United States Patent
Hachtel et al.

(10) Patent No.: US 9,156,796 B2
(45) Date of Patent: Oct. 13, 2015

(54) BENZOIMIDAZOLE-CARBOXYLIC ACID AMIDE DERIVATIVES AS APJ RECEPTOR MODULATORS

(71) Applicant: SANOFI, Paris (FR)

(72) Inventors: Stephanie Hachtel, Frankfurt am Main (DE); Paulus Wohlfart, Frankfurt am Main (DE); John Weston, Frankfurt am Main (DE); Marco Mueller, Frankfurt am Main (DE); Elisabeth Defossa, Frankfurt am Main (DE); Katharina Mertsch, Frankfurt am Main (DE); Jian-Hui Weng, Oro Valley, AZ (US); Robert Alan Binnie, Tucson, AZ (US); Farid Abdul-Latif, Oro Valley, AZ (US); William Jerome Bock, Tucson, AZ (US); Armin Walser, Tucson, AZ (US)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/031,427

(22) Filed: Sep. 19, 2013

(65) Prior Publication Data

US 2014/0094450 A1 Apr. 3, 2014

(51) Int. Cl.
| | |
|---|---|
| *C07D 235/08* | (2006.01) |
| *C07D 405/06* | (2006.01) |
| *C07D 409/06* | (2006.01) |
| *C07D 417/06* | (2006.01) |
| *C07D 409/14* | (2006.01) |
| *C07D 413/14* | (2006.01) |
| *C07D 403/06* | (2006.01) |
| *C07D 413/06* | (2006.01) |
| *C07D 417/14* | (2006.01) |
| *C07D 411/06* | (2006.01) |
| *C07D 451/04* | (2006.01) |
| *C07D 487/06* | (2006.01) |
| *C07D 455/02* | (2006.01) |
| *C07D 487/08* | (2006.01) |

(52) U.S. Cl.
CPC ............ *C07D 235/08* (2013.01); *C07D 403/06* (2013.01); *C07D 405/06* (2013.01); *C07D 409/06* (2013.01); *C07D 409/14* (2013.01); *C07D 411/06* (2013.01); *C07D 413/06* (2013.01); *C07D 413/14* (2013.01); *C07D 417/06* (2013.01); *C07D 417/14* (2013.01); *C07D 451/04* (2013.01); *C07D 455/02* (2013.01); *C07D 487/06* (2013.01); *C07D 487/08* (2013.01)

(58) Field of Classification Search
USPC .................................................... 548/304.7
See application file for complete search history.

(56) References Cited

FOREIGN PATENT DOCUMENTS

| EP | 1 903 052 A2 | 3/2008 |
|---|---|---|
| WO | WO 99/40072 A1 | 8/1999 |
| WO | WO 03/014377 A2 | 2/2003 |
| WO | WO 03/053938 A1 | 7/2003 |
| WO | WO 2004/108688 A1 | 12/2004 |
| WO | WO 2008/153701 A1 | 12/2008 |

OTHER PUBLICATIONS

Evan A. Ashley et al., The endogenous peptide apelin potently improves cardiac contractility and reduces cardiac loading in vivo, Cardiovascular Research, (2005), vol. 65, pp. 73-82.
Gareth Barnes et al., Translation promise of the apelin-APJ system, Heart, (2010), vol. 96, pp. 1011-1016.
Jeremie Boucher et al., Apelin, a Newly Identified Adipokine Up-Regulated by Insulin and Obesity, Endocrinology, (Apr. 2005), vol. 146, pp. 1764-1771.
Hyung J. Chun et al., Apelin signaling antagonizes Ang II effects in mouse models of atherosclerosis, The Journal of Clinical Investigation, (Oct. 2008), vol. 118, No. 10, pp. 3343-3354.
Tieying Dai et al., Apelin increases contractility in failing cardiac muscle, European Journal of Pharmacology, (2006), vol. 553, pp. 222-228.
Nadia De Mota et al., Cloning, Pharmacological Characterization and Brain Distribution of the Rat Apelin Receptor, Neuroendocrinology, (2000), vol. 72, pp. 400-407.
Cedric Dray et al., Apelin Stimulates Glucose Utilization in Normal and Obese Insulin-Resistant Mice, Cell Metabolism, (Nov. 5, 2008), vol. 8, pp. 437-445.
Klara Farkasfalvi et al., Direct effects of apelin on cardiomyocyte contractility and electrophysiology, Biochemical and Biophysical Research Communications, (2007), vol. 357, pp. 889-895.

(Continued)

*Primary Examiner* — Laura L. Stockton
(74) *Attorney, Agent, or Firm* — Morrison & Foerster LLP

(57) ABSTRACT

The present invention relates to benzoimidazole-carboxylic acid amide compounds of the formula I,

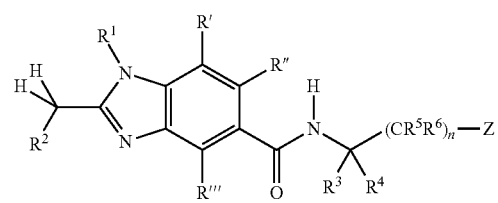

in which R', R'', R''', $R^1$, $R^2$, $R^3$, $R^4$, $R^5$, $R^6$ and Z are defined as indicated below. The compounds of the formula I are APJ receptor modulators, and are useful for the treatment of diseases associated with increased blood pressure for example. The invention furthermore relates to the use of compounds of the formula I, in particular as active ingredients in pharmaceuticals, and pharmaceutical compositions comprising them.

11 Claims, No Drawings

(56) References Cited

OTHER PUBLICATIONS

Gabor Foldes et al., Circulating and cardiac levels of apelin, the novel ligand of the orphan receptor APJ, in patients with heart failure, Biochemical and Biophysical Research Communications, (2003), vol. 308, pp. 480-485.

Masaki Hosoya et al., Molecular and Functional Characteristics of APJ, The Journal of Biological Chemistry, (Jul. 14, 2000), vol. 275, No. 28, pp. 21061-21067.

Junji Ishida et al., Regulatory Roles of APJ, a Seven-transmembrane Receptor Related to Angiotensin-type 1 Receptor in Blood Pressure in Vivo, The Journal of Biological Chemistry, (Jun. 18, 2004), vol. 279, No. 25, pp. 26274-26279.

Alan G. Japp et al., Vascular Effects of Apelin in Vivo in Man, Journal of the American College of Cardiology, (Sep. 9, 2008), vol. 52, No. 11, pp. 908-913.

A.G. Japp et al., Acute Cardiovascular Effects of Apelin in Humans: Potential Role in Patients With Chronic Heart Failure, Circulation, Journal of the American Heart Association, (2010), vol. 121, pp. 1818-1827.

Hiroyasu Kidoya et al., Apelin induces enlarged and nonleaky blood vessels for functional recovery from ischemia, Blood, (Apr. 15, 2010), vol. 115, No. 15, pp. 3166-3174.

Matthias J. Kleinz et al., Immunocytochemical localisation of the apelin receptor, APJ, to human cardiomyocytes, vascular smooth muscle and endothelial cells, Regulatory Peptides, (2005), vol. 126, pp. 233-240.

Matthias J. Kleinz et al., Apelin reduces myocardial reperfusion injury independently of PI3K/Akt and P70S6 kinase, Regulatory Peptides, (2008), vol. 146, pp. 271-277.

Keiji Kuba et al., Impaired Heart Contractility in Apelin Gene-Deficient Mice Associated with Aging and Pressure Overload, Circulation Research, (2007), vol. 101, pp. e32-e42.

Nicholas J. Leeper et al., Apelin prevents aortic aneurysm formation by inhibiting macrophage inflammation, American Journal of Physiology—Heart and Circulatory Physiology, (Mar. 20, 2009), vol. 296, pp. H1329-H1335.

Janet J. Maguire et al., [Pyr1] Apelin-13 Identified as the Predominant Apelin Isoform in the Human Heart: Vasoactive Mechanisms and Inotropic Action in Disease, Hypertension, (Sep. 2009), vol. 54, pp. 598-604.

Andrew D. Medhurst et al., Pharmacological and immunohistochemical characterization of the APJ receptor and its endogenous ligand apelin, Journal of Neurochemistry, (2003), vol. 84, pp. 1162-1172.

Cedric Mesmin et al., Liquid chromatography/tandem mass spectrometry assay for the absolute quantification of The expected circulating apelin peptides in human plasma, Rapid Communications in Mass Spectrometry, (2010), vol. 24, pp. 2875-2884.

Brian F. O'Dowd et al., A human gene that shows identity with the gene encoding the angiotensin receptor is located on chromosome 11, Gene, (1993), vol. 136, pp. 355-360.

Annabelle Reaux-Le Goazigo et al., Dehydration-Induced Cross-Regulation of Apelin and Vasopressin Immunoreactivity Levels in Magnocellular Hypothalamic Neurons, Endocrinology, (Sep. 2004), vol. 145, No. 9, pp. 4392-4400.

James C. Simpkin et al., Apelin-13 and apelin-36 exhibit direct cardioprotective activity against ischemia-reperfusion injury, Basic Research in Cardiology, (2007), vol. 102, pp. 518-528.

Christopher C. T. Smith et al., Temporal Changes in Myocardial Salvage Kinases During Reperfusion Following Ischemia: Studies Involving the Cardioprotective Adipocytokine Apelin, Cardiovas Drugs Ther, (2007), vol. 21, pp. 409-414.

Istvan Szokodi et al., Apelin, the Novel Endogenous Ligand of the Orphan Receptor APJ, Regulates Cardiac Contractility, Circulation Research, (2002), vol. 91, pp. 434-440.

Kazuhiko Tatemoto et al., Isolation and Characterization of a Novel Endogenous Peptide Ligand for the Human APJ Receptor, Biochemical and Biophysical Research Communications, (1998), vol. 251, pp. 471-476.

Chen Wang WE146 et al., Apelin decreases the SR Ca2+ content but enhances the amplitude of [Ca2+]i transient and contractions during twitches in isolated rat cardiac myocytes, Am J Physiol Heart Circ Physiol, (2008), vol. 294, pp. H2540-H2546.

Patrick Yue et al., Apelin is necessary for the maintenance of insulin sensitivity, Am J Physiol Endocrinol Metab, (2010), vol. 298, pp. E59-E67.

Tatsuo Hashimoto et al., Requirement of Apelin-Apelin Receptor System for Oxidative Stress-Linked Atherosclerosis, The American Journal of Pathology, (Nov. 2007), vol. 171, No. 5, pp. 1705-1712.

BENZOIMIDAZOLE-CARBOXYLIC ACID AMIDE DERIVATIVES AS APJ RECEPTOR MODULATORS

The present invention relates to benzoimidazole-carboxylic acid amide compounds of the formula I,

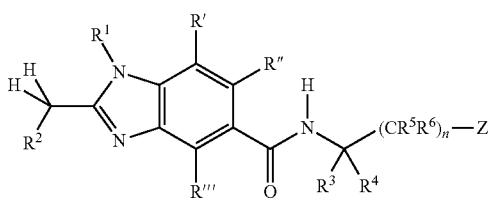

in which R', R", R''', $R^1$, $R^2$, $R^3$, $R^4$, $R^5$, $R^6$ and Z are defined as indicated below. The compounds of the formula I are APJ receptor modulators, and are useful for the treatment of diseases associated with increased blood pressure for example. The invention furthermore relates to the use of compounds of the formula I, in particular as active ingredients in pharmaceuticals, and pharmaceutical compositions comprising them.

The apelin receptor (AplnR alias APJ alias Agtrl-1) is a G-protein-coupled receptor first identified in 1993 (O'Dowd et al. Gene 1993; 136:355-60). It is expressed in several tissues, including the endothelium, myocardium, vascular smooth muscle, adipose tissue and throughout the brain (Farkasfalvi et al. Biochem Biophys Res Commun 2007; 357:889-95; Hosoya et al. J Biol Chem 2000; 275:21061-7; Kleinz et al. Regul Pept 2005; 126:233-240; Medhurst et al., J Neurochem 2003; 84:1162-1172; De Mota et al. Neuroendocrinology 2000; 72:400-407). The peptidic ligands for this receptor named apelins were first deorphaned in 1998 (Tatemoto et al. Biochem Biophys Res Commun 1998; 251:471-476). All apelins stem from a single precursor, a 77 amino acid prepropeptide that is cleaved by unknown proteases into smaller peptides. Apelins bear a conserved c-terminal sequence forming a unique activating pharmacophore on the apelin receptor. Several publications describe quantifications of apelin peptides in plasma samples from different patient populations using a commercially available immunoassay. However, in the light of a recent publication describing a more accurate combined liquid chromatography and tandem mass spectrometry assay for the absolute quantification of different apelin peptides all the immunoassay results may need to be revised. (Mesmin et al. Rapid Commun Mass Spectrom. 2010; 24: 2875-2884). Surprisingly these authors could not detect five major forms of circulating apelins in amounts indicated by the immunoassay. The main sources for plasma apelins are currently unclear, although vascular endothelium, atria of the heart and adipocytes are likely to be significant contributors (Földes et al. Biochem Biophys Res Commun 2003; 308:480-485; Bocher et al. Endocrinology 2005; 146:1764-1771. Epub 2005 Jan. 27). 10

Administrations of apelins cause vasodilatation in different pre-clinical models and accordingly, intravenous administration in rodents reduces mean arterial blood pressure, systemic venous tone and cardiac pre- and afterload (for a review see Barnes et al. Heart 2010, 96:1011-1016). Vasodilatation to apelin in rodents is dependent on endothelium and mediated through nitric oxide and prostacyclin dependent pathways. Ishida and colleagues demonstrated in 2004, that a functional knockdown of the apelin receptor abolished blood pressure lowering effects of apelins, confirming that vascular effects of apelins are mediated by the apelin receptor specifically (Ishida et al. 2004, J Biol Chem; 279:25, 25274-25279).

The vascular effects of apelin in pre-clinical studies translate into similar effects in humans (Japp et al., 2008 J Am Coll Cardiol 2008; 52:908-913; Japp et al. Circulation 2010; 121: 1818-1827). Infusions of apelins increased forearm and coronary blood flow and lowered mean arterial pressure and peripheral vascular resistance in heart failure patients and healthy control subjects in heart failure patients without raising heart rates. An increased cardiax index could be noted, which may be explained by either direct effects on the cardiac muscle (see below) and/or reduction of pre- and afterload in the peripheral circulation. In man, vasodilatation by apelins is reduced by two thirds during nitric oxide synthase inhibition but is unaffected by prostacyclin inhibition.

The apelin receptor has been linked to direct cardiac actions. In vitro, exogenous apelin increases contractility at subnanomolar concentrations in atrial strips (Maguire et al. Hypertension 2009; 54:598-604) and whole rat hearts (Szokodi et al. Circ. Res. 2002; 91, 434-440). In healthy rodents, acute apelin infusion increases myocardial contractility independently of its effects on loading conditions. Uniquely among current inotropic agents, chronic dosing causes a sustained increase in cardiac output without inducing left ventricular hypertrophy (Ashley et al. Cardiovasc Res 2005; 65:73-82). While apelin-deficient mice display normal or only slightly impaired basal cardiac function at early life cycles, they demonstrate progressive cardiac dysfunction from 6 months of age and develop severe heart failure when subjected to chronic pressure overload (Kuba et al. Circ Res 2007; 101, e§2-42).

Controversial results have been published regarding the involvement of intracellular calcium on the contractility effects of apelin in cardiomyocytes. Two groups described that intracellular calcium is not a signalling mechanism. However, others reported at least a modest increase in the amplitude of the intracellular calcium ion transients in failing rat trabeculae and isolated cardiomyocytes (Dai et al. Eur J Pharmacol 2006; 553; 222-228; Wang et al. Am J Physiol heart circ Physiol 2008; 294; H2540-46.

Additionally, effects of apelins in pre-clinical models have been described. Apelins may have an important counter-regulatory role to vasopressin and hence fluid homoeostasis. Apelin and the APJ receptor are both expressed also in the kidney and many areas of the brain. Synthesis in certain brain regions involved in fluid homeostasis are regulated by vasopressin. To the contrary, intracerebral injection of apelin directly inhibits vasopressin release leading to a 40% reduction in plasma vasopressin concentrations (Reaux-Le Goazigo et al. Endocrinology 2004; 145:4392-4400).

A link of apelins to metabolic syndrome is suggested by pre-clinical data. Apelins are produced by adipose tissue and may influence glucose and lipid metabolism as adipocytokines (Boucher et al. Endocrinology 2005; 146:1764-1771). Acute intravenous administration of $^1$pyr-apelin-13 stimulates glucose utilization in normal and obese insulin-resistant mice (Dray C et al. Cell Metab 2008; 8:437-445). These acute effects were explained by a direct effect of $^1$pyr-apelin-13 on glucose uptake into skeletal muscle. Mice deficient for the apelins have reduced insulin sensitivity which can be corrected by sub-chronic supplementation with apelin via minipumps. Furthermore in insulin resistant homozygous leptin receptor mutant mice (db/db mice) a similar sub-chronic administration results in improved glucose utilization (Yue et al. Am J Physiol Endocrinol Metab 2009; 298:E59-67). Results with glucose utilization in apelin receptor knockout mice have not been published. Furthermore it is not reported yet, whether apelins significantly affect glucose handling in man.

The clinical and pre-clinical profile suggests applications of apelin receptor agonists in different patient populations and indications. In heart failure, apelins demonstrate a unique hemodynamic profile in enhancing myocardial contractility without inducing left ventricular hypertrophy. In parallel, ventricular pre- and afterload is reduced by reduced peripheral resistance. In pre-clincal models, apelin increases contractility at least to the same extent in the failing compared to normal myocardium (Dai et al. Eur J Phammacol 2006; 553: 222-228). Irrespective of changes in receptor and ligand expression, these studies indicate agonism of the receptor is not diminished in situations of established heart failure. First data from clinical studies with acute apelin infusions are promising. In contrast to acetylcholine, another vaso-active principle, vascular and cardiac hemodynamic effects of apelins are preserved in chronic heart failure patients (Japp et al. Circulation 2010; 121:1818-1827). These patients received optimal pharmacological treatment, suggesting that the effects of apelin were additive to established heart failure therapies like ACE-Inhibitors and/or β-blockers. Regarding therapies targeting the diseased heart, acute beneficial effects of apelins after acute myocardial infarction may be envisaged. Two groups reported that in pre-clinical models of acute myocardial ischemia and reperfusion administration of apelins at reperfusion strongly reduces myocardial injury (Kleinz et al. Regul Pept 2008; 146:271-277; Simpkin et al. Basic Res Cardiol 2007; 102:518-28). Both groups published opposing results regarding the underlying signaling of this cardioprotective mechanism. Simpkin et al favor a mechanism based on activation of phosphatide-3-kinase, AKT kinase and P70S6 kinase, whereas Kleinz et al could not confirm activation of this pathway However, signaling pathways independent of PI-3-kinase, AKT-kinase and p70S6 kinase may also explain the benefical effects of apelin receptor agonists in ischemia-reperfusion injury. Apelin increases both phosphorylation and activity of key components within reperfusion injury salvage kinase pathway (Smith et al. Cardiovasc Drugs Ther 2007; 21:409-414). This pro-survival pathway is known to be associated with reduced ischemia-reperfusion-injury by preserving mitochondrial function. Despite the fact, preconditioning agents are difficult to implement in clinical practice, apelin receptor agonists may be administered with the reperfusion solution directly after acute myocardial infarction and thereby display potential benefits in both restoring cardiac survival and function. Another application, especially of oral bioavailable small molecule apelin receptor agonists, could be to start in a patient with an acute myocardial infarction with an intravenous formulation during reperfusion and continue later, e.g. outside the clinic, with an oral bioavailable formulation of the same drug component. Furthermore, intravenous or oral administration of apelin receptor agonists could be envisaged in patients with acute heart failure. Very often acute heart failure develops in the progression of chronic heart failure spontaneously as acute episodes of disease worsening but without signs of myocardial infarction. Patients are then hospitalized and stabilized during hospitalization by agents increasing the contracility of the disease heart muscle. Apelin receptor agonists display a unique hemodynamic profile suggesting a safe and efficient use in such patients.

Agonists of the apelin receptor may also represent a novel class of anti-hypertensive agents. In preclinical models, administration of apelin peptides lowers blood pressure, greatly enhanced in hypertensive animals compared with normotensive controls. In first clinical studies modest but significant effects on blood pressure lowering could be demonstrated in normotensive middle-aged subjects. Whether intravenously applied apelin peptides lower blood pressure stronger in hypertensive patient populations, similar to the situation in normotensive vs. hypertensive rats, needs to be evaluated. Application of apelin peptides in hypertensive patients is strongly limited by the need of intravenous administration route. However, small molecule apelin receptor agonists as claimed in this patent application may have a much wider application in these patients due to better oral bioavailiblity.

Apelin receptor agonists appear to have beneficial effects on additional vascular based diseases. In atherosclerotic mice deficient for the Apolipoprotein-E, apelin infusion inhibits atherosclerosis progress and completely abrogates angiotensin II-accelerated detrimental effects independent of blood pressure (Chun et al. J Clin Invest 2008; 118:3343-3354). And in double knockout mice, deficient in for the apelin receptor ligand and Apolipoprotein-E, accelerated atherosclerosis could be observed compared versus single Apolipoprotein-E-knockout. It needs to be mentioned, that also pro-atherosclerotic effects of the apelin receptor have been described in a combined mice knockout-model of the apelin receptor and apolipoprotein-E ApoE (Hashimoto et al. Am J Pathol 2007:108:1432-1438). Overall these results are difficult to reconcile: Most probably very different fat feeding regimens or different genetic backgrounds and so called off-target genetic effects best explain the observed differences. Independent of effects on atherosclerosis progression, apelin treatment resulted in reduced aneurysm by 50% in a mouse model of abdominal aortic aneurysms (Leeper et al. Am J Physiol Heart Circ Physiol 2009; 296:H1329-1335), an effect explained by the authors by a direct anti-inflammatory effect within the vessel wall.

Furthermore, apelin receptor agonists may play an important role in maturation of newly formed blood vessels. Kidoya et al (Blood 2010; 115; 3166-3174) recently described in a model of vascular remodelling after hindlimb ischemia in mice, that apelins induce the maturation into enlarged and non-leaky blood vessels for functional recovery. Especially pathologically increased vascular permeability induced by VEGF under hypoxic conditions seems to be corrected by apelins.

In humans, apelins cause nitric oxide-mediated vasodilatation in forearm resistance vessels of healthy subjects. Based on promising preclinical data, the role of apelin receptor agonists in preventing human vascular disease merits further investigations. These investigations will be strongly facilitated by small molecule apelin receptor agonists, as claimed in this patent application, because the oral bioavailability allows for much easier chronic administration routes.

In patients with metabolic syndrome and diabetes, apelin receptor agonists may provide additional benefits. Apelins are produced also by adipose tissue and influence glucose and lipid metabolism as adipocytokines. Mice with no apelin receptor ligands have reduced insulin sensitivity which can be corrected by the administration of exogenous apelin. Acute and sub-chronic positive effects of apelins on glucose utlizations following a glucose load have been described in insulin-resistant animal strains. Although the translation of these effects to man needs to be performed, apelin receptor agonists may offer additional therapeutic options especially in insulin-resistant patients, insufficiently dealing with increased plasma glucose load in metabolic syndrome and diabetes. The simultaneous beneficial effects on blood glucose lowering and vascular and cardiac homeostasis are a unique advantage to therapeutic priniciples affecting blood glucose alone and open an avenue to macro- and microvascualar diabetic late complications, like diabetic cardiomyopathies, diabetic retinophathy, diabetic macular edema, diabetic nephrophathy and diabetic neuropathy. Oral bioavailable small molecule apelin receptor agonist would strongly boost these areas of applications because they would be not restricted to intravenous or subcutaneous administration routes.

There continues to be a need for further effective low molecular weight APJ modulators, in particular in view of safety and selectivity. The present invention satisfies this need by providing the Benzoimidazole-carboxylic acid compounds of the formula I.

Benzoimidazole-carboxylic acid derivatives which are useful for pharmaceutical applications, have already been disclosed, for example in WO03053938 (NovoNordisk), WO2004108688 (Astra Zeneca), WO99040072, WO03014377 (Boehringer Ingelheim) and in WO2008153701 (Schering Corp.).

Accordingly, a subject of the present invention is a compound of the formula I,

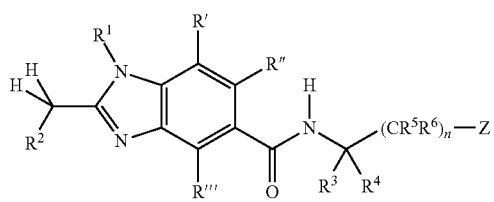

I wherein
R', R", R''' are independently of each other H, halogen, $CF_3$, $OCF_3$, O—$(C_1-C_3)$-alkyl;
$R^1$ is
a) $(C_4-C_7)$-alkyl;
b) $(C_5-C_7)$-cycloalkyl, which is unsubstituted or mono-substituted by $(C_1-C_2)$-alkyl, or $CF_3$;
c) methylene-cyclohexyl;
d) phenyl, which is unsbutstituted or mono-substituted by methyl or Cl;
$R^2$ is
a) a 5-membered heteroaryl which contains 1 or 2 identical or different ring heteroatoms chosen from N, O and S, wherein said 5-membered heteroaryl is unsubstituted or mono-substituted by Cl or $(C_1-C_4)$-alkyl;
b) phenyl;
c) $(C_5-C_6)$-cycloalkyl; or
d) tetrahydrofuranyl;
$R^3$ is H, or $(C_1-C_2)$-alkyl;
and
$R^4$ is
a) $(C_3-C_5)$-alkyl, which may be optionally substituted by 1-3 F or S—$(C_1-C_4)$-alkyl,
b) $(C_0-C_1)$-alkylene-$(C_3-C_7)$-cycloalkyl, wherein said cycloalkyl is unsubstituted or mono- or di-substituted by methyl;
c) $(C_0-C_2)$-alkylene-phenyl, wherein said phenyl is unsubstituted or mono- or di-substituted by F, Cl, $(C_1-C_4)$-alkyl or $CF_3$; or
d) thienyl;
or
$R^3$ and $R^4$ are, together with the carbon atom to which they are attached, a 5- to 7-membered cycloalkyl ring, which is unsubstituted or mono-substituted by $(C_1-C_4)$-alkyl;
$R^5$ is H, $(C_1-C_4)$-alkyl or OH;
$R^6$H or $(C_1-C_4)$-alkyl;
n is 0, 1 or 2; and
Z is
$CO_2$—$R^7$, $OR^8$, $C(O)NR^9R^{10}$, $S(O)_2NR^{11}R^{12}$,

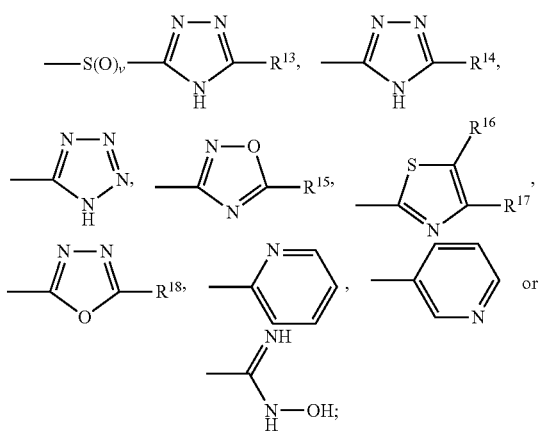

wherein
v is 0 or 2;
$R^7$ is H or $(C_1-C_4)$-alkyl;
$R^8$ is H or $(C_1-C_4)$-alkyl;
$R^9$ is H, $(C_1-C_4)$-alkyl or ethylene-O—$(C_1-C_4)$-alkyl;
and
$R^{10}$ is
a) H;
b) $(C_1-C_6)$-alkyl, which is unsubstituted or mono-substituted by $CF_3$;
c) $(C_1-C_2)$-alkyl, which is substituted by CN or $CO_2R^{19}$
wherein
$R^{19}$ is H or $(C_1-C_6)$-alkyl;
d) $(C_2-C_4)$-alkyl, which is mono-substituted by a substituent selected from the group consisting of S-methyl, $SO_2NR^{20}R^{21}$, O—$R^{22}$ and $NR^{23}R^{24}$;
wherein
$R^{20}$ is H;
$R^{21}$ is H;
$R^{22}$ is H, $(C_1-C_3)$-alkyl, methylene-cyclopropyl, methylene-phenyl, or methylene-2-tetrahydrofurane;
$R^{23}$ is H or $(C_1-C_2)$-alkyl;
$R^{24}$ is $(C_1-C_2)$-alkyl or $SO_2$-methyl;
e) $(C_3-C_5)$-cycloalkyl, which is unsubstituted or mono-substituted by phenyl;
f) $(C_0-C_2)$-alkylene-heterocycloalkyl, wherein said heterocylcoalkyl is five or six membered and contains 1 or 2 O atoms in non-adjacent positions, and wherein sad heterocycloalkyl is unsubstituted or geminally disubstituted with a spiro cyclopentyl ring or a spiro cyclohexyl ring;
g) $(C_2-C_5)$-alkylene-heterocycloalkyl, wherein said heterocycloalkyl is a five-, six- or seven-membered ring, which contains at least one N atom, and which is attached via said N-atom, and which may additionally contain one heteroatom selected from the group consisting of O, $S(O)_x$ or $NR^{25}$ in a position not adjacent to the N atom, by which the ring is attached to the alkylene, and wherein any carbon atom within said heterocycloalkyl is unsubstituted or substituted by 1 or 2 substituents selected from the group consisting of $(C_1-C_3)$alkyl, or methylene-phenyl;
wherein
x is 2;
$R^{25}$ is H, $(C_1-C_2)$alkyl, methylene-phenyl or phenyl, which is unsubstituted or substituted by 1 or 2 substituents selected from the group consisting of F, Cl and O—$(C_1-C_4)$-alkyl;
h) $(C_0-C_3)$-alkylene-heterocycloalkyl, wherein said heterocycloalkyl is a five- or six-membered ring, which contains at least one N atom, and which is not attached via said N-atom, and which may additionally contain one O atom in a position not adjacent to the N atom, and wherein said N-atom is unsubstituted or substituted by a substituent selected from the group consisting of
  i) $(C_1-C_4)$-alkyl, which is unsubstituted or mono-substituted by O$(C_1-C_4)$-alkyl;
  ii) methylene-cyclohexyl;
  iii) $(C_0-C_2)$-alkylene-phenyl, wherein phenyl is unsubstituted or substituted by 1 or 2 substituents selected from the group consisting of F and O$(C_1-C_4)$-alkyl;
  iv) $(C_0-C_1)$-alkylene-pyridyl;
  v) pyrimidinyl;
i) 8-methyl-8-aza-bicyclo[3.2.1]oct-3yl;
j) 9-methyl-9-aza-bicyclo[3.3.1]non-3-yl;
k) methylene-4-(octahydro-quinolizinyl);
l) $(C_0-C_2)$-alkylene-phenyl, wherein phenyl is unsubstituted or monosubstituted by substituents chosen from the group consisting of F, O$(C_1-C_4)$-alkyl, N$((C_1-C_4)$-alkyl$)_2$, 4-morpholinyl and methylene-(4-methyl-piperidin)-1-yl or disubstituted on adjacent positions by the group —O(CH$_2$)O—;
m) $(C_1-C_2)$-alkylene-heteroaryl, wherein said heteroaryl ring is a five- or six-membered ring containing 1, 2, 3 or 4 heteroatoms selected from O, S or N; and wherein said heteroaryl ring is unsubstituted or mono-substituted by oxo (=O);
or
$R^9$ and $R^{10}$ together with the N-atom carrying them are
a) a four-, five- or six-membered heterocylcoalkyl ring containing only the N atom, to which $R^9$ and $R^{10}$ are attached, which is unsubstituted or mono-substituted by a substituent selected from the group consisting of
  i) $(C_0-C_1)$-alkylene-OR$^{26}$, wherein $R^{26}$ is H, $(C_1-C_3)$ alkyl or methylene-phenyl;
  ii) CO$_2$R$^{27}$, wherein $R^{27}$ is H or $(C_1-C_6)$-alkyl;
  ii) NR$^{28}$R$^{29}$, wherein $R^{28}$ is $(C_1-C_2)$-alkyl and $R^{29}$ is $(C_1-C_2)$-alkyl, methylene-phenyl or ethylene-N$((C_1-C_4)$-alkyl$)_2$;
  iii) 1-piperidinyl, which is unsubstituted or mono-substituted by methyl;
  iv) 1-piperazinyl, which is unsubstituted or mono-substituted by methyl;
  v) 4-morpholinyl;
  vi) 1-azepanyl;
  vii) 2-(2,3-dihydro-1H-isoindolyl);
b) a six- or seven-membered heterocycloalkyl ring containing the N atom, to which $R^9$ and $R^{10}$ are attached and one additional heteroatom selected from O, S or NR$^{30}$ in a position non-adjacent to the N atom, to which $R^9$ and $R^{10}$ are attached, wherein the carbon atoms in said heterocycloalkyl ring are unsubstituted or mono- or disubstituted by methyl and wherein
$R^{30}$ is
  i) H;
  ii) $(C_1-C_4)$-alkyl;
  iii) $(C_5-C_6)$-cycloalkyl;
  iv) phenyl, which is unsubstituted or mono-substituted by F, CF$_3$ or O—$(C_1-C_4)$-alkyl;
  v) methylene-phenyl, which is unsubstituted or mono- or di-substituted by F or Cl or disubstituted on adjacent positions by the group —O(CH$_2$)O—;
  vi) pyridyl;
c) a 2,5-diaza-bicyclo[2.2.1]heptyl-ring, which is unsubstituted or substituted on the second N atom in 5-position by a substituent selected from the group consisting of $(C_1-C_4)$-alkyl, methylene-cyclopentyl, phenyl, which is unsubstituted or mono-substituted by F, methylene-phenyl, wherein phenyl is unsubstituted or mono-substituted by O—$(C_1-C_4)$-alkyl or CF$_3$,
$R^{11}$ is H;
$R^{12}$ is $(C_1-C_4)$-alkyl;
$R^{13}$ is H;
$R^{14}$ is CF$_3$ or methylene-O—$(C_1-C_4)$-alkyl;
$R^{15}$ is cyclopryopyl or phenyl;
$R^{16}$ is H or $(C_1-C_4)$-alkyl;
$R^{17}$ is H or $(C_1-C_4)$-alkyl;
and
$R^{18}$ is $(C_1-C_4)$-alkyl;
in any of its stereoisomeric forms, or a mixture of stereoisomeric forms in any ratio, or a physiologically acceptable salt thereof, or a physiologically acceptable solvate of any of them.

Structural elements such as groups, substituents, hetero ring members, numbers or other features, for example alkyl groups, groups like $R^1$, $R^2$, $R^3$ etc., which can occur several times in the compounds of the formula I, can all independently of one another have any of the indicated meanings and can in each case be identical to or different from one another. For example, the alkyl groups in a dialkylamino group can be identical or different.

As used here, the terms "including" and "comprising" are used in their open, non-limiting sense. As used herein, the terms "$(C_1-C_8)$" or "$(C_6-C_8)$" and so forth, refer to moieties having 1 to 8 or 5 to 8 carbon atoms, respectively. Within terms like "$(C_0-C_6)$-alkyl" or "$(C_0-C_6)$-alkylen" "$C_0$-alkyl" or "$(C_0)$-alkylen" refer to a bond, or in case of an unsubstituted "$(C_0)$-alkyl" it refers to a hydrogen.

The term "alkyl", as used herein, refers to saturated, monovalent hydrocarbon radicals. The term "alkenyl", as used herein, refers to monovalent hydrocarbon radicals, which contain at least one carbon-carbon double bond, wherein each double bond can have E- or Z-configuration. The term "alkinyl", as used herein, refers to monovalent hydrocarbon radicals, which contain at least one carbon-carbon triple bond. The alkyl, alkenyl and alkynyl groups can be linear, i.e. straight-chain, or branched. This also applies when they are part of other groups, for example alkyloxy groups (=alkoxy groups, O-alkylgroups), alkyloxycarbonyl groups or alkyl-substituted amino groups, or when they are substituted. Depending on the respective definition, the number of carbon atoms in an alkyl group can be 1, 2, 3, 4, 5, 6, 7 or 8, or 1, 2, 3, 4, 5 or 6, or 1, 2, 3 or 4, or 1, 2 or 3. Examples of alkyl are methyl, ethyl, propyl including n-propyl and isopropyl, butyl including n-butyl, sec-butyl, isobutyl and tert-butyl, pentyl including n-pentyl, 1-methylbutyl, isopentyl, neopentyl and tert-pentyl, hexyl including n-hexyl, 3,3-dimethylbutyl and isohexyl, heptyl and octyl. Double bonds and triple bonds in alkenyl groups and alkynyl groups can be present in any positions. In one embodiment of the invention, alkenyl groups contain one double bond and alkynyl groups contain one triple bond. In one embodiment of the invention, an alkenyl group or alkynyl group contains at least three carbon atoms and is bonded to the remainder of the molecule via a carbon atom which is not part of a double bond or triple bond. Examples of alkenyl and alkynyl are ethenyl, prop-1-enyl, prop-2-enyl (=allyl), but-2-enyl, 2-methylprop-2-enyl, 3-methylbut-2-enyl, hex-3-enyl, hex-4-enyl, prop-2-ynyl (=propargyl), but-2-ynyl, but-3-ynyl, hex-4-ynyl or hex-5-ynyl. Substituted alkyl groups, alkenyl groups and alkynyl groups can be substituted in any positions, provided that the respective compound is sufficiently stable and is suitable for the desired purpose such as use as a drug substance. The prerequisite that a specific group and a compound of the formula I are sufficiently stable and suitable for the desired purpose such as use as a drug substance, applies in general with respect to the definitions of all groups in the compounds of the formula I.

Independently of one another and independently of any other substituents, alkyl groups, divalent alkyl groups, alkenyl groups, alkynyl groups, cycloalkyl groups and heterocycloalkyl groups are optionally substituted by one or more fluorine substituents which can be located in any positions, i.e., the said groups can be unsubstituted by fluorine substituents or substituted by fluorine substituents, for example by 1, 2, 3, 4, 5, 6, 7, 8, 9, 10, 11, 12 or 13, or by 1, 2, 3, 4, 5, 6, 7, 8 or 9, or by 1, 2, 3, 4, 5, 6 or 7, or by 1, 2, 3, 4 or 5, or by 1, 2 or 3, or by 1 or 2, fluorine substituents. Examples of fluorine-substituted said groups are trifluoromethyl, 2-fluoroethyl, 2,2,2-trifluoroethyl, pentafluoroethyl, 3,3,3-trifluoropropyl, 2,2,3,3,3-pentafluoropropyl, 4,4,4-trifluorobutyl, heptafluoroisopropyl, —CHF—, —$CF_2$—, —$CF_2$—$CH_2$—, —$CH_2$—$CF_2$—, —$CF_2$—$CF_2$—, —$CF(CH_3)$—, —$C(CF_3)_2$—, —$C(CH_3)_2$—$CF_2$—, —$CF_2$—$C(CH_3)_2$—, 1-fluoro-cyclopropyl, 2,2-difluorocyclopropyl, 3,3-difluorocyclobutyl, 1-fluorocyclohexyl, 4,4-difluorocyclohexyl, 3,3,4,4,5,5-hexafluorocyclohexyl. Examples of alkyloxy groups in which the alkyl moiety is fluorine-substituted, are trifluoromethoxy, 2,2,2-trifluoro-ethoxy, pentafluoroethoxy and 3,3,3-trifluoropropoxy.

The term "alkanediyl" or "alkylene", as used herein, refers to saturated, divalent hydrocarbon radicals. The term "alkenediyl", as used herein, refers to divalent hydrocarbon radicals, which contain at least one carbon-carbon double bond, wherein each double bond can have E- or Z-configuration. The term "alkindiyl", as used herein, refers to divalent hydrocarbon radicals, which contain at least one carbon-carbon triple bond. As far as applicable, the preceding explanations regarding alkyl, alkenyl and alkinyl groups apply correspondingly to alkanediyl, alkendiyl and alkindiyl groups, which thus can likewise be linear and branched. Examples of divalent alkyl groups are —$CH_2$— (=methylene), —$CH_2$—$CH_2$—, —$CH_2$—$CH_2$—$CH_2$—, —$CH_2$—$CH_2$—$CH_2$—$CH_2$—, —$CH(CH_3)$—, —$C(CH_3)_2$—, —$CH(CH_3)$—$CH_2$—, —$CH_2$—$CH(CH_3)$—, —$C(CH_3)_2$—$CH_2$—, —$CH_2$—$C(CH_3)_2$—.

The term "cycloalkyl", as used herein, unless otherwise indicated, refers to a monovalent radical of a saturated or partially saturated hydrocarbon ring system, which can be monocyclic, bicyclic or tricyclic, i.e. which can contain one, two or three rings. The bicyclic or tricyclic ring system can be a fused ring system, in which two adjacent rings share two adjacent carbon atoms. The bicyclic or tricyclic ring system can be a spiro ring system or a di-spiro-ring system, in which two adjacent rings share a single carbon atom. The tricyclic ring system can also be a bicyclic spiro ring system, to which another ring is fused, that means that the latter ring and the ring in the spiro ring system, to which it is attached, share two adjacent carbon atoms; herein the latter ring can be an aromatic, saturated or partially saturated ring. The bicyclic or tricyclic system can also be a non-fused or bridged ring system, in which two adjacent rings share two non-adjacent carbon atoms. The bicyclic or tricyclic ring can be attached by any ring atom except a spiro- or a bridgehead atom.

In a monocyclic cycloalkyl group the number of ring carbon atoms can be 3, 4, 5, 6, 7 or 8. In one embodiment of the invention, the number of ring carbon atoms in a cycloalkyl group, independently of the number of ring carbon atoms in any other cycloalkyl group, is 3, 4, 5 or 6, in another embodiment 3, 4 or 5, in another embodiment 3 or 4, in another embodiment 3, in another embodiment 5, 6 or 7, in another embodiment 5 or 6, in another embodiment 6 or 7, in another embodiment 5, in another embodiment 6. Examples of cycloalkyl groups are cyclopropyl, cyclobutyl, cyclopentyl, cyclohexyl, cycloheptyl and cyclooctyl.

In a bicyclic cycloalkyl group the number of ring carbon atoms can be 6, 7, 8, 9, 10, 11 or 12. In one embodiment of the invention, the number of ring carbon atoms in a bicyclic cycloalkyl group can be 7, 8, 9, 10 or 11, in another embodiment 8, 9 or 10. In a tricyclic cycloalkyl group the number of ring carbon atoms can be 7, 8, 9, 10, 11, 12, 13, 14 or 15. In one embodiment of the invention, the number of ring carbon atoms in a tricyclic cycloalkyl group can be 10, 11 or 12.

Exemplary bicyclic or tricyclic fused ring cycloalkyls are derived from, but not limited to, the following ring systems: bicyclo[3.1.0]hexane, bicyclo[4.1.0]heptane, bicycle-[5.1.0]octane, bicyclo[3.2.0]heptane, bicyclo[4.2.0]octane, octahydro-pentalene, octa-hydro-indene, decahydro-azulene, decahydro-naphthalene, decahydro-benzocycloheptene, dodecahydro-heptalene, 1,2,3,3a,4,6a-hexahydro-pentalene, 1,2,3,4-tetrahydro-pentalene, 2,3,3a,4,5,7a-hexahydro-1H-indene, 2,3,3a,4,7,7a-hexahydro-1H-indene, 3a,4,5,6,7,7a-hexahydro-1H-indene, 4,5,6,7-tetrahydro-1H-indene, indane, 1,2,3,4,4a,5,6,8a-octahydro-naphthalene, 1,2,3,4,4a,5,8,8a-octahydro-naphthalene, 1,2,4a,5,8,8a-hexahydro-naphthalene, 1,4,4a,5,8,8a-hexahydro-naphthalene, 1,2,3,4-tetrahydro-naphthalene, 2,3,4,4a,5,6,9,9a-octahydro-1H-benzocycloheptene, 2,3,4,4a,5,9a-hexahydro-1H-benzocycloheptene, 4,4a,5,6,7,8,9,9a-octahydro-1H-benzocycloheptene, 6,7,8,9-tetrahydro-5H-benzocycloheptene, 1,2,3,4,5,5a,6,7,8,10a-decahydro-heptalene, dodecahydro-as-indacene and 2,3,3a,4,9,9a-hexahydro-1H-cyclopenta[b]naphthalene.

Exemplary bicyclic or tricyclic spiro ring cycloalkyls are derived from, but not limited to, the following ring systems: spiro[2.4]heptane, spiro[2.5]octane, spiro[2.6]nonane, spiro[3.3]heptane, spiro[3.4]octane, spiro[3.5]nonane, spiro[3.6]decane, spiro[4.4]nonane, spiro[4.5]decane, spiro[4.6]undecane, spiro[5.5]undecane, spiro[5.6]dodecane, spiro[6.6]tridecane, dispiro[2.2.4.2]dodecane, dispiro[2.2.3.2]undecane, dispiro-[2.1.4.2]undecane and spiro[5.5]undec-2-ene.

Exemplary non-fused or bridged bicyclic or tricyclic ring cycloalkyls are derived from, but not limited to, the following ring systems: bicyclo[2.2.1]heptane, bicyclo[2.2.2]octane, bicyclo[3.2.1]octane, bicyclo[3.2.2]nonane and adamantane.

The term "heterocycloalkyl" or "heterocyclyl", as used herein, unless otherwise indicated, refers to a cycloalkyl as defined above, in which 1, 2, 3 or 4 carbon atoms are replaced by nitrogen, oxygen or sulfur atoms, provided that a spiro atom is always a carbon atom and a bridgehead atom is either a carbon or a nitrogen atom and provided that the heterocycloalkyl system is stable and suitable as a subgroup for the desired purpose of the compound of the formula I such as use as a drug substance. Depending on the definition of the respective heterocyclic group, in one embodiment of the invention the number of ring heteroatoms which can be present in a heterocyclic group, independently of the number of ring heteroatoms in any other heterocyclic group, is 1, 2, 3 or 4, in another embodiment 1, 2 or 3, in another embodiment 1 or 2, in another embodiment 1, 2 or 3, in another embodiment 1, wherein the ring heteroatoms can be identical or different. The heterocycloalkyl group can be attached by any ring carbon atom or saturated ring nitrogen atom, with the exception of spiro- or bridgehead atoms. A ring sulfur atom in a heterocycloalkyl group can carry zero, one or two oxo groups, it is a non-oxidized sulfur atom S in case it does not carry any oxo group, or it is an S(O) group (=sulfoxide group, S-oxide group) in case it carries one oxo group, or it is an $S(O)_2$ group (=sulfone group, S,S-dioxide group) in case it carries two oxo groups.

Exemplary monocyclic heterocycloalkyls are derived from, but not limited to, the following ring systems: aziridine, oxirane, azetidine, oxetane, pyrrolidine, tetrahydrofurane, tetrahydrothiophene, 4,5-dihydrothiazole, piperidine, piperazine, morpholine, thiomorpholine, tetrahydropyran, 1,4-dioxane, 1,4-oxathiane, 1,2,3,6-tetrahydro-pyridine, azepane, 2,3,4,7-tetrahydro-1H-azepine, 2,7-dihydro-1H-azepine, 1,4-diazepane, 1,4-oxazepane, 1,4-thiazepane and 1,4-dioxepane.

In one embodiment monocyclic heterocycloalkyls are derived from azetidine, pyrrolidine, piperidine, piperazine, morpholine or 1,4-diazepane.

Exemplary bicyclic fused ring heterocycloalkyls are derived from, but not limited to, the following ring systems: 3-aza-bicyclo[3.1.0]hexane, 2-aza-bicyclo[4.1.0]heptane, 2-oxa-5-aza-bicyclo[5.1.0]octane, 3-aza-bicyclo[3.2.0]heptane, 2-aza-bicyclo[4.2.0]-octane, octahydro-pyrrolo[3,4-c]pyrrole, octahydro-pyrrolo[3,4-b]pyrrole, octahydro-pyrrolo[3,4-b]pyridine, octahydro-thieno[3,4-b]pyrazine, octahydro-furo[3,4-b]pyridine, octahydro-cyclopenta[1,4]oxazine, octahydro-pyrrolo[1,2-a]pyrimidine, octahydro-pyrrolo[1,2-a]pyrazine, octahydro-cyclopenta[e][1,4]oxazepine, decahydro-quinoxaline, decahydro-[1,6]naphthyridine, octahydro-benzo[1,4]oxazine, octahydro-benzo[1,4]thiazine, octahydro-pyrido[1,2-a]pyrazine, octahydro-pyrano[3,2-b]pyridine, decahydro-1-oxa-9-aza-benzocycloheptene, 1,2,3,3a,6,6a-hexahydro-cyclopenta[b]pyrrole, 5,6-dihydro-4H-cyclopenta[b]thiophene, 2,3,4,4a,7,7a-hexahydro-1H-[2]pyrindine, 2,4a,5,6,7,7a-hexahydro-1H-[1]pyrindine, 2,3,3a,4,7,7a-hexahydro-1H-indole, 1,2,3,4-tetrahydro-quinoxaline, 4,5,6,7-tetrahydro-benzofuran, benzo[1,3]dioxole, 3,4,4a,7,8,8a-hexahydro-2H-benzo[1,4]oxazine, 1,2,3,4,4a,5,8,8a-octahydro-quinoxaline, 4a,5,8,8a-tetrahydro-2H-thiopyrano[3,2-b]pyridine and 1,2,3,4-tetrahydro-[1,5]naphthyridine.

Exemplary non-fused or bridged bicyclic or tricyclic ring heterocycloalkyls are derived from, but not limited to, the following ring systems: 2-aza-bicyclo[2.2.1]heptane, 1-aza-bicyclo[2.2.2]octane, 8-aza-bicyclo[3.2.1]octane, 3-aza-bicyclo[3.2.1]octane, 9-aza-bicyclo[3.3.1]nonane, 2,5-diaza-bicyclo[2.2.1]heptane, 2,5-diaza-bicyclo[2.2.2]-octane, 3,8-diaza-bicyclo[3.2.1]octane and 3,7-diaza-bicyclo[3.3.1]nonane.

The term "aryl", as used herein, refers to a radical derived from an aromatic hydrocarbon by removal of one hydrogen, such as phenyl or naphthyl (=naphthalenyl).

The term "heteroaryl" or "hetaryl" as used herein, refers to a radical derived from an aromatic mono- or bicyclic ring system, in which 1, 2, 3, 4 or 5 carbon atoms are replaced by heteroatoms. The ring heteroatoms are generally chosen from N, O and S, wherein N includes ring nitrogen atoms which carry a hydrogen atom or a substituent as well as ring nitrogen atoms which do not carry a hydrogen atom or a substituent. Ring heteroatoms can be located in any position, provided that the heterocyclic system is stable and suitable as a subgroup for the desired purpose of the compound of the formula I such as use as a drug substance. Heteroaryl radicals are derived from 5-membered or 6-membered monocyclic rings or 8-membered, 9-membered or 10-membered bicyclic rings, in another embodiment 5-membered or 6-membered monocyclic rings or 9-membered or 10-membered bicyclic rings, in another embodiment 5-membered or 6-membered monocyclic rings.

Exemplary heteroaryl systems are derived from, but not limited to, the following ring systems: pyrrole, furan, thiophene, imidazole, pyrazole, oxazole (=[1,3]oxazole), isoxazole (=[1,2]oxazole), thiazole (=[1,3]thiazole), isothiazole (=[1,2]thiazole), [1,2,3]triazole, [1,2,4]triazole, [1,2,4]oxadiazole, [1,3,4]oxadiazole, [1,2,4]thiadiazole, [1,3,4]thiadiazole, tetrazole, pyridine, pyridazine, pyrimidine, pyrazine, [1,2,3]triazine, [1,2,4]triazine, [1,3,5]triazine, indole, isoindole, benzofuran, benzothiophene [1,3]benzoxazole, [1,3]benzothiazole, benzoimidazole, indazole, quinoline, isoquinoline, cinnoline, quinazoline, quinoxaline, phthalazine, different naphthyridines, e.g. [1,8]naphthyridine, different thienopyridines, e.g. thieno[2,3-b]pyridine and purine.

Groups like phenyl, naphthyl (=naphthalenyl) and residues of aromatic heterocycles which are optionally substituted by one or more substituents, can be unsubstituted or substituted, for example by 1, 2, 3, 4 or 5, or by 1, 2, 3 or 4, or by 1, 2 or 3, or by 1 or 2, or by 1, identical or different substituents which can be located in any positions. Aromatic nitrogen heterocycles which in the parent ring system carry a hydrogen atom on a ring nitrogen atom in a 5-membered ring, such as a pyrrole, imidazole, indole or benzoimidazole ring, for example, can be substituted on ring carbon atoms and/or on such ring nitrogen atoms. In one embodiment of the invention, substituents on such ring nitrogen atoms are chosen from $(C_1-C_4)$-alkyl groups, i.e. such ring nitrogen atoms in aromatic heterocycles carry a hydrogen atom or a $(C_1-C_4)$-alkyl substituent. When it is stated with respect to ring nitrogen atoms in aromatic heterocycles and any other heterocycles that they can carry a hydrogen atom or a substituent, such ring nitrogen atoms either carry a hydrogen atom or a substituent or they do not carry a hydrogen atom or substituent. Ring nitrogen atoms which carry a hydrogen atom or a substituent, occur in a nitrogen-containing aromatic 5-membered ring as is present in pyrrole, imidazole, indole or benzoimidazole, for example, and in a non-aromatic ring including a saturated ring. Ring nitrogen atoms which do not carry a hydrogen atom or a substituent unless they are present in positively charged form, including any further ring nitrogen atoms in addition to ring nitrogen atoms which carry a hydrogen atom or a substituent, occur in an aromatic ring as is present in thiazole, imidazole, pyridine or benzoimidazole, for example, and in a non-aromatic ring in which they are part of a double bond, and they occur as ring nitrogen atoms via which a ring is bonded. Suitable ring nitrogen atoms in aromatic heterocycles in the compounds of the formula I, such as the ring nitrogen atom in a pyridine ring or a quinoline ring, can in general also be present as N-oxide or as quaternary salt, for example as N—$(C_1-C_4)$-alkyl salt such as N-methyl salt, wherein in one embodiment of the invention the counter anion in such quaternary salt is a physiologically acceptable anion which is derived from an acid that forms a physiologically acceptable salt.

In monosubstituted phenyl groups, the substituent can be located in the 2-position, the 3-position or the 4-position. In disubstituted phenyl groups, the substituents can be located in 2,3-position, 2,4-position, 2,5-position, 2,6-position, 3,4-position or 3,5-position. In trisubstituted phenyl groups, the substituents can be located in 2,3,4-position, 2,3,5-position, 2,3,6-position, 2,4,5-position, 2,4,6-position or 3,4,5-position. Naphthyl can be 1-naphthyl (=naphthalen-1-yl) or 2-naphthyl (=naphthalen-2-yl). In monosubstituted 1-naphthyl groups, the substituent can be located in the 2-, 3-, 4-, 5-, 6-, 7- or 8-position. In monosubstituted 2-naphthyl groups, the substituent can be located in the 1-, 3-, 4-, 5-, 6-, 7- or 8-position. In disubstituted naphthyl groups, the substituents can likewise be located in any positions both in the ring via which the naphthyl group is bonded and/or in the other ring.

Ring heteroatoms can be located in any positions, provided that the heterocyclic system is known in the art and is stable and suitable as a subgroup for the desired purpose of the compound of the formula I such as use as a drug substance. In one embodiment of the invention, two ring oxygen atoms cannot be present in adjacent ring positions of any heterocycle, in another embodiment two ring heteroatoms chosen from oxygen and sulfur cannot be present in adjacent ring positions of any heterocycle. Substituents on heterocyclic groups can be located in any positions. For example, in a pyridin-2-yl group substituents can be located in the 3-position and/or 4-position and/or 5-position and/or 6-position, in a pyridin-3-yl group substituent can be located in the 2-position and/or 4-position and/or 5-position and/or 6-position, in a pyridin-4-yl group substituents can be located in the 2-position and/or 3-position and/or 5-position and/or 6-position.

Halogen is fluorine, chlorine, bromine or iodine. In one embodiment of the invention, any halogen in a compound of the formula I is independently of any other halogen chosen from fluorine, chlorine and bromine, in another embodiment from fluorine and chlorine, and in yet another embodiment it is fluorine, and in yet another embodiment it is chlorine.

When an oxo group is bonded to a carbon atom, it replaces two hydrogen atoms on a carbon atom of the parent system. Thus, if a $CH_2$ group in a chain or a ring is substituted by oxo, i.e. by a doubly bonded oxygen atom, it becomes a CO group. Evidently, an oxo group cannot occur as a substituent on a carbon atom in an aromatic ring such as in a phenyl group, for example. When a ring sulfur atom in a heterocyclic group can carry one or two oxo groups, it is a non-oxidized sulfur atom S in case it does not carry any oxo group, or it is an S(O) group (=sulfoxide group, S-oxide group) in case it carries one oxo group, or it is an $S(O)_2$ group (=sulfone group, S,S-dioxide group) in case it carries two oxo groups.

The present invention includes all stereoisomeric forms of the compounds of the formula I and their salts and solvates. With respect to each chiral center, independently of any other chiral center, the compounds of the formula I can be present in S configuration or substantially S configuration, or in R configuration or substantially R configuration, or as a mixture of the S isomer and the R isomer in any ratio. The invention includes all possible enantiomers and diastereomers and mixtures of two or more stereoisomers, for example mixtures of enantiomers and/or diastereomers, in all ratios. Thus, compounds according to the invention which can exist as enantiomers can be present in enantiomerically pure form, both as levorotatory and as dextrorotatory antipodes, and in the form of mixtures of the two enantiomers in all ratios including racemates. In the case of a E/Z isomerism, or cis/trans isomerism, for example on double bonds or rings such as cycloalkyl rings, the invention includes both the E form and Z form, or the cis form and the trans form, as well as mixtures of these forms in all ratios. In one embodiment of the invention, a compound which can occur in two or more stereoisomeric forms is a pure, or substantially pure, individual stereoisomer.

The preparation of individual stereoisomers can be carried out, for example, by separation of a mixture of isomers by customary methods, for example by chromatography or crystallization, by the use of stereochemically uniform starting materials in the synthesis, or by stereoselective synthesis. Optionally, a derivatization can be carried out before a separation of stereoisomers. The separation of a mixture of stereoisomers can be carried out at the stage of the compound of the formula I or at the stage of a starting material or an intermediate during the synthesis. The present invention also includes all tautomeric forms of the compounds of the formula I and their salts and solvates.

In case the compounds of the formula I contain one or more acidic and/or basic groups, i.e. salt-forming groups, the invention also includes their corresponding physiologically or toxicologically acceptable salts, i.e. non-toxic salts, in particular their pharmaceutically acceptable salts.

The present invention furthermore includes all solvates of compounds of the formula I, for example hydrates or adducts with alcohols such as $(C_1-C_4)$-alkanols, active metabolites of the compounds of the formula I, and also prodrugs and derivatives of the compounds of the formula I which in vitro may not necessarily exhibit pharmacological activity but which in vivo are converted into pharmacologically active compounds, for example esters or amides of carboxylic acid groups.

In another group of embodiments of the compounds of the formula I
R', R", R''' are independently of each other H, halogen, $CF_3$, $OCF_3$, O—$(C_1-C_3)$-alkyl, preferably
R', R", R''' are independently of each other H, F, Cl, $CF_3$, $OCF_3$, O—$CH_3$; more preferably
R', R", R''' are independently of each other H, F, Cl; most preferably
R', R", R''' are H.

In another group of embodiments of the compounds of the formula I
$R^1$ is
a) $(C_4-C_7)$-alkyl;
b) $(C_5-C_7)$-cycloalkyl, which is unsubstituted or mono-substituted by $(C_1-C_2)$-alkyl, or $CF_3$;
c) methylene-cyclohexyl;
d) phenyl, which is unsubstituted or mono-substituted by methyl or Cl; preferably
$R^1$ is
a) iso-buytyl, sec-butyl, 1-ethyl-propyl, 2-methyl-butyl, 1,3-dimethyl-butyl, 1-isopropyl-2-methyl-propyl;
b) cyclopentyl, 2-methyl-cyclopentyl, cyclohexyl, 2-methyl-cyclohexyl, 2-(trifluoromethyl)-cyclohexyl, 2-ethyl-cyclohexyl, cycloheptyl;
c) methylene-cyclohexyl;
d) phenyl, 2-chloro-phenyl, 4-tolyl; more preferably
$R^1$ is
a) 1-ethyl-propyl;
b) 2-methyl-cyclopentyl, 2-methyl-cyclohexyl; most preferably
$R^1$ is
a) 1-ethyl-propyl,
b) 2-methyl-cyclohexyl.

In another group of embodiments of the compounds of the formula I
$R^2$ is
a) a 5-membered heteroaryl which contains 1 or 2 identical or different ring heteroatoms chosen from N, O and S, wherein said 5-membered heteroaryl is unsubstituted or mono-substituted by Cl or Me;
b) phenyl;
c) $(C_5-C_6)$-cycloalkyl; or
d) tetrahydrofuranyl; preferably $R^2$ is
a) 2-furanyl, 3-furanyl, 2-thienyl, 3-thienyl, 4-thiazolyl, 5-thiazoloyl, 1-pyrazolyl; 5-isoxazolyl, 5-methyl-thien-2-yl, 5-chloro-thien-2-yl
b) phenyl;
c) $(C_5-C_6)$-cycloalkyl; or
d) 2-tetrahydrofuranyl; more preferably
$R^2$ is 2-furanyl, 3-furanyl, 2-thienyl, 3-thienyl, 4-thiazolyl, 5-thiazoloyl, even more preferably
$R^2$ is 2-furanyl, 2-thienyl; most preferably
$R^2$ is 2-thienyl.

In another group of embodiments of the compounds of the formula I
$R^3$ is H, or $(C_1-C_2)$-alkyl;
and
$R^4$ is
a) $(C_3-C_5)$-alkyl, which may be optionally substituted by 1-3 F or S—$CH_3$,
b) $(C_0-C_1)$-alkylene-$(C_3-C_7)$-cycloalkyl, wherein said cycloalkyl is unsubstituted or mono- or di-substituted by methyl;
c) $(C_0-C_2)$-alkylene-phenyl, wherein said phenyl is unsubstituted or mono- or di-substituted by F, Cl, Me or $CF_3$; or
d) thienyl; preferably
$R^3$ is H, or $(C_1-C_2)$-alkyl;
and
$R^4$ is
a) $(C_3-C_5)$-alkyl, which may be optionally substituted by 1-3 F or S—$CH_3$,
b) $(C_0-C_1)$-alkylene-$(C_3-C_7)$-cycloalkyl, wherein said cycloalkyl is unsubstituted or mono- or di-substituted by methyl;
c) $(C_0-C_2)$-alkylene-phenyl, wherein said phenyl is unsubstituted or mono- or di-substituted by F, Cl, Me or $CF_3$; or
d) thienyl; more preferably
$R^3$ is H or $CH_3$;
and
$R^4$ is
a) $(C_3-C_5)$-alkyl, which may be optionally substituted by 1-3 F or S-Me,
b) methylene-$(C_4-C_6)$-cycloalkyl; most preferably
$R^3$ is H;
and
$R^4$ is
a) $(C_4-C_5)$-alkyl;
b) methylene-$(C_4-C_6)$-cycloalkyl.

In another group of embodiments of the compounds of the formula I
$R^3$ and $R^4$
are, together with the carbon atom to which they are attached, a 5- to 7-membered cycloalkyl ring, which is unsubstituted or mono-substituted by $CH_3$; preferably
$R^3$ and $R^4$
are, together with the carbon atom to which they are attached, a 5- to 7-membered cycloalkyl ring.

In another group of embodiments of the compounds of the formula I
$R^5$ is H, $CH_3$ or OH;
$R^6$ H or $CH_3$;
n is 0, 1 or 2; preferably
$R^5$ is H;
$R^6$ H;
n is 0, 1 or 2.

In another group of embodiments of the compounds of the formula I
$R^5$ is H, $CH_3$ or OH;
$R^6$ H or $CH_3$;
n is 1 or 2; preferably
$R^5$ is H;
$R^6$ H;
n is 1 or 2.

In another group of embodiments of the compounds of the formula I
$R^5$ is H, $CH_3$ or OH;
$R^6$ H or $CH_3$;
n is 0 or 1; preferably
$R^5$ is H;
$R^6$ H;
n is 0 or 1.

In another group of embodiments of the compounds of the formula I
$R^5$ is H, $CH_3$ or OH;
$R^6$ H or $CH_3$;
n is 2; preferably
$R^5$ is H;
$R^6$ H;
n is 2.

In another group of embodiments of the compounds of the formula I
$R^5$ is H, $CH_3$ or OH;
$R^6$ H or $CH_3$;
n is 1; preferably
$R^5$ is H;
$R^6$ H;
n is 1.

In another group of embodiments of the compounds of the formula I
n is 0.

In another group of embodiments of the compounds of the formula I $R^5$ is H or $CH_3$;
$R^6$ H;
n is 0, 1 or 2; preferably
$R^5$ is H or $CH_3$;
$R^6$ H or $CH_3$;
n is 1 or 2.

In another group of embodiments of the compounds of the formula I
$R^5$ is H or OH;
$R^6$ H;
n is 0, 1 or 2; preferably
$R^5$ is H or OH;
$R^6$ H or $CH_3$;
n is 1 or 2.

In another group of embodiments of the compounds of the formula I
Z is
$CO_2$—$R^7$, $OR^8$, $C(O)NR^9R^{10}$, $S(O)_2NR^{11}R^{12}$,

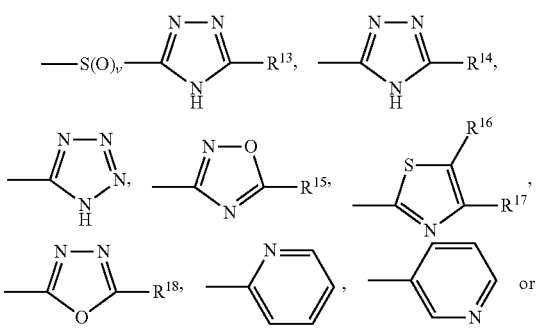

-continued

[structure: C(=NH)-N(H)-OH group]

wherein v is 0 or 2; preferably
Z is
CO$_2$—R$^7$, OR$^8$, C(O)NR$^9$R$^{10}$, S(O)$_2$NR$^{11}$R$^{12}$,

[structures: —S(O)$_v$-triazolyl-R$^{13}$; triazolyl-R$^{14}$; tetrazolyl; oxadiazolyl-R$^{15}$; thiazolyl with R$^{16}$, R$^{17}$; oxadiazolyl-R$^{18}$; pyridyl; pyridyl]

or

[structure: C(=NH)-N(H)-OH group]

wherein
v is 0 or 2; more preferably
Z is CO$_2$—R$^7$, OR$^8$, C(O)NR$^9$R$^{10}$, S(O)$_2$NR$^{11}$R$^{12}$ or 5-tetrazolyl, even more preferably
Z is CO$_2$—H, OH, C(O)NR$^9$R$^{10}$, or 5-tetrazolyl; most preferably
Z is CO$_2$—H.

Another group of embodiments are compounds of the formula I, wherein
R$^7$ is H or (C$_1$-C$_4$)-alkyl; preferably
R$^7$ is H.

Another group of embodiments are compounds of the formula I, wherein
R$^8$ is H or (C$_1$-C$_4$)-alkyl; preferably
R$^8$ is H.

Another group of embodiments are compounds of the formula I, wherein
R$^9$ is H, CH$_3$ or ethylene-O-methyl;
and
R$^{10}$ is
a) H
b) (C$_1$-C$_6$)-alkyl, which is unsubstituted or mono-substituted by CF$_3$;
c) (C$_1$-C$_2$)-alkyl, which is substituted by CN or CO$_2$R$^{19}$ wherein
R$^{19}$ is H or (C$_1$-C$_6$)-alkyl;
d) (C$_2$-C$_4$)-alkyl, which is mono-substituted by a substituent selected from the group consisting of S-methyl, SO$_2$NR$^{20}$R$^{21}$, O—R$^{22}$ and NR$^{23}$R$^{24}$;
wherein
R$^{20}$ is H;
R$^{21}$ is H;
R$^{22}$ is H, methylene-cyclopropyl, methylene-phenyl, or methylene-2-tetrahydrofurane;
R$^{23}$ is H or (C$_1$-C$_2$)-alkyl;
R$^{24}$ is (C$_1$-C$_2$)-alkyl or SO$_2$-methyl;
e) (C$_3$-C$_5$)-cycloalkyl, which is unsubstituted or mono-substituted by phenyl;
f) (C$_0$-C$_2$)-alkylene-heterocycloalkyl, wherein said heterocyloalkyl is five or six membered and contains 1 or 2 O atoms in non-adjacent positions, and wherein sad heterocycloalkyl is unsubstituted or geminally disubstituted with a spiro cyclopentyl ring
g) (C$_2$-C$_5$)-alkylene-heterocycloalkyl, wherein said heterocycloalkyl is a five-, six- or seven-membered ring, which contains at least one N atom, and which is attached via said N-atom, and which may additionally contain one heteroatom selected from the group consisting of O, S(O)$_x$ or NR$^{25}$ in a position not adjacent to the N atom, by which the ring is attached to the alkylene, and wherein any carbon atom within said heterocycloalkyl is unsubstituted or substituted by 1 or 2 substituents selected from the group consisting of (C$_1$-C$_3$)alkyl, or methylene-phenyl;
wherein
x is 2;
R$^{25}$ is H, (C$_1$-C$_2$)alkyl, methylene-phenyl or phenyl, which is unsubstituted or substituted by 1 or 2 substituents selected from the group consisting of F, Cl and OMe;
h) (C$_0$-C$_3$)-alkylene-heterocycloalkyl, wherein said heterocycloalkyl is a five- or six-membered ring, which contains at least one N atom, and which is not attached via said N-atom, and which may additionally contain one O atom in a position not adjacent to the N atom, and wherein said N-atom is unsubstituted or substituted by a substituent selected from the group consisting of
i) (C$_1$-C$_4$)-alkyl, which is unsubstituted or mono-substituted by —O-methyl;
ii) methylene-cyclohexyl;
iii) (C$_0$-C$_2$)-alkylene-phenyl, wherein phenyl is unsubstituted or substituted by 1 or 2 substituents selected from the group consisting of F and O-methyl;
iv) (C$_0$-C$_1$)-alkylene-pyridyl;
v) pyrimidinyl;
i) 8-methyl-8-aza-bicyclo[3.2.1]oct-3yl;
j) 9-methyl-9-aza-bicyclo[3.3.1]non-3-yl;
k) methylene-4-(octahydro-quinolizinyl);
l) (C$_0$-C$_2$)-alkylene-phenyl, wherein phenyl is unsubstituted or monosubstituted by substituents chosen from the group consisting of F, O-methyl, N(methyl)$_2$, 4-morpholinyl and methylene-(4-methyl-piperidin)-1-yl or disubstituted on adjacent positions by the group —O(CH$_2$)O—;
m) (C$_1$-C$_2$)-alkylene-heteroaryl, wherein said heteroaryl ring is a five- or six-membered ring containing 1, 2, 3 or 4 heteroatoms selected from O, S or N; and wherein said heteroaryl ring is unsubstituted or mono-substituted by oxo (═O);
or
R$^9$ and R$^{10}$ together with the N-atom carrying them are
a) a four-, five- or six-membered heterocylcoalkyl ring containing only the N atom, to which R$^9$ and R$^{10}$ are attached, which is unsubstituted or mono-substituted by a substituent selected from the group consisting of
i) (C$_0$-C$_1$)-alkylene-OR$^{26}$, wherein R$^{26}$ is H, (C$_1$-C$_3$) alkyl or methylene-phenyl;
ii) CO$_2$R$^{27}$, wherein R$^{27}$ is H or (C$_1$-C$_6$)-alkyl;
iii) NR$^{28}$R$^{29}$, wherein R$^{28}$ is (C1-C2)-alkyl and R$^{29}$ is (C1-C2)-alkyl, methylene-phenyl or ethylene-NMe$_2$;
iv) 1-piperidinyl, which is unsubstituted or mono-substituted by methyl;
v) 1-piperazinyl, which is unsubstituted or mono-substituted by methyl;
vi) 4-morpholinyl;
vii) 1-azepanyl;
vii) 2-(2,3-dihydro-1H-isoindolyl);

b) a six- or seven-membered heterocycloalkyl ring containing the N atom, to which $R^9$ and $R^{10}$ are attached and one additional heteroatom selected from O, S or $NR^{30}$ in a position non-adjacent to the N atom, to which $R^9$ and $R^{10}$ are attached, wherein the carbon atoms in said heterocycloalkyl ring are unsubstituted or mono- or disubstituted by methyl and wherein
$R^{30}$ is
i) H;
ii) $(C_1-C_4)$-alkyl;
iii) $(C_5-C_6)$-cycloalkyl;
iv) phenyl, which is unsubstituted or mono-substituted by F, $CF_3$ or OMe;
v) methylene-phenyl, which is unsubstituted or mono- or di-substituted by F or Cl or disubstituted on adjacent positions by the group $—O(CH_2)O—$;
vi) pyridyl;
c) a 2,5-diaza-bicyclo[2.2.1]heptyl-ring, which is unsubstituted or substituted on the second N atom in 5-position by a substituent selected from the group consisting of $(C_1-C_4)$-alkyl, methylene-cyclopentyl, phenyl, which is unsubstituted or mono-substituted by F, methylene-phenyl, wherein phenyl is unsubstituted or mono-substituted by $OCH_3$ or $CF_3$;
$R^{11}$ is H;
$R^{12}$ is $CH_3$;
$R^{13}$ is H;
$R^{14}$ is $CF_3$ or methylene-$OCH_3$;
$R^{15}$ is cyclopryopyl or phenyl;
$R^{16}$ is H or $CH_3$;
$R^{17}$ is H or $CH_3$
and
$R^{18}$ is $CH_3$;
in any of its stereoisomeric forms, or a mixture of stereoisomeric forms in any ratio, or a physiologically acceptable salt thereof, or a physiologically acceptable solvate of any of them.

Another group of embodiments are compounds of the formula I, wherein
$R^9$ is H, $CH_3$ or ethylene-$OCH_3$;
and
$R^{10}$ is
a) H
b) $(C_1-C_6)$-alkyl, which is unsubstituted or mono-substituted by $CF_3$;
c) $(C_1-C_2)$-alkyl, which is substituted by CN or $CO_2R^{19}$ wherein
$R^{19}$ is H;
d) $(C_2-C_4)$-alkyl, which is mono-substituted by a substituent selected from the group consisting of SMe, $SO_2NR^{20}R^{21}$, $O—R^{22}$ and $NR^{23}R^{24}$;
wherein
$R^{20}$ is H;
$R^{21}$ is H;
$R^{22}$ is H, $(C_1-C_3)$-alkyl, methylene-cyclopropyl, methylene-phenyl, or methylene-2-tetrahydrofurane;
$R^{23}$ is H or $(C_1-C_2)$-alkyl,
$R^{24}$ is $(C_1-C_2)$-alkyl or $SO_2$ $CH_3$;
e) $(C_3-C_5)$-cycloalkyl, which is unsubstituted or mono-substituted by phenyl;
f) $(C_0-C_2)$-alkylene-heterocycloalkyl, wherein said heterocylcoalkyl is five or six membered and contains 1 or 2 O atoms in non-adjacent positions, and wherein said heterocycloalkyl is unsubstituted or geminally disubstituted with a spiro cyclopentyl ring or with a spiro cyclohexyl ring;

g) $(C_2-C_5)$-alkylene-heterocycloalkyl, wherein said heterocycloalkyl is a five-, six- or seven-membered ring, which contains at least one N atom, and which is attached via said N-atom, and which may additionally contain one heteroatom selected from the group consisting of O, $S(O)_x$ or $NR^{25}$ in a position not adjacent to the N atom, by which the ring is attached to the alkylene, and wherein any carbon atom within said heterocycloalkyl is unsubstituted or substituted by 1 or 2 substituents selected from the group consisting of $(C_1-C_3)$alkyl, or methylene-phenyl; wherein
x is 2;
$R^{25}$ is $(C_1-C_2)$alkyl, methylene-phenyl or phenyl, which is substituted by 1 or 2 substituents selected from the group consisting of F, Cl and $OCH_3$;
h) $(C_0-C_3)$-alkylene-heterocycloalkyl, wherein said heterocycloalkyl is a five- or six-membered ring, which contains at least one N atom, and which is not attached via said N-atom, and which may additionally contain one O atom in a position not adjacent to the N atom, and wherein said N-atom is unsubstituted or substituted by a substituent selected from the group consisting of
i) $(C_1-C_4)$-alkyl, which is unsubstituted or mono-substituted by $OCH_3$;
ii) methylene-cyclohexyl;
iii) $(C_0-C_2)$-alkylene-phenyl, wherein phenyl is unsubstituted or substituted by 1 or 2 substituents selected from the group consisting of F and $OCH_3$;
iv) $(C_0-C_1)$-alkylene-pyridyl;
v) pyrimidinyl;
i) 8-methyl-8-aza-bicyclo[3.2.1]oct-3yl;
j) 9-methyl-9-aza-bicyclo[3.3.1]non-3-yl;
k) methylene-4-(octahydro-quinolizinyl);
l) $(C_0-C_2)$-alkylene-phenyl, wherein phenyl is unsubstituted or monosubstituted by substituents chosen from the group consisting of F, $OCH_3$, $N(CH_3)_2$, 4-morpholinyl and methylene-(4-methyl-piperidin)-1-yl or disubstituted on adjacent positions by the group $—O(CH_2)O—$;
m) $(C_1-C_2)$-alkylene-heteroaryl, wherein said heteroaryl ring is a five- or six-membered ring containing 1, 2, 3 or 4 heteroatoms selected from O, S or N; and wherein said heteroaryl ring is unsubstituted or mono-substituted by oxo (=O);
or
$R^9$ and $R^{10}$ together with the N-atom carrying them are
a) a four-, five- or six-membered heterocylcoalkyl ring containing only the N atom, to which $R^9$ and $R^{10}$ are attached, which is unsubstituted or mono-substituted by a substituent selected from the group consisting of
i) $(C_0-C_1)$-alkylene-$OR^{26}$, wherein $R^{26}$ is H, $(C_1-C_3)$ alkyl or methylene-phenyl;
ii) $CO_2R^{27}$, wherein $R^{27}$ is H;
ii) $NR^{28}R^{29}$, wherein $R^{28}$ is $(C_1-C_2)$-alkyl and $R^{29}$ is $(C_1-C_2)$-alkyl, methylene-phenyl or ethylene-N $(CH_3)_2$;
iii) 1-piperidinyl, which is mono-substituted by methyl;
iv) 1-piperazinyl, which is unsubstituted or mono-substituted by methyl;
v) 4-morpholinyl;
vi) 1-azepanyl;
vii) 2-(2,3-dihydro-1H-isoindolyl);
b) a six- or seven-membered heterocycloalkyl ring containing the N atom, to which $R^9$ and $R^{13}$ are attached and one additional heteroatom selected from O, S or $NR^{30}$ in a position non-adjacent to the N atom, to which $R^9$ and $R^{10}$ are attached, wherein the carbon atoms in said heterocycloalkyl ring are unsubstituted or mono- or disubstituted by methyl and wherein $R^{30}$ is
  i) $(C_1-C_4)$-alkyl;
  ii) $(C_5-C_6)$-cycloalkyl;
  iii) phenyl, which is unsubstituted or mono-substituted by F, $CF_3$ or $OCH_3$;
  iv) methylene-phenyl, which is unsubstituted or mono- or di-substituted by F or Cl or disubstituted on adjacent positions by the group —$O(CH_2)O$—;
  v) pyridyl;
c) a 2,5-diaza-bicyclo[2.2.1]heptyl-ring, which is substituted on the second N atom in 5-position by a substituent selected from the group consisting of $(C_1-C_4)$-alkyl, methylene-cyclopentyl, phenyl, which is mono-substituted by F, methylene-phenyl, wherein phenyl is unsubstituted or mono-substituted by $OCH_3$ or $CF_3$;
$R^{11}$ is H;
$R^{12}$ is $CH_3$;
$R^{13}$ is H;
$R^{14}$ is $CF_3$ or methylene-$OCH_3$;
$R^{15}$ is cyclopryopyl or phenyl;
$R^{16}$ is H or $CH_3$;
$R^{17}$ is H or $CH_3$;
and
$R^{18}$ is $CH_3$;
in any of its stereoisomeric forms, or a mixture of stereoisomeric forms in any ratio, or a physiologically acceptable salt thereof, or a physiologically acceptable solvate of any of them.

Another group of embodiments are compounds of the formula I, wherein
$R^9$ is H, $CH_3$;
and
$R^{10}$ is
a) H
b) $(C_1-C_6)$-alkyl, which is unsubstituted or mono-substituted by $CF_3$;
c) $(C_1-C_2)$-alkyl, which is substituted by CN or $CO_2R^{19}$
  wherein
  $R^{19}$ is H;
d) $(C_2-C_4)$-alkyl, which is mono-substituted by a substituent selected from the group consisting of $SCH_3$, $SO_2NR^{20}R^{21}$, O—$R^{22}$ and $NR^{23}R^{24}$;
  wherein
  $R^{20}$ is H;
  $R^{21}$ is H;
  $R^{22}$ is H, $(C_1-C_3)$-alkyl, methylene-cyclopropyl, methylene-phenyl, or methylene-2-tetrahydrofurane;
  $R^{23}$ is H or $(C_1-C_2)$-alkyl;
  $R^{24}$ is $(C_1-C_2)$-alkyl or $SO_2CH_3$;
e) cyclobutyl, cyclopentyl or 2-phenyl-cyclopropyl;
f) $(C_0-C_2)$-alkylene-heterocycloalkyl, wherein said heterocylcoalkyl is selected from the group consisting of 2-tetrahydrofuranyl, 3-tetrahydrofuranyl, 2-tetrahydropyranyl, 3-tetrahydropyranyl, 4-tetrahydropyranyl and 1,4-dioxan-2-yl;
g) $(C_2-C_5)$-alkylene-heterocycloalkyl, wherein said heterocycloalkyl is selected from the group consisting of 1-pyrrolidinyl, 1-piperidinyl, 1-azepanyl, 4-morpholinyl 1,1-dioxo-thiomorpholin-4-yl, and 1-piperazinyl; wherein said heterocycloalkyl is unsubstituted or substituted by 1 or 2 substituents selected from the group consisting of $(C_1-C_2)$alkyl, or methylene-phenyl;
h) $(C_0-C_3)$-alkylene-heterocycloalkyl, wherein said heterocycloalkyl is selected from the group consisting of 3-pyrrolidinyl, 2-piperidinyl, 3-piperidinyl, 4-piperidinyl and 2-morpholinyl and wherein said heterocycloalkyl is substituted by a substituent selected from the group consisting of
  i) $(C_1-C_4)$-alkyl;
  ii) methylene-cyclohexyl;
  iii) $(C_0-C_2)$-alkylene-phenyl;
  iv) $(C_0-C_1)$-alkylene-pyridyl;
  v) pyrimidinyl;
i) 8-methyl-8-aza-bicyclo[3.2.1]oct-3yl;
j) 9-methyl-9-aza-bicyclo[3.3.1]non-3-yl;
k) methylene-4-(octahydro-quinolizinyl);
l) $(C_0-C_2)$-alkylene-phenyl, wherein phenyl is unsubstituted or monosubstituted by substituents chosen from the group consisting of F, $OCH_3$, $N(CH_3)_2$;
m) $(C_1-C_2)$-alkylene-heteroaryl, wherein said heteroaryl ring is selected from the group consisting of 2-thienyl, 2-furanyl, 2-thiazolyl, 2-oxazolyl, 5-tetrazolyl and 5-Oxo-4,5-dihydro-1H-[1,2,4]triazol-3-yl;
or
$R^9$ and $R^{10}$ together with the N-atom carrying them are
a) azetidinyl substituted by $CO_2H$;
b) pyrrolidinyl, which is unsubstituted or mono-substituted by a substituent selected from the group consisting of
  i) OH;
  ii) methylene-$OCH_3$;
  iii) methylene-O-methylene-phenyl;
  iv) $CO_2H$;
  v) $NR^{28}R^{29}$, wherein $R^{28}$ is $(C_1-C_2)$-alkyl and $R^{29}$ is $(C_1-C_2)$-alkyl;
  vi) 1-piperazinyl, which is unsubstituted or mono-substituted by methyl;
c) piperidinyl, which is mono-substituted by a substituent selected from the group consisting of
  i) O—$(C_1-C_3)$alkyl;
  ii) methylene-$OCH_3$;
  iii) $NR^{28}R^{29}$, wherein $R^{28}$ is $(C_1-C_2)$-alkyl and $R^{29}$ is methylene-phenyl or ethylene-$N(CH_3)_2$
  iv) 1-piperidinyl, which is mono-substituted by methyl;
  v) 1-piperazinyl, which is unsubstituted or mono-substituted by methyl;
  vi) 4-morpholinyl;
  vii) 1-azepanyl;
  viii) 2-(2,3-dihydro-1H-isoindolyl);
d) 4-morpholinyl, which is disubstituted by methyl;
e) 4-thiomorpholinyl;
f) piperazinyl, which is mono-substituted by a substituent selected from the group consisting of
  i) $(C_1-C_4)$-alkyl;
  ii) $(C_5-C_6)$-cycloalkyl;
  iii) phenyl, which is unsubstituted or mono-substituted by F, $CF_3$ or $OCH_3$;
  iv) methylene-phenyl, which is unsubstituted or disubstituted on adjacent positions by the group —$O(CH_2)O$—;
  v) pyridyl;
g) azepanyl, which is substituted by methylene-phenyl, which is unsubstituted or mono- or di-substituted by F or Cl;
c) a 2,5-diaza-bicyclo[2.2.1]heptyl-ring, which is substituted on the second N atom in 5-position by a substituent selected from the group consisting of $(C_1-C_4)$-alkyl, methylene-cyclopentyl, phenyl, which is mono-substituted by F, methylene-phenyl, wherein phenyl is unsubstituted or mono-substituted by $OCH_3$ or $CF_3$;
$R^{11}$ is H;
$R^{12}$ is $CH_3$;
$R^{13}$ is H;

$R^{14}$ is $CF_3$ or methylene-$OCH_3$;
$R^{15}$ is cyclopryopyl or phenyl;
$R^{16}$ is H or $CH_3$;
$R^{17}$ is H or $CH_3$;
and
$R^{18}$ is $CH_3$;
in any of its stereoisomeric forms, or a mixture of stereoisomeric forms in any ratio, or a physiologically acceptable salt thereof, or a physiologically acceptable solvate of any of them.

Another group of embodiments are compounds of the formula I
wherein
$R^9$ is H;
and
$R^{10}$ is
a) H
b) $(C_1-C_6)$-alkyl;
c) $(C_1-C_2)$-alkyl, which is substituted by CN or $CO_2R^{19}$
  wherein
  $R^{19}$ is H;
d) $(C_2-C_4)$-alkyl, which is mono-substituted by a substituent selected from the group consisting of $SCH_3$, $SO_2NR^{20}R^{21}$, $O-R^{22}$ and $NR^{23}R^{24}$;
  wherein
  $R^{20}$ is H;
  $R^{21}$ is H;
  $R^{22}$ is H, $(C_1-C_3)$-alkyl, methylene-cyclopropyl, methylene-phenyl, or methylene-2-tetrahydrofurane;
  $R^{23}$ is H or $(C_1-C_2)$-alkyl;
  $R^{24}$ is $(C_1-C_2)$-alkyl or $SO_2CH_3$;
e) cyclobutyl, or cyclopentyl;
f) $(C_0-C_2)$-alkylene-heterocycloalkyl, wherein said heterocylcoalkyl is selected from the group consisting of 2-tetrahydrofuranyl, 3-tetrahydrofuranyl, 2-tetrahydropyranyl, 3-tetrahydropyranyl, 4-tetrahydropyranyl and 1,4-dioxan-2-yl;
g) $(C_2-C_5)$-alkylene-heterocycloalkyl, wherein said heterocycloalkyl is selected from the group consisting of 1-pyrrolidinyl, 1-piperidinyl, 1-azepanyl, 4-morpholinyl 1,1-dioxo-thiomorpholin-4-yl, and 1-piperazinyl; wherein said heterocycloalkyl is unsubstituted or substituted by 1 or 2 substituents selected from the group consisting of $(C_1-C_2)$alkyl, or methylene-phenyl;
h) $(C_0-C_3)$-alkylene-heterocycloalkyl, wherein said heterocycloalkyl is selected from the group consisting of 3-pyrrolidinyl, 2-piperidinyl, 3-piperidinyl, 4-piperidinyl and 2-morpholinyl and wherein said heterocycloalkyl is substituted by a substituent selected from the group consisting of
  i) $(C_1-C_4)$-alkyl;
  ii) methylene-cyclohexyl;
  iii) $(C_0-C_2)$-alkylene-phenyl;
  iv) $(C_0-C_1)$-alkylene-pyridyl;
  v) pyrimidinyl;
l) $(C_0-C_2)$-alkylene-phenyl, wherein phenyl is unsubstituted or monosubstituted by substituents chosen from the group consisting of F, $OCH_3$, $N(CH_3)_2$;
m) $(C_1-C_2)$-alkylene-heteroaryl, wherein said heteroaryl ring is selected from the group consisting of 2-thienyl, 2-furanyl, 2-thiazolyl, 2-oxazolyl, 5-tetrazolyl and 5-Oxo-4,5-dihydro-1H-[1,2,4]-triazol-3-yl;
or
$R^9$ and $R^{10}$ together with the N-atom carrying them are
a) azetidinyl substituted by $CO_2H$;
b) pyrrolidinyl, which is unsubstituted or mono-substituted by a substituent selected from the group consisting of
  i) OH;
  ii) methylene-$OCH_3$;
  iii) methylene-O-methylene-phenyl;
  iv) $CO_2H$;
  v) $NR^{28}R^{29}$, wherein $R^{28}$ is $(C_1-C_2)$-alkyl and $R^{29}$ is $(C_1-C_2)$-alkyl;
  vi) 1-piperazinyl, which is unsubstituted or mono-substituted by methyl;
c) piperidinyl, which is mono-substituted by a substituent selected from the group consisting of
  i) $O-(C_1-C_3)$alkyl;
  ii) methylene-$OCH_3$;
  iii) $NR^{28}R^{29}$, wherein $R^{28}$ is (C1-C2)-alkyl and $R^{29}$ is methylene-phenyl or ethylene-$N(CH_3)_2$
  iv) 1-piperidinyl, which is mono-substituted by methyl;
  v) 1-piperazinyl, which is unsubstituted or mono-substituted by methyl;
  vi) 4-morpholinyl;
  vii) 1-azepanyl;
  viii) 2-(2,3-dihydro-1H-isoindolyl);
d) 4-morpholinyl, which is disubstituted by methyl;
e) 4-thiomorpholinyl;
f) piperazinyl, which, which is mono-substituted by a substituent selected from the group consisting of
  i) $(C_1-C_4)$-alkyl;
  ii) $(C_5-C_6)$-cycloalkyl;
  iii) phenyl, which is unsubstituted or mono-substituted by F, $CF_3$ or $OCH_3$;
  iv) methylene-phenyl, which is unsubstituted or disubstituted on adjacent positions by the group —$O(CH_2)O$—;
  v) pyridyl;
g) azepanyl, which is substituted by methylene-phenyl, which is unsubstituted or mono- or di-substituted by F or Cl;
c) a 2,5-diaza-bicyclo[2.2.1]heptyl-ring, which is substituted on the second N atom in 5-position by a substituent selected from the group consisting of $(C_1-C_4)$-alkyl, methylene-cyclopentyl, phenyl, which is mono-substituted by F, methylene-phenyl, wherein phenyl is unsubstituted or mono-substituted by $OCH_3$ or $CF_3$;
$R^{11}$ is H;
$R^{12}$ is $CH_3$;
$R^{13}$ is H;
$R^{14}$ is $CF_3$ or methylene-$OCH_3$;
$R^{15}$ is cyclopryopyl or phenyl;
$R^{16}$ is H or $CH_3$;
$R^{17}$ is H or $CH_3$;
and
$R^{18}$ is $CH_3$;
in any of its stereoisomeric forms, or a mixture of stereoisomeric forms in any ratio, or a physiologically acceptable salt thereof, or a physiologically acceptable solvate of any of them.

Another group of embodiments are compounds of the formula I

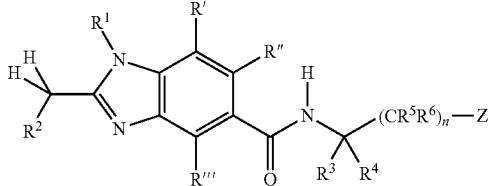

wherein
R', R", R''' are H;
R$^1$ is 1-ethyl-propyl;
R$^2$ is 3-thienyl;
R$^3$ is H;
R$^4$ is 2-methyl-propyl;
n is 0;
and
Z is CO$_2$—R$^7$, C(O)NR$^9$R$^{10}$.

Another group of embodiments are compounds of the formula I

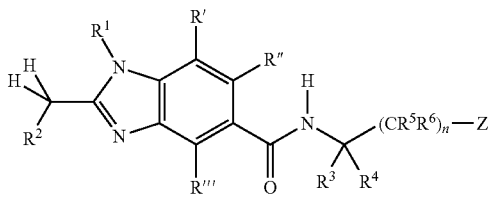

wherein
R', R", R''' are H;
R$^1$ is 1-ethyl-propyl;
R$^2$ is 3-thienyl;
R$^3$ is H;
R$^4$ is 2-methyl-propyl;
n is 0, 1, 2;
and
Z is C(O)NR$^9$R$^{10}$.

Another group of embodiments are compounds of the formula I wherein
R', R", R''' are H;
R$^1$ is 1-ethyl-propyl or 2-methyl-cyclohexyl;
R$^2$ is 3-thienyl;
R$^3$ is H, or (C$_1$-C$_2$)-alkyl;
and
R$^4$ is
a) (C$_3$-C$_5$)-alkyl, which may be optionally substituted by 1-3 F or S—(C$_1$-C$_4$)-alkyl,
b) (C$_0$-C$_1$)-alkylene-(C$_3$-C$_7$)-cycloalkyl, wherein said cycloalkyl is unsubstituted or mono- or di-substituted by methyl;
or
R$^3$ and R$^4$
are, together with the carbon atom to which they are attached, a 5- to 7-membered cycloalkyl ring, which is unsubstituted or mono-substituted by (C$_1$-C$_4$)-alkyl;
n is 0; and
Z is CO$_2$—H;

Another group of embodiments are compounds of the formula I wherein
R', R", R''' are H;
R$^1$ is 1-ethyl-propyl or 2-methyl-cyclohexyl;
R$^2$ is 3-thienyl;
R$^3$ is H, or (C$_1$-C$_2$)-alkyl; and
R$^4$ is
a) (C$_3$-C$_5$)-alkyl, which may be optionally substituted by 1-3 F or S—(C$_1$-C$_4$)-alkyl,
b) (C$_0$-C$_1$)-alkylene-(C$_3$-C$_7$)-cycloalkyl, wherein said cycloalkyl is unsubstituted or mono- or di-substituted by methyl;
or
R$^3$ and R$^4$
are, together with the carbon atom to which they are attached, a 5- to 7-membered cycloalkyl ring, which is unsubstituted or mono-substituted by (C$_1$-C$_4$)-alkyl;
R$^5$ is H, (C$_1$-C$_4$)-alkyl or OH;
R$^6$ H or (C$_1$-C$_4$)-alkyl;
n is 1;
and
Z is CO$_2$—H.

Another group of embodiments are compounds of the formula I wherein
R', R", R''' are H;
R$^1$ is 1-ethyl-propyl or 2-methyl-cyclohexyl;
R$^2$ is 3-thienyl;
R$^3$ is H, or (C$_1$-C$_2$)-alkyl;
and
R$^4$ is
a) (C$_3$-C$_5$)-alkyl, which may be optionally substituted by 1-3 F or S—(C$_1$-C$_4$)-alkyl,
b) (C$_0$-C$_1$)-alkylene-(C$_3$-C$_7$)-cycloalkyl, wherein said cycloalkyl is unsubstituted or mono- or di-substituted by methyl;
or
R$^3$ and R$^4$
are, together with the carbon atom to which they are attached, a 5- to 7-membered cycloalkyl ring, which is unsubstituted or mono-substituted by (C$_1$-C$_4$)-alkyl;
R$^5$ is H, (C$_1$-C$_4$)-alkyl or OH;
R$^6$ H or (C$_1$-C$_4$)-alkyl;
n is 2;
and
Z is CO$_2$—H.

Another group of embodiments are compounds of the formula I wherein
R', R", R''' are H;
R$^1$ is 1-ethyl-propyl;
R$^2$ is 3-thienyl;
R$^3$ is H, or (C$_1$-C$_2$)-alkyl;
and
R$^4$ is
a) (C$_3$-C$_5$)-alkyl, which may be optionally substituted by 1-3 F or S—(C$_1$-C$_4$)-alkyl,
b) (C$_0$-C$_1$)-alkylene-(C$_3$-C$_7$)-cycloalkyl, wherein said cycloalkyl is unsubstituted or mono- or di-substituted by methyl;
or
R$^3$ and R$^4$
are, together with the carbon atom to which they are attached, a 5- to 7-membered cycloalkyl ring, which is unsubstituted or mono-substituted by (C$_1$-C$_4$)-alkyl;
R$^5$ is H, (C$_1$-C$_4$)-alkyl or OH;
R$^6$ H or (C$_1$-C$_4$)-alkyl;
n is 1 or 2;
and
Z is OR$^8$, S(O)$_2$NR$^{11}$R$^{12}$, CN,

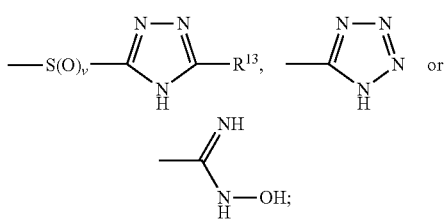

wherein v is 0 or 2;
R⁸ is H;
R¹¹ is H;
R¹² is CH₃; and
R¹³ is H.

Another group of embodiments are compounds of the formula I wherein
R', R'', R''' are H;
R¹ is 1-ethyl-propyl;
R² is 3-thienyl;
R³ is H;
R⁴ is 2-methyl-propyl;
n is 0;
and
Z is C(O)NR⁹R¹⁰.
 wherein
 R⁹ is H or methyl;
 and
 R¹⁰ is
 c) (C₁-C₂)-alkyl, which is substituted by CN
 d) (C₂-C₄)-alkyl, which is mono-substituted by a substituent selected from NR²³R²⁴;
  wherein
  R²³ is H;
  R²⁴ is (C₁-C₂)-alkyl or SO₂Methyl;
 m) (C₁-C₂)-alkylene-heteroaryl, wherein said heteroaryl ring is a five- or six-membered ring containing 1, 2, 3 or 4 heteroatoms selected from O, S or N; and wherein said heteroaryl ring is unsubstituted or mono-substituted by oxo (=O);
 or
 R⁹ and R¹⁰ together with the N-atom carrying them are
 a) a four-, five- or six-membered heterocylcoalkyl ring containing only the N atom, to which R⁹ and R¹⁰ are attached, which is unsubstituted or mono-substituted by a substituent selected from the group consisting of
  i) (C₀-C₁)-alkylene-OR²⁶, wherein R²⁶ is H;
  ii) CO₂R²⁷, wherein R²⁷ is H.

Another group of embodiments are compounds of the formula I wherein
R', R'', R''' are H;
R¹ is 1-ethyl-propyl;
R² is 3-thienyl;
R³ is H;
R⁴ is 2-methyl-propyl;
n is 0;
and
Z is C(O)NR⁹R¹⁰;
 wherein
 R⁹ is H or methyl;
 and
 R¹⁰ is
 a) (C₁-C₂)-alkyl, which is substituted by CN;
 b) (C₂-C₄)-alkyl, which is mono-substituted by a substituent selected from NR²³R²⁴;
  wherein
  R²³ is H;
  R²⁴ is (C₁-C₂)-alkyl or SO₂Methyl;
 c) (C₁-C₂)-alkylene-heteroaryl, wherein said heteroaryl ring is selected from 5-Oxo-4,5-dihydro-1H-[1,2,4]triazol-3-yl;
 or
 R⁹ and R¹⁰ together with the N-atom carrying them are
 a) a four-, five- or six-membered heterocylcoalkyl ring containing only the N atom, to which R⁹ and R¹⁰ are attached, which is unsubstituted or mono-substituted by a substituent selected from the group consisting of
  i) (C₀-C₁)-alkylene-OR²⁶, wherein R²⁶ is H;
  ii) CO₂R²⁷, wherein R²⁷ is H.

In another embodiment compounds of the formula I are encompassed selected from the group consisting of 1  1-{[1-(1-Ethyl-propyl)-2-thiophen-2-ylmethyl-1H-benzoimidazole-5-carbonyl]-amino}-cycloheptanecarboxylic acid
2  2-{[1-(1-Ethyl-propyl)-2-furan-2-ylmethyl-1H-benzoimidazole-5-carbonyl]-amino}-2-methyl-3-phenyl-propionic acid
3  (S)-3-Cyclohexyl-2-{[2-cyclopentylmethyl-1-(1-ethyl-propyl)-1H-benzoimidazole-5-carbonyl]-amino}-propionic acid
4  2-{[1-(1-Ethyl-propyl)-2-thiophen-2-ylmethyl-1H-benzoimidazole-5-carbonyl]-amino}-2-methyl-3-phenyl-propionic acid
5  2-{[1-(1-Ethyl-propyl)-2-thiophen-2-ylmethyl-1H-benzoimidazole-5-carbonyl]-amino}-2,3-dimethyl-butyric acid
6  1-{[1-(1-Ethyl-propyl)-2-thiophen-2-ylmethyl-1H-benzoimidazole-5-carbonyl]-amino}-cyclopentanecarboxylic acid
7  2-{[1-(1-Ethyl-propyl)-2-thiophen-2-ylmethyl-1H-benzoimidazole-5-carbonyl]-amino}-2-phenyl-butyric acid
8  (S)-3-Cyclohexyl-2-{[1-(1-ethyl-propyl)-2-furan-2-ylmethyl-1H-benzoimidazole-5-carbonyl]-amino}-propionic acid
9  (R)-3-Cyclohexyl-2-{[1-(1-ethyl-propyl)-2-furan-2-ylmethyl-1H-benzoimidazole-5-carbonyl]-amino}-propionic acid
10 (R)-3-Cyclohexyl-2-[{2-cyclopentylmethyl-1-(1-ethyl-propyl)-1H-benzoimidazole-5-carbonyl]-amino}-propionic acid
11 3-Cyclopentyl-2-{[1-(1-ethyl-propyl)-2-thiophen-2-ylmethyl-1H-benzoimidazole-5-carbonyl]-amino}-propionic acid
12 2-{[1-(1-Ethyl-propyl)-2-thiophen-2-ylmethyl-1H-benzoimidazole-5-carbonyl]-amino}-2,4-dimethyl-pentanoic acid
13 2-{[1-(1-Ethyl-propyl)-2-furan-2-ylmethyl-1H-benzoimidazole-5-carbonyl]-amino}-2,4-dimethyl-pentanoic acid
14 2-{[1-(1-Ethyl-propyl)-2-furan-2-ylmethyl-1H-benzoimidazole-5-carbonyl]-amino}-2-methyl-4-methylsulfanyl-butyric acid
15 (S)-3-Cyclohexyl-2-{[1-(2-methyl-cyclohexyl)-2-thiophen-2-ylmethyl-1H-benzoimidazole-5-carbonyl]-amino}-propionic acid
16 (S)-2-{[1-(2-Methyl-cyclohexyl)-2-thiophen-2-ylmethyl-1H-benzoimidazole-5-carbonyl]-amino}-hexanoic acid
17 (S)-3-Cyclohexyl-2-{[2-thiophen-2-ylmethyl-1-(2-trifluoromethyl-cyclohexyl)-1H-benzoimidazole-5-carbonyl]-amino}-propionic acid
18 (S)-2-{[1-(1-Ethyl-propyl)-2-thiophen-2-ylmethyl-1H-benzoimidazole-5-carbonyl]-amino}-hexanoic acid 19 (S)-2-{[1-(1-Ethyl-propyl)-2-thiophen-2-ylmethyl-1H-benzoimidazole-5-carbonyl]-amino}-3-(4-fluoro-phenyl)-propionic acid 20 (S)-3-(4-Chloro-phenyl)-2-{[1-(1-ethyl-propyl)-2-thiophen-2-ylmethyl-1H-benzoimidazole-5-carbonyl]-amino}-propionic acid 21 (S)-3-Cyclopropyl-2-{[1-(1-ethyl-propyl)-2-thiophen-2-ylmethyl-1H-benzoimidazole-5-carbonyl]-amino}-propionic acid 22 (S)-3-Cyclobutyl-2-{[1-(1-ethyl-propyl)-2-thiophen-2-ylmethyl-1H-benzoimidazole-5-carbonyl]-amino}-propionic acid 23 (S)-3-Cyclobutyl-2-{[1-((1R,2R)-2-methyl-cyclohexyl)-2-thiophen-2-ylmethyl-1H-benzoimidazole-5-carbonyl]-amino}-propionic acid 24 1-{[1-(1-Ethyl-propyl)-2-thiophen-2-ylmethyl-1H-benzoimidazole-5-carbonyl]-amino}-cyclohexanecarboxylic acid 25 2-{[1-(1-Ethyl-propyl)-2-thiophen-2-ylmethyl-1H-benzoimidazole-5-carbonyl]-amino}-2-methyl-pentanoic acid 26 2-{[1-(1-Ethyl-propyl)-2-thiophen-2-ylmethyl-1H-benzoimidazole-5-carbonyl]-amino}-5,5,5-trifluoro-pentanoic acid 27 5,5,5-Trifluoro-2-{[1-((1R,2R)-2-methyl-cyclohexyl)-2-thiophen-2-ylmethyl-1H-benzoimidazole-5-carbonyl]-amino}-pentanoic acid 28 2-{[1-(1-Ethyl-propyl)-2-thiophen-2-ylmethyl-1H-benzoimidazole-5-carbonyl]-amino}-4-phenyl-butyric acid 29 3-(4,4-Dimethyl-cyclohexyl)-2-{[1-(1-ethyl-propyl)-2-thiophen-2-ylmethyl-1H-benzoimidazole-5-carbonyl]-amino}-propionic acid 30 3-(4-Ethyl-phenyl)-2-{[1-(1-ethyl-propyl)-2-thiophen-2-ylmethyl-1H-benzoimidazole-5-carbonyl]-amino}-propionic acid 31 2-{[1-(1-Ethyl-propyl)-2-thiophen-2-ylmethyl-1H-benzoimidazole-5-carbonyl]-amino}-3-(4-trifluoromethyl-phenyl)-propionic acid 32 (S)-3-(3,4-Dichloro-phenyl)-2-{[1-(1-ethyl-propyl)-2-thiophen-2-ylmethyl-1H-benzoimidazole-5-carbonyl]-amino}-propionic acid 33 3-(4,4-Dimethyl-cyclohexyl)-2-{[1-((1R,2R)-2-methyl-cyclohexyl)-2-thiophen-2-ylmethyl-1H-benzoimidazole-5-carbonyl]-amino}-propionic acid 34 1-{[1-(1-Ethyl-propyl)-2-thiophen-2-ylmethyl-1H-benzoimidazole-5-carbonyl]-amino}-4-methyl-cyclohexanecarboxylic acid 35 4-Methyl-1-{[1-((1R,2R)-2-methyl-cyclohexyl)-2-thiophen-2-ylmethyl-1H-benzoimidazole-5-carbonyl]-amino}-cyclohexanecarboxylic acid 36 2-{[1-(1-Ethyl-propyl)-2-thiophen-2-ylmethyl-1H-benzoimidazole-5-carbonyl]-amino}-3-(4-methyl-cyclohexyl)-propionic acid 37 (S)-3-Cyclohexyl-2-{[1-((1R,2R)-2-methyl-cyclohexyl)-2-thiazol-5-ylmethyl-1H-benzoimidazole-5-carbonyl]-amino}-propionic acid 38 1-{[1-((1R,2R)-2-Methyl-cyclohexyl)-2-thiophen-2-ylmethyl-1H-benzoimidazole-5-carbonyl]-amino}-cyclohexanecarboxylic acid 39 3-Cycloheptyl-2-{[1-(1-ethyl-propyl)-2-thiophen-2-ylmethyl-1H-benzoimidazole-5-carbonyl]-amino}-propionic acid 40 3-Cycloheptyl-2-{[1-((1R,2R)-2-methyl-cyclohexyl)-2-thiophen-2-ylmethyl-1H-benzoimidazole-5-carbonyl]-amino}-propionic acid 41 3-{[1-(1-Ethyl-propyl)-2-furan-2-ylmethyl-1H-benzoimidazole-5-carbonyl]-amino}-4-methyl-pentanoic acid 42 3-{[1-(1-Ethyl-propyl)-2-furan-2-ylmethyl-1H-benzoimidazole-5-carbonyl]-amino}-3-phenyl-propionic acid 43 3-{[2-Cyclopentylmethyl-1-(1-ethyl-propyl)-1H-benzoimidazole-5-carbonyl]-amino}-3-phenyl-propionic acid 44 3-Cyclohexyl-3-{[1-(1-ethyl-propyl)-2-thiophen-2-ylmethyl-1H-benzoimidazole-5-carbonyl]-amino}-propionic acid 45 3-{[1-(1-Ethyl-propyl)-2-thiophen-2-ylmethyl-1H-benzoimidazole-5-carbonyl]-amino}-heptanoic acid 46 4-Cyclohexyl-3-{[1-(1-ethyl-propyl)-2-thiophen-2-ylmethyl-1H-benzoimidazole-5-carbonyl]-amino}-butyric acid 47 3-{[1-(1-Ethyl-propyl)-2-thiophen-2-ylmethyl-1H-benzoimidazole-5-carbonyl]-amino}-5,5-dimethyl-hexanoic acid 48 (R)-3-{[1-(1-Ethyl-propyl)-2-thiophen-2-ylmethyl-1H-benzoimidazole-5-carbonyl]-amino}-5-methyl-hexanoic acid 49 (S)-3-{[1-(1-Ethyl-propyl)-2-pyrazol-1-ylmethyl-1H-benzoimidazole-5-carbonyl]-amino}-5-methyl-hexanoic acid 50 (S)-3-{[1-(1-Ethyl-propyl)-2-thiazol-5-ylmethyl-1H-benzoimidazole-5-carbonyl]-amino}-5-methyl-hexanoic acid 51 4-Cyclohexyl-3-{[1-((1R,2R)-2-methyl-cyclohexyl)-2-thiophen-2-ylmethyl-1H-benzoimidazole-5-carbonyl]-amino}-butyric acid 52 4-Cyclohexyl-3-{[1-((1S,2S)-2-methyl-cyclohexyl)-2-thiophen-2-ylmethyl-1H-benzoimidazole-5-carbonyl]-amino}-butyric acid 53 (3R,4S)-4-Methyl-3-{[1-((1R,2R)-2-methyl-cyclohexyl)-2-thiophen-2-ylmethyl-1H-benzoimidazole-5-carbonyl]-amino}-hexanoic acid 54 (3R,4S)-3-{[1-(1-Ethyl-propyl)-2-thiophen-2-ylmethyl-1H-benzoimidazole-5-carbonyl]-amino}-4-methyl-hexanoic acid 55 3-{[1-((1R,2R)-2-Methyl-cyclohexyl)-2-thiophen-2-ylmethyl-1H-benzoimidazole-5-carbonyl]-amino}-hexanoic acid 56 3-{[1-((1R,2R)-2-Methyl-cyclohexyl)-2-thiophen-2-ylmethyl-1H-benzoimidazole-5-carbonyl]-amino}-heptanoic acid 57 3-Cyclohexyl-3-{[1-((1R,2R)-2-methyl-cyclohexyl)-2-thiophen-2-ylmethyl-1H-benzoimidazole-5-carbonyl]-amino}-propionic acid 58 3-{[1-(1-Ethyl-propyl)-2-thiophen-2-ylmethyl-1H-benzoimidazole-5-carbonyl]-amino}-2,2-dimethyl-heptanoic acid 59 4-Ethyl-3-{[1-(1-ethyl-propyl)-2-thiophen-2-ylmethyl-1H-benzoimidazole-5-carbonyl]-amino}-hexanoic acid 60 (S)-4-Cyclopentyl-3-{[1-(1-ethyl-propyl)-2-thiophen-2-ylmethyl-1H-benzoimidazole-5-carbonyl]-amino}-butyric acid 61 (S)-4-Cyclopentyl-3-{[1-((1R,2R)-2-methyl-cyclohexyl)-2-thiophen-2-ylmethyl-1H-benzoimidazole-5-carbonyl]-amino}-butyric acid 62 3-{[1-(1-Ethyl-propyl)-2-thiophen-2-ylmethyl-1H-benzoimidazole-5-carbonyl]-amino}-2,2,5-trimethyl-hexanoic acid 63 3-{[1-(1-Ethyl-propyl)-2-thiophen-2-ylmethyl-1H-benzoimidazole-5-carbonyl]-amino}-2,2-dimethyl-hexanoic acid 64  (1-{[1-(1-Ethyl-propyl)-2-thiophen-2-ylmethyl-1H-benzoimidazole-5-carbonyl]-amino}-cyclohexyl)-acetic acid
65  4-Cyclohexyl-3-{[1-((1R,2R)-2-methyl-cyclohexyl)-2-thiazol-5-ylmethyl-1H-benzoimidazole-5-carbonyl]-amino}-butyric acid
66  (1-{[1-((1R,2R)-2-Methyl-cyclohexyl)-2-thiophen-2-ylmethyl-1H-benzoimidazole-5-carbonyl]-amino}-cyclohexyl)-acetic acid
67  (2R,3S)-3-{[1-(1-Ethyl-propyl)-2-thiophen-2-ylmethyl-1H-benzoimidazole-5-carbonyl]-amino}-2-hydroxy-5-methyl-hexanoic acid
68  (2S,3S)-3-{[1-(1-Ethyl-propyl)-2-thiophen-2-ylmethyl-1H-benzoimidazole-5-carbonyl]-amino}-2-hydroxy-5-methyl-hexanoic acid
69  (R)-6-Methyl-4-{[2-thiophen-2-ylmethyl-1-(2-trifluoromethyl-cyclohexyl)-1H-benzoimidazole-5-carbonyl]-amino}-heptanoic acid
70  (R)-6-Methyl-4-{[1-((1R,2R)-2-methyl-cyclohexyl)-2-thiophen-2-ylmethyl-1H-benzoimidazole-5-carbonyl]-amino}-heptanoic acid
71  (4R,5S)-4-{[1-(1-Ethyl-propyl)-2-thiophen-2-ylmethyl-1H-benzoimidazole-5-carbonyl]-amino}-5-methyl-heptanoic acid
72  (4R,5S)-5-Methyl-4-{[1-((1R,2R)-2-methyl-cyclohexyl)-2-thiophen-2-ylmethyl-1H-benzoimidazole-5-carbonyl]-amino}-heptanoic acid
73  (3R,4S)-5-Cyclohexyl-4-{[1-(1-ethyl-propyl)-2-thiophen-2-ylmethyl-1H-benzoimidazole-5-carbonyl]-amino}-3-hydroxy-pentanoic acid
74  (3R,4S)-5-Cyclohexyl-3-hydroxy-4-{[1-((1R,2R)-2-methyl-cyclohexyl)-2-thiophen-2-ylmethyl-1H-benzoimidazole-5-carbonyl]-amino}-pentanoic acid
75  (3S,4S)-4-{[1-(1-Ethyl-propyl)-2-thiophen-2-ylmethyl-1H-benzoimidazole-5-carbonyl]-amino}-3-hydroxy-6-methyl-heptanoic acid
76  (3R,4S)-4-{[1-(1-Ethyl-propyl)-2-thiophen-2-ylmethyl-1H-benzoimidazole-5-carbonyl]-amino}-3-hydroxy-6-methyl-heptanoic acid
77  (3R,4S)-3-Hydroxy-6-methyl-4-{[4-((1R,2R)-2-methyl-cyclohexyl)-2-thiophen-2-ylmethyl-1H-benzoimidazole-5-carbonyl]-amino}-heptanoic acid
78  (3S,4S)-3-Hydroxy-6-methyl-4-{[1-((1R,2R)-2-methyl-cyclohexyl)-2-thiophen-2-ylmethyl-1H-benzoimidazole-5-carbonyl]-amino}-heptanoic acid
79  (3S,4S)-5-Cyclohexyl-4-{[1-(1-ethyl-propyl)-2-thiophen-2-ylmethyl-1H-benzoimidazole-5-carbonyl]-amino}-3-hydroxy-pentanoic acid
80  (S)-2-{[1-(1-Ethyl-propyl)-2-(tetrahydro-furan-2-ylmethyl)-1H-benzoimidazole-5-carbonyl]-amino}-4-methyl-pentanoic acid
81  (S)-2-{[1-(1-Ethyl-propyl)-2-furan-2-ylmethyl-1H-benzoimidazole-5-carbonyl]-amino}-4-methyl-pentanoic acid
82  (S)-2-{[2-(5-Chloro-thiophen-2-ylmethyl)-1-(1-ethyl-propyl)-1H-benzoimidazole-5-carbonyl}-amino]-4-methyl-pentanoic acid
83  (S)-2-[(1-Cyclohexylmethyl-2-thiophen-2-ylmethyl-1H-benzoimidazole-5-carbonyl)-amino]-4-methyl-pentanoic acid
84  (S)-2-{[1-(1-Ethyl-propyl)-2-thiazol-4-ylmethyl-1H-benzoimidazole-5-carbonyl]-amino}-4-methyl-pentanoic acid
85  (2S,3S)-2-{[1-(1-Ethyl-propyl)-2-thiazol-4-ylmethyl-1H-benzoimidazole-5-carbonyl]-amino}-3-methyl-pentanoic acid
86  (S)-2-{[2-Furan-2-ylmethyl-1-(2-methyl-cyclohexyl)-1H-benzoimidazole-5-carbonyl]-amino}-4-methyl-pentanoic acid
87  (S)-4-Methyl-2-{[2-thiophen-2-ylmethyl-1-(2-trifluoromethyl-cyclohexyl)-1H-benzoimidazole-5-carbonyl]-amino}-pentanoic acid
88  (S)-2-{[2-Thiophen-2-ylmethyl-1-(2-trifluoromethyl-cyclohexyl)-1H-benzoimidazole-5-carbonyl]-amino}-pentanoic acid
89  (S)-3-Phenyl-2-{[2-thiophen-2-ylmethyl-1-(2-trifluoromethyl-cyclohexyl)-1H-benzoimidazole-5-carbonyl]-amino}-propionic acid
90  (S)-4-Methyl-2-{[1-(2-methyl-cyclopentyl)-2-thiophen-2-ylmethyl-1H-benzoimidazole-5-carbonyl]-amino}-pentanoic acid
91  (S)-2-{[1-((1R,2R)-2-Methyl-cyclohexyl)-2-thiophen-2-ylmethyl-1H-benzoimidazole-5-carbonyl]-amino}-pentanoic acid
92  (2S,3S)-3-Methyl-2-{[1-((1R,2R)-2-methyl-cyclohexyl)-2-thiophen-2-ylmethyl-1H-benzoimidazole-5-carbonyl]-amino}-pentanoic acid
93  (S)-2-{[1-(2-Ethyl-cyclohexyl)-2-thiophen-2-ylmethyl-1H-benzoimidazole-5-carbonyl]-amino}-4-methyl-pentanoic acid
94  (S)-2-{[1-(1-Ethyl-propyl)-2-thiophen-2-ylmethyl-1H-benzoimidazole-5-carbonyl]-amino}-pentanoic acid
95  (S)-3-{[1-(1-Ethyl-propyl)-2-thiophen-2-ylmethyl-1H-benzoimidazole-5-carbonyl]-amino}-5-methyl-hexanoic acid
96  (S)-3-{[1-(1-Ethyl-propyl)-2-furan-2-ylmethyl-1H-benzoimidazole-5-carbonyl]-amino}-5-methyl-hexanoic acid
97  (S)-3-[(1-Cyclohexylmethyl-2-thiophen-2-ylmethyl-1H-benzoimidazole-5-carbonyl)-amino]-5-methyl-hexanoic acid
98  (S)-3-{[1-(1-Ethyl-propyl)-2-thiazol-4-ylmethyl-1'-1-benzoimidazole-5-carbonyl]-amino}-5-methyl-hexanoic acid
99  (S)-3-{[2-Furan-2-ylmethyl-1-(2-methyl-cyclohexyl)-1H-benzoimidazole-5-carbonyl]-amino}-5-methyl-hexanoic acid
100 (S)-3-{[1-(1-Ethyl-propyl)-2-thiophen-2-ylmethyl-1H-benzoimidazole-5-carbonyl]-amino}-4-phenyl-butyric acid
101 (S)-5-Methyl-3-{[1-(2-methyl-cyclohexyl)-2-thiophen-2-ylmethyl-1H-benzoimidazole-5-carbonyl]-amino}hexanoic acid
102 (S)-5-Methyl-3-{[2-thiophen-2-ylmethyl-1-(2-trifluoromethyl-cyclohexyl)-1H-benzoimidazole-5-carbonyl]-amino}-hexanoic acid
103 (S)-4-Phenyl-3-{[2-thiophen-2-ylmethyl-1-(2-trifluoromethyl-cyclohexyl)-1H-benzoimidazole-5-carbonyl]-amino}-butyric acid
104 (S)-5-Methyl-3-{[1-(2-methyl-cyclopentyl)-2-thiophen-2-ylmethyl-1H-benzoimidazole-5-carbonyl]-amino}-hexanoic acid
105 (S)-3-{[1-(1-Ethyl-propyl)-2-isoxazol-5-ylmethyl-1H-benzoimidazole-5-carbonyl]-amino}-5-methyl-hexanoic acid
106 (S)-5-Methyl-3-{[1-((1R,2R)-2-methyl-cyclohexyl)-2-thiazol-5-ylmethyl-1H-benzoimidazole-5-carbonyl]-amino}-hexanoic acid
107 (S)-3-{[1-(1-Ethyl-propyl)-2-thiophen-2-ylmethyl-1H-benzoimidazole-5-carbonyl]-amino}-5-methyl-hexanoic acid
108 (S)-2-[(1-Cyclohexyl-2-thiophen-2-ylmethyl-1H-benzoimidazole-5-carbonyl)-amino]-4-methyl-pentanoic acid 109 (S)-2-{[2-Cyclopentylmethyl-1-(2-methyl-butyl)-1H-benzoimidazole-5-carbonyl]-amino}-4-methyl-pentanoic acid
110 (S)-2-[(1-Cyclopentyl-2-thiophen-2-ylmethyl-1H-benzoimidazole-5-carbonyl)-amino]-4-methyl-pentanoic acid
111 (S)-2-[(1-Cycloheptyl-2-thiophen-2-ylmethyl-1H-benzoimidazole-5-carbonyl)-amino]-4-methyl-pentanoic acid
112 (S)-2-[(1-Cyclohexyl-2-cyclopentylmethyl-1H-benzoimidazole-5-carbonyl)-amino]-4-methyl-pentanoic acid
113 (S)-4-Methyl-2-{[1-(2-methyl-butyl)-2-thiophen-2-ylmethyl-1H-benzoimidazole-5-carbonyl]-amino}-pentanoic acid
114 (S)-2-{[1-(1-Ethyl-propyl)-2-thiophen-2-ylmethyl-1H-benzoimidazole-5-carbonyl]-amino}-4-methyl-pentanoic acid
115 (S)-4-Methyl-2-[(2-thiophen-2-ylmethyl-1-p-tolyl-1H-benzoimidazole-5-carbonyl)-amino]-pentanoic acid
116 (S)-2-{[2-Benzyl-1-(1-ethyl-propyl)-1H-benzoimidazole-5-carbonyl]-amino}-4-methyl-pentanoic acid
117 (S)-2-{[1-(1-Ethyl-propyl)-2-thiophen-3-ylmethyl-1H-benzoimidazole-5-carbonyl]-amino}-4-methyl-pentanoic acid
118 (S)-2-{[1-(1-Ethyl-propyl)-2-furan-3-ylmethyl-1H-benzoimidazole-5-carbonyl]-amino}-4-methyl-pentanoic acid
119 (S)-2-{[1-(1-Ethyl-propyl)-2-(5-methyl-thiophen-2-ylmethyl)-1H-benzoimidazole-5-carbonyl]-amino}-4-methyl-pentanoic acid
120 (S)-2-{[2-Cyclohexylmethyl-1-(1-ethyl-propyl)-1H-benzoimidazole-5-carbonyl]-amino}-4-methyl-pentanoic acid
121 (S)-2-{[1-(1-Ethyl-propyl)-2-thiophen-2-ylmethyl-1H-benzoimidazole-5-carbonyl]-amino}-3-methyl-pentanoic acid
122 (S)-2-{[1-(1-Ethyl-propyl)-2-thiophen-2-ylmethyl-1H-benzoimidazole-5-carbonyl]-amino}-3-methyl-butyric acid
123 (S)-2-{[1-(1-Ethyl-propyl)-2-thiophen-2-ylmethyl-1H-benzoimidazole-5-carbonyl]-amino}-4-methylsulfanyl-butyric acid
124 (S)-2-{[1-(1-Ethyl-propyl)-2-thiophen-2-ylmethyl-1H-benzoimidazole-5-carbonyl]-amino}-3-phenyl-propionic acid
125 (S)-3-Cyclohexyl-2-{[1-(1-ethyl-propyl)-2-thiophen-2-ylmethyl-1H-benzoimidazole-5-carbonyl]-amino}-propionic acid
126 2-{[1-(1-Ethyl-propyl)-2-thiophen-2-ylmethyl-1H-benzoimidazole-5-carbonyl]-amino}-4,4-dimethyl-pentanoic acid
127 (S)-2-[(1-Isobutyl-2-thiophen-2-ylmethyl-1H-benzoimidazole-5-carbonyl)-amino]-4-methyl-pentanoic acid
128 (S)-2-[(2-Cyclopentylmethyl-1-isobutyl-1H-benzoimidazole-5-carbonyl)-amino]-4-methyl-pentanoic acid
129 (S)-2-{[2-Cyclopentylmethyl-1-(1-ethyl-propyl)-1H-benzoimidazole-5-carbonyl]-amino}-4-methyl-pentanoic acid
130 (S)-2-{[1-(1-Ethyl-propyl)-2-thiophen-2-ylmethyl-1H-benzoimidazole-5-carbonyl]-amino}-5-methyl-hexanoic acid
131 (S)-2-{[2-Furan-3-ylmethyl-1-(2-methyl-cyclohexyl)-1H-benzoimidazole-5-carbonyl]amino}-4-methyl-pentanoic acid
132 (S)-4-Methyl-2-[(1-phenyl-2-thiophen-2-ylmethyl-1H-benzoimidazole-5-carbonyl)-amino]-pentanoic acid
133 (S)-3-Cyclohexyl-2-{[2-cyclohexylmethyl-1-(2-methyl-butyl)-1H-benzoimidazole-5-carbonyl]-amino}-propionic acid
134 (S)-3-Cyclohexyl-2-[(2-cyclohexylmethyl-1-isobutyl-1H-benzoimidazole-5-carbonyl)-amino]-propionic acid
135 (S)-2-{[2-Cyclohexylmethyl-1-(2-methyl-butyl)-1H-benzoimidazole-5-carbonyl]-amino}-4-methyl-pentanoic acid
136 (S)-4-Methyl-2-[(1-phenyl-2-thiophen-3-ylmethyl-1H-benzoimidazole-5-carbonyl)-amino]-pentanoic acid
137 (S)-4-Methyl-2-{[1-(2-methyl-butyl)-2-thiophen-3-ylmethyl-1H-benzoimidazole-5-carbonyl]-amino}-pentanoic acid
138 (S)-2-[(1-Cyclohexyl-2-furan-3-ylmethyl-1H-benzoimidazole-5-carbonyl)-amino]-4-methyl-pentanoic acid
139 (S)-4-Methyl-2-{[1-(2-methyl-cyclohexyl)-2-thiophen-3-ylmethyl-1H-benzoimidazole-5-carbonyl]-amino}-pentanoic acid
140 (S)-2-[(1-sec-Butyl-2-thiophen-2-ylmethyl-1H-benzoimidazole-5-carbonyl)-amino]-3-cyclohexyl-propionic acid
141 (S)-3-Cyclohexyl-2-{[2-cyclohexylmethyl-1-(1-ethyl-propyl)-1H-benzoimidazole-5-carbonyl]-amino}-propionic acid
142 (S)-2-[(1-sec-Butyl-2-thiophen-3-ylmethyl-1H-benzoimidazole-5-carbonyl)-amino]-4-methyl-pentanoic acid
143 (S)-2-{[2-Benzyl-1-(2-methyl-cyclohexyl)-1H-benzoimidazole-5-carbonyl]-amino}-4-methyl-pentanoic acid
144 (S)-4-Methyl-2-{[1-(2-methyl-cyclohexyl)-2-(5-methyl-thiophen-2-ylmethyl)-1H-benzoimidazole-5-carbonyl]-amino}-pentanoic acid
145 (S)-3-Cyclohexyl-2-{[1-(2-methyl-butyl)-2-thiophen-2-ylmethyl-1H-benzoimidazole-5-carbonyl]-amino}-propionic acid
146 (S)-4-Methyl-2-{[1-(2-methyl-cyclohexyl)-2-thiophen-2-ylmethyl-1H-benzoimidazole-5-carbonyl]-amino}-pentanoic acid
147 (S)-2-[(1-sec-Butyl-2-thiophen-2-ylmethyl-1H-benzoimidazole-5-carbonyl)-amino]-4-methyl-pentanoic acid
148 (S)-2-[(2-Benzyl-1-cyclohexyl-1H-benzoimidazole-5-carbonyl)-amino]-4-methyl-pentanoic acid
149 (S)-2-[(1-sec-Butyl-2-cyclopentylmethyl-1H-benzoimidazole-5-carbonyl)-amino]-4-methyl-pentanoic acid
150 (S)-2-{[2-Cyclopentylmethyl-1-(2-methyl-cyclohexyl)-1H-benzoimidazole-5-carbonyl]-amino}-4-methyl-pentanoic acid
151 (S)-3-Cyclohexyl-2-{[1-(1-ethyl-propyl)-2-(tetrahydrofuran-2-ylmethyl)-1H-benzoimidazole-5-carbonyl]-amino}-propionic acid
152 (S)-2-[(1-Cyclohexyl-2-thiophen-3-ylmethyl-1H-benzoimidazole-5-carbonyl)-amino]-4-methyl-pentanoic acid
153 (2S,3R)-2-{[1-(1-Ethyl-propyl)-2-thiophen-2-ylmethyl-1H-benzoimidazole-5-carbonyl]-amino}-3-methyl-pentanoic acid
154 (S)-3-{[1-(1-Ethyl-propyl)-2-furan-3-ylmethyl-1H-benzoimidazole-5-carbonyl]-amino}-5-methyl-hexanoic acid
155 3-{[1-(1-Ethyl-propyl)-2-thiophen-2-ylmethyl-1H-benzoimidazole-5-carbonyl]-amino}-hexanoic acid 156 (S)-3-{[1-(1-Ethyl-propyl)-2-thiophen-3-ylmethyl-1H-benzoimidazole-5-carbonyl]-amino}-5-methyl-hexanoic acid
157 (S)-3-{[2-Benzyl-1-(1-ethyl-propyl)-1H-benzoimidazole-5-carbonyl]-amino}-5-methyl-hexanoic acid
158 (S)-3-{[2-Cyclopentylmethyl-1-(1-ethyl-propyl)-1H-benzoimidazole-5-carbonyl]-amino}-5-methyl-hexanoic acid
159 (S)-3-{[2-Cyclopentylmethyl-1-(2-methyl-butyl)-1H-benzoimidazole-5-carbonyl]-amino}-5-methyl-hexanoic acid
160 (S)-3-{[1-(1-Ethyl-propyl)-2-(tetrahydro-furan-2-ylmethyl)-1H-benzoimidazole-5-carbonyl]-amino}-5-methyl-hexanoic acid
161 (R)-3-{[1-(1-Ethyl-propyl)-2-thiophen-2-ylmethyl-1H-benzoimidazole-5-carbonyl]-amino}-4-methyl-pentanoic acid
162 (R)-4-{[1-(1-Ethyl-propyl)-2-thiophen-2-ylmethyl-1H-benzoimidazole-5-carbonyl]-amino}-5-methyl-hexanoic acid
163 (R)-4-{[1-(1-Ethyl-propyl)-2-thiophen-2-ylmethyl-1H-benzoimidazole-5-carbonyl]amino}-6-methyl-heptanoic acid
164 (S)-2-{[1-(1-Isopropyl-2-methyl-propyl)-2-thiophen-2-ylmethyl-1H-benzoimidazole-5-carbonyl]-amino}-4-methyl-pentanoic acid
165 (S)-2-{[1-(2-Chloro-phenyl)-2-thiophen-2-ylmethyl-1H-benzoimidazole-5-carbonyl]-amino}-4-methyl-pentanoic acid
166 (S)-2-{[1-(1,3-Dimethyl-butyl)-2-thiophen-2-ylmethyl-1H-benzoimidazole-5-carbonyl]-amino}-4-methyl-pentanoic acid
399 1-(1-Ethyl-propyl)-2-thiophen-2-ylmethyl-1H-benzoimidazole-5-carboxylic acid {(S)-3-methyl-1-[(1H-tetrazol-5-ylmethyl)-carbamoyl]-butyl}-amide
400 1-(1-Ethyl-propyl)-2-thiophen-2-ylmethyl-1H-benzoimidazole-5-carboxylic acid {(S)-3-methyl-1-[2-(1H-tetrazol-5-yl)-ethylcarbamoyl]-butyl}-amide
401 1-(1-Ethyl-propyl)-2-thiophen-2-ylmethyl-1H-benzoimidazole-5-carboxylic acid [(S)-3-methyl-1-(2-sulfamoyl-ethylcarbamoyl)-butyl]-amide
402 1-(1-Ethyl-propyl)-2-thiophen-2-ylmethyl-1H-benzoimidazole-5-carboxylic acid [(S)-1-(2-methanesulfonylamino-ethylcarbamoyl)-3-methyl-butyl]-amide
403 1-(1-Ethyl-propyl)-2-thiophen-2-ylmethyl-1H-benzoimidazole-5-carboxylic acid [(S)-1-(cyanomethyl-carbamoyl)-3-methyl-butyl]-amide
404 1-(1-Ethyl-propyl)-2-thiophen-2-ylmethyl-1H-benzoimidazole-5-carboxylic acid [(S)-1-(2-cyano-ethylcarbamoyl)-3-methyl-butyl]-amide
405 1-(1-Ethyl-propyl)-2-thiophen-2-ylmethyl-1H-benzoimidazole-5-carboxylic acid {(S)-3-methyl-1-[methyl-(5-oxo-4,5-dihydro-1H-[1,2,4]triazol-3-ylmethyl)-carbamoyl]-butyl}-amide
406 1-(1-Ethyl-propyl)-2-thiophen-2-ylmethyl-1H-benzoimidazole-5-carboxylic acid {(S)-3-methyl-1-[2-(5-oxo-4,5-dihydro-1H-[1,2,4]triazol-3-yl)-ethylcarbamoyl]-butyl}-amide
408 ((S)-2-{[1-(1-Ethyl-propyl)-2-thiophen-2-ylmethyl-1H-benzoimidazole-5-carbonyl]-amino}-4-methyl-pentanoylamino)-acetic acid
409 (S)-1-((S)-2-{[1-(1-Ethyl-propyl)-2-thiophen-2-ylmethyl-1H-benzoimidazole-5-carbonyl]-amino}-4-methyl-pentanoyl)-pyrrolidine-2-carboxylic acid
410 (R)-1-((S)-2-{[1-(1-Ethyl-propyl)-2-thiophen-2-ylmethyl-1H-benzoimidazole-5-carbonyl]-amino}-4-methyl-pentanoyl)-pyrrolidine-2-carboxylic acid
411 1-((S)-2-{[1-(1-Ethyl-propyl)-2-thiophen-2-ylmethyl-1H-benzoimidazole-5-carbonyl]-amino}-4-methyl-pentanoyl)-azetidine-3-carboxylic acid
412 (S)-4-Methyl-2-{[1-((1R,2R)-2-methyl-cyclohexyl)-2-thiophen-2-ylmethyl-1H-benzoimidazole-5-carbonyl]-amino}-pentanoic acid
413 (S)-4-Methyl-2-{[1-((1S,2S)-2-methyl-cyclohexyl)-2-thiophen-2-ylmethyl-1H-benzoimidazole-5-carbonyl]-amino}-pentanoic acid
414 (S)-4-Methyl-2-{[1-((1R,2S)-2-methyl-cyclohexyl)-2-thiophen-2-ylmethyl-1H-benzoimidazole-5-carbonyl]-amino}-pentanoic acid
415 (S)-4-Methyl-2-{[1-((1S,2R)-2-methyl-cyclohexyl)-2-thiophen-2-ylmethyl-1H-benzoimidazole-5-carbonyl]-amino}-pentanoic acid
416 (S)-2-{[2-Furan-2-ylmethyl-1-(2-methyl-cyclohexyl)-1H-benzoimidazole-5-carbonyl]-amino}-4-methyl-pentanoic acid
417 (S)-2-{[2-Furan-2-ylmethyl-1-(2-methyl-cyclohexyl)-1H-benzoimidazole-5-carbonyl]-amino}-4-methyl-pentanoic acid
418 (S)-2-{[2-Furan-2-ylmethyl-1-(2-methyl-cyclohexyl)-1H-benzoimidazole-5-carbonyl]amino}-4-methyl-pentanoic acid
419 (S)-2-{[2-Furan-2-ylmethyl-1-(2-methyl-cyclohexyl)-1H-benzoimidazole-5-carbonyl]-amino}-4-methyl-pentanoic acid
420 (S)-2-{[1-(2-Methyl-cyclohexyl)-2-thiophen-2-ylmethyl-1H-benzoimidazole-5-carbonyl]-amino}-hexanoic acid
421 (S)-2-{[1-(2-Methyl-cyclohexyl)-2-thiophen-2-ylmethyl-1H-benzoimidazole-5-carbonyl]-amino}-hexanoic acid
422 (S)-2-{[1-(2-Methyl-cyclohexyl)-2-thiophen-2-ylmethyl-1H-benzoimidazole-5-carbonyl]-amino}-hexanoic acid
423 (S)-2-{[1-(2-Methyl-cyclohexyl)-2-thiophen-2-ylmethyl-1H-benzoimidazole-5-carbonyl]-amino}-hexanoic acid
424 (S)-3-Cyclohexyl-2-{[1-(2-methyl-cyclohexyl)-2-thiophen-2-ylmethyl-1H-benzoimidazole-5-carbonyl]-amino}-propionic acid
425 (S)-3-Cyclohexyl-2-{[1-(2-methyl-cyclohexyl)-2-thiophen-2-ylmethyl-1H-benzoimidazole-5-carbonyl]-amino}-propionic acid
426 (S)-3-Cyclohexyl-2-{[1-(2-methyl-cyclohexyl)-2-thiophen-2-ylmethyl-1H-benzoimidazole-5-carbonyl]-amino}-propionic acid
427 (S)-3-Cyclohexyl-2-{[1-(2-methyl-cyclohexyl)-2-thiophen-2-ylmethyl-1H-benzoimidazole-5-carbonyl]-amino}-propionic acid
428 (S)-4-Methyl-2-{[1-(2-methyl-cyclopentyl)-2-thiophen-2-ylmethyl-1H-benzoimidazole-5-carbonyl]-amino}-pentanoic acid
429 (S)-4-Methyl-2-{[1-(2-methyl-cyclopentyl)-2-thiophen-2-ylmethyl-1H-benzoimidazole-5-carbonyl]-amino}-pentanoic acid
430 (S)-4-Methyl-2-{[1-(2-methyl-cyclopentyl)-2-thiophen-2-ylmethyl-1H-benzoimidazole-5-carbonyl]-amino}-pentanoic acid
431 (S)-4-Methyl-2-{[1-(2-methyl-cyclopentyl)-2-thiophen-2-ylmethyl-1H-benzoimidazole-5-carbonyl]-amino}-pentanoic acid
432 (S)-3-{[2-Furan-2-ylmethyl-1-(2-methyl-cyclohexyl)-1H-benzoimidazole-5-carbonyl]-amino}-5-methyl-hexanoic acid 433 (S)-3-{[2-Furan-2-ylmethyl-1-(2-methyl-cyclohexyl)-1H-benzoimidazole-5-carbonyl]-amino}-5-methyl-hexanoic acid 434 (S)-3-{[2-Furan-2-ylmethyl-1-(2-methyl-cyclohexyl)-1H-benzoimidazole-5-carbonyl]-amino}-5-methyl-hexanoic acid 435 (S)-3-{[2-Furan-2-ylmethyl-1-(2-methyl-cyclohexyl)-1H-benzoimidazole-5-carbonyl]-amino}-5-methyl-hexanoic acid 436 (S)-5-Methyl-3-{[1-(2-methyl-cyclohexyl)-2-thiophen-2-ylmethyl-1H-benzoimidazole-5-carbonyl]-amino}-hexanoic acid 437 (S)-5-Methyl-3-{[1-(2-methyl-cyclohexyl)-2-thiophen-2-ylmethyl-1H-benzoimidazole-5-carbonyl]-amino}-hexanoic acid 438 (S)-5-Methyl-3-{[1-(2-methyl-cyclohexyl)-2-thiophen-2-ylmethyl-1H-benzoimidazole-5-carbonyl]-amino}-hexanoic acid 439 (S)-5-Methyl-3-{[1-(2-methyl-cyclohexyl)-2-thiophen-2-ylmethyl-1H-benzoimidazole-5-carbonyl]-amino}-hexanoic acid 440 (R)-2-{[1-(1-Ethyl-propyl)-2-thiophen-2-ylmethyl-1H-benzoimidazole-5-carbonyl]-amino}-2,4-dimethyl-pentanoic acid 441 (S)-2-{[1-(1-Ethyl-propyl)-2-thiophen-2-ylmethyl-1H-benzoimidazole-5-carbonyl]-amino}-2,4-dimethyl-pentanoic acid 442 3-Cyclopentyl-2-{[1-((1R,2R)-2-methyl-cyclohexyl)-2-thiophen-2-ylmethyl-1H-benzoimidazole-5-carbonyl]-amino}-propionic acid 443 3-Cyclopentyl-2-{[1-((1R,2R)-2-methyl-cyclohexyl)-2-thiophen-2-ylmethyl-1H-benzoimidazole-5-carbonyl]-amino}-propionic acid 444 (S)-3-(4,4-Dimethyl-cyclohexyl)-2-{[1-(1-ethyl-propyl)-2-thiophen-2-ylmethyl-1H-benzoimidazole-5-carbonyl]-amino}-propionic acid 445 (R)-3-(4,4-Dimethyl-cyclohexyl)-2-{[1-(1-ethyl-propyl)-2-thiophen-2-ylmethyl-1H-benzoimidazole-5-carbonyl]-amino}-propionic acid 446 3-(4,4-Dimethyl-cyclohexyl)-2-{[1-((1R,2R)-2-methyl-cyclohexyl)-2-thiophen-2-ylmethyl-1H-benzoimidazole-5-carbonyl]-amino}-propionic acid 447 3-(4,4-Dimethyl-cyclohexyl)-2-{[1-((1R,2R)-2-methyl-cyclohexyl)-2-thiophen-2-ylmethyl-1H-benzoimidazole-5-carbonyl]-amino}-propionic acid 448 (S)-3-Cycloheptyl-2-{[1-(1-ethyl-propyl)-2-thiophen-2-ylmethyl-1H-benzoimidazole-5-carbonyl]-amino}-propionic acid 449 (R)-3-Cycloheptyl-2-{[1-(1-ethyl-propyl)-2-thiophen-2-ylmethyl-1H-benzoimidazole-5-carbonyl]-amino}-propionic acid 450 3-Cycloheptyl-2-{[1-((1R,2R)-2-methyl-cyclohexyl)-2-thiophen-2-ylmethyl-1H-benzoimidazole-5-carbonyl]-amino}-propionic acid 451 3-Cycloheptyl-2-{[1-((1R,2R)-2-methyl-cyclohexyl)-2-thiophen-2-ylmethyl-1H-benzoimidazole-5-carbonyl]-amino}-propionic acid 452 (S)-3-{[1-(1-Ethyl-propyl)-2-thiophen-2-ylmethyl-1H-benzoimidazole-5-carbonyl]-amino}-heptanoic acid 453 (R)-3-{[1-(1-Ethyl-propyl)-2-thiophen-2-ylmethyl-1H-benzoimidazole-5-carbonyl]-amino}-heptanoic acid 454 (S)-4-Cyclohexyl-3-{[1-(1-ethyl-propyl)-2-thiophen-2-ylmethyl-1H-benzoimidazole-5-carbonyl]-amino}-butyric acid 455 (R)-4-Cyclohexyl-3-{[1-(1-ethyl-propyl)-2-thiophen-2-ylmethyl-1H-benzoimidazole-5-carbonyl]-amino}-butyric acid 456 4-Cyclohexyl-3-{[1-((1R,2R)-2-methyl-cyclohexyl)-2-thiophen-2-ylmethyl-1H-benzoimidazole-5-carbonyl]-amino}-butyric acid 457 4-Cyclohexyl-3-{[1-((1R,2R)-2-methyl-cyclohexyl)-2-thiophen-2-ylmethyl-1H-benzoimidazole-5-carbonyl]-amino}-butyric acid 458 3-{[1-((1R,2R)-2-Methyl-cyclohexyl)-2-thiophen-2-ylmethyl-1H-benzoimidazole-5-carbonyl]-amino}-hexanoic acid 459 3-{[1-((1R,2R)-2-Methyl-cyclohexyl)-2-thiophen-2-ylmethyl-1H-benzoimidazole-5-carbonyl]-amino}-hexanoic acid 460 3-{[1-((1R,2R)-2-Methyl-cyclohexyl)-2-thiophen-2-ylmethyl-1H-benzoimidazole-5-carbonyl]-amino}-heptanoic acid 461 3-{[1-((1R,2R)-2-Methyl-cyclohexyl)-2-thiophen-2-ylmethyl-1H-benzoimidazole-5-carbonyl]-amino}-heptanoic acid 462 3-Cyclohexyl-3-{[1-((1R,2R)-2-methyl-cyclohexyl)-2-thiophen-2-ylmethyl-1H-benzoimidazole-5-carbonyl]-amino}-propionic acid 463 3-Cyclohexyl-3-{[1-((1R,2R)-2-methyl-cyclohexyl)-2-thiophen-2-ylmethyl-1H-benzoimidazole-5-carbonyl]-amino}-propionic acid 464 (R)-3-{[1-(1-Ethyl-propyl)-2-thiophen-2-ylmethyl-1H-benzoimidazole-5-carbonyl]-amino}-2,2,5-trimethyl-hexanoic acid 465 (S)-3-{[1-(1-Ethyl-propyl)-2-thiophen-2-ylmethyl-1H-benzoimidazole-5-carbonyl]-amino}-2,2,5-trimethyl-hexanoic acid 466 (R)-3-{[1-(1-Ethyl-propyl)-2-thiophen-2-ylmethyl-1H-benzoimidazole-5-carbonyl]-amino}-2,2-dimethyl-hexanoic acid 467 (S)-3-{[1-(1-Ethyl-propyl)-2-thiophen-2-ylmethyl-1H-benzoimidazole-5-carbonyl]-amino}-2,2-dimethyl-hexanoic acid 468 (S)-3-{[1-(1-Ethyl-propyl)-2-thiophen-2-ylmethyl-1H-benzoimidazole-5-carbonyl]-amino}-2,2-dimethyl-heptanoic acid 469 (R)-3-{[1-(1-Ethyl-propyl)-2-thiophen-2-ylmethyl-1H-benzoimidazole-5-carbonyl]-amino}-2,2-dimethyl-heptanoic acid 472 1-(1-Ethyl-propyl)-2-thiophen-2-ylmethyl-1H-benzoimidazole-5-carboxylic acid [(S)-3-methyl-1-(1H-tetrazol-5-ylmethyl)-butyl]-amide 473 1-(1-Ethyl-propyl)-2-thiophen-2-ylmethyl-1H-benzoimidazole-5-carboxylic acid [(S)-1-(N-hydroxycarbamimidoylmethyl)-3-methyl-butyl]-amide 483 1-(1-Ethyl-propyl)-2-thiophen-2-ylmethyl-1H-benzoimidazole-5-carboxylic acid [(S)-3-methyl-1-(4H-[1,2,4]triazol-3-ylsulfanylmethyl)-butyl]-amide 484 1-(1-Ethyl-propyl)-2-thiophen-2-ylmethyl-1H-benzoimidazole-5-carboxylic acid [(S)-3-methyl-1-(4H-[1,2,4]triazole-3-sulfonylmethyl)-butyl]-amide 485 1-(1-Ethyl-propyl)-2-thiophen-2-ylmethyl-1H-benzoimidazole-5-carboxylic acid ((S)-3-methyl-1-methylsulfamoylmethyl-butyl)-amide.

The number denotes the example number of the respective compound.

In another embodiment compounds of the formula I are encompassed selected from the group consisting of 1 1-{[1-(1-Ethyl-propyl)-2-thiophen-2-ylmethyl-1H-benzoimidazole-5-carbonyl]-amino}-cycloheptanecarboxylic acid 2 (S)-3-Cyclohexyl-2-{[2-cyclopentylmethyl-1-(1-ethyl-propyl)-1H-benzoimidazole-5-carbonyl]-amino}-propionic acid 6 1-{[1-(1-Ethyl-propyl)-2-thiophen-2-ylmethyl-1H-benzoimidazole-5-carbonyl]-amino}-cyclopentanecarboxylic acid 8 (S)-3-Cyclohexyl-2-{[1-(1-ethyl-propyl)-2-furan-2-ylmethyl-1H-benzoimidazole-5-carbonyl]-amino}-propionic acid 9 (R)-3-Cyclohexyl-2-{[1-(1-ethyl-propyl)-2-furan-2-ylmethyl-1H-benzoimidazole-5-carbonyl]-amino}-propionic acid 10 (R)-3-Cyclohexyl-2-{[2-cyclopentylmethyl-1-(1-ethyl-propyl)-1H-benzoimidazole-5-carbonyl]-amino}-propionic acid 11 3-Cyclopentyl-2-{[1-(1-ethyl-propyl)-2-thiophen-2-ylmethyl-1H-benzoimidazole-5-carbonyl]-amino}-propionic acid 12 2-{[1-(1-Ethyl-propyl)-2-thiophen-2-ylmethyl-1H-benzoimidazole-5-carbonyl]-amino}-2,4-dimethyl-pentanoic acid 13 2-{[1-(1-Ethyl-propyl)-2-furan-2-ylmethyl-1H-benzoimidazole-5-carbonyl]-amino}-2,4-dimethyl-pentanoic acid 14 2-{[1-(1-Ethyl-propyl)-2-furan-2-ylmethyl-1H-benzoimidazole-5-carbonyl]-amino}-2-methyl-4-methylsulfanyl-butyric acid 15 (S)-3-Cyclohexyl-2-{[1-(2-methyl-cyclohexyl)-2-thiophen-2-ylmethyl-1H-benzoimidazole-5-carbonyl]-amino}-propionic acid 16 (S)-2-{[1-(2-Methyl-cyclohexyl)-2-thiophen-2-ylmethyl-1H-benzoimidazole-5-carbonyl]-amino}-hexanoic acid 17 (S)-3-Cyclohexyl-2-{[2-thiophen-2-ylmethyl-1-(2-trifluoromethyl-cyclohexyl)-1H-benzoimidazole-5-carbonyl]-amino}-propionic acid 18 (S)-2-{[1-(1-Ethyl-propyl)-2-thiophen-2-ylmethyl-1H-benzoimidazole-5-carbonyl]-amino}-hexanoic acid 21 (S)-3-Cyclopropyl-2-{[1-(1-ethyl-propyl)-2-thiophen-2-ylmethyl-1H-benzoimidazole-5-carbonyl]-amino}-propionic acid 22 (S)-3-Cyclobutyl-2-{[1-(1-ethyl-propyl)-2-thiophen-2-ylmethyl-1H-benzoimidazole-5-carbonyl]-amino}-propionic acid 23 (S)-3-Cyclobutyl-2-{[1-((1R,2R)-2-methyl-cyclohexyl)-2-thiophen-2-ylmethyl-1H-benzoimidazole-5-carbonyl]-amino}-propionic acid 24 1-{[1-(1-Ethyl-propyl)-2-thiophen-2-ylmethyl-1H-benzoimidazole-5-carbonyl]-amino}-cyclohexanecarboxylic acid 25 2-{[1-(1-Ethyl-propyl)-2-thiophen-2-ylmethyl-1H-benzoimidazole-5-carbonyl]-amino}-2-methyl-pentanoic acid 26 2-{[1-(1-Ethyl-propyl)-2-thiophen-2-ylmethyl-1H-benzoimidazole-5-carbonyl]-amino}-5,5,5-trifluoro-pentanoic acid 27 5,5,5-Trifluoro-2-{[1-((1R,2R)-2-methyl-cyclohexyl)-2-thiophen-2-ylmethyl-1H-benzoimidazole-5-carbonyl]-amino}-pentanoic acid 29 3-(4,4-Dimethyl-cyclohexyl)-2-{[1-(1-ethyl-propyl)-2-thiophen-2-ylmethyl-1H-benzoimidazole-5-carbonyl]-amino}-propionic acid 33 3-(4,4-Dimethyl-cyclohexyl)-2-{[1-((1R,2R)-2-methyl-cyclohexyl)-2-thiophen-2-ylmethyl-1H-benzoimidazole-5-carbonyl]-amino}-propionic acid 34 1-{[1-(1-Ethyl-propyl)-2-thiophen-2-ylmethyl-1H-benzoimidazole-5-carbonyl]-amino}-4-methyl-cyclohexanecarboxylic acid 35 4-Methyl-1-{[1-((1R,2R)-2-methyl-cyclohexyl)-2-thiophen-2-ylmethyl-1H-benzoimidazole-5-carbonyl]-amino}-cyclohexanecarboxylic acid 36 2-{[1-(1-Ethyl-propyl)-2-thiophen-2-ylmethyl-1H-benzoimidazole-5-carbonyl]-amino}-3-(4-methyl-cyclohexyl)-propionic acid 37 (S)-3-Cyclohexyl-2-{[1-((1R,2R)-2-methyl-cyclohexyl)-2-thiazol-5-ylmethyl-1H-benzoimidazole-5-carbonyl]-amino}-propionic acid 38 1-{[1-((1R,2R)-2-Methyl-cyclohexyl)-2-thiophen-2-ylmethyl-1H-benzoimidazole-5-carbonyl]-amino}-cyclohexanecarboxylic acid 39 3-Cycloheptyl-2-{[1-(1-ethyl-propyl)-2-thiophen-2-ylmethyl-1H-benzoimidazole-5-carbonyl]-amino}-propionic acid 40 3-Cycloheptyl-2-{[1-((1R,2R)-2-methyl-cyclohexyl)-2-thiophen-2-ylmethyl-1H-benzoimidazole-5-carbonyl]-amino}-propionic acid 41 3-{[1-(1-Ethyl-propyl)-2-furan-2-ylmethyl-1H-benzoimidazole-5-carbonyl]-amino}-4-methyl-pentanoic acid 42 3-{[1-(1-Ethyl-propyl)-2-furan-2-ylmethyl-1H-benzoimidazole-5-carbonyl]-amino}-3-phenyl-propionic acid 44 3-Cyclohexyl-3-{[1-(1-ethyl-propyl)-2-thiophen-2-ylmethyl-1H-benzoimidazole-5-carbonyl]-amino}-propionic acid 45 3-{[1-(1-Ethyl-propyl)-2-thiophen-2-ylmethyl-1H-benzoimidazole-5-carbonyl]-amino}-heptanoic acid 46 4-Cyclohexyl-3-{[1-(1-ethyl-propyl)-2-thiophen-2-ylmethyl-1H-benzoimidazole-5-carbonyl]-amino}-butyric acid 47 3-{[1-(1-Ethyl-propyl)-2-thiophen-2-ylmethyl-1H-benzoimidazole-5-carbonyl]-amino}-5,5-dimethyl-hexanoic acid 48 (R)-3-{[1-(1-Ethyl-propyl)-2-thiophen-2-ylmethyl-1H-benzoimidazole-5-carbonyl]-amino}-5-methyl-hexanoic acid 50 (S)-3-{[1-(1-Ethyl-propyl)-2-thiazol-5-ylmethyl-1H-benzoimidazole-5-carbonyl]-amino}-5-methyl-hexanoic acid 51 4-Cyclohexyl-3-{[1-((1R,2R)-2-methyl-cyclohexyl)-2-thiophen-2-ylmethyl-1H-benzoimidazole-5-carbonyl]-amino}-butyric acid 52 4-Cyclohexyl-3-{[1-((1S,2S)-2-methyl-cyclohexyl)-2-thiophen-2-ylmethyl-1H-benzoimidazole-5-carbonyl]-amino}-butyric acid 53 (3R,4S)-4-Methyl-3-{[1-((1R,2R)-2-methyl-cyclohexyl)-2-thiophen-2-ylmethyl-1H-benzoimidazole-5-carbonyl]-amino}-hexanoic acid 54 (3R,4S)-3-{[1-(1-Ethyl-propyl)-2-thiophen-2-ylmethyl-1H-benzoimidazole-5-carbonyl]-amino}-4-methyl-hexanoic acid 55 3-{[1-((1R,2R)-2-Methyl-cyclohexyl)-2-thiophen-2-ylmethyl-1H-benzoimidazole-5-carbonyl]-amino}-hexanoic acid 56 3-{[1-((1R,2R)-2-Methyl-cyclohexyl)-2-thiophen-2-ylmethyl-1H-benzoimidazole-5-carbonyl]-amino}-heptanoic acid 57 3-Cyclohexyl-3-{[1-((1R,2R)-2-methyl-cyclohexyl)-2-thiophen-2-ylmethyl-1H-benzoimidazole-5-carbonyl]-amino}-propionic acid 58 3-{[1-(1-Ethyl-propyl)-2-thiophen-2-ylmethyl-1H-benzoimidazole-5-carbonyl]-amino}-2,2-dimethyl-heptanoic acid 59 4-Ethyl-3-{[1-(1-ethyl-propyl)-2-thiophen-2-ylmethyl-1H-benzoimidazole-5-carbonyl]-amino}-hexanoic acid 60 (S)-4-Cyclopentyl-3-{[1-(1-ethyl-propyl)-2-thiophen-2-ylmethyl-1H-benzoimidazole-5-carbonyl]-amino}-butyric acid 61  (S)-4-Cyclopentyl-3-{[1-((1R,2R)-2-methyl-cyclohexyl)-2-thiophen-2-ylmethyl-1H-benzoimidazole-5-carbonyl]-amino}-butyric acid
62  3-{[1-(1-Ethyl-propyl)-2-thiophen-2-ylmethyl-1H-benzoimidazole-5-carbonyl]-amino}-2,2,5-trimethyl-hexanoic acid
63  3-{[1-(1-Ethyl-propyl)-2-thiophen-2-ylmethyl-1H-benzoimidazole-5-carbonyl]-amino}-2,2-dimethyl-hexanoic acid
64  (1-{[1-(1-Ethyl-propyl)-2-thiophen-2-ylmethyl-1H-benzoimidazole-5-carbonyl]-amino}-cyclohexyl)-acetic acid
65  4-Cyclohexyl-3-{[1-((1R,2R)-2-methyl-cyclohexyl)-2-thiazol-5-ylmethyl-1H-benzoimidazole-5-carbonyl]-amino}-butyric acid
66  (1-{[1-((1R,2R)-2-Methyl-cyclohexyl)-2-thiophen-2-ylmethyl-1H-benzoimidazole-5-carbonyl]-amino}-cyclohexyl)-acetic acid
67  (2R,3S)-3-{[1-(1-Ethyl-propyl)-2-thiophen-2-ylmethyl-1H-benzoimidazole-5-carbonyl]-amino}-2-hydroxy-5-methyl-hexanoic acid
68  (2S,3S)-3-{[1-(1-Ethyl-propyl)-2-thiophen-2-ylmethyl-1H-benzoimidazole-5-carbonyl]-amino}-2-hydroxy-5-methyl-hexanoic acid
69  (R)-6-Methyl-4-{[2-thiophen-2-ylmethyl-1-(2-trifluoromethyl-cyclohexyl)-1H-benzoimidazole-5-carbonyl]-amino}-heptanoic acid
70  (R)-6-Methyl-4-{[1-((1R,2R)-2-methyl-cyclohexyl)-2-thiophen-2-ylmethyl-1H-benzoimidazole-5-carbonyl]-amino}-heptanoic acid
71  (4R,5S)-4-{[1-(1-Ethyl-propyl)-2-thiophen-2-ylmethyl-1H-benzoimidazole-5-carbonyl]-amino}-5-methyl-heptanoic acid
72  (4R,5S)-5-Methyl-4-{[1-((1R,2R)-2-methyl-cyclohexyl)-2-thiophen-2-ylmethyl-1H-benzoimidazole-5-carbonyl]-amino}-heptanoic acid
73  (3R,4S)-5-Cyclohexyl-4-{[1-(1-ethyl-propyl)-2-thiophen-2-ylmethyl-1H-benzoimidazole-5-carbonyl]-amino}-3-hydroxy-pentanoic acid
74  (3R,4S)-5-Cyclohexyl-3-hydroxy-4-{[1-((1R,2R)-2-methyl-cyclohexyl)-2-thiophen-2-ylmethyl-1H-benzoimidazole-5-carbonyl]-amino}-pentanoic acid
75  (3S,4S)-4-{[1-(1-Ethyl-propyl)-2-thiophen-2-ylmethyl-1H-benzoimidazole-5-carbonyl]-amino}-3-hydroxy-6-methyl-heptanoic acid
76  (3R,4S)-4-{[1-(1-Ethyl-propyl)-2-thiophen-2-ylmethyl-1H-benzoimidazole-5-carbonyl]-amino}-3-hydroxy-6-methyl-heptanoic acid
77  (3R,4S)-3-Hydroxy-6-methyl-4-{[1-((1R,2R)-2-methyl-cyclohexyl)-2-thiophen-2-ylmethyl-1H-benzoimidazole-5-carbonyl]-amino}-heptanoic acid
78  (3S,4S)-3-Hydroxy-6-methyl-4-{[1-((1R,2R)-2-methyl-cyclohexyl)-2-thiophen-2-ylmethyl-1H-benzoimidazole-5-carbonyl]-amino}-heptanoic acid
79  (3S,4S)-5-Cyclohexyl-4-{[1-(1-ethyl-propyl)-2-thiophen-2-ylmethyl-1H-benzoimidazole-5-carbonyl]-amino}-3-hydroxy-pentanoic acid
80  (S)-2-{[1-(1-Ethyl-propyl)-2-(tetrahydro-furan-2-ylmethyl)-1H-benzoimidazole-5-carbonyl]-amino}-4-methyl-pentanoic acid
81  (S)-2-{[1-(1-Ethyl-propyl)-2-furan-2-ylmethyl-1H-benzoimidazole-5-carbonyl]-amino}-4-methyl-pentanoic acid
84  (S)-2-{[1-(1-Ethyl-propyl)-2-thiazol-4-ylmethyl-1H-benzoimidazole-5-carbonyl]-amino}-4-methyl-pentanoic acid
85  (2S,3S)-2-{[1-(1-Ethyl-propyl)-2-thiazol-4-ylmethyl-1H-benzoimidazole-5-carbonyl]-amino}-3-methyl-pentanoic acid
86  (S)-2-{[2-Furan-2-ylmethyl-1-(2-methyl-cyclohexyl)-1H-benzoimidazole-5-carbonyl]-amino}-4-methyl-pentanoic acid
87  (S)-4-Methyl-2-{[2-thiophen-2-ylmethyl-1-(2-trifluoromethyl-cyclohexyl)-1H-benzoimidazole-5-carbonyl]-amino}-pentanoic acid
88  (S)-2-{[2-Thiophen-2-ylmethyl-1-(2-trifluoromethyl-cyclohexyl)-1H-benzoimidazole-5-carbonyl]-amino}-pentanoic acid
90  (S)-4-Methyl-2-{[1-(2-methyl-cyclopentyl)-2-thiophen-2-ylmethyl-1H-benzoimidazole-5-carbonyl]-amino}-pentanoic acid
91  (S)-2-{[1-((1R,2R)-2-Methyl-cyclohexyl)-2-thiophen-2-ylmethyl-1H-benzoimidazole-5-carbonyl]-amino}-pentanoic acid
92  (2S,3S)-3-Methyl-2-{[1-((1R,2R)-2-methyl-cyclohexyl)-2-thiophen-2-ylmethyl-1H-benzoimidazole-5-carbonyl]-amino}-pentanoic acid
93  (S)-2-{[1-(2-Ethyl-cyclohexyl)-2-thiophen-2-ylmethyl-1H-benzoimidazole-5-carbonyl]-amino}-4-methyl-pentanoic acid
94  (S)-2-{[1-(1-Ethyl-propyl)-2-thiophen-2-ylmethyl-1H-benzoimidazole-5-carbonyl]-amino}-pentanoic acid
95  (S)-3-{[1-(1-Ethyl-propyl)-2-thiophen-2-ylmethyl-1H-benzoimidazole-5-carbonyl]-amino}-5-methyl-hexanoic acid
96  (S)-3-{[1-(1-Ethyl-propyl)-2-furan-2-ylmethyl-1H-benzoimidazole-5-carbonyl]-amino}-5-methyl-hexanoic acid
98  (S)-3-{[1-(1-Ethyl-propyl)-2-thiazol-4-ylmethyl-1H-benzoimidazole-5-carbonyl]-amino}-5-methyl-hexanoic acid
99  (S)-3-{[2-Furan-2-ylmethyl-1-(2-methyl-cyclohexyl)-1H-benzoimidazole-5-carbonyl]-amino}-5-methyl-hexanoic acid
101  (S)-5-Methyl-3-{[1-(2-methyl-cyclohexyl)-2-thiophen-2-ylmethyl-1H-benzoimidazole-5-carbonyl]-amino}-hexanoic acid
102  (S)-5-Methyl-3-{[2-thiophen-2-ylmethyl-1-(2-trifluoromethyl-cyclohexyl)-1H-benzoimidazole-5-carbonyl]-amino}-hexanoic acid
103  (S)-4-Phenyl-3-{[2-thiophen-2-ylmethyl-1-(2-trifluoromethyl-cyclohexyl)-1H-benzoimidazole-5-carbonyl]-amino}-butyric acid
104  (S)-5-Methyl-3-{[1-(2-methyl-cyclopentyl)-2-thiophen-2-ylmethyl-1H-benzoimidazole-5-carbonyl]-amino}-hexanoic acid
105  (S)-3-{[1-(1-Ethyl-propyl)-2-isoxazol-5-ylmethyl-1H-benzoimidazole-5-carbonyl]-amino}-5-methyl-hexanoic acid
106  (S)-5-Methyl-3-{[1-((1R,2R)-2-methyl-cyclohexyl)-2-thiazol-5-ylmethyl-1H-benzoimidazole-5-carbonyl]-amino}-hexanoic acid
107  (S)-3-{[1-(1-Ethyl-propyl)-2-thiophen-2-ylmethyl-1H-benzoimidazole-5-carbonyl]-amino}-5-methyl-hexanoic acid
108  (S)-2-[(1-Cyclohexyl-2-thiophen-2-ylmethyl-1H-benzoimidazole-5-carbonyl)-amino]-4-methyl-pentanoic acid
109  (S)-2-{[2-Cyclopentylmethyl-1-(2-methyl-butyl)-1H-benzoimidazole-5-carbonyl]-amino}-4-methyl-pentanoic acid
110  (S)-2-[(1-Cyclopentyl-2-thiophen-2-ylmethyl-1H-benzoimidazole-5-carbonyl)-amino]-4-methyl-pentanoic acid 111 (S)-2-[(1-Cycloheptyl-2-thiophen-2-ylmethyl-1H-benzoimidazole-5-carbonyl)-amino]-4-methyl-pentanoic acid 114 (S)-2-{[1-(1-Ethyl-propyl)-2-thiophen-2-ylmethyl-1H-benzoimidazole-5-carbonyl]-amino}-4-methyl-pentanoic acid 117 (S)-2-{[1-(1-Ethyl-propyl)-2-thiophen-3-ylmethyl-1H-benzoimidazole-5-carbonyl]-amino}-4-methyl-pentanoic acid 118 (S)-2-{[1-(1-Ethyl-propyl)-2-furan-3-ylmethyl-1H-benzoimidazole-5-carbonyl]-amino}-4-methyl-pentanoic acid 121 (S)-2-{[1-(1-Ethyl-propyl)-2-thiophen-2-ylmethyl-1H-benzoimidazole-5-carbonyl]-amino}-3-methyl-pentanoic acid 122 (S)-2-{[1-(1-Ethyl-propyl)-2-thiophen-2-ylmethyl-1H-benzoimidazole-5-carbonyl]-amino}-3-methyl-butyric acid 123 (S)-2-{[1-(1-Ethyl-propyl)-2-thiophen-2-ylmethyl-1H-benzoimidazole-5-carbonyl]-amino}-4-methylsulfanyl-butyric acid 125 (S)-3-Cyclohexyl-2-{[1-(1-ethyl-propyl)-2-thiophen-2-ylmethyl-1H-benzoimidazole-5-carbonyl]-amino}-propionic acid 126 2-{[1-(1-Ethyl-propyl)-2-thiophen-2-ylmethyl-1H-benzoimidazole-5-carbonyl]-amino}-4,4-dimethyl-pentanoic acid 129 (S)-2-{[2-Cyclopentylmethyl-1-(1-ethyl-propyl)-1H-benzoimidazole-5-carbonyl]-amino}-4-methyl-pentanoic acid 130 (S)-2-{[1-(1-Ethyl-propyl)-2-thiophen-2-ylmethyl-1H-benzoimidazole-5-carbonyl]-amino}-5-methyl-hexanoic acid 131 (S)-2-{[2-Furan-3-ylmethyl-1-(2-methyl-cyclohexyl)-1H-benzoimidazole-5-carbonyl]-amino}-4-methyl-pentanoic acid 139 (S)-4-Methyl-2-{[1-(2-methyl-cyclohexyl)-2-thiophen-3-ylmethyl-1H-benzoimidazole-5-carbonyl]-amino}-pentanoic acid 146 (S)-4-Methyl-2-{[1-(2-methyl-cyclohexyl)-2-thiophen-2-ylmethyl-1H-benzoimidazole-5-carbonyl]-amino}-pentanoic acid 150 (S)-2-{[2-Cyclopentylmethyl-1-(2-methyl-cyclohexyl)-1H-benzoimidazole-5-carbonyl]-amino}-4-methyl-pentanoic acid 151 (S)-3-Cyclohexyl-2-{[1-(1-ethyl-propyl)-2-(tetrahydro-furan-2-ylmethyl)-1H-benzoimidazole-5-carbonyl]-amino}-propionic acid 153 (2S,3R)-2-{[1-(1-Ethyl-propyl)-2-thiophen-2-ylmethyl-1H-benzoimidazole-5-carbonyl]-amino}-3-methyl-pentanoic acid 154 (S)-3-{[1-(1-Ethyl-propyl)-2-furan-3-ylmethyl-1H-benzoimidazole-5-carbonyl]-amino}-5-methyl-hexanoic acid 155 3-{[1-(1-Ethyl-propyl)-2-thiophen-2-ylmethyl-1H-benzoimidazole-5-carbonyl]-amino}-hexanoic acid 156 (S)-3-{[1-(1-Ethyl-propyl)-2-thiophen-3-ylmethyl-1H-benzoimidazole-5-carbonyl]-amino}-5-methyl-hexanoic acid 158 (S)-3-{[2-Cyclopentylmethyl-1-(1-ethyl-propyl)-1H-benzoimidazole-5-carbonyl]-amino}-5-methyl-hexanoic acid 160 (S)-3-{[1-(1-Ethyl-propyl)-2-(tetrahydro-furan-2-ylmethyl)-1H-benzoimidazole-5-carbonyl]-amino}-5-methyl-hexanoic acid 161 (R)-3-{[1-(1-Ethyl-propyl)-2-thiophen-2-ylmethyl-1H-benzoimidazole-5-carbonyl]-amino}-4-methyl-pentanoic acid 162 (R)-4-{[1-(1-Ethyl-propyl)-2-thiophen-2-ylmethyl-1H-benzoimidazole-5-carbonyl]-amino}-5-methyl-hexanoic acid 163 (R)-4-{[1-(1-Ethyl-propyl)-2-thiophen-2-ylmethyl-1H-benzoimidazole-5-carbonyl]-amino}-6-methyl-heptanoic acid 399 1-(1-Ethyl-propyl)-2-thiophen-2-ylmethyl-1H-benzoimidazole-5-carboxylic acid {(S)-3-methyl-1-[(1H-tetrazol-5-ylmethyl)-carbamoyl]-butyl}-amide 400 1-(1-Ethyl-propyl)-2-thiophen-2-ylmethyl-1H-benzoimidazole-5-carboxylic acid {(S)-3-methyl-1-[2-(1H-tetrazol-5-yl)-ethylcarbamoyl]-butyl}-amide 401 1-(1-Ethyl-propyl)-2-thiophen-2-ylmethyl-1H-benzoimidazole-5-carboxylic acid [(S)-3-methyl-1-(2-sulfamoyl-ethylcarbamoyl)-butyl]-amide 402 1-(1-Ethyl-propyl)-2-thiophen-2-ylmethyl-1H-benzoimidazole-5-carboxylic acid [(S)-1-(2-methanesulfonylamino-ethylcarbamoyl)-3-methyl-butyl]-amide 403 1-(1-Ethyl-propyl)-2-thiophen-2-ylmethyl-1'-1-benzoimidazole-5-carboxylic acid [(S)-1-(cyanomethyl-carbamoyl)-3-methyl-butyl]-amide 404 1-(1-Ethyl-propyl)-2-thiophen-2-ylmethyl-1H-benzoimidazole-5-carboxylic acid [(S)-1-(2-cyano-ethylcarbamoyl)-3-methyl-butyl]-amide 405 1-(1-Ethyl-propyl)-2-thiophen-2-ylmethyl-1H-benzoimidazole-5-carboxylic acid 404 {(S)-3-methyl-1-[methyl-(5-oxo-4,5-dihydro-1H-[1,2,4]triazol-3-ylmethyl)-carbamoyl]-butyl}-amide 406 1-(1-Ethyl-propyl)-2-thiophen-2-ylmethyl-1H-benzoimidazole-5-carboxylic acid {(S)-3-methyl-1-[2-(5-oxo-4,5-dihydro-1H-[1,2,4]-triazol-3-yl)-ethylcarbamoyl]-butyl}-amide 408 ((S)-2-{[1-(1-Ethyl-propyl)-2-thiophen-2-ylmethyl-1H-benzoimidazole-5-carbonyl]-amino}-4-methyl-pentanoylamino)-acetic acid 409 (S)-1-(S)-2-{[1-(1-Ethyl-propyl)-2-thiophen-2-ylmethyl-1H-benzoimidazole-5-carbonyl]-amino}-4-methyl-pentanoyl)-pyrrolidine-2-carboxylic acid 410 (R)-1-((S)-2-{[1-(1-Ethyl-propyl)-2-thiophen-2-ylmethyl-1H-benzoimidazole-5-carbonyl]-amino}-4-methyl-pentanoyl)-pyrrolidine-2-carboxylic acid 411 1-((S)-2-{[1-(1-Ethyl-propyl)-2-thiophen-2-ylmethyl-1H-benzoimidazole-5-carbonyl]-amino}-4-methyl-pentanoyl)-azetidine-3-carboxylic acid 412 (S)-4-Methyl-2-{[1-((1R,2R)-2-methyl-cyclohexyl)-2-thiophen-2-ylmethyl-1H-benzoimidazole-5-carbonyl]-amino}-pentanoic acid 413 (S)-4-Methyl-2-{[1-((1S,2S)-2-methyl-cyclohexyl)-2-thiophen-2-ylmethyl-1H-benzoimidazole-5-carbonyl]-amino}-pentanoic acid 414 (S)-4-Methyl-2-{[1-((1R,2S)-2-methyl-cyclohexyl)-2-thiophen-2-ylmethyl-1H-benzoimidazole-5-carbonyl]-amino}-pentanoic acid 415 (S)-4-Methyl-2-{[1-((1S,2R)-2-methyl-cyclohexyl)-2-thiophen-2-ylmethyl-1H-benzoimidazole-5-carbonyl]-amino}-pentanoic acid 416 (S)-2-{[2-Furan-2-ylmethyl-1-(2-methyl-cyclohexyl)-1H-benzoimidazole-5-carbonyl]-amino}-4-methyl-pentanoic acid 417 (S)-2-{[2-Furan-2-ylmethyl-1-(2-methyl-cyclohexyl)-1H-benzoimidazole-5-carbonyl]-amino}-4-methyl-pentanoic acid 418 (S)-2-{[2-Furan-2-ylmethyl-1-(2-methyl-cyclohexyl)-1H-benzoimidazole-5-carbonyl]-amino}-4-methyl-pentanoic acid 419 (S)-2-{[2-Furan-2-ylmethyl-1-(2-methyl-cyclohexyl)-1H-benzoimidazole-5-carbonyl]-amino}-4-methyl-pentanoic acid
420 (S)-2-{[1-(2-Methyl-cyclohexyl)-2-thiophen-2-ylmethyl-1H-benzoimidazole-5-carbonyl]-amino}-hexanoic acid
421 (S)-2-{[1-(2-Methyl-cyclohexyl)-2-thiophen-2-ylmethyl-1H-benzoimidazole-5-carbonyl]-amino}-hexanoic acid
422 (S)-2-{[1-(2-Methyl-cyclohexyl)-2-thiophen-2-ylmethyl-1H-benzoimidazole-5-carbonyl]-amino}-hexanoic acid
423 (S)-2-{[1-(2-Methyl-cyclohexyl)-2-thiophen-2-ylmethyl-1H-benzoimidazole-5-carbonyl]-amino}-hexanoic acid
424 (S)-3-Cyclohexyl-2-{[1-(2-methyl-cyclohexyl)-2-thiophen-2-ylmethyl-1H-benzoimidazole-5-carbonyl]-amino}-propionic acid
425 (S)-3-Cyclohexyl-2-{[1-(2-methyl-cyclohexyl)-2-thiophen-2-ylmethyl-1H-benzoimidazole-5-carbonyl]-amino}-propionic acid
426 (S)-3-Cyclohexyl-2-{[1-(2-methyl-cyclohexyl)-2-thiophen-2-ylmethyl-1H-benzoimidazole-5-carbonyl]-amino}-propionic acid
427 (S)-3-Cyclohexyl-2-{[1-(2-methyl-cyclohexyl)-2-thiophen-2-ylmethyl-1H-benzoimidazole-5-carbonyl]-amino}-propionic acid
428 (S)-4-Methyl-2-{[1-(2-methyl-cyclopentyl)-2-thiophen-2-ylmethyl-1H-benzoimidazole-5-carbonyl]-amino}-pentanoic acid
429 (S)-4-Methyl-2-{[1-(2-methyl-cyclopentyl)-2-thiophen-2-ylmethyl-1H-benzoimidazole-5-carbonyl]-amino}-pentanoic acid
430 (S)-4-Methyl-2-{[1-(2-methyl-cyclopentyl)-2-thiophen-2-ylmethyl-1H-benzoimidazole-5-carbonyl]-amino}-pentanoic acid
431 (S)-4-Methyl-2-{[1-(2-methyl-cyclopentyl)-2-thiophen-2-ylmethyl-1H-benzoimidazole-5-carbonyl]-amino}-pentanoic acid
432 (S)-3-{[2-Furan-2-ylmethyl-1-(2-methyl-cyclohexyl)-1H-benzoimidazole-5-carbonyl]-amino}-5-methyl-hexanoic acid
433 (S)-3-{[2-Furan-2-ylmethyl-1-(2-methyl-cyclohexyl)-1H-benzoimidazole-5-carbonyl]-amino}-5-methyl-hexanoic acid
434 (S)-3-{[2-Furan-2-ylmethyl-1-(2-methyl-cyclohexyl)-1H-benzoimidazole-5-carbonyl]-amino}-5-methyl-hexanoic acid
435 (S)-3-{[2-Furan-2-ylmethyl-1-(2-methyl-cyclohexyl)-1H-benzoimidazole-5-carbonyl]-amino}-5-methyl-hexanoic acid
436 (S)-5-Methyl-3-{[1-(2-methyl-cyclohexyl)-2-thiophen-2-ylmethyl-1H-benzoimidazole-5-carbonyl]-amino}-hexanoic acid
437 (S)-5-Methyl-3-{[1-(2-methyl-cyclohexyl)-2-thiophen-2-ylmethyl-1H-benzoimidazole-5-carbonyl]-amino}-hexanoic acid
438 (S)-5-Methyl-3-{[1-(2-methyl-cyclohexyl)-2-thiophen-2-ylmethyl-1H-benzoimidazole-5-carbonyl]-amino}-hexanoic acid
439 (S)-5-Methyl-3-{[1-(2-methyl-cyclohexyl)-2-thiophen-2-ylmethyl-1H-benzoimidazole-5-carbonyl]-amino}-hexanoic acid
440 (R)-2-{[1-(1-Ethyl-propyl)-2-thiophen-2-ylmethyl-1H-benzoimidazole-5-carbonyl]-amino}-2,4-dimethyl-pentanoic acid
441 (S)-2-{[1-(1-Ethyl-propyl)-2-thiophen-2-ylmethyl-1H-benzoimidazole-5-carbonyl]-amino}-2,4-dimethyl-pentanoic acid
442 3-Cyclopentyl-2-{[1-((1R,2R)-2-methyl-cyclohexyl)-2-thiophen-2-ylmethyl-1H-benzoimidazole-5-carbonyl]-amino}-propionic acid
443 3-Cyclopentyl-2-{[1-((1R,2R)-2-methyl-cyclohexyl)-2-thiophen-2-ylmethyl-1H-benzoimidazole-5-carbonyl]-amino}-propionic acid
448 (S)-3-Cycloheptyl-2-{[1-(1-ethyl-propyl)-2-thiophen-2-ylmethyl-1H-benzoimidazole-5-carbonyl]-amino}-propionic acid
449 (R)-3-Cycloheptyl-2-{[1-(1-ethyl-propyl)-2-thiophen-2-ylmethyl-1H-benzoimidazole-5-carbonyl]-amino}-propionic acid
450 3-Cycloheptyl-2-{[1-((1R,2R)-2-methyl-cyclohexyl)-2-thiophen-2-ylmethyl-1H-benzoimidazole-5-carbonyl]-amino}-propionic acid
451 3-Cycloheptyl-2-{[1-((1R,2R)-2-methyl-cyclohexyl)-2-thiophen-2-ylmethyl-1H-benzoimidazole-5-carbonyl]-amino}-propionic acid
452 (S)-3-{[1-(1-Ethyl-propyl)-2-thiophen-2-ylmethyl-1H-benzoimidazole-5-carbonyl]-amino}-heptanoic acid
453 (R)-3-{[1-(1-Ethyl-propyl)-2-thiophen-2-ylmethyl-1H-benzoimidazole-5-carbonyl]-amino}-heptanoic acid
454 (S)-4-Cyclohexyl-3-{[1-(1-ethyl-propyl)-2-thiophen-2-ylmethyl-1H-benzoimidazole-5-carbonyl]-amino}-butyric acid
455 (R)-4-Cyclohexyl-3-{[1-(1-ethyl-propyl)-2-thiophen-2-ylmethyl-1H-benzoimidazole-5-carbonyl]-amino}-butyric acid
456 4-Cyclohexyl-3-{[1-((1R,2R)-2-methyl-cyclohexyl)-2-thiophen-2-ylmethyl-1H-benzoimidazole-5-carbonyl]-amino}-butyric acid
457 4-Cyclohexyl-3-{[1-((1R,2R)-2-methyl-cyclohexyl)-2-thiophen-2-ylmethyl-1H-benzoimidazole-5-carbonyl]-amino}-butyric acid
458 3-{[1-((1R,2R)-2-Methyl-cyclohexyl)-2-thiophen-2-ylmethyl-1H-benzoimidazole-5-carbonyl]-amino}-hexanoic acid
459 3-{[1-((1R,2R)-2-Methyl-cyclohexyl)-2-thiophen-2-ylmethyl-1H-benzoimidazole-5-carbonyl]-amino}-hexanoic acid
460 3-{[1-((1R,2R)-2-Methyl-cyclohexyl)-2-thiophen-2-ylmethyl-1H-benzoimidazole-5-carbonyl]-amino}-heptanoic acid
461 3-{[1-((1R,2R)-2-Methyl-cyclohexyl)-2-thiophen-2-ylmethyl-1H-benzoimidazole-5-carbonyl]-amino}-heptanoic acid
462 3-Cyclohexyl-3-{[1-((1R,2R)-2-methyl-cyclohexyl)-2-thiophen-2-ylmethyl-1H-benzoimidazole-5-carbonyl]-amino}-propionic acid
463 3-Cyclohexyl-3-{[1-((1R,2R)-2-methyl-cyclohexyl)-2-thiophen-2-ylmethyl-1H-benzoimidazole-5-carbonyl]-amino}-propionic acid
464 (R)-3-{[1-(1-Ethyl-propyl)-2-thiophen-2-ylmethyl-1H-benzoimidazole-5-carbonyl]-amino}-2,2,5-trimethyl-hexanoic acid
465 (S)-3-{[1-(1-Ethyl-propyl)-2-thiophen-2-ylmethyl-1H-benzoimidazole-5-carbonyl]-amino}-2,2,5-trimethyl-hexanoic acid
466 (R)-3-{[1-(1-Ethyl-propyl)-2-thiophen-2-ylmethyl-1H-benzoimidazole-5-carbonyl]-amino}-2,2-dimethyl-hexanoic acid
467 (S)-3-{[1-(1-Ethyl-propyl)-2-thiophen-2-ylmethyl-1H-benzoimidazole-5-carbonyl]-amino}-2,2-dimethyl-hexanoic acid 468 (S)-3-{[1-(1-Ethyl-propyl)-2-thiophen-2-ylmethyl-1H-benzoimidazole-5-carbonyl]-amino}-2,2-di methyl-heptanoic acid 469 (R)-3-{[1-(1-Ethyl-propyl)-2-thiophen-2-ylmethyl-1H-benzoimidazole-5-carbonyl]-amino}-2,2-dimethyl-heptanoic acid 472 1-(1-Ethyl-propyl)-2-thiophen-2-ylmethyl-1H-benzoimidazole-5-carboxylic acid [(S)-3-methyl-1-(1H-tetrazol-5-ylmethyl)-butyl]-amide 473 1-(1-Ethyl-propyl)-2-thiophen-2-ylmethyl-1H-benzoimidazole-5-carboxylic acid [(S)-1-(N-hydroxycarbamimidoylmethyl)-3-methyl-butyl]-amide 483 1-(1-Ethyl-propyl)-2-thiophen-2-ylmethyl-1H-benzoimidazole-5-carboxylic acid [(S)-3-methyl-1-(4H-[1,2,4]triazol-3-ylsulfanylmethyl)-butyl]-amide 484 1-(1-Ethyl-propyl)-2-thiophen-2-ylmethyl-1H-benzoimidazole-5-carboxylic acid [(S)-3-methyl-1-(4H-[1,2,4]triazole-3-sulfonylmethyl)-butyl]-amide 485 1-(1-Ethyl-propyl)-2-thiophen-2-ylmethyl-1H-benzoimidazole-5-carboxylic acid ((S)-3-methyl-1-methylsulfamoylmethyl-butyl)-amide.

The number denotes the example number of the respective compound.

In another embodiment compounds of the formula I are encompassed selected from the group consisting of 1 1-{[1-(1-Ethyl-propyl)-2-thiophen-2-ylmethyl-1H-benzoimidazole-5-carbonyl]-amino}-cycloheptanecarboxylic acid 3 (S)-3-Cyclohexyl-2-{[2-cyclopentylmethyl-1-(1-ethyl-propyl)-1H-benzoimidazole-5-carbonyl]-amino}-propionic acid 6 1-{[1-(1-Ethyl-propyl)-2-thiophen-2-ylmethyl-1H-benzoimidazole-5-carbonyl]-amino}-cyclopentanecarboxylic acid 8 (S)-3-Cyclohexyl-2-{[1-(1-ethyl-propyl)-2-furan-2-ylmethyl-1H-benzoimidazole-5-carbonyl]-amino}-propionic acid 9 (R)-3-Cyclohexyl-2-{[1-(1-ethyl-propyl)-2-furan-2-ylmethyl-1H-benzoimidazole-5-carbonyl]-amino}-propionic acid 10 (R)-3-Cyclohexyl-2-{[2-cyclopentylmethyl-1-(1-ethyl-propyl)-1H-benzoimidazole-5-carbonyl]-amino}-propionic acid 11 3-Cyclopentyl-2-{[1-(1-ethyl-propyl)-2-thiophen-2-ylmethyl-1H-benzoimidazole-5-carbonyl]-amino}-propionic acid 12 2-{[1-(1-Ethyl-propyl)-2-thiophen-2-ylmethyl-1H-benzoimidazole-5-carbonyl]-amino}-2,4-dimethyl-pentanoic acid 13 2-{[1-(1-Ethyl-propyl)-2-furan-2-ylmethyl-1H-benzoimidazole-5-carbonyl]-amino}-2,4-dimethyl-pentanoic acid 14 2-{[1-(1-Ethyl-propyl)-2-furan-2-ylmethyl-1H-benzoimidazole-5-carbonyl]-amino}-2-methyl-4-methylsulfanyl-butyric acid 15 (S)-3-Cyclohexyl-2-{[1-(2-methyl-cyclohexyl)-2-thiophen-2-ylmethyl-1H-benzoimidazole-5-carbonyl]-amino}-propionic acid 16 (S)-2-{[1-(2-Methyl-cyclohexyl)-2-thiophen-2-ylmethyl-1H-benzoimidazole-5-carbonyl]-amino}-hexanoic acid 17 (S)-3-Cyclohexyl-2-{[2-thiophen-2-ylmethyl-1-(2-trifluoromethyl-cyclohexyl)-1H-benzoimidazole-5-carbonyl]-amino}-propionic acid 18 (S)-2-{[1-(1-Ethyl-propyl)-2-thiophen-2-ylmethyl-1H-benzoimidazole-5-carbonyl]-amino}-hexanoic acid 21 (S)-3-Cyclopropyl-2-{[1-(1-ethyl-propyl)-2-thiophen-2-ylmethyl-1H-benzoimidazole-5-carbonyl]-amino}-propionic acid 22 (S)-3-Cyclobutyl-2-{[1-(1-ethyl-propyl)-2-thiophen-2-ylmethyl-1H-benzoimidazole-5-carbonyl]-amino}-propionic acid 23 (S)-3-Cyclobutyl-2-{[1-((1R,2R)-2-methyl-cyclohexyl)-2-thiophen-2-ylmethyl-1H-benzoimidazole-5-carbonyl]-amino}-propionic acid 24 1-{[1-(1-Ethyl-propyl)-2-thiophen-2-ylmethyl-1H-benzoimidazole-5-carbonyl]-amino}-cyclohexanecarboxylic acid 25 2-{[1-(1-Ethyl-propyl)-2-thiophen-2-ylmethyl-1H-benzoimidazole-5-carbonyl]-amino}-2-methyl-pentanoic acid 26 2-{[1-(1-Ethyl-propyl)-2-thiophen-2-ylmethyl-1H-benzoimidazole-5-carbonyl]-amino}-5,5,5-trifluoro-pentanoic acid 27 5,5,5-Trifluoro-2-{[1-((1R,2R)-2-methyl-cyclohexyl)-2-thiophen-2-ylmethyl-1H-benzoimidazole-5-carbonyl]-amino}-pentanoic acid 29 3-(4,4-Dimethyl-cyclohexyl)-2-{[1-(1-ethyl-propyl)-2-thiophen-2-ylmethyl-1H-benzoimidazole-5-carbonyl]-amino}-propionic acid 33 3-(4,4-Dimethyl-cyclohexyl)-2-{[1-((1R,2R)-2-methyl-cyclohexyl)-2-thiophen-2-ylmethyl-1H-benzoimidazole-5-carbonyl]-amino}-propionic acid 34 1-{[1-(1-Ethyl-propyl)-2-thiophen-2-ylmethyl-1H-benzoimidazole-5-carbonyl]-amino}-4-methyl-cyclohexanecarboxylic acid 35 4-Methyl-1-{[1-((1R,2R)-2-methyl-cyclohexyl)-2-thiophen-2-ylmethyl-1H-benzoimidazole-5-carbonyl]-amino}-cyclohexanecarboxylic acid 36 2-{[1-(1-Ethyl-propyl)-2-thiophen-2-ylmethyl-1H-benzoimidazole-5-carbonyl]-amino}-3-(4-methyl-cyclohexyl)-propionic acid 37 (S)-3-Cyclohexyl-2-{[1-((1R,2R)-2-methyl-cyclohexyl)-2-thiazol-5-ylmethyl-1H-benzoimidazole-5-carbonyl]-amino}-propionic acid 38 1-{[1-((1R,2R)-2-Methyl-cyclohexyl)-2-thiophen-2-ylmethyl-1H-benzoimidazole-5-carbonyl]-amino}-cyclohexanecarboxylic acid 39 3-Cycloheptyl-2-{[1-(1-ethyl-propyl)-2-thiophen-2-ylmethyl-1H-benzoimidazole-5-carbonyl]-amino}-propionic acid 40 3-Cycloheptyl-2-{[1-((1R,2R)-2-methyl-cyclohexyl)-2-thiophen-2-ylmethyl-1H-benzoimidazole-5-carbonyl]-amino}-propionic acid 41 3-{[1-(1-Ethyl-propyl)-2-furan-2-ylmethyl-1H-benzoimidazole-5-carbonyl]-amino}-4-methyl-pentanoic acid 42 3-{[1-(1-Ethyl-propyl)-2-furan-2-ylmethyl-1H-benzoimidazole-5-carbonyl]-amino}-3-phenyl-propionic acid 44 3-Cyclohexyl-3-{[1-(1-ethyl-propyl)-2-thiophen-2-ylmethyl-1H-benzoimidazole-5-carbonyl]-amino}-propionic acid 45 3-{[1-(1-Ethyl-propyl)-2-thiophen-2-ylmethyl-1H-benzoimidazole-5-carbonyl]-amino}-heptanoic acid 46 4-Cyclohexyl-3-{[1-(1-ethyl-propyl)-2-thiophen-2-ylmethyl-1H-benzoimidazole-5-carbonyl]-amino}-butyric acid 47 3-{[1-(1-Ethyl-propyl)-2-thiophen-2-ylmethyl-1H-benzoimidazole-5-carbonyl]-amino}-5,5-dimethyl-hexanoic acid 48  (R)-3-{[1-(1-Ethyl-propyl)-2-thiophen-2-ylmethyl-1H-benzoimidazole-5-carbonyl]-amino}-5-methyl-hexanoic acid
50  (S)-3-{[1-(1-Ethyl-propyl)-2-thiazol-5-ylmethyl-1'-1-benzoimidazole-5-carbonyl]-amino}-5-methyl-hexanoic acid
51  4-Cyclohexyl-3-{[1-((1R,2R)-2-methyl-cyclohexyl)-2-thiophen-2-ylmethyl-1H-benzoimidazole-5-carbonyl]-amino}-butyric acid
52  4-Cyclohexyl-3-{[1-((1S,2S)-2-methyl-cyclohexyl)-2-thiophen-2-ylmethyl-1H-benzoimidazole-5-carbonyl]-amino}-butyric acid
53  (3R,4S)-4-Methyl-3-{[1-((1R,2R)-2-methyl-cyclohexyl)-2-thiophen-2-ylmethyl-1H-benzoimidazole-5-carbonyl]-amino}-hexanoic acid
54  (3R,4S)-3-{[1-(1-Ethyl-propyl)-2-thiophen-2-ylmethyl-1H-benzoimidazole-5-carbonyl]-amino}-4-methyl-hexanoic acid
55  3-{[1-((1R,2R)-2-Methyl-cyclohexyl)-2-thiophen-2-ylmethyl-1H-benzoimidazole-5-carbonyl]-amino}-hexanoic acid
56  3-{[1-((1R,2R)-2-Methyl-cyclohexyl)-2-thiophen-2-ylmethyl-1H-benzoimidazole-5-carbonyl]-amino}-heptanoic acid
57  3-Cyclohexyl-3-{[1-((1R,2R)-2-methyl-cyclohexyl)-2-thiophen-2-ylmethyl-1H-benzoimidazole-5-carbonyl]-amino}-propionic acid
58  3-{[1-(1-Ethyl-propyl)-2-thiophen-2-ylmethyl-1H-benzoimidazole-5-carbonyl]-amino}-2,2-dimethyl-heptanoic acid
59  4-Ethyl-3-{[1-(1-ethyl-propyl)-2-thiophen-2-ylmethyl-1H-benzoimidazole-5-carbonyl]-amino}-hexanoic acid
60  (S)-4-Cyclopentyl-3-{[1-(1-ethyl-propyl)-2-thiophen-2-ylmethyl-1H-benzoimidazole-5-carbonyl]-amino}-butyric acid
61  (S)-4-Cyclopentyl-3-{[1-((1R,2R)-2-methyl-cyclohexyl)-2-thiophen-2-ylmethyl-1H-benzoimidazole-5-carbonyl]-amino}-butyric acid
62  3-{[1-(1-Ethyl-propyl)-2-thiophen-2-ylmethyl-1H-benzoimidazole-5-carbonyl]-amino}-2,2,5-trimethyl-hexanoic acid
63  3-{[1-(1-Ethyl-propyl)-2-thiophen-2-ylmethyl-1H-benzoimidazole-5-carbonyl]-amino}-2,2-dimethyl-hexanoic acid
64  (1-{[1-(1-Ethyl-propyl)-2-thiophen-2-ylmethyl-1H-benzoimidazole-5-carbonyl]-amino}-cyclohexyl)-acetic acid
65  4-Cyclohexyl-3-{[1-((1R,2R)-2-methyl-cyclohexyl)-2-thiazol-5-ylmethyl-1H-benzoimidazole-5-carbonyl]-amino}-butyric acid
66  (1-{[1-((1R,2R)-2-Methyl-cyclohexyl)-2-thiophen-2-ylmethyl-1H-benzoimidazole-5-carbonyl]-amino}-cyclohexyl)-acetic acid
67  (2R,3S)-3-{[1-(1-Ethyl-propyl)-2-thiophen-2-ylmethyl-1H-benzoimidazole-5-carbonyl]-amino}-2-hydroxy-5-methyl-hexanoic acid
68  (2S,3S)-3-{[1-(1-Ethyl-propyl)-2-thiophen-2-ylmethyl-1H-benzoimidazole-5-carbonyl]-amino}-2-hydroxy-5-methyl-hexanoic acid
69  (R)-6-Methyl-4-{[2-thiophen-2-ylmethyl-1-(2-trifluoromethyl-cyclohexyl)-1H-benzoimidazole-5-carbonyl]-amino}-heptanoic acid
70  (R)-6-Methyl-4-{[1-((1R,2R)-2-methyl-cyclohexyl)-2-thiophen-2-ylmethyl-1H-benzoimidazole-5-carbonyl]-amino}-heptanoic acid
71  (4R,5S)-4-{[1-(1-Ethyl-propyl)-2-thiophen-2-ylmethyl-1H-benzoimidazole-5-carbonyl]-amino}-5-methyl-heptanoic acid
72  (4R,5S)-5-Methyl-4-{[1-((1R,2R)-2-methyl-cyclohexyl)-2-thiophen-2-ylmethyl-1H-benzoimidazole-5-carbonyl]-amino}-heptanoic acid
73  (3R,4S)-5-Cyclohexyl-4-{[1-(1-ethyl-propyl)-2-thiophen-2-ylmethyl-1H-benzoimidazole-5-carbonyl]-amino}-3-hydroxy-pentanoic acid
74  (3R,4S)-5-Cyclohexyl-3-hydroxy-4-{[1-((1R,2R)-2-methyl-cyclohexyl)-2-thiophen-2-ylmethyl-1H-benzoimidazole-5-carbonyl]-amino}-pentanoic acid
75  (3S,4S)-4-{[1-(1-Ethyl-propyl)-2-thiophen-2-ylmethyl-1H-benzoimidazole-5-carbonyl]-amino}-3-hydroxy-6-methyl-heptanoic acid
76  (3R,4S)-4-{[1-(1-Ethyl-propyl)-2-thiophen-2-ylmethyl-1H-benzoimidazole-5-carbonyl]-amino}-3-hydroxy-6-methyl-heptanoic acid
77  (3R,4S)-3-Hydroxy-6-methyl-4-{[1-((1R,2R)-2-methyl-cyclohexyl)-2-thiophen-2-ylmethyl-1H-benzoimidazole-5-carbonyl]-amino}-heptanoic acid
78  (3S,4S)-3-Hydroxy-6-methyl-4-{[1-((1R,2R)-2-methyl-cyclohexyl)-2-thiophen-2-ylmethyl-1H-benzoimidazole-5-carbonyl]-amino}-heptanoic acid
79  (3S,4S)-5-Cyclohexyl-4-{[1-(1-ethyl-propyl)-2-thiophen-2-ylmethyl-1H-benzoimidazole-5-carbonyl]-amino}-3-hydroxy-pentanoic acid
80  (S)-2-{[1-(1-Ethyl-propyl)-2-(tetrahydro-furan-2-ylmethyl)-1H-benzoimidazole-5-carbonyl]-amino}-4-methyl-pentanoic acid
81  (S)-2-{[1-(1-Ethyl-propyl)-2-furan-2-ylmethyl-1H-benzoimidazole-5-carbonyl]-amino}-4-methyl-pentanoic acid
84  (S)-2-{[1-(1-Ethyl-propyl)-2-thiazol-4-ylmethyl-1H-benzoimidazole-5-carbonyl]-amino}-4-methyl-pentanoic acid
85  (2S,3S)-2-{[1-(1-Ethyl-propyl)-2-thiazol-4-ylmethyl-1H-benzoimidazole-5-carbonyl]-amino}-3-methyl-pentanoic acid
86  (S)-2-{[2-Furan-2-ylmethyl-1-(2-methyl-cyclohexyl)-1H-benzoimidazole-5-carbonyl]-amino}-4-methyl-pentanoic acid
87  (S)-4-Methyl-2-{[2-thiophen-2-ylmethyl-1-(2-trifluoromethyl-cyclohexyl)-1H-benzoimidazole-5-carbonyl]-amino}-pentanoic acid
88  (S)-2-{[2-Thiophen-2-ylmethyl-1-(2-trifluoromethyl-cyclohexyl)-1H-benzoimidazole-5-carbonyl]-amino}-pentanoic acid
90  (S)-4-Methyl-2-{[1-(2-methyl-cyclopentyl)-2-thiophen-2-ylmethyl-1H-benzoimidazole-5-carbonyl]-amino}-pentanoic acid
    (S)-2-{[1-((1R,2R)-2-Methyl-cyclohexyl)-2-thiophen-2-ylmethyl-1H-benzoimidazole-5-carbonyl]-amino}-pentanoic acid
92  (2S,3S)-3-Methyl-2-{[1-((1R,2R)-2-methyl-cyclohexyl)-2-thiophen-2-ylmethyl-1H-benzoimidazole-5-carbonyl]-amino}-pentanoic acid
93  (S)-2-{[1-(2-Ethyl-cyclohexyl)-2-thiophen-2-ylmethyl-1H-benzoimidazole-5-carbonyl]-amino}-4-methyl-pentanoic acid
94  (S)-2-{[1-(1-Ethyl-propyl)-2-thiophen-2-ylmethyl-1H-benzoimidazole-5-carbonyl]-amino}-pentanoic acid
95  (S)-3-{[1-(1-Ethyl-propyl)-2-thiophen-2-ylmethyl-1H-benzoimidazole-5-carbonyl]-amino}-5-methyl-hexanoic acid
96  (S)-3-{[1-(1-Ethyl-propyl)-2-furan-2-ylmethyl-1H-benzoimidazole-5-carbonyl]-amino}-5-methyl-hexanoic acid
98  (S)-3-{[1-(1-Ethyl-propyl)-2-thiazol-4-ylmethyl-1H-benzoimidazole-5-carbonyl]-amino}-5-methyl-hexanoic acid 99  (S)-3-{[2-Furan-2-ylmethyl-1-(2-methyl-cyclohexyl)-1H-benzoimidazole-5-carbonyl]-amino}-5-methyl-hexanoic acid
101  (S)-5-Methyl-3-{[1-(2-methyl-cyclohexyl)-2-thiophen-2-ylmethyl-1H-benzoimidazole-5-carbonyl]-amino}-hexanoic acid
102  (S)-5-Methyl-3-{[2-thiophen-2-ylmethyl-1-(2-trifluoromethyl-cyclohexyl)-1H-benzoimidazole-5-carbonyl]-amino}-hexanoic acid
104  (S)-5-Methyl-3-{[1-(2-methyl-cyclopentyl)-2-thiophen-2-ylmethyl-1H-benzoimidazole-5-carbonyl]-amino}-hexanoic acid
106  (S)-5-Methyl-3-{[1-((1R,2R)-2-methyl-cyclohexyl)-2-thiazol-5-ylmethyl-1H-benzoimidazole-5-carbonyl]-amino}-hexanoic acid
107  (S)-3-{[1-(1-Ethyl-propyl)-2-thiophen-2-ylmethyl-1H-benzoimidazole-5-carbonyl]-amino}-5-methyl-hexanoic acid
108  (S)-2-[(1-Cyclohexyl-2-thiophen-2-ylmethyl-1H-benzoimidazole-5-carbonyl)-amino]-4-methyl-pentanoic acid
109  (S)-2-{[2-Cyclopentylmethyl-1-(2-methyl-butyl)-1H-benzoimidazole-5-carbonyl]-amino}-4-methyl-pentanoic acid
110  (S)-2-[(1-Cyclopentyl-2-thiophen-2-ylmethyl-1H-benzoimidazole-5-carbonyl)-amino]-4-methyl-pentanoic acid
111  (S)-2-[(1-Cycloheptyl-2-thiophen-2-ylmethyl-1H-benzoimidazole-5-carbonyl)-amino]-4-methyl-pentanoic acid
114  (S)-2-{[1-(1-Ethyl-propyl)-2-thiophen-2-ylmethyl-1H-benzoimidazole-5-carbonyl]-amino}-4-methyl-pentanoic acid
117  (S)-2-{[1-(1-Ethyl-propyl)-2-thiophen-3-ylmethyl-1H-benzoimidazole-5-carbonyl]-amino}-4-methyl-pentanoic acid
118  (S)-2-{[1-(1-Ethyl-propyl)-2-furan-3-ylmethyl-1H-benzoimidazole-5-carbonyl]-amino}-4-methyl-pentanoic acid
121  (S)-2-{[1-(1-Ethyl-propyl)-2-thiophen-2-ylmethyl-1H-benzoimidazole-5-carbonyl]-amino}-3-methyl-pentanoic acid
123  (S)-2-{[1-(1-Ethyl-propyl)-2-thiophen-2-ylmethyl-1H-benzoimidazole-5-carbonyl]-amino}-4-methylsulfanyl-butyric acid
125  (S)-3-Cyclohexyl-2-{[1-(1-ethyl-propyl)-2-thiophen-2-ylmethyl-1H-benzoimidazole-5-carbonyl]-amino}-propionic acid
130  (S)-2-{[1-(1-Ethyl-propyl)-2-thiophen-2-ylmethyl-1H-benzoimidazole-5-carbonyl]-amino}-5-methyl-hexanoic acid
131  (S)-2-{[2-Furan-3-ylmethyl-1-(2-methyl-cyclohexyl)-1H-benzoimidazole-5-carbonyl]-amino}-4-methyl-pentanoic acid
139  (S)-4-Methyl-2-{[1-(2-methyl-cyclohexyl)-2-thiophen-3-ylmethyl-1H-benzoimidazole-5-carbonyl]-amino}-pentanoic acid
146  (S)-4-Methyl-2-{[1-(2-methyl-cyclohexyl)-2-thiophen-2-ylmethyl-1H-benzoimidazole-5-carbonyl]-amino}-pentanoic acid
151  (S)-3-Cyclohexyl-2-{[1-(1-ethyl-propyl)-2-(tetrahydro-furan-2-ylmethyl)-1H-benzoimidazole-5-carbonyl]-amino}-propionic acid
153  (2S,3R)-2-{[1-(1-Ethyl-propyl)-2-thiophen-2-ylmethyl-1H-benzoimidazole-5-carbonyl]-amino}-3-methyl-pentanoic acid
154  (S)-3-{[1-(1-Ethyl-propyl)-2-furan-3-ylmethyl-1H-benzoimidazole-5-carbonyl]-amino}-5-methyl-hexanoic acid
155  3-{[1-(1-Ethyl-propyl)-2-thiophen-2-ylmethyl-1H-benzoimidazole-5-carbonyl]-amino}-hexanoic acid
158  (S)-3-{[2-Cyclopentylmethyl-1-(1-ethyl-propyl)-1H-benzoimidazole-5-carbonyl]-amino}-5-methyl-hexanoic acid
160  (S)-3-{[1-(1-Ethyl-propyl)-2-(tetrahydro-furan-2-ylmethyl)-1H-benzoimidazole-5-carbonyl]-amino}-5-methyl-hexanoic acid
161  (R)-3-{[1-(1-Ethyl-propyl)-2-thiophen-2-ylmethyl-1H-benzoimidazole-5-carbonyl]-amino}-4-methyl-pentanoic acid
162  (R)-4-{[1-(1-Ethyl-propyl)-2-thiophen-2-ylmethyl-1H-benzoimidazole-5-carbonyl]-amino}-5-methyl-hexanoic acid
163  (R)-4-{[1-(1-Ethyl-propyl)-2-thiophen-2-ylmethyl-1H-benzoimidazole-5-carbonyl]-amino}-6-methyl-heptanoic acid
412  (S)-4-Methyl-2-{[1-((1R,2R)-2-methyl-cyclohexyl)-2-thiophen-2-ylmethyl-1H-benzoimidazole-5-carbonyl]-amino}-pentanoic acid
413  (S)-4-Methyl-2-{[1-((1S,2S)-2-methyl-cyclohexyl)-2-thiophen-2-ylmethyl-1H-benzoimidazole-5-carbonyl]-amino}-pentanoic acid
414  (S)-4-Methyl-2-{[1-((1R,2S)-2-methyl-cyclohexyl)-2-thiophen-2-ylmethyl-1H-benzoimidazole-5-carbonyl]-amino}-pentanoic acid
415  (S)-4-Methyl-2-{[1-((1S,2R)-2-methyl-cyclohexyl)-2-thiophen-2-ylmethyl-1H-benzoimidazole-5-carbonyl]-amino}-pentanoic acid
416  (S)-2-{[2-Furan-2-ylmethyl-1-(2-methyl-cyclohexyl)-1H-benzoimidazole-5-carbonyl]-amino}-4-methyl-pentanoic acid
417  (S)-2-{[2-Furan-2-ylmethyl-1-(2-methyl-cyclohexyl)-1H-benzoimidazole-5-carbonyl]-amino}-4-methyl-pentanoic acid
418  (S)-2-{[2-Furan-2-ylmethyl-1-(2-methyl-cyclohexyl)-1H-benzoimidazole-5-carbonyl]-amino}-4-methyl-pentanoic acid
419  (S)-2-{[2-Furan-2-ylmethyl-1-(2-methyl-cyclohexyl)-1H-benzoimidazole-5-carbonyl]-amino}-4-methyl-pentanoic acid
420  (S)-2-{[1-(2-Methyl-cyclohexyl)-2-thiophen-2-ylmethyl-1H-benzoimidazole-5-carbonyl]-amino}-hexanoic acid
421  (S)-2-{[1-(2-Methyl-cyclohexyl)-2-thiophen-2-ylmethyl-1H-benzoimidazole-5-carbonyl]-amino}-hexanoic acid
422  (S)-2-{[1-(2-Methyl-cyclohexyl)-2-thiophen-2-ylmethyl-1H-benzoimidazole-5-carbonyl]-amino}-hexanoic acid
423  (S)-2-{[1-(2-Methyl-cyclohexyl)-2-thiophen-2-ylmethyl-1H-benzoimidazole-5-carbonyl]-amino}-hexanoic acid
424  (S)-3-Cyclohexyl-2-{[1-(2-methyl-cyclohexyl)-2-thiophen-2-ylmethyl-1H-benzoimidazole-5-carbonyl]-amino}-propionic acid
425  (S)-3-Cyclohexyl-2-{[1-(2-methyl-cyclohexyl)-2-thiophen-2-ylmethyl-1H-benzoimidazole-5-carbonyl]-amino}-propionic acid
426  (S)-3-Cyclohexyl-2-{[1-(2-methyl-cyclohexyl)-2-thiophen-2-ylmethyl-1H-benzoimidazole-5-carbonyl]-amino}-propionic acid
427  (S)-3-Cyclohexyl-2-{[1-(2-methyl-cyclohexyl)-2-thiophen-2-ylmethyl-1H-benzoimidazole-5-carbonyl]-amino}-propionic acid 428 (S)-4-Methyl-2-{[1-(2-methyl-cyclopentyl)-2-thiophen-2-ylmethyl-1H-benzoimidazole-5-carbonyl]-amino}-pentanoic acid
429 (S)-4-Methyl-2-{[1-(2-methyl-cyclopentyl)-2-thiophen-2-ylmethyl-1H-benzoimidazole-5-carbonyl]-amino}-pentanoic acid
430 (S)-4-Methyl-2-{[1-(2-methyl-cyclopentyl)-2-thiophen-2-ylmethyl-1H-benzoimidazole-5-carbonyl]-amino}-pentanoic acid
431 (S)-4-Methyl-2-{[1-(2-methyl-cyclopentyl)-2-thiophen-2-ylmethyl-1H-benzoimidazole-5-carbonyl]-amino}-pentanoic acid
432 (S)-3-{[2-Furan-2-ylmethyl-1-(2-methyl-cyclohexyl)-1H-benzoimidazole-5-carbonyl]-amino}-5-methyl-hexanoic acid
433 (S)-3-{[2-Furan-2-ylmethyl-1-(2-methyl-cyclohexyl)-1H-benzoimidazole-5-carbonyl]-amino}-5-methyl-hexanoic acid
434 (S)-3-{[2-Furan-2-ylmethyl-1-(2-methyl-cyclohexyl)-1H-benzoimidazole-5-carbonyl]-amino}-5-methyl-hexanoic acid
435 (S)-3-{[2-Furan-2-ylmethyl-1-(2-methyl-cyclohexyl)-1H-benzoimidazole-5-carbonyl]-amino}-5-methyl-hexanoic acid
436 (S)-5-Methyl-3-{[1-(2-methyl-cyclohexyl)-2-thiophen-2-ylmethyl-1H-benzoimidazole-5-carbonyl]-amino}-hexanoic acid
437 (S)-5-Methyl-3-{[1-(2-methyl-cyclohexyl)-2-thiophen-2-ylmethyl-1H-benzoimidazole-5-carbonyl]-amino}-hexanoic acid
438 (S)-5-Methyl-3-{[1-(2-methyl-cyclohexyl)-2-thiophen-2-ylmethyl-1H-benzoimidazole-5-carbonyl]-amino}-hexanoic acid
439 (S)-5-Methyl-3-{[1-(2-methyl-cyclohexyl)-2-thiophen-2-ylmethyl-1H-benzoimidazole-5-carbonyl]-amino}-hexanoic acid
440 (R)-2-{[1-(1-Ethyl-propyl)-2-thiophen-2-ylmethyl-1H-benzoimidazole-5-carbonyl]-amino}-2,4-dimethyl-pentanoic acid
441 (S)-2-{[1-(1-Ethyl-propyl)-2-thiophen-2-ylmethyl-1H-benzoimidazole-5-carbonyl]-amino}-2,4-dimethyl-pentanoic acid
442 3-Cyclopentyl-2-{[1-((1R,2R)-2-methyl-cyclohexyl)-2-thiophen-2-ylmethyl-1H-benzoimidazole-5-carbonyl]-amino}-propionic acid
443 3-Cyclopentyl-2-{[1-((1R,2R)-2-methyl-cyclohexyl)-2-thiophen-2-ylmethyl-1H-benzoimidazole-5-carbonyl]-amino}-propionic acid
448 (S)-3-Cycloheptyl-2-{[1-(1-ethyl-propyl)-2-thiophen-2-ylmethyl-1H-benzoimidazole-5-carbonyl]-amino}-propionic acid
449 (R)-3-Cycloheptyl-2-{[1-(1-ethyl-propyl)-2-thiophen-2-ylmethyl-1H-benzoimidazole-5-carbonyl]-amino}-propionic acid
450 3-Cycloheptyl-2-{[1-((1R,2R)-2-methyl-cyclohexyl)-2-thiophen-2-ylmethyl-1H-benzoimidazole-5-carbonyl]-amino}-propionic acid
451 3-Cycloheptyl-2-{[1-((1R,2R)-2-methyl-cyclohexyl)-2-thiophen-2-ylmethyl-1H-benzoimidazole-5-carbonyl]-amino}-propionic acid
452 (S)-3-{[1-(1-Ethyl-propyl)-2-thiophen-2-ylmethyl-1H-benzoimidazole-5-carbonyl]-amino}-heptanoic acid
453 (R)-3-{[1-(1-Ethyl-propyl)-2-thiophen-2-ylmethyl-1H-benzoimidazole-5-carbonyl]-amino}-heptanoic acid
454 (S)-4-Cyclohexyl-3-{[1-(1-ethyl-propyl)-2-thiophen-2-ylmethyl-1H-benzoimidazole-5-carbonyl]-amino}-butyric acid
455 (R)-4-Cyclohexyl-3-{[1-(1-ethyl-propyl)-2-thiophen-2-ylmethyl-1H-benzoimidazole-5-carbonyl]-amino}-butyric acid
456 4-Cyclohexyl-3-{[1-((1R,2R)-2-methyl-cyclohexyl)-2-thiophen-2-ylmethyl-1H-benzoimidazole-5-carbonyl]-amino}-butyric acid
457 4-Cyclohexyl-3-{[1-((1R,2R)-2-methyl-cyclohexyl)-2-thiophen-2-ylmethyl-1H-benzoimidazole-5-carbonyl]-amino}-butyric acid
458 3-{[1-((1R,2R)-2-Methyl-cyclohexyl)-2-thiophen-2-ylmethyl-1H-benzoimidazole-5-carbonyl]-amino}-hexanoic acid
459 3-{[1-((1R,2R)-2-Methyl-cyclohexyl)-2-thiophen-2-ylmethyl-1H-benzoimidazole-5-carbonyl]-amino}-hexanoic acid
460 3-{[1-((1R,2R)-2-Methyl-cyclohexyl)-2-thiophen-2-ylmethyl-1H-benzoimidazole-5-carbonyl]-amino}-heptanoic acid
461 3-{[1-((1R,2R)-2-Methyl-cyclohexyl)-2-thiophen-2-ylmethyl-1H-benzoimidazole-5-carbonyl]-amino}-heptanoic acid
462 3-Cyclohexyl-3-{[1-((1R,2R)-2-methyl-cyclohexyl)-2-thiophen-2-ylmethyl-1H-benzoimidazole-5-carbonyl]-amino}-propionic acid
463 3-Cyclohexyl-3-{[1-((1R,2R)-2-methyl-cyclohexyl)-2-thiophen-2-ylmethyl-1H-benzoimidazole-5-carbonyl]-amino}-propionic acid
464 (R)-3-{[1-(1-Ethyl-propyl)-2-thiophen-2-ylmethyl-1H-benzoimidazole-5-carbonyl]-amino}-2,2,5-trimethyl-hexanoic acid
465 (S)-3-{[1-(1-Ethyl-propyl)-2-thiophen-2-ylmethyl-1H-benzoimidazole-5-carbonyl]-amino}-2,2,5-trimethyl-hexanoic acid
466 (R)-3-{[1-(1-Ethyl-propyl)-2-thiophen-2-ylmethyl-1H-benzoimidazole-5-carbonyl]-amino}-2,2-dimethyl-hexanoic acid
467 (S)-3-{[1-(1-Ethyl-propyl)-2-thiophen-2-ylmethyl-1H-benzoimidazole-5-carbonyl]-amino}-2,2-dimethyl-hexanoic acid
468 (S)-3-{[1-(1-Ethyl-propyl)-2-thiophen-2-ylmethyl-1H-benzoimidazole-5-carbonyl]-amino}-2,2-dimethyl-heptanoic acid
469 (R)-3-{[1-(1-Ethyl-propyl)-2-thiophen-2-ylmethyl-1H-benzoimidazole-5-carbonyl]-amino}-2,2-dimethyl-heptanoic acid.

The number denotes the example number of the respective compound.

In another embodiment compounds of the formula I are encompassed selected from the group consisting of
1  1-{[1-(1-Ethyl-propyl)-2-thiophen-2-ylmethyl-1H-benzoimidazole-5-carbonyl]-amino}-cycloheptanecarboxylic acid
6  1-{[1-(1-Ethyl-propyl)-2-thiophen-2-ylmethyl-1H-benzoimidazole-5-carbonyl]-amino}-cyclopentanecarboxylic acid
11  3-Cyclopentyl-2-{[1-(1-ethyl-propyl)-2-thiophen-2-ylmethyl-1H-benzoimidazole-5-carbonyl]-amino}-propionic acid
12  2-{[1-(1-Ethyl-propyl)-2-thiophen-2-ylmethyl-1H-benzoimidazole-5-carbonyl]-amino}-2,4-dimethyl-pentanoic acid
15  (S)-3-Cyclohexyl-2-{[1-(2-methyl-cyclohexyl)-2-thiophen-2-ylmethyl-1H-benzoimidazole-5-carbonyl]-amino}-propionic acid
16 (S)-2-{[1-(2-Methyl-cyclohexyl)-2-thiophen-2-ylmethyl-1H-benzoimidazole-5-carbonyl]-amino}-hexanoic acid 18 (S)-2-{[1-(1-Ethyl-propyl)-2-thiophen-2-ylmethyl-1H-benzoimidazole-5-carbonyl]-amino}-hexanoic acid
21 (S)-3-Cyclopropyl-2-{[1-(1-ethyl-propyl)-2-thiophen-2-ylmethyl-1H-benzoimidazole-5-carbonyl]-amino}-propionic acid
22 (S)-3-Cyclobutyl-2-{[1-(1-ethyl-propyl)-2-thiophen-2-ylmethyl-1H-benzoimidazole-5-carbonyl]-amino}-propionic acid
23 (S)-3-Cyclobutyl-2-{[1-((1R,2R)-2-methyl-cyclohexyl)-2-thiophen-2-ylmethyl-1H-benzoimidazole-5-carbonyl]-amino}-propionic acid
24 1-{[1-(1-Ethyl-propyl)-2-thiophen-2-ylmethyl-1H-benzoimidazole-5-carbonyl]-amino}-cyclohexanecarboxylic acid
25 2-{[1-(1-Ethyl-propyl)-2-thiophen-2-ylmethyl-1H-benzoimidazole-5-carbonyl]-amino}-2-methyl-pentanoic acid
26 2-{[1-(1-Ethyl-propyl)-2-thiophen-2-ylmethyl-1H-benzoimidazole-5-carbonyl]-amino}-5,5,5-trifluoro-pentanoic acid
27 5,5,5-Trifluoro-2-{[1-((1R,2R)-2-methyl-cyclohexyl)-2-thiophen-2-ylmethyl-1H-benzoimidazole-5-carbonyl]-amino}-pentanoic acid
29 3-(4,4-Dimethyl-cyclohexyl)-2-{[1-(1-ethyl-propyl)-2-thiophen-2-ylmethyl-1H-benzoimidazole-5-carbonyl]-amino}-propionic acid
33 3-(4,4-Dimethyl-cyclohexyl)-2-{[1-((1R,2R)-2-methyl-cyclohexyl)-2-thiophen-2-ylmethyl-1H-benzoimidazole-5-carbonyl]-amino}-propionic acid
34 1-{[1-(1-Ethyl-propyl)-2-thiophen-2-ylmethyl-1H-benzoimidazole-5-carbonyl]-amino}-4-methyl-cyclohexanecarboxylic acid
35 4-Methyl-1-{[1-((1R,2R)-2-methyl-cyclohexyl)-2-thiophen-2-ylmethyl-1H-benzoimidazole-5-carbonyl]-amino}-cyclohexanecarboxylic acid
36 2-{[1-(1-Ethyl-propyl)-2-thiophen-2-ylmethyl-1H-benzoimidazole-5-carbonyl]-amino}-3-(4-methyl-cyclohexyl)-propionic acid
38 1-{[1-((1R,2R)-2-Methyl-cyclohexyl)-2-thiophen-2-ylmethyl-1H-benzoimidazole-5-carbonyl]-amino}-cyclohexanecarboxylic acid
39 3-Cycloheptyl-2-{[1-(1-ethyl-propyl)-2-thiophen-2-ylmethyl-1H-benzoimidazole-5-carbonyl]-amino}-propionic acid
40 3-Cycloheptyl-2-{[1-((1R,2R)-2-methyl-cyclohexyl)-2-thiophen-2-ylmethyl-1H-benzoimidazole-5-carbonyl]-amino}-propionic acid
44 3-Cyclohexyl-3-{[1-(1-ethyl-propyl)-2-thiophen-2-ylmethyl-1H-benzoimidazole-5-carbonyl]-amino}-propionic acid
45 3-{[1-(1-Ethyl-propyl)-2-thiophen-2-ylmethyl-1H-benzoimidazole-5-carbonyl]-amino}-heptanoic acid
46 4-Cyclohexyl-3-{[1-(1-ethyl-propyl)-2-thiophen-2-ylmethyl-1H-benzoimidazole-5-carbonyl]-amino}-butyric acid
47 3-{[1-(1-Ethyl-propyl)-2-thiophen-2-ylmethyl-1H-benzoimidazole-5-carbonyl]-amino}-5,5-dimethyl-hexanoic acid
48 (R)-3-{[1-(1-Ethyl-propyl)-2-thiophen-2-ylmethyl-1H-benzoimidazole-5-carbonyl]-amino}-5-methyl-hexanoic acid
51 4-Cyclohexyl-3-{[1-((1R,2R)-2-methyl-cyclohexyl)-2-thiophen-2-ylmethyl-1H-benzoimidazole-5-carbonyl]-amino}-butyric acid
52 4-Cyclohexyl-3-{[1-((1S,2S)-2-methyl-cyclohexyl)-2-thiophen-2-ylmethyl-1H-benzoimidazole-5-carbonyl]-amino}-butyric acid
53 (3R,4S)-4-Methyl-3-{[1-((1R,2R)-2-methyl-cyclohexyl)-2-thiophen-2-ylmethyl-1H-benzoimidazole-5-carbonyl]-amino}-hexanoic acid
54 (3R,4S)-3-{[1-(1-Ethyl-propyl)-2-thiophen-2-ylmethyl-1H-benzoimidazole-5-carbonyl]-amino}-4-methyl-hexanoic acid
55 3-{[1-((1R,2R)-2-Methyl-cyclohexyl)-2-thiophen-2-ylmethyl-1H-benzoimidazole-5-carbonyl]-amino}-hexanoic acid
56 3-{[1-((1R,2R)-2-Methyl-cyclohexyl)-2-thiophen-2-ylmethyl-1H-benzoimidazole-5-carbonyl]-amino}-heptanoic acid
57 3-Cyclohexyl-3-{[1-((1R,2R)-2-methyl-cyclohexyl)-2-thiophen-2-ylmethyl-1H-benzoimidazole-5-carbonyl]-amino}-propionic acid
58 3-{[1-(1-Ethyl-propyl)-2-thiophen-2-ylmethyl-1H-benzoimidazole-5-carbonyl]-amino}-2,2-dimethyl-heptanoic acid
59 4-Ethyl-3-{[1-(1-ethyl-propyl)-2-thiophen-2-ylmethyl-1H-benzoimidazole-5-carbonyl]-amino}-hexanoic acid
60 (S)-4-Cyclopentyl-3-{[1-(1-ethyl-propyl)-2-thiophen-2-ylmethyl-1H-benzoimidazole-5-carbonyl]-amino}-butyric acid
61 (S)-4-Cyclopentyl-3-{[1-((1R,2R)-2-methyl-cyclohexyl)-2-thiophen-2-ylmethyl-1H-benzoimidazole-5-carbonyl]-amino}-butyric acid
62 3-{[1-(1-Ethyl-propyl)-2-thiophen-2-ylmethyl-1H-benzoimidazole-5-carbonyl]-amino}-2,2,5-trimethyl-hexanoic acid
63 3-{[1-(1-Ethyl-propyl)-2-thiophen-2-ylmethyl-1H-benzoimidazole-5-carbonyl]-amino}-2,2-dimethyl-hexanoic acid
64 (1-{[1-(1-Ethyl-propyl)-2-thiophen-2-ylmethyl-1H-benzoimidazole-5-carbonyl]-amino}-cyclohexyl)-acetic acid
66 (1-{[1-((1R,2R)-2-Methyl-cyclohexyl)-2-thiophen-2-ylmethyl-1H-benzoimidazole-5-carbonyl]-amino}-cyclohexyl)-acetic acid
67 (2R,3S)-3-{[1-(1-Ethyl-propyl)-2-thiophen-2-ylmethyl-1H-benzoimidazole-5-carbonyl]-amino}-2-hydroxy-5-methyl-hexanoic acid
68 (2S,3S)-3-{[1-(1-Ethyl-propyl)-2-thiophen-2-ylmethyl-1H-benzoimidazole-5-carbonyl]-amino}-2-hydroxy-5-methyl-hexanoic acid
70 (R)-6-Methyl-4-{[1-((1R,2R)-2-methyl-cyclohexyl)-2-thiophen-2-ylmethyl-1H-benzoimidazole-5-carbonyl]-amino}-heptanoic acid
71 (4R,5S)-4-{[1-(1-Ethyl-propyl)-2-thiophen-2-ylmethyl-1H-benzoimidazole-5-carbonyl]-amino}-5-methyl-heptanoic acid
72 (4R,5S)-5-Methyl-4-{[1-((1R,2R)-2-methyl-cyclohexyl)-2-thiophen-2-ylmethyl-1H-benzoimidazole-5-carbonyl]-amino}-heptanoic acid
73 (3R,4S)-5-Cyclohexyl-4-{[1-(1-ethyl-propyl)-2-thiophen-2-ylmethyl-1H-benzoimidazole-5-carbonyl]-amino}-3-hydroxy-pentanoic acid
74 (3R,4S)-5-Cyclohexyl-3-hydroxy-4-{[1-((1R,2R)-2-methyl-cyclohexyl)-2-thiophen-2-ylmethyl-1H-benzoimidazole-5-carbonyl]-amino}-pentanoic acid
75 (3S,4S)-4-{[1-(1-Ethyl-propyl)-2-thiophen-2-ylmethyl-1H-benzoimidazole-5-carbonyl]-amino}-3-hydroxy-6-methyl-heptanoic acid
76 (3R,4S)-4-{[1-(1-Ethyl-propyl)-2-thiophen-2-ylmethyl-1H-benzoimidazole-5-carbonyl]-amino}-3-hydroxy-6-methyl-heptanoic acid
77 (3R,4S)-3-Hydroxy-6-methyl-4-{[4-((1R,2R)-2-methyl-cyclohexyl)-2-thiophen-2-ylmethyl-1H-benzoimidazole-5-carbonyl]-amino}-heptanoic acid 78 (3S,4S)-3-Hydroxy-6-methyl-4-{[1-((1R,2R)-2-methyl-cyclohexyl)-2-thiophen-2-ylmethyl-1H-benzoimidazole-5-carbonyl]-amino}-heptanoic acid
79 (3S,4S)-5-Cyclohexyl-4-{[1-(1-ethyl-propyl)-2-thiophen-2-ylmethyl-1H-benzoimidazole-5-carbonyl]-amino}-3-hydroxy-pentanoic acid
91 (S)-2-{[1-((1R,2R)-2-Methyl-cyclohexyl)-2-thiophen-2-ylmethyl-1H-benzoimidazole-5-carbonyl]-amino}-pentanoic acid
92 (2S,3S)-3-Methyl-2-{[1-((1R,2R)-2-methyl-cyclohexyl)-2-thiophen-2-ylmethyl-1H-benzoimidazole-5-carbonyl]-amino}-pentanoic acid
93 (S)-2-{[1-(2-Ethyl-cyclohexyl)-2-thiophen-2-ylmethyl-1H-benzoimidazole-5-carbonyl]-amino}-4-methyl-pentanoic acid
94 (S)-2-{[1-(1-Ethyl-propyl)-2-thiophen-2-ylmethyl-1H-benzoimidazole-5-carbonyl]-amino}-pentanoic acid
95 (S)-3-{[1-(1-Ethyl-propyl)-2-thiophen-2-ylmethyl-1H-benzoimidazole-5-carbonyl]-amino}-5-methyl-hexanoic acid
101 (S)-5-Methyl-3-{[1-(2-methyl-cyclohexyl)-2-thiophen-2-ylmethyl-1H-benzoimidazole-5-carbonyl]-amino}hexanoic acid
107 (S)-3-{[1-(1-Ethyl-propyl)-2-thiophen-2-ylmethyl-1H-benzoimidazole-5-carbonyl]-amino}-5-methyl-hexanoic acid
114 (S)-2-{[1-(1-Ethyl-propyl)-2-thiophen-2-ylmethyl-1H-benzoimidazole-5-carbonyl]-amino}-4-methyl-pentanoic acid
121 (S)-2-{[1-(1-Ethyl-propyl)-2-thiophen-2-ylmethyl-1H-benzoimidazole-5-carbonyl]-amino}-3-methyl-pentanoic acid
123 (S)-2-{[1-(1-Ethyl-propyl)-2-thiophen-2-ylmethyl-1H-benzoimidazole-5-carbonyl]-amino}-4-methylsulfanyl-butyric acid
125 (S)-3-Cyclohexyl-2-{[1-(1-ethyl-propyl)-2-thiophen-2-ylmethyl-1H-benzoimidazole-5-carbonyl]-amino}-propionic acid
130 (S)-2-{[1-(1-Ethyl-propyl)-2-thiophen-2-ylmethyl-1H-benzoimidazole-5-carbonyl]-amino}-5-methyl-hexanoic acid
139 (S)-4-Methyl-2-{[1-(2-methyl-cyclohexyl)-2-thiophen-3-ylmethyl-1H-benzoimidazole-5-carbonyl]-amino}-pentanoic acid
146 (S)-4-Methyl-2-{[1-(2-methyl-cyclohexyl)-2-thiophen-2-ylmethyl-1H-benzoimidazole-5-carbonyl]-amino}-pentanoic acid
153 (2S,3R)-2-{[1-(1-Ethyl-propyl)-2-thiophen-2-ylmethyl-1H-benzoimidazole-5-carbonyl]-amino}-3-methyl-pentanoic acid
155 3-{[1-(1-Ethyl-propyl)-2-thiophen-2-ylmethyl-1H-benzoimidazole-5-carbonyl]-amino}-hexanoic acid
161 (R)-3-{[1-(1-Ethyl-propyl)-2-thiophen-2-ylmethyl-1H-benzoimidazole-5-carbonyl]-amino}-4-methyl-pentanoic acid
162 (R)-4-{[1-(1-Ethyl-propyl)-2-thiophen-2-ylmethyl-1H-benzoimidazole-5-carbonyl]-amino}-5-methyl-hexanoic acid
163 (R)-4-{[1-(1-Ethyl-propyl)-2-thiophen-2-ylmethyl-1H-benzoimidazole-5-carbonyl]amino}-6-methyl-heptanoic acid
412 (S)-4-Methyl-2-{[1-((1R,2R)-2-methyl-cyclohexyl)-2-thiophen-2-ylmethyl-1H-benzoimidazole-5-carbonyl]-amino}-pentanoic acid
413 (S)-4-Methyl-2-{[1-((1S,2S)-2-methyl-cyclohexyl)-2-thiophen-2-ylmethyl-1H-benzoimidazole-5-carbonyl]-amino}-pentanoic acid
414 (S)-4-Methyl-2-{[1-((1R,2S)-2-methyl-cyclohexyl)-2-thiophen-2-ylmethyl-1H-benzoimidazole-5-carbonyl]-amino}-pentanoic acid
415 (S)-4-Methyl-2-{[1-((1S,2R)-2-methyl-cyclohexyl)-2-thiophen-2-ylmethyl-1H-benzoimidazole-5-carbonyl]-amino}-pentanoic acid
420 (S)-2-{[1-(2-Methyl-cyclohexyl)-2-thiophen-2-ylmethyl-1H-benzoimidazole-5-carbonyl]-amino}-hexanoic acid
421 (S)-2-{[1-(2-Methyl-cyclohexyl)-2-thiophen-2-ylmethyl-1H-benzoimidazole-5-carbonyl]-amino}-hexanoic acid
422 (S)-2-{[1-(2-Methyl-cyclohexyl)-2-thiophen-2-ylmethyl-1H-benzoimidazole-5-carbonyl]-amino}-hexanoic acid
423 (S)-2-{[1-(2-Methyl-cyclohexyl)-2-thiophen-2-ylmethyl-1H-benzoimidazole-5-carbonyl]-amino}-hexanoic acid
424 (S)-3-Cyclohexyl-2-{[1-(2-methyl-cyclohexyl)-2-thiophen-2-ylmethyl-1H-benzoimidazole-5-carbonyl]-amino}-propionic acid
425 (S)-3-Cyclohexyl-2-{[1-(2-methyl-cyclohexyl)-2-thiophen-2-ylmethyl-1H-benzoimidazole-5-carbonyl]-amino}-propionic acid
426 (S)-3-Cyclohexyl-2-{[1-(2-methyl-cyclohexyl)-2-thiophen-2-ylmethyl-1H-benzoimidazole-5-carbonyl]-amino}-propionic acid
427 (S)-3-Cyclohexyl-2-{[1-(2-methyl-cyclohexyl)-2-thiophen-2-ylmethyl-1H-benzoimidazole-5-carbonyl]-amino}-propionic acid
436 (S)-5-Methyl-3-{[1-(2-methyl-cyclohexyl)-2-thiophen-2-ylmethyl-1H-benzoimidazole-5-carbonyl]-amino}-hexanoic acid
437 (S)-5-Methyl-3-{[1-(2-methyl-cyclohexyl)-2-thiophen-2-ylmethyl-1H-benzoimidazole-5-carbonyl]-amino}-hexanoic acid
438 (S)-5-Methyl-3-{[1-(2-methyl-cyclohexyl)-2-thiophen-2-ylmethyl-1H-benzoimidazole-5-carbonyl]-amino}-hexanoic acid
439 (S)-5-Methyl-3-{[1-(2-methyl-cyclohexyl)-2-thiophen-2-ylmethyl-1H-benzoimidazole-5-carbonyl]-amino}-hexanoic acid
440 (R)-2-{[1-(1-Ethyl-propyl)-2-thiophen-2-ylmethyl-1H-benzoimidazole-5-carbonyl]-amino}-2,4-dimethyl-pentanoic acid
441 (S)-2-{[1-(1-Ethyl-propyl)-2-thiophen-2-ylmethyl-1H-benzoimidazole-5-carbonyl]-amino}-2,4-dimethyl-pentanoic acid
442 3-Cyclopentyl-2-{[1-((1R,2R)-2-methyl-cyclohexyl)-2-thiophen-2-ylmethyl-1H-benzoimidazole-5-carbonyl]-amino}-propionic acid
443 3-Cyclopentyl-2-{[1-((1R,2R)-2-methyl-cyclohexyl)-2-thiophen-2-ylmethyl-1H-benzoimidazole-5-carbonyl]-amino}-propionic acid
448 (S)-3-Cycloheptyl-2-{[1-(1-ethyl-propyl)-2-thiophen-2-ylmethyl-1H-benzoimidazole-5-carbonyl]-amino}-propionic acid
449 (R)-3-Cycloheptyl-2-{[1-(1-ethyl-propyl)-2-thiophen-2-ylmethyl-1H-benzoimidazole-5-carbonyl]-amino}-propionic acid
450 3-Cycloheptyl-2-{[1-((1R,2R)-2-methyl-cyclohexyl)-2-thiophen-2-ylmethyl-1H-benzoimidazole-5-carbonyl]-amino}-propionic acid
451 3-Cycloheptyl-2-{[1-((1R,2R)-2-methyl-cyclohexyl)-2-thiophen-2-ylmethyl-1H-benzoimidazole-5-carbonyl]-amino}-propionic acid 452 (S)-3-{[1-(1-Ethyl-propyl)-2-thiophen-2-ylmethyl-1H-benzoimidazole-5-carbonyl]-amino}-heptanoic acid
453 (R)-3-{[1-(1-Ethyl-propyl)-2-thiophen-2-ylmethyl-1H-benzoimidazole-5-carbonyl]-amino}-heptanoic acid
454 (S)-4-Cyclohexyl-3-{[1-(1-ethyl-propyl)-2-thiophen-2-ylmethyl-1H-benzoimidazole-5-carbonyl]-amino}-butyric acid
455 (R)-4-Cyclohexyl-3-{[1-(1-ethyl-propyl)-2-thiophen-2-ylmethyl-1H-benzoimidazole-5-carbonyl]-amino}-butyric acid
456 4-Cyclohexyl-3-{[1-((1R,2R)-2-methyl-cyclohexyl)-2-thiophen-2-ylmethyl-1H-benzoimidazole-5-carbonyl]-amino}-butyric acid
457 4-Cyclohexyl-3-{[1-((1R,2R)-2-methyl-cyclohexyl)-2-thiophen-2-ylmethyl-1H-benzoimidazole-5-carbonyl]-amino}-butyric acid
458 3-{[1-((1R,2R)-2-Methyl-cyclohexyl)-2-thiophen-2-ylmethyl-1H-benzoimidazole-5-carbonyl]-amino}-hexanoic acid
459 3-{[1-((1R,2R)-2-Methyl-cyclohexyl)-2-thiophen-2-ylmethyl-1H-benzoimidazole-5-carbonyl]-amino}-hexanoic acid
460 3-{[1-((1R,2R)-2-Methyl-cyclohexyl)-2-thiophen-2-ylmethyl-1H-benzoimidazole-5-carbonyl]-amino}-heptanoic acid
461 3-{[1-((1R,2R)-2-Methyl-cyclohexyl)-2-thiophen-2-ylmethyl-1H-benzoimidazole-5-carbonyl]-amino}-heptanoic acid
462 3-Cyclohexyl-3-{[1-((1R,2R)-2-methyl-cyclohexyl)-2-thiophen-2-ylmethyl-1H-benzoimidazole-5-carbonyl]-amino}-propionic acid
463 3-Cyclohexyl-3-{[1-((1R,2R)-2-methyl-cyclohexyl)-2-thiophen-2-ylmethyl-1H-benzoimidazole-5-carbonyl]-amino}-propionic acid
464 (R)-3-{[1-(1-Ethyl-propyl)-2-thiophen-2-ylmethyl-1H-benzoimidazole-5-carbonyl]-amino}-2,2,5-trimethyl-hexanoic acid
465 (S)-3-{[1-(1-Ethyl-propyl)-2-thiophen-2-ylmethyl-1H-benzoimidazole-5-carbonyl]-amino}-2,2,5-trimethyl-hexanoic acid
466 (R)-3-{[1-(1-Ethyl-propyl)-2-thiophen-2-ylmethyl-1H-benzoimidazole-5-carbonyl]-amino}-2,2-dimethyl-hexanoic acid
467 (S)-3-{[1-(1-Ethyl-propyl)-2-thiophen-2-ylmethyl-1H-benzoimidazole-5-carbonyl]-amino}-2,2-dimethyl-hexanoic acid
468 (S)-3-{[1-(1-Ethyl-propyl)-2-thiophen-2-ylmethyl-1H-benzoimidazole-5-carbonyl]-amino}-2,2-dimethyl-heptanoic acid
469 (R)-3-{[1-(1-Ethyl-propyl)-2-thiophen-2-ylmethyl-1H-benzoimidazole-5-carbonyl]-amino}-2,2-dimethyl-heptanoic acid The number denotes the example number of the respective compound.

Uses

The present invention provides novel and potent APJ modulators. The efficacy of the compounds of the formula I can be demonstrated in the pharmacological test described below and in other tests which are known to a person skilled in the art.

Selective APJ modulators are useful to substitute or complement apelins in their physiological actions and act in many tissues mediated by the specific interaction with the APJ receptor. Among different uses for such APJ receptor modulation, four major areas of interesting uses include direct cardiac and cardiovascular effects, effects on metabolic dysfunction, diabetes and related complications, effects on the body's fluid homeostasis, and effects on the vasculature and vascular formation First, selective APJ modulators are useful in preventing and treating cardiovascular diseases. These include coronary heart disease, stroke, and heart failure. Heart Failure itself comprises a bundle of clinical syndromes such as systolic heart failure, diastolic heart failure, diabetic heart failure and heart failure with preserved ejection fraction, cardiomyopathy, myocardial infarction, left ventricular dysfunction including left ventricular dysfunction after myocardial infarction, cardiac hypertrophy, myocardial remodeling including myocardial remodeling after infarction or after cardiac surgery, and valvular heart diseases, A second major area includes metabolic dysfunction, diabetes and related complications. This area includes diseases with metabolic syndrome, insulin resistance, diabetes melittus and diabetic late complications. Diabetic late complications comprise all end organ damages of micro- or macrovascular origin, such as diabetic macro- and microvasculopathies, diabetic nephropathy, diabetic retinopathy, diabetic neuropathies, and cardiac autonomic neuropathy.

The third major area of uses includes diseases with disturbed body's fluid homeostasis by CNS dependent and -independent effects, such as acute and chronic renal failure or hypertension. Hypertension itself comprises a bundle of syndromes such as pulmonary hypertension, portal hypertension and systolic hypertension.

A fourth major area of use contain diseases with vascular pathology, e.g. with increased vascular permeability and non-functional blood vessels. APJ modulators are useful to treat vascular hypertrophy, vascular remodeling including vascular stiffness, atherosclerosis, peripheral arterial occlusive disease (PAOD), restenosis, thrombosis and vascular permeability disorders, ischemia and/or reperfusion damage including ischemia and/or reperfusion damage of the heart, kidney and retina Beside these four major areas of uses, APJ modulators may be useful in pulmonary, liver, renal and retinal diseases, such as chronic obstructive pulmonary disease (COPD), asthma, acute respiratory dystress syndrome (ARDS), liver cirrhosis, and macular degeneration;

The treatment of diseases is to be understood as meaning both the therapy of existing pathological changes or malfunctions of the organism or of existing symptoms with the aim of relief, alleviation or cure, and the prophylaxis or prevention of pathological changes or malfunctions of the organism or of symptoms in humans or animals which are susceptible thereto and are in need of such a prophylaxis or prevention, with the aim of a prevention or suppression of their occurrence or of an attenuation in the case of their occurrence. For example, in patients who on account of their disease history are susceptible to myocardial infarction, by means of the prophylactic or preventive medicinal treatment the occurrence or re-occurrence of a myocardial infarction can be prevented or its extent and sequalae decreased, or in patients who are susceptible to attacks of asthma, by means of the prophylactic or preventive medicinal treatment such attacks can be prevented or their severity decreased. The treatment of diseases can occur both in acute cases and in chronic cases.

Combination with Other Pharmacological Actives

The compounds of the formula I and their physiologically acceptable salts and solvates can also be used in combination with other pharmaceutical active compounds, especially those approved for the treatment in the named major area of uses. In such a combination use the compounds of the formula I and/or their physiologically acceptable salts and/or solvates and one or more other pharmaceutical active compounds can be present in one and the same pharmaceutical composition or in two or more pharmaceutical compositions for separate, simultaneous or sequential administration.

They can be combined with an inventive compound of the formula I, especially for a synergistic improvement in action. The active ingredient combination can be administered either by separate administration of the active ingredients to the patient or in the form of combination products in which a plurality of active ingredients are present in one pharmaceutical preparation. When the active ingredients are administered by separate administration of the active ingredients, this can be done simultaneously or successively. Most of the active ingredients mentioned hereinafter are disclosed in the USP Dictionary of USAN and International Drug Names, US Pharmacopeia, Rockville 2006 or Rote Liste 2011.

A subject of the present invention also is the said combination use of any one or more of the compounds of the formula I disclosed herein and their physiologically acceptable salts and solvates, with any one or more, for example one or two, of the mentioned other pharmaceutical active compounds.

Examples of combination of compounds of the formula I with cardiovascular active compounds include all aldosterone antagonists, aquaretics, angiotensin converting enzyme (ACE) inhibitors, angiotensin receptor blockers, beta blockers, digoxin, nitric oxide donors, nitrates, hydralazines, ionotropes, vasopressin receptor antagonists, soluble guanylate cyclase activators, statins, anti-arrhythmics, endothelin receptor antagonists, calcium antagonists, phosphodiesterase inhibitors including phosphodiesterase type 5 (PDE5) inhibitors, and renin inhibitors. Examples are further all approved anti-hypertensives and nephro-protectives, e.g. as mentioned in the Rote Liste 2011, and all diuretics as mentioned in the Rote Liste 2011, chapter 36;

Examples of such other pharmaceutical active compounds in the area of metabolic dysfunction and diabetes are all pharmaceutical active compounds approved to treat such diseases. Among them are insulin and insulin derivatives, for example Lantus® Levemir® (insulin detemir), Humalog® (Insulin Lispro), insulin degludec, insulin aspart, polyethylene glycosidized (PEGylated) Insulin Lispro as described in WO2009152128, Flumulin™, VIAject™, SuliXen™, VIAject™ or those as described in WO2005005477 (Novo Nordisk), fast-acting insulins (see U.S. Pat. No. 6,221,633), inhalable insulins, for example Exubera®, Nasulin™, or oral insulins, for example IN-105 (Nobex) or Oral-lyn™ (Generex Biotechnology), or Technosphere® insulin (MannKind) or Cobalamin™ oral insulin or ORMD-0801 or insulins or insulin precursors as described in WO2007128815, WO2007128817, WO2008034881, WO2008049711, WO2008145721, WO2009034117, WO2009060071, WO2009133099 or insulins which can be administered transdermally; additionally included are also those insulin derivatives which are bonded to albumin by a bifunctional linker, as described, for example, in WO2009121884; Furthermore combination of the compounds of the formula I with GLP-1 derivatives and GLP-1 agonists are useful. Examples are exenatide or specific formulations thereof, as described, for example, in WO2008061355, WO2009080024, WO2009080032, liraglutide, taspoglutide (R-1583), albiglutide, lixisenatide or those which have been disclosed in WO 98/08871, WO2005027978, WO2006037810 by Novo Nordisk A/S, in WO 01/04156 by Zealand or in WO 00/34331 by Beaufour-Ipsen, pramlintide acetate (Symlin; Amylin Pharmaceuticals), inhalable GLP-1 (MKC-253 from MannKind), AVE-0010, BIM-51077 (R-1583, ITM-077), PC-DAC:exendin-4 (an exendin-4 analog which is bonded covalently to recombinant human albumin), biotinylated exendin (WO2009107900), a specific formulation of exendin-4 as described in US2009238879, CVX-73, CVX-98 and CVx-96 (GLP-1 analogs which are bonded covalently to a monoclonal antibody which has specific binding sites for the GLP-1 peptide), CNTO-736 (a GLP-1 analog which is bonded to a domain which includes the Fc portion of an antibody), PGC-GLP-1 (GLP-1 bonded to a nanocarrier), agonists or modulators, as described, for example, in D. Chen et al., Proc. Natl. Acad. Sci. USA 104 (2007) 943, those as described in WO2006124529, WO2007124461, WO2008062457, WO2008082274, WO2008101017, WO2008081418, WO2008112939, WO2008112941, WO2008113601, WO2008116294, WO2008116648, WO2008119238, WO2008148839, US2008299096, WO2008152403, WO2009030738, WO2009030771, WO2009030774, WO2009035540, WO2009058734, WO2009111700, WO2009125424, WO2009129696, WO2009149148, peptides, for example obinepitide (TM-30338), orally active GLP-1 analogs (e.g. NN9924 from Novo Nordisk), amylin receptor agonists, as described, for example, in WO2007104789, WO2009034119, analogs of the human GLP-1, as described in WO2007120899, WO2008022015, WO2008056726, chimeric pegylated peptides containing both GLP-1 and glucagon residues, as described, for example, in WO2008101017, WO2009155257, WO2009155258, glycosylated GLP-1 derivatives as described in WO2009153960, and orally active hypoglycemic ingredients.

Antidiabetics additionally include poly- or monoclonal antibodies directed, for example, against interleukin 1 beta (IL-1β), for example XOMA-052. Antidiabetics additionally include peptides which can bind to the human pro-islet peptide (HIP) receptor, as described, for example, in WO2009049222. Antidiabetics also include agonists of the glucose-dependent insulinotropic polypeptide (GIP) receptor, as described, for example, in WO2006121860. Antidiabetics also include the glucose-dependent insulinotropic polypeptide (GIP), and also analogous compounds, as described, for example, in WO2008021560, WO2010016935, WO2010016936, WO2010016938, WO2010016940, WO2010016944. Additionally included are analogs and theivatives of human pancreatic polypeptide, as described, for example, in WO2009007714. Antidiabetics additionally include encapsulated insulin-producing porcine cells, for example DiabeCell®. Antidiabetics also include analogs and derivatives of fibroblast growth factor 21 (FGF-21), as described, for example, in WO2009149171, WO2010006214.

Combination of the compounds of the formula I with antidiabetics also include orally active hypoglycemic ingredients preferably include sulfonylureas, biguanidines, meglitinides, oxadiazolidinediones, thiazolidinediones, PPAR and RXR modulators, inhibitors of dipeptidyl peptidase-IV (DPP-IV), insulin sensitizers, glucosidase inhibitors, inhibitors of glycogen phosphorylase, glucagon receptor antagonists, glucokinase activators, inhibitors of fructose 1,6-bisphosphatase, modulators of glucose transporter 4 (GLUT4), inhibitors of glutamine:fructose-6-phosphate amidotransferase (GFAT), orally active GLP-1 agonists.

Combination of the compounds of the formula I with potassium channel openers are useful, for example pinacidil, cromakalim, diazoxide, diazoxide choline salt, or those as described in R. D. Carr et al., Diabetes 52, 2003, 2513.2518, in J. B. Hansen et al., Current Medicinal Chemistry 11, 2004, 1595-1615, in T. M. Tagmose et al., J. Med. Chem. 47, 2004, 3202-3211 or in M. J. Coghlan et al., J. Med. Chem. 44, 2001, 1627-1653, or those which have been disclosed in WO 97/26265 and WO 99/03861 by Novo Nordisk A/S, and active ingredients which act on the ATP-dependent potassium channel of the beta cells, In one embodiment of the invention, the compound of the formula I is administered in combination with insulin.

In another embodiment of the invention, the compound of the formula I is administered in combination with an insulin sensitizer, for example PN-2034 or ISIS-113715.

In one embodiment, the compound of the formula I is administered in combination with an active ingredient which acts on the ATP-dependent potassium channel of the beta cells, for example sulfonylureas, for example tolbutamide, glibenclamide, glipizide, gliclazide or glimepiride, or those formulations as described, for example, in EP2103302.

In one embodiment, the compound of the formula I is administered in combination with a tablet which comprises both glimepiride, which is released rapidly, and metformin, which is released over a longer period (as described, for example, in US2007264331, WO2008050987, WO2008062273).

In one embodiment, the compound of the formula I is administered in combination with a biguanide, for example metformin or one of its salts.

In a further embodiment, the compound of the formula I is administered in combination with a guanidine, for example benzylguanidine or one of its salts, or those guanidines as described in WO2009087395.

In another embodiment, the compound of the formula I is administered in combination with a meglitinide, for example repaglinide, nateglinide or mitiglinide.

In a further embodiment, the compound of the formula I is administered with a combination of mitiglinide with a glitazone, e.g. pioglitazone hydrochloride.

In a further embodiment, the compound of the formula I is administered with a combination of mitiglinide with an alpha-glucosidase inhibitor.

In a further embodiment, the compound of the formula I is administered in combination with antidiabetic compounds, as described in WO2007095462, WO2007101060, WO2007105650.

In a further embodiment, the compound of the formula I is administered in combination with antihypoglycemic compounds, as described in WO2007137008, WO2008020607.

In one embodiment, the compound of the formula I is administered in combination with a thiazolidinedione, for example troglitazone, ciglitazone, pioglitazone, rosiglitazone or the compounds disclosed in WO 97/41097 by Dr. Reddy's Research Foundation, especially 5-[[4-[(3,4-dihydro-3-methyl-4-oxo-2-quinazolinylmethoxy]-phenyl]methyl]-2,4-thiazolidinedione.

In one embodiment of the invention, the compound of the formula I is administered in combination with a PPAR gamma agonist, for example rosiglitazone, pioglitazone, JTT-501, GI 262570, R-483, CS-011 (rivoglitazone), DRL-17564, DRF-2593 (balaglitazone), INT-131, T-2384, or those as described in WO2005086904, WO2007060992, WO2007100027, WO2007103252, WO2007122970, WO2007138485, WO2008006319, WO2008006969, WO2008010238, WO2008017398, WO2008028188, WO2008066356, WO2008084303, WO2008089461-WO2008089464, WO2008093639, WO2008096769, WO2008096820, WO2008096829, US2008194617, WO2008099944, WO2008108602, WO2008109334, WO2008110062, WO2008126731, WO2008126732, WO2008137105, WO2009005672, WO2009038681, WO2009046606, WO2009080821, WO2009083526, WO2009102226, WO2009128558, WO2009139340.

In one embodiment of the invention, the compound of the formula I is administered in combination with Competact™, a solid combination of pioglitazone hydrochloride with metformin hydrochloride.

In one embodiment of the invention, the compound of the formula I is administered in combination with Tandemact™, a solid combination of pioglitazone with glimepiride.

In a further embodiment of the invention, the compound of the formula I is administered in combination with a solid combination of pioglitazone hydrochloride with an angiotensin II agonist, for example TAK-536.

In one embodiment of the invention, the compound of the formula I is administered in combination with a PPAR alpha agonist or mixed PPAR alpha/PPAR delta agonist, for example GW9578, GW-590735, K-111, LY-674, KRP-101, DRF-10945, LY-518674, CP-900691, BMS-687453, BMS-711939, or those as described in WO2001040207, WO2002096894, WO2005097076, WO2007056771, WO2007087448, WO2007089667, WO2007089557, WO2007102515, WO2007103252, JP2007246474, WO2007118963, WO2007118964, WO2007126043, WO2008006043, WO2008006044, WO2008012470, WO2008035359, WO2008087365, WO2008087366, WO2008087367, WO2008117982, JP2009023975, WO2009033561, WO2009047240, WO2009072581, WO2009080248, WO2009080242, WO2009149819, WO2009149820, WO2009147121, WO2009153496, WO2010008299, WO2010014771.

In one embodiment of the invention, the compound of the formula I is administered in combination with a mixed PPAR alpha/gamma agonist, for example naveglitazar, aleglitazar, LY-510929, ONO-5129, E-3030, AVE 8042, AVE 8134, AVE 0847, AVE 0897, CKD-501 (lobeglitazone sulfate), MBX-213, KY-201, BMS-759509, or as described in WO 00/64888, WO 00/64876, WO03/020269, WO2004024726, WO2007099553, US2007276041, WO2007085135, WO2007085136, WO2007141423, WO2008016175, WO2008053331, WO2008109697, WO2008109700, WO2008108735, WO2009026657, WO2009026658, WO2009149819, WO2009149820 or in J. P. Berger et al., TRENDS in Pharmacological Sciences 28(5), 244-251, 2005.

In one embodiment of the invention, the compound of the formula I is administered in combination with a PPAR delta agonist, for example GW-501516, or as described in WO2006059744, WO2006084176, WO2006029699, WO2007039172-WO2007039178, WO2007071766, WO2007101864, US2007244094, WO2007119887, WO2007141423, US2008004281, WO2008016175, WO2008066356, WO2008071311, WO2008084962, US2008176861, WO2009012650, US2009137671, WO2009080223, WO2009149819, WO2009149820, WO2010000353.

In one embodiment of the invention, the compound of the formula I is administered in combination with a pan-SPPARM (selective PPAR modulator alpha, gamma, delta), for example GFT-505, indeglitazar, or those as described in WO2008035359, WO2009072581.

In one embodiment, the compound of the formula I is administered in combination with metaglidasen or with MBX-2044 or other partial PPAR gamma agonists/antagonists.

In one embodiment, the compound of the formula I is administered in combination with an α-glucosidase inhibitor, for example miglitol or acarbose, or those as described, for example, in WO2007114532, WO2007140230, US2007287674, US2008103201, WO2008065796, WO2008082017, US2009076129.

In one embodiment, the compound of the formula I is administered in combination with an inhibitor of glycogen phosphorylase, for example PSN-357 or FR-258900, or those as described in WO2003084922, WO2004007455, WO2005073229-31, WO2005067932, WO2008062739, WO2008099000, WO2008113760, WO2009016118, WO2009016119, WO2009030715, WO2009045830, WO2009045831, WO2009127723.

In another embodiment, the compound of the formula I is administered in combination with an inhibitor of the interaction of liver glycogen phosphorylase with the protein PPP1R3 (GL subunit of glycogen-associated protein phosphatase 1 (PP1)), as described, for example, in WO2009030715.

In one embodiment, the compound of the formula I is administered in combination with glucagon receptor antagonists, for example A-770077 or NNC-25-2504 or as described in WO2004100875, WO2005065680, WO2006086488, WO2007047177, WO2007106181, WO2007111864, WO2007120270, WO2007120284, WO2007123581, WO2007136577, WO2008042223, WO2008098244, WO2009057784, WO2009058662, WO2009058734, WO2009110520, WO2009120530, WO2009140342, WO2010019828.

In a further embodiment, the compound of the formula I is administered in combination with an antisense compound, e.g. ISIS-325568, which inhibits the production of the glucagon receptor.

In one embodiment, the compound of the formula I is administered in combination with activators of glucokinase, for example LY-2121260 (WO2004063179), PSN-105, PSN-110, GKA-50, or those as described, for example, in WO2004072031, WO2004072066, WO2005080360, WO2005044801, WO2006016194, WO2006058923, WO2006112549, WO2006125972, WO2007017549, WO2007017649, WO2007007910, WO2007007040-42, WO2007006760-61, WO2007006814, WO2007007886, WO2007028135, WO2007031739, WO2007041365, WO2007041366, WO2007037534, WO2007043638, WO2007053345, WO2007051846, WO2007051845, WO2007053765, WO2007051847, WO2007061923, WO2007075847, WO2007089512, WO2007104034, WO2007117381, WO2007122482, WO2007125103, WO2007125105, US2007281942, WO2008005914, WO2008005964, WO2008043701, WO2008044777, WO2008047821, US2008096877, WO2008050117, WO2008050101, WO2008059625, US2008146625, WO2008078674, WO2008079787, WO2008084043, WO2008084044, WO2008084872, WO2008089892, WO2008091770, WO2008075073, WO2008084043, WO2008084044, WO2008084872, WO2008084873, WO2008089892, WO2008091770, JP2008189659, WO2008104994, WO2008111473, WO2008116107, WO2008118718, WO2008120754, US2008280875, WO2008136428, WO2008136444, WO2008149382, WO2008154563, WO2008156174, WO2008156757, US2009030046, WO2009018065, WO2009023718, WO2009039944, WO2009042435, WO2009046784, WO2009046802, WO2009047798, WO2009063821, WO2009081782, WO2009082152, WO2009083553, WO2009091014, US2009181981, WO2009092432, WO2009099080, WO2009106203, WO2009106209, WO2009109270, WO2009125873, WO2009127544, WO2009127546, WO2009128481, WO2009133687, WO2009140624, WO2010013161, WO2010015849, WO2010018800.

In one embodiment, the compound of the formula I is administered in combination with an inhibitor of gluconeogenesis, as described, for example, in FR-225654, WO2008053446.

In one embodiment, the compound of the formula I is administered in combination with inhibitors of fructose 1,6-bisphosphatase (FBPase), for example MB-07729, CS-917 (MB-06322) or MB-07803, or those as described in WO2006023515, WO2006104030, WO2007014619, WO2007137962, WO2008019309, WO2008037628, WO2009012039, EP2058308, WO2009068467, WO2009068468.

In one embodiment, the compound of the formula I is administered in combination with modulators of glucose transporter 4 (GLUT4), for example KST-48 (D.-O. Lee et al.: Arzneim.-Forsch. Drug Res. 54 (12), 835 (2004)).

In one embodiment, the compound of the formula I is administered in combination with inhibitors of glutamine: fructose-6-phosphate amidotransferase (GFAT), as described, for example, in WO2004101528.

In one embodiment, the compound of the formula I is administered in combination with inhibitors of dipeptidyl peptidase-IV (DPP-IV), for example vildagliptin (LAF-237), sitagliptin (MK-0431), sitagliptin phosphate, saxagliptin (BMS-477118), GSK-823093, PSN-9301, SYR-322, SYR-619, TA-6666, TS-021, GRC-8200 (melogliptin), GW-825964X, KRP-104, DP-893, ABT-341, ABT-279 or another salt thereof, S-40010, S-40755, PF-00734200, BI-1356, PHX-1149, DSP-7238, alogliptin benzoate, linagliptin, melogliptin, carmegliptin, or those compounds as described in WO2003074500, WO2003106456, WO2004037169, WO200450658, WO2005037828, WO2005058901, WO2005012312, WO2005/012308, WO2006039325, WO2006058064, WO2006015691, WO2006015701, WO2006015699, WO2006015700, WO2006018117, WO2006099943, WO2006099941, JP2006160733, WO2006071752, WO2006065826, WO2006078676, WO2006073167, WO2006068163, WO2006085685, WO2006090915, WO2006104356, WO2006127530, WO2006111261, US2006890898, US2006803357, US2006303661, WO2007015767 (LY-2463665), WO2007024993, WO2007029086, WO2007063928, WO2007070434, WO2007071738, WO2007071576, WO2007077508, WO2007087231, WO2007097931, WO2007099385, WO2007100374, WO2007112347, WO2007112669, WO2007113226, WO2007113634, WO2007115821, WO2007116092, US2007259900, EP1852108, US2007270492, WO2007126745, WO2007136603, WO2007142253, WO2007148185, WO2008017670, US2008051452, WO2008027273, WO2008028662, WO2008029217, JP2008031064, JP2008063256, WO2008033851, WO2008040974, WO2008040995, WO2008060488, WO2008064107, WO2008066070, WO2008077597, JP2008156318, WO2008087560, WO2008089636, WO2008093960, WO2008096841, WO2008101953, WO2008118848, WO2008119005, WO2008119208, WO2008120813, WO2008121506, WO2008130151, WO2008131149, WO2009003681, WO2009014676, WO2009025784, WO2009027276, WO2009037719, WO2009068531, WO2009070314, WO2009065298, WO2009082134, WO2009082881, WO2009084497, WO2009093269, WO2009099171, WO2009099172, WO2009111239, WO2009113423, WO2009116067, US2009247532, WO2010000469, WO2010015664.

In one embodiment, the compound of the formula I is administered in combination with Janumet™, a solid combination of sitagliptin phosphate with metformin hydrochloride.

In one embodiment, the compound of the formula I is administered in combination with Eucreas®, a solid combination of vildagliptin with metformin hydrochloride.

In a further embodiment, the compound of the formula I is administered in combination with a solid combination of alogliptin benzoate with pioglitazone.

In one embodiment, the compound of the formula I is administered in combination with a solid combination of a salt of sitagliptin with metformin hydrochloride.

In one embodiment, the compound of the formula I is administered in combination with a combination of a DPP-IV inhibitor with omega-3 fatty acids or omega-3 fatty acid esters, as described, for example, in WO2007128801.

In one embodiment, the compound of the formula I is administered in combination with a combination of a DPP-IV inhibitor with metformin hydrochloride, as described, for example, in WO2009121945.

In one embodiment, the compound of the formula I is administered in combination with a combination of a DPP-IV inhibitor with a GPR-119 agonist, as described, for example, in WO2009123992.

In one embodiment, the compound of the formula I is administered in combination with a combination of a DPP-IV inhibitor with miglitol, as described, for example, in WO2009139362.

In one embodiment, the compound of the formula I is administered in combination with a solid combination of a salt of sitagliptin with metformin hydrochloride.

In one embodiment, the compound of the formula I is administered in combination with a solid combination of alopliptin benzoate with pioglitazone hydrochloride.

In one embodiment, the compound of the formula I is administered in combination with a substance which enhances insulin secretion, for example KCP-265 (WO2003097064), or those as described in WO2007026761, WO2008045484, US2008194617, WO2009109259, WO2009109341.

In one embodiment, the compound of the formula I is administered in combination with agonists of the glucose-dependent insulinotropic receptor (GDIR), for example APD-668.

In one embodiment of the invention, the compound of the formula I is administered in combination with an ATP citrate lyase inhibitor, for example SB-204990.

In one embodiment, the compound of the formula I is administered in combination with modulators of the sodium-dependent glucose transporter 1 and/or 2 (SGLT1, SGLT2), for example KGA-2727, T-1095, SGL-0010, AVE 2268, SAR 7226, SGL-5083, SGL-5085, SGL-5094, ISIS-388626, sergliflozin, dapagliflozin or remogliflozin etabonate, canagliflozin, or as described, for example, in WO2004007517, WO200452903, WO200452902, PCT/EP2005/005959, WO2005085237, JP2004359630, WO2005121161, WO2006018150, WO2006035796, WO2006062224, WO2006058597, WO2006073197, WO2006080577, WO2006087997, WO2006108842, WO2007000445, WO2007014895, WO2007080170, WO2007093610, WO2007126117, WO2007128480, WO2007129668, US2007275907, WO2007136116, WO2007143316, WO2007147478, WO2008001864, WO2008002824, WO2008013277, WO2008013280, WO2008013321, WO2008013322, WO2008016132, WO2008020011, JP2008031161, WO2008034859, WO2008042688, WO2008044762, WO2008046497, WO2008049923, WO2008055870, WO2008055940, WO2008069327, WO2008070609, WO2008071288, WO2008072726, WO2008083200, WO2008090209, WO2008090210, WO2008101586, WO2008101939, WO2008116179, WO2008116195, US2008242596, US2008287529, WO2009026537, WO2009049731, WO2009076550, WO2009084531, WO2009096503, WO2009100936, WO2009121939, WO2009124638, WO2009128421, WO2009135673, WO2010009197, WO2010018435, WO2010018438, WO2011023755 or by A. L. Handlon in Expert Opin. Ther. Patents (2005) 15(11); 1531-1540.

In a further embodiment of the invention, the compound of the formula I is administered in combination with a solid combination of an SGLT inhibitor with a DPP-IV inhibitor, as described in WO2009091082.

In one embodiment, the compound of the formula I is administered in combination with a stimulator of glucose transport, as described, for example, in WO2008136392, WO2008136393.

In one embodiment, the compound of the formula I is administered in combination with inhibitors of 11-beta-hydroxysteroid dehydrogenase 1 (11β-HSD1), for example BVT-2733, JNJ-25918646, INCB-13739, INCB-20817, DIO-92 ((−)-ketoconazole) or those as described, for example, in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004058730, WO2004065351, WO2004089367, WO2004089380, WO2004089470-71, WO2004089896, WO2005016877, WO2005063247, WO2005097759, WO2006010546, WO2006012227, WO2006012173, WO2006017542, WO2006034804, WO2006040329, WO2006051662, WO2006048750, WO2006049952, WO2006048331, WO2006050908, WO2006024627, WO2006040329, WO2006066109, WO2006074244, WO2006078006, WO2006106423, WO2006132436, WO2006134481, WO2006134467, WO2006135795, WO2006136502, WO2006138508, WO2006138695, WO2006133926, WO2007003521, WO2007007688, US2007066584, WO2007029021, WO2007047625, WO2007051811, WO2007051810, WO2007057768, WO2007058346, WO2007061661, WO2007068330, WO2007070506, WO2007087150, WO2007092435, WO2007089683, WO2007101270, WO2007105753, WO2007107470, WO2007107550, WO2007111921, US2007207985, US2007208001, WO2007115935, WO2007118185, WO2007122411, WO2007124329, WO2007124337, WO2007124254, WO2007127688, WO2007127693, WO2007127704, WO2007127726, WO2007127763, WO2007127765, WO2007127901, US2007270424, JP2007291075, WO2007130898, WO2007135427, WO2007139992, WO2007144394, WO2007145834. WO2007145835, WO2007146761, WO2008000950, WO2008000951, WO2008003611, WO2008005910, WO2008006702, WO2008006703, WO2008011453, WO2008012532, WO2008024497, WO2008024892, WO2008032164, WO2008034032, WO2008043544, WO2008044656, WO2008046758, WO2008052638, WO2008053194, WO2008071169, WO2008074384, WO2008076336, WO2008076862, WO2008078725, WO2008087654, WO2008088540, WO2008099145, WO2008101885, WO2008101886, WO2008101907, WO2008101914, WO2008106128, WO2008110196, WO2008119017, WO2008120655, WO2008127924, WO2008130951, WO2008134221, WO2008142859, WO2008142986, WO2008157752, WO2009001817, WO2009010416, WO2009017664, WO2009020140, WO2009023180, WO2009023181, WO2009023664, WO2009026422, WO2009038064, WO2009045753, WO2009056881, WO2009059666, WO2009061498, WO2009063061, WO2009070497, WO2009074789, WO2009075835, WO2009088997, WO2009090239, WO2009094169, WO2009098501, WO2009100872, WO2009102428, WO2009102460, WO2009102761, WO2009106817, WO2009108332, WO2009112691, WO2009112845, WO2009114173, WO2009117109, US2009264401, WO2009118473, WO2009131669, WO2009132986, WO2009134384, WO2009134387, WO2009134392, WO2009134400, WO2009135581, WO2009138386, WO2010006940, WO2010010157, WO2010010174, WO2010011917.

In one embodiment, the compound of the formula I is administered in combination with inhibitors of protein tyrosine phosphatase-1B (PTP-1B), as described, for example, in WO200119830-31, WO200117516, WO2004506446, WO2005012295, WO2005116003, WO2005116003, WO2006007959, DE 10 2004 060542A, WO2007009911, WO2007028145, WO2007067612-615, WO2007081755, WO2007115058, US2008004325, WO2008033455, WO2008033931, WO2008033932, WO2008033934, WO2008089581, WO2008148744, WO2009032321, WO2009109999, WO2009109998.

In a further embodiment, the compound of the formula I is administered in combination with stimulators of tyrosine kinase B (Trk-B), as described, for example, in WO2010014613.

In a further embodiment, the compound of the formula I is administered in combination with beta 3 agonists (also called beta-3 adrenoceptor agonists), as described, for example, in Physiol. Behav. 2004 Sep. 15; 82(2-3):489-96, J Clin Invest (1998) 101: 2387-93, Curr. Pharma. Des. 2001 September; 7(14):1433-49, Bioorganic & Medicinal Chemistry Letters volume 14, number 13, Jul. 5, 2004, pages 3525-3529 (BMS-201620).

In one embodiment of the invention, the compound of the formula I is administered in combination with an agonist of GPR109A (HM74A receptor agonists; NAR agonists (nicotinic acid receptor agonists)), for example nicotinic acid or extended release niacin in conjunction with MK-0524A (laropiprant) or MK-0524, or those compounds as described in WO2004041274, WO2006045565, WO2006045564, WO2006069242, WO2006085108, WO2006085112, WO2006085113, WO2006124490, WO2006113150, WO2007002557, WO2007017261, WO2007017262, WO2007017265, WO2007015744, WO2007027532, WO2007092364, WO2007120575, WO2007134986, WO2007150025, WO2007150026, WO2008016968, WO2008051403, WO2008086949, WO2008091338, WO2008097535, WO2008099448, US2008234277, WO2008127591.

In another embodiment of the invention, the compound of the formula I is administered in combination with a solid combination of niacin with simvastatin.

In another embodiment of the invention, the compound of the formula I is administered in combination with nicotinic acid or "extended release niacin" in conjunction with MK-0524A (laropiprant).

In a further embodiment of the invention, the compound of the formula I is administered in combination with nicotinic acid or "extended release niacin" in conjunction with MK-0524A (laropiprant) and with simvastatin.

In one embodiment of the invention, the compound of the formula I is administered in combination with nicotinic acid or another nicotinic acid receptor agonist and a prostaglandin DP receptor antagonist, for example those as described in WO2008039882.

In another embodiment of the invention, the compound of the formula I is administered in combination with a solid combination of niacin with meloxicam, as described, for example, in WO2009149056.

In another embodiment of the invention, the compound of the formula I is administered in combination with an agonist of GPR116, as described, for example, in WO2006067531, WO2006067532.

In one embodiment, the compound of the formula I is administered in combination with modulators of GPR40, as described, for example, in WO2007013689, WO2007033002, WO2007106469, US2007265332, WO2007123225, WO2007131619, WO2007131620, WO2007131621, US2007265332, WO2007131622, WO2007136572, WO2008001931, WO2008030520, WO2008030618, WO2008054674, WO2008054675, WO2008066097, US2008176912, WO2008130514, WO2009038204, WO2009039942, WO2009039943, WO2009048527, WO2009054479, WO2009058237, WO2009111056, WO2010012650.

In one embodiment, the compound of the formula I is administered in combination with modulators of GPR119 (G-protein-coupled glucose-dependent insulinotropic receptor), for example PSN-119-1, PSN-821, PSN-119-2, MBX-2982 or those as described, for example, in WO2004065380, WO2005061489 (PSN-632408), WO2006083491, WO2007003960-62 and WO2007003964, WO2007035355, WO2007116229, WO2007116230, WO2008005569, WO2008005576, WO2008008887, WO2008008895, WO2008025798, WO2008025799, WO2008025800, WO2008070692, WO2008076243, WO200807692, WO2008081204, WO2008081205, WO2008081206, WO2008081207, WO2008081208, WO2008083238, WO2008085316, WO2008109702, WO2008130581, WO2008130584, WO2008130615, WO2008137435, WO2008137436, WO2009012275, WO2009012277, WO2009014910, WO2009034388, WO2009038974, WO2009050522, WO2009050523, WO2009055331, WO2009105715, WO2009105717, WO2009105722, WO2009106561, WO2009106565, WO2009117421, WO2009125434, WO2009126535, WO2009129036, US2009286812, WO2009143049, WO2009150144, WO2010001166, WO2010004343, WO2010004344, WO2010004345, WO2010004346, WO2010004347, WO2010004348, WO2010008739, WO2010006191, WO2010009183, WO2010009195, WO2010009207, WO2010009208, WO2010014593.

In a further embodiment, the compound of the formula I is administered in combination with modulators of GPR120, as described, for example, in EP1688138, WO2008066131, WO2008066131, WO2008103500, WO2008103501, WO2008139879, WO2009038204, WO2009147990, WO2010008831.

In another embodiment, the compound of the formula I is administered in combination with antagonists of GPR105, as described, for example, in WO2009000087, WO2009070873.

In a further embodiment, the compound of the formula I is administered in combination with agonists of GPR43, for example ESN-282.

In one embodiment, the compound of the formula I is administered in combination with inhibitors of hormone-sensitive lipase (HSL) and/or phospholipases, as described, for example, in WO2005073199, WO2006074957, WO2006087309, WO2006111321, WO2007042178, WO2007119837, WO2008122352, WO2008122357, WO2009009287.

In one embodiment, the compound of the formula I is administered in combination with inhibitors of endothelial lipase, as described, for example, in WO2007045393, WO2007110216, WO2011157827.

In one embodiment, the compound of the formula I is administered in combination with a phospholipase A2 inhibitor, for example darapladib or A-002, or those as described in WO2008048866, WO20080488867, US2009062369.

In one embodiment, the compound of the formula I is administered in combination with myricitrin, a lipase inhibitor (WO2007119827).

In one embodiment, the compound of the formula I is administered in combination with an inhibitor of glycogen synthase kinase-3 beta (GSK-3 beta), as described, for example, in US2005222220, WO2005085230, WO2005111018, WO2003078403, WO2004022544, WO2003106410, WO2005058908, US2005038023, WO2005009997, US2005026984, WO2005000836, WO2004106343, EP1460075, WO2004014910, WO2003076442, WO2005087727, WO2004046117, WO2007073117, WO2007083978, WO2007120102, WO2007122634, WO2007125109, WO2007125110, US2007281949, WO2008002244, WO2008002245, WO2008016123, WO2008023239, WO2008044700, WO2008056266, WO2008057940, WO2008077138, EP1939191, EP1939192, WO2008078196, WO2008094992, WO2008112642, WO2008112651, WO2008113469, WO2008121063, WO2008121064, EP-1992620, EP-1992621, EP1992624, EP-1992625, WO2008130312, WO2009007029, EP2020232, WO2009017452, WO2009035634, WO2009035684, WO2009038385, WO2009095787, WO2009095788, WO2009095789, WO2009095792, WO2009145814, US2009291982, WO2009154697, WO2009156857, WO2009156859, WO2009156860, WO2009156861, WO2009156863, WO2009156864, WO2009156865, WO2010013168, WO2010014794.

In one embodiment, the compound of the formula I is administered in combination with an inhibitor of phosphoenolpyruvate carboxykinase (PEPCK), for example those as described in WO2004074288.

In one embodiment, the compound of the formula I is administered in combination with an inhibitor of phosphoinositide kinase-3 (PI3K), for example those as described in WO2008027584, WO2008070150, WO2008125833, WO2008125835, WO2008125839, WO2009010530, WO2009026345, WO2009071888, WO2009071890, WO2009071895.

In one embodiment, the compound of the formula I is administered in combination with an inhibitor of serum/glucocorticoid-regulated kinase (SGK), as described, for example, in WO2006072354, WO2007093264, WO2008009335, WO2008086854, WO2008138448.

In one embodiment, the compound of the formula I is administered in combination with a modulator of the glucocorticoid receptor, as described, for example, in WO2008057855, WO2008057856, WO2008057857, WO2008057859, WO2008057862, WO2008059867, WO2008059866, WO2008059865, WO2008070507, WO2008124665, WO2008124745, WO2008146871, WO2009015067, WO2009040288, WO2009069736, WO2009149139.

In one embodiment, the compound of the formula I is administered in combination with a modulator of the mineralocorticoid receptor (MR), for example drospirenone, or those as described in WO2008104306, WO2008119918.

In one embodiment, the compound of the formula I is administered in combination with an inhibitor of protein kinase C beta (PKC beta), for example ruboxistaurin, or those as described in WO2008096260, WO2008125945.

In one embodiment, the compound of the formula I is administered in combination with an inhibitor of protein kinase D, for example doxazosin (WO2008088006).

In a further embodiment, the compound of the formula I is administered in combination with an activator/modulator of the AMP-activated protein kinase (AMPK), as described, for example, in WO2007062568, WO2008006432, WO2008016278, WO2008016730, WO2008020607, WO2008083124, WO2008136642, WO2009019445, WO2009019446, WO2009019600, WO2009028891, WO2009065131, WO2009076631, WO2009079921, WO2009100130, WO2009124636, WO2009135580, WO2009152909.

In one embodiment, the compound of the formula I is administered in combination with an inhibitor of ceramide kinase, as described, for example, in WO2007112914, WO2007149865.

In a further embodiment, the compound of the formula I is administered in combination with an inhibitor of MAPK-interacting kinase 1 or 2 (MNK1 or 2), as described, for example, in WO2007104053, WO2007115822, WO2008008547, WO2008075741.

In one embodiment, the compound of the formula I is administered in combination with inhibitors of "I-kappaB kinase" (IKK inhibitors), as described, for example, in WO2001000610, WO2001030774, WO2004022057, WO2004022553, WO2005097129, WO2005113544, US2007244140, WO2008099072, WO2008099073, WO2008099073, WO2008099074, WO2008099075, WO2009066693, WO2009075277, WO2009089042, WO2009120801.

In another embodiment, the compound of the formula I is administered in combination with inhibitors of NF-kappaB (NFKB) activation, for example salsalate.

In a further embodiment, the compound of the formula I is administered in combination with inhibitors of ASK-1 (apoptosis signal-regulating kinase 1), as described, for example, in WO2008016131, WO2009123986.

In one embodiment of the invention, the compound of the formula I is administered in combination with an HMG-CoA reductase inhibitor such as simvastatin, fluvastatin, pravastatin, lovastatin, atorvastatin, cerivastatin, rosuvastatin, pitavastatin, L-659699, BMS-644950, NCX-6560, or those as described in US2007249583, WO2008083551, WO2009054682.

In a further embodiment of the invention, the compound of the formula I is administered in combination with a farnesoid X receptor (FXR) modulator, for example WAY-362450 or those as described in WO2003099821, WO2005056554, WO2007052843, WO2007070796, WO2007092751, JP2007230909, WO2007095174, WO2007140174, WO2007140183, WO2008000643, WO2008002573, WO2008025539, WO2008025540, JP2008214222, JP2008273847, WO2008157270, US2008299118, US2008300235, WO2009005998, WO2009012125, WO2009027264, WO2009062874, US2009131409, US2009137554, US2009163552, WO2009127321, EP2128158.

In another embodiment of the invention, the compound of the formula I is administered in combination with a ligand of the liver X receptor (LXR), as described, for example, in WO2007092965, WO2008041003, WO2008049047, WO2008065754, WO2008073825, US2008242677, WO2009020683, US2009030082, WO2009021868, US2009069373, WO2009024550, WO2009040289, WO2009086123, WO2009086129, WO2009086130, WO2009086138, WO2009107387, US2009247587, WO2009133692, WO2008138438, WO2009144961, WO2009150109.

In one embodiment of the invention, the compound of the formula I is administered in combination with a fibrate, for example fenofibrate, clofibrate, bezafibrate, or those as described in WO2008093655.

In one embodiment of the invention, the compound of the formula I is administered in combination with fibrates, for example the choline salt of fenofibrate (SLV-348; Trilipix™).

In one embodiment of the invention, the compound of the formula I is administered in combination with fibrates, for example the choline salt of fenofibrate (Trilipix™) and an HMG-CoA reductase inhibitor, for example rosuvastatin.

In a further embodiment of the invention, the compound of the formula I is administered in combination with bezafibrate and diflunisal.

In a further embodiment of the invention, the compound of the formula I is administered in combination with a solid combination of fenofibrate or a salt thereof with simvastatin, rosuvastatin, fluvastatin, lovastatin, cerivastatin, pravastatin, pitavastatin or atorvastatin.

In a further embodiment of the invention, the compound of the formula I is administered in combination with Synordia®, a solid combination of fenofibrate with metformin.

In another embodiment of the invention, the compound of the formula I is administered in combination with a solid combination of metformin with an MTP inhibitor, as described in WO2009090210.

In one embodiment of the invention, the compound of the formula I is administered in combination with a cholesterol reabsorption inhibitor, for example ezetimibe, tiqueside, pamaqueside, FM-VP4 (sitostanol/campesterol ascorbyl phosphate; Forbes Medi-Tech, WO2005042692, WO2005005453), MD-0727 (Microbia Inc., WO2005021497, WO2005021495) or with compounds as described in WO2002066464, WO2005000353 (Kotobuki Pharmaceutical Co. Ltd.) or WO2005044256 or WO2005062824 (Merck & Co.) or WO2005061451 and WO2005061452 (AstraZeneca AB) and WO2006017257 (Phenomix) or WO2005033100 (Lipideon Biotechnology AG), or as described in WO2002050060, WO2002050068, WO2004000803, WO2004000804, WO2004000805, WO2004087655, WO2004097655, WO2005047248, WO2006086562, WO2006102674, WO2006116499, WO2006121861, WO2006122186, WO2006122216, WO2006127893, WO2006137794, WO2006137796, WO2006137782, WO2006137793, WO2006137797, WO2006137795, WO2006137792, WO2006138163, WO2007059871, US2007232688, WO2007126358, WO2008033431, WO2008033465, WO2008052658, WO2008057336, WO2008085300, WO2008104875, US2008280836, WO2008108486.

In one embodiment of the invention, the compound of the formula I is administered in combination with an NPC1L1 antagonist, for example those as described in WO2008033464, WO2008033465.

In one embodiment of the invention, the compound of the formula I is administered in combination with Vytorin™, a solid combination of ezetimibe with simvastatin.

In one embodiment of the invention, the compound of the formula I is administered in combination with a solid combination of ezetimibe with atorvastatin.

In one embodiment of the invention, the compound of the formula I is administered in combination with a solid combination of ezetimibe with fenofibrate.

In one embodiment of the invention, the further active ingredient is a diphenylazetidinone derivative, as described, for example, in U.S. Pat. No. 6,992,067 or U.S. Pat. No. 7,205,290.

In a further embodiment of the invention, the further active ingredient is a diphenylazetidinone derivative, as described, for example, in U.S. Pat. No. 6,992,067 or U.S. Pat. No. 7,205,290, combined with a statin, for example simvastatin, fluvastatin, pravastatin, lovastatin, cerivastatin, atorvastatin, pitavastatin or rosuvastatin.

In one embodiment of the invention, the compound of the formula t is administered in combination with a solid combination of lapaquistat, a squalene synthase inhibitor, with atorvastatin.

In a further embodiment of the invention, the compound of the formula I is administered in combination with a conjugate consisting of the HMG-CoA reductase inhibitor atorvastatin with the renin inhibitor aliskiren (WO2009090158).

In one embodiment of the invention, the compound of the formula I is administered in combination with a CETP inhibitor, for example torcetrapib, anacetrapib or JTT-705 (dalcetrapib), or those as described in WO2006002342, WO2006010422, WO2006012093, WO2006073973, WO2006072362, WO2007088996, WO2007088999, US2007185058, US2007185113, US2007185154, US2007185182, WO2006097169, WO2007041494, WO2007090752, WO2007107243, WO2007120621, US2007265252, US2007265304, WO2007128568, WO2007132906, WO2008006257, WO2008009435, WO2008018529, WO2008058961, WO2008058967, WO2008059513, WO2008070496, WO2008115442, WO2008111604, WO2008129951, WO2008141077, US2009118287, WO2009062371, WO2009071509.

In one embodiment of the invention, the compound of the formula I is administered in combination with bile acid reabsorption inhibitors (inhibitors of the intestinal bile acid transporter (IBAT)) (see, for example, U.S. Pat. No. 6,245,744, U.S. Pat. No. 6,221,897 or WO00/61568), for example HMR 1741, or those as described in DE 10 2005 033099.1 and DE 10 2005 033100.9, DE 10 2006 053635, DE 10 2006 053637, WO2007009655-56, WO2008058628, WO2008058629, WO2008058630, WO2008058631.

In one embodiment, the compound of the formula I is administered in combination with agonists of GPBAR1 (G-protein-coupled bile acid receptor 1; TGR5), for example INT-777 or those as described, for example, in US20060199795, WO2007110237, WO2007127505, WO2008009407, WO2008067219, WO2008067222, FR2908310, WO2008091540, WO2008097976, US2009054304, WO2009026241, WO2009146772, WO2010014739, WO2010014836.

In one embodiment, the compound of the formula I is administered in combination with modulators of histone deacetylase, for example ursodeoxycholic acid, as described in WO2009011420.

In one embodiment, the compound of the formula I is administered in combination with inhibitors/modulators of the TRPM5 channel (TRP cation channel M5), as described, for example, in WO2008097504, WO2009038722.

In one embodiment, the compound of the formula I is administered in combination with inhibitors/modulators of the TRPA1 channel (TRP cation channel A1), as described, for example, in US2009176883, WO2009089083, WO2009144548.

In one embodiment, the compound of the formula I is administered in combination with inhibitors/modulators of the TRPV3 channel (TRP cation channel V3), as described, for example, in WO2009084034, WO2009130560.

In one embodiment of the invention, the compound of the formula I is administered in combination with a polymeric bile acid adsorber, for example cholestyramine, colesevelam hydrochloride.

In one embodiment of the invention, the compound of the formula I is administered in combination with colesevelam hydrochloride and metformin or a sulfonylurea or insulin.

In one embodiment of the invention, the compound of the formula I is administered in combination with tocotrienol and insulin or an insulin derivative.

In one embodiment of the invention, the compound of the formula I is administered in combination with a chewing gum comprising phytosterols (Reductol™)

In one embodiment of the invention, the compound of the formula I is administered in combination with an inhibitor of the microsomal triglyceride transfer protein (MTP inhibitor), for example implitapide, BMS-201038, R-103757, AS-1552133, SLx-4090, AEGR-733, JTT-130, or those as described in WO2005085226, WO2005121091, WO2006010423, WO2006113910, WO2007143164, WO2008049806, WO2008049808, WO2008090198, WO2008100423, WO2009014674.

In a further embodiment of the invention, the compound of the formula I is administered in combination with a combination of a cholesterol absorption inhibitor, for example ezetimibe, and an inhibitor of the triglyceride transfer protein (MTP inhibitor), for example implitapide, as described in WO2008030382 or in WO2008079398.

In one embodiment of the invention, the compound of the formula I is administered in combination with an active antihypertriglyceridemic ingredient, for example those as described in WO2008032980.

In another embodiment of the invention, the compound of the formula I is administered in combination with an antagonist of the somatostatin 5 receptor (SST5 receptor), for example those as described in WO2006094682.

In one embodiment of the invention, the compound of the formula I is administered in combination with an ACAT inhibitor, for example avasimibe, SMP-797 or KY-382, or those as described in WO2008087029, WO2008087030, WO2008095189, WO2009030746, WO2009030747, WO2009030750, WO2009030752, WO2009070130, WO2009081957, WO2009081957.

In a further embodiment of the invention, the compound of the formula I is administered in combination with an inhibitor of liver carnitine palmitoyltransferase-1 (L-CPT1), as described, for example, in WO2007063012, WO2007096251 (ST-3473), WO2008015081, US2008103182, WO2008074692, WO2008145596, WO2009019199, WO2009156479, WO2010008473.

In another embodiment of the invention, the compound of the formula I is administered in combination with an inhibitor of carnitin O-palmitoyltransferase II (CPT2), as described, for example, in US2009270500, US2009270505, WO2009132978, WO2009132979.

In a further embodiment of the invention, the compound of the formula I is administered in combination with a modulator of serine palmitoyltransferase (SPT), as described, for example, in WO2008031032, WO2008046071, WO2008083280, WO2008084300.

In one embodiment of the invention, the compound of the formula I is administered in combination with a squalene synthetase inhibitor, for example BMS-188494, TAK-475 (lapaquistat acetate), or as described in WO2005077907, JP2007022943, WO2008003424, WO2008132846, WO2008133288, WO2009136396.

In one embodiment of the invention, the compound of the formula I is administered in combination with ISIS-301012 (mipomersen), an antisense oligonucleotide which is capable of regulating the apolipoprotein B gene.

In one embodiment of the invention, the compound of the formula I is administered in combination with apolipoprotein (ApoB) SNALP, a therapeutic product which comprises an siRNA (directed against the ApoB gene).

In one embodiment of the invention, the compound of the formula I is administered in combination with a stimulator of the ApoA-1 gene, as described, for example, in WO2008092231.

In one embodiment of the invention, the compound of the formula I is administered in combination with a modulator of the synthesis of apolipoprotein C-III, for example ISIS-APOCIIIRx.

In one embodiment of the invention, the compound of the formula I is administered in combination with an LDL receptor inducer (see U.S. Pat. No. 6,342,512), for example HMR1171, HMR1586, or those as described in WO2005097738, WO2008020607.

In another embodiment of the invention, the compound of the formula I is administered in combination with an HDL cholesterol-elevating agent, for example those as described in WO2008040651, WO2008099278, WO2009071099, WO2009086096, US2009247550.

In one embodiment of the invention, the compound of the formula I is administered in combination with an ABCA1 expression enhancer, as described, for example, in WO2006072393, WO2008062830, WO2009100326.

In one embodiment of the invention, the compound of the formula I is administered in combination with a lipoprotein lipase modulator, for example ibrolipim (NO-1886).

In one embodiment of the invention, the compound of the formula I is administered in combination with a lipoprotein (a) antagonist, for example gemcabene (CI-1027).

In one embodiment of the invention, the compound of the formula I is administered in combination with a lipase inhibitor, for example orlistat or cetilistat (ATL-962).

In one embodiment of the invention, the compound of the formula I is administered in combination with an adenosine A1 receptor agonist (adenosine A1 R), for example CVT-3619 or those as described, for example, in EP1258247, EP1375508, WO2008028590, WO2008077050, WO2009050199, WO2009080197, WO2009100827, WO2009112155.

In one embodiment of the invention, the compound of the formula I is administered in combination with an adenosine A2B receptor agonist (adenosine A2B R), for example ATL-801.

In another embodiment of the invention, the compound of the formula I is administered in combination with a modulator of adenosine A2A and/or adenosine A3 receptors, as described, for example, in WO2007111954,

WO2007121918, WO2007121921, WO2007121923, WO2008070661, WO2009010871.

In a further embodiment of the invention, the compound of the formula I is administered in combination with a ligand of the adenosine A1/A2B receptors, as described, for example, in WO2008064788, WO2008064789, WO2009080198, WO2009100827, WO2009143992.

In one embodiment of the invention, the compound of the formula I is administered in combination with an adenosine A2B receptor antagonist (adenosine A2B R), as described in US2007270433, WO2008027585, WO2008080461, WO2009037463, WO2009037467, WO2009037468, WO2009118759.

In one embodiment, the compound of the formula I is administered in combination with inhibitors of acetyl-CoA carboxylase (ACC1 and/or ACC2), for example those as described in WO199946262, WO200372197, WO2003072197, WO2005044814, WO2005108370, JP2006131559, WO2007011809, WO2007011811, WO2007013691, WO2007095601-603, WO2007119833, WO2008065508, WO2008069500, WO2008070609, WO2008072850, WO2008079610, WO2008088688, WO2008088689, WO2008088692, US2008171761, WO2008090944, JP2008179621, US2008200461, WO2008102749, WO2008103382, WO2008121592, WO2009082346, US2009253725, JP2009196966, WO2009144554, WO2009144555, WO2010003624, WO2010002010.

In another embodiment, the compound of the formula I is administered in combination with modulators of microsomal acyl-CoA:glycerol-3-phosphate acyltransferase 3 (GPAT3, described in WO2007100789) or with modulators of microsomal acyl-CoA:glycerol-3-phosphate acyltransferase 4 (GPAT4, described in WO2007100833) or with modulators of mitochondrial glycerol-3-phosphate O-acyltransferase, described in WO2010005922.

In a further embodiment, the compound of the formula I is administered in combination with modulators of xanthine oxidoreductase (XOR).

In another embodiment, the compound of the formula I is administered in combination with inhibitors of soluble epoxide hydrolase (sEH), as described, for example, in WO2008051873, WO2008051875, WO2008073623, WO2008094869, WO2008112022, WO2008011872, WO2009049154, WO2009049157, WO2009049165, WO2009073772, WO2009097476, WO2009111207, WO2009129508, WO2009151800.

In a further embodiment, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists, for example 4-[(4-aminoquinazolin-2-ylamino)methyl]-cyclohexylmethylnaphthalene-1-sulfonamide hydrochloride (CGP 71683A) or velneperit or those as described in WO2009110510;

NPY-5 receptor antagonists/receptor modulators, such as L-152804 or the compound "NPY-5-BY" from Banyu, or as described, for example, in WO2006001318, WO2007103295, WO2007125952, WO2008026563, WO2008026564, WO2008052769, WO2008092887, WO2008092888, WO2008092891, WO2008129007, WO2008134228, WO2009054434, WO2009095377, WO2009131096;

NPY-4 receptor antagonists, as described, for example, in WO2007038942;

NPY-2 receptor antagonists/modulators, as described, for example, in WO2007038943, WO2009006185, US2009099199, US2009099243, US2009099244, WO2009079593, WO2009079597;

peptide YY 3-36 (PYY3-36) or analogous compounds, for example CJC-1682 (PYY3-36 conjugated with human serum albumin via Cys34) or CJC-1643 (derivative of PYY3-36, which is conjugated in vivo to serum albumin), or those as described in WO2005080424, WO2006095166, WO2008003947, WO2009080608;

NPY-2 receptor agonists, as described, for example, in WO2009080608;

derivatives of the peptide obestatin, as described by WO2006096847;

CB1R (cannabinoid receptor 1) antagonists/inverse agonists, for example rimonabant, surinabant (SR147778), SLV-319 (ibipinabant), AVE-1625, taranabant (MK-0364) or salts thereof, otenabant (CP-945,598), rosonabant, V-24343 or those compounds as described in, for example, EP 0656354, WO 00/15609, WO2001/64632-64634, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509, WO2005077897, WO2006018662, WO2006047516, WO2006060461, WO2006067428, WO2006067443, WO2006087480, WO2006087476, WO2006100208, WO2006106054, WO2006111849, WO2006113704, WO2007009705, WO2007017124, WO2007017126, WO2007018459, WO2007018460, WO2007016460, WO2007020502, WO2007026215, WO2007028849, WO2007031720, WO2007031721, WO2007036945, WO2007038045, WO2007039740, US20070015810, WO2007046548, WO2007047737, WO2007057687, WO2007062193, WO2007064272, WO2007079681, WO2007084319, WO2007084450, WO2007086080, EP1816125, US2007213302, WO2007095513, WO2007096764, US2007254863, WO2007119001, WO2007120454, WO2007121687, WO2007123949, US2007259934, WO2007131219, WO2007133820, WO2007136571, WO2007136607, WO2007136571, US7297710, WO2007138050, WO2007139464, WO2007140385, WO2007140439, WO2007146761, WO2007148061, WO2007148062, US2007293509, WO2008004698, WO2008017381, US2008021031, WO2008024284, WO2008031734, WO2008032164, WO2008034032, WO2008035356, WO2008036021, WO2008036022, WO2008039023, WO2998043544, WO2008044111, WO2008048648, EP1921072-A1, WO2008053341, WO2008056375, WO2008059207, WO2008059335, WO2008062424, WO2008068423, WO2008068424, WO2008070305, WO2008070306, WO2008074816, WO2008074982, WO2008075012, WO2008075013, WO2008075019, WO2008075118, WO2008076754, WO2008081009, WO2008084057, EP1944295, US2008090809, US2008090810, WO2008092816, WO2008094473, WO2008094476, WO2008099076, WO2008099139, WO2008101995, US2008207704, WO2008107179, WO2008109027, WO2008112674, WO2008115705, WO2008118414, WO2008119999, WO200812000, WO2008121257, WO2008127585, WO2008129157, WO2008130616, WO2008134300, US2008262066, US2008287505, WO2009005645, WO2009005646, WO2009005671, WO2009023292, WO2009023653, WO2009024819, WO2009033125, EP2042175, WO2009053548-WO2009053553, WO2009054923, WO2009054929, WO2009059264, WO2009073138, WO2009074782, WO2009075691, WO2009078498, WO2009087285, WO2009074782, WO2009097590, WO2009097995, WO2009097996, WO2009097998, WO2009097999, WO2009098000, WO2009106708, US2009239909, WO2009118473, US2009264436, US2009264476, WO2009130234, WO2009131814, WO2009131815, US2009286758, WO2009141532, WO2009141533, WO2009153569, WO2010003760, WO2010012437, WO2010019762;

cannabinoid receptor 1/cannabinoid receptor 2 (CB1,/CB2) modulating compounds, for example delta-9-tetrahydrocannabivarin, or those as described, for example, in WO2007001939, WO2007044215, WO2007047737, WO2007095513, WO2007096764, WO2007112399, WO2007112402, WO2008122618, WO2009007697, WO2009012227, WO2009087564, WO2009093018, WO2009095752, WO2009120660, WO2010012964;

cannabinoid receptor 2 (CB2) modulating compounds, for example those as described, for example, in WO2008063625, WO2008157500, WO2009004171, WO2009032754, WO2009055357, WO2009061652, WO2009063495, WO2009067613, WO2009114566;

modulators of FAAH (fatty acid amide hydrolase), as described, for example, in WO2007140005, WO2008019357, WO2008021625, WO2008023720, WO2008030532, WO2008129129, WO2008145839, WO2008145843, WO2008147553, WO2008153752, WO2009011904, WO2009048101, WO2009084970, WO2009105220, WO2009109504, WO2009109743, WO2009117444, WO2009127944, WO2009138416, WO2009151991, WO2009152025, WO2009154785, WO2010005572, WO2010017079;

inhibitors of fatty acid synthase (FAS), as described, for example, in WO2008057585, WO2008059214, WO2008075064, WO2008075070, WO2008075077, WO2009079860;

inhibitors of LCE (long chain fatty acid elongase)/long chain fatty acid CoA ligase, as described, for example, in WO2008120653, WO2009038021, WO2009044788, WO2009081789, WO2009099086;

vanilloid-1 receptor modulators (modulators of TRPV1), as described, for example, in WO2007091948, WO2007129188, WO2007133637, WO2008007780, WO2008010061, WO2008007211, WO2008010061, WO2008015335, WO2008018827, WO2008024433, WO2008024438, WO2008032204, WO2008050199, WO2008059339, WO2008059370, WO2008066664, WO2008075150, WO2008090382, WO2008090434, WO2008093024, WO2008107543, WO2008107544, WO2008110863, WO2008125295, WO2008125296, WO2008125337, WO2008125342, WO2008132600, WO2008133973, WO2009010529, WO2009010824, WO2009016241, WO2009023539, WO2009038812, WO2009050348, WO2009055629, WO2009055749, WO2009064449, WO2009081222, WO2009089057, WO2009109710, WO2009112677, WO2009112678, WO2009112679, WO2009121036, WO2009124551, WO2009136625, WO2010002209;

modulators, ligands, antagonists or inverse agonists of the opioid receptors, for example GSK-982 or those as described, for example, in WO2007047397, WO2008021849, WO2008021851, WO2008032156, WO2008059335, WO2008125348, WO2008125349, WO2008142454, WO2009030962, WO2009103552, WO2009115257;

modulators of the "orphan opioid (ORL-1) receptor", as described, for example, in US2008249122, WO2008089201;

agonists of the prostaglandin receptor, for example bimatoprost or those compounds as described in WO2007111806;

MC4 receptor agonists (melanocortin-4 receptor agonists, MC4R agonists, for example N-[2-(3a-benzyl-2-methyl-3-oxo-2,3,3a,4,6,7-hexahydro-pyrazolo[4,3-c]pyridin-5-yl)-1-(4-chlorophenyl)-2-oxoethyl]-1-amino-1,2,3,4-tetrahydronaphthalene-2-carboxamide; (WO 01/91752)) or LB53280, LB53279, LB53278 or THIQ, MB243, RY764, CHIR-785, PT-141, MK-0493, or those as described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2004089307, WO2005042516, WO2005040109, WO2005030797, US20040224901, WO200501921, WO200509184, WO2005000339, EP1460069, WO2005047253, WO2005047251, WO2005118573, EP1538159, WO2004072076, WO2004072077, WO2006021655-57, WO2007009894, WO2007015162, WO2007041061, WO2007041052, JP2007131570, EP-1842846, WO2007096186, WO2007096763, WO2007141343, WO2008007930, WO2008017852, WO2008039418, WO2008087186, WO2008087187, WO2008087189, WO2008087186-WO2008087190, WO2008090357, WO2008142319, WO2009015867, WO2009061411, US2009076029, US2009131465, WO2009071101, US2009305960, WO2009144432, WO2009151383, WO2010015972;

MC4 receptor modulators (melanocortin-4 receptor modulators), as described, for example, in WO2009010299, WO2009074157;

orexin receptor 1 antagonists (OX1R antagonists), orexin receptor 2 antagonists (OX2R antagonists) or mixed OX1R/OX2R antagonists (e.g. 1-(2-methylbenzoxazol-6-yl)-3-[1,5] naphthyridin-4-ylurea hydrochloride (SB-334867-A), or those as described, for example, in WO200196302, WO200185693, WO2004085403, WO2005075458, WO2006067224, WO2007085718, WO2007088276, WO2007116374, WO2007122591, WO2007126934, WO2007126935, WO2008008517, WO2008008518, WO2008008551, WO2008020405, WO2008026149, WO2008038251, US2008132490, WO2008065626, WO2008078291, WO2008087611, WO2008081399, WO2008108991, WO2008107335, US2008249125, WO2008147518, WO2008150364, WO2009003993, WO2009003997, WO2009011775, WO2009016087, WO2009020642, WO2009058238, US2009186920, US2009203736, WO2009092642, WO2009100994, WO2008104155, WO2009124956, WO2009133522, WO2009156951, WO2010017260);

histamine H3 receptor antagonists/inverse agonists (e.g. 3-cyclohexyl-1-(4,4-dimethyl-1,4,6,7-tetrahydroimidazo[4, 5-c]pyridin-5-yl)propan-1-one oxalic acid salt (WO 00/63208), or those as described in WO200064884, WO2005082893, WO2005123716, US2005171181 (e.g. PF-00389027), WO2006107661, WO2007003804, WO2007016496, WO2007020213, WO2007049798, WO2007055418, WO2007057329, WO2007062999, WO2007065820, WO2007068620, WO2007068641, WO2007075629, WO2007080140, WO2007082840, WO2007088450, WO2007088462, WO2007094962, WO2007099423, WO2007100990, WO2007105053, WO2007106349, WO2007110364, WO2007115938, WO2007131907, WO2007133561, US2007270440, WO2007135111, WO2007137955, US2007281923, WO2007137968, WO2007138431, WO2007146122, WO2008005338, WO2008012010, WO2008015125, WO2008045371, EPI 757594, WO2008068173, WO2008068174, US20080171753, WO2008072703, WO2008072724, US2008188484, US2008188486, US2008188487, WO2008109333, WO2008109336, WO2008126886, WO2008154126, WO2008151957, US2008318952, WO2009003003, WO2009013195, WO2009036132, WO2009039431, WO2009045313, WO2009058300, WO2009063953, WO2009067401, WO2009067405, WO2009067406, US2009163464, WO2009100120, WO2009105206, WO2009121812, WO2009126782, WO2010011653, WO2010011657);

histamine H1/histamine H3 modulators, for example betahistine or its dihydrochloride;

modulators of the histamine H3 transporter or of the histamine H3/serotonin transporter, as described, for example, in WO2008002816, WO2008002817, WO2008002818, WO2008002820;

modulators of vesicular monoamine transporter 2 (VMAT2), as described, for example, in WO2009126305;

histamine H4 modulators, as described, for example, in WO2007117399, US2009156613;

CRF antagonists (e.g. [2-methyl-9-(2,4,6-trimethylphenyl)-9H-1,3,9-triazafluoren-4-yl]dipropylamine (WO 00/66585) or those CRF1 antagonists as described in WO2007105113, WO2007133756, WO2008036541, WO2008036579, WO2008083070, WO2010015628, WO2010015655);

CRF BP antagonists (e.g. urocortin);

urocortin agonists;

modulators of the beta-3 adrenoceptor, for example 1-(4-chloro-3-methanesulfonylmethylphenyl)-2-[2-(2,3-dimethyl-1H-indol-6-yloxy)ethylamino]ethanol hydrochloride (WO 01/83451) or solabegron (GW-427353) or N-5984 (KRP-204), or those as described in JP2006111553, WO2002038543, WO2002038544, WO2007048840-843, WO2008015558, EP1947103, WO2008132162;

MSH (melanocyte-stimulating hormone) agonists;

MCH (melanine-concentrating hormone) receptor antagonists (for example NBI-845, A-761, A-665798, A-798, ATC-0175, T-226296, T-71 (AMG-071, AMG-076), GW-856464, NGD-4715, ATC-0453, ATC-0759, GW-803430, or those compounds as described in WO2005085200, WO2005019240, WO2004011438, WO2004012648, WO2003015769, WO2004072025, WO2005070898, WO2005070925, WO2004039780, WO2004092181, WO2003033476, WO2002006245, WO2002089729, WO2002002744, WO2003004027, FR2868780, WO2006010446, WO2006038680, WO2006044293, WO2006044174, JP2006176443, WO2006018280, WO2006018279, WO2006118320, WO2006130075, WO2007018248, WO2007012661, WO2007029847, WO2007024004, WO2007039462, WO2007042660, WO2007042668, WO2007042669, US2007093508, US2007093509, WO2007048802, JP2007091649, WO2007092416; WO2007093363-366, WO2007114902, WO2007114916, WO2007141200, WO2007142217, US2007299062, WO2007146758, WO2007146759, WO2008001160, WO2008016811, WO2008020799, WO2008022979, WO2008038692, WO2008041090, WO2008044632, WO2008047544, WO2008061109, WO2008065021, WO2008068265, WO2008071646, WO2008076562, JP2008088120, WO2008086404, WO2008086409, US2008269110, WO2008140239, WO2009021740, US2009011994, US2009082359, WO2009041567, WO2009076387, WO2009089482, WO2009103478, WO2009119726, WO2009120655, WO2009123194, WO2009137270, WO2009146365, WO2009154132);

CCK-A (CCK-1) modulators (for example {2-[4-(4-chloro-2,5-dimethoxyphenyl)-5-(2-cyclohexylethyl)-thiazol-2-ylcarbamoyl]-5,7-dimethylindol-1-yl}acetic acid trifluoroacetic acid salt (WO 99/15525) or SR-146131 (WO 0244150) or SSR-125180) or those as described in WO2005116034, WO2007120655, WO2007120688, WO2007120718, WO2008091631;

serotonin reuptake inhibitors (e.g. dexfenfluramine), or those as described in WO2007148341, WO2008034142, WO2008081477, WO2008120761, WO2008141081, WO2008141082, WO2008145135, WO2008150848, WO2009043834, WO2009077858;

mixed serotonin/dopamine reuptake inhibitors (e.g. bupropion), or those as described in WO2008063673, or solid combinations of bupropion with naltrexone or bupropion with zonisamide;

mixed reuptake inhibitors, for example DOV-21947 or those as described in WO2009016214, WO2009016215, WO2009077584, WO2009098208, WO2009098209, WO2009106769, WO2009109517, WO2009109518, WO2009109519, WO2009109608, WO2009145357, WO2009149258;

mixed serotoninergic and noradrenergic compounds (e.g. WO 00/71549);

5-HT receptor agonists, for example 1-(3-ethylbenzofuran-7-yl)piperazine oxalic acid salt (WO 01/09111);

mixed dopamine/norepinephrine/acetylcholine reuptake inhibitors (e.g. tesofensine), or those as described, for example, in WO2006085118, WO2008150480;

dopamine antagonists, as described, for example, in WO2008079838, WO2008079839, WO2008079847, WO2008079848;

norepinephrine reuptake inhibitors, as described, for example, in US2008076724, WO2009062318;

5-HT1A receptor modulators, as described, for example, in WO2009006227, WO2009137679, WO2009137732;

5-HT2A receptor antagonists, as described, for example, in WO2007138343;

5-HT2C receptor agonists (for example lorcaserine hydrochloride (APD-356) or BVT-933, or those as described in WO200077010, WO200077001-02, WO2005019180, WO2003064423, WO200242304, WO2005035533, WO2005082859, WO2006004937, US2006025601, WO2006028961, WO2006077025, WO2006103511, WO2007028132, WO2007084622, US2007249709; WO2007132841, WO2007140213, WO2008007661, WO2008007664, WO2008009125, WO2008010073, WO2008108445, WO2009063991, WO2009063992, WO2009063993, WO2009079765);

5-HT6 receptor modulators, for example E-6837, BVT-74316, PF-3246799 or PRX-07034, or those as described, for example, in WO2005058858, WO2007054257, WO2007107373, WO2007108569, WO2007108742-744, WO2008003703, WO2008027073, WO2008034815, WO2008054288, EP1947085, WO2008084491, WO2008084492, WO2008092665, WO2008092666, WO2008101247, WO2008110598, WO2008116831, WO2008116833, WO2008117169, WO2008136017, WO2008147812, EP2036888, WO2009013010, WO2009034581, WO2009053997, WO2009056632, WO2009073118, WO2009115515, WO2009135925, WO2009135927, WO2010000456, WO2010012806, EP2145887;

agonists of estrogen receptor gamma (ERRγ agonists), as described, for example, in WO2007131005, WO2008052709;

agonists of estrogen receptor alpha (ERRα/ERR1 agonists), as described, for example, in WO2008109727;

agonists of estrogen receptor beta (ERRβ agonists), as described, for example, in WO2009055734, WO2009100335, WO2009127686;

sigma-1 receptor antagonists, as described, for example, in WO2007098953, WO2007098961, WO2008015266, WO2008055932, WO2008055933, WO2009071657;

muscarin 3 receptor (M3R) antagonists, as described, for example, in WO2007110782, WO2008041184;

bombesin receptor agonists (BRS-3 agonists), as described, for example, in WO2008051404, WO2008051405, WO2008051406, WO2008073311;

galanin receptor antagonists;

growth hormone (e.g. human growth hormone or AOD-9604);

growth hormone releasing compounds (tert-butyl 6-benzyloxy-1-(2-diisopropylaminoethylcarbamoyl)-3,4-dihydro-1H-isoquinoline-2-carboxylate (WO 01/85695));

growth hormone secretagogue receptor antagonists (ghrelin antagonists), for example A-778193, or those as described in WO2005030734, WO2007127457, WO2008008286, WO2009056707;

growth hormone secretagogue receptor modulators (ghrelin modulators), for example JMV-2959, JMV-3002, JMV-2810, JMV-2951, or those as described in WO2006012577 (e.g. YIL-781 or YIL-870), WO2007079239, WO2008092681, WO2008145749, WO2008148853, WO2008148854, WO2008148856, WO2009047558, WO2009071283, WO2009115503;

TRH agonists (see, for example, EP 0 462 884);

decoupling protein 2 or 3 modulators (as described, for example, in WO2009128583);

chemical decouplers (e.g. WO2008059023, WO2008059024, WO2008059025, WO2008059026);

leptin receptor agonists (see, for example, Lee, Daniel W.; Leinung, Matthew C.; Rozhayskaya-Arena, Marina; Grasso, Patricia. Leptin agonists as a potential approach to the treatment of obesity. Drugs of the Future (2001), 26(9), 873-881);

leptin receptor modulators, as described, for example, in WO2009019427, WO2009071658, WO2009071668, WO2009071677, WO2009071678, WO2009147211, WO2009147216, WO2009147219, WO2009147221;

DA agonists (bromocriptin, bromocriptin mesylate, doprexin) or those as described in US2009143390;

lipase/amylase inhibitors (e.g. WO 00/40569, WO2008107184, WO2009049428, WO2009125819), inhibitors of diacylglycerol O-acyltransferases (DGATs), for example BAY-74-4113, or as described, for example, in US2004/0224997, WO2004094618, WO200058491, WO2005044250, WO2005072740, JP2005206492, WO2005013907, WO2006004200, WO2006019020, WO2006064189, WO2006082952, WO2006120125, WO2006113919, WO2006134317, WO2007016538, WO2007060140, JP2007131584, WO2007071966, WO2007126957, WO2007137103, WO2007137107, WO2007138304, WO2007138311, WO2007141502, WO2007141517, WO2007141538, WO2007141545, WO2007144571, WO2008011130, WO2008011131, WO2008039007, WO2008048991, WO2008067257, WO2008099221, WO2008129319, WO2008141976, WO2008148840, WO2008148849, WO2008148851, WO2008148868, WO2009011285, WO2009016462, WO2009024821, US2009076275, WO2009040410, WO2009071483, WO2009081195, WO2009119534, WO2009126624, WO2009126861, WO2010007046, WO2010017040, WO2010086551;

inhibitors of monoacylglycerol acyltransferase (2-acyiglycerol O-acyltransferase; MGAT), as described, for example, in WO2008038768;

inhibitors of fatty acid synthase (FAS), for example C75, or those as described in WO2004005277, WO2008006113;

inhibitors of stearoyl-CoA delta9 desaturase (SCD1), as described, for example, in WO2007009236, WO2007044085, WO2007046867, WO2007046868, WO2007050124, WO2007056846, WO2007071023, WO2007130075, WO2007134457, WO2007136746, WO2007143597, WO2007143823, WO2007143824, WO2008003753, WO2008017161, WO2008024390, WO2008029266, WO2008036715, WO2008043087, WO2008044767, WO2008046226, WO2008056687, WO2008062276, WO2008064474, WO2008074824, WO2008074832, WO2008074833, WO2008074834, WO2008074835, WO2008089580, WO2008096746, WO2008104524, WO2008116898, US2008249100, WO2008120744, WO2008120759, WO2008123469, WO2008127349, WO2008128335, WO2008135141, WO2008139845, WO2008141455, US20080255130, US2008255161, WO2008141455, WO2009010560, WO2009016216, WO2009012573, WO2009024287, JP2009019013, WO2009037542, WO2009056556, WO2009060053, WO2009060054, WO2009070533, WO2009073973, WO2009103739, WO2009117659, WO2009117676, US2009253693, US2009253738, WO2009124259, WO2009126123, WO2009126527, WO2009129625, WO2009137201, WO2009150196, WO2009156484, WO2010006962, WO2010007482;

inhibitors of fatty acid desaturase 1 (delta5 desaturase), as described, for example, in WO2008089310;

inhibitors of monoglyceride lipase (MGL), as described in WO2008145842;

hypoglycemic/hypertriglyceridemic indoline compounds, as described in WO2008039087, WO2009051119;

inhibitors of "adipocyte fatty acid-binding protein aP2", for example BMS-309403 or those as described in WO2009028248;

activators of adiponectin secretion, as described, for example, in WO2006082978, WO2008105533, WO2008136173;

promoters of adiponectin production, as described, for example, in WO2007125946, WO2008038712;

modified adiponectins, as described, for example, in WO2008121009;

oxyntomodulin or analogs thereof (for example, TKS-1225);

oleoyl-estrone or agonists or partial agonists of the thyroid hormone receptor (thyroid hormone receptor agonists), for example: KB-2115 (eprotirome), QRX-431 (sobetirome) or DITPA, or those as described in WO20058279, WO200172692, WO200194293, WO2003084915, WO2004018421, WO2005092316, WO2007003419, WO2007009913, WO2007039125, WO2007110225, WO2007110226, WO2007128492, WO2007132475, WO2007134864, WO2008001959, WO2008106213, JP2009155261;

or agonists of the thyroid hormone receptor beta (TR-beta), for example MB-07811 or MB-07344, or those as described in WO2008062469.

In one embodiment of the invention, the compound of the formula I is administered in combination with a combination of eprotirome with ezetimibe.

In one embodiment of the invention, the compound of the formula I is administered in combination with an inhibitor of site-1 protease (S1P), for example PF-429242.

In a further embodiment of the invention, the compound of the formula I is administered in combination with a modulator of the "trace amine associated receptor 1" (TAAR1), as described, for example, in US2008146523, WO2008092785.

In one embodiment of the invention, the compound of the formula I is administered in combination with an inhibitor of growth factor receptor bound protein 2 (GRB2), as described, for example, in WO2008067270.

In a further embodiment of the invention, the compound of the formula I is administered in combination with an RNAi (siRNA) therapeutic agent directed against PCSK9 (proprotein convertase subtilisin/kexin type 9).

In one embodiment, the compound of the formula I is administered in combination with Omacor® or Lovaza™ (omega-3 fatty acid ester; highly concentrated ethyl ester of eicosapentaenoic acid and of docosahexaenoic acid).

In one embodiment, the compound of the formula I is administered in combination with lycopene.

In one embodiment of the invention, the compound of the formula I is administered in combination with an antioxidant, for example OPC-14117, AGI-1067 (succinobucol), probucol, tocopherol, ascorbic acid, β-carotene or selenium, or those as described in WO2009135918.

In one embodiment of the invention, the compound of the formula I is administered in combination with a vitamin, for example vitamin B6 or vitamin B12.

In one embodiment, the compound of the formula I is administered in combination with more than one of the aforementioned compounds, for example in combination with a sulfonylurea and metformin, a sulfonylurea and acarbose, repaglinide and metformin (PrandiMet™), insulin and a sulfonylurea, insulin and metformin, insulin and troglitazone, insulin and lovastatin, etc.

In a further embodiment, the compound of the formula I is administered in combination with an activator of soluble guanylate cyclase (sGC), as described, for example, in WO2009032249.

In another embodiment, the compound of the formula I is administered in combination with an inhibitor of carboanhydrase type 2 (carbonic anhydrase type 2), for example those as described in WO2007065948, WO2009050252.

In another embodiment, the compound of the formula I is administered in combination with topiramat or a derivative thereof, as described in WO2008027557, US2009304789.

In a further embodiment, the compound of the formula I is administered in combination with a solid combination of topiramat with phentermin (Qnexa™)

In a further embodiment, the compound of the formula I is administered in combination with an antisense compound, e.g. ISIS-377131, which inhibits the production of the glucocorticoid receptor.

In another embodiment, the compound of the formula I is administered in combination with an aldosterone synthase inhibitor and an antagonist of the glucocorticoid receptor, a cortisol synthesis inhibitor and/or an antagonist of the corticotropin releasing factor, as described, for example, in EP1886695, WO2008119744.

In one embodiment, the compound of the formula I is administered in combination with an agonist of the RUP3 receptor, as described, for example, in WO2007035355, WO2008005576.

In another embodiment, the compound of the formula I is administered in combination with an activator of the gene which codes for ataxia telangiectasia mutated (ATM) protein kinase, for example chloroquine.

In one embodiment, the compound of the formula I is administered in combination with a tau protein kinase 1 inhibitor (TPK1 inhibitor), as described, for example, in WO2007119463, WO2009035159, WO2009035162.

In one embodiment, the compound of the formula I is administered in combination with a "c-Jun N-terminal kinase" inhibitor (JNK inhibitor), for example B1-78D3 or those as described, for example, in WO2007125405, WO2008028860, WO2008118626.

In one embodiment, the compound of the formula I is administered in combination with an endothelin A receptor antagonist, for example avosentan (SPP-301).

In one embodiment, the compound of the formula I is administered in combination with inhibitors of neutral endopeptidase (NEP inhibitors), as described, for example, in WO2009138122, WO2009135526.

In one embodiment, the compound of the formula I is administered in combination with modulators of the glucocorticoid receptor (GR), for example KB-3305 or those compounds as described, for example, in WO2005090336, WO2006071609, WO2006135826, WO2007105766, WO2008120661, WO2009040288, WO2009058944, WO2009108525, WO2009111214.

In one embodiment, the further active ingredient is varenicline tartrate, a partial agonist of the alpha 4-beta 2 nicotinic acetylcholine receptor.

In one embodiment, the further active ingredient is an agonist of the alpha 7-nicotinic acetylcholine receptor, as described, for example, in WO2009018551, WO2009071519, WO2009071576, WO2009071577.

In one embodiment, the further active ingredient is trodusquemine.

In one embodiment, the further active ingredient is a modulator of the enzyme SIRT1 and/or SIRT3 (an $NAD^+$-dependent protein deacetylase); this active ingredient may, for example, be resveratrol in suitable formulations, or those compounds as specified in WO2007019416 (e.g. SRT-1720), WO2008073451, WO2008156866, WO2008156869, WO2009026701, WO2009049018, WO2009058348, WO2009061453, WO2009134973, WO2009146358, WO2010003048.

In one embodiment of the invention, the further active ingredient is DM-71 (N-acetyl-L-cysteine with bethanechol).

In one embodiment, the compound of the formula I is administered in combination with antihypercholesterolemic compounds, as described, for example, in WO2004000803, WO2006000804, WO2004000805, WO2004087655, WO2005113496, WO2007059871, WO2007107587, WO2007111994, WO2008052658, WO2008106600, WO2008113796, US2008280836, WO2009113952, US2009312302.

In a further embodiment, the compound of the formula I is administered in combination with inhibitors of SREBP (sterol regulatory element-binding protein), for example fatostatin, or those as described, for example, in WO2008097835.

In another embodiment, the compound of the formula I is administered in combination with a cyclic peptide agonist of the VPAC2 receptor, as described, for example, in WO2007101146, WO2007133828.

In a further embodiment, the compound of the formula I is administered in combination with an agonist of the endothelin receptor, as described, for example, in WO2007112069.

In a further embodiment, the compound of the formula I is administered in combination with AKP-020 (bis(ethylmaltolato)oxovanadium(IV)).

In another embodiment, the compound of the formula I is administered in combination with tissue-selective androgen receptor modulators (SARM), as described, for example, in WO2007099200, WO2007137874.

In a further embodiment, the compound of the formula I is administered in combination with an AGE (advanced glycation endproduct) inhibitor, as described, for example, in JP2008024673.

In one embodiment of the invention, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In another embodiment of the invention, the further active ingredient is metreleptin (recombinant methionyl-leptin) combined with pramlintide.

In a further embodiment of the invention, the further active ingredient is the tetrapeptide ISF-402.

In one embodiment, the further active ingredient is dexamphetamine or amphetamine.

In one embodiment, the further active ingredient is fenfluramine or dexfenfluramine.

In another embodiment, the further active ingredient is sibutramine or those derivatives as described in WO2008034142.

In one embodiment, the further active ingredient is mazindol or phentermin.

In a further embodiment, the further active ingredient is geniposidic acid (WO2007100104) or derivatives thereof (JP2008106008).

In another embodiment, the further active ingredient is a neuropeptide FF2 agonist, as described, for example, in WO2009038012.

In one embodiment, the further active ingredient is a nasal calcium channel blocker, for example diltiazem, or those as described in U.S. Pat. No. 7,138,107.

In one embodiment, the further active ingredient is an inhibitor of sodium-calcium ion exchange, for example those as described in WO2008028958, WO2008085711.

In a further embodiment, the further active ingredient is a blocker of calcium channels, for example of CaV3.2 or CaV2.2, as described in WO2008033431, WO2008033447, WO2008033356, WO2008033460, WO2008033464, WO2008033465, WO2008033468, WO2008073461.

In one embodiment, the further active ingredient is a modulator of a calcium channel, for example those as described in WO2008073934, WO2008073936, WO2009107660.

In one embodiment, the further active ingredient is an inhibitor of the calcium metabolism, for example those as described in US2009124680.

In one embodiment, the further active ingredient is a blocker of the "T-type calcium channel", as described, for example, in WO2008033431, WO2008110008, US2008280900, WO2008141446, US2009270338, WO2009146540, US2009325979, WO2009146539.

In one embodiment, the further active ingredient is an inhibitor of KCNQ potassium channel 2 or 3, for example those as described in US2008027049, US2008027090.

In one embodiment, the further active ingredient is a modulator of KCNN potassium channel 1, 2 or 3 (modulators of the SK1, SK2 and/or SK3 channel), for example those as described in US2009036475.

In one embodiment, the further active ingredient is an inhibitor of the potassium Kv1.3 ion channel, for example those as described in WO2008040057, WO2008040058, WO2008046065, WO2009043117.

In one embodiment, the further active ingredient is a potassium channel modulator, for example those as described in WO2008135447, WO2008135448, WO2008135591, WO2009099820.

In a further embodiment, the further active ingredient is a hyperpolarization-activated cyclic nucleotide-gated (HCN) potassium-sodium channel inhibitor, for example those as described in US2009069296.

In another embodiment, the further active ingredient is an inhibitor of the sodium-potassium-2 chloride (NKCCl) cotransporter, for example those as described in WO2009130735.

In another embodiment, the further active ingredient is a voltage-gated sodium channel inhibitor, for example those as described in WO2009049180, WO2009049181.

In another embodiment, the further active ingredient is a modulator of the MCP-1 receptor (monocyte chemoattractant protein-1 (MCP-1)), for example those as described in WO2008014360, WO2008014381.

In one embodiment, the further active ingredient is a modulator of somatostatin receptor 3 (SSTR3), for example those as described in WO2009011836.

In one embodiment, the further active ingredient is a modulator of somatostatin receptor 5 (SSTR5), for example those as described in WO2008019967, US2008064697, US2008249101, WO2008000692, US2008293756, WO2008148710.

In one embodiment, the further active ingredient is a modulator of somatostatin receptor 2 (SSTR2), for example those as described in WO2008051272.

In one embodiment, the further active ingredient is a compound which is capable of reducing the amount of retinol-binding protein 4 (RBP4), for example those as described in WO2009051244, WO2009145286.

In one embodiment, the further active ingredient is an erythropoietin-mimetic peptide which acts as an erythropoietin (EPO) receptor agonist. Such molecules are described, for example, in WO2008042800.

In a further embodiment, the further active ingredient is an anorectic/a hypoglycemic compound, for example those as described in WO2008035305, WO2008035306, WO2008035686.

In one embodiment, the further active ingredient is an inductor of lipoic acid synthetase, for example those as described in WO2008036966, WO2008036967.

In one embodiment, the further active ingredient is a stimulator of endothelial nitric oxide synthase (eNOS), for example those as described in WO2008058641, WO2008074413.

In one embodiment, the further active ingredient is a modulator of carbohydrate and/or lipid metabolism, for example those as described in WO2008059023, WO2008059024, WO2008059025, WO2008059026.

In a further embodiment, the further active ingredient is an angiotensin II receptor antagonist, for example those as described in WO2008062905, WO2008067378, WO2008062905.

In one embodiment, the further active ingredient is an agonist of the sphingosine 1-phosphate receptor (S1P), for example those as described in WO2008064315, WO2008074820, WO2008074821, WO2008135522, WO2009019167, WO2009043013, WO2009080663, WO2009085847, WO2009151529, WO2009151621, WO2009151626, WO2009154737.

In one embodiment, the further active ingredient is an agent which retards gastric emptying, for example 4-hydroxyisoleucine (WO2008044770).

In one embodiment, the further active ingredient is a trytophan-5-hydroxylase inhibitor-1 (TPH1 inhibitor), which modulates gastrointestinal motility, as described, for example, in WO2009014972.

In one embodiment, the further active ingredient is a muscle-relaxing substance, as described, for example, in WO2008090200.

In a further embodiment, the further active ingredient is an inhibitor of monoamine oxidase B (MAO-B), for example those as described in WO2008092091, WO2009066152.

In a further embodiment, the further active ingredient is an inhibitor of monoamine oxidase A (MAO-A), for example those as described in WO2009030968.

In another embodiment, the further active ingredient is an inhibitor of the binding of cholesterol and/or triglycerides to the SCP-2 protein (sterol carrier protein-2), for example those as described in US2008194658.

In a further embodiment, the further active ingredient is a compound which binds to the β-subunit of the trimeric GTP-binding protein, for example those as described in WO2008126920.

In one embodiment, the further active ingredient is a urate anion exchanger inhibitor 1, as described, for example, in WO2009070740.

In one embodiment, the further active ingredient is a modulator of the ATP transporter, as described, for example, in WO2009108657.

In another embodiment, the further active ingredient is lisofylline, which prevents autoimmune damage to insulin-producing cells.

In yet another embodiment, the further active ingredient is an extract from *Bidens pilosa* with the ingredient cytopiloyne as described in EP1955701.

In one embodiment, the further active ingredient is an inhibitor of glucosylceramide synthase, as described, for example, in WO2008150486.

In a further embodiment of the invention, the further active ingredient is a glycosidase inhibitor, as described, for example, in WO2009117829, WO2009155753.

In another embodiment, the further active ingredient is an ingredient from the plant *Hoodia Gordonii*, as described in US2009042813, EP2044852.

In one embodiment, the further active ingredient is an antidiabetic, for example D-tagatose.

In one embodiment, the further active ingredient is a zinc complex of curcumin, as described in WO2009079902.

In one embodiment, the further active ingredient is an inhibitor of the "cAMP response element binding protein" (CREB), as described in WO2009143391.

In another embodiment, the further active ingredient is an antagonist of the bradykinin B1 receptor, as described in WO2009124746.

In a further embodiment, the further active ingredient is a compound which is capable of modulating diabetic peripheral neuropathy (DPN). Such modulators are, for example, FK-1706 or SB-509, or those as described in WO1989005304, WO2009092129, WO2010002956.

In one embodiment, the further active ingredient is a compound which is capable of modulating diabetic nephropathy. Such compounds are described, for example, in WO2009089545, WO2009153261.

In one embodiment, the further active ingredient is an inhibitor (e.g. an anti-CD38 antibody) of CD38, as described in US2009196825.

In one embodiment, the further active ingredient is an inhibitor of human fibroblast growth factor receptor 4 (FGFR4), as described, for example, in WO2009046141.

In a further embodiment of the invention, the further active ingredient is a compound which protects the beta cell, for example 1 4-alpha-lipolyl-andrographolide (AL-1).

In yet another embodiment of the invention, the further active ingredient is the INGAP (islet neogenesis associated protein) peptide, a peptide which reestablishes insulin production in patients with diabetes mellitus.

In one embodiment of the invention, the further active ingredient is a modulator of the CFTR (cystic fibrosis transmembrane conductance regulator), as described, for example, in US2009246137, US2009264433, US2009264441, US2009264471, US2009264481, US2009264486, WO2010019239.

In one embodiment of the invention, the further active ingredient is a compound which stimulates/modulates insulin release, for example those as described in WO2009109258, WO2009132739, US2009281057, WO2009157418.

In one embodiment of the invention, the further active ingredient is an extract from *Hippophae rhamnoides*, as described, for example, in WO2009125071.

In one embodiment of the invention, the further active ingredient is an from *Huanglian* and *Ku Ding Cha*, as described, for example, in WO2009133458.

In another embodiment, the further active ingredient is a root extract from *Cipadessa baccifera*, as described in US2009238900.

In one embodiment of the invention, the further active ingredients are borapetoside A and/or borapetoside C, which can be isolated from the plant SDH-V, a species of *Tinospora crispa*, as described, for example, in US2010016213.

In one embodiment, the compound of the formula I is administered in combination with bulking agents, preferably insoluble bulking agents (see, for example, Carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

It will be appreciated that every suitable combination of the compounds of the invention with one or more of the aforementioned compounds and optionally one or more other pharmacologically active substances is considered to be covered within the scope of protection conferred by the present invention.

FM-VP4
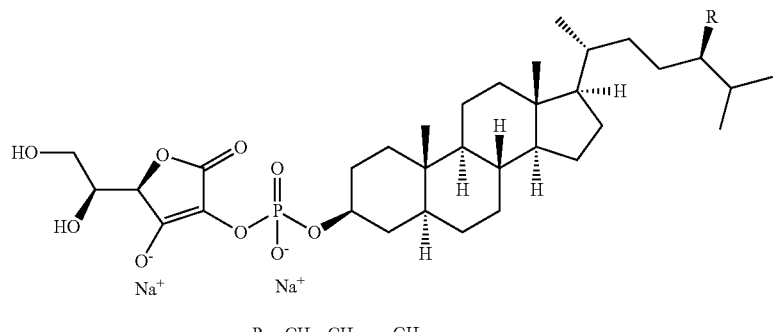
R = CH₃; CH₂—CH₃
JTT-501
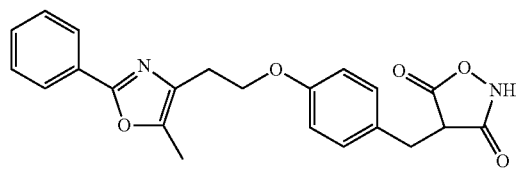
GI 262570
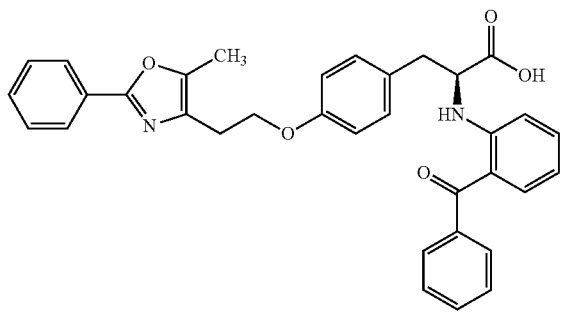
CS-011
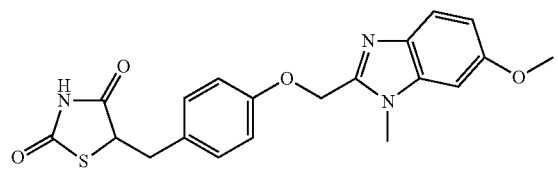
Rivoglitazone
GW-9578
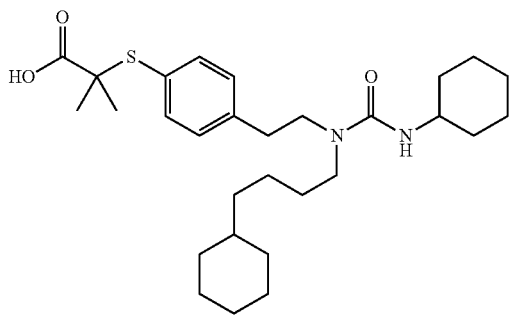
K-111
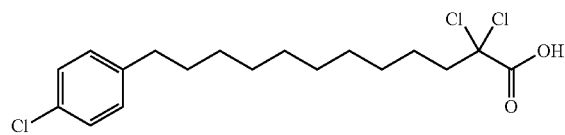
LY-518674
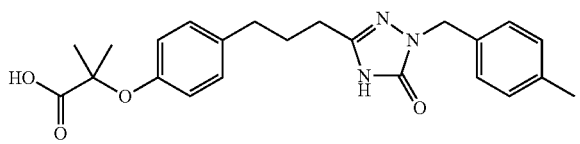
KRP-101
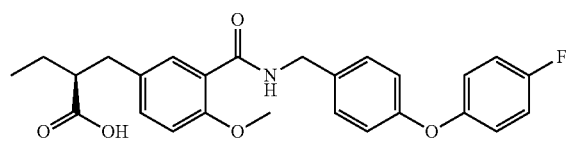
LY-510929
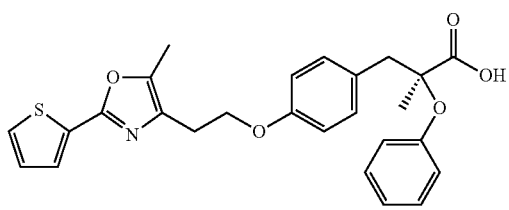

-continued
GW-501516
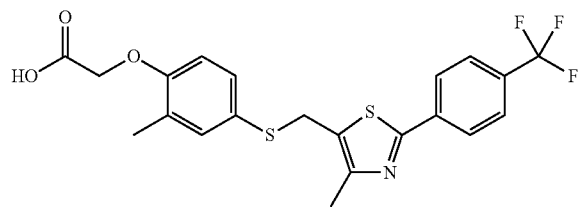
BMS-201038
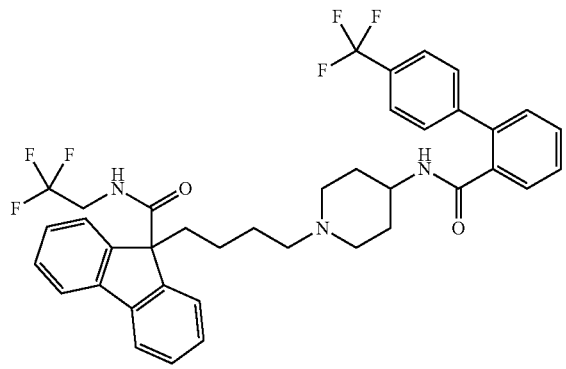
R-103757
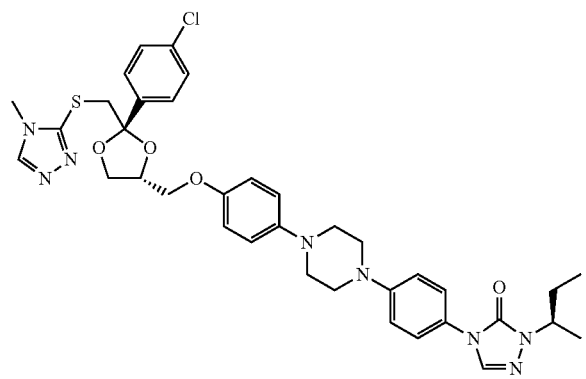
JTT-705
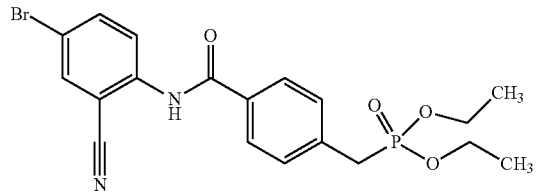
OPC-14117
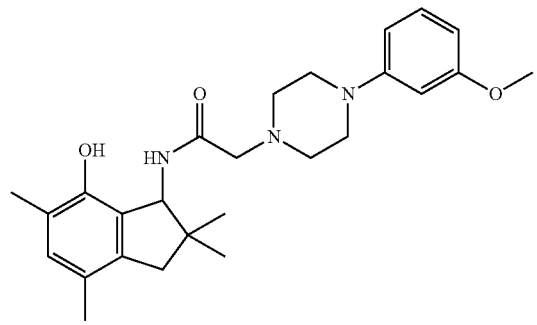
NO-1886
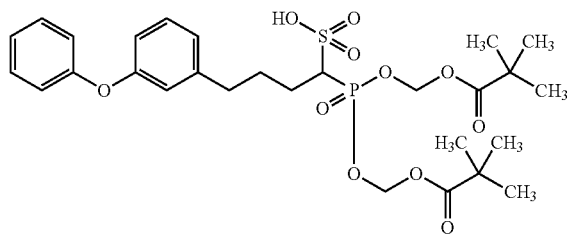
SB-204990
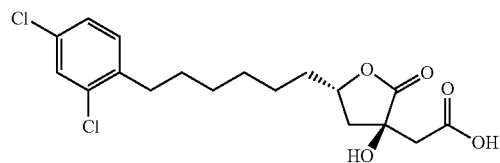
BMS-188494
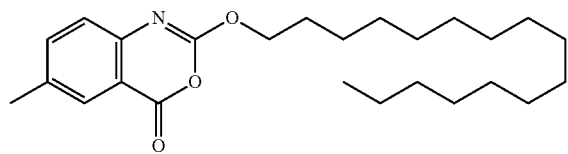
CI-1027
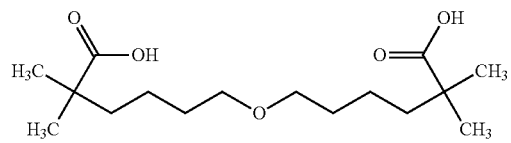
ATL-962

-continued
FR-258900
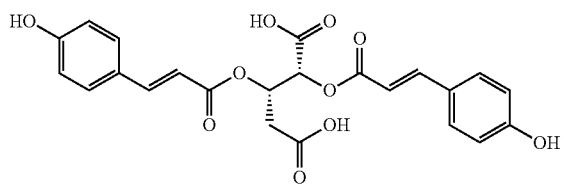
NNC-25-2504
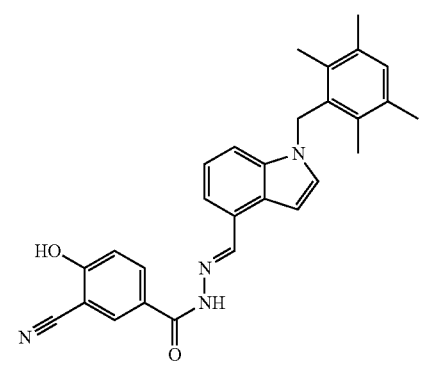
LY-2121260
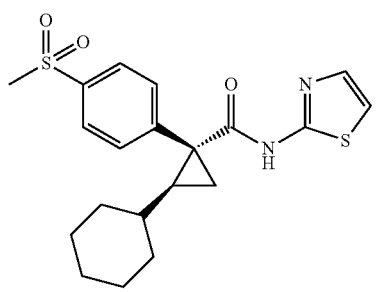
GKA-50
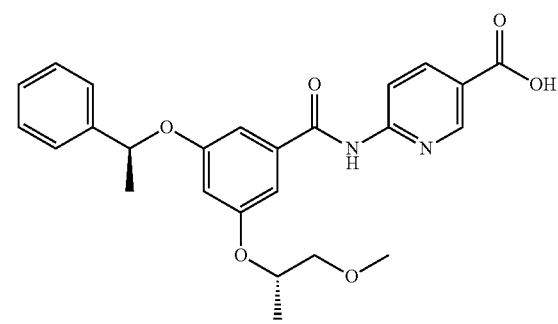
FR-225654
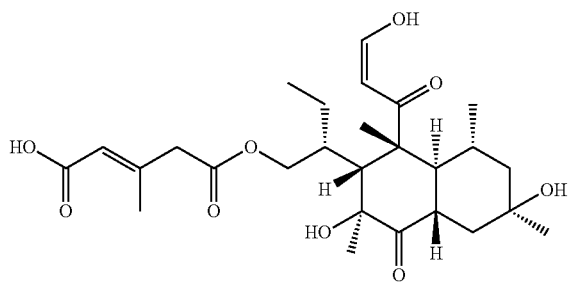
KST-48
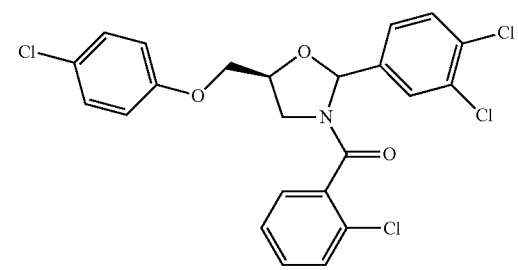
BMS-477118
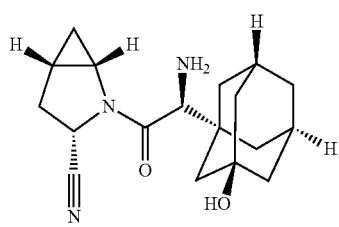
BVT-2733
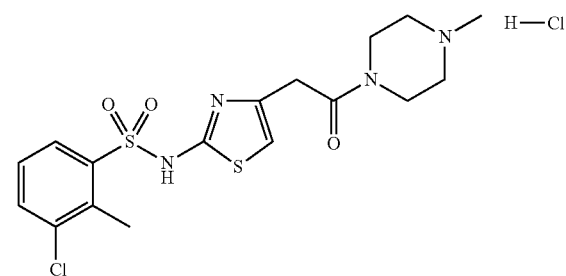
T-1095
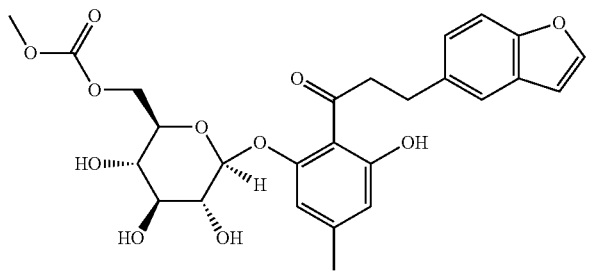
SPP-301
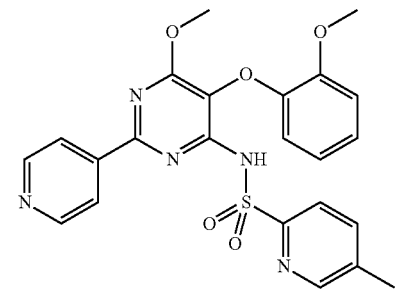

-continued
THIQ
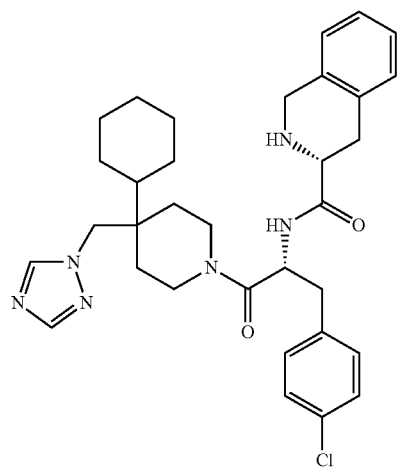
MB243
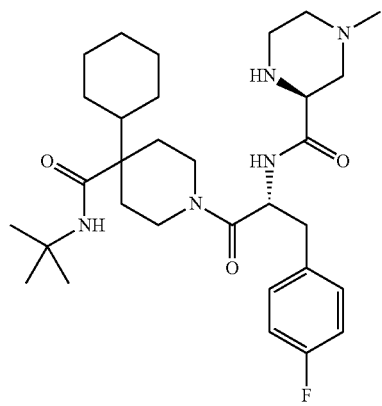
RY764
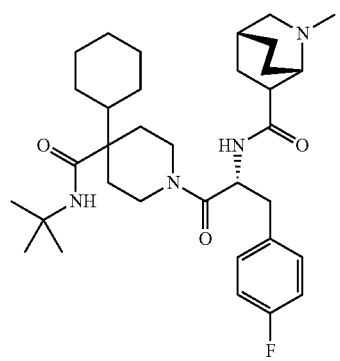
CHIR-785
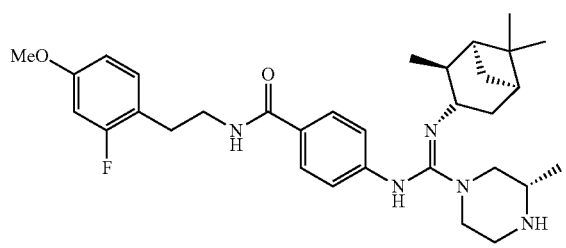
A-761
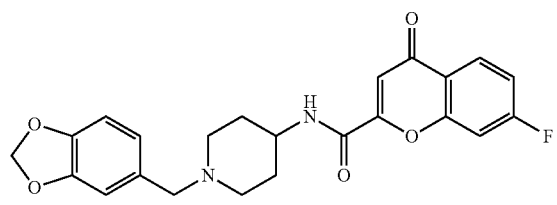
A-665798
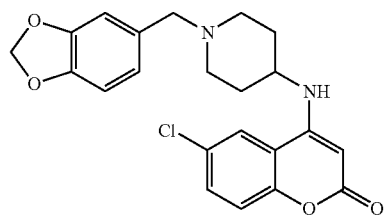
ATC-0175
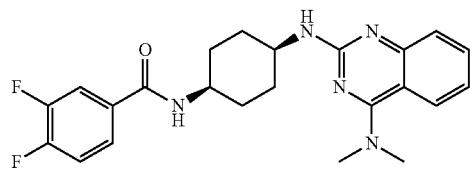
T-226296
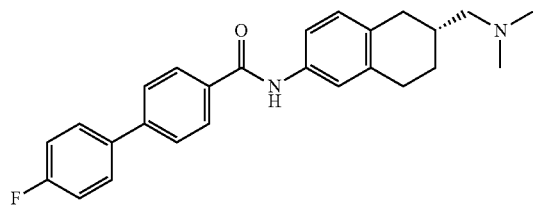
GW-803430
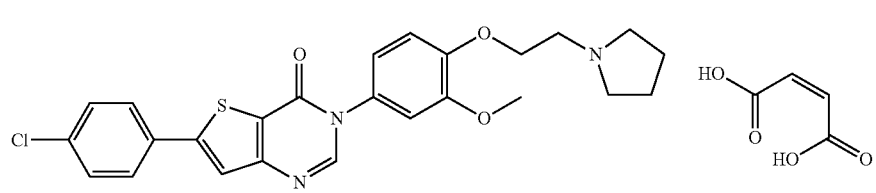

AOD-9604
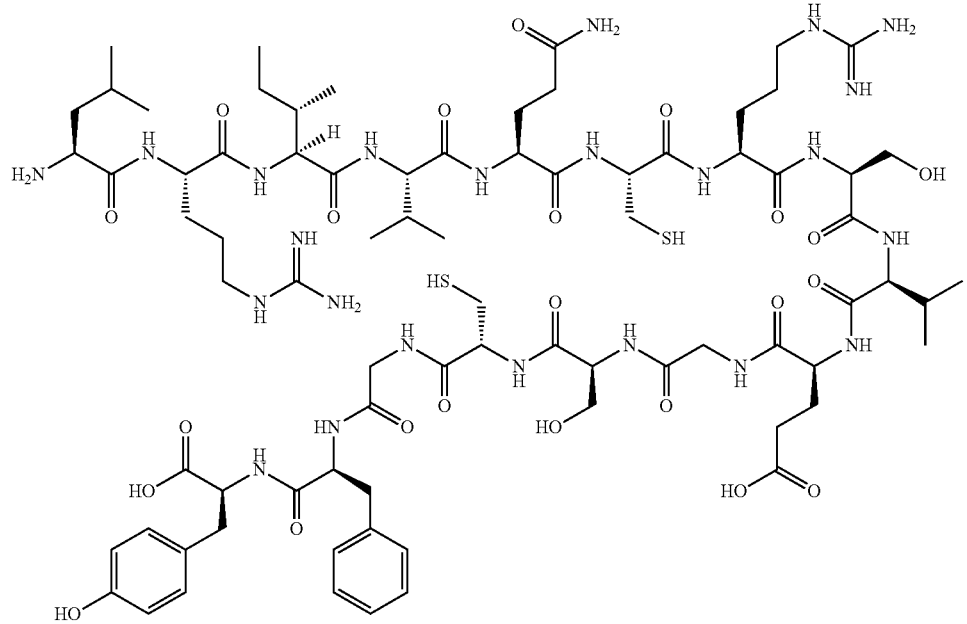
A-778193
C75
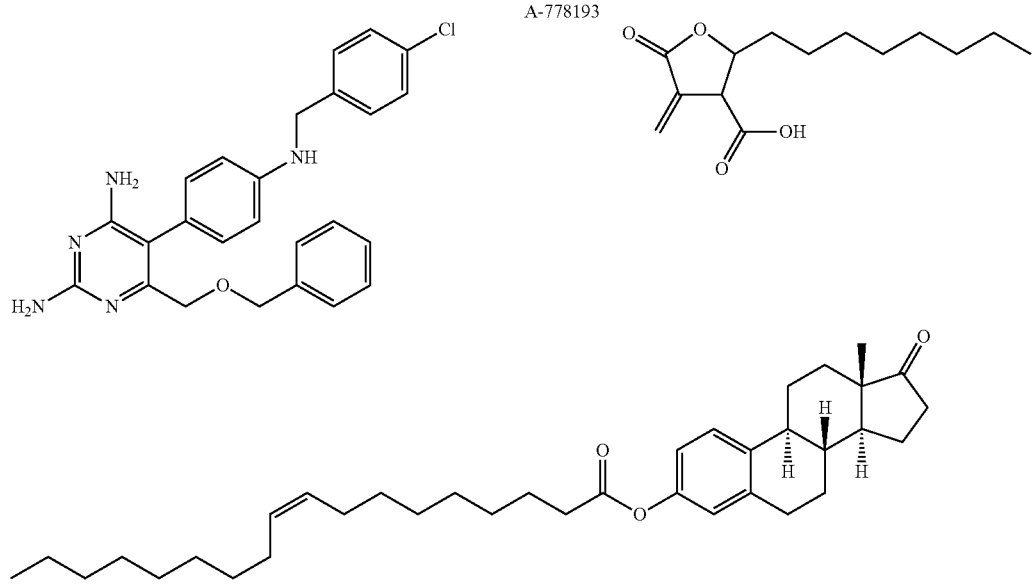
Oleoyl-Estron
KB-2115
KCP-265
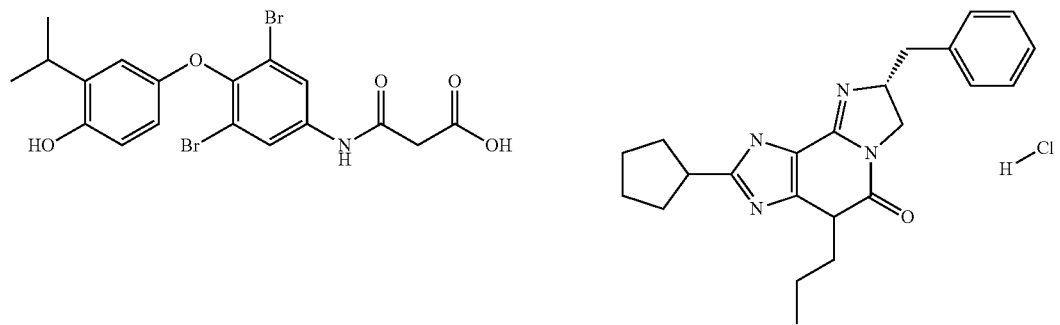

-continued
SMP-797
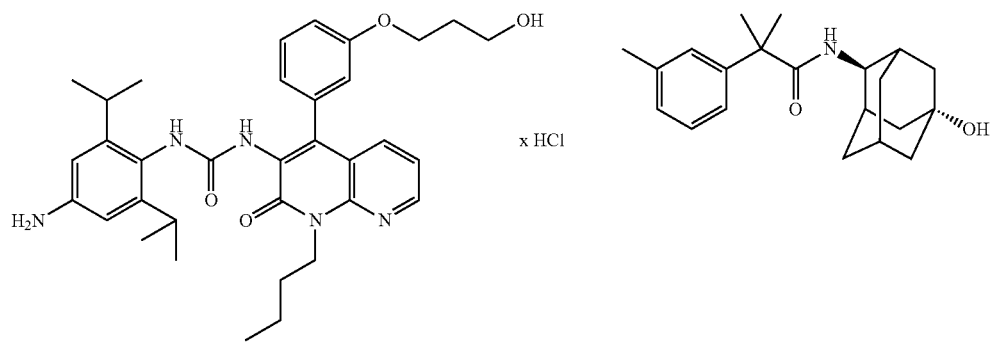
x HCl
JNJ-25918646
PSN-632408
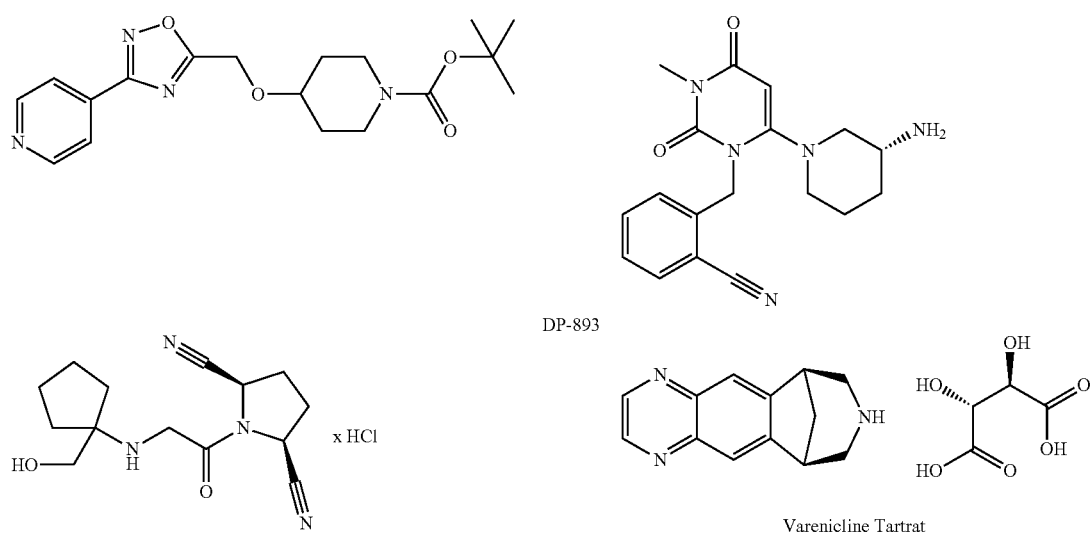
SYR-322
DP-893
x HCl
Varenicline Tartrat
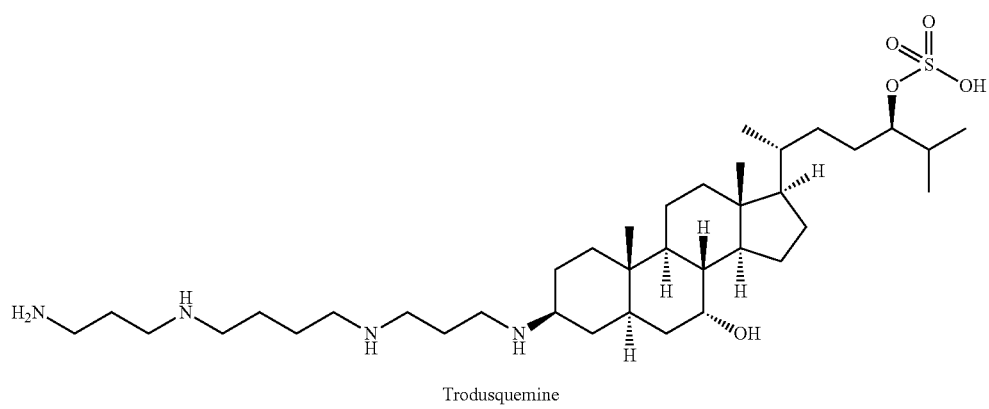
Trodusquemine
x HCl
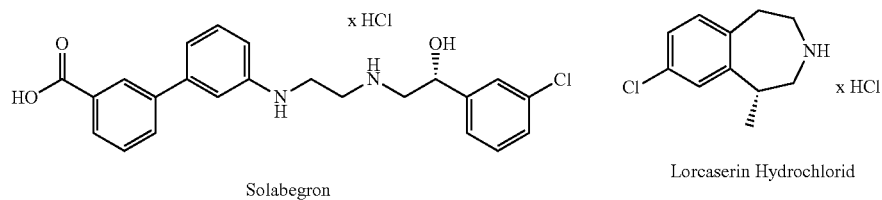
Solabegron
Lorcaserin Hydrochlorid -continued
L-152804
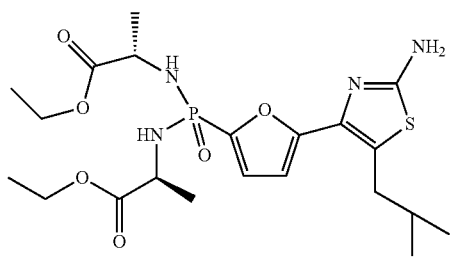
MB-06322
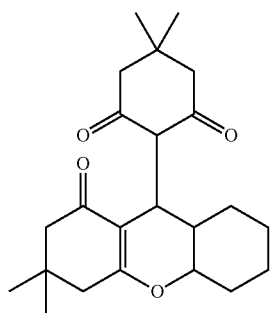
CS-917
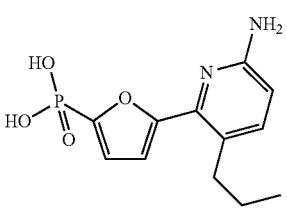
MB-07803
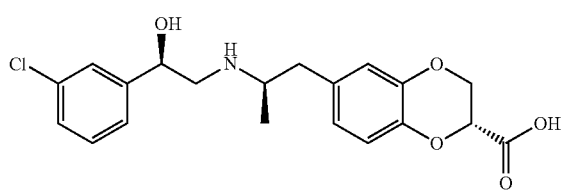
A-769662
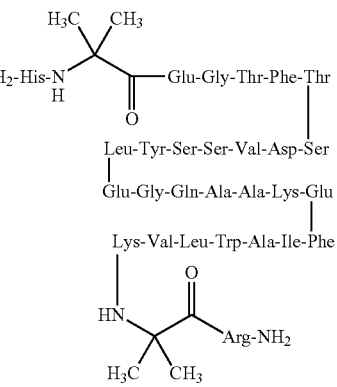
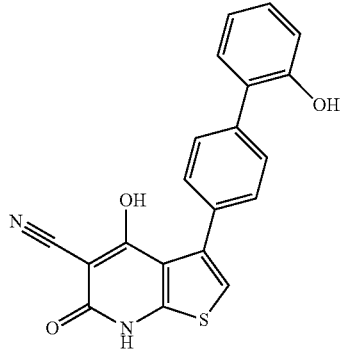
TAK-536
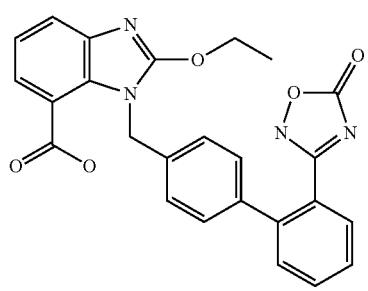
E-6837
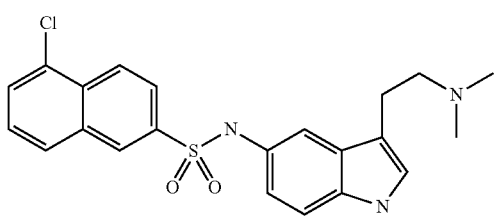
tesofensine
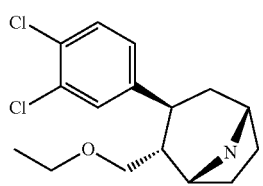
BVT-74316
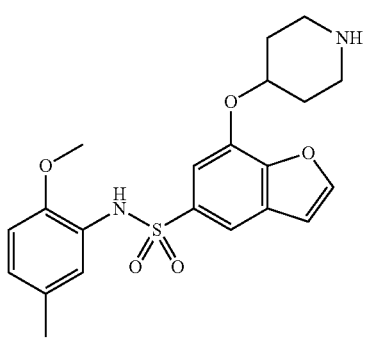

-continued
ABT-341
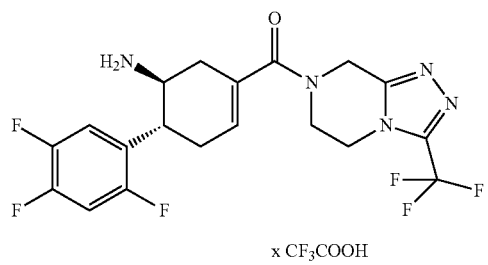
x CF₃COOH
MK-0364
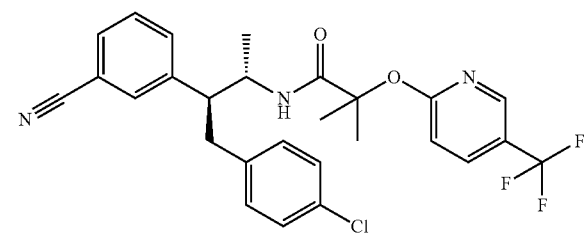
ABT-279
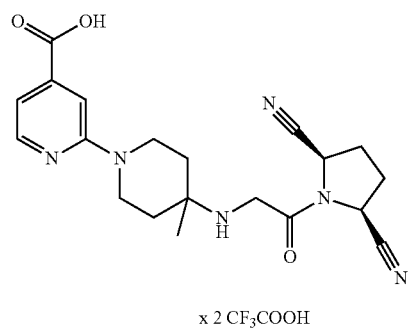
x 2 CF₃COOH
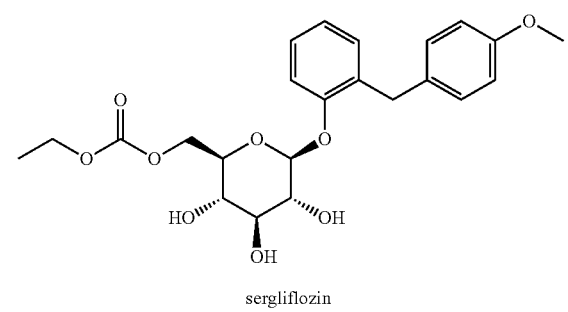
sergliflozin
SLV-319
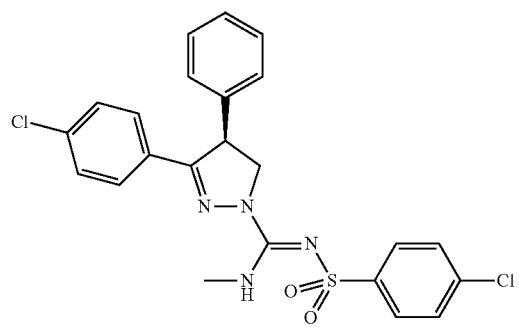
AVE 1625
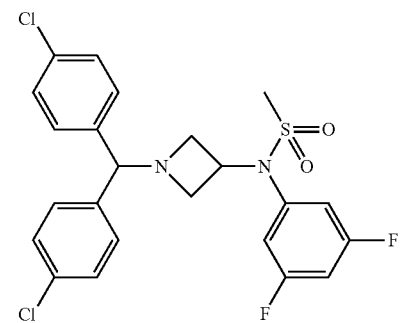
(proposed INN: drinabant)
TAK-475
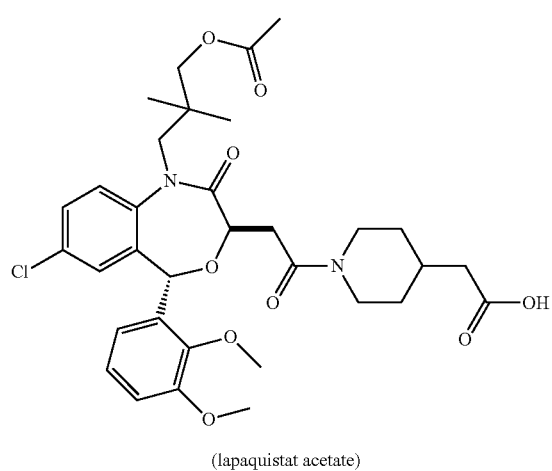
(lapaquistat acetate)
AS-1552133
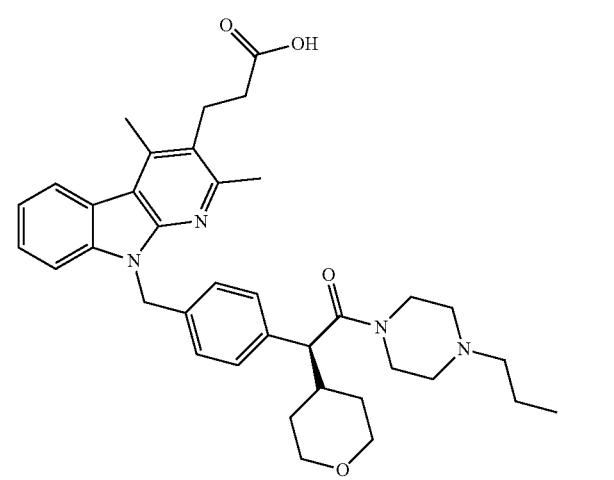

-continued
MB-07344
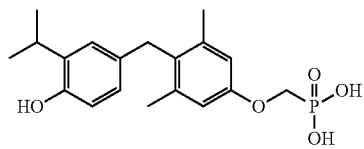
CKD-501
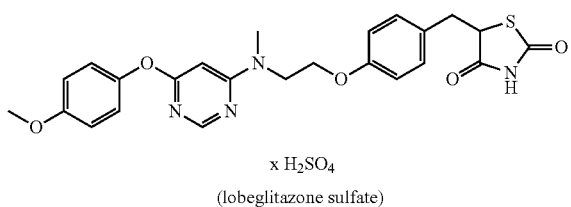
x H₂SO₄
(lobeglitazone sulfate)
MB-07811
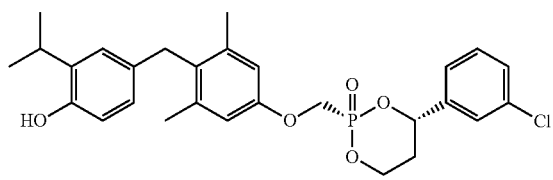
JMV-2959
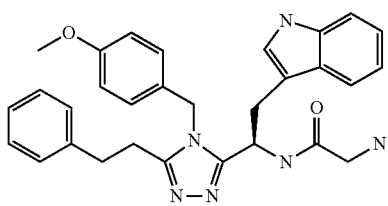
JMV-3002
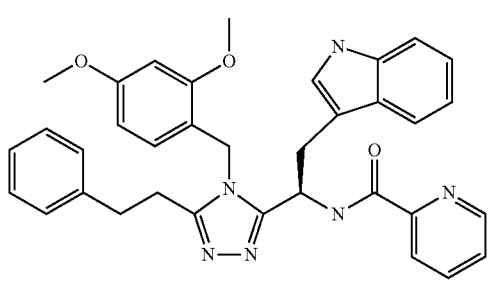
JMV-2810
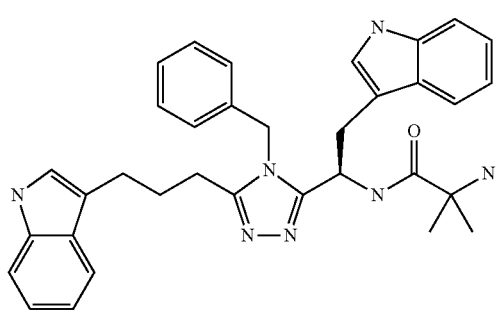
JMV-2951
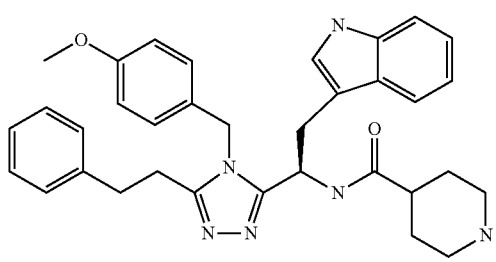
BMS-309403
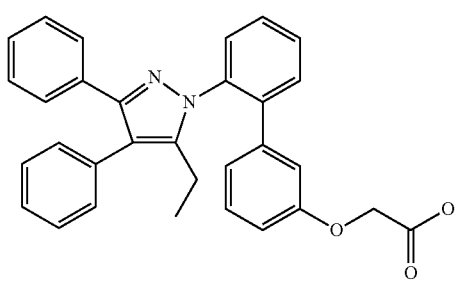
PSN-119-1
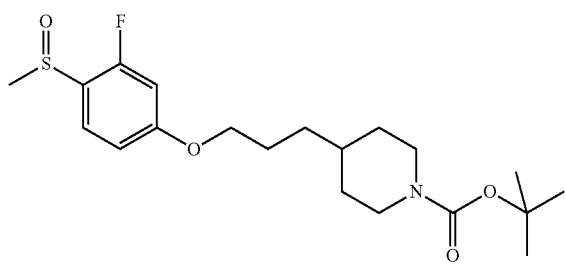
S-40755
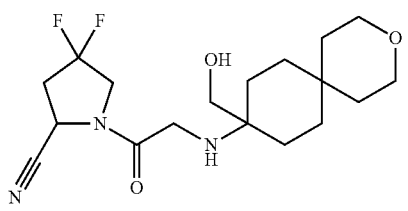

-continued
LY-2463665
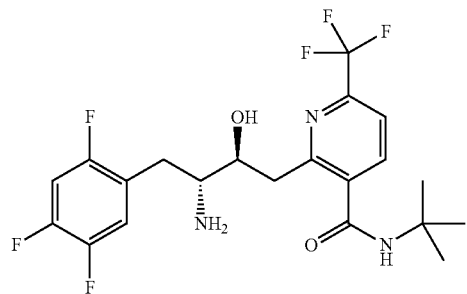
BMS-512148
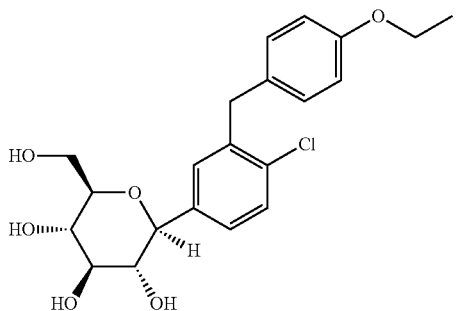
dapagliflozin,
BI-1356
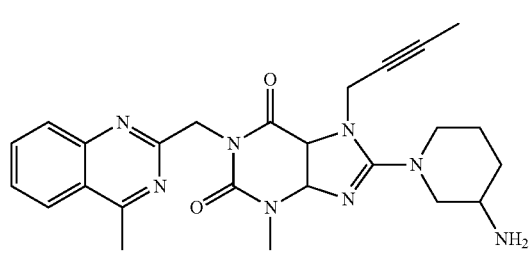
PF-429242
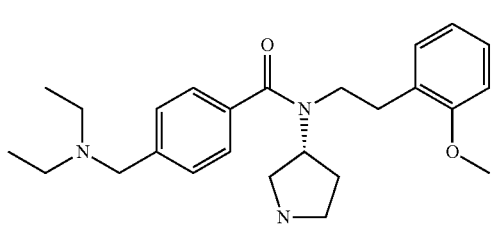
SLV-348
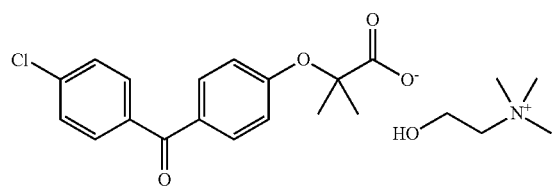
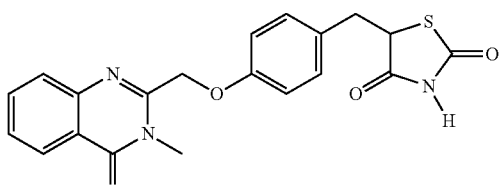
balaglitazone
"NPY-5-BY"
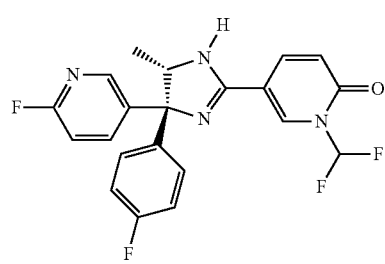
BMS-711939
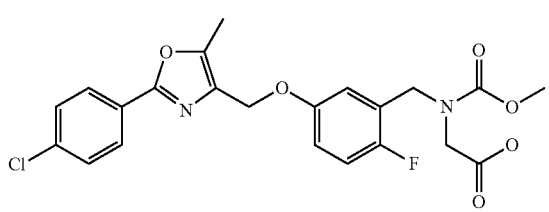
BMS-687453
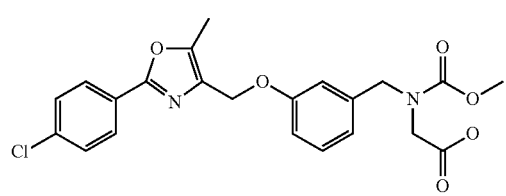
ST-3473
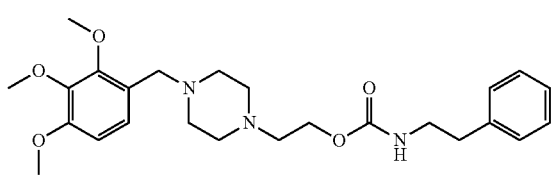
DOV-21947
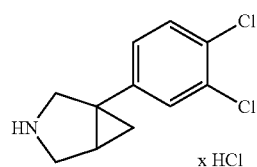
DM-71

-continued
AEGR-733
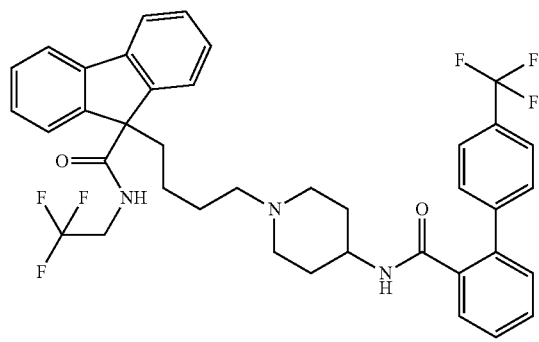
KY-382
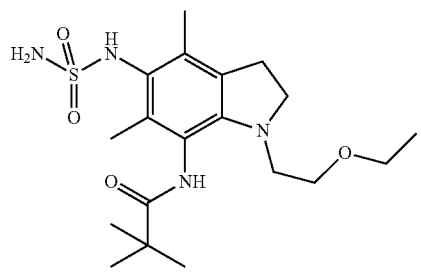
YIL-781
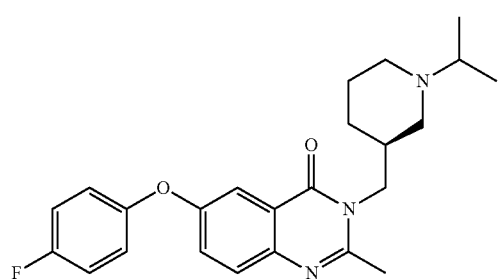
YIL-870
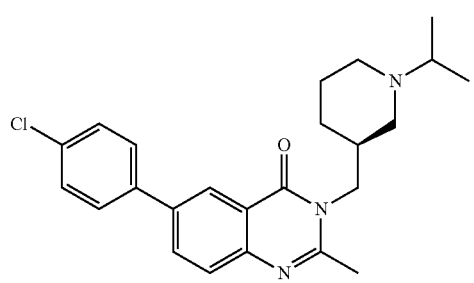
PRX-07034
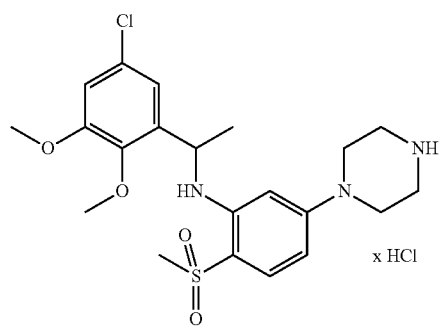
PF-00389027
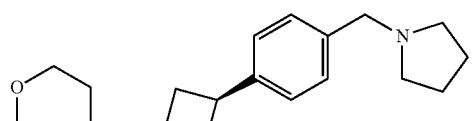
KB-3305
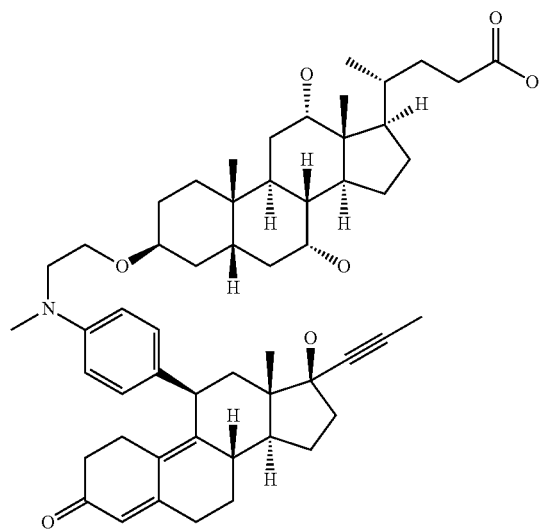
ISF-402
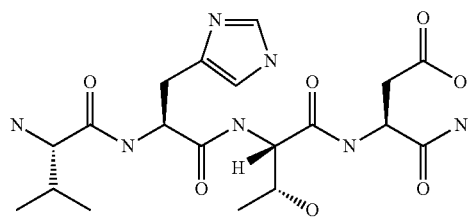

-continued
SRT-1720
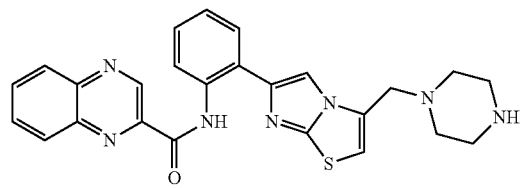
darapladib
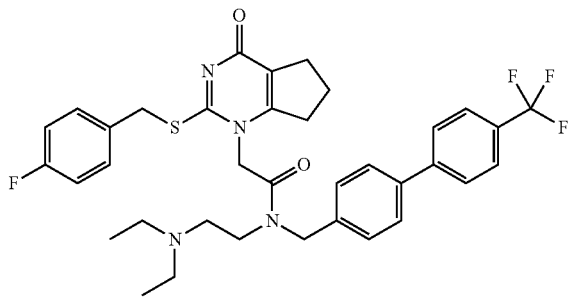
A-002
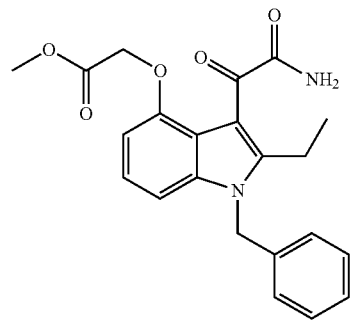
DITPA
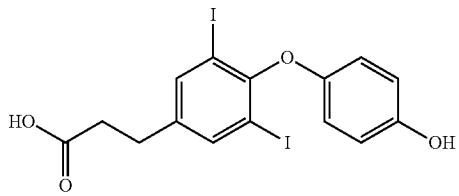
DGAT-1 inhibitor from WO2007137103
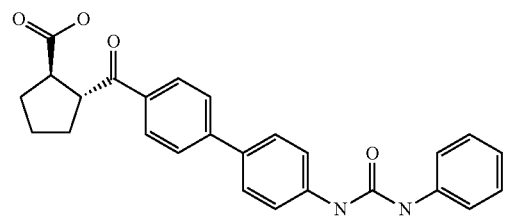
AMG-071
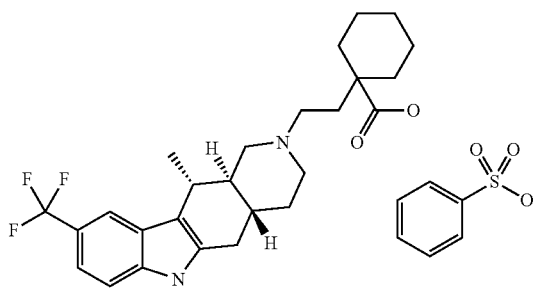
sobetirome
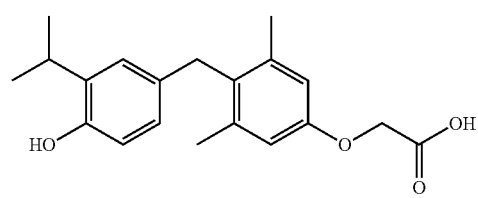
salsalate
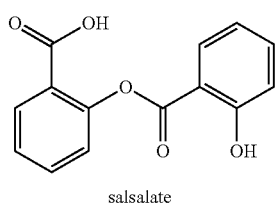
INT-131
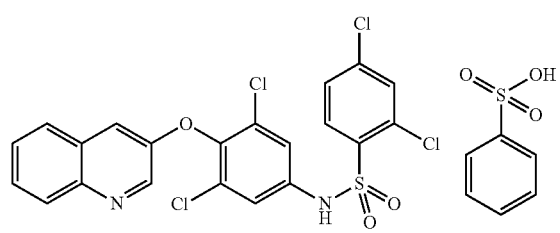
dalcetrapib
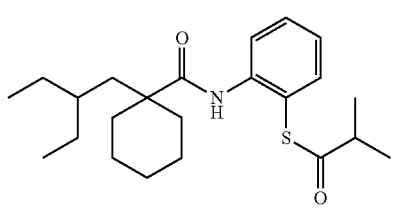

-continued
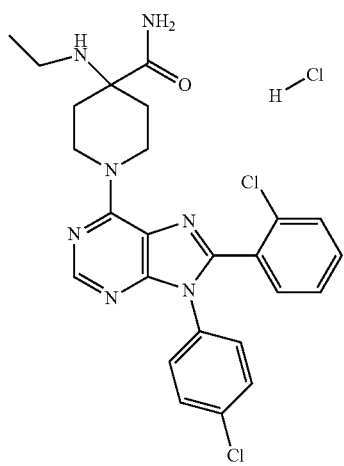
otenabant
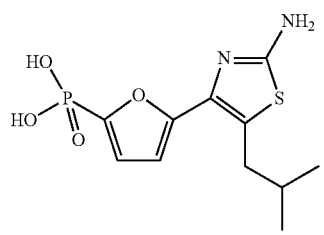
MB-07229
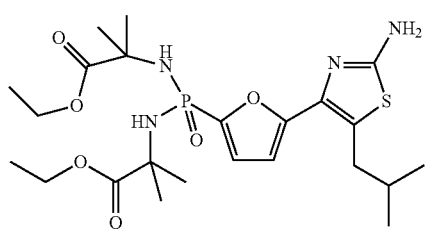
MB-07803
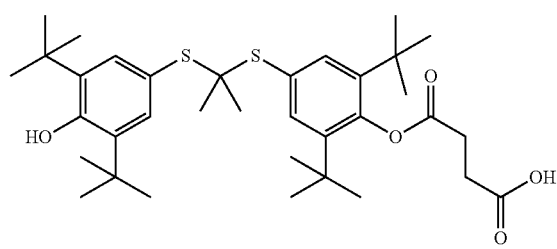
succinobucol
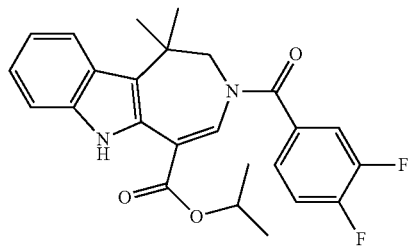
WAY-362450
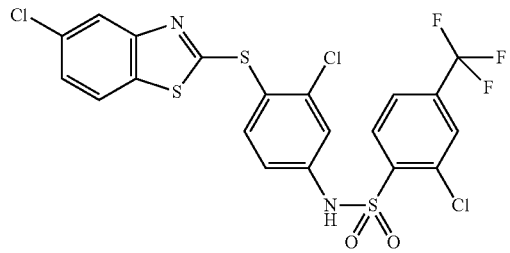
T-2384
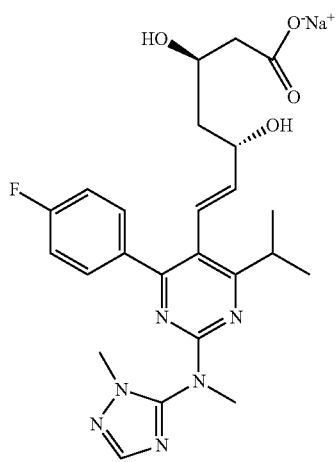
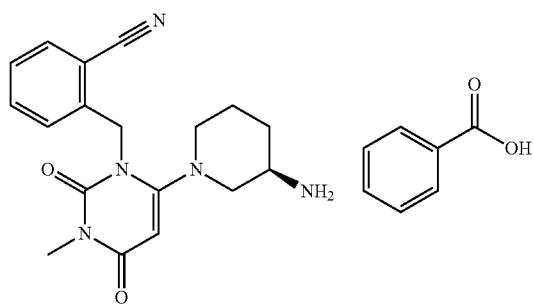
BMS-644950
alogliptin benzoate -continued
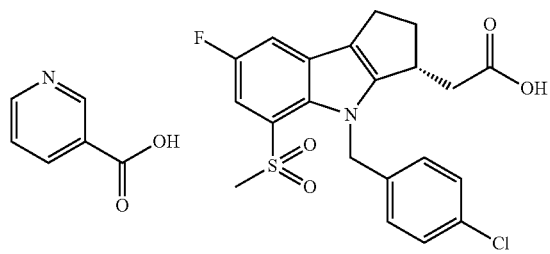
nicotinic acid/laropiprant
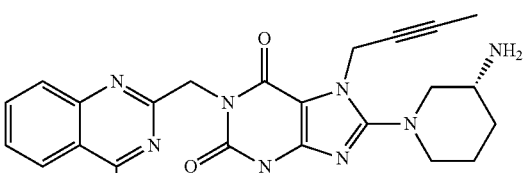
linagliptin
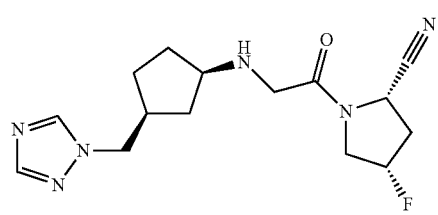
melogliptin
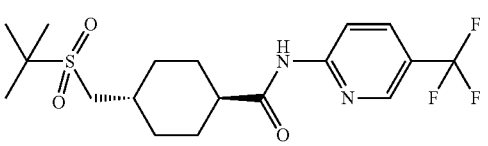
velneperit
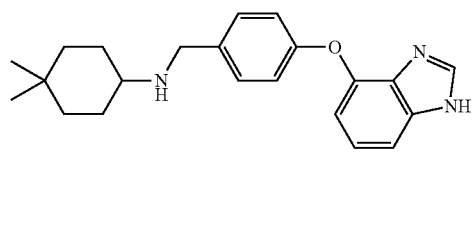
GSK-982
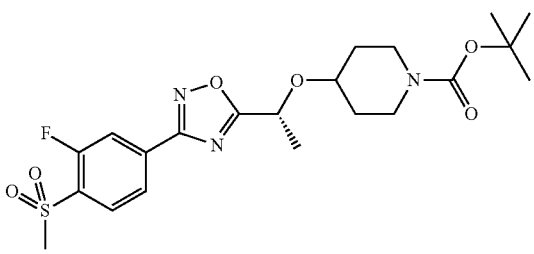
PSN-119-2
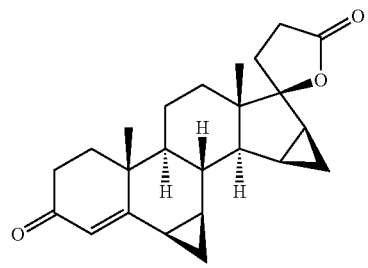
drospirenone
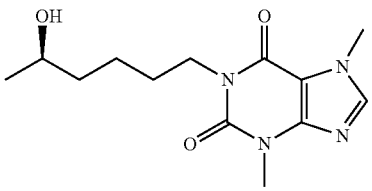
lisofylline
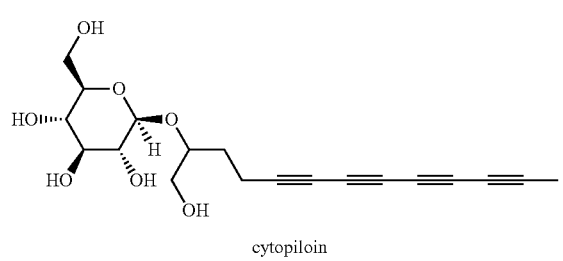
cytopiloin
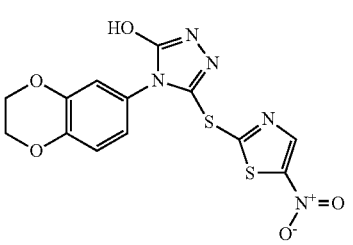
BI-78D3

119
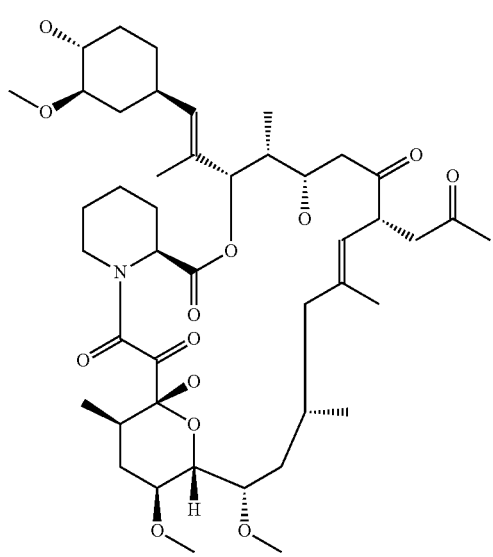
FK-1706
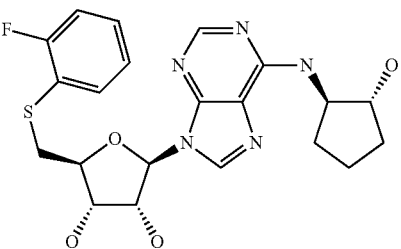
CVT-3619
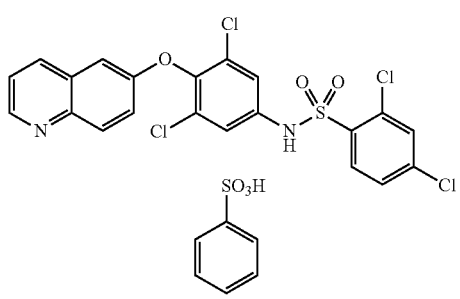
INT-131
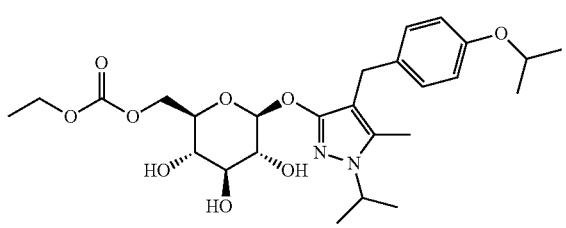
remogliflozin
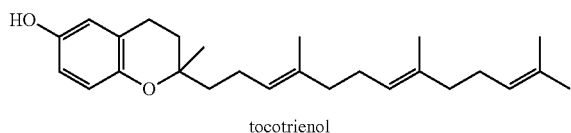
tocotrienol
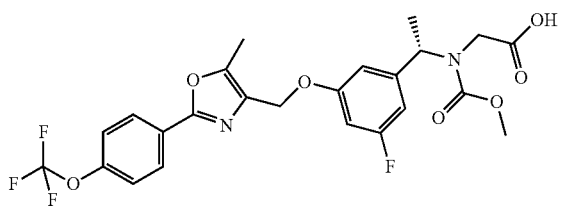
BMS-759509
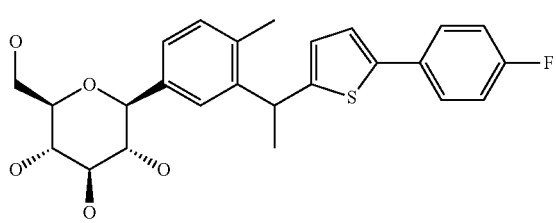
canagliflozin
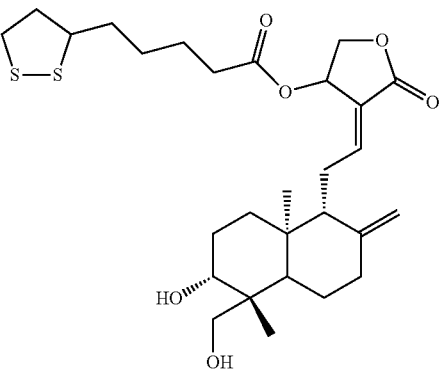
(AL-1)
14-alpha-lipolyl-andrographolide

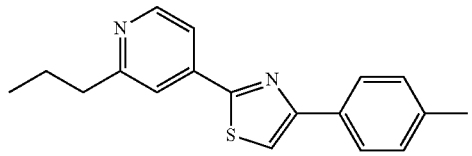

fatostatin

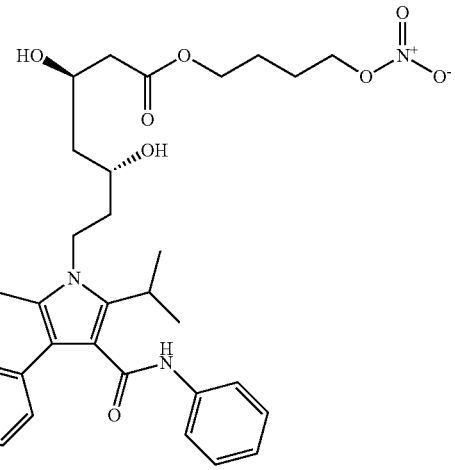

NCX-6560

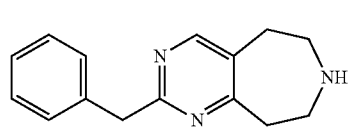

PF-3246799

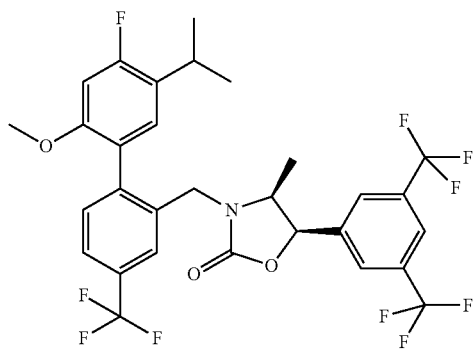

anacetrapib

Also suitable are the following active ingredients for combination preparations:
all antiepileptics specified in the Rote Liste 2011, chapter 15;
all antihypertensives specified in the Rote Liste 2011, chapter 17;
all hypotonics specified in the Rote Liste 2011, chapter 19;
all anticoagulants specified in the Rote Liste 2011, chapter 20;
all arteriosclerosis drugs specified in the Rote Liste 2011, chapter 25;
all beta receptors, calcium channel blockers and inhibitors of the renin angiotensin system specified in the Rote Liste 2011, chapter 27;
all diuretics and perfusion-promoting drugs specified in the Rote Liste 2011, chapter 36 and 37;
all withdrawal drugs/drugs for the treatment of addictive disorders specified in the Rote Liste 2011, chapter 39;
all coronary drugs and gastrointestinal drugs specified in the Rote Liste 2011, chapter 55 and 60;
all migraine drugs, neuropathy preparations and Parkinson's drugs specified in the Rote Liste 2011, chapter 61, 66 and 70.

It will be appreciated that every suitable combination of the compounds of the invention with one or more of the aforementioned compounds and optionally one or more other pharmacologically active substances is considered to be covered within the scope of protection conferred by the present invention.

Pharmaceutical Compositions

APJ modulators can be administered to animals, in particular to mammals including humans, as pharmaceuticals by themselves, in mixtures with one another, or in the form of pharmaceutical compositions. The administration can be carried out orally, for example in the form of tablets, film-coated tablets, sugar-coated tablets, granules, hard and soft gelatin capsules, solutions including aqueous, alcoholic and oily solutions, juices, drops, syrups, emulsions or suspensions, rectally, for example in the form of suppositories, or parenterally, for example in the form of solutions for subcutaneous, intramuscular or intravenous injection or infusion, in particular aqueous solutions.

Suitable pharmaceutical compounds for oral administration may be in the form of separate units, for example capsules, cachets, lozenges or tablets, each of which contains a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surfactant(s)/dispersant(s) in a suitable machine. Molded tablets can be produced by molding the compound, which is in powder form and has been moistened with an inert liquid diluent, in a suitable machine.

Pharmaceutical compositions which are suitable for peroral (sublingual) administration comprise lozenges which contain a compound of formula I with a flavoring, typically sucrose, and gum arabic or tragacanth, and pastilles which comprise the compound in an inert base such as gelatin and glycerol or sucrose and gum arabic.

Coated formulations and coated slow-release formulations, especially acid- and gastric juice-resistant formulations, also belong within the framework of the invention. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Pharmaceutical compositions suitable for rectal administration are preferably in the form of single-dose suppositories. These can be produced by mixing a compound of formula I with one or more conventional solid carriers, for example cocoa butter, and shaping resulting mixture.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain 0.1 to 5% by weight of the active compound.

Other suitable administration forms are, for example, percutaneous or topical administration, for example in the form of ointments, creams, tinctures, sprays, powders or transdermal therapeutic systems, or inhalative administration, for example in the form of nasal sprays or aerosol mixtures, or forms such as microcapsules, implants or rods.

Pharmaceutical compositions suitable for topical use on the skin are preferably in the form of ointment, cream, lotion, paste, spray, aerosol or oil. The carriers used may be petrolatum, lanolin, polyethylene glycols, alcohols and combinations of two or more of these substances. The active ingredient is generally present in a concentration of 0.1 to 15% by weight of the composition, for example 0.5 to 2%.

Transdermal administration is also possible. Pharmaceutical compositions suitable for transdermal uses may be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular option is for the active ingredient to be released by electrotransport or iontophoresis as described, for example, in Pharmaceutical Research, 2(6): 318 (1986).

APJ modulators can additionally be used in systems for local drug delivery, for example in coated stents for preventing or reducing in-stent restenosis or by applying them locally by means of a catheter. The appropriate administration form depends, among others, on the disease to be treated and on its severity.

The dosing of APJ modulators to achieve the desirable therapeutic effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of body weight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, 0.1 ng to 100 mg, typically 1 ng to 100 mg, per milliliter. Single doses may contain, for example, 1 mg to 10 g of the active ingredient. Thus, ampoules for injections may contain, for example, from 1 mg to 100 mg, and orally administrable single-dose formulations, for example tablets or capsules, may contain, for example, from 1.0 to 1000 mg, typically from 10 to 600 mg. For treatment of the abovementioned conditions, the compounds of the formula I themselves may be used as the compound, but they are preferably present with a compatible carrier in the form of a pharmaceutical composition. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Another subject of the present invention are processes for the preparation of the compounds of the formula I and their salts and solvates, by which the compounds are obtainable and which are outlined in the following.

The invention further relates to the following processes for preparing the compounds of the formula I.

Compounds of formula I can be prepared as described in Scheme 1

Scheme 1

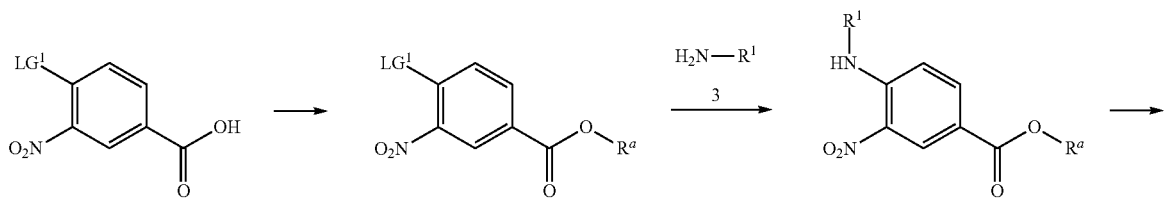

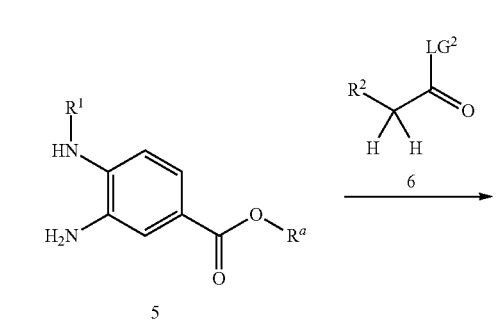
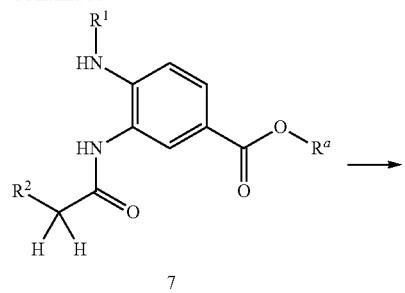
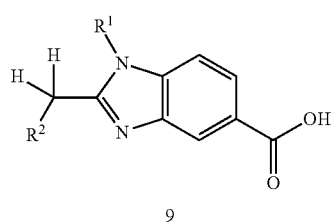

which comprises
a) protection of an acid of formula 1 to form an ester of formula 2,
b) substitution of a leaving group of a compound of formula 2 with an amine of formula 3 to form a compound of formula 4,
c) reduction of the nitro-group of formula 4 to a compound of formula 5,
d) reaction of a compound of formula 5 with a compound of formula 6 to form an amide of formula 7
e) cyclization of a compound of formula 7 to a benzimidazole of formula 8,
f) cleavage of the ester of formula 8 to form an acid of formula 9,
g) coupling of an acid of formula 9 with an amino compound of formula 10 to an amide of formula 12 and
h) converting a compound of formula 12 to a compound of formula I, or alternatively,
coupling of an acid of formula 9 with an amino compound of formula 11 to a compound of formula I;
wherein in the compounds of the formulae 1, 2, 3, 4, 5, 6, 7, 8, 9, 10, 11 and 12
$R^1$, $R^2$, $R^3$, $R^4$, $R^5$, $R^6$, n and Z are defined as in formula I,
$R^a$ is alkyl having 1, 2, 3, 4, 5 or 6 carbon atoms, e.g. Me, Et, nPr, iPr, n-Bu, sec-Bu or tert.-Bu, or —CH$_2$-phenyl, which may be substituted, e.g. Bn or para-Methoxybenzyl,
$R^b$ is $CO_2R^c$, with $R^c$ being alkyl having 1, 2, 3, 4, 5 or 6 carbon atoms, e.g. Me, Et, nPr, iPr, n-Bu, sec-Bu or tert.-Bu, or —CH$_2$-phenyl, which may be substituted, e.g. Bn or para-Methoxybenzyl, $LG^1$ is a leaving group, which can undergo nucleophilic aromatic substitution with an amin, e.g. F, Cl, Br, CN, OMs, OTf or OTs and
$LG^2$ is OH or a leaving group, which can undergo nucleophilic substitution with an aromatic amine, e.g. (C$_1$-C$_4$)-alkoxy, F, Cl, Br or OC(O)—(C$_1$-C$_4$)-alkyl, or -pentafluorphenoxy.

The protection of an acid of formula 1 to form an ester of formula 2 are per se well known to the skilled person and can be carried out under standard conditions according to, or analogously to, procedures described in the literature, for example in P. J. Kocienski, Protecting Groups, Georg Thieme Verlag, Stuttgart, 1994 or T. W. Greene, P. G. M. Wuts, Protective Groups in Organic Synthesis, John Wiley, New York, 1999), preferably the protection is achieved by reacting the acid of formula 1 with the respective alcohol under acidic conditions to obtain a methyl or ethyl ester.

The substitution of a leaving group of a compound of formula 2 with an amine of formula 3 to form a compound of formula 4 is generally carried out under neat conditions or in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or an ester such as ethyl acetate or ethyl butanoate or an amide such as N,N-dimethylformamide, N,N-dimethylacetamide or N-methyl-pyridone or a in mixture of solvents, it is carried out preferably in the presence of an additional base, for example an amine base such as TEA, DIPEA or N-methylmorpholin or an alkaline metal- or alkaline earth metal-bicarbonate, -carbonate or -hydroxide, such as sodium, potassium or lithium hydrogen carbonate, carbonate or hydroxide or cesium carbonate. The reaction temperature is generally from 0° C. to 250° C., preferably from 20° C. to 250°, more preferably from 20° C. to 150° C. The reaction time is generally from 15 min to 6 days, preferably from 15 min to 16 h, depending on the composition of the mixture and the chosen temperature range.

The reduction of the nitro-group of formula 4 to a compound of formula 5 is generally carried out in the presence of a suitable catalyst, e.g. a palladium catalyst or a Raney-Nickel catalyst or a homogeneous palladium complex, either under hydrogen atmosphere, usually at ambient pressure or at elevated pressure up to 50 bar, preferably at pressures up to 5 bar or in the presence of a different hydrogen source such as formic acid in a suitable solvent, preferably an alcohol, such as methanol, ethanol or propanol, or an ester, such as ethyl acetate or ethyl butanoate, an ether such as tetrahydrofurane, 1,4-dioxane, dibutylether, diisopropylether, methyl-tert-butylether, dimethoxyethane, or mixtures of solvents at reaction temperatures from 0° C. to 250° C., preferably from 20° C. to 150°, more preferably from 20° C. to 60° C., with reaction times generally from 15 min to 6 days, preferably from 15 min to 16 h, depending on the composition of the mixture and the chosen temperature range, or alternatively it is carried out in the presence of tin(II) chloride in a suitable solvent such as an ester, e.g. ethyl acetate or ethyl butanoate, at reaction temperatures from 0° C. to 250° C., preferably from 20° C. to 150°, more preferably from 20° C. to 80° C., with reaction times generally from 15 min to 6 days, preferably from 15 min to 16 h, depending on the composition of the mixture and the chosen temperature range.

The reaction of a compound of formula 5 with a compound of formula 6, in which $LG^2$ is OH, to form an amide of formula 7 is generally carried out in the presence of activating agents, such as CDI, DCC, EDC, HOAt, HOBt, HATU, TOTU, TBTU, BEP, PyBOP or combinations thereof, and optionally an additional base, such as TEA, DIPEA or N-methylmorpholin in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or an ester such as ethyl acetate or ethyl butanoate or an amide such as N,N-dimethylformamide or N,N-dimethylacetamide or N-methyl-pyridone or a in mixture of solvents. The reaction temperature is generally from −30° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range. The acids of formula 6 can be subjected to the reaction in form of their salts, for example their sodium salts. As far as applicable and unless otherwise indicated, it applies to all acidic or basic compounds occurring in the preparation of the compounds of the formula I that they can be present in form of their salts. The reaction of a compound of formula 5 with a compound of formula 6, in which $LG^2$ is a leaving group, which can undergo nucleophilic substitution with an aromatic amine, e.g. $(C_1-C_4)$-alkoxy, F, Cl, Br or OC(O)—$(C_1-C_4)$-alkyl, or -pentafluorphenoxy, is generally carried out in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or an ester such as ethyl acetate or ethyl butanoate or an amide such as N,N-dimethylformamide or N,N-dimethylacetamide or N-methyl-pyridone or a in mixture of solvents and optionally in the presence of an additional base, such as TEA, DIPEA or N-methylmorpholin The reaction temperature is generally from 0° C. to 250° C., preferably from 0° C. to 150°, more preferably from 20° C. to 100° C. The reaction time is generally from 15 min to 6 days, preferably from 15 min to 16 h, depending on the composition of the mixture and the chosen temperature range.

The cyclization of a compound of formula 7 to a benzimidazole of formula 8 is generally performed under neat conditions or in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, preferably in the presence of an acid, such as hydrochloric acid or trifluoro acetic acid or sulfuric acid, more preferably in the presence of hydrochloric acid in anhydrous dioxane, the reaction temperature is generally from 0° C. to 250° C., preferably from 20° C. to 250°, more preferably from 80° C. to 200° C. and the reaction time is generally from 5 min to 6 days, preferably from 5 min to 16 h, depending on the composition of the mixture and the chosen temperature range.

The cleavage of the ester of formula 8 to form an acid of formula 9 can be performed by known to the skilled person and can be carried out under standard conditions according to, or analogously to, procedures described in the literature, for example in P. J. Kocienski, Protecting Groups, Georg Thieme Verlag, Stuttgart, 1994 or T. W. Greene, P. G. M. Wuts, Protective Groups in Organic Synthesis, John Wiley, New York, 1999), preferably by reacting the ester of formula 8 with aqueous acids, such as hydrochloric acid or sulfuric acid or with aqueous bases, such as an alkaline metal- or alkaline earth metal-carbonate or -hydroxide, such as sodium, potassium or lithium carbonate or hydroxide or cesium carbonate, optionally in the presence of an additional solvent, such as an ether such as tetrahydrofurane, 1,4-dioxane, dibutylether, diisopropylether, methyl-tert-butylether, dimethoxyethane or an alcohol, such as methanol, ethanol or propanol, or mixtures of solvents. The reaction temperature is generally from 0° C. to 250° C., preferably from 20° C. to 150°, more preferably from 20° C. to 100° C. The reaction time is generally from 15 min to 6 days, preferably from 15 min to 16 h, depending on the composition of the mixture and the chosen temperature range.

The coupling of an acid of formula 9 with an amino compound of formula 10 to an amide of formula 12 is generally performed in the presence of activating agents, such as CDI, DCC, EDC, HOAt, HOBt, HATU, TOTU, TBTU, BEP, PyBOP or combinations thereof, and optionally an additional base, such as TEA, DIPEA or N-methylmorpholin in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or an ester such as ethyl acetate or ethyl butanoate or an amide such as N,N-dimethylformamide or N,N-dimethylacetamide or N-methyl-pyridone or a in mixture of solvents. The reaction temperature is generally from −30° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range. The acids of formula 9 can be subjected to the reaction in form of their salts, for example their sodium salts. They can also be transformed into an activated derivative prior to the coupling with the amine, for example into an acid chloride or an acid anhydride by standard transformations. The amines of formula 10 can be subjected to the reaction in form of their salts, for example as hydrochloride or triflate salts, in which case usually an additional equivalent of the base is added to the reaction.

The conversion of a compound of formula 12 to a compound of formula I, can be performed in one step or in several steps, depending on the meaning of the groups $R^b$ and Z.

If $R^b$ is $CO_2R^c$, with $R^c$ being alkyl having 1, 2, 3, 4, 5 or 6 carbon atoms, e.g. Me, Et, nPr, iPr, n-Bu, sec-Bu or tert.-Bu, or —$CH_2$-phenyl, which may be substituted, e.g. Bn or para-Methoxybenzyl, and Z is $CO_2H$, the conversion of a compound of formula 12 to a compound of formula I can be performed by methods known to the skilled person and can be carried out under standard conditions according to, or analogously to, procedures described in the literature, for example in P. J. Kocienski, Protecting Groups, Georg Thieme Verlag, Stuttgart, 1994 or T. W. Greene, P. G. M. Wuts, Protective Groups in Organic Synthesis, John Wiley, New York, 1999), preferably by reacting the ester of formula 8 with acids, such as hydrochloric acid, trifluoro acetic acid or sulfuric acid or with aqueous bases, such as an alkaline metal- or alkaline earth metal-carbonate or -hydroxide, such as sodium, potassium or lithium carbonate or hydroxide or cesium carbonate, optionally in the presence of an additional solvent, such as an ether such as tetrahydrofurane, 1,4-dioxane, dibutylether, diisopropylether, methyl-tert-butylether, dimethoxyethane or an alcohol, such as methanol, ethanol or propanol, or mixtures of solvents. The reaction temperature is generally from 0° C. to 250° C., preferably from 20° C. to 150°, more preferably from 20° C. to 100° C. The reaction time is generally from 15 min to 6 days, preferably from 15 min to 16 h, depending on the composition of the mixture and the chosen temperature range.

If $R^b$ is $CO_2R^c$, with $R^c$ being alkyl having 1, 2, 3, 4, 5 or 6 carbon atoms, e.g. Me, Et, nPr, iPr, n-Bu, sec-Bu or tert.-Bu, or —$CH_2$-phenyl, which may be substituted, e.g. Bn or para-Methoxybenzyl, and Z is $CONR^7R^8$, the conversion of a compound of formula 12 to a compound of formula I can be performed in several steps. The first step consists of the cleavage of the ester of formula 12 as described immediately above, followed by a reaction with an amine $HNR^{7a}R^{8a}$, wherein $R^{7a}$ and $R^{8a}$ are, independently of each other, either defined as the groups $R^7$ and $R^8$ in the compounds of formula I or they are precursors of the groups $R^7$ and $R^8$ in formula I, they can for example contain functional groups in protected form or functional groups which can be converted to obtain the final groups $R^7$ and $R^8$. This reaction with an amine $HNR^{7a}R^{8a}$ is generally performed in the presence of activating agents, such as CDI, DCC, EDC, HOAt, HOBt, HATU, TOTU, TBTU, BEP, PyBOP or combinations thereof, and optionally an additional base, such as TEA, DIPEA or N-methylmorpholin in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or an ester such as ethyl acetate or ethyl butanoate or an amide such as N,N-dimethylformamide or N,N-dimethylacetamide or N-methyl-pyridone or a in mixture of solvents. The reaction temperature is generally from −30° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range. The resulting product can already be a compound of formula I, if $R^{7a}$ is $R^7$ and $R^{8a}$ is $R^8$. If the resulting product is not already a compound of formula I, it can be transformed into a compound of formula I depending on the meaning of the groups $R^{7a}$ and $R^{8a}$. If the groups $R^{7a}$ and/or $R^{8a}$ contain protecting groups that can be cleaved by hydrogenation, e.g. a benzyl group or a 4-methoxybenzyl group, the transformation to a compound of formula I can be a catalytic hydrogenation or a transfer hydrogenation. If the groups $R^{7a}$ and/or $R^{8a}$ contain protecting groups that can be cleaved by treatment with acid, e.g. a tert-butyl group, the transformation to a compound of formula I can be an acidic deprotection. If the groups $R^{7a}$ and/or $R^{8a}$ contain protecting groups that can be cleaved by treatment with base e.g. a methyl or ethyl ester, the transformation to a compound of formula I can be a basic hydrolysis. All deprotection reactions used in the above-described transformations of precursors of compounds of formula I, in which the groups $R^{7a}$ and/or $R^{8a}$ contain protecting groups, to compounds of formula I are per se well known to the skilled person and can be carried out under standard conditions according to, or analogously to, procedures described in the literature, for example in P. J. Kocienski, Protecting Groups, Georg Thieme Verlag, Stuttgart, 1994 or T. W. Greene, P. G. M. Wuts, Protective Groups in Organic Synthesis, John Wiley, New York, 1999).

Alternatively, the coupling of an acid of formula 9 with an amino compound of formula 11 can directly result in a compound of formula I. This transformation is generally performed in the presence of activating agents, such as CDI, DCC, EDC, HOAt, HOBt, HATU, TOTU, TBTU, BEP, PyBOP or combinations thereof, and optionally an additional base, such as TEA, DIPEA or N-methylmorpholin in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or an ester such as ethyl acetate or ethyl butanoate or an amide such as N,N-dimethylformamide or N,N-dimethylacetamide or N-methyl-pyridone or a in mixture of solvents. The reaction temperature is generally from −30° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range.

Alternatively compounds of formula I can be prepared as described in Scheme 2

Scheme 2

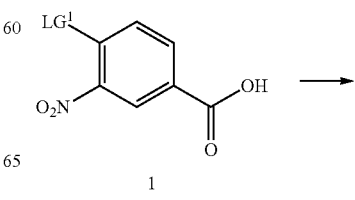

1

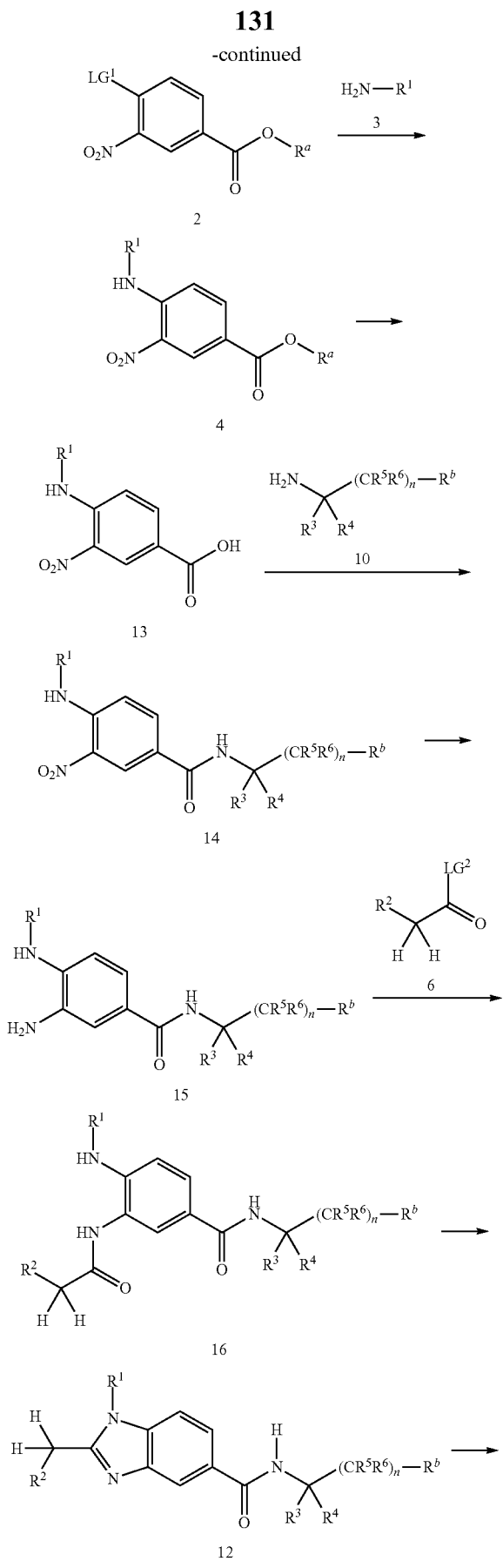

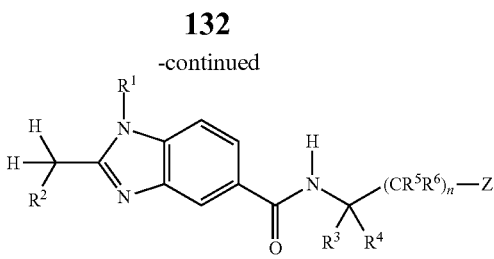

which comprises
a) protection of an acid of formula 1 to form an ester of formula 2,
b) substitution of a leaving group of a compound of formula 2 with an amine of formula 3 to form a compound of formula 4,
c) cleavage of an ester of formula 4 to an acid of formula 13,
d) reaction of a compound of formula 13 with an amine of formula 10 to form an amide of formula 14,
e) reduction of the nitro-group of a compound of formula 14 to a compound of formula 15,
f) reaction of a compound of formula 15 with a compound of formula 6 to form an amide of formula 16,
g) cyclization of a compound of formula 16 to a benzimidazole of formula 12,
h) converting a compound of formula 12 to a compound of formula I,
wherein in the compounds of the formulae 1, 2, 3, 4, 6, 10, 12, 13, 14, 15 and 16
$R^1$, $R^2$, $R^3$, $R^4$, $R^5$, $R^6$, n and Z are defined as in formula I,
$R^a$ is alkyl having 1, 2, 3, 4, 5 or 6 carbon atoms, e.g. Me, Et, nPr, iPr, n-Bu, sec-Bu or tert.-Bu, or —$CH_2$-phenyl, which may be substituted, e.g. Bn or para-Methoxybenzyl,
$R^b$ is $CO_2R^c$, with $R^c$ being alkyl having 1, 2, 3, 4, 5 or 6 carbon atoms, e.g. Me, Et, nPr, iPr, n-Bu, sec-Bu or tert.-Bu, or —$CH_2$-phenyl, which may be substituted, e.g. Bn or para-Methoxybenzyl,
$LG^1$ is a leaving group, which can undergo nucleophilic aromatic substitution with an amine, e.g. F, Cl, Br, CN, OMs, OTf or OTs and
$LG^2$ is OH or a leaving group, which can undergo nucleophilic substitution with an aromatic amine, e.g. ($C_1$-$C_4$)-alkoxy, F, Cl, Br or OC(O)—($C_1$-$C_4$)-alkyl, or -pentafluorphenoxy.

The protection of an acid of formula 1 to form an ester of formula 2 can be performed by methods known to the skilled person and can be carried out under standard conditions according to, or analogously to, procedures described in the literature, for example in P. J. Kocienski, Protecting Groups, Georg Thieme Verlag, Stuttgart, 1994 or T. W. Greene, P. G. M. Wuts, Protective Groups in Organic Synthesis, John Wiley, New York, 1999), preferably by reacting the acid of formula 1 with the respective alcohol under acidic conditions.

The substitution of a leaving group of a compound of formula 2 with an amine of formula 3 to form a compound of formula 4 is generally carried out under neat conditions or in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or an ester such as ethyl acetate or ethyl butanoate or an amide such as N,N-dimethylformamide or N,N-dimethylacetamide or N-methyl-pyridone or a in mixture of solvents, it is carried out preferably in the presence of an additional base, for example an amine base such as TEA, DIPEA or N-methylmorpholin or an alkaline metal- or alkaline earth metal-bicarbonate, -carbonate or -hydroxide, such as sodium, potassium or lithium hydrogen carbonate, carbonate or hydroxide or cesium carbonate. The reaction temperature is generally from 0° C. to 250° C., preferably from 20° C. to 250°, more preferably from 20° C. to 150° C. The reaction time is generally from 15 min to 6 days, preferably from 15 min to 16 h, depending on the composition of the mixture and the chosen temperature range.

The cleavage of the ester of formula 4 to form an acid of formula 13 can be performed by methods known to the skilled person and can be carried out under standard conditions according to, or analogously to, procedures described in the literature, for example in P. J. Kocienski, Protecting Groups, Georg Thieme Verlag, Stuttgart, 1994 or T. W. Greene, P. G. M. Wuts, Protective Groups in Organic Synthesis, John Wiley, New York, 1999), preferably by reacting the ester of formula 4 with aqueous acids, such as hydrochloric acid or sulfuric acid or with aqueous bases, such as an alkaline metal- or alkaline earth metal-carbonate or -hydroxide, such as sodium, potassium or lithium carbonate or hydroxide or cesium carbonate, optionally in the presence of an additional solvent, such as an ether such as tetrahydrofurane, 1,4-dioxane, dibutylether, diisopropylether, methyl-tert-butylether, dimethoxyethane or an alcohol, such as methanol, ethanol or propanol, or mixtures of solvents. The reaction temperature is generally from 0° C. to 250° C., preferably from 20° C. to 150°, more preferably from 20° C. to 100° C. The reaction time is generally from 15 min to 6 days, preferably from 15 min to 16 h, depending on the composition of the mixture and the chosen temperature range.

The coupling of an acid of formula 13 with an amino compound of formula 10 to an amide of formula 14 is generally performed in the presence of activating agents, such as CDI, DCC, EDC, HOAt, HOBt, HATU, TOTU, TBTU, BEP, PyBOP or combinations thereof, and optionally an additional base, such as TEA, DIPEA or N-methylmorpholin in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or an ester such as ethyl acetate or ethyl butanoate or an amide such as N,N-dimethylformamide or N,N-dimethylacetamide or N-methyl-pyridone or a in mixture of solvents. The reaction temperature is generally from −30° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range. The acids of formula 13 can be subjected to the reaction in form of their salts, for example their sodium salts. They can also be transformed into an activated derivative prior to the coupling with the amine, for example into an acid chloride or an acid anhydride by standard transformations. The amines of formula 10 can be subjected to the reaction in form of their salts, for example as hydrochloride or triflate salts, in which case usually an additional equivalent of the base is added to the reaction.

The reduction of the nitro-group of formula 14 to a compound of formula 15 is generally carried out in the presence of a suitable catalyst, e.g. a palladium catalyst or a Raney-Nickel catalyst or a homogeneous palladium complex, either under hydrogen atmosphere, usually at ambient pressure or at elevated pressure up to 50 bar, preferably at pressures up to 5 bar or in the presence of a different hydrogen source such as formic acid in a suitable solvent, preferably an alcohol, such as methanol, ethanol or propanol, or an ester, such as ethyl acetate or ethyl butanoate, an ether such as tetrahydrofurane, 1,4-dioxane, dibutylether, diisopropylether, methyl-tert-butylether, dimethoxyethane, or mixtures of solvents at reaction temperatures from 0° C. to 250° C., preferably from 20° C. to 150°, more preferably from 20° C. to 60° C., with reaction times generally from 15 min to 6 days, preferably from 15 min to 16 h, depending on the composition of the mixture and the chosen temperature range, or alternatively it is carried out in the presence of tin(II) chloride in a suitable solvent such as an ester, e.g. ethyl acetate or ethyl butanoate, at reaction temperatures from 0° C. to 250° C., preferably from 20° C. to 150°, more preferably from 20° C. to 80° C., with reaction times generally from 15 min to 6 days, preferably from 15 min to 16 h, depending on the composition of the mixture and the chosen temperature range.

The reaction of a compound of formula 15 with a compound of formula 6, in which $LG^2$ is OH, to form an amide of formula 16 is generally carried out in the presence of activating agents, such as CDI, DCC, EDC, HOAt, HOBt, HATU, TOTU, TBTU, BEP, PyBOP or combinations thereof, and optionally an additional base, such as TEA, DIPEA or N-methylmorpholin in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or an ester such as ethyl acetate or ethyl butanoate or an amide such as N,N-dimethylformamide or N,N-dimethylacetamide or N-methyl-pyridone or a in mixture of solvents. The reaction temperature is generally from −30° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range. The acids of formula 6 can be subjected to the reaction in form of their salts, for example their sodium salts. The reaction of a compound of formula 15 with a compound of formula 6, in which $LG^2$ is a leaving group, which can undergo nucleophilic substitution with an aromatic amine, e.g. ($C_1$-$C_4$)-alkoxy, F, Cl, Br or OC(O)—($C_1$-$C_4$)-alkyl, or -pentafluorphenoxy, is generally carried out in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or an ester such as ethyl acetate or ethyl butanoate or an amide such as N,N-dimethylformamide or N,N-dimethylacetamide or N-methyl-pyridone or a in mixture of solvents and optionally in the presence of an additional base, such as TEA, DIPEA or N-methylmorpholin The reaction temperature is generally from 0° C. to 250° C., preferably from 0° C. to 150°, more preferably from 20° C. to 100° C. The reaction time is generally from 15 min to 6 days, preferably from 15 min to 16 h, depending on the composition of the mixture and the chosen temperature range.

The cyclization of a compound of formula 16 to a benzimidazole of formula 12 is generally performed under neat conditions or in an appropriate inert solvent, for example a hydrocarbon or a chlorinated hydrocarbon such as benzene; toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, preferably in the presence of an acid, such as hydrochloric acid or trifluoro acetic acid or sulfuric acid, more preferably in the presence of hydrochloric acid in anhydrous dioxane, the reaction temperature is generally from 0° C. to 250° C., preferably from 20° C. to 250°, more preferably from 80° C. to 200° C. and the reaction time is generally from 5 min to 6 days, preferably from 5 min to 16 h, depending on the composition of the mixture and the chosen temperature range.

The conversion of a compound of formula 12 to a compound of formula I can be performed as it was described for the reaction sequence in Scheme 1.

Alternatively compounds of formula I can be prepared as described in Scheme 3 d) reaction of a compound of formula 15 with a compound of formula 6 to form an amide of formula 16, e) cyclization of a compound of formula 16 to a benzimidazole of formula 12, and f) converting a compound of formula 12 to a compound of formula I, or alternatively, the conversion of a compound of formula 16 to a compound of formula 17 and subsequently the cyclization of a compound of formula 17 to a compound of formula I,

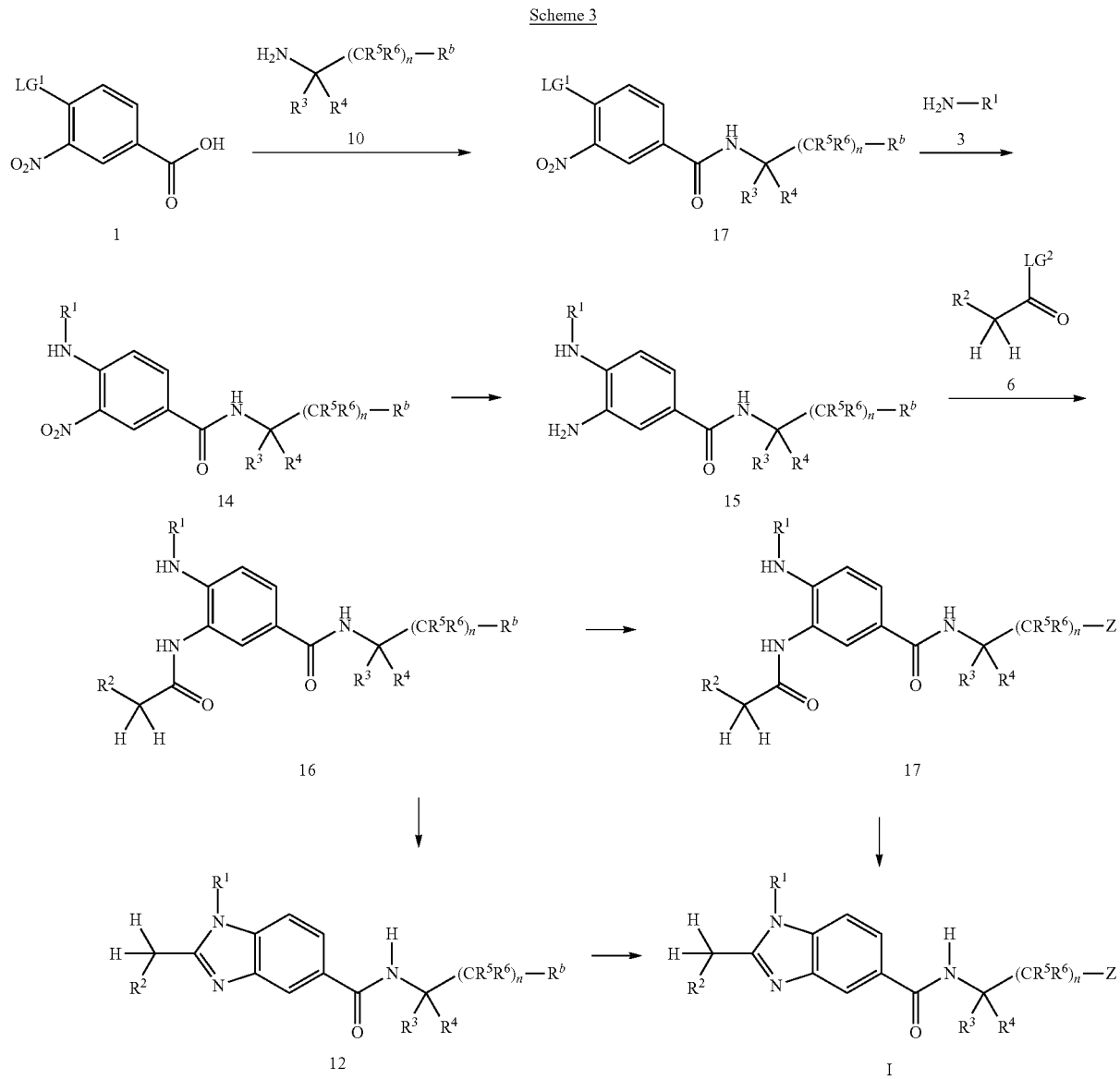

Scheme 3 which comprises
a) reaction of a compound of formula 1 with an amine of formula 10 to form an amide of formula 17,
b) substitution of a leaving group of a compound of formula 17 with an amine of formula 3 to form a compound of formula 14,
c) reduction of the nitro-group of formula 14 to a compound of formula 15, wherein in the compounds of the formulae 1, 3, 6, 10, 12, 14, 15, 16 and 17
$R^1$, $R^2$, $R^3$, $R^4$, $R^5$, $R^6$, n and Z are defined as in formula I,
$R^a$ is alkyl having 1, 2, 3, 4, 5 or 6 carbon atoms, e.g. Me, Et, nPr, iPr, n-Bu, sec-Bu or tert.-Bu, or —CH$_2$-phenyl, which may be substituted, e.g. Bn or para-Methoxybenzyl,
$R^b$ is CO$_2$R$^c$, with R$^c$ being alkyl having 1, 2, 3, 4, 5 or 6 carbon atoms, e.g. Me, Et, nPr, iPr, n-Bu, sec-Bu or tert.-

Bu, or —CH$_2$-phenyl, which may be substituted, e.g. Bn or para-Methoxybenzyl, or R$^c$ is a solid support, like a Wang resin.

LG$^1$ is a leaving group, which can undergo nucleophilic aromatic substitution with an amine, e.g. F, Cl, Br, CN, OMs, OTf or OTs and LG$^2$ is OH or a leaving group, which can undergo nucleophilic substitution with an aromatic amine, e.g. (C$_1$-C$_4$)-alkoxy, F, Cl, Br or OC(O)—(C$_1$-C$_4$)-alkyl, or -pentafluorphenoxy.

The coupling of an acid of formula 1 with an amino compound of formula 10 to an amide of formula 17 is generally performed in the presence of activating agents, such as CDI, DCC, EDC, HOAt, HOBt, HATU, TOTU, TBTU, BEP, PyBOP or combinations thereof, and optionally an additional base, such as TEA, DIPEA or N-methylmorpholin in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or an ester such as ethyl acetate or ethyl butanoate or an amide such as N,N-dimethylformamide or N,N-dimethylacetamide or N-methyl-pyridone or a in mixture of solvents. The reaction temperature is generally from −30° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range. The acids of formula 1 can be subjected to the reaction in form of their salts, for example their sodium salts. They can also be transformed into an activated derivative prior to the coupling with the amine, for example into an acid chloride or an acid anhydride by standard transformations. The amines of formula 10 can be subjected to the reaction in form of their salts, for example as hydrochloride or triflate salts, in which case usually an additional equivalent of the base is added to the reaction.

The substitution of a leaving group of a compound of formula 17 with an amine of formula 3 to form a compound of formula 14 is generally carried out under neat conditions or in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or an ester such as ethyl acetate or ethyl butanoate or an amide such as N,N-dimethylformamide or N,N-dimethylacetamide or N-methyl-pyridone or a in mixture of solvents, it is carried out preferably in the presence of an additional base, for example an amine base such as TEA, DIPEA or N-methylmorpholin or an alkaline metal- or alkaline earth metal-bicarbonate, -carbonate or -hydroxide, such as sodium, potassium or lithium hydrogen carbonate, carbonate or hydroxide or cesium carbonate. The reaction temperature is generally from 0° C. to 250° C., preferably from 20° C. to 250°, more preferably from 20° C. to 150° C. The reaction time is generally from 15 min to 6 days, preferably from 15 min to 16 h, depending on the composition of the mixture and the chosen temperature range.

The reduction of the nitro-group of formula 14 to a compound of formula 15 is generally carried out in the presence of a suitable catalyst, e.g. a palladium catalyst or a Raney-Nickel catalyst or a homogeneous palladium complex, either under hydrogen atmosphere, usually at ambient pressure or at elevated pressure up to 50 bar, preferably at pressures up to 5 bar or in the presence of a different hydrogen source such as formic acid in a suitable solvent, preferably an alcohol, such as methanol, ethanol or propanol, or an ester, such as ethyl acetate or ethyl butanoate, an ether such as tetrahydrofurane, 1,4-dioxane, dibutylether, diisopropylether, methyl-tert-butylether, dimethoxyethane, or mixtures of solvents at reaction temperatures from 0° C. to 250° C., preferably from 20° C. to 150°, more preferably from 20° C. to 60° C., with reaction times generally from 15 min to 6 days, preferably from 15 min to 16 h, depending on the composition of the mixture and the chosen temperature range, or alternatively it is carried out in the presence of tin(II) chloride in a suitable solvent such as an ester, e.g. ethyl acetate or ethyl butanoate, at reaction temperatures from 0° C. to 250° C., preferably from 20° C. to 150°, more preferably from 20° C. to 80° C., with reaction times generally from 15 min to 6 days, preferably from 15 min to 16 h, depending on the composition of the mixture and the chosen temperature range.

The reaction of a compound of formula 15 with a compound of formula 6, in which LG$^2$ is OH, to form an amide of formula 16 is generally carried out in the presence of activating agents, such as CDI, DCC, EDC, HOAt, HOBt, HATU, TOTU, TBTU, BEP, PyBOP or combinations thereof, and optionally an additional base, such as TEA, DIPEA or N-methylmorpholin in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or an ester such as ethyl acetate or ethyl butanoate or an amide such as N,N-dimethylformamide or N,N-dimethylacetamide or N-methyl-pyridone or a in mixture of solvents. The reaction temperature is generally from −30° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range. The acids of formula 6 can be subjected to the reaction in form of their salts, for example their sodium salts. The reaction of a compound of formula 15 with a compound of formula 6, in which LG$^2$ is a leaving group, which can undergo nucleophilic substitution with an aromatic amine, e.g. (C$_1$-C$_4$)-alkoxy, F, Cl, Br or OC(O)—(C$_1$-C$_4$)-alkyl, or -pentafluorphenoxy, is generally carried out in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or an ester such as ethyl acetate or ethyl butanoate or an amide such as N,N-dimethylformamide or N,N-dimethylacetamide or N-methyl-pyridone or a in mixture of solvents and optionally in the presence of an additional base, such as TEA, DIPEA or N-methylmorpholin The reaction temperature is generally from 0° C. to 250° C., preferably from 0° C. to 150°, more preferably from 20° C. to 100° C. The reaction time is generally from 15 min to 6 days, preferably from 15 min to 16 h, depending on the composition of the mixture and the chosen temperature range.

The cyclization of a compound of formula 16 to a benzimidazole of formula 12 is generally performed under neat conditions or in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, preferably in the presence of an acid, such as hydrochloric acid or trifluoro acetic acid or sulfuric acid, more preferably in the presence of hydrochloric acid in anhydrous dioxane, the reaction temperature is generally from 0° C. to 250° C., preferably from 20° C. to 250°, more preferably from 80° C. to 200° C. and the reaction time is generally from 5 min to 6 days, preferably from 5 min to 16 h, depending on the composition of the mixture and the chosen temperature range.

The conversion of a compound of formula 12 to a compound of formula I can be performed as it was described for the reaction sequence in Scheme 1.

Alternatively, the conversion of a compound of formula 16 to a compound of formula 17, wherein $R^b$ is $CO_2R^c$, with $R^c$ being alkyl having 1, 2, 3, 4, 5 or 6 carbon atoms, e.g. Me, Et, nPr, iPr, n-Bu, sec-Bu or tert.-Bu, or —$CH_2$-phenyl, which may be substituted, e.g. Bn or para-Methoxybenzyl, or $R^c$ is a solid support, like a Wang resin, and Z is $CO_2H$ can be performed by methods known to the skilled person and can be carried out under standard conditions according to, or analogously to, procedures described in the literature, for example in P. J. Kocienski, Protecting Groups, Georg Thieme Verlag, Stuttgart, 1994 or T. W. Greene, P. G. M. Wuts, Protective Groups in Organic Synthesis, John Wiley, New York, 1999), preferably by reacting the ester of formula 12 with acids, such as hydrochloric acid, trifluoro acetic acid or sulfuric acid or with aqueous bases, such as an alkaline metal- or alkaline earth metal-carbonate or -hydroxide, such as sodium, potassium or lithium carbonate or hydroxide or cesium carbonate, optionally in the presence of an additional solvent, such as an ether such as tetrahydrofurane, 1,4-dioxane, dibutylether, diisopropylether, methyl-tert-butylether, dimethoxyethane or an alcohol, such as methanol, ethanol or propanol, or mixtures of solvents. The reaction temperature is generally from 0° C. to 250° C., preferably from 20° C. to 150°, more preferably from 20° C. to 100° C. The reaction time is generally from 15 min to 6 days, preferably from 15 min to 16 h, depending on the composition of the mixture and the chosen temperature range. Subsequently, the cyclization of a compound of formula 17 to a compound of formula I, wherein Z is $CO_2H$, is generally performed under neat conditions or in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, preferably in the presence of an acid, such as hydrochloric acid or trifluoro acetic acid or sulfuric acid, more preferably in the presence of hydrochloric acid in anhydrous dioxane, the reaction temperature is generally from 0° C. to 250° C., preferably from 20° C. to 250°, more preferably from 80° C. to 200° C. and the reaction time is generally from 5 min to 6 days, preferably from 5 min to 16 h, depending on the composition of the mixture and the chosen temperature range.

Alternative processes for preparing the compounds are described in the examples and are also part of the invention.

The starting compounds of the formulae 1, 3, 6 and 10 are commercially available or can be prepared by a skilled artisan according to procedures described in the literature.

Another subject of the present invention are the novel intermediates occurring in the synthesis of the compounds of the formula I in any of their stereoisomeric forms or a mixture of stereoisomeric forms in any ratio, and their salts, and solvates of any of them, and their use as intermediates. The invention also includes all tautomeric forms of the said intermediates and starting compounds. All explanations given above and embodiments specified above with respect to the compounds of the formula I apply correspondingly to the said intermediates. Another subject of the invention are in particular the novel specific intermediates disclosed herein. Independently thereof whether they are disclosed as a free compound and/or as a specific salt, they are a subject of the invention both in the form of the free compounds and in the form of their salts, and if a specific salt is disclosed, additionally in the form of this specific salt, and in the form of solvates of any of them.

All reactions used in the above-described syntheses of the compounds of the formula I are per se well known to the skilled person and can be carried out under standard conditions according to, or analogously to, procedures described in the literature, for example in Houben-Weyl, Methoden der Organischen Chemie (Methods of Organic Chemistry), Thieme-Verlag, Stuttgart, or Organic Reactions, John Wiley & Sons, New York. If desired, the obtained compounds of the formula I, as well as any intermediate compounds, can be purified by customary purification procedures, for example by recrystallization or chromatography. As already mentioned, all starting compounds and intermediates employed into the above-described syntheses which contain an acidic or basic group, can also be employed in the form of salts, and all intermediates and final target compounds can also be obtained in the form of salts. As likewise mentioned above, depending on the circumstances of the specific case, in order to avoid an unwanted course of a reaction or side reactions during the synthesis of a compound it can generally be necessary or advantageous to temporarily block functional groups by introducing protective groups and deprotect them at a later stage of the synthesis, or to introduce functional groups in the form of precursor groups which later are converted into the desired functional groups. As examples of protecting groups amino-protecting groups may be mentioned which can be acyl groups or alkyloxycarbonyl groups, for example a tert-butyloxycarbonyl group (=Boc) which can be removed by treatment with trifluoroacetic acid (=TFA), a benzyloxycarbonyl group which can be removed by catalytic hydrogenation, or a fluoren-9-ylmethoxycarbonyl group which can be removed by treatment with piperidine, and protecting groups of carboxylic acid groups which can be protected as ester groups, such as Cert-butyl esters which can be deprotected by treatment with trifluoroacetic acid, or benzyl esters which can be deprotected by catalytic hydrogenation. As an example of a precursor group the nitro group may be mentioned, which can be converted into an amino group by reduction, for example by catalytic hydrogenation, or a furane group, which can be converted to a tetrahydrofurane group for example by catalytic hydrogenation. Such synthesis strategies, and protective groups and precursor groups which are suitable in a specific case, are known to the skilled person.

LIST OF ABBREVIATIONS 2-bromo-1-ethyl-pyridinium tetrafluoroborate BEP
Bromo-tris-pyrrolidino-phosphoniumhexafluorophosphate PyBoP
Dichloromethane DCM
Diethylamine DEA
4-Dimethylaminopyridine DMAP
N,N-Diisopropylethylamine DIPEA
N,N'-Diisopropylcarbodiimid DIC
1-(3-Dimethylaminopropyl)-3-ethylcarbodiimide-Hydrochloride EDC
N,N-Dimethylformamide DMF
Electron spray ionisation Positive mode ESI+ or ESI
Ethanol EtOH
Ethyl acetate EtOAc
Heptane Hep
High pressure liquid chromatography HPLC
Hour/s h 1-Hydroxyazabenzotriazole HOAT
1-Hydroxybenzotriazole HOBT
Liquid chromatography LC
Methanol MeOH
Mass spectroscopy MS
O-(7-Azabenzotriazol-1-yl)-N,N,N',N'-tetramethyl HATU
uronium hexafluorophosphate
preconditioned precond.
iso-Propanol iPrOH
Retention time Rt
Reversed phase RP
Room temperature rt
Separation sep.
Tetrahydrofuran THF
Triethylamine TEA
Trifluoroacetic acid TFA The following examples illustrate the invention.

When example compounds containing a basic group were purified by HPLC on reversed phase (RP) column material, and, as costumary, the eluent was a mixture of water, acetonitrile and trifluoro acetic acid, acetic acid or formic acid, they were in part obtained in the form of the acid addition salt with trifluoro acetic acid, acetic acid or formic acid, depending on the details of the workup such as evaporation or lyophilization conditions. In the names of the example compounds and their formulae any such contained trifluoro acetic acid, acetic acid or formic acid is not specified. Likewise, when the example compounds containing a basic group were treated with hydrochloric acid during workup, they were in part obtained as their hydrochloric acid salts, depending on further evaporation or lyophilization conditions. In the names of the example compounds and their formulae any such contained hydrochloric acid is not specified.

Description of the analytical LCMS methods:

1_1_1:
Agilent 1100, Zorbax, 3.5 uM, 2*50 mm,
A: H2O+0.05% TFA, B: Methanol+0.05% TFA,
97:3 (0 min) to 80:20 (0.2 min), and to 0:100 (hold from 3.7 min to 4.1 min), and to 97:3 (hold from 4.11 to 4.60 min)
1.2 ml/min, column temperature: 50° C.
ABI Sciex, API 100, single Quadrupole, 1 scan/second, 160 to 800

1_2_1:
Agilent 1100, Zorbax, 3.5 uM, 2*50 mm,
A: H2O+0.05% TFA, B: Methanol+0.05% TFA,
97:3 (0 min) to 80:20 (0.2 min), and to 0:100 (hold from 3.7 min to 4.1 min), and to 97:3 (hold from 4.11 to 4.60 min)
1.0 ml/min/RT
ABI Sciex, API 100, single Quadrupole, 1 scan/second, 160 to 800

2_1_1:
Javelin C18, 2*20 mm (use two columns), 5u
A: H2O+0.1% TFA, B: CH3CN+0.08% TFA,
98:2 (hold from 0 min to 0.2 min) to 20:80 (5.0 min), and to 0:100 (5.2 mins, hold from 5.2 min to 5.4 min), and to 98:2 (6.2 min, hold from 6.2 min to 6.4 min)
1.0 ml/min/RT
ABI Sciex, API 100, single Quadrupole, 2 s scantime, 120 to 1000

3_1_1:
Merck Chromolith FastGrad. RP-18e, 50×2 mm, 0.05% TFA: AcN+0.05% TFA
98:2 (0.2 min) to 2:98 (2.4 min) to 2:98 (3.2 min) to 98:2 (3.3 min) to 98:2 (4 min), 2.0 ml/min;
2.0 ml/min, 50° C.; Waters LCT classic TOF-MS, 0.33 s scantime for mass 175-1500

3_2_1:
Merck Chromolith FastGrad. RP-18e, 50×2 mm, 0.05% TFA: AcN+0.05% TFA 98:2 (0.2 min) to 2:98 (2.4 min) to 2:98 (3.2 min) to 98:2 (3.3 min) to 98:2 (4 min), 2.4 ml/min;
2.4 ml/min, 50° C.; Waters LCT classic TOF-MS, 0.33 s scantime for mass 175-1500

4_1_1:
Waters UPLC BEH C18 2.1*50 mm; 1.7u, H2O+0.1% FA:AcN+0.08% FA 95:5 (0 min) to 5:95 (1.1 min) to 5:95 (1.7 min) to 95:5 (1.8 min) to 95:5 (2 min), 0.9 ml/min 55° C.; Waters SQD Single Quadrupol, 0.5 s scantime for mass 120-1200

5_1_1:
Waters XBridge C18 4.6*50 mm; 2.5u, H2O+0.1% FA:AcN+ 0.08% FA 97:3 (0 min) to 40:60 (3.5 min) to 2:98 (4 min) to 2:98 (5 min) to 97:3 (5.2 min) to 97:3 (6.5 min); 1.3 ml/min/ RT; Waters Ultima Triple Quad MS, 0.75 s scantime for mass 100-1200

5_2_1:
Waters XBridge C18 4.6*50 mm; 2.5u, H2O+0.1% FA:AcN+ 0.1% FA 97:3 (0 min) to 40:60 (3.5 min) to 2:98 (4 min) to 2:98 (5 min) to 97:3 (5.2 min) to 97:3 (6.5 min); 1.3 ml/min 45° C.; Waters ZQ Single Quadrupol, 0.5 s scantime for mass 100-1200

5_3_1:
Waters XBridge C18 4.6*50 mm; 2.5u, H2O+0.05% TFA: AcN+0.05% TFA 95:5 (0 min) to 95:5 (0.2 min) to 5:95 (2.4 min) to 5:95 (3.2 min), to 95:5 (3.3 min) to 95:5 (4.0 min); 1.7 ml/min, 40° C.; Waters LCT classic TOF-MS, 0.33 s scantime for mass 175-1500

5_4_1:
Waters XBridge C18, 4.6*50, 2.5μ, H2O+0.05% TFA:AcN+ 0.05% TFA 95:5 (0 min) to 95:5 (0.2 min) to 5:95 (2.4 min) to 5:95 (3.5 min), to 95:5 (3.6 min) to 95:5 (4.5 min), 1.7 ml/min, 40° C.; Waters LCT classic TOF-MS, 0.33 s scantime for mass 175-1500

5_5_1:
Waters XBridge C18, 4.6*50, 2.5μ, H2O+0.05% TFA:AcN+ 0.05% TFA 95:5 (0 min) to 95:5 (0.2 min) to 5:95 (2.4 min) to 5:95 (3.5 min), to 95:5 (3.6 min) to 95:5 (4.5 min), 1.7 ml/min, 50° C.; Waters LCT classic TOF-MS, 0.33 s scantime for mass 175-1500

5_6_1:
Waters XBridge C18, 4.6*50, 2.5μ, H2O+0.05% TFA:AcN+ 0.05% TFA 95:5 (0 min) to 5:95 (2.6 min) to 5:95 (3.0 min) to 95:5 (3.1 min), to 95:5 (4.0 min), 1.7 ml/min, 40° C.; Waters LCT classic TOF-MS, 0.33 s scantime for mass 175-1500

5_7_1:
Waters XBridge C18, 4.6*50, 2.5μ, H2O+0.05% TFA:AcN+ 0.05% TFA 95:5 (0 min) to 95:5 (0.3 min) to 5:95 (3.5 min) to 5:95 (4 min); 1.7 ml/min, 40° C.; Waters LCT classic TOF-MS, 0.33 s scantime for mass 175-1500

6_1_1:
YMC-Pack Jsphere H80 33*2.1, 4u, H2O+0.05% TFA:AcN+ 0.05% TFA 95:5 (0 min) to 5:95 (3.7 min); 1 ml/min; RT; Waters LCT classic TOF-MS, 8-channel Mux, 0.15 s scantime for mass 100-1500

6_2_1:
YMC-Pack Jsphere H80 33*2.1, 4u, H2O+0.1% FA:AcN+ 0.08% FA 95:5 (0 min) to 5:95 (2.5 min); 1.3 ml/min RT; Waters Ultima Triple Quad MS, 0.8 s scantime for mass 100-1200

6_2_2:
YMC-Pack Jsphere H80 33*2.1, 4u, H2O+0.1% FA:AcN+ 0.08% FA 95:5 (0 min) to 5:95 (2.5 min); 1.3 ml/min RT; Waters Ultima Triple Quad MS, 0.5 s scantime for mass 100-1200

6_3_1:
YMC-Pack Jsphere H80 33*2.1, 4u, H2O+0.05% TFA:AcN+ 0.05% TFA 95:5 (0 min) to 5:95 (2.5 min) to 95:5 (3.2 min); 1.3 ml/min RT; Waters LCT classic TOF-MS, 0.33 s scantime for mass 170-1300
6_4_1:
YMC-Pack Jsphere H80 33*2.1, 4u, H2O+0.05% TFA:AcN+ 0.05% TFA 95:5 (0 min) to 5:95 (2.5 min); 1.3 ml/min RT; Waters LCT classic TOF-MS, 0.33 s scantime for mass 170-1300
6_5_1:
YMC-Pack Jsphere H80 33*2.1, 4u, H2O+0.05% TFA:AcN+ 0.05% TFA 95:5 (0 min) to 95:5 (0.5 min) to 5:95 (3.5 min) to 5:95 (4 min); 1.3 ml/min RT; Waters LCT classic TOF-MS, 0.33 s scantime for mass 175-1500
6_6_1:
YMC-Pack Jsphere H80 33*2.1, 4u, H2O+0.05% TFA: CH3OH+0.05% TFA 98:2 (1 min) to 5:95 (5.0 min) to 5:95 (6.25 min); 1.0 ml/min/RT; Waters LCT classic TOF-MS, 8-channel Mux, 0.15 s scantime for mass 100-1500
7_1_1:
Column: YMC-Pack Jsphere ODS H80 20×2.1 mm, 4 um, flow: 1.0 ml/min; gradient (eluent A=H2O+0.05% TFA, eluent B=acetonitrile) from A:B 96:4 to 5:95 in 2.0 min, then 5:95 until 2.4 min, then to 96:4 until 2.45 min; ionization ESI+(scan for mass 110-1000)
8_1_1:
Column: Phenomenex 10×2 mm, 4 μm; flow: 1.1 ml/min; gradient (eluent A=H₂O+0.05% TFA, eluent B=acetonitrile) from A:B 93:7 to 5:95 in 1.2 min, then 5:95 until 1.4 min, then to 93:7 until 1.45 min; ionization ESI+ (scan for mass 110-1000).

EXAMPLE 1

1-{[1-(1-Ethyl-propyl)-2-thiophen-2-ylmethyl-1H-benzoimidazole-5-carbonyl]-amino}-cycloheptanecarboxylic acid

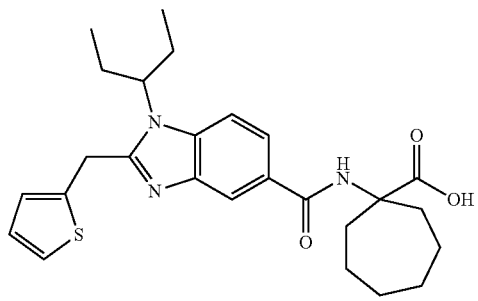 [SMILES: CCC(CC)n1c(Cc2cccs2)nc2cc(C(=O)NC3(C(=O)O)CCCCCC3)ccc21]

a) 1-{[1-(1-Ethyl-propyl)-2-thiophen-2-ylmethyl-1H-benzimidazole-5-carbonyl]-amino}-cycloheptanecarboxylic acid methyl ester

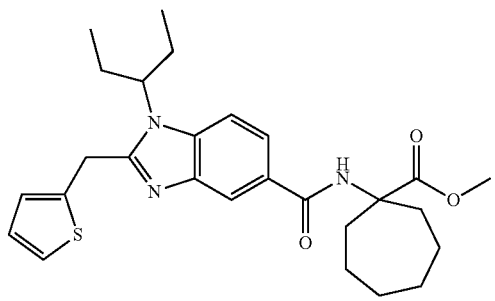 [SMILES: CCC(CC)n1c(Cc2cccs2)nc2cc(C(=O)NC3(C(=O)OC)CCCCCC3)ccc21]

To a solution of 160 mg of 1-(1-ethyl-propyl)-2-thiophen-2-ylmethyl-1H-benzoimidazole-5-carboxylic acid (The preparation of intermediates is described below) in 3 ml of dry DMF 73 mg of HOAT, 131 mg of EDC and 0.16 ml of DIPEA were added at 0° C. After 15 min 100 mg of methyl 1-amino-cycloheptanecarboxylate-hydrochloride and 0.16 ml of DIPEA were added and the reaction was stirred at it for 16 h. The reaction was then poured into water and the pH was adjusted to 3 by the addition of 2 M aqueous hydrochloric acid. The reaction was extracted with ethyl acetate three times. The combined organic phases were washed with saturated aqueous sodium bicarbonate solution and brine, dried over magnesium sulphate and concentrated. The crude product was purified by HPLC to yield 200 mg (85%) of 1-{[1-(1-Ethyl-propyl)-2-thiophen-2-ylmethyl-1H-benzimidazole-5-carbonyl]-amino}-cycloheptanecarboxylic acid methyl ester.

$C_{27}H_{35}N_3O_3S$ (481.66), LCMS (method 3_2_1): Rt=1.46 min, m/z=482.26 [M+H]$^+$ b) 1-{[1-(1-Ethyl-propyl)-2-thiophen-2-ylmethyl-1H-benzoimidazole-5-carbonyl]-amino}-cycloheptanecarboxylic acid

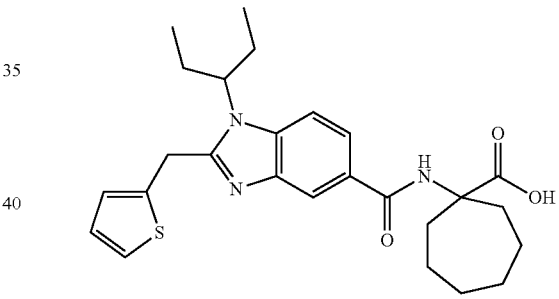

400 mg of 1-{[1-(1-ethyl-propyl)-2-thiophen-2-ylmethyl-1H-benzoimidazole-5-carbonyl]-amino}-cycloheptanecarboxylic acid methyl ester were dissolved in 4 ml ethanol and 2 ml THF and 4 ml of 2 M aqueous sodium hydroxide solution were added. After stirring at room temperature over night, the reaction mixture was brought to pH 3 by addition of 2 M aqueous hydrochloric acid and extracted with ethyl acetate three times. The combined organic phases were dried over magnesium sulphate and concentrated to yield 100 mg (26%) of 1-{[1-(1-ethyl-propyl)-2-thiophen-2-ylmethyl-1H-benzoimidazole-5-carbonyl]-amino}-cycloheptanecarboxylic acid.

$C_{26}H_{33}N_3O_3S$ (467.63), LCMS (method 3_2_1): Rt=1.38 min, m/z=468.21 [M+H]$^+$ The following examples were prepared in analogy to example 1:

| Exp. No. | Chemical Name | Structure | m/z [M + H]⁺ | LCMS method | R$_t$ [min] |
|---|---|---|---|---|---|
| 2 | 2-{[1-(1-Ethyl-propyl)-2-furan-2-ylmethyl-1H-benzoimidazole-5-carbonyl]-amino}-2-methyl-3-phenyl-propionic acid | 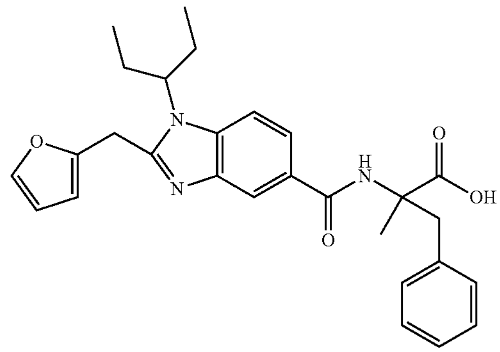 [SMILES: CCC(CC)n1c(Cc2ccco2)nc2cc(C(=O)NC(C)(Cc3ccccc3)C(=O)O)ccc21] | 474.1 | 6_1_1 | 1.68 |
| 3 | (S)-3-Cyclohexyl-2-{[2-cyclopentylmethyl-1-(1-ethyl-propyl)-1H-benzoimidazole-5-carbonyl]-amino}-propionic acid | 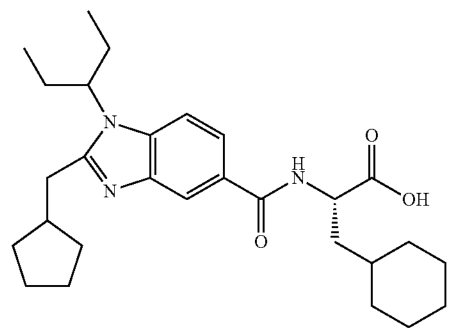 [SMILES: CCC(CC)n1c(CC2CCCC2)nc2cc(C(=O)N[C@@H](CC3CCCCC3)C(=O)O)ccc21] | 468.3 | 6_1_1 | 1.87 |
| 4 | 2-{[1-(1-Ethyl-propyl)-2-thiophen-2-ylmethyl-1H-benzoimidazole-5-carbonyl]-amino}-2-methyl-3-phenyl-propionic acid | 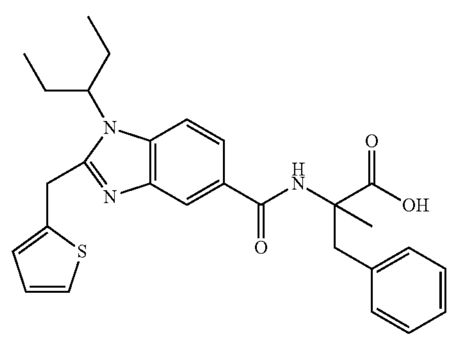 [SMILES: CCC(CC)n1c(Cc2cccs2)nc2cc(C(=O)NC(C)(Cc3ccccc3)C(=O)O)ccc21] | 490.2 | 6_4_1 | 1.5 |
| 5 | 2-{[1-(1-Ethyl-propyl)-2-thiophen-2-ylmethyl-1H-benzoimidazole-5-carbonyl]-amino}-2,3-dimethyl-butyric acid | 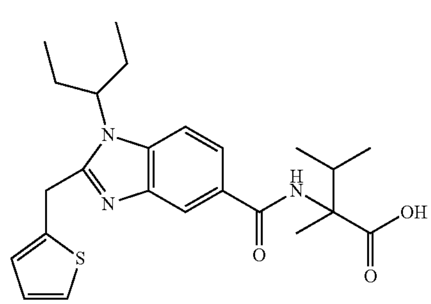 [SMILES: CCC(CC)n1c(Cc2cccs2)nc2cc(C(=O)NC(C)(C(=O)O)C(C)C)ccc21] | 440.7 | 6_2_2 | 1.81 |

-continued

| Exp. No. | Chemical Name | Structure | m/z [M + H]+ | LCMS method | R_t [min] |
|---|---|---|---|---|---|
| 6 | 1-{[1-(1-Ethyl-propyl)-2-thiophen-2-ylmethyl-1H-benzoimidazole-5-carbonyl]-amino}-cyclopentanecarboxylic acid | 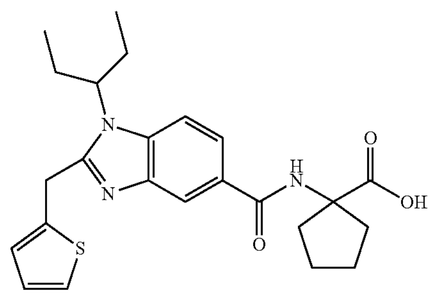 [SMILES: CCC(CC)n1c(Cc2cccs2)nc2cc(C(=O)NC3(C(=O)O)CCCC3)ccc21] | 438.7 | 6_2_2 | 1.75 |
| 7 | 2-{[1-(1-Ethyl-propyl)-2-thiophen-2-ylmethyl-1H-benzoimidazole-5-carbonyl]-amino}-2-phenyl-butyric acid | 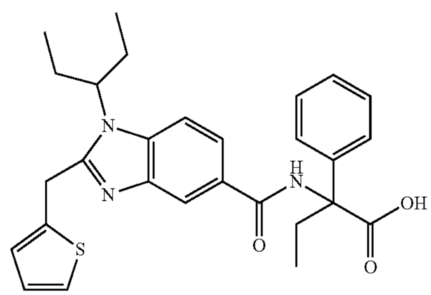 | 490.4 | 6_4_1 | 1.55 |
| 8 | (S)-3-Cyclohexyl-2-{[1-(1-ethyl-propyl)-2-furan-2-ylmethyl-1H-benzoimidazole-5-carbonyl]-amino}-propionic acid | 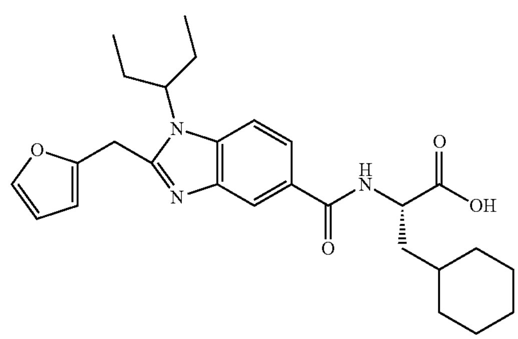 [SMILES: CCC(CC)n1c(Cc2ccco2)nc2cc(C(=O)N[C@@H](CC3CCCCC3)C(=O)O)ccc21] | 466.3 | 6_4_1 | 1.55 |
| 9 | (R)-3-Cyclohexyl-2-{[1-(1-ethyl-propyl)-2-furan-2-ylmethyl-1H-benzoimidazole-5-carbonyl]-amino}-propionic acid | 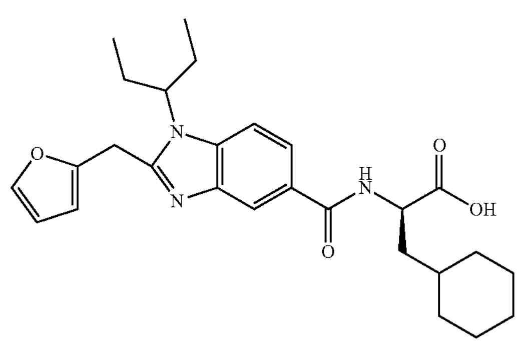 [SMILES: CCC(CC)n1c(Cc2ccco2)nc2cc(C(=O)N[C@H](CC3CCCCC3)C(=O)O)ccc21] | 466.3 | 6_4_1 | 1.57 |

-continued

| Exp. No. | Chemical Name | Structure | m/z [M + H]⁺ | LCMS method | R_t [min] |
|---|---|---|---|---|---|
| 10 | (R)-3-Cyclohexyl-2-{[2-cyclopentylmethyl-1-(1-ethyl-propyl)-1H-benzoimidazole-5-carbonyl]-amino}-propionic acid | 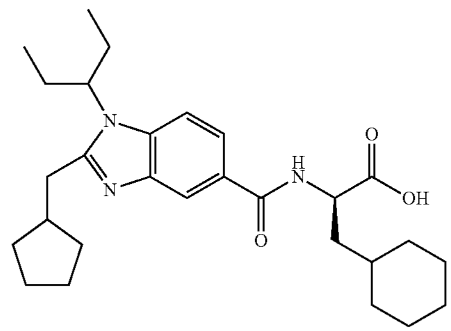 [SMILES: CCC(CC)n1c(CC2CCCC2)nc2cc(C(=O)N[C@H](CC3CCCCC3)C(=O)O)ccc21] | 468.3 | 6_3_1 | 1.58 |
| 11 | 3-Cyclopentyl-2-{[1-(1-ethyl-propyl)-2-thiophen-2-ylmethyl-1H-benzoimidazole-5-carbonyl]-amino}-propionic acid | 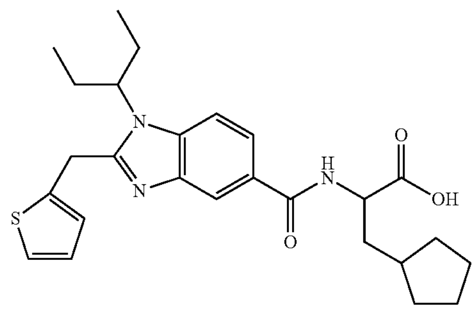 [SMILES: CCC(CC)n1c(Cc2cccs2)nc2cc(C(=O)NC(CC3CCCC3)C(=O)O)ccc21] | 468.3 | 6_1_1 | 1.74 |
| 12 | 2-{[1-(1-Ethyl-propyl)-2-thiophen-2-ylmethyl-1H-benzoimidazole-5-carbonyl]-amino}-2,4-dimethyl-pentanoic acid | 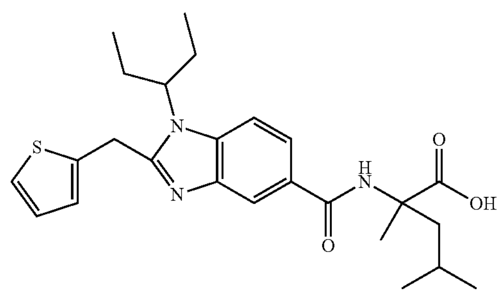 | 456.19 | 6_5_1 | 2.05 |
| 13 | 2-{[1-(1-Ethyl-propyl)-2-furan-2-ylmethyl-1H-benzoimidazole-5-carbonyl]-amino}-2,4-dimethyl-pentanoic acid | 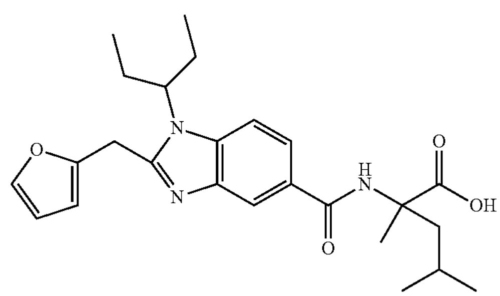 [SMILES: CCC(CC)n1c(Cc2ccco2)nc2cc(C(=O)NC(C)(CC(C)C)C(=O)O)ccc21] | 440.21 | 6_5_1 | 2.00 |
| 14 | 2-{[1-(1-Ethyl-propyl)-2-furan-2-ylmethyl-1H-benzoimidazole-5-carbonyl]-amino}-2-methyl-4-methylsulfanyl-butyric acid | 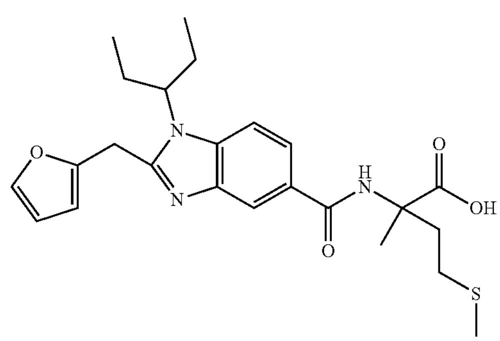 [SMILES: CCC(CC)n1c(Cc2ccco2)nc2cc(C(=O)NC(C)(CCSC)C(=O)O)ccc21] | 458.2 | 6_5_1 | 1.89 |

-continued

| Exp. No. | Chemical Name | Structure | m/z [M + H]+ | LCMS method | R_t [min] |
|---|---|---|---|---|---|
| 15 | (S)-3-Cyclohexyl-2-{[1-(2-methyl-cyclohexyl)-2-thiophen-2-ylmethyl-1H-benzoimidazole-5-carbonyl]-amino}-propionic acid | 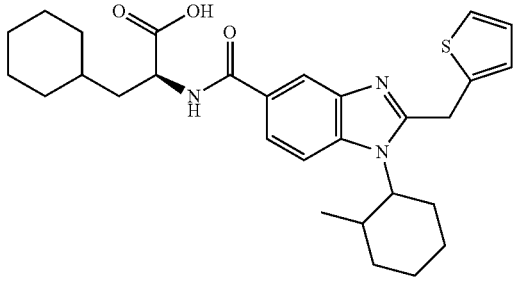 [SMILES: CC1CCCCC1n1c(Cc2cccs2)nc2cc(C(=O)N[C@@H](CC3CCCCC3)C(=O)O)ccc21] | 508.3 | 5_7_1 | 3.12 |
| 16 | (S)-2-{[1-(2-Methyl-cyclohexyl)-2-thiophen-2-ylmethyl-1H-benzoimidazole-5-carbonyl]-amino}-hexanoic acid | 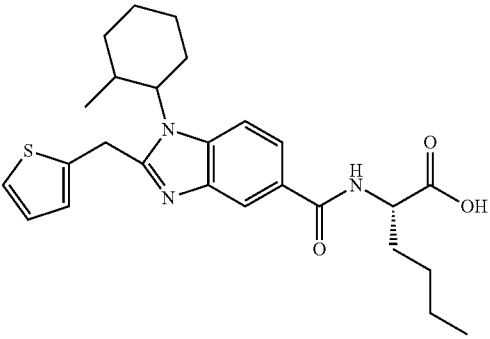 [SMILES: CCCC[C@H](NC(=O)c1ccc2c(c1)nc(Cc1cccs1)n2C1CCCCC1C)C(=O)O] | 512.4 | 5_1_1 | 4.41 |
| 17 | (S)-3-Cyclohexyl-2-{[2-thiophen-2-ylmethyl-1-(2-trifluoromethyl-cyclohexyl)-1H-benzoimidazole-5-carbonyl]-amino}-propionic acid | 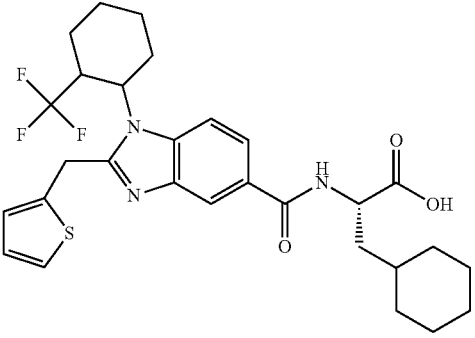 [SMILES: O=C(N[C@@H](CC1CCCCC1)C(=O)O)c1ccc2c(c1)nc(Cc1cccs1)n2C1CCCCC1C(F)(F)F] | 562.5 | 5_2_1 | 4.75 |
| 18 | (S)-2-{[1-(1-Ethyl-propyl)-2-thiophen-2-ylmethyl-1H-benzoimidazole-5-carbonyl]-amino}-hexanoic acid | 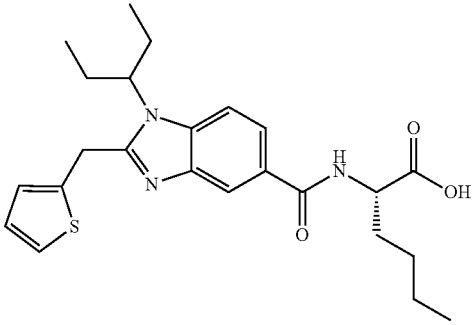 [SMILES: CCCC[C@H](NC(=O)c1ccc2c(c1)nc(Cc1cccs1)n2C(CC)CC)C(=O)O] | 442.2 | 4_1_1 | 1.19 |

| Exp. No. | Chemical Name | Structure | m/z [M + H]⁺ | LCMS method | R_t [min] |
|---|---|---|---|---|---|
| 19 | (S)-2-{[1-(1-Ethyl-propyl)-2-thiophen-2-ylmethyl-1H-benzoimidazole-5-carbonyl]-amino}-3-(4-fluoro-phenyl)-propionic acid | 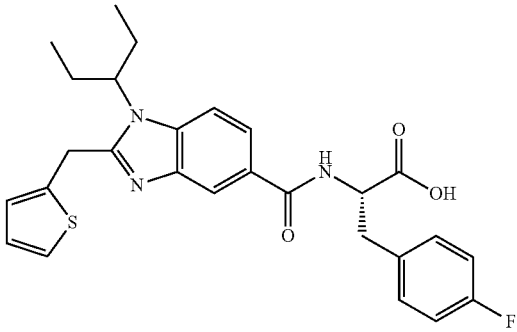 [SMILES: CCC(CC)n1c(Cc2cccs2)nc2cc(C(=O)N[C@@H](Cc3ccc(F)cc3)C(=O)O)ccc21] | 494.3 | 4_1_1 | 1.18 |
| 20 | (S)-3-(4-Chloro-phenyl)-2-{[1-(1-ethyl-propyl)-2-thiophen-2-ylmethyl-1H-benzoimidazole-5-carbonyl]-amino}-propionic acid | 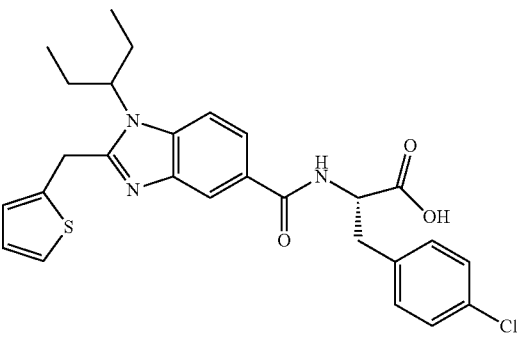 [SMILES: CCC(CC)n1c(Cc2cccs2)nc2cc(C(=O)N[C@@H](Cc3ccc(Cl)cc3)C(=O)O)ccc21] | 510.2 | 4_1_1 | 1.21 |
| 21 | (S)-3-Cyclopropyl-2-{[1-(1-ethyl-propyl)-2-thiophen-2-ylmethyl-1H-benzoimidazole-5-carbonyl]-amino}-propionic acid | 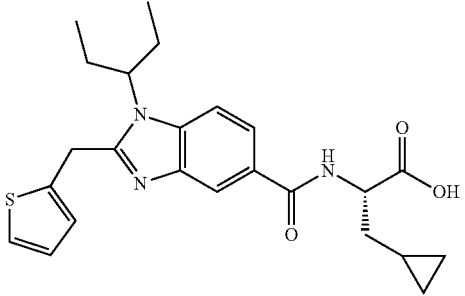 [SMILES: CCC(CC)n1c(Cc2cccs2)nc2cc(C(=O)N[C@@H](CC3CC3)C(=O)O)ccc21] | 440.2 | 3_1_1 | 1.42 |
| 22 | (S)-3-Cyclobutyl-2-{[1-(1-ethyl-propyl)-2-thiophen-2-ylmethyl-1H-benzoimidazole-5-carbonyl]-amino}-propionic acid | 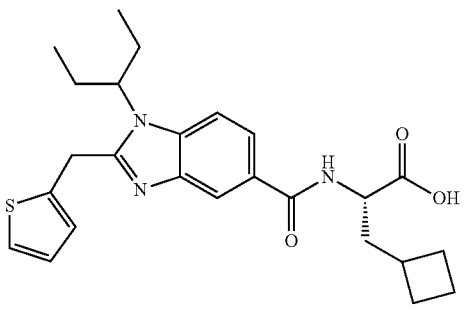 [SMILES: CCC(CC)n1c(Cc2cccs2)nc2cc(C(=O)N[C@@H](CC3CCC3)C(=O)O)ccc21] | 454.2 | 3_1_1 | 1.49 |
| 23 | (S)-3-Cyclobutyl-2-{[1-((1R,2R)-2-methyl-cyclohexyl)-2-thiophen-2-ylmethyl-1H-benzoimidazole-5-carbonyl]-amino}-propionic acid | 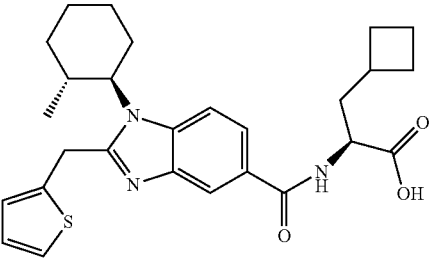 [SMILES: C[C@@H]1CCCC[C@H]1n1c(Cc2cccs2)nc2cc(C(=O)N[C@@H](CC3CCC3)C(=O)O)ccc21] | 480.2 | 3_1_1 | 1.56 |

-continued

| Exp. No. | Chemical Name | Structure | m/z [M + H]⁺ | LCMS method | R_t [min] |
|---|---|---|---|---|---|
| 24 | 1-{[1-(1-Ethyl-propyl)-2-thiophen-2-ylmethyl-1H-benzoimidazole-5-carbonyl]-amino}-cyclohexanecarboxylic acid | 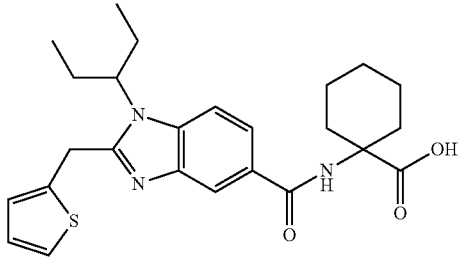 [SMILES: CCC(CC)n1c(Cc2cccs2)nc2cc(C(=O)NC3(C(=O)O)CCCCC3)ccc21] | 454.3 | 6_6_1 | 2.87 |
| 25 | 2-{[1-(1-Ethyl-propyl)-2-thiophen-2-ylmethyl-1H-benzoimidazole-5-carbonyl]-amino}-2-methyl-pentanoic acid | 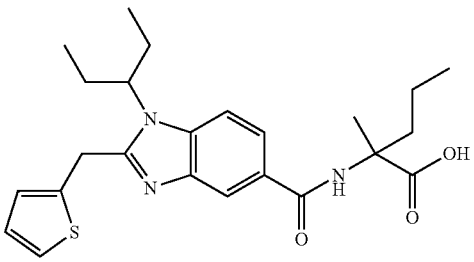 [SMILES: CCCC(C)(NC(=O)c1ccc2c(c1)nc(Cc1cccs1)n2C(CC)CC)C(=O)O] | 442.3 | 6_6_1 | 2.84 |
| 26 | 2-{[1-(1-Ethyl-propyl)-2-thiophen-2-ylmethyl-1H-benzoimidazole-5-carbonyl]-amino}-5,5,5-trifluoro-pentanoic acid | 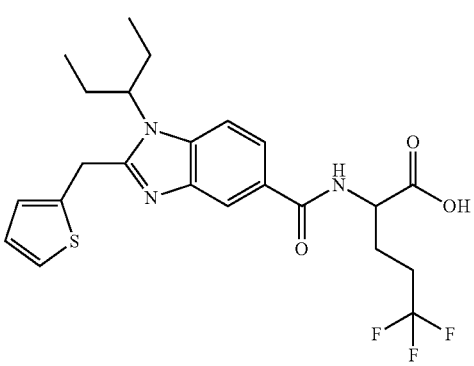 [SMILES: CCC(CC)n1c(Cc2cccs2)nc2cc(C(=O)NC(CCC(F)(F)F)C(=O)O)ccc21] | 482.1 | 3_1_1 | 1.46 |
| 27 | 5,5,5-Trifluoro-2-{[1-((1R,2R)-2-methyl-cyclohexyl)-2-thiophen-2-ylmethyl-1H-benzoimidazole-5-carbonyl]-amino}-pentanoic acid | 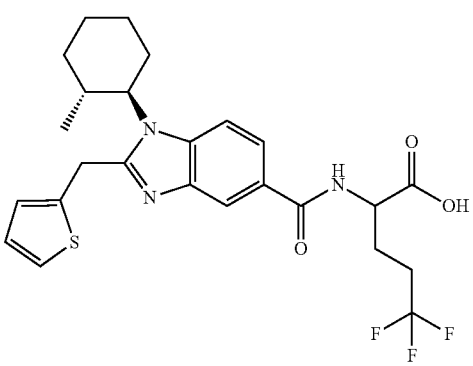 [SMILES: C[C@@H]1CCCC[C@H]1n1c(Cc2cccs2)nc2cc(C(=O)NC(CCC(F)(F)F)C(=O)O)ccc21] | 508.1 | 3_1_1 | 1.54 |

-continued

| Exp. No. | Chemical Name | Structure | m/z [M + H]+ | LCMS method | R_t [min] |
|---|---|---|---|---|---|
| 28 | 2-{[1-(1-Ethyl-propyl)-2-thiophen-2-ylmethyl-1H-benzoimidazole-5-carbonyl]-amino}-4-phenyl-butyric acid | 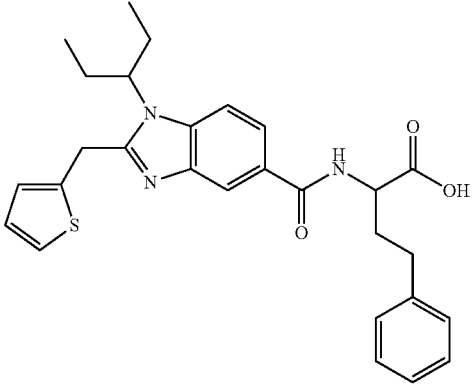 [SMILES: CCC(CC)n1c(Cc2cccs2)nc2cc(C(=O)NC(CCc3ccccc3)C(=O)O)ccc21] | 490.3 | 6_6_1 | 3.04 |
| 29 | 3-(4,4-Dimethyl-cyclohexyl)-2-{[1-(1-ethyl-propyl)-2-thiophen-2-ylmethyl-1H-benzoimidazole-5-carbonyl]-amino}-propionic acid | 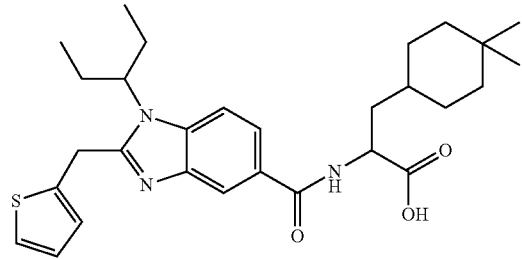 [SMILES: CCC(CC)n1c(Cc2cccs2)nc2cc(C(=O)NC(CC3CCC(C)(C)CC3)C(=O)O)ccc21] | 510.3 | 3_1_1 | 1.68 |
| 30 | 3-(4-Ethyl-phenyl)-2-{[1-(1-ethyl-propyl)-2-thiophen-2-ylmethyl-1H-benzoimidazole-5-carbonyl]-amino}-propionic acid | 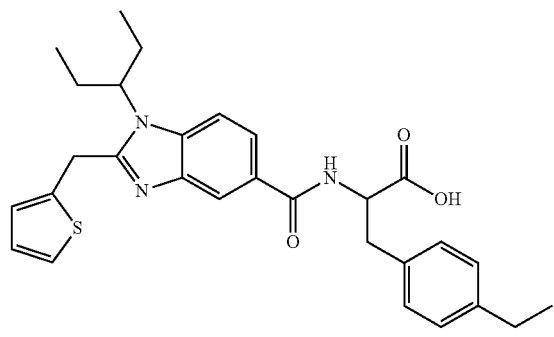 [SMILES: CCc1ccc(CC(NC(=O)c2ccc3c(c2)nc(Cc2cccs2)n3C(CC)CC)C(=O)O)cc1] | 504.2 | 3_1_1 | 1.57 |
| 31 | 2-{[1-(1-Ethyl-propyl)-2-thiophen-2-ylmethyl-1H-benzoimidazole-5-carbonyl]-amino}-3-(4-trifluoromethyl-phenyl)-propionic acid | 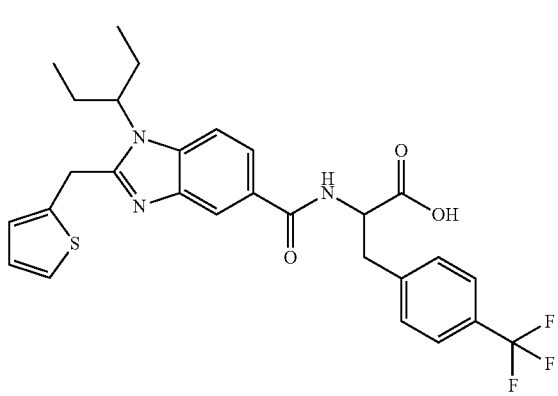 [SMILES: CCC(CC)n1c(Cc2cccs2)nc2cc(C(=O)NC(Cc3ccc(C(F)(F)F)cc3)C(=O)O)ccc21] | 544.2 | 4_1_1 | 1.24 |

-continued

| Exp. No. | Chemical Name | Structure | m/z [M + H]+ | LCMS method | R_t [min] |
|---|---|---|---|---|---|
| 32 | (S)-3-(3,4-Dichloro-phenyl)-2-{[1-(1-ethyl-propyl)-2-thiophen-2-ylmethyl-1H-benzoimidazole-5-carbonyl]-amino}-propionic acid | 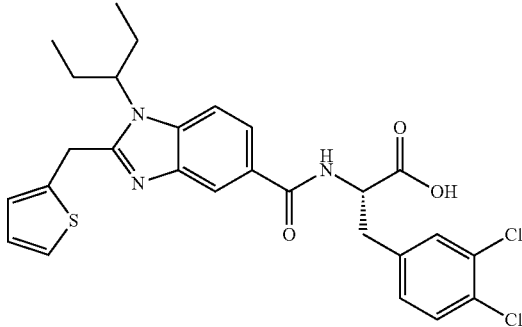 [SMILES: CCC(CC)n1c(Cc2cccs2)nc2cc(C(=O)N[C@@H](Cc3ccc(Cl)c(Cl)c3)C(=O)O)ccc21] | 544.2 | 4_1_1 | 1.25 |
| 33 | 3-(4,4-Dimethyl-cyclohexyl)-2-{[1-((1R,2R)-2-methyl-cyclohexyl)-2-thiophen-2-ylmethyl-1H-benzoimidazole-5-carbonyl]-amino}-propionic acid | 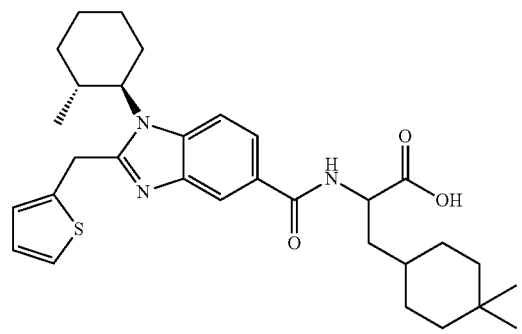 [SMILES: C[C@@H]1CCCC[C@H]1n1c(Cc2cccs2)nc2cc(C(=O)NC(CC3CCC(C)(C)CC3)C(=O)O)ccc21] | 536.3 | 3_1_1 | 1.73 |
| 34 | 1-{[1-(1-Ethyl-propyl)-2-thiophen-2-ylmethyl-1H-benzoimidazole-5-carbonyl]-amino}-4-methyl-cyclohexanecarboxylic acid | 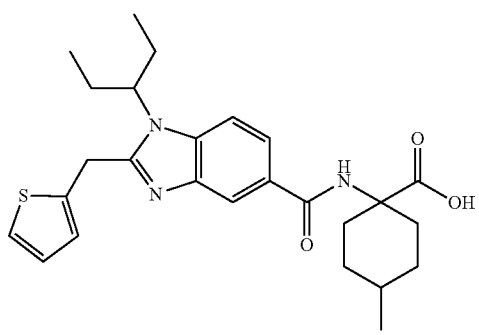 [SMILES: CCC(CC)n1c(Cc2cccs2)nc2cc(C(=O)NC3(C(=O)O)CCC(C)CC3)ccc21] | 466.3 | 5_2_1 | 4.22 |
| 35 | 4-Methyl-1-{[1-((1R,2R)-2-methyl-cyclohexyl)-2-thiophen-2-ylmethyl-1H-benzoimidazole-5-carbonyl]-amino}-cyclohexanecarboxylic acid | 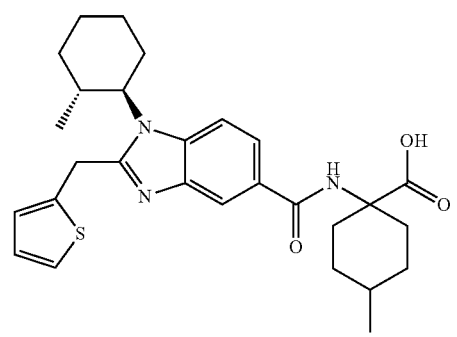 [SMILES: CC1CCC(NC(=O)c2ccc3c(c2)nc(Cc2cccs2)n3[C@@H]2CCCC[C@H]2C)(C(=O)O)CC1] | 494.2 | 3_1_1 | 1.55 |

-continued

| Exp. No. | Chemical Name | Structure | m/z [M + H]+ | LCMS method | R_t [min] |
|---|---|---|---|---|---|
| 36 | 2-{[1-(1-Ethyl-propyl)-2-thiophen-2-ylmethyl-1H-benzoimidazole-5-carbonyl]-amino}-3-(4-methyl-cyclohexyl)-propionic acid | 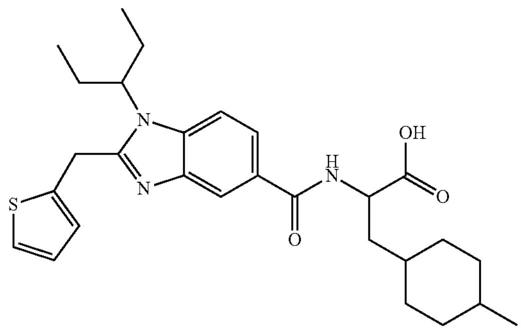 [SMILES: CCC(CC)n1c(Cc2cccs2)nc2cc(C(=O)NC(CC3CCC(C)CC3)C(=O)O)ccc21] | 496.3 | 3_1_1 | 1.62 |
| 37 | (S)-3-Cyclohexyl-2-{[1-((1R,2R)-2-methyl-cyclohexyl)-2-thiazol-5-ylmethyl-1H-benzoimidazole-5-carbonyl]-amino}-propionic acid | 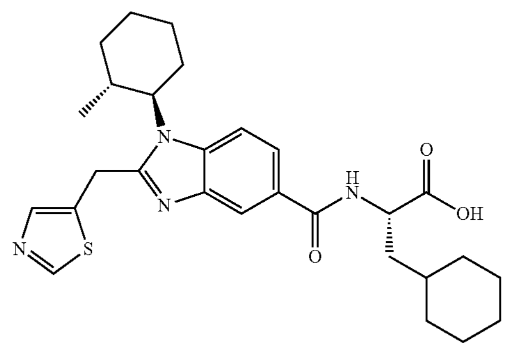 [SMILES: C[C@@H]1CCCC[C@H]1n1c(Cc2cncs2)nc2cc(C(=O)N[C@@H](CC3CCCCC3)C(=O)O)ccc21] | 509.2 | 4_1_1 | 1.26 |
| 38 | 1-{[1-((1R,2R)-2-Methyl-cyclohexyl)-2-thiophen-2-ylmethyl-1H-benzoimidazole-5-carbonyl]-amino}-cyclohexanecarboxylic acid | 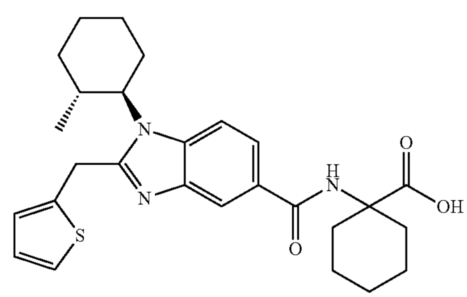 [SMILES: C[C@@H]1CCCC[C@H]1n1c(Cc2cccs2)nc2cc(C(=O)NC3(C(=O)O)CCCCC3)ccc21] | 478.5 | 4_1_1 | 1.27 |
| 39 | 3-Cycloheptyl-2-{[1-(1-ethyl-propyl)-2-thiophen-2-ylmethyl-1H-benzoimidazole-5-carbonyl]-amino}-propionic acid | 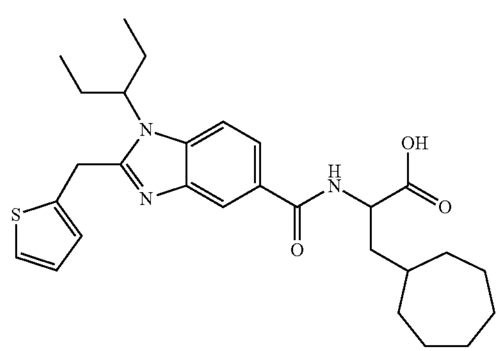 [SMILES: CCC(CC)n1c(Cc2cccs2)nc2cc(C(=O)NC(CC3CCCCCC3)C(=O)O)ccc21] | 496.4 | 4_1_1 | 1.32 |

| Exp. No. | Chemical Name | Structure | m/z [M + H]⁺ | LCMS method | R_t [min] |
|---|---|---|---|---|---|
| 40 | 3-Cycloheptyl-2-{[1-((1R,2R)-2-methyl-cyclohexyl)-2-thiophen-2-ylmethyl-1H-benzoimidazole-5-carbonyl]-amino}-propionic acid | 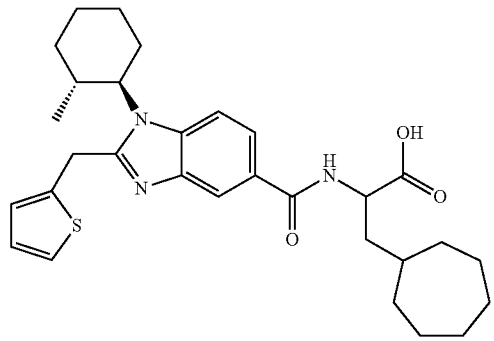 [SMILES: C[C@@H]1CCCC[C@H]1n1c(Cc2cccs2)nc2cc(C(=O)NC(CC3CCCCCC3)C(=O)O)ccc21] | 522.6 | 4_1_1 | 1.37 |
| 41 | 3-{[1-(1-Ethyl-propyl)-2-furan-2-ylmethyl-1H-benzoimidazole-5-carbonyl]-amino}-4-methyl-pentanoic acid | 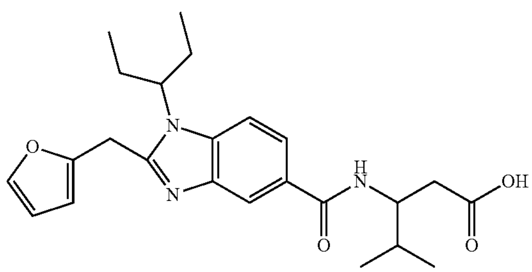 [SMILES: CCC(CC)n1c(Cc2ccco2)nc2cc(C(=O)NC(CC(=O)O)C(C)C)ccc21] | 426.2 | 6_1_1 | 1.43 |
| 42 | 3-{[1-(1-Ethyl-propyl)-2-furan-2-ylmethyl-1H-benzoimidazole-5-carbonyl]-amino}-3-phenyl-propionic acid | 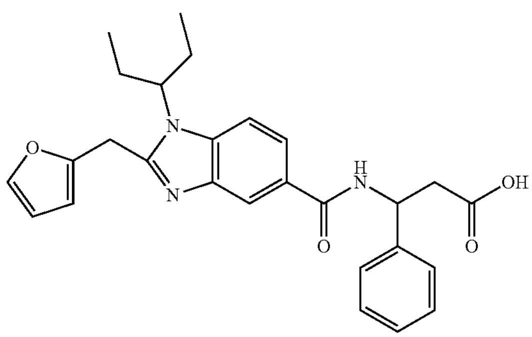 | 460.3 | 6_1_1 | 1.50 |
| 43 | 3-{[2-Cyclopentylmethyl-1-(1-ethyl-propyl)-1H-benzoimidazole-5-carbonyl]-amino}-3-phenyl-propionic acid | 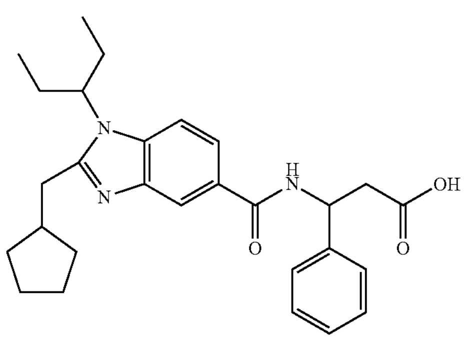 [SMILES: CCC(CC)n1c(CC2CCCC2)nc2cc(C(=O)NC(CC(=O)O)c3ccccc3)ccc21] | 462.2 | 6_1_1 | 1.62 |

-continued

| Exp. No. | Chemical Name | Structure | m/z [M + H]+ | LCMS method | R_t [min] |
|---|---|---|---|---|---|
| 44 | 3-Cyclohexyl-3-{[1-(1-ethyl-propyl)-2-thiophen-2-ylmethyl-1H-benzoimidazole-5-carbonyl]-amino}-propionic acid | 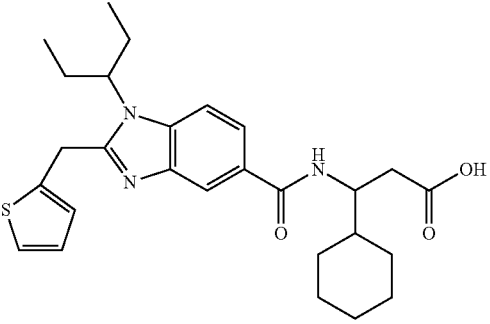 [SMILES: CCC(CC)n1c(Cc2cccs2)nc2cc(C(=O)NC(CC(=O)O)C3CCCCC3)ccc21] | 482.4 | 6_1_1 | 1.70 |
| 45 | 3-{[1-(1-Ethyl-propyl)-2-thiophen-2-ylmethyl-1H-benzoimidazole-5-carbonyl]-amino}-heptanoic acid | 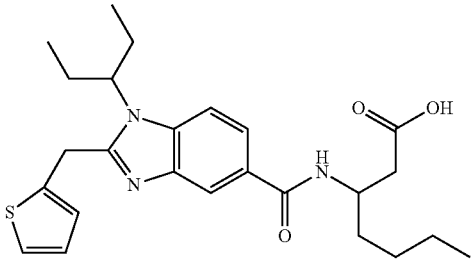 | 456.1 | 5_7_1 | 2.71 |
| 46 | 4-Cyclohexyl-3-{[1-(1-ethyl-propyl)-2-thiophen-2-ylmethyl-1H-benzoimidazole-5-carbonyl]-amino}-butyric acid | 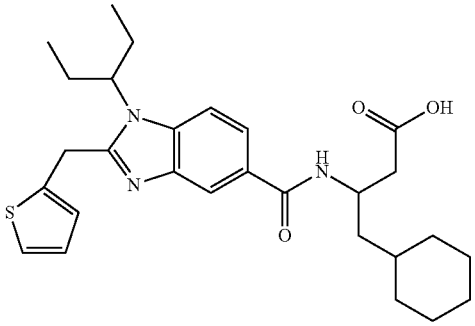 [SMILES: CCC(CC)n1c(Cc2cccs2)nc2cc(C(=O)NC(CC(=O)O)CC3CCCCC3)ccc21] | 496.2 | 5_7_1 | 2.93 |
| 47 | 3-{[1-(1-Ethyl-propyl)-2-thiophen-2-ylmethyl-1H-benzoimidazole-5-carbonyl]-amino}-5,5-dimethyl-hexanoic acid | 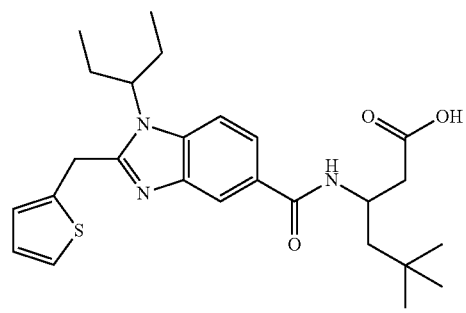 [SMILES: CCC(CC)n1c(Cc2cccs2)nc2cc(C(=O)NC(CC(=O)O)CC(C)(C)C)ccc21] | 470.1 | 5_7_1 | 2.78 |
| 48 | (R)-3-{[1-(1-Ethyl-propyl)-2-thiophen-2-ylmethyl-1H-benzoimidazole-5-carbonyl]-amino}-5-methyl-hexanoic acid | 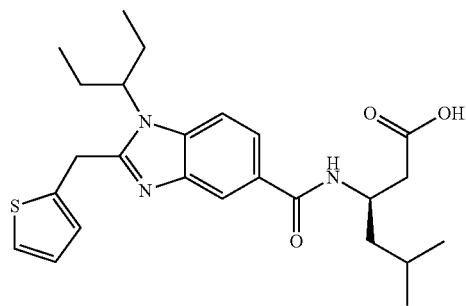 [SMILES: CCC(CC)n1c(Cc2cccs2)nc2cc(C(=O)N[C@@H](CC(=O)O)CC(C)C)ccc21] | 456.2 | 5_7_1 | 2.75 |

| Exp. No. | Chemical Name | Structure | m/z [M + H]+ | LCMS method | R_t [min] |
|---|---|---|---|---|---|
| 49 | (S)-3-{[1-(1-Ethyl-propyl)-2-pyrazol-1-ylmethyl-1H-benzoimidazole-5-carbonyl]-amino}-5-methyl-hexanoic acid | 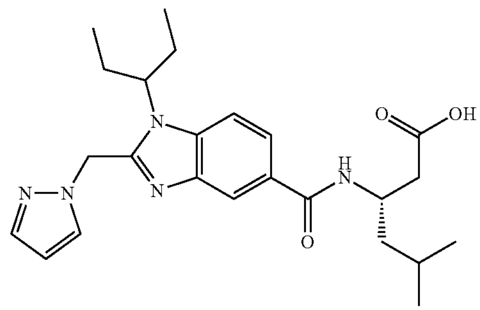 [SMILES: CCC(CC)n1c(Cn2cccn2)nc2cc(C(=O)N[C@H](CC(=O)O)CC(C)C)ccc21] | 440.2 | 5_3_1 | 1.96 |
| 50 | (S)-3-{[1-(1-Ethyl-propyl)-2-thiazol-5-ylmethyl-1H-benzoimidazole-5-carbonyl]-amino}-5-methyl-hexanoic acid | 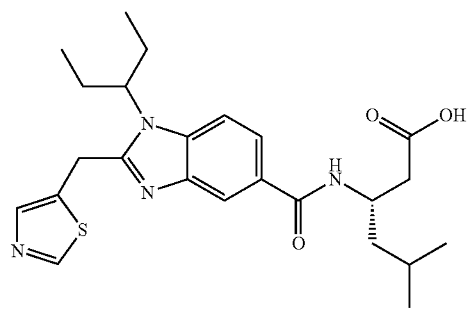 [SMILES: CCC(CC)n1c(Cc2cncs2)nc2cc(C(=O)N[C@H](CC(=O)O)CC(C)C)ccc21] | 457.1 | 5_3_1 | 1.88 |
| 51 | 4-Cyclohexyl-3-{[1-((1R,2R)-2-methyl-cyclohexyl)-2-thiophen-2-ylmethyl-1H-benzoimidazole-5-carbonyl]-amino}-butyric acid | 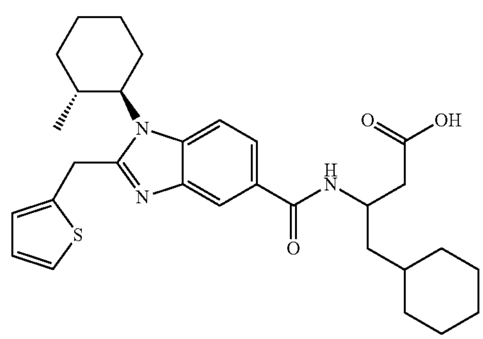 [SMILES: C[C@@H]1CCCC[C@H]1n1c(Cc2cccs2)nc2cc(C(=O)NC(CC(=O)O)CC3CCCCC3)ccc21] | 522.3 | 5_3_1 | 2.29 |
| 52 | 4-Cyclohexyl-3-{[1-((1S,2S)-2-methyl-cyclohexyl)-2-thiophen-2-ylmethyl-1H-benzoimidazole-5-carbonyl]-amino}-butyric acid | 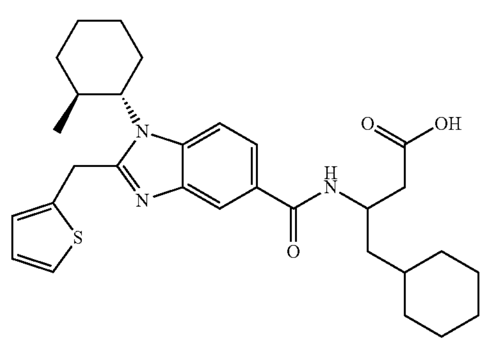 [SMILES: C[C@H]1CCCC[C@@H]1n1c(Cc2cccs2)nc2cc(C(=O)NC(CC(=O)O)CC3CCCCC3)ccc21] | 522.2 | 5_5_1 | 2.25 |

-continued

| Exp. No. | Chemical Name | Structure | m/z [M + H]+ | LCMS method | R_t [min] |
|---|---|---|---|---|---|
| 53 | (3R,4S)-4-Methyl-3-{[1-((1R,2R)-2-methyl-cyclohexyl)-2-thiophen-2-ylmethyl-1H-benzoimidazole-5-carbonyl]-amino}-hexanoic acid | 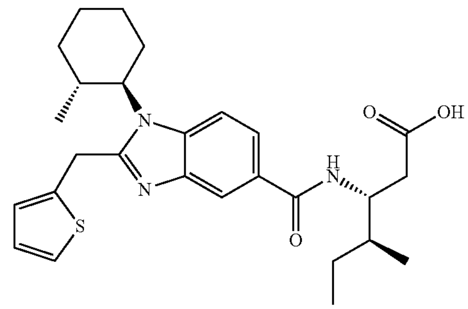 [SMILES: CC[C@H](C)[C@@H](CC(=O)O)NC(=O)c1ccc2c(c1)nc(Cc1cccs1)n2[C@@H]1CCCC[C@H]1C] | 482.3 | 5_5_1 | 2.12 |
| 54 | (3R,4S)-3-{[1-(1-Ethyl-propyl)-2-thiophen-2-ylmethyl-1H-benzoimidazole-5-carbonyl]-amino}-4-methyl-hexanoic acid | 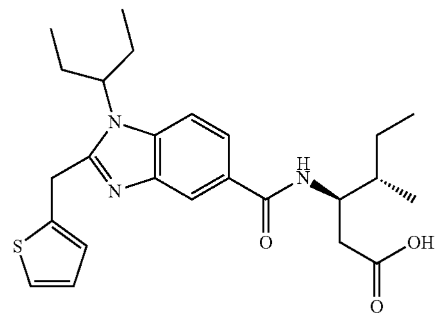 [SMILES: CCC(CC)n1c(Cc2cccs2)nc2cc(C(=O)N[C@H](CC(=O)O)[C@@H](C)CC)ccc21] | 454.1 | 5_2_1 | 3.94 |
| 55 | 3-{[1-((1R,2R)-2-Methyl-cyclohexyl)-2-thiophen-2-ylmethyl-1H-benzoimidazole-5-carbonyl]-amino}-hexanoic acid | 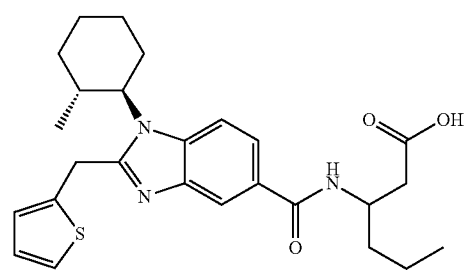 [SMILES: CCCC(CC(=O)O)NC(=O)c1ccc2c(c1)nc(Cc1cccs1)n2[C@@H]1CCCC[C@H]1C] | 468.3 | 5_5_1 | 2.06 |
| 56 | 3-{[1-((1R,2R)-2-Methyl-cyclohexyl)-2-thiophen-2-ylmethyl-1H-benzoimidazole-5-carbonyl]-amino}-heptanoic acid | 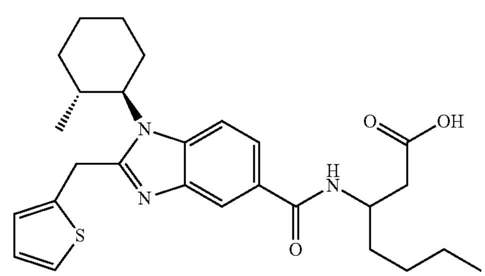 [SMILES: CCCCC(CC(=O)O)NC(=O)c1ccc2c(c1)nc(Cc1cccs1)n2[C@@H]1CCCC[C@H]1C] | 480.1 | 5_2_1 | 4.33 |
| 57 | 3-Cyclohexyl-3-{[1-((1R,2R)-2-methyl-cyclohexyl)-2-thiophen-2-ylmethyl-1H-benzoimidazole-5-carbonyl]-amino}-propionic acid | 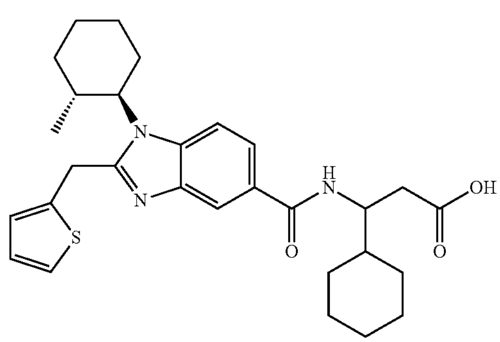 [SMILES: C[C@@H]1CCCC[C@H]1n1c(Cc2cccs2)nc2cc(C(=O)NC(CC(=O)O)C3CCCCC3)ccc21] | 508.3 | 3_2_1 | 1.50 |

-continued

| Exp. No. | Chemical Name | Structure | m/z [M + H]+ | LCMS method | R_t [min] |
|---|---|---|---|---|---|
| 58 | 3-{[1-(1-Ethyl-propyl)-2-thiophen-2-ylmethyl-1H-benzoimidazole-5-carbonyl]-amino}-2,2-dimethyl-heptanoic acid | 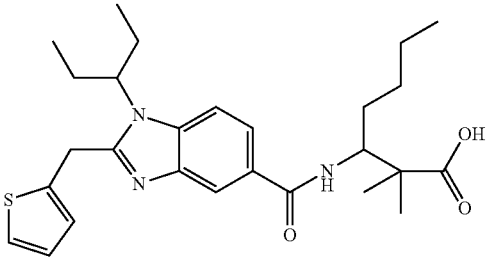 [SMILES: CCCCC(NC(=O)c1ccc2c(c1)nc(Cc1cccs1)n2C(CC)CC)C(C)(C)C(=O)O] | 484.2 | 3_1_1 | 1.52 |
| 59 | 4-Ethyl-3-{[1-(1-ethyl-propyl)-2-thiophen-2-ylmethyl-1H-benzoimidazole-5-carbonyl]-amino}-hexanoic acid | 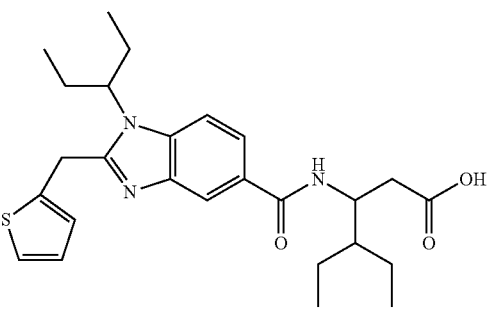 [SMILES: CCC(CC)C(CC(=O)O)NC(=O)c1ccc2c(c1)nc(Cc1cccs1)n2C(CC)CC] | 470.4 | 4_1_1 | 1.20 |
| 60 | (S)-4-Cyclopentyl-3-{[1-(1-ethyl-propyl)-2-thiophen-2-ylmethyl-1H-benzoimidazole-5-carbonyl]-amino}-butyric acid | 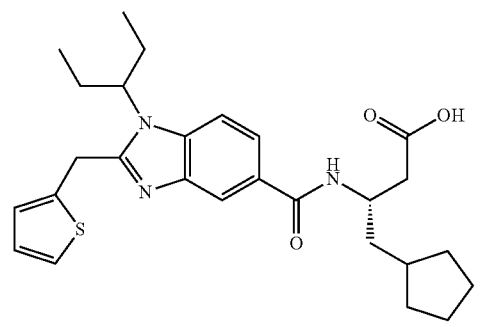 [SMILES: CCC(CC)n1c(Cc2cccs2)nc2cc(C(=O)N[C@H](CC(=O)O)CC3CCCC3)ccc21] | 482.3 | 3_1_1 | 1.55 |
| 61 | (S)-4-Cyclopentyl-3-{[1-((1R,2R)-2-methyl-cyclohexyl)-2-thiophen-2-ylmethyl-1H-benzoimidazole-5-carbonyl]-amino}-butyric acid | 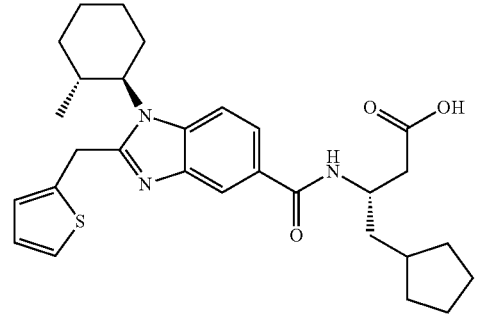 [SMILES: C[C@@H]1CCCC[C@H]1n1c(Cc2cccs2)nc2cc(C(=O)N[C@H](CC(=O)O)CC3CCCC3)ccc21] | 508.3 | 3_1_1 | 1.60 |
| 62 | 3-{[1-(1-Ethyl-propyl)-2-thiophen-2-ylmethyl-1H-benzoimidazole-5-carbonyl]-amino}-2,2,5-trimethyl-hexanoic acid | 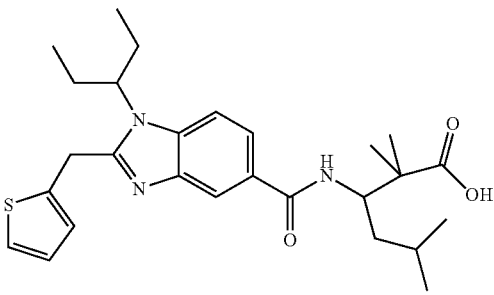 [SMILES: CCC(CC)n1c(Cc2cccs2)nc2cc(C(=O)NC(CC(C)C)C(C)(C)C(=O)O)ccc21] | 484.3 | 6_6_1 | 3.04 |

-continued

| Exp. No. | Chemical Name | Structure | m/z [M + H]+ | LCMS method | R_t [min] |
|---|---|---|---|---|---|
| 63 | 3-{[1-(1-Ethyl-propyl)-2-thiophen-2-ylmethyl-1H-benzoimidazole-5-carbonyl]-amino}-2,2-dimethyl-hexanoic acid | 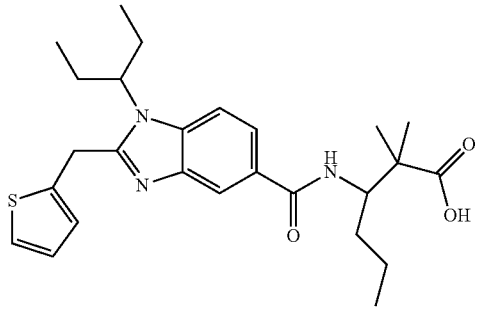 [SMILES: CCCC(NC(=O)c1ccc2c(c1)nc(Cc1cccs1)n2C(CC)CC)C(C)(C)C(=O)O] | 470.3 | 6_6_1 | 2.87 |
| 64 | (1-{[1-(1-Ethyl-propyl)-2-thiophen-2-ylmethyl-1H-benzoimidazole-5-carbonyl]-amino}-cyclohexyl)-acetic acid | 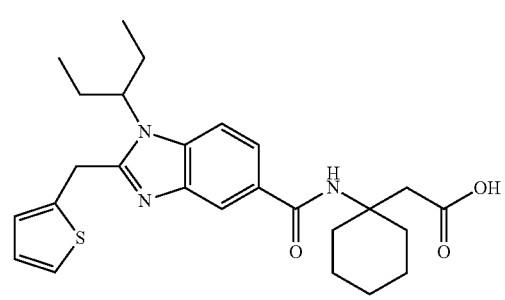 [SMILES: CCC(CC)n1c(Cc2cccs2)nc2cc(C(=O)NC3(CC(=O)O)CCCCC3)ccc21] | 468.3 | 6_6_1 | 2.85 |
| 65 | 4-Cyclohexyl-3-{[1-((1R,2R)-2-methyl-cyclohexyl)-2-thiazol-5-ylmethyl-1H-benzoimidazole-5-carbonyl]-amino}-butyric acid | 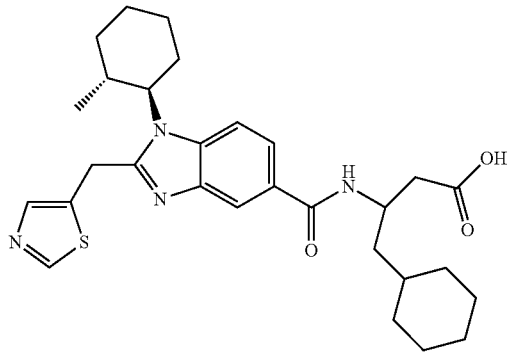 [SMILES: C[C@@H]1CCCC[C@H]1n1c(Cc2cncs2)nc2cc(C(=O)NC(CC(=O)O)CC3CCCCC3)ccc21] | 523.3 | 4_1_1 | 1.24 |
| 66 | (1-{[1-((1R,2R)-2-Methyl-cyclohexyl)-2-thiophen-2-ylmethyl-1H-benzoimidazole-5-carbonyl]-amino}-cyclohexyl)-acetic acid | 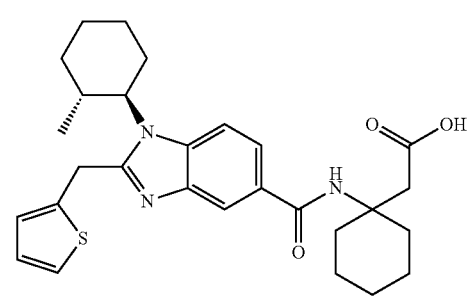 [SMILES: C[C@@H]1CCCC[C@H]1n1c(Cc2cccs2)nc2cc(C(=O)NC3(CC(=O)O)CCCCC3)ccc21] | 494.3 | 4_1_1 | 1.26 |
| 67 | (2R,3S)-3-{[1-(1-Ethyl-propyl)-2-thiophen-2-ylmethyl-1H-benzoimidazole-5-carbonyl]-amino}-2-hydroxy-5-methyl-hexanoic acid | 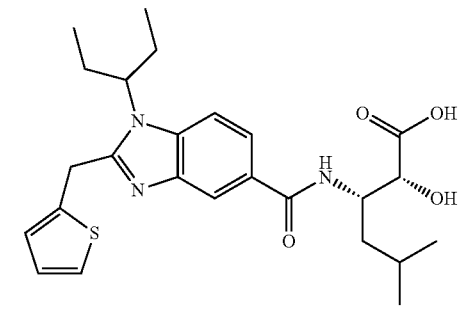 [SMILES: CCC(CC)n1c(Cc2cccs2)nc2cc(C(=O)N[C@@H](CC(C)C)[C@@H](O)C(=O)O)ccc21] | 472.4 | 4_1_1 | 1.19 |

| Exp. No. | Chemical Name | Structure | m/z [M + H]+ | LCMS method | R$_t$ [min] |
|---|---|---|---|---|---|
| 68 | (2S,3S)-3-{[1-(1-Ethyl-propyl)-2-thiophen-2-ylmethyl-1H-benzoimidazole-5-carbonyl]-amino}-2-hydroxy-5-methyl-hexanoic acid | 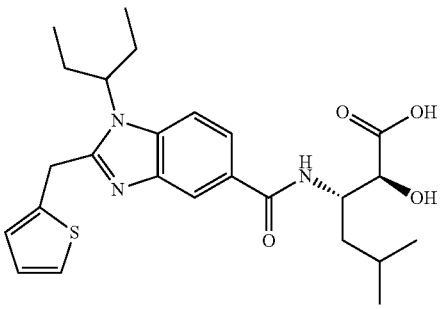 [SMILES: CCC(CC)n1c(Cc2cccs2)nc2cc(C(=O)N[C@@H](CC(C)C)[C@H](O)C(=O)O)ccc21] | 472.3 | 4_1_1 | 1.20 |
| 69 | (R)-6-Methyl-4-{[2-thiophen-2-ylmethyl-1-(2-trifluoromethyl-cyclohexyl)-1H-benzoimidazole-5-carbonyl]-amino}-heptanoic acid | 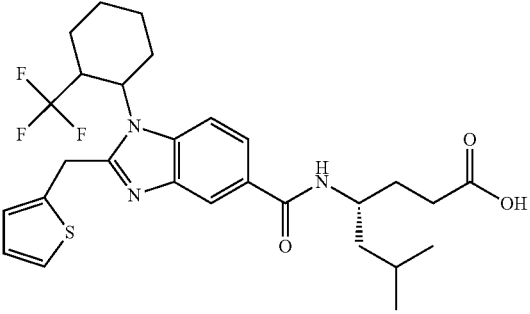 [SMILES: CC(C)C[C@@H](CCC(=O)O)NC(=O)c1ccc2c(c1)nc(Cc1cccs1)n2C1CCCCC1C(F)(F)F] | 550.5 | 5_2_1 | 4.57 |
| 70 | (R)-6-Methyl-4-{[1-((1R,2R)-2-methyl-cyclohexyl)-2-thiophen-2-ylmethyl-1H-benzoimidazole-5-carbonyl]-amino}-heptanoic acid | 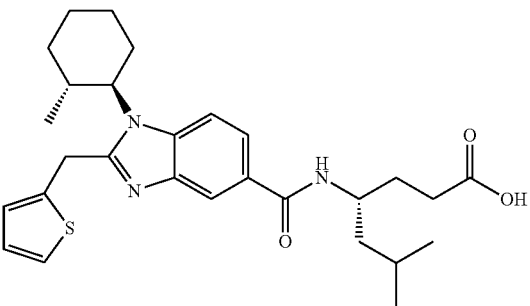 [SMILES: CC(C)C[C@@H](CCC(=O)O)NC(=O)c1ccc2c(c1)nc(Cc1cccs1)n2[C@@H]1CCCC[C@H]1C] | 496.3 | 5_5_1 | 2.14 |
| 71 | (4R,5S)-4-{[1-(1-Ethyl-propyl)-2-thiophen-2-ylmethyl-1H-benzoimidazole-5-carbonyl]-amino}-5-methyl-heptanoic acid | 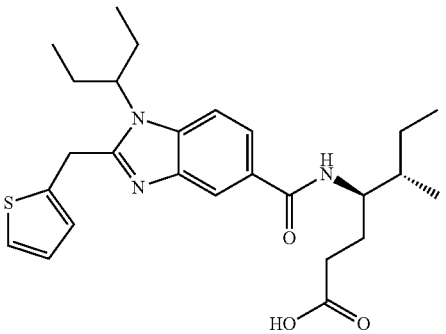 [SMILES: CCC(CC)n1c(Cc2cccs2)nc2cc(C(=O)N[C@H](CCC(=O)O)[C@@H](C)CC)ccc21] | 470.2 | 6_6_1 | 2.89 |

-continued

| Exp. No. | Chemical Name | Structure | m/z [M + H]+ | LCMS method | R_t [min] |
|---|---|---|---|---|---|
| 72 | (4R,5S)-5-Methyl-4-{[1-((1R,2R)-2-methyl-cyclohexyl)-2-thiophen-2-ylmethyl-1H-benzoimidazole-5-carbonyl]-amino}-heptanoic acid | 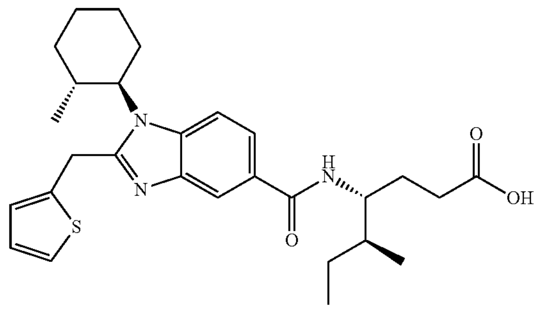 [SMILES: CC[C@H](C)[C@@H](CCC(=O)O)NC(=O)c1ccc2c(c1)nc(Cc1cccs1)n2[C@@H]1CCCC[C@H]1C] | 496.3 | 3_1_1 | 1.55 |
| 73 | (3R,4S)-5-Cyclohexyl-4-{[1-(1-ethyl-propyl)-2-thiophen-2-ylmethyl-1H-benzoimidazole-5-carbonyl]-amino}-3-hydroxy-pentanoic acid | 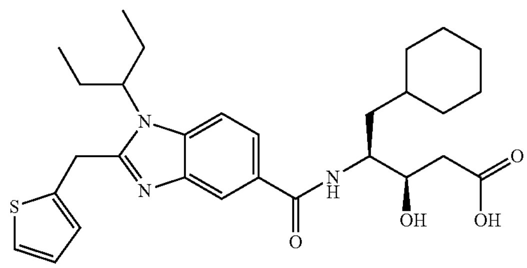 [SMILES: CCC(CC)n1c(Cc2cccs2)nc2cc(C(=O)N[C@@H](CC3CCCCC3)[C@H](O)CC(=O)O)ccc21] | 526.3 | 5_2_1 | 4.30 |
| 74 | (3R,4S)-5-Cyclohexyl-3-hydroxy-4-{[1-((1R,2R)-2-methyl-cyclohexyl)-2-thiophen-2-ylmethyl-1H-benzoimidazole-5-carbonyl]-amino}-pentanoic acid | 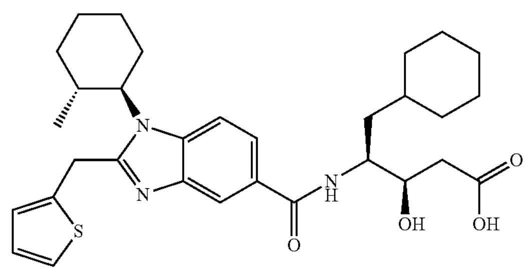 [SMILES: C[C@@H]1CCCC[C@H]1n1c(Cc2cccs2)nc2cc(C(=O)N[C@@H](CC3CCCCC3)[C@H](O)CC(=O)O)ccc21] | 552.5 | 4_1_1 | 1.27 |
| 75 | (3S,4S)-4-{[1-(1-Ethyl-propyl)-2-thiophen-2-ylmethyl-1H-benzoimidazole-5-carbonyl]-amino}-3-hydroxy-6-methyl-heptanoic acid | 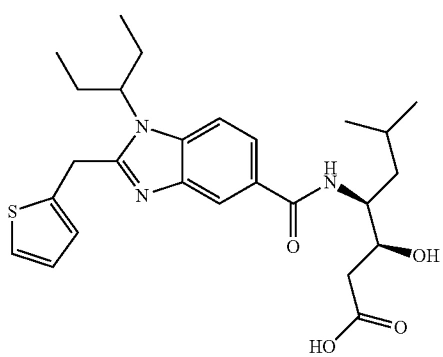 [SMILES: CCC(CC)n1c(Cc2cccs2)nc2cc(C(=O)N[C@@H](CC(C)C)[C@@H](O)CC(=O)O)ccc21] | 486.4 | 4_1_1 | 1.20 |
| 76 | (3R,4S)-4-{[1-(1-Ethyl-propyl)-2-thiophen-2-ylmethyl-1H-benzoimidazole-5-carbonyl]-amino}-3-hydroxy-6-methyl-heptanoic acid | 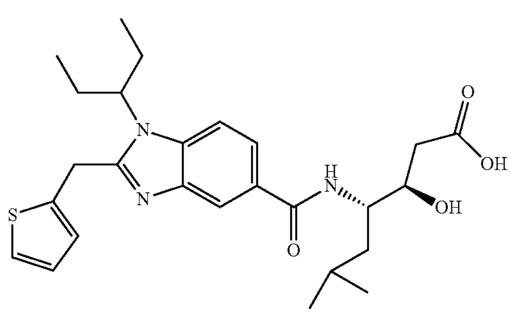 [SMILES: CCC(CC)n1c(Cc2cccs2)nc2cc(C(=O)N[C@@H](CC(C)C)[C@H](O)CC(=O)O)ccc21] | 486.4 | 4_1_1 | 1.20 |

| Exp. No. | Chemical Name | Structure | m/z [M + H]⁺ | LCMS method | R_t [min] |
|---|---|---|---|---|---|
| 77 | (3R,4S)-3-Hydroxy-6-methyl-4-{[1-((1R,2R)-2-methyl-cyclohexyl)-2-thiophen-2-ylmethyl-1H-benzoimidazole-5-carbonyl]-amino}-heptanoic acid | 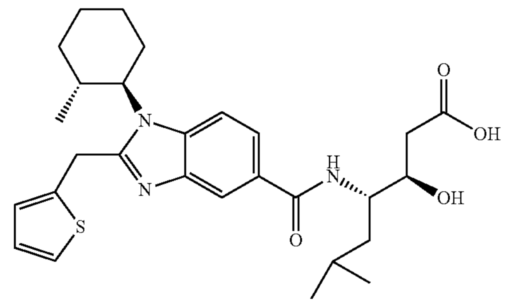 [SMILES: CC(C)C[C@H](NC(=O)c1ccc2c(c1)nc(Cc1cccs1)n2[C@@H]1CCCC[C@H]1C)[C@H](O)CC(=O)O] | 512.4 | 4_1_1 | 1.25 |
| 78 | (3S,4S)-3-Hydroxy-6-methyl-4-{[1-((1R,2R)-2-methyl-cyclohexyl)-2-thiophen-2-ylmethyl-1H-benzoimidazole-5-carbonyl]-amino}-heptanoic acid | 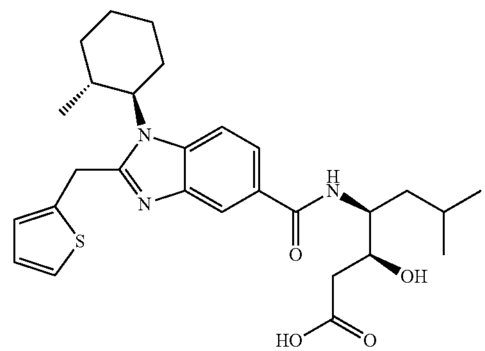 [SMILES: CC(C)C[C@H](NC(=O)c1ccc2c(c1)nc(Cc1cccs1)n2[C@@H]1CCCC[C@H]1C)[C@@H](O)CC(=O)O] | 512.4 | 4_1_1 | 1.25 |
| 79 | (3S,4S)-5-Cyclohexyl-4-{[1-(1-ethyl-propyl)-2-thiophen-2-ylmethyl-1H-benzoimidazole-5-carbonyl]-amino}-3-hydroxy-pentanoic acid | 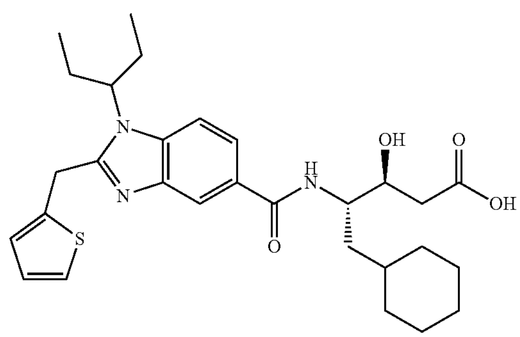 [SMILES: CCC(CC)n1c(Cc2cccs2)nc2cc(C(=O)N[C@@H](CC3CCCCC3)[C@@H](O)CC(=O)O)ccc21] | 526.4 | 4_1_1 | 1.27 |

EXAMPLE 80

(S)-2-{[1-(1-Ethyl-propyl)-2-(tetrahydro-furan-2-ylmethyl)-1H-benzoimidazole-5-carbonyl]-amino}-4-methyl-pentanoic acid

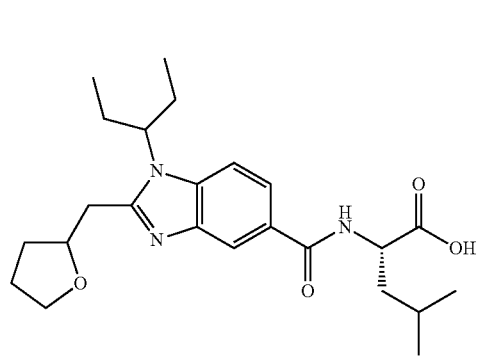 [SMILES: CCC(CC)n1c(CC2CCCO2)nc2cc(C(=O)N[C@@H](CC(C)C)C(=O)O)ccc21]

a) (S)-2-{[1-(1-Ethyl-propyl)-2-(tetrahydro-furan-2-ylmethyl)-1H-benzoimidazole-5-carbonyl]-amino}-4-methyl-pentanoic acid tert-butyl ester

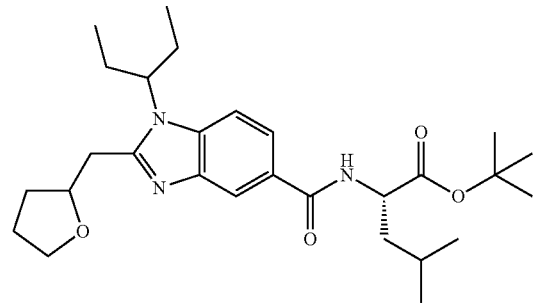 [SMILES: CCC(CC)n1c(CC2CCCO2)nc2cc(C(=O)N[C@@H](CC(C)C)C(=O)OC(C)(C)C)ccc21]

To a solution of 55 mg of 1-(1-Ethyl-propyl)-2-(tetrahydro-furan-2-ylmethyl)-1H-benzoimidazole-5-carboxylic acid in 1 ml of dry DMF 26 mg of HOBT, 37 mg of EDC and 0.05 ml of DIPEA were added at 0° C. After 15 min 100 mg of L-leucine tert-butyl ester-hydrochloride and 0.05 ml of DIPEA were added and the reaction was stirred at rt for 16 h. The reaction was then poured into water and the pH was adjusted to 3 by the addition of 2 M aqueous hydrochloric acid. The reaction was extracted with ethyl acetate three times. The combined organic phases were washed with saturated aqueous sodium bicarbonate solution and brine, dried over magnesium sulphate and concentrated. 75 mg (88%) of (S)-2-{[1-(1-Ethyl-propyl)-2-(tetrahydro-furan-2-ylmethyl)-1H-benzoimidazole-5-carbonyl]-amino}-4-methyl-pentanoic acid tert-butyl ester were obtained.

$C_{28}H_{43}N_3O_3$ (485.67), LCMS (method 7_1_1): Rt=1.30 min, m/z=486.45 $[M+H]^+$ b) (S)-2-{[1-(1-Ethyl-propyl)-2-(tetrahydro-furan-2-ylmethyl)-1H-benzoimidazole-5-carbonyl]-amino}-4-methyl-pentanoic acid 75 mg of (S)-2-{[1-(1-Ethyl-propyl)-2-(tetrahydro-furan-2-ylmethyl)-1H-benzoimidazole-5-carbonyl]-amino}-4-methyl-pentanoic acid tert-butyl ester were dissolved in 0.6 ml dichloromethane and 0.18 µl of trifluoroacetic acid were added. After stirring at room temperature over night the reaction mixture was concentrated. The residue was dissolved in 1 M aqueous sodium hydroxide solution, and precipitated by addition of 2 M aqueous hydrochloric acid. The solid was taken up in ethyl acetate, dried over sodium sulphate and concentrated. The obtained residue was precipitated by addition of pentane. 23 mg (35%) of (S)-2-{[1-(1-Ethyl-propyl)-2-(tetrahydro-furan-2-ylmethyl)-1H-benzoimidazole-5-carbonyl]-amino}-4-methyl-pentanoic acid were obtained.

$C_{24}H_{35}N_3O_4$ (429.26), LCMS (method 6_3_1): Rt=1.28 min, m/z=430.24 $[M+H]^+$

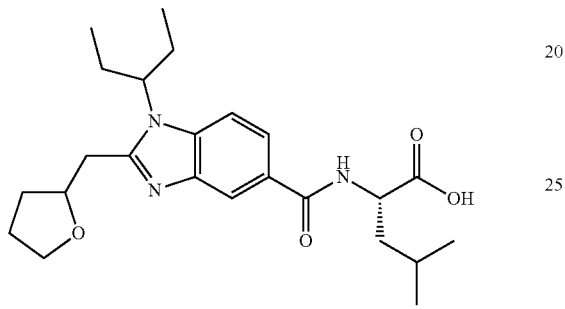

The following examples were prepared in analogy to example 80:

| Exp. No. | Chemical Name | Structure | m/z $[M + H]^+$ | LCMS method | $R_t$ [min] |
|---|---|---|---|---|---|
| 81 | (S)-2-{[1-(1-Ethyl-propyl)-2-furan-2-ylmethyl-1H-benzoimidazole-5-carbonyl]-amino}-4-methyl-pentanoic acid | 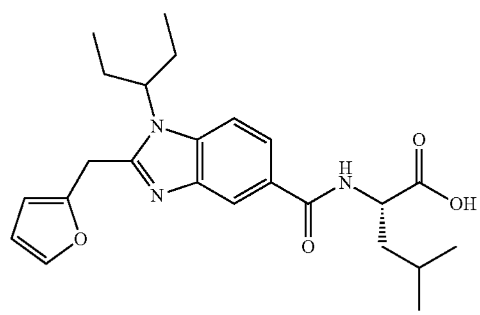 [SMILES: CCC(CC)n1c(Cc2ccco2)nc2cc(C(=O)N[C@@H](CC(C)C)C(=O)O)ccc21] | 426.2 | 6_4_1 | 1.43 |
| 82 | (S)-2-{[2-(5-Chloro-thiophen-2-ylmethyl)-1-(1-ethyl-propyl)-1H-benzoimidazole-5-carbonyl]-amino}-4-methyl-pentanoic acid | 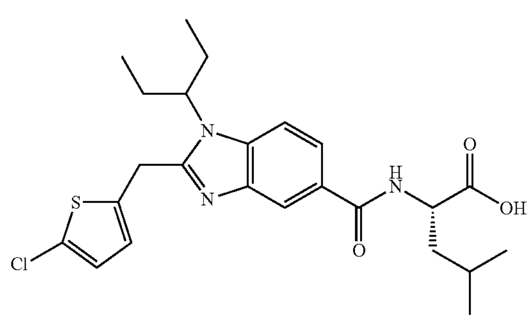 [SMILES: CCC(CC)n1c(Cc2ccc(Cl)s2)nc2cc(C(=O)N[C@@H](CC(C)C)C(=O)O)ccc21] | 476.2 | 6_3_1 | 1.53 |

-continued

| Exp. No. | Chemical Name | Structure | m/z [M + H]+ | LCMS method | R_t [min] |
|---|---|---|---|---|---|
| 83 | (S)-2-[(1-Cyclohexylmethyl-2-thiophen-2-ylmethyl-1H-benzoimidazole-5-carbonyl)-amino]-4-methyl-pentanoic acid | 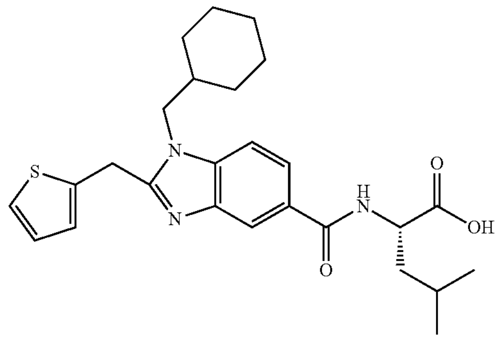 [SMILES: CC(C)C[C@H](NC(=O)c1ccc2c(c1)nc(Cc1cccs1)n2CC1CCCCC1)C(=O)O] | 468.1 | 6_3_1 | 1.51 |
| 84 | (S)-2-{[1-(1-Ethyl-propyl)-2-thiazol-4-ylmethyl-1H-benzoimidazole-5-carbonyl]-amino}-4-methyl-pentanoic acid | 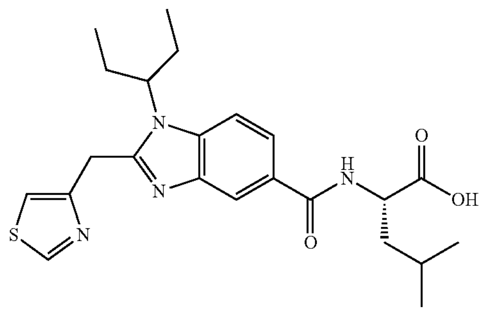 [SMILES: CCC(CC)n1c(Cc2cscn2)nc2cc(C(=O)N[C@@H](CC(C)C)C(=O)O)ccc21] | 443.2 | 6_3_1 | 1.28 |
| 85 | (2S,3S)-2-{[1-(1-Ethyl-propyl)-2-thiazol-4-ylmethyl-1H-benzoimidazole-5-carbonyl]-amino}-3-methyl-pentanoic acid | 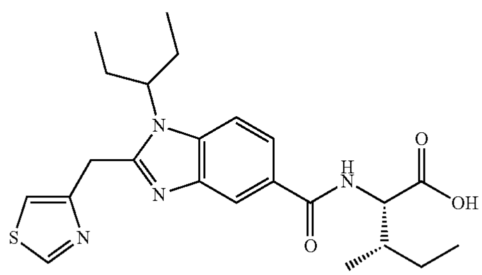 [SMILES: CCC(CC)n1c(Cc2cscn2)nc2cc(C(=O)N[C@H](C(=O)O)[C@@H](C)CC)ccc21] | 443.2 | 6_3_1 | 1.21 |
| 86 | (S)-2-{[2-Furan-2-ylmethyl-1-(2-methyl-cyclohexyl)-1H-benzoimidazole-5-carbonyl]-amino}-4-methyl-pentanoic acid | 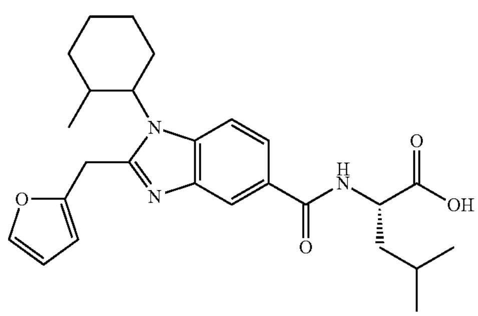 [SMILES: CC(C)C[C@H](NC(=O)c1ccc2c(c1)nc(Cc1ccco1)n2C1CCCCC1C)C(=O)O] | 452.2 | 6_3_1 | 1.49 |
| 87 | (S)-4-Methyl-2-{[2-thiophen-2-ylmethyl-1-(2-trifluoromethyl-cyclohexyl)-1H-benzoimidazole-5-carbonyl]-amino}-pentanoic acid | 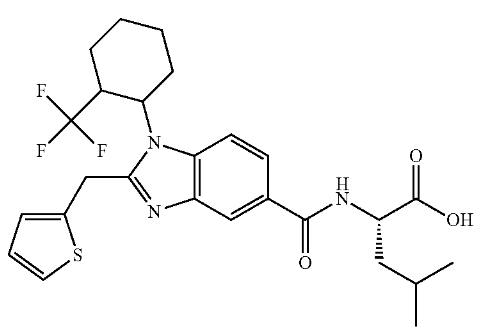 [SMILES: CC(C)C[C@H](NC(=O)c1ccc2c(c1)nc(Cc1cccs1)n2C1CCCCC1C(F)(F)F)C(=O)O] | 522.2 | 6_6_1 | 3.22 |

-continued

| Exp. No. | Chemical Name | Structure | m/z [M + H]+ | LCMS method | R_t [min] |
|---|---|---|---|---|---|
| 88 | (S)-2-{[2-Thiophen-2-ylmethyl-1-(2-trifluoromethyl-cyclohexyl)-1H-benzoimidazole-5-carbonyl]-amino}-pentanoic acid | 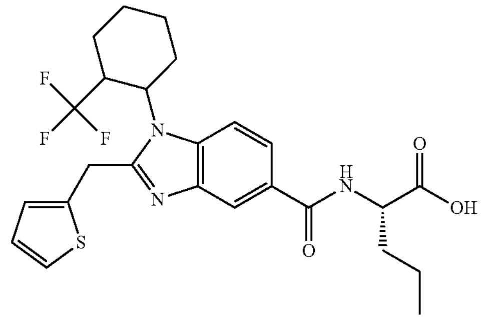 [SMILES: CCC[C@H](NC(=O)c1ccc2c(c1)nc(Cc1cccs1)n2C1CCCCC1C(F)(F)F)C(=O)O] | 508.4 | 5_2_1 | 4.37 |
| 89 | (S)-3-Phenyl-2-{[2-thiophen-2-ylmethyl-1-(2-trifluoromethyl-cyclohexyl)-1H-benzoimidazole-5-carbonyl]-amino}-propionic acid | 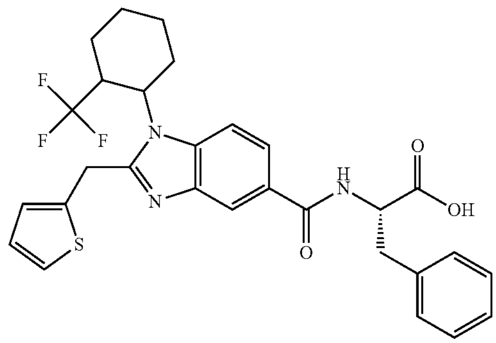 [SMILES: O=C(N[C@@H](Cc1ccccc1)C(=O)O)c1ccc2c(c1)nc(Cc1cccs1)n2C1CCCCC1C(F)(F)F] | 556.4 | 5_2_1 | 4.52 |
| 90 | (S)-4-Methyl-2-{[1-(2-methyl-cyclopentyl)-2-thiophen-2-ylmethyl-1H-benzoimidazole-5-carbonyl]-amino}-pentanoic acid | 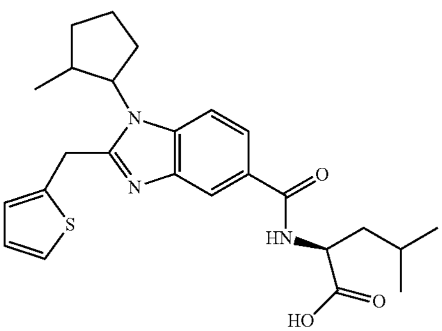 [SMILES: CC(C)C[C@H](NC(=O)c1ccc2c(c1)nc(Cc1cccs1)n2C1CCCC1C)C(=O)O] | 454.2 | 6_6_1 | 2.93 |
| 91 | (S)-2-{[1-((1R,2R)-2-Methyl-cyclohexyl)-2-thiophen-2-ylmethyl-1H-benzoimidazole-5-carbonyl]-amino}-pentanoic acid | 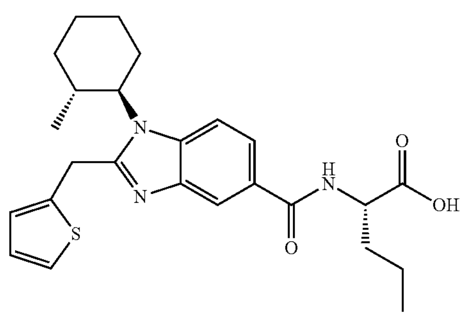 [SMILES: CCC[C@H](NC(=O)c1ccc2c(c1)nc(Cc1cccs1)n2[C@@H]1CCCC[C@H]1C)C(=O)O] | 454.2 | 6_6_1 | 2.90 |
| 92 | (2S,3S)-3-Methyl-2-{[1-((1R,2R)-2-methyl-cyclohexyl)-2-thiophen-2-ylmethyl-1H-benzoimidazole-5-carbonyl]-amino}-pentanoic acid | 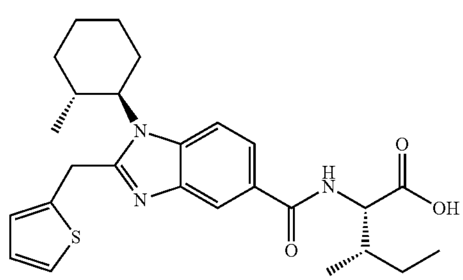 [SMILES: CC[C@H](C)[C@H](NC(=O)c1ccc2c(c1)nc(Cc1cccs1)n2[C@@H]1CCCC[C@H]1C)C(=O)O] | 468.2 | 5_5_1 | 2.12 |

-continued

| Exp. No. | Chemical Name | Structure | m/z [M + H]⁺ | LCMS method | R_t [min] |
|---|---|---|---|---|---|
| 93 | (S)-2-{[1-(2-Ethyl-cyclohexyl)-2-thiophen-2-ylmethyl-1H-benzoimidazole-5-carbonyl]-amino}-4-methyl-pentanoic acid | 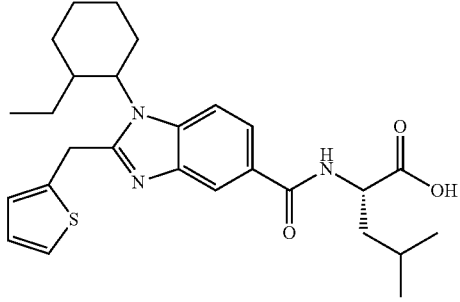 [SMILES: CCC1CCCCC1n1c(Cc2cccs2)nc2cc(C(=O)N[C@@H](CC(C)C)C(=O)O)ccc21] | 482.3 | 5_5_1 | 2.18 |
| 94 | (S)-2-{[1-(1-Ethyl-propyl)-2-thiophen-2-ylmethyl-1H-benzoimidazole-5-carbonyl]-amino}-pentanoic acid | 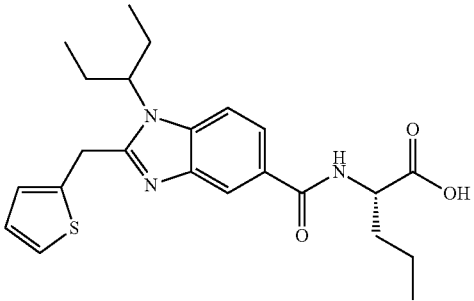 [SMILES: CCC[C@H](NC(=O)c1ccc2c(c1)nc(Cc1cccs1)n2C(CC)CC)C(=O)O] | 426.2 | 4_1_1 | 1.16 |
| 95 | (S)-3-{[1-(1-Ethyl-propyl)-2-thiophen-2-ylmethyl-1H-benzoimidazole-5-carbonyl]-amino}-5-methyl-hexanoic acid | 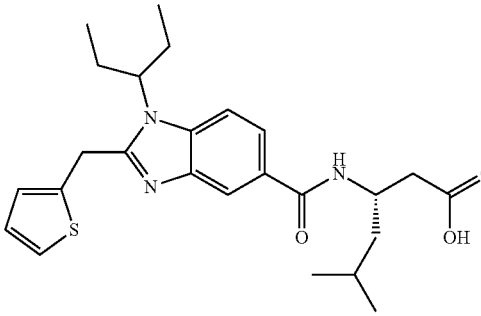 | 456.2 | 6_3_1 | 1.39 |
| 96 | (S)-3-{[1-(1-Ethyl-propyl)-2-furan-2-ylmethyl-1H-benzoimidazole-5-carbonyl]-amino}-5-methyl-hexanoic acid | 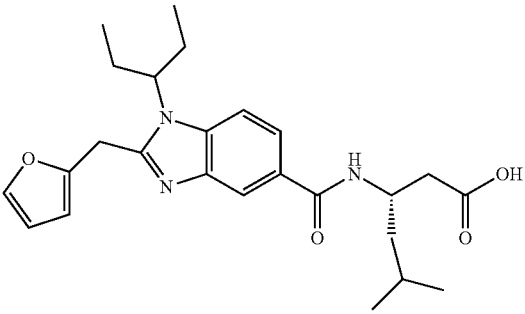 [SMILES: CCC(CC)n1c(Cc2ccco2)nc2cc(C(=O)N[C@H](CC(=O)O)CC(C)C)ccc21] | 440.3 | 6_4_1 | 1.39 |

-continued

| Exp. No. | Chemical Name | Structure | m/z [M + H]+ | LCMS method | R_t [min] |
|---|---|---|---|---|---|
| 97 | (S)-3-[(1-Cyclohexylmethyl-2-thiophen-2-ylmethyl-1H-benzoimidazole-5-carbonyl)-amino]-5-methyl-hexanoic acid | 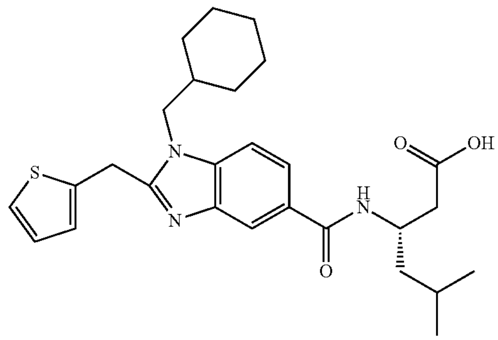 [SMILES: CC(C)C[C@@H](CC(=O)O)NC(=O)c1ccc2c(c1)nc(Cc1cccs1)n2CC1CCCCC1] | 482.1 | 6_3_1 | 1.50 |
| 98 | (S)-3-{[1-(1-Ethyl-propyl)-2-thiazol-4-ylmethyl-1H-benzoimidazole-5-carbonyl]-amino}-5-methyl-hexanoic acid | Chiral | 457.2 | 6_3_1 | 1.26 |
| 99 | (S)-3-{[2-Furan-2-ylmethyl-1-(2-methyl-cyclohexyl)-1H-benzoimidazole-5-carbonyl]-amino}-5-methyl-hexanoic acid | 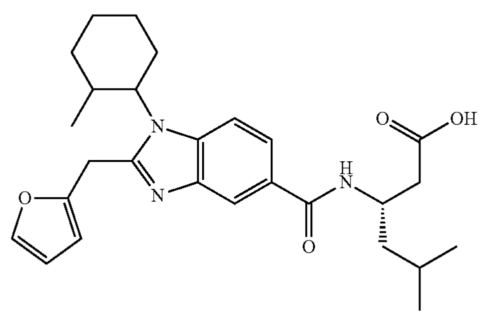 [SMILES: CC(C)C[C@@H](CC(=O)O)NC(=O)c1ccc2c(c1)nc(Cc1ccco1)n2C1CCCCC1C] | 466.2 | 6_3_1 | 1.47 |
| 100 | (S)-3-{[1-(1-Ethyl-propyl)-2-thiophen-2-ylmethyl-1H-benzoimidazole-5-carbonyl]-amino}-4-phenyl-butyric acid | 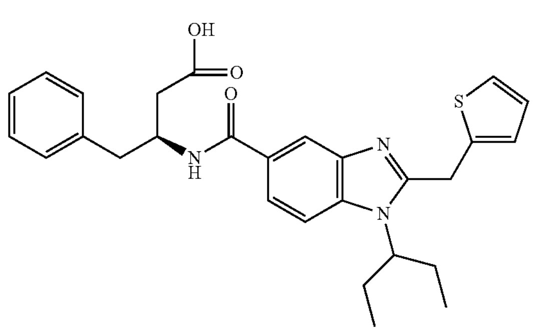 [SMILES: CCC(CC)n1c(Cc2cccs2)nc2cc(C(=O)N[C@H](CC(=O)O)Cc3ccccc3)ccc21] | 490.1 | 5_7_1 | 2.70 |

-continued

| Exp. No. | Chemical Name | Structure | m/z [M + H]+ | LCMS method | R$_t$ [min] |
|---|---|---|---|---|---|
| 101 | (S)-5-Methyl-3-{[1-(2-methyl-cyclohexyl)-2-thiophen-2-ylmethyl-1H-benzoimidazole-5-carbonyl]-amino}-hexanoic acid | 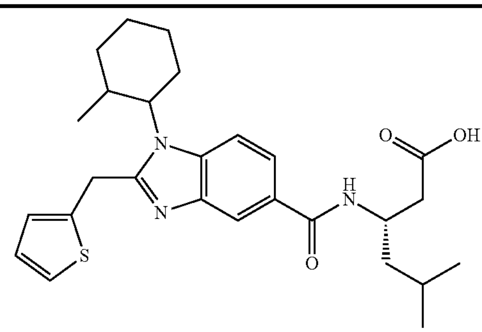 | 961.6 | 5_1_1 | 4.44 |
| 102 | (S)-5-Methyl-3-{[2-thiophen-2-ylmethyl-1-(2-trifluoromethyl-cyclohexyl)-1H-benzoimidazole-5-carbonyl]-amino}-hexanoic acid | 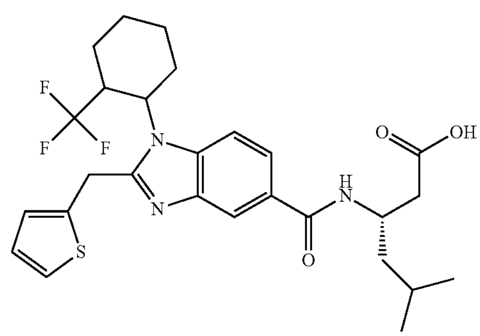 [SMILES: CC(C)C[C@@H](CC(=O)O)NC(=O)c1ccc2c(c1)nc(Cc1cccs1)n2C1CCCCC1C(F)(F)F] | 536.5 | 5_2_1 | 4.52 |
| 103 | (S)-4-Phenyl-3-{[2-thiophen-2-ylmethyl-1-(2-trifluoromethyl-cyclohexyl)-1H-benzoimidazole-5-carbonyl]-amino}-butyric acid | 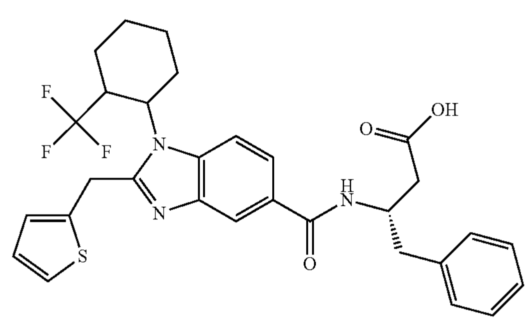 [SMILES: O=C(O)C[C@H](Cc1ccccc1)NC(=O)c1ccc2c(c1)nc(Cc1cccs1)n2C1CCCCC1C(F)(F)F] | 570.5 | 5_2_1 | 4.49 |
| 104 | (S)-5-Methyl-3-{[1-(2-methyl-cyclopentyl)-2-thiophen-2-ylmethyl-1H-benzoimidazole-5-carbonyl]-amino}-hexanoic acid | 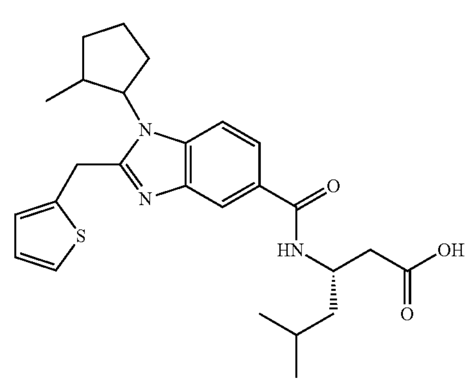 [SMILES: CC(C)C[C@@H](CC(=O)O)NC(=O)c1ccc2c(c1)nc(Cc1cccs1)n2C1CCCC1C] | 468.2 | 5_3_1 | 2.07 |

| Exp. No. | Chemical Name | Structure | m/z [M + H]+ | LCMS method | R$_t$ [min] |
|---|---|---|---|---|---|
| 105 | (S)-3-{[1-(1-Ethyl-propyl)-2-isoxazol-5-ylmethyl-1H-benzoimidazole-5-carbonyl]-amino}-5-methyl-hexanoic acid | 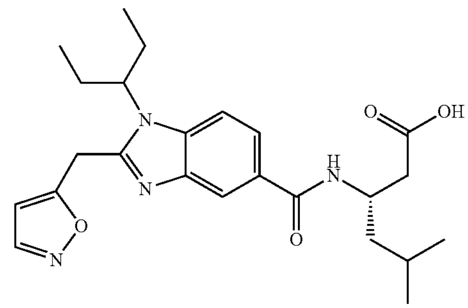 [SMILES: CCC(CC)n1c(Cc2ccno2)nc2cc(C(=O)N[C@H](CC(=O)O)CC(C)C)ccc21] | 441.4 | 4_1_1 | 1.12 |
| 106 | (S)-5-Methyl-3-{[1-((1R,2R)-2-methyl-cyclohexyl)-2-thiazol-5-ylmethyl-1H-benzoimidazole-5-carbonyl]-amino}-hexanoic acid | 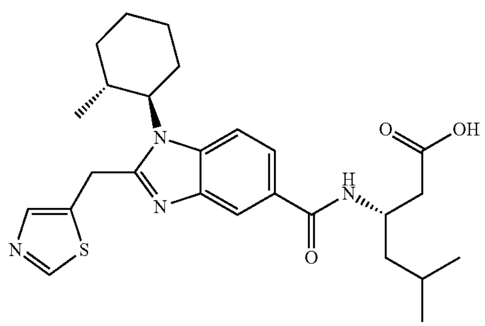 [SMILES: CC(C)C[C@@H](CC(=O)O)NC(=O)c1ccc2c(c1)nc(Cc1cncs1)n2[C@@H]1CCCC[C@H]1C] | 483.3 | 4_1_1 | 1.17 |

EXAMPLE 107

(S)-3-{[1-(1-Ethyl-propyl)-2-thiophen-2-ylmethyl-1H-benzoimidazole-5-carbonyl]-amino}-5-methyl-hexanoic acid

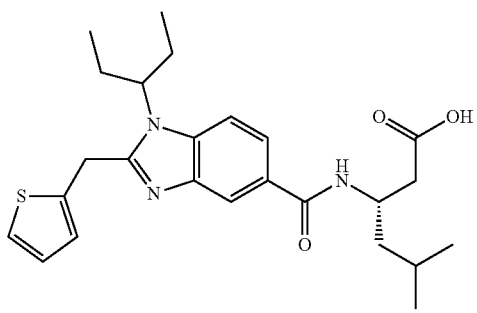 [SMILES: CCC(CC)n1c(Cc2cccs2)nc2cc(C(=O)N[C@H](CC(=O)O)CC(C)C)ccc21]

To 300 mg of Wang resin (NovaBioChem 70-90 mesh, loading capacity 1.3 mmol/g), 430 mg of (S)-3-(9H-Fluoren-9-ylmethoxycarbonylamino)-5-methyl-hexanoic acid, 173 mg of DIC, and 14 mg of DMAP were added in DMF in a 20 ml scintillation bottle. The reaction was kept at rt for 18 h. To deprotect the Fmoc-group 50% Piperidine in DMF was added and the reaction was kept for 30 min at rt. Afterwards the resin was washed thoroughly with DMF. For the amide formation the resin was reacted with 217 mg 4-Fluoro-3-nitrobenzoic acid, 185 mg HOBt, and 173 mg DIC in DMF for 18 h at rt. In the next step nucleophilic substitution was achieved by reacting the resin with 680 mg of 1-Ethyl-propylamine in DMF at it for 24 h. Subsequently, the reduction of the nitro group took place by reaction with 10 ml of 1M SnCl2 in DMF at rt for 23 h. Then, to the resin in dry DMF were added 139 mg 2-thienyl acetic acid, 371 mg of HATU and 250 mg of DIPEA and the reaction was left at it for 4 h to achieve amide formation. The cleavage from the resin took place by reaction with 3 ml of 95% aqueous TFA for 2 hrs. Then additional 2 ml of aqueous of 95% TFA, 3 ml of acetonitrile and 3 ml water were added and the cleavage solution was heated to 60° C. for 24 h. After filtration the solvents were removed and the resulting residue was purified by HPLC to afford 37 mg (8%) of (S)-3-{[1-(1-Ethyl-propyl)-2-thiophen-2-ylmethyl-1H-benzoimidazole-5-carbonyl]-amino}-5-methyl-hexanoic acid.

$C_{25}H_{33}N_3O_3S$ (455.62), LCMS (method 6_1_1): Rt=1.62 min, m/z=456.40 [M+H]+

The following examples were prepared in analogy to example 107:

| Exp. No. | Chemical Name | Structure | m/z [M + H]+ | LCMS method | R_t [min] |
|---|---|---|---|---|---|
| 108 | (S)-2-[(1-Cyclohexyl-2-thiophen-2-ylmethyl-1H-benzoimidazole-5-carbonyl)-amino]-4-methyl-pentanoic acid | 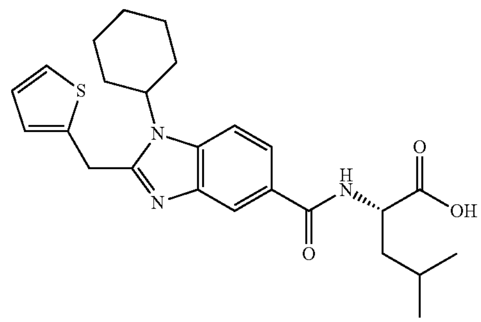 [SMILES: CC(C)C[C@H](NC(=O)c1ccc2c(c1)nc(Cc1cccs1)n2C1CCCCC1)C(=O)O] | 454.2 | 2_1_1 | 3.81 |
| 109 | (S)-2-{[2-Cyclopentylmethyl-1-(2-methyl-butyl)-1H-benzoimidazole-5-carbonyl]-amino}-4-methyl-pentanoic acid | 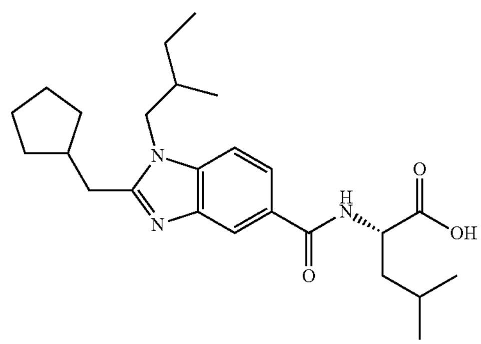 [SMILES: CCC(C)Cn1c(CC2CCCC2)nc2cc(C(=O)N[C@@H](CC(C)C)C(=O)O)ccc21] | 428.3 | 2_1_1 | 3.11 |
| 110 | (S)-2-[(1-Cyclopentyl-2-thiophen-2-ylmethyl-1H-benzoimidazole-5-carbonyl)-amino]-4-methyl-pentanoic acid | 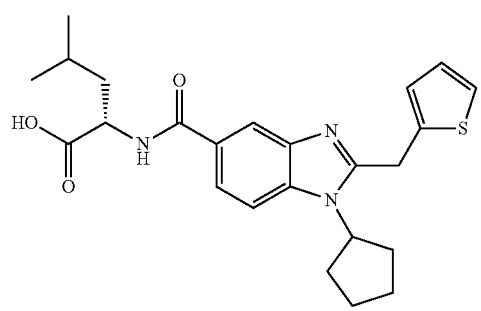 [SMILES: CC(C)C[C@H](NC(=O)c1ccc2c(c1)nc(Cc1cccs1)n2C1CCCC1)C(=O)O] | 440.3 | 2_1_1 | 2.78 |
| 111 | (S)-2-[(1-Cycloheptyl-2-thiophen-2-ylmethyl-1H-benzoimidazole-5-carbonyl)-amino]-4-methyl-pentanoic acid | 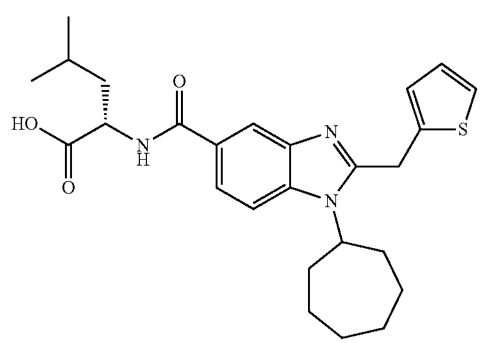 [SMILES: CC(C)C[C@H](NC(=O)c1ccc2c(c1)nc(Cc1cccs1)n2C1CCCCCC1)C(=O)O] | 468.3 | 2_1_1 | 3.08 |

-continued

| Exp. No. | Chemical Name | Structure | m/z [M + H]+ | LCMS method | R_t [min] |
|---|---|---|---|---|---|
| 112 | (S)-2-[(1-Cyclohexyl-2-cyclopentylmethyl-1H-benzoimidazole-5-carbonyl)-amino]-4-methyl-pentanoic acid | 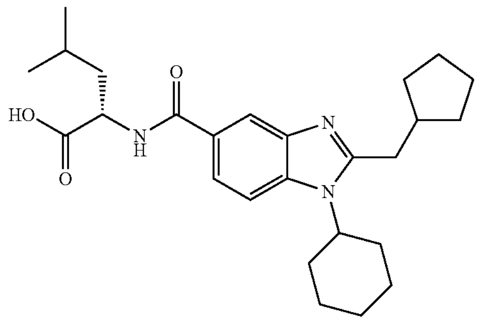 [SMILES: CC(C)C[C@H](NC(=O)c1ccc2c(c1)nc(CC1CCCC1)n2C1CCCCC1)C(=O)O] | 400.3 | 2_1_1 | 3.08 |
| 113 | (S)-4-Methyl-2-{[1-(2-methyl-butyl)-2-thiophen-2-ylmethyl-1H-benzoimidazole-5-carbonyl]-amino}-pentanoic acid | 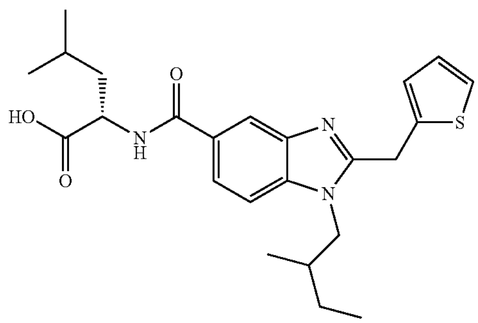 [SMILES: CCC(C)Cn1c(Cc2cccs2)nc2cc(C(=O)N[C@@H](CC(C)C)C(=O)O)ccc21] | 442.3 | 2_1_1 | 2.89 |
| 114 | (S)-2-{[1-(1-Ethyl-propyl)-2-thiophen-2-ylmethyl-1H-benzoimidazole-5-carbonyl]-amino}-4-methyl-pentanoic acid | 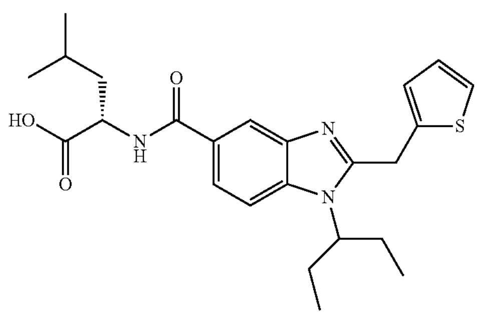 [SMILES: CCC(CC)n1c(Cc2cccs2)nc2cc(C(=O)N[C@@H](CC(C)C)C(=O)O)ccc21] | 442.3 | 2_1_1 | 2.79 |
| 115 | (S)-4-Methyl-2-[(2-thiophen-2-ylmethyl-1-p-tolyl-1H-benzoimidazole-5-carbonyl)-amino]-pentanoic acid | 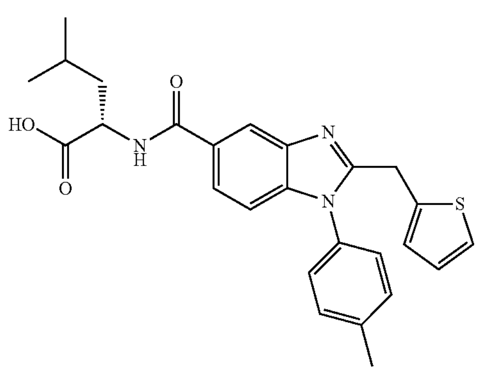 [SMILES: Cc1ccc(-n2c(Cc3cccs3)nc3cc(C(=O)N[C@@H](CC(C)C)C(=O)O)ccc32)cc1] | 462.3 | 2_1_1 | 3.02 |

-continued

| Exp. No. | Chemical Name | Structure | m/z [M + H]+ | LCMS method | R_t [min] |
|---|---|---|---|---|---|
| 116 | (S)-2-{[2-Benzyl-1-(1-ethyl-propyl)-1H-benzoimidazole-5-carbonyl]-amino}-4-methyl-pentanoic acid | 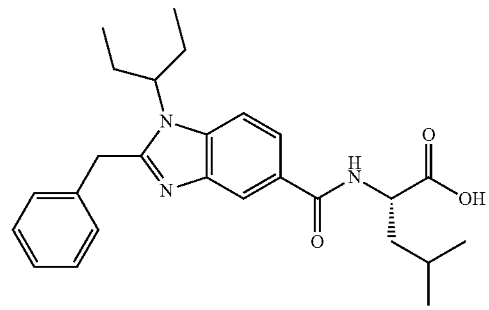 [SMILES: CCC(CC)n1c(Cc2ccccc2)nc2cc(C(=O)N[C@@H](CC(C)C)C(=O)O)ccc21] | 436.2 | 2_1_1 | 4.11 |
| 117 | (S)-2-{[1-(1-Ethyl-propyl)-2-thiophen-3-ylmethyl-1H-benzoimidazole-5-carbonyl]-amino}-4-methyl-pentanoic acid | 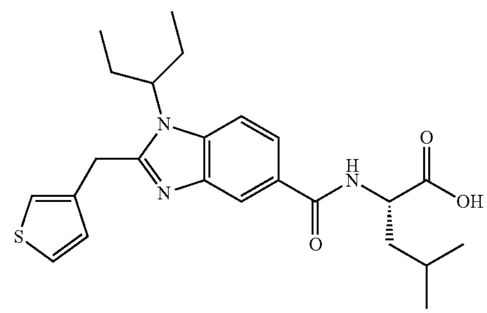 [SMILES: CCC(CC)n1c(Cc2ccsc2)nc2cc(C(=O)N[C@@H](CC(C)C)C(=O)O)ccc21] | 442.2 | 2_1_1 | 3.30 |
| 118 | (S)-2-{[1-(1-Ethyl-propyl)-2-furan-3-ylmethyl-1H-benzoimidazole-5-carbonyl]-amino}-4-methyl-pentanoic acid | 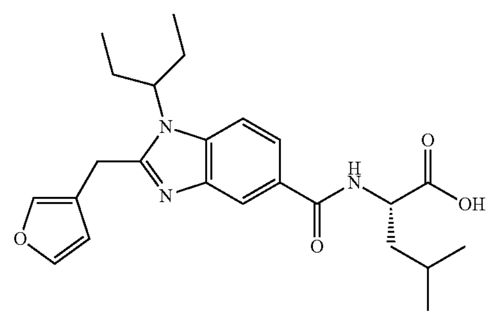 [SMILES: CCC(CC)n1c(Cc2ccoc2)nc2cc(C(=O)N[C@@H](CC(C)C)C(=O)O)ccc21] | 426.2 | 2_1_1 | 3.13 |
| 119 | (S)-2-{[1-(1-Ethyl-propyl)-2-(5-methyl-thiophen-2-ylmethyl)-1H-benzoimidazole-5-carbonyl]-amino}-4-methyl-pentanoic acid | 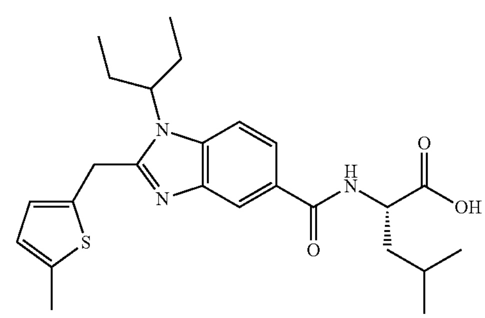 [SMILES: CCC(CC)n1c(Cc2ccc(C)s2)nc2cc(C(=O)N[C@@H](CC(C)C)C(=O)O)ccc21] | 456.2 | 2_1_1 | 4.27 |
| 120 | (S)-2-{[2-Cyclohexylmethyl-1-(1-ethyl-propyl)-1H-benzoimidazole-5-carbonyl]-amino}-4-methyl-pentanoic acid | 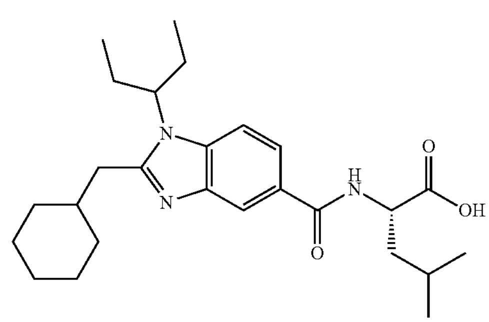 [SMILES: CCC(CC)n1c(CC2CCCCC2)nc2cc(C(=O)N[C@@H](CC(C)C)C(=O)O)ccc21] | 442.2 | 2_1_1 | 3.58 |

-continued

| Exp. No. | Chemical Name | Structure | m/z [M + H]+ | LCMS method | R_t [min] |
|---|---|---|---|---|---|
| 121 | (S)-2-{[1-(1-Ethyl-propyl)-2-thiophen-2-ylmethyl-1H-benzoimidazole-5-carbonyl]-amino}-3-methyl-pentanoic acid | 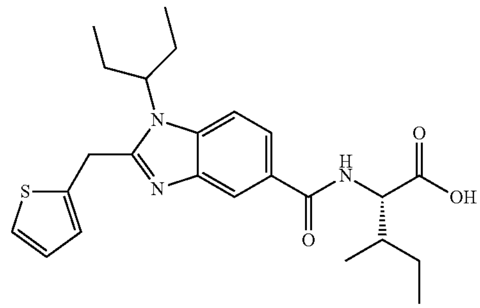 [SMILES: CCC(C)[C@H](NC(=O)c1ccc2c(c1)nc(Cc1cccs1)n2C(CC)CC)C(=O)O] | 442.2 | 2_1_1 | 3.23 |
| 122 | (S)-2-{[1-(1-Ethyl-propyl)-2-thiophen-2-ylmethyl-1H-benzoimidazole-5-carbonyl]-amino}-3-methyl-butyric acid | 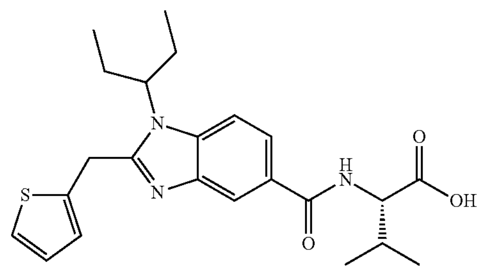 [SMILES: CCC(CC)n1c(Cc2cccs2)nc2cc(C(=O)N[C@H](C(=O)O)C(C)C)ccc21] | 428.2 | 2_1_1 | 3.02 |
| 123 | (S)-2-{[1-(1-Ethyl-propyl)-2-thiophen-2-ylmethyl-1H-benzoimidazole-5-carbonyl]-amino}-4-methylsulfanyl-butyric acid | 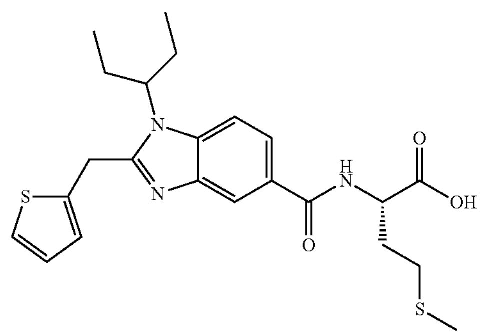 [SMILES: CCC(CC)n1c(Cc2cccs2)nc2cc(C(=O)N[C@@H](CCSC)C(=O)O)ccc21] | 460.2 | 2_1_1 | 3.08 |
| 124 | (S)-2-{[1-(1-Ethyl-propyl)-2-thiophen-2-ylmethyl-1H-benzoimidazole-5-carbonyl]-amino}-3-phenyl-propionic acid | 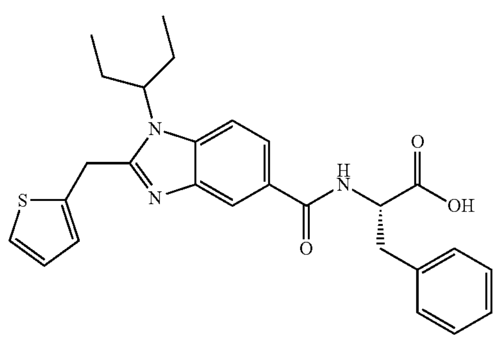 [SMILES: CCC(CC)n1c(Cc2cccs2)nc2cc(C(=O)N[C@@H](Cc3ccccc3)C(=O)O)ccc21] | 476.3 | 2_1_1 | 3.33 |
| 125 | (S)-3-Cyclohexyl-2-{[1-(1-ethyl-propyl)-2-thiophen-2-ylmethyl-1H-benzoimidazole-5-carbonyl]-amino}-propionic acid | 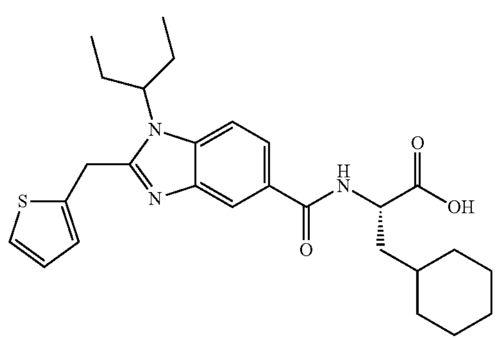 [SMILES: CCC(CC)n1c(Cc2cccs2)nc2cc(C(=O)N[C@@H](CC3CCCCC3)C(=O)O)ccc21] | 482.3 | 2_1_1 | 3.71 |

-continued

| Exp. No. | Chemical Name | Structure | m/z [M + H]+ | LCMS method | R_t [min] |
|---|---|---|---|---|---|
| 126 | 2-{[1-(1-Ethyl-propyl)-2-thiophen-2-ylmethyl-1H-benzoimidazole-5-carbonyl]-amino}-4,4-dimethyl-pentanoic acid | 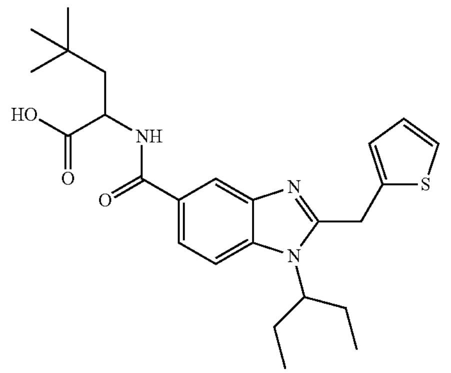 [SMILES: CCC(CC)n1c(Cc2cccs2)nc2cc(C(=O)NC(CC(C)(C)C)C(=O)O)ccc21] | 456.2 | 2_1_1 | 3.43 |
| 127 | (S)-2-[(1-Isobutyl-2-thiophen-2-ylmethyl-1H-benzoimidazole-5-carbonyl)-amino]-4-methyl-pentanoic acid | 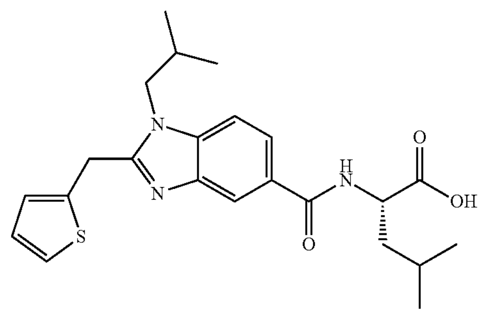 [SMILES: CC(C)C[C@H](NC(=O)c1ccc2c(c1)nc(Cc1cccs1)n2CC(C)C)C(=O)O] | 428.2 | 2_1_1 | 3.86 |
| 128 | (S)-2-[(2-Cyclopentylmethyl-1-isobutyl-1H-benzoimidazole-5-carbonyl)-amino]-4-methyl-pentanoic acid | 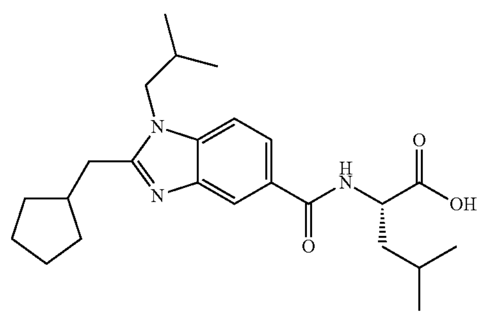 [SMILES: CC(C)C[C@H](NC(=O)c1ccc2c(c1)nc(CC1CCCC1)n2CC(C)C)C(=O)O] | 414.3 | 1_1_1 | 3.29 |
| 129 | (S)-2-{[2-Cyclopentylmethyl-1-(1-ethyl-propyl)-1H-benzoimidazole-5-carbonyl]-amino}-4-methyl-pentanoic acid | 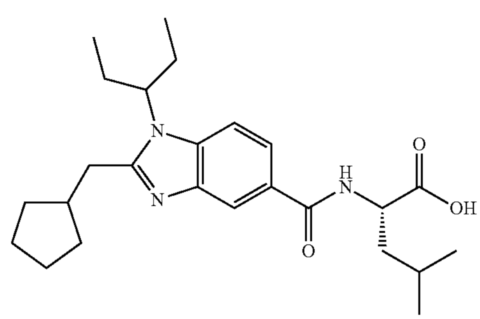 | 428.2 | 2_1_1 | 4.24 |

-continued

| Exp. No. | Chemical Name | Structure | m/z [M + H]+ | LCMS method | R_r [min] |
|---|---|---|---|---|---|
| 130 | (S)-2-{[1-(1-Ethyl-propyl)-2-thiophen-2-ylmethyl-1H-benzoimidazole-5-carbonyl]-amino}-5-methyl-hexanoic acid | 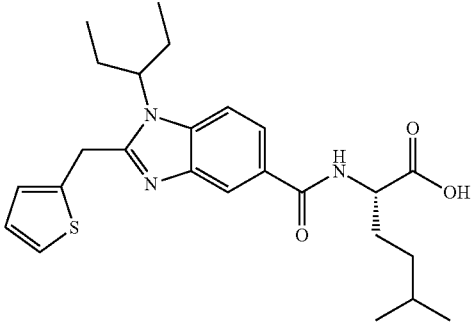 [SMILES: CCC(CC)n1c(Cc2cccs2)nc2cc(C(=O)N[C@@H](CCC(C)C)C(=O)O)ccc21] | 456.2 | 2_1_1 | 4.32 |
| 131 | (S)-2-{[2-Furan-3-ylmethyl-1-(2-methyl-cyclohexyl)-1H-benzoimidazole-5-carbonyl]-amino}-4-methyl-pentanoic acid | 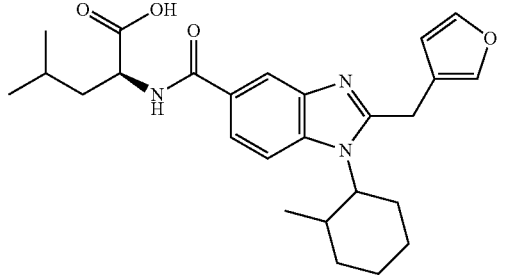 [SMILES: CC(C)C[C@H](NC(=O)c1ccc2c(c1)nc(Cc1ccoc1)n2C1CCCCC1C)C(=O)O] | 452.2 | 2_1_1 | 4.18 |
| 132 | (S)-4-Methyl-2-[(1-phenyl-2-thiophen-2-ylmethyl-1H-benzoimidazole-5-carbonyl)-amino]-pentanoic acid | 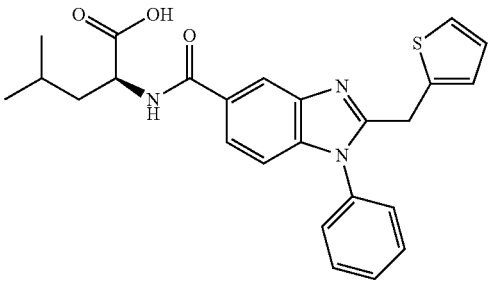 [SMILES: CC(C)C[C@H](NC(=O)c1ccc2c(c1)nc(Cc1cccs1)n2-c1ccccc1)C(=O)O] | 448.2 | 2_1_1 | 4.12 |
| 133 | (S)-3-Cyclohexyl-2-{[2-cyclohexylmethyl-1-(2-methyl-butyl)-1H-benzoimidazole-5-carbonyl]-amino}-propionic acid | 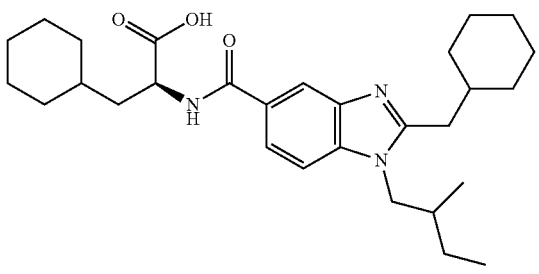 [SMILES: CCC(C)Cn1c(CC2CCCCC2)nc2cc(C(=O)N[C@@H](CC3CCCCC3)C(=O)O)ccc21] | 482.3 | 2_1_1 | 5.10 |
| 134 | (S)-3-Cyclohexyl-2-[(2-cyclohexylmethyl-1-isobutyl-1H-benzoimidazole-5-carbonyl)-amino]-propionic acid | 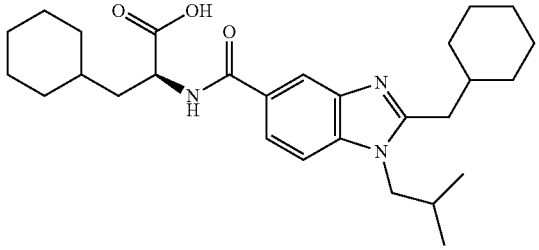 [SMILES: CC(C)Cn1c(CC2CCCCC2)nc2cc(C(=O)N[C@@H](CC3CCCCC3)C(=O)O)ccc21] | 468.3 | 2_1_1 | 4.87 |

-continued

| Exp. No. | Chemical Name | Structure | m/z [M + H]+ | LCMS method | R_t [min] |
|---|---|---|---|---|---|
| 135 | (S)-2-{[2-Cyclohexylmethyl-1-(2-methyl-butyl)-1H-benzoimidazole-5-carbonyl]-amino}-4-methyl-pentanoic acid | 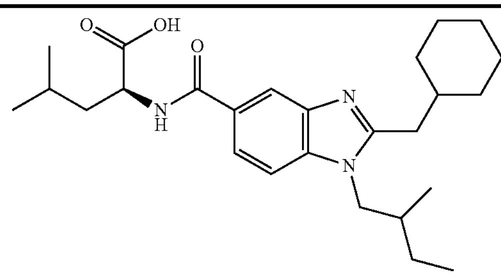 | 442.2 | 2_1_1 | 4.60 |
| 136 | (S)-4-Methyl-2-[(1-phenyl-2-thiophen-3-ylmethyl-1H-benzoimidazole-5-carbonyl)-amino]-pentanoic acid | 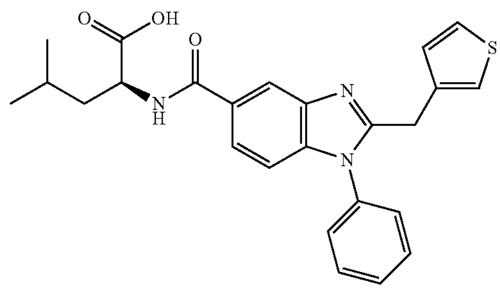 [SMILES: CC(C)C[C@H](NC(=O)c1ccc2c(c1)nc(Cc1ccsc1)n2-c1ccccc1)C(=O)O] | 448.2 | 2_1_1 | 4.04 |
| 137 | (S)-4-Methyl-2-{[1-(2-methyl-butyl)-2-thiophen-3-ylmethyl-1H-benzoimidazole-5-carbonyl]-amino}-pentanoic acid | 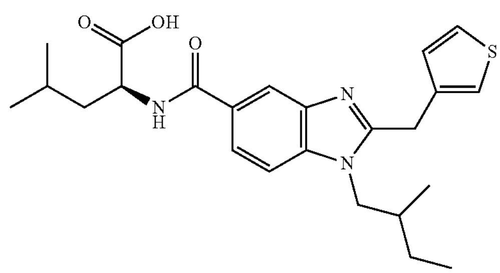 [SMILES: CCC(C)Cn1c(Cc2ccsc2)nc2cc(C(=O)N[C@@H](CC(C)C)C(=O)O)ccc21] | 442.2 | 2_1_1 | 4.14 |
| 138 | (S)-2-[(1-Cyclohexyl-2-furan-3-ylmethyl-1H-benzoimidazole-5-carbonyl)-amino]-4-methyl-pentanoic acid | 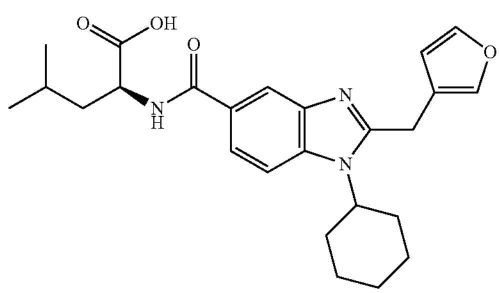 [SMILES: CC(C)C[C@H](NC(=O)c1ccc2c(c1)nc(Cc1ccoc1)n2C1CCCCC1)C(=O)O] | 438.3 | 6_6_1 | 2.84 |
| 139 | (S)-4-Methyl-2-{[1-(2-methyl-cyclohexyl)-2-thiophen-3-ylmethyl-1H-benzoimidazole-5-carbonyl]-amino}-pentanoic acid | 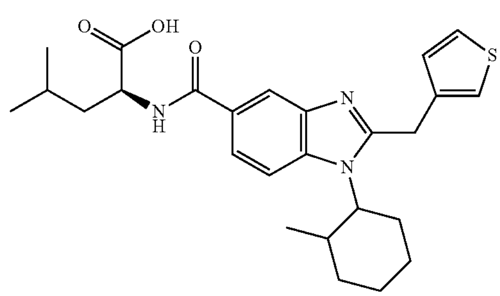 [SMILES: CC(C)C[C@H](NC(=O)c1ccc2c(c1)nc(Cc1ccsc1)n2C1CCCCC1C)C(=O)O] | 468.2 | 2_1_1 | 4.40 |

-continued

| Exp. No. | Chemical Name | Structure | m/z [M + H]⁺ | LCMS method | R$_t$ [min] |
|---|---|---|---|---|---|
| 140 | (S)-2-[(1-sec-Butyl-2-thiophen-2-ylmethyl-1H-benzoimidazole-5-carbonyl)-amino]-3-cyclohexyl-propionic acid | 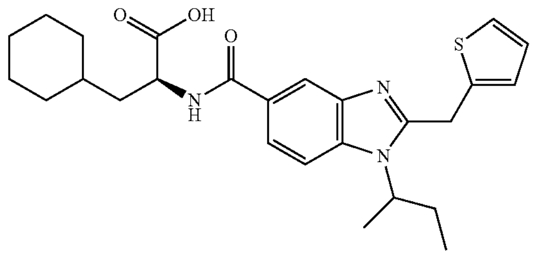 [SMILES: CCC(C)n1c(Cc2cccs2)nc2cc(C(=O)N[C@@H](CC3CCCCC3)C(=O)O)ccc21] | 468.2 | 2_1_1 | 4.41 |
| 141 | (S)-3-Cyclohexyl-2-{[2-cyclohexylmethyl-1-(1-ethyl-propyl)-1H-benzoimidazole-5-carbonyl]-amino}-propionic acid | 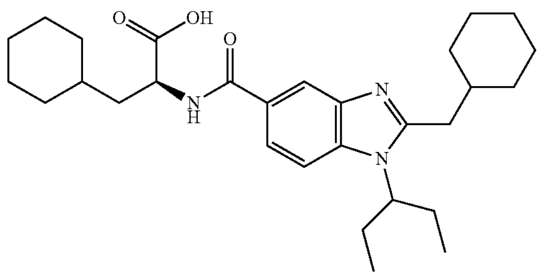 [SMILES: CCC(CC)n1c(CC2CCCCC2)nc2cc(C(=O)N[C@@H](CC3CCCCC3)C(=O)O)ccc21] | 482.3 | 2_1_1 | 5.00 |
| 142 | (S)-2-[(1-sec-Butyl-2-thiophen-3-ylmethyl-1H-benzoimidazole-5-carbonyl)-amino]-4-methyl-pentanoic acid | 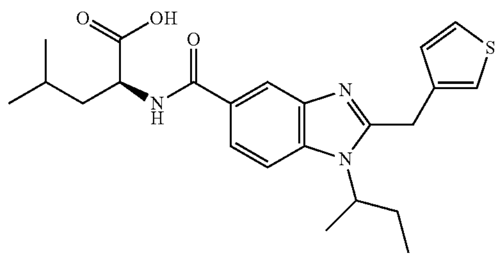 [SMILES: CCC(C)n1c(Cc2ccsc2)nc2cc(C(=O)N[C@@H](CC(C)C)C(=O)O)ccc21] | 428.2 | 2_1_1 | 3.82 |
| 143 | (S)-2-{[2-Benzyl-1-(2-methyl-cyclohexyl)-1H-benzoimidazole-5-carbonyl]-amino}-4-methyl-pentanoic acid | 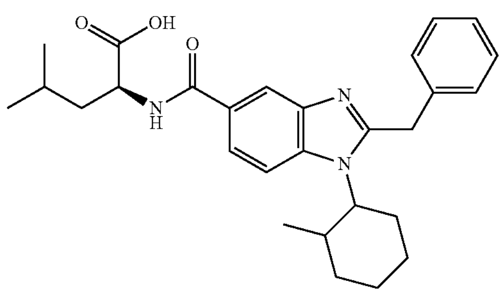 [SMILES: CC(C)C[C@H](NC(=O)c1ccc2c(c1)nc(Cc1ccccc1)n2C1CCCCC1C)C(=O)O] | 462.2 | 2_1_1 | 4.47 |
| 144 | (S)-4-Methyl-2-{[1-(2-methyl-cyclohexyl)-2-(5-methyl-thiophen-2-ylmethyl)-1H-benzoimidazole-5-carbonyl]-amino}-pentanoic acid | 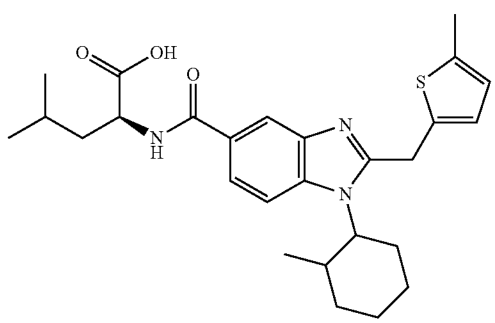 [SMILES: Cc1ccc(Cc2nc3cc(C(=O)N[C@@H](CC(C)C)C(=O)O)ccc3n2C2CCCCC2C)s1] | 482.2 | 2_1_1 | 4.65 |

-continued

| Exp. No. | Chemical Name | Structure | m/z [M + H]+ | LCMS method | R_t [min] |
|---|---|---|---|---|---|
| 145 | (S)-3-Cyclohexyl-2-{[1-(2-methyl-butyl)-2-thiophen-2-ylmethyl-1H-benzoimidazole-5-carbonyl]-amino}-propionic acid | 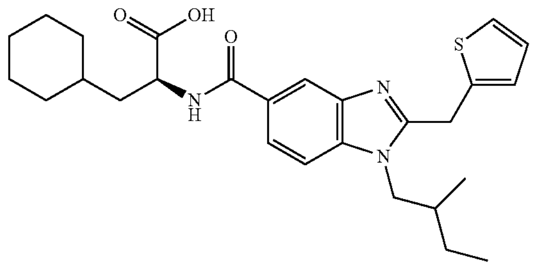 [SMILES: CCC(C)Cn1c(Cc2cccs2)nc2cc(C(=O)N[C@@H](CC3CCCCC3)C(=O)O)ccc21] | 482.2 | 2_1_1 | 4.71 |
| 146 | (S)-4-Methyl-2-{[1-(2-methyl-cyclohexyl)-2-thiophen-2-ylmethyl-1H-benzoimidazole-5-carbonyl]-amino}-pentanoic acid | 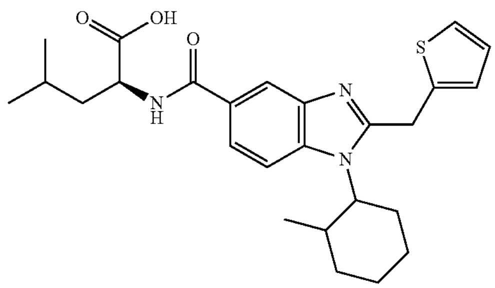 [SMILES: CC(C)C[C@H](NC(=O)c1ccc2c(c1)nc(Cc1cccs1)n2C1CCCCC1C)C(=O)O] | 468.2 | 6_3_1 | 1.50 |
| 147 | (S)-2-[(1-sec-Butyl-2-thiophen-2-ylmethyl-1H-benzoimidazole-5-carbonyl)-amino]-4-methyl-pentanoic acid | 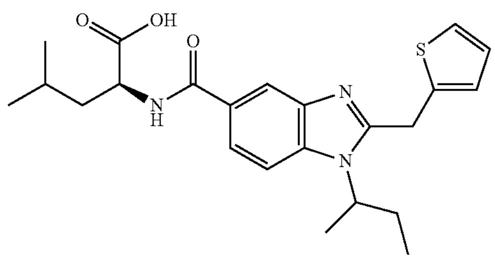 [SMILES: CCC(C)n1c(Cc2cccs2)nc2cc(C(=O)N[C@@H](CC(C)C)C(=O)O)ccc21] | 428.2 | 2_1_1 | 3.81 |
| 148 | (S)-2-[(2-Benzyl-1-cyclohexyl-1H-benzoimidazole-5-carbonyl)-amino]-4-methyl-pentanoic acid | 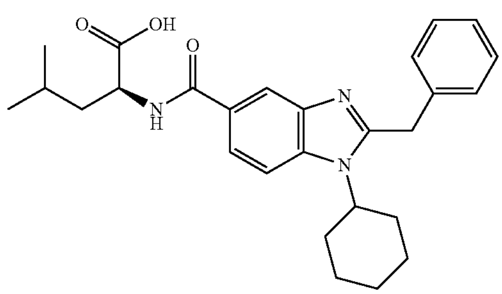 [SMILES: CC(C)C[C@H](NC(=O)c1ccc2c(c1)nc(Cc1ccccc1)n2C1CCCCC1)C(=O)O] | 448.2 | 2_1_1 | 4.31 |
| 149 | (S)-2-[(1-sec-Butyl-2-cyclopentylmethyl-1H-benzoimidazole-5-carbonyl)-amino]-4-methyl-pentanoic acid | 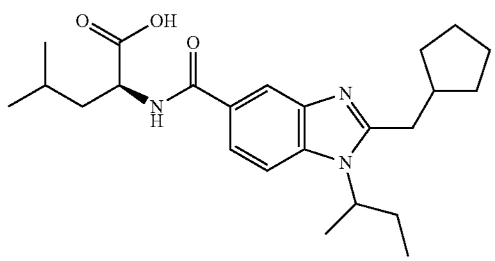 [SMILES: CCC(C)n1c(CC2CCCC2)nc2cc(C(=O)N[C@@H](CC(C)C)C(=O)O)ccc21] | 414.2 | 2_1_1 | 4.03 |

-continued

| Exp. No. | Chemical Name | Structure | m/z [M + H]+ | LCMS method | R$_t$ [min] |
|---|---|---|---|---|---|
| 150 | (S)-2-{[2-Cyclopentylmethyl-1-(2-methyl-cyclohexyl)-1H-benzoimidazole-5-carbonyl]-amino}-4-methyl-pentanoic acid | 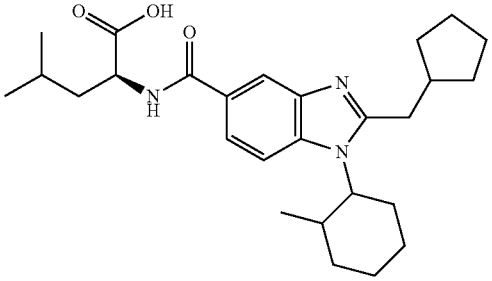 [SMILES: CC(C)C[C@H](NC(=O)c1ccc2c(c1)nc(CC1CCCC1)n2C1CCCCC1C)C(=O)O] | 454.3 | 2_1_1 | 4.61 |
| 151 | (S)-3-Cyclohexyl-2-{[1-(1-ethyl-propyl)-2-(tetrahydro-furan-2-ylmethyl)-1H-benzoimidazole-5-carbonyl]-amino}-propionic acid | 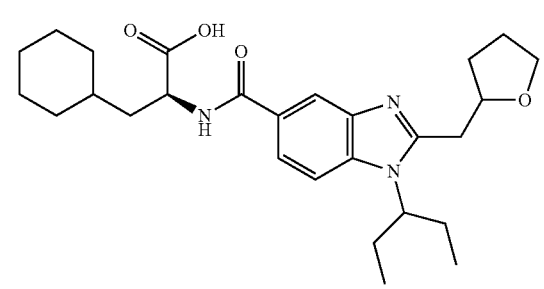 [SMILES: CCC(CC)n1c(CC2CCCO2)nc2cc(C(=O)N[C@@H](CC3CCCCC3)C(=O)O)ccc21] | 470.2 | 2_1_1 | 2.90 |
| 152 | (S)-2-[(1-Cyclohexyl-2-thiophen-3-ylmethyl-1H-benzoimidazole-5-carbonyl)-amino]-4-methyl-pentanoic acid | 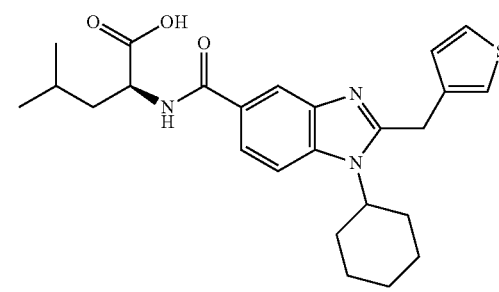 | 454.2 | 2_1_1 | 4.23 |
| 153 | (2S,3R)-2-{[1-(1-Ethyl-propyl)-2-thiophen-2-ylmethyl-1H-benzoimidazole-5-carbonyl]-amino}-3-methyl-pentanoic acid | 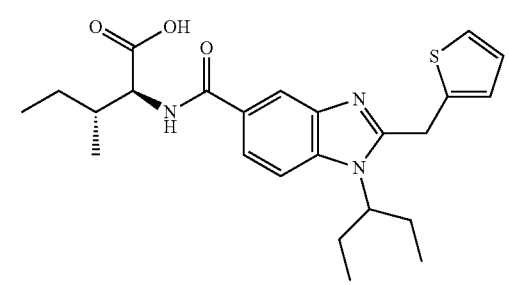 [SMILES: CCC(CC)n1c(Cc2cccs2)nc2cc(C(=O)N[C@H](C(=O)O)[C@H](C)CC)ccc21] | 442.2 | 2_1_1 | 3.95 |
| 154 | (S)-3-{[1-(1-Ethyl-propyl)-2-furan-3-ylmethyl-1H-benzoimidazole-5-carbonyl]-amino}-5-methyl-hexanoic acid | 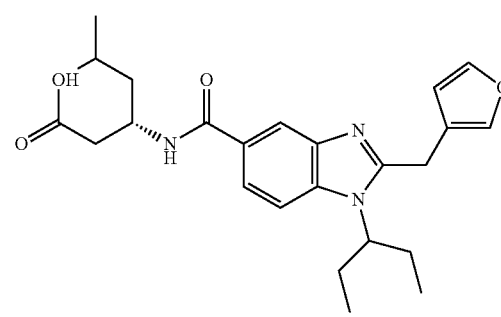 | 440.3 | 6_6_1 | 2.75 |

-continued

| Exp. No. | Chemical Name | Structure | m/z [M + H]+ | LCMS method | R_f [min] |
|---|---|---|---|---|---|
| 155 | 3-{[1-(1-Ethyl-propyl)-2-thiophen-2-ylmethyl-1H-benzoimidazole-5-carbonyl]-amino}-hexanoic acid | 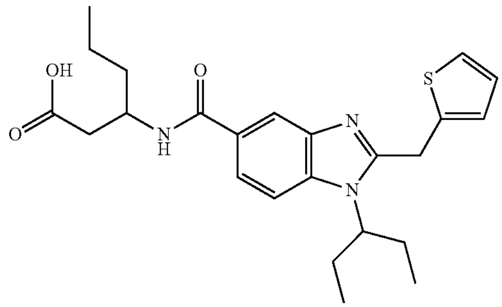 [SMILES: CCCC(CC(=O)O)NC(=O)c1ccc2c(c1)nc(Cc1cccs1)n2C(CC)CC] | 442.2 | 2_1_1 | 3.75 |
| 156 | (S)-3-{[1-(1-Ethyl-propyl)-2-thiophen-3-ylmethyl-1H-benzoimidazole-5-carbonyl]-amino}-5-methyl-hexanoic acid | 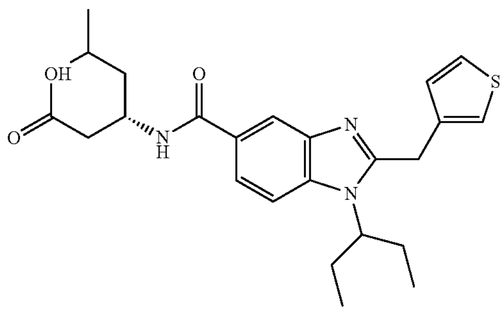 [SMILES: CCC(CC)n1c(Cc2ccsc2)nc2cc(C(=O)N[C@@H]3CC(=O)OC(C)C3)ccc21] | 456.2 | 2_1_1 | 4.02 |
| 157 | (S)-3-{[2-Benzyl-1-(1-ethyl-propyl)-1H-benzoimidazole-5-carbonyl]-amino}-5-methyl-hexanoic acid | 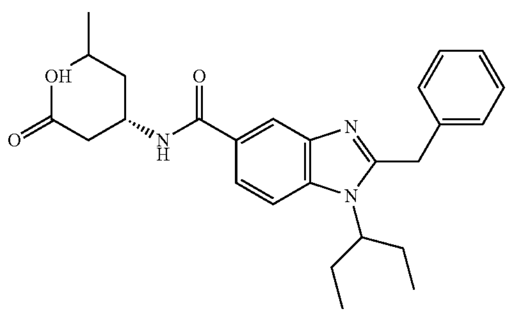 [SMILES: CCC(CC)n1c(Cc2ccccc2)nc2cc(C(=O)N[C@@H]3CC(=O)OC(C)C3)ccc21] | 450.4 | 6_6_1 | 2.89 |
| 158 | (S)-3-{[2-Cyclopentylmethyl-1-(1-ethyl-propyl)-1H-benzoimidazole-5-carbonyl]-amino}-5-methyl-hexanoic acid | 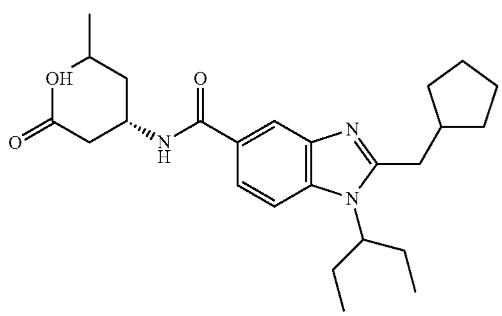 | 442.2 | 2_1_1 | 4.23 |
| 159 | (S)-3-{[2-Cyclopentylmethyl-1-(2-methyl-butyl)-1H-benzoimidazole-5-carbonyl]-amino}-5-methyl-hexanoic acid | 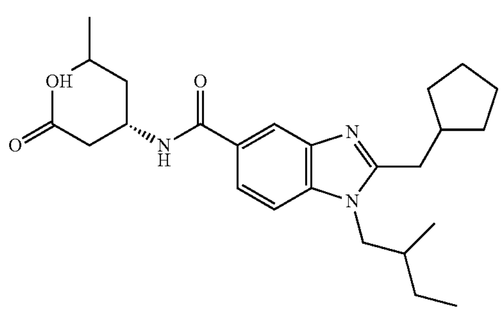 [SMILES: CCC(C)Cn1c(CC2CCCC2)nc2cc(C(=O)N[C@@H]3CC(=O)OC(C)C3)ccc21] | 442.3 | 2_1_1 | 4.37 |

| Exp. No. | Chemical Name | Structure | m/z [M + H]+ | LCMS method | R_t [min] |
|---|---|---|---|---|---|
| 160 | (S)-3-{[1-(1-Ethyl-propyl)-2-(tetrahydro-furan-2-ylmethyl)-1H-benzoimidazole-5-carbonyl]-amino}-5-methyl-hexanoic acid | 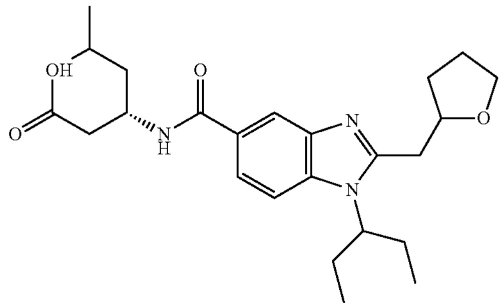 [SMILES: CCC(CC)n1c(CC2CCCO2)nc2cc(C(=O)N[C@@H]3CC(=O)OC(C)C3)ccc21] | 444.2 | 2_1_1 | 3.66 |
| 161 | (R)-3-{[1-(1-Ethyl-propyl)-2-thiophen-2-ylmethyl-1H-benzoimidazole-5-carbonyl]-amino}-4-methyl-pentanoic acid | 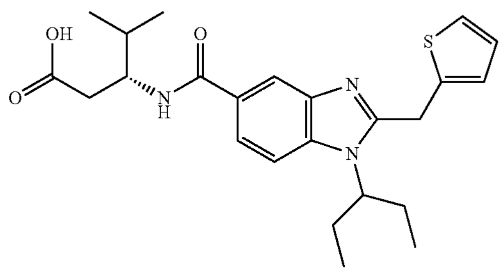 [SMILES: CCC(CC)n1c(Cc2cccs2)nc2cc(C(=O)N[C@H](CC(=O)O)C(C)C)ccc21] | 442.2 | 2_1_1 | 2.53 |
| 162 | (R)-4-{[1-(1-Ethyl-propyl)-2-thiophen-2-ylmethyl-1H-benzoimidazole-5-carbonyl]-amino}-5-methyl-hexanoic acid | 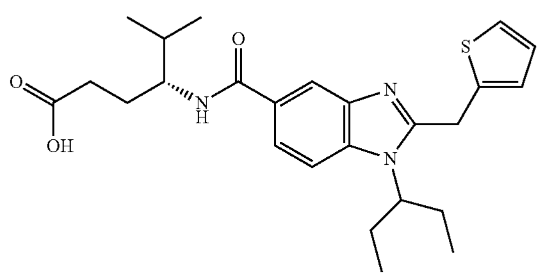 [SMILES: CCC(CC)n1c(Cc2cccs2)nc2cc(C(=O)N[C@H](CCC(=O)O)C(C)C)ccc21] | 456.2 | 2_1_1 | 3.79 |
| 163 | (R)-4-{[1-(1-Ethyl-propyl)-2-thiophen-2-ylmethyl-1H-benzoimidazole-5-carbonyl]-amino}-6-methyl-heptanoic acid | 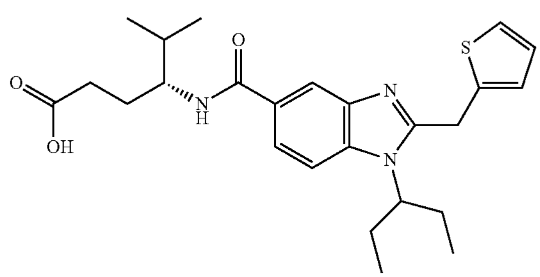 [SMILES: CCC(CC)n1c(Cc2cccs2)nc2cc(C(=O)N[C@H](CCC(=O)O)C(C)C)ccc21] | 470.3 | 6_4_1 | 1.43 |

EXAMPLE 164

(S)-2-{[1-(1-Isopropyl-2-methyl-propyl)-2-thiophen-2-ylmethyl-1H-benzoimidazole-5-carbonyl]-amino}-4-methyl-pentanoic acid

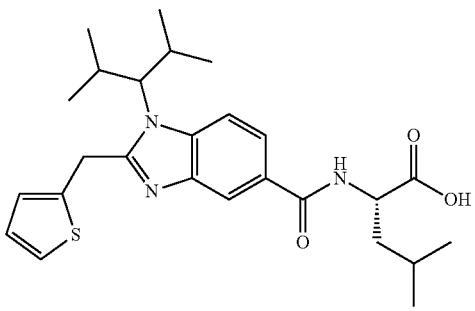 [SMILES: CC(C)C[C@H](NC(=O)c1ccc2c(c1)nc(Cc1cccs1)n2C(C(C)C)C(C)C)C(=O)O]

a) (S)-2-[4-(1-Isopropyl-2-methyl-propylamino)-3-(2-thiophen-2-yl-acetylamino)-benzoylamino]-4-methyl-pentanoic acid tert-butyl ester

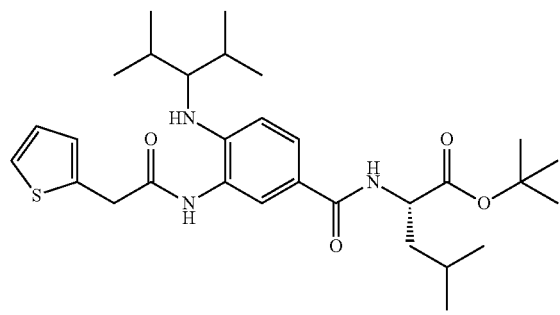 [SMILES: CC(C)C[C@H](NC(=O)c1ccc(NC(C(C)C)C(C)C)c(NC(=O)Cc2cccs2)c1)C(=O)OC(C)(C)C]

To a solution of 469 mg of thiophen-2-yl-acetic acid in 7.5 ml of dry DMF 449 mg of HOAT, 633 mg of EDC and 0.75 ml of DIPEA were added at 0° C. After 30 min 1259 mg of (S)-2-[3-Amino-4-(1-isopropyl-2-methyl-propylamino)-benzoylamino]-4-methyl-pentanoic acid tert-butyl ester and 0.75 ml of DIPEA were added and the reaction was stirred at it for 16 h. The reaction was then poured into water and extracted with ethyl acetate three times. The combined organic phases were washed with saturated aqueous sodium bicarbonate solution and brine, dried over magnesium sulphate and concentrated. The crude product was purified by HPLC to yield 250 mg (15%)) (S)-2-[4-(1-Isopropyl-2-methyl-propylamino)-3-(2-thiophen-2-yl-acetylamino)-benzoylamino]-4-methyl-pentanoic acid tert-butyl ester
$C_{30}H_{45}N_3O_4S$ (543.77), LCMS (method 6_3_1): Rt=2.35 min, m/z=544.27 [M+H]$^+$ b) (S)-2-{[1-(1-Isopropyl-2-methyl-propyl)-2-thiophen-2-ylmethyl-1H-benzoimidazole-5-carbonyl]-amino}-4-methyl-pentanoic acid

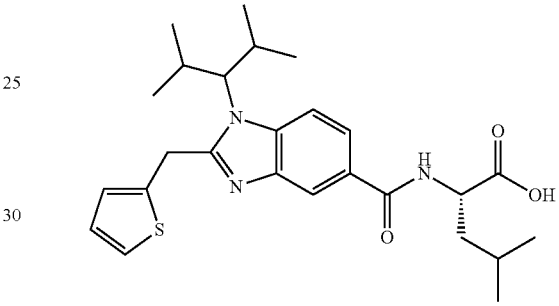

80 mg of (S)-2-[4-(1-Isopropyl-2-methyl-propylamino)-3-(2-thiophen-2-yl-acetyl-amino)-benzoylamino]-4-methyl-pentanoic acid tert-butyl ester and 2 ml of hydrochloric acid (4M in dioxin) were heated in a microwave reactor for 2 min to 100° C. and for 15 min to 130° C. The reaction was then concentrated in vacuo and the resulting residue purified by HPLC to obtain 3 mg (4%) of (S)-2-{[1-(1-Isopropyl-2-methyl-propyl)-2-thiophen-2-ylmethyl-1H-benzoimidazole-5-carbonyl]-amino}-4-methyl-pentanoic acid.
$C_{26}H_{35}N_3O_3S$ (469.65), LCMS (method 6_3_1): Rt=1.50 min, m/z=470.23 [M+H]$^+$ The following examples were prepared in analogy to example 164:

| Exp. No. | Chemical Name | Structure | m/z [M + H]$^+$ | LCMS method | R$_t$ [min] |
|---|---|---|---|---|---|
| 165 | (S)-2-{[1-(2-Chloro-phenyl)-2-thiophen-2-ylmethyl-1H-benzoimidazole-5-carbonyl]-amino}-4-methyl-pentanoic acid | 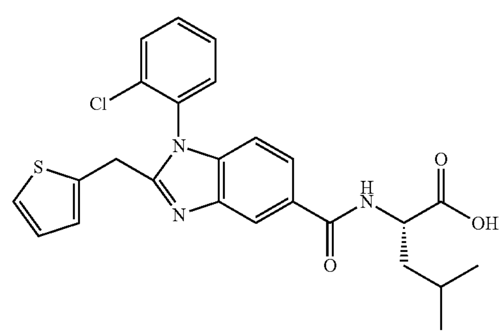 [SMILES: CC(C)C[C@H](NC(=O)c1ccc2c(c1)nc(Cc1cccs1)n2-c1ccccc1Cl)C(=O)O] | 482.1 | 6_3_1 | 1.66 |

-continued

| Exp. No. | Chemical Name | Structure | m/z [M + H]⁺ | LCMS method | R_t [min] |
|---|---|---|---|---|---|
| 166 | (S)-2-{[1-(1,3-Dimethyl-butyl)-2-thiophen-2-ylmethyl-1H-benzoimidazole-5-carbonyl]-amino}-4-methyl-pentanoic acid | 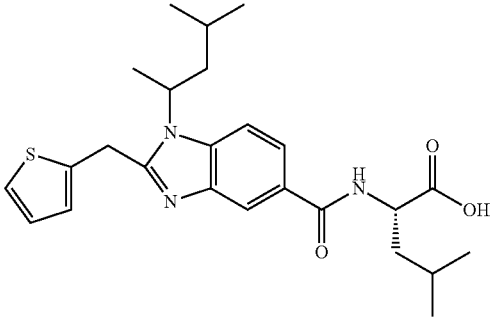 [SMILES: CC(C)CC(C)n1c(Cc2cccs2)nc2cc(C(=O)N[C@@H](CC(C)C)C(=O)O)ccc21] | 456.2 | 6_3_1 | 1.48 |

EXAMPLE 167

2-Cyclopentylmethyl-1-(1-ethyl-propyl)-1H-benzoimidazole-5-carboxylic acid ((S)-1-cyclohexylmethyl-2-hydroxy-ethyl)-amide

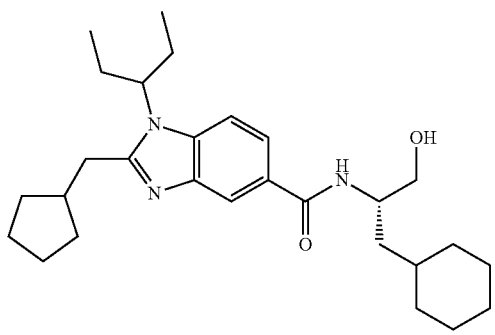 [SMILES: CCC(CC)n1c(CC2CCCC2)nc2cc(C(=O)N[C@H](CO)CC3CCCCC3)ccc21]

47 mg of (S)-2-amino-3-cyclohexyl-propan-1-ol and 0.14 ml DIPEA were dissolved in 2 ml dry THF. The mixture was cooled to −10° C. and 67 mg of 2-cyclopentylmethyl-1-(1-ethyl-propyl)-1H-benzoimidazole-5-carbonyl chloride in 1 ml of dry THF were added. The mixture was stirred under exclusion of moisture for 15 min at −10° C. and then at RT over night. It was then filtered, the filter was washed with 10 ml ethyl acetate. The filtrate was evaporated, the residue was taken up in 20 ml ethyl acetate and extracted with 20 ml 5% NaHCO3. The organic phase was dried and evaporated and the residue was purified by HPLC to yield 24 mg (27%) of 2-cyclopentylmethyl-1-(1-ethyl-propyl)-1H-benzoimidazole-5-carboxylic acid ((S)-1-cyclohexylmethyl-2-hydroxy-ethyl)-amide.

$C_{28}H_{43}N_3O_2$ (453.67), LCMS (method 6_3_1): Rt=1.57 min, m/z=454.31 [M+H]⁺

The following examples were prepared in analogy to example 167:

| Exp. No. | Chemical Name | Structure | m/z [M + H]⁺ | LCMS method | R_t [min] |
|---|---|---|---|---|---|
| 168 | 1-Cyclohexyl-2-thiophen-2-ylmethyl-1H-benzoimidazole-5-carboxylic acid ((S)-1-carbamoyl-3-methyl-butyl)-amide | 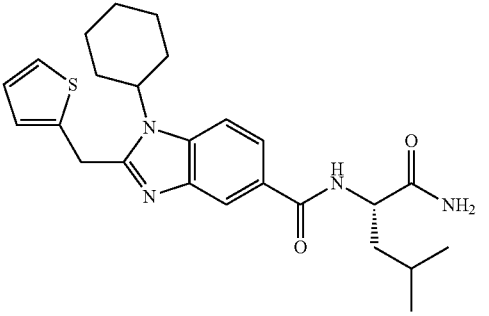 [SMILES: CC(C)C[C@H](NC(=O)c1ccc2c(c1)nc(Cc1cccs1)n2C1CCCCC1)C(N)=O] | 453.2 | 2_1_1 | 2.84 |

-continued

| Exp. No. | Chemical Name | Structure | m/z [M + H]+ | LCMS method | R_t [min] |
|---|---|---|---|---|---|
| 169 | 2-Cyclopentylmethyl-1-(1-ethyl-propyl)-1H-benzoimidazole-5-carboxylic acid (1-carbamoyl-3-methyl-butyl)-amide | 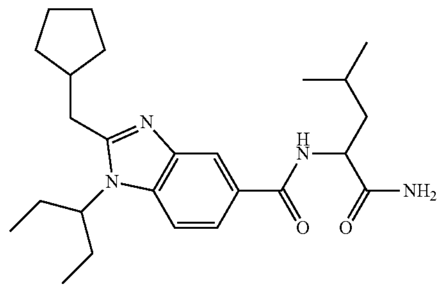 [SMILES: CCC(CC)n1c(CC2CCCC2)nc2cc(C(=O)NC(CC(C)C)C(N)=O)ccc21] | 427.3 | 6_3_1 | 1.35 |
| 170 | 1-(1-Ethyl-propyl)-2-thiophen-2-ylmethyl-1H-benzoimidazole-5-carboxylic acid (carbamoyl-phenyl-methyl)-amide | 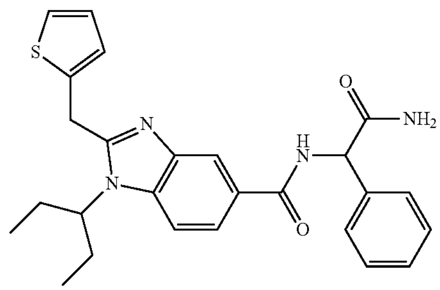 [SMILES: CCC(CC)n1c(Cc2cccs2)nc2cc(C(=O)NC(C(N)=O)c3ccccc3)ccc21] | 461.2 | 6_3_1 | 1.33 |
| 171 | 1-(1-Ethyl-propyl)-2-thiophen-2-ylmethyl-1H-benzoimidazole-5-carboxylic acid (1-carbamoyl-3-methyl-butyl)-amide | 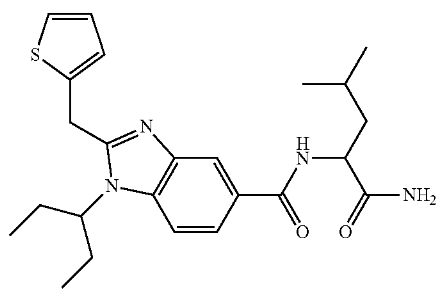 [SMILES: CCC(CC)n1c(Cc2cccs2)nc2cc(C(=O)NC(CC(C)C)C(N)=O)ccc21] | 441.3 | 6_1_1 | 1.56 |
| 172 | 1-(1-Ethyl-propyl)-2-thiazol-4-ylmethyl-1H-benzoimidazole-5-carboxylic acid ((S)-1-carbamoyl-3-methyl-butyl)-amide | 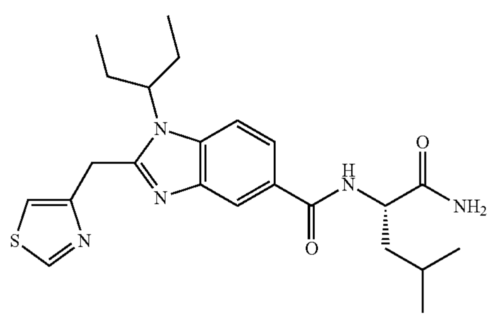 [SMILES: CCC(CC)n1c(Cc2cscn2)nc2cc(C(=O)N[C@@H](CC(C)C)C(N)=O)ccc21] | 442.4 | 6_1_1 | 1.24 |
| 173 | 1-(1-Ethyl-propyl)-2-thiophen-2-ylmethyl-1H-benzoimidazole-5-carboxylic acid ((S)-1-carbamoyl-2-cyclohexyl-ethyl)-amide | 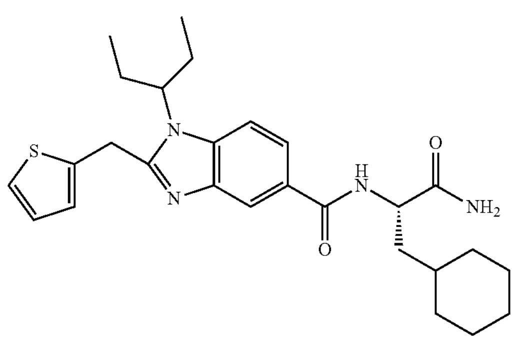 [SMILES: CCC(CC)n1c(Cc2cccs2)nc2cc(C(=O)N[C@@H](CC3CCCCC3)C(N)=O)ccc21] | 481.5 | 6_2_1 | 1.98 |

-continued

| Exp. No. | Chemical Name | Structure | m/z [M + H]+ | LCMS method | R_t [min] |
|---|---|---|---|---|---|
| 174 | 1-(1-Ethyl-propyl)-2-thiophen-2-ylmethyl-1H-benzoimidazole-5-carboxylic acid (1-carbamoylmethyl-3-methyl-butyl)-amide | 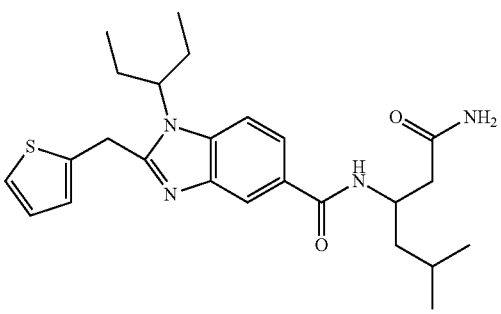 [SMILES: CCC(CC)n1c(Cc2cccs2)nc2cc(C(=O)NC(CC(N)=O)CC(C)C)ccc21] | 455.2 | 6_3_1 | 1.34 |
| 175 | 2-Cyclopentylmethyl-1-(1-ethyl-propyl)-1H-benzoimidazole-5-carboxylic acid ((S)-1-hydroxymethyl-3-methyl-butyl)-amide | 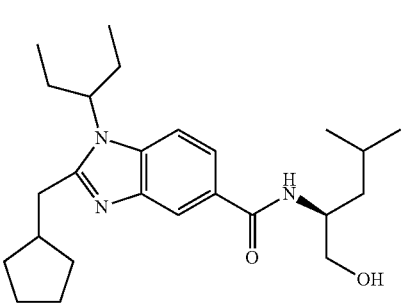 [SMILES: CCC(CC)n1c(CC2CCCC2)nc2cc(C(=O)N[C@H](CO)CC(C)C)ccc21] | 414.2 | 6_3_1 | 1.42 |
| 176 | 2-Cyclopentylmethyl-1-(1-ethyl-propyl)-1H-benzoimidazole-5-carboxylic acid ((R)-1-hydroxymethyl-3-methyl-butyl)-amide | 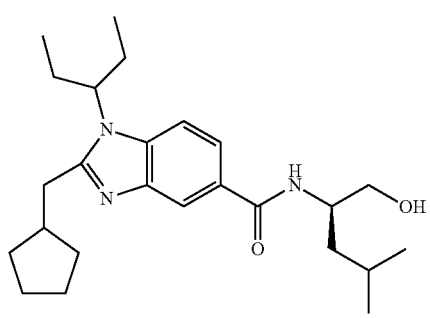 [SMILES: CCC(CC)n1c(CC2CCCC2)nc2cc(C(=O)N[C@@H](CO)CC(C)C)ccc21] | 414.3 | 6_3_1 | 1.42 |
| 177 | 1-(1-Ethyl-propyl)-2-thiophen-2-ylmethyl-1H-benzoimidazole-5-carboxylic acid ((S)-1-cyclohexylmethyl-2-hydroxy-ethyl)-amide | 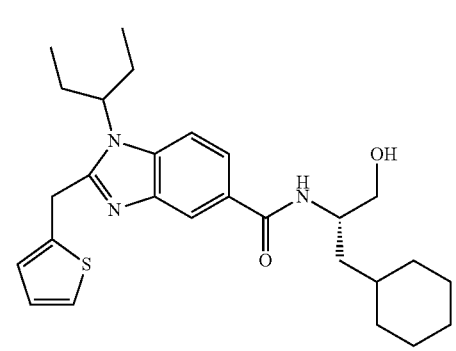 [SMILES: CCC(CC)n1c(Cc2cccs2)nc2cc(C(=O)N[C@H](CO)CC3CCCCC3)ccc21] | 468.2 | 6_4_1 | 1.58 |
| 178 | 2-Cyclopentylmethyl-1-(1-ethyl-propyl)-1H-benzoimidazole-5-carboxylic acid ((S)-1-hydroxymethyl-3-methylsulfanyl-propyl)-amide | 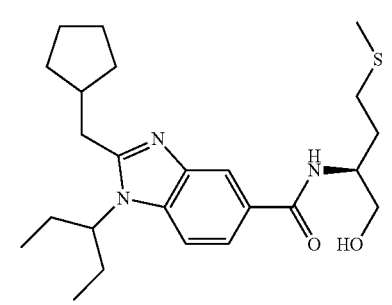 [SMILES: CCC(CC)n1c(CC2CCCC2)nc2cc(C(=O)N[C@H](CO)CCSC)ccc21] | 432.2 | 6_3_1 | 1.30 |

| Exp. No. | Chemical Name | Structure | m/z [M + H]⁺ | LCMS method | R_t [min] |
|---|---|---|---|---|---|
| 179 | 2-Cyclopentylmethyl-1-(1-ethyl-propyl)-1H-benzoimidazole-5-carboxylic acid (1-hydroxymethyl-cyclopentyl)-amide | 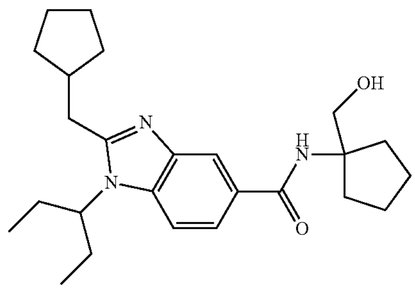 [SMILES: CCC(CC)n1c(CC2CCCC2)nc2cc(C(=O)NC3(CO)CCCC3)ccc21] | 412.2 | 6_3_1 | 1.37 |
| 180 | 2-Cyclopentylmethyl-1-(1-ethyl-propyl)-1H-benzoimidazole-5-carboxylic acid ((1S,2S)-1-hydroxymethyl-2-methyl-butyl)-amide | 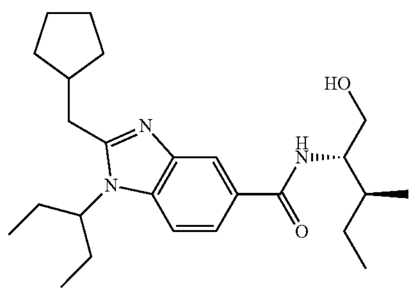 [SMILES: CCC(CC)n1c(CC2CCCC2)nc2cc(C(=O)N[C@H](CO)[C@@H](C)CC)ccc21] | 414.3 | 6_3_1 | 1.41 |
| 181 | 2-Cyclopentylmethyl-1-(1-ethyl-propyl)-1H-benzoimidazole-5-carboxylic acid (1-hydroxymethyl-butyl)-amide | 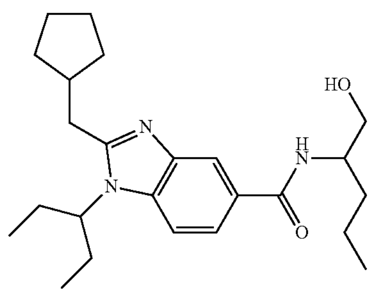 [SMILES: CCCC(CO)NC(=O)c1ccc2c(c1)nc(CC1CCCC1)n2C(CC)CC] | 400.3 | 6_3_1 | 1.32 |
| 182 | 2-Cyclopentylmethyl-1-(1-ethyl-propyl)-1H-benzoimidazole-5-carboxylic acid (1-hydroxymethyl-pentyl)-amide | 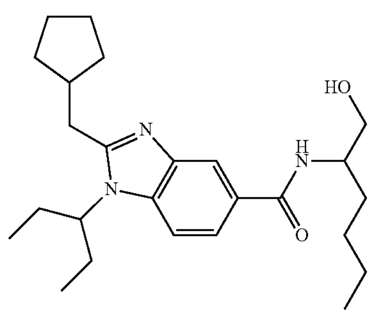 [SMILES: CCCCC(CO)NC(=O)c1ccc2c(c1)nc(CC1CCCC1)n2C(CC)CC] | 414.3 | 6_3_1 | 1.39 |
| 183 | 2-Cyclopentylmethyl-1-(1-ethyl-propyl)-1H-benzoimidazole-5-carboxylic acid ((R)-1-hydroxymethyl-pentyl)-amide | 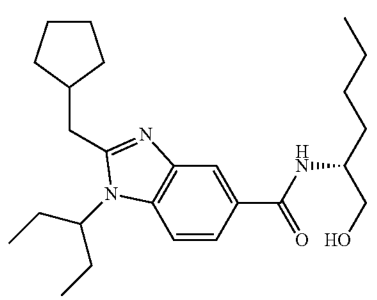 [SMILES: CCCC[C@H](CO)NC(=O)c1ccc2c(c1)nc(CC1CCCC1)n2C(CC)CC] | 414.3 | 6_3_1 | 1.39 |

| Exp. No. | Chemical Name | Structure | m/z [M + H]+ | LCMS method | R_t [min] |
|---|---|---|---|---|---|
| 184 | 2-Cyclopentylmethyl-1-(1-ethyl-propyl)-1H-benzoimidazole-5-carboxylic acid ((S)-1-hydroxymethyl-pentyl)-amide | 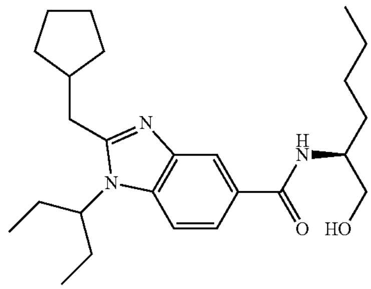 [SMILES: CCCC[C@@H](CO)NC(=O)c1ccc2c(c1)nc(CC1CCCC1)n2C(CC)CC] | 414.3 | 6_3_1 | 1.40 |
| 185 | 2-Cyclopentylmethyl-1-(1-ethyl-propyl)-1H-benzoimidazole-5-carboxylic acid ((R)-1-hydroxymethyl-butyl)-amide | 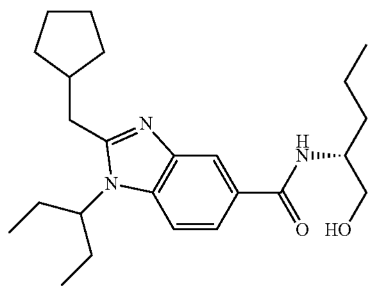 [SMILES: CCC[C@H](CO)NC(=O)c1ccc2c(c1)nc(CC1CCCC1)n2C(CC)CC] | 400.3 | 6_3_1 | 1.32 |
| 186 | 2-Cyclopentylmethyl-1-(1-ethyl-propyl)-1H-benzoimidazole-5-carboxylic acid ((S)-1-hydroxymethyl-butyl)-amide | 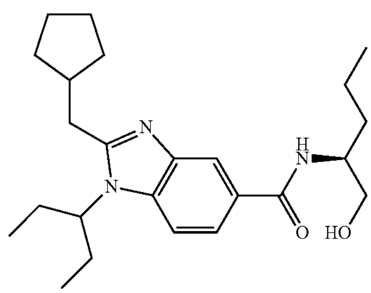 [SMILES: CCC[C@@H](CO)NC(=O)c1ccc2c(c1)nc(CC1CCCC1)n2C(CC)CC] | 400.3 | 6_3_1 | 1.33 |
| 187 | 2-Cyclopentylmethyl-1-(1-ethyl-propyl)-1H-benzoimidazole-5-carboxylic acid ((S)-1-hydroxymethyl-2-methyl-propyl)-amide | 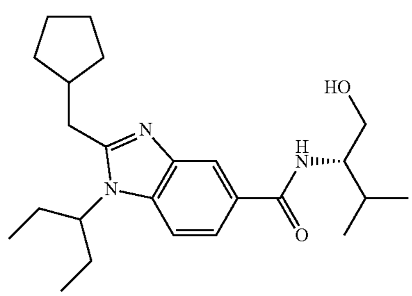 [SMILES: CCC(CC)n1c(CC2CCCC2)nc2cc(C(=O)N[C@H](CO)C(C)C)ccc21] | 400.3 | 6_1_1 | 1.51 |
| 188 | 1-(1-Ethyl-propyl)-2-thiophen-2-ylmethyl-1H-benzoimidazole-5-carboxylic acid ((S)-1-hydroxymethyl-3-methylsulfanyl-propyl)-amide | 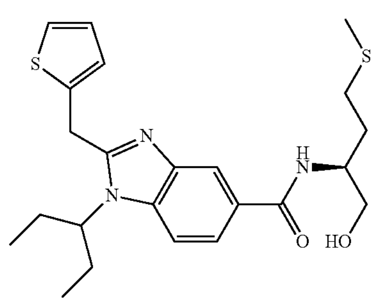 [SMILES: CCC(CC)n1c(Cc2cccs2)nc2cc(C(=O)N[C@H](CO)CCSC)ccc21] | 446.2 | 6_3_1 | 1.26 |

-continued

| Exp. No. | Chemical Name | Structure | m/z [M + H]⁺ | LCMS method | R_t [min] |
|---|---|---|---|---|---|
| 189 | 1-(1-Ethyl-propyl)-2-thiophen-2-ylmethyl-1H-benzoimidazole-5-carboxylic acid (1-hydroxymethyl-2-methyl-propyl)-amide | 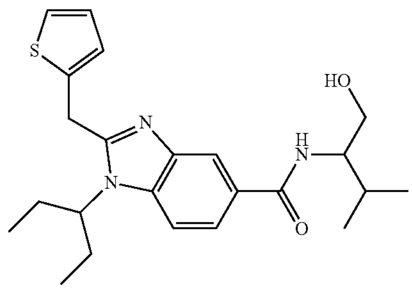 [SMILES: CCC(CC)n1c(Cc2cccs2)nc2cc(C(=O)NC(CO)C(C)C)ccc21] | 414.2 | 6_3_1 | 1.26 |
| 190 | 1-(1-Ethyl-propyl)-2-thiophen-2-ylmethyl-1H-benzoimidazole-5-carboxylic acid ((S)-1-hydroxymethyl-2-methyl-propyl)-amide | 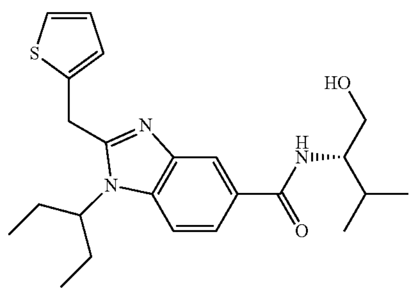 | 414.2 | 6_3_1 | 1.26 |
| 191 | 1-(1-Ethyl-propyl)-2-thiophen-2-ylmethyl-1H-benzoimidazole-5-carboxylic acid ((R)-1-hydroxymethyl-3-methyl-butyl)-amide | 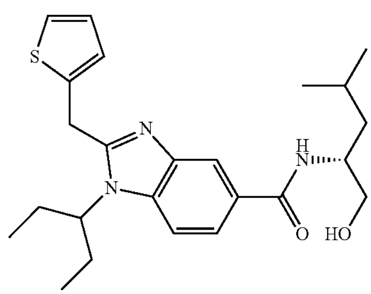 [SMILES: CCC(CC)n1c(Cc2cccs2)nc2cc(C(=O)N[C@@H](CO)CC(C)C)ccc21] | 428.2 | 6_3_1 | 1.35 |
| 192 | 1-(1-Ethyl-propyl)-2-thiophen-2-ylmethyl-1H-benzoimidazole-5-carboxylic acid ((S)-1-hydroxymethyl-2,2-dimethyl-propyl)-amide | 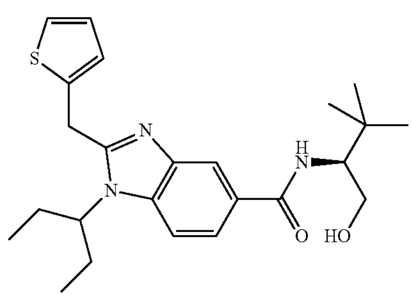 [SMILES: CCC(CC)n1c(Cc2cccs2)nc2cc(C(=O)N[C@H](CO)C(C)(C)C)ccc21] | 428.2 | 6_3_1 | 1.32 |
| 193 | 1-(1-Ethyl-propyl)-2-thiophen-2-ylmethyl-1H-benzoimidazole-5-carboxylic acid (1-hydroxymethyl-cyclopentyl)-amide | 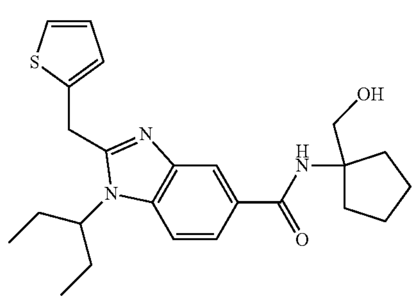 [SMILES: CCC(CC)n1c(Cc2cccs2)nc2cc(C(=O)NC3(CO)CCCC3)ccc21] | 426.2 | 6_3_1 | 1.30 |

-continued

| Exp. No. | Chemical Name | Structure | m/z [M + H]+ | LCMS method | R_t [min] |
|---|---|---|---|---|---|
| 194 | 1-(1-Ethyl-propyl)-2-thiophen-2-ylmethyl-1H-benzoimidazole-5-carboxylic acid ((1S,2S)-1-hydroxymethyl-2-methyl-butyl)-amide | 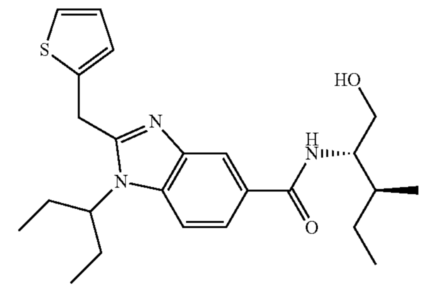 [SMILES: CCC(CC)n1c(Cc2cccs2)nc2cc(C(=O)N[C@H](CO)[C@@H](C)CC)ccc21] | 428.2 | 6_3_1 | 1.34 |
| 195 | 1-(1-Ethyl-propyl)-2-thiophen-2-ylmethyl-1H-benzoimidazole-5-carboxylic acid ((R)-1-hydroxymethyl-3-methylsulfanyl-propyl)-amide | 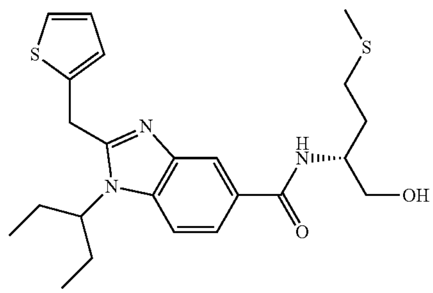 [SMILES: CCC(CC)n1c(Cc2cccs2)nc2cc(C(=O)N[C@@H](CO)CCSC)ccc21] | 446.5 | 6_2_1 | 1.71 |
| 196 | 1-(1-Ethyl-propyl)-2-thiophen-2-ylmethyl-1H-benzoimidazole-5-carboxylic acid (1-hydroxymethyl-butyl)-amide | 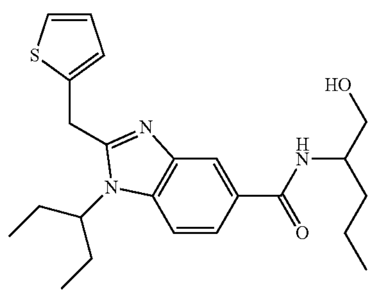 [SMILES: CCCC(CO)NC(=O)c1ccc2c(c1)nc(Cc1cccs1)n2C(CC)CC] | 414.1 | 6_3_1 | 1.27 |
| 197 | 1-(1-Ethyl-propyl)-2-thiophen-2-ylmethyl-1H-benzoimidazole-5-carboxylic acid (1-hydroxymethyl-pentyl)-amide | 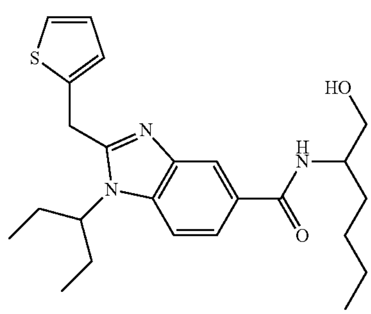 [SMILES: CCCCC(CO)NC(=O)c1ccc2c(c1)nc(Cc1cccs1)n2C(CC)CC] | 428.2 | 6_3_1 | 1.36 |
| 198 | 1-(1-Ethyl-propyl)-2-thiophen-2-ylmethyl-1H-benzoimidazole-5-carboxylic acid ((R)-1-hydroxymethyl-pentyl)-amide | 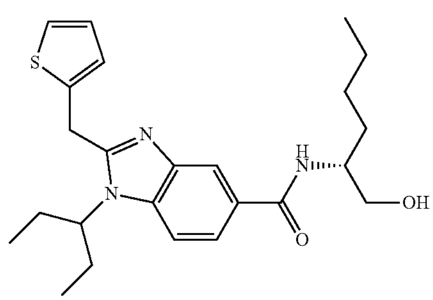 | 428.2 | 6_3_1 | 1.40 |

-continued

| Exp. No. | Chemical Name | Structure | m/z [M + H]+ | LCMS method | R_t [min] |
|---|---|---|---|---|---|
| 199 | 1-(1-Ethyl-propyl)-2-thiophen-2-ylmethyl-1H-benzoimidazole-5-carboxylic acid ((S)-1-hydroxymethyl-pentyl)-amide | 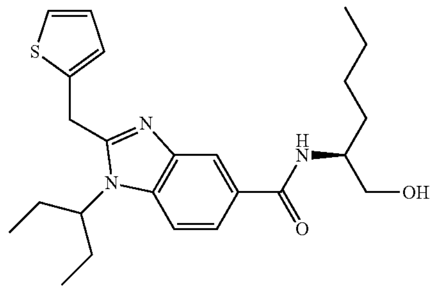 [SMILES: CCCC[C@@H](CO)NC(=O)c1ccc2c(c1)nc(Cc1cccs1)n2C(CC)CC] | 428.3 | 6_1_1 | 1.61 |
| 200 | 1-(1-Ethyl-propyl)-2-thiophen-2-ylmethyl-1H-benzoimidazole-5-carboxylic acid ((R)-1-hydroxymethyl-butyl)-amide | 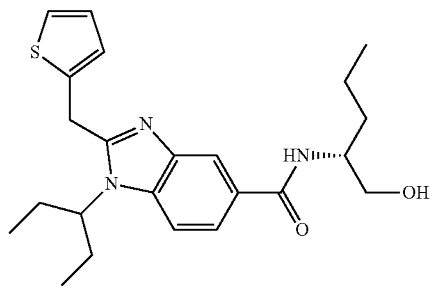 [SMILES: CCC[C@H](CO)NC(=O)c1ccc2c(c1)nc(Cc1cccs1)n2C(CC)CC] | 414.2 | 6_1_1 | 1.48 |
| 201 | 1-(1-Ethyl-propyl)-2-thiophen-2-ylmethyl-1H-benzoimidazole-5-carboxylic acid ((S)-1-hydroxymethyl-butyl)-amide | 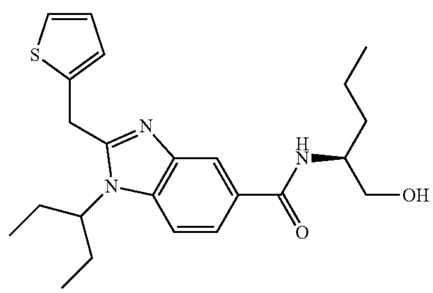 [SMILES: CCC[C@@H](CO)NC(=O)c1ccc2c(c1)nc(Cc1cccs1)n2C(CC)CC] | 414.2 | 6_1_1 | 1.51 |
| 202 | 1-(1-Ethyl-propyl)-2-thiophen-2-ylmethyl-1H-benzoimidazole-5-carboxylic acid (2-hydroxy-1-phenyl-ethyl)-amide | 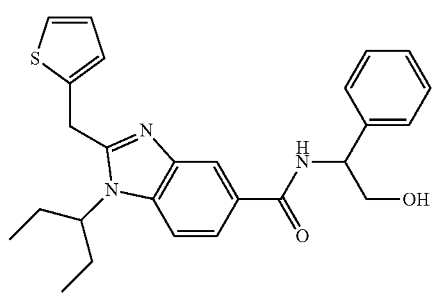 [SMILES: CCC(CC)n1c(Cc2cccs2)nc2cc(C(=O)NC(CO)c3ccccc3)ccc21] | 448.2 | 6_1_1 | 1.58 |
| 203 | 1-(1-Ethyl-propyl)-2-thiophen-2-ylmethyl-1H-benzoimidazole-5-carboxylic acid ((R)-1-cyclohexyl-2-hydroxy-ethyl)-amide | 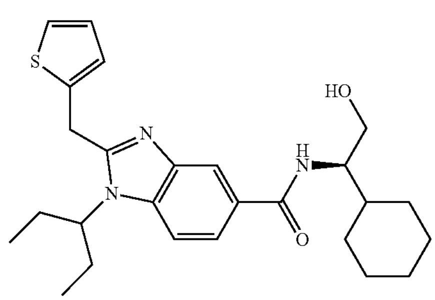 [SMILES: CCC(CC)n1c(Cc2cccs2)nc2cc(C(=O)N[C@@H](CO)C3CCCCC3)ccc21] | 454.3 | 6_1_1 | 1.73 |

| Exp. No. | Chemical Name | Structure | m/z [M + H]+ | LCMS method | R_t [min] |
|---|---|---|---|---|---|
| 204 | 1-(1-Ethyl-propyl)-2-thiophen-2-ylmethyl-1H-benzoimidazole-5-carboxylic acid ((S)-1-cyclohexyl-2-hydroxy-ethyl)-amide | 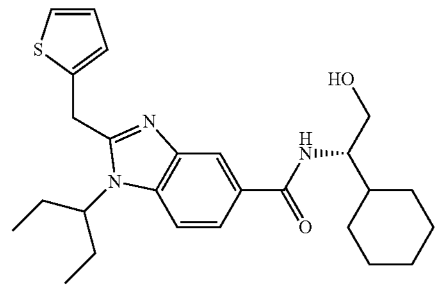 [SMILES: CCC(CC)n1c(Cc2cccs2)nc2cc(C(=O)N[C@H](CO)C3CCCCC3)ccc21] | 454.3 | 6_1_1 | 1.71 |
| 205 | 1-(1-Ethyl-propyl)-2-thiazol-4-ylmethyl-1H-benzoimidazole-5-carboxylic acid ((S)-1-hydroxymethyl-3-methyl-butyl)-amide | 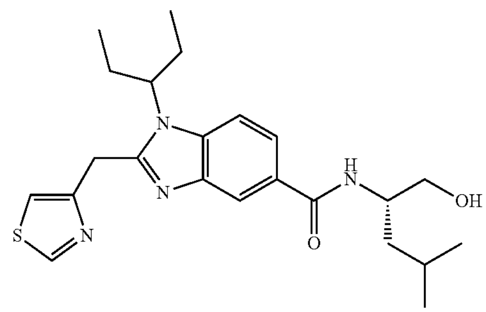 [SMILES: CCC(CC)n1c(Cc2cscn2)nc2cc(C(=O)N[C@H](CO)CC(C)C)ccc21] | 429.4 | 6_1_1 | 1.35 |
| 206 | 1-(1-Ethyl-propyl)-2-thiazol-4-ylmethyl-1H-benzoimidazole-5-carboxylic acid ((S)-1-methoxymethyl-3-methyl-butyl)-amide | 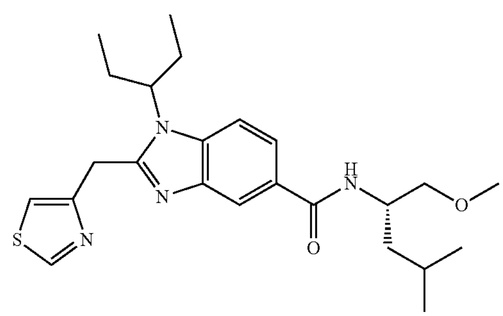 [SMILES: CCC(CC)n1c(Cc2cscn2)nc2cc(C(=O)N[C@H](COC)CC(C)C)ccc21] | 443.4 | 6_1_1 | 1.52 |
| 207 | 1-(1-Ethyl-propyl)-2-thiophen-2-ylmethyl-1H-benzoimidazole-5-carboxylic acid ((S)-1-methoxymethyl-3-methyl-butyl)-amide | 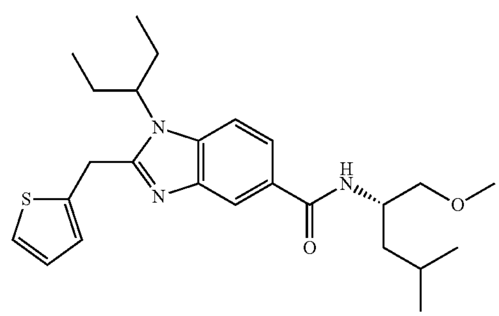 [SMILES: CCC(CC)n1c(Cc2cccs2)nc2cc(C(=O)N[C@H](COC)CC(C)C)ccc21] | 442.4 | 6_1_1 | 1.74 |
| 208 | 1-(1-Ethyl-propyl)-2-thiophen-2-ylmethyl-1H-benzoimidazole-5-carboxylic acid ((S)-1-ethoxymethyl-3-methyl-butyl)-amide | 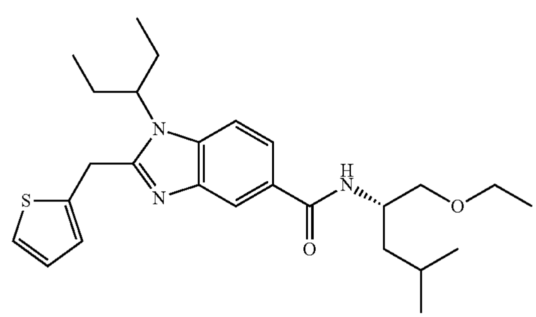 [SMILES: CCOC[C@H](CC(C)C)NC(=O)c1ccc2c(c1)nc(Cc1cccs1)n2C(CC)CC] | 456.2 | 6_4_1 | 1.60 |

| Exp. No. | Chemical Name | Structure | m/z [M + H]+ | LCMS method | R_t [min] |
|---|---|---|---|---|---|
| 209 | 1-(1-Ethyl-propyl)-2-thiophen-2-ylmethyl-1H-benzoimidazole-5-carboxylic acid ((S)-1-hydroxymethyl-3-methyl-butyl)-amide | 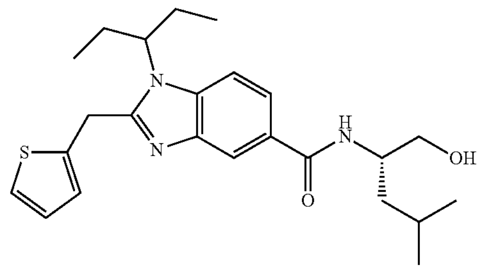 [SMILES: CCC(CC)n1c(Cc2cccs2)nc2cc(C(=O)N[C@H](CO)CC(C)C)ccc21] | 428.2 | 6_4_1 | 1.38 |
| 210 | 1-(1-Ethyl-propyl)-2-thiophen-2-ylmethyl-1H-benzoimidazole-5-carboxylic acid ((S)-1-butoxymethyl-3-methyl-butyl)-amide | 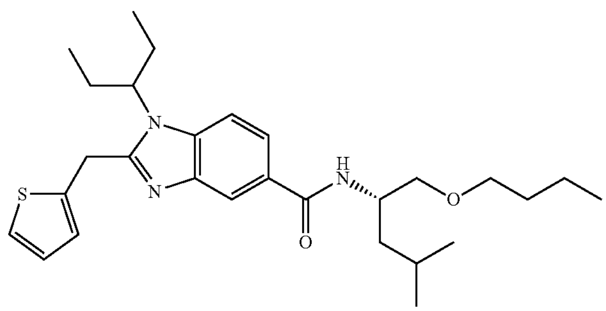 [SMILES: CCCCOC[C@H](CC(C)C)NC(=O)c1ccc2c(c1)nc(Cc1cccs1)n2C(CC)CC] | 484.2 | 6_4_1 | 1.56 |
| 211 | 1-(2-Methyl-cyclohexyl)-2-thiophen-2-ylmethyl-1H-benzoimidazole-5-carboxylic acid ((S)-1-hydroxymethyl-3-methyl-butyl)-amide | 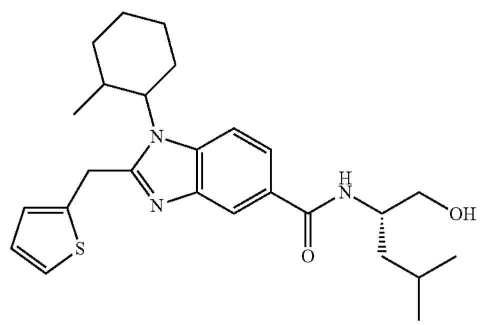 [SMILES: CC(C)C[C@@H](CO)NC(=O)c1ccc2c(c1)nc(Cc1cccs1)n2C1CCCCC1C] | 453.3 | 5_7_1 | 2.55 |
| 212 | 1-(1-Ethyl-propyl)-2-thiophen-2-ylmethyl-1H-benzoimidazole-5-carboxylic acid (3-hydroxy-1-thiophen-3-yl-propyl)-amide | 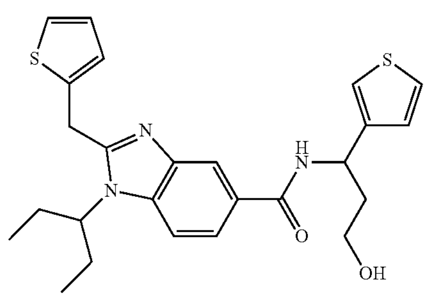 [SMILES: CCC(CC)n1c(Cc2cccs2)nc2cc(C(=O)NC(CCO)c3ccsc3)ccc21] | 468.2 | 6_1_1 | 1.61 |
| 213 | 1-(1-Ethyl-propyl)-2-thiophen-2-ylmethyl-1H-benzoimidazole-5-carboxylic acid (1-cyclopropyl-3-hydroxy-propyl)-amide | 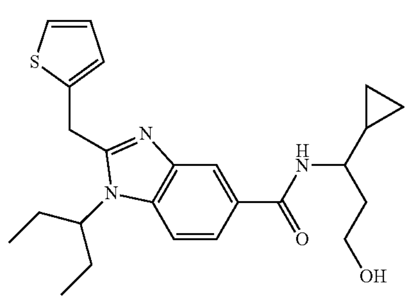 [SMILES: CCC(CC)n1c(Cc2cccs2)nc2cc(C(=O)NC(CCO)C3CC3)ccc21] | 426.3 | 6_1_1 | 1.48 |

-continued

| Exp. No. | Chemical Name | Structure | m/z [M + H]+ | LCMS method | R$_t$ [min] |
|---|---|---|---|---|---|
| 214 | 1-(1-Ethyl-propyl)-2-thiophen-2-ylmethyl-1H-benzoimidazole-5-carboxylic acid [1-(2-hydroxy-ethyl)-butyl]-amide | 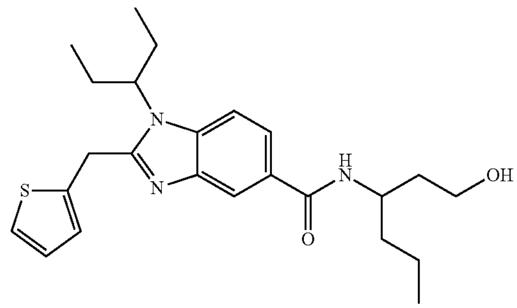 [SMILES: CCCC(CCO)NC(=O)c1ccc2c(c1)nc(Cc1cccs1)n2C(CC)CC] | 428.2 | 5_7_1 | 2.75 |

EXAMPLE 215

1-(1-Ethyl-propyl)-2-thiophen-2-ylmethyl-1H-benzoimidazole-5-carboxylic acid ((S)-1-cyclobutylcarbamoyl-3-methyl-butyl)-amide

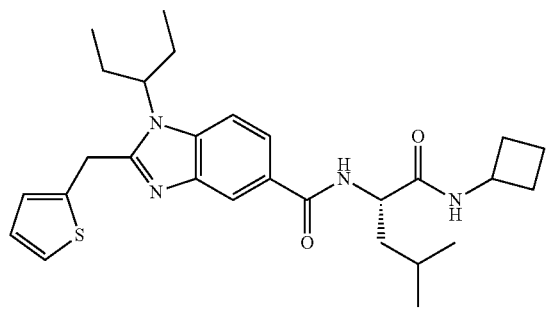 [SMILES: CCC(CC)n1c(Cc2cccs2)nc2cc(C(=O)N[C@@H](CC(C)C)C(=O)NC3CCC3)ccc21]

Into a reaction vial were placed 10 mg of cyclobutylamine, 20 mg of HOAt, 53 mg of (S)-2-{[1-(1-Ethyl-propyl)-2-thiophen-2-ylmethyl-1H-benzoimidazole-5-carbonyl]-amino}-4-methyl-pentanoic acid. Then 0.11 ml DIPEA in 1 ml DMF were added, followed by 67 mg PyBrOP in 0.5 ml DMF. The reaction was shaken at RT over night, then filtered and purified by HPLC to yield 39 mg (74%) of 1-(1-ethyl-propyl)-2-thiophen-2-ylmethyl-1H-benzoimidazole-5-carboxylic acid ((S)-1-cyclobutylcarbamoyl-3-methyl-butyl)-amide.

$C_{28}H_{28}N_{14}O_2S$ (494.70), LCMS (method 6_3_1): Rt=1.50 min, m/z=495.18 [M+H]+

The following examples were prepared in analogy to example 215:

| Exp. No. | Chemical Name | Structure | m/z [M + H]+ | LCMS method | R$_t$ [min] |
|---|---|---|---|---|---|
| 216 | 1-(2-Methyl-cyclohexyl)-2-thiophen-2-ylmethyl-1H-benzoimidazole-5-carboxylic acid ((S)-1-dimethylcarbamoyl-3-methyl-butyl)-amide | 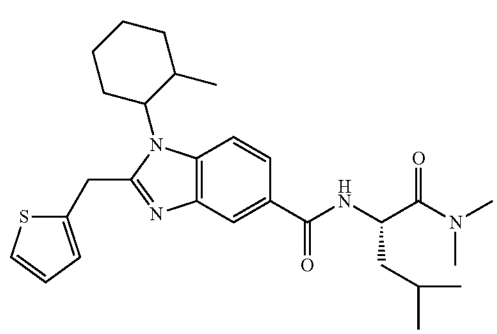 [SMILES: CC(C)C[C@H](NC(=O)c1ccc2c(c1)nc(Cc1cccs1)n2C1CCCCC1C)C(=O)N(C)C] | 495.3 | 2_1_1 | 3.50 |

| Exp. No. | Chemical Name | Structure | m/z [M + H]⁺ | LCMS method | R_t [min] |
|---|---|---|---|---|---|
| 217 | 1-(1-Ethyl-propyl)-2-thiophen-2-ylmethyl-1H-benzoimidazole-5-carboxylic acid [(S)-3-methyl-1-(thiomorpholine-4-carbonyl)-butyl]-amide | 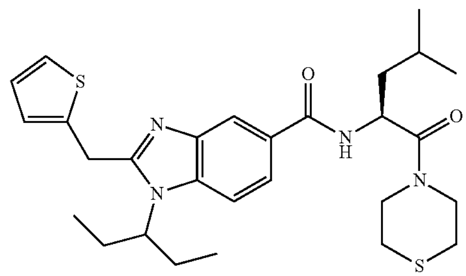 [SMILES: CCC(CC)n1c(Cc2cccs2)nc2cc(C(=O)N[C@@H](CC(C)C)C(=O)N3CCSCC3)ccc21] | 527.1 | 6_3_1 | 1.54 |
| 218 | 1-(1-Ethyl-propyl)-2-thiophen-2-ylmethyl-1H-benzoimidazole-5-carboxylic acid ((S)-1-sec-butylcarbamoyl-3-methyl-butyl)-amide | 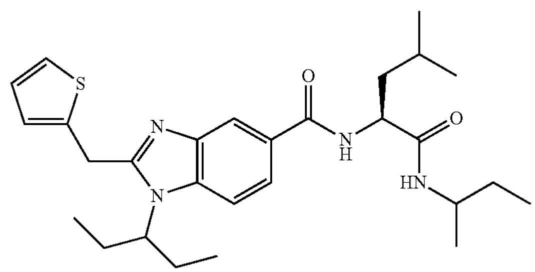 [SMILES: CCC(C)NC(=O)[C@H](CC(C)C)NC(=O)c1ccc2c(c1)nc(Cc1cccs1)n2C(CC)CC] | 497.2 | 6_3_1 | 1.52 |
| 219 | 1-(1-Ethyl-propyl)-2-thiophen-2-ylmethyl-1H-benzoimidazole-5-carboxylic acid {(S)-3-methyl-1-[2-(1-methyl-pyrrolidin-2-yl)-ethylcarbamoyl]-butyl}-amide | 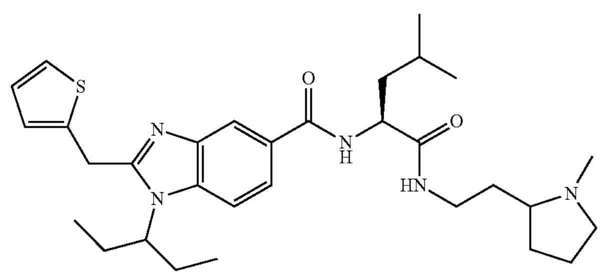 [SMILES: CCC(CC)n1c(Cc2cccs2)nc2cc(C(=O)N[C@@H](CC(C)C)C(=O)NCCC3CCCN3C)ccc21] | 552.3 | 6_3_1 | 1.25 |
| 220 | 1-(1-Ethyl-propyl)-2-thiophen-2-ylmethyl-1H-benzoimidazole-5-carboxylic acid ((S)-1-benzylcarbamoyl-3-methyl-butyl)-amide | 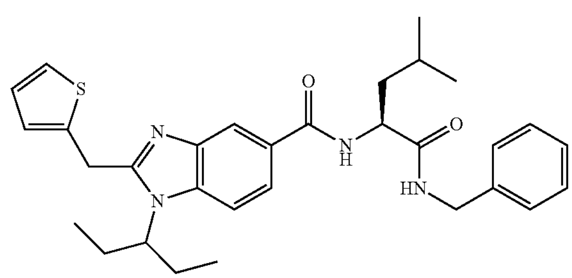 [SMILES: CCC(CC)n1c(Cc2cccs2)nc2cc(C(=O)N[C@@H](CC(C)C)C(=O)NCc3ccccc3)ccc21] | 531.2 | 6_3_1 | 1.58 |
| 221 | 1-(1-Ethyl-propyl)-2-thiophen-2-ylmethyl-1H-benzoimidazole-5-carboxylic acid {(S)-1-[(furan-2-ylmethyl)-carbamoyl]-3-methyl-butyl}-amide | 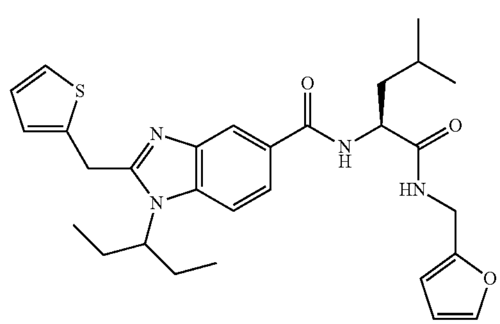 [SMILES: CCC(CC)n1c(Cc2cccs2)nc2cc(C(=O)N[C@@H](CC(C)C)C(=O)NCc3ccco3)ccc21] | 521.2 | 6_3_1 | 1.52 |

-continued

| Exp. No. | Chemical Name | Structure | m/z [M + H]+ | LCMS method | R_t [min] |
|---|---|---|---|---|---|
| 222 | 1-(1-Ethyl-propyl)-2-thiophen-2-ylmethyl-1H-benzoimidazole-5-carboxylic acid {(S)-3-methyl-1-[(thiophen-2-ylmethyl)-carbamoyl]-butyl}-amide | 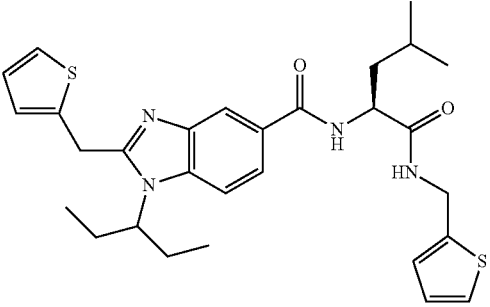 [SMILES: CCC(CC)n1c(Cc2cccs2)nc2cc(C(=O)N[C@@H](CC(C)C)C(=O)NCc3cccs3)ccc21] | 537.1 | 6_3_1 | 1.57 |
| 223 | 1-(1-Ethyl-propyl)-2-thiophen-2-ylmethyl-1H-benzoimidazole-5-carboxylic acid [(S)-3-methyl-1-(2-thiophen-2-yl-ethylcarbamoyl)-butyl]-amide | 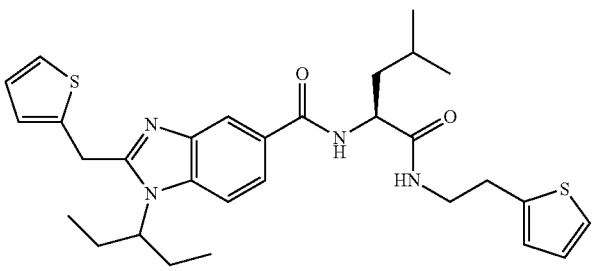 [SMILES: CCC(CC)n1c(Cc2cccs2)nc2cc(C(=O)N[C@@H](CC(C)C)C(=O)NCCc3cccs3)ccc21] | 551.2 | 6_3_1 | 1.59 |
| 224 | 1-(1-Ethyl-propyl)-2-thiophen-2-ylmethyl-1H-benzoimidazole-5-carboxylic acid [(S)-1-(3-dimethylamino-propylcarbamoyl)-3-methyl-butyl]-amide | 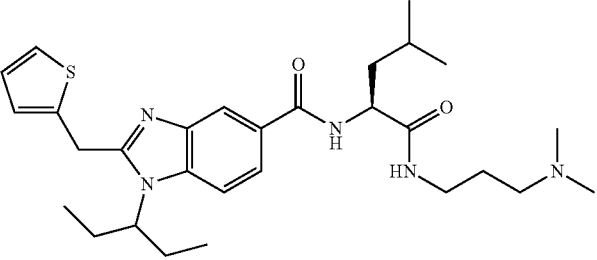 [SMILES: CCC(CC)n1c(Cc2cccs2)nc2cc(C(=O)N[C@@H](CC(C)C)C(=O)NCCCN(C)C)ccc21] | 526.3 | 6_3_1 | 1.21 |
| 225 | 1-(1-Ethyl-propyl)-2-thiophen-2-ylmethyl-1H-benzoimidazole-5-carboxylic acid [(S)-3-methyl-1-(4-methyl-piperazine-1-carbonyl)-butyl]-amide | 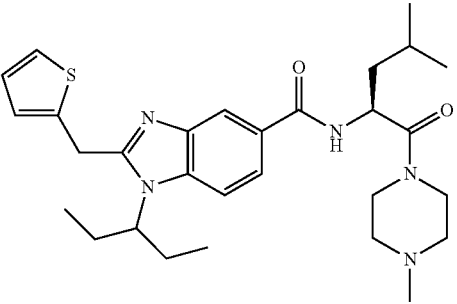 [SMILES: CCC(CC)n1c(Cc2cccs2)nc2cc(C(=O)N[C@@H](CC(C)C)C(=O)N3CCN(C)CC3)ccc21] | 524.3 | 6_3_1 | 1.21 |
| 226 | 1-(1-Ethyl-propyl)-2-thiophen-2-ylmethyl-1H-benzoimidazole-5-carboxylic acid [(S)-1-(1-ethyl-propylcarbamoyl)-3-methyl-butyl]-amide | 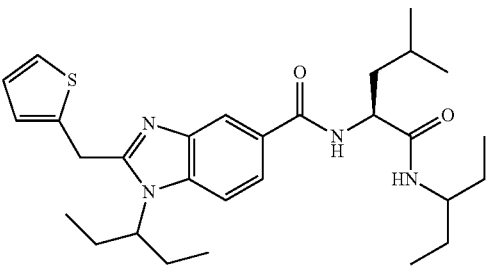 [SMILES: CCC(CC)NC(=O)[C@H](CC(C)C)NC(=O)c1ccc2c(c1)nc(Cc1cccs1)n2C(CC)CC] | 511.2 | 6_3_1 | 1.60 |

| Exp. No. | Chemical Name | Structure | m/z [M + H]+ | LCMS method | R_t [min] |
|---|---|---|---|---|---|
| 227 | 1-(1-Ethyl-propyl)-2-thiophen-2-ylmethyl-1H-benzoimidazole-5-carboxylic acid {(S)-3-methyl-1-[3-(4-methyl-piperazin-1-yl)-propylcarbamoyl]-butyl}-amide | 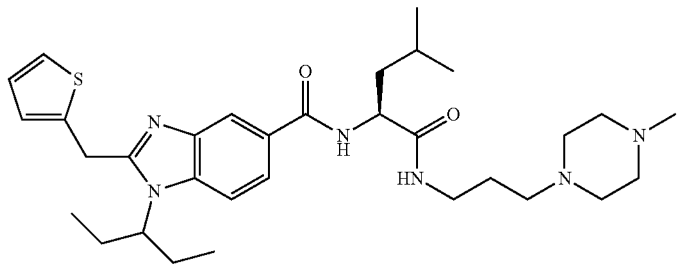 [SMILES: CCC(CC)n1c(Cc2cccs2)nc2cc(C(=O)N[C@@H](CC(C)C)C(=O)NCCCN3CCN(C)CC3)ccc21] | 581.3 | 6_3_1 | 1.17 |
| 228 | 1-(1-Ethyl-propyl)-2-thiophen-2-ylmethyl-1H-benzoimidazole-5-carboxylic acid [(S)-1-(4-fluoro-phenylcarbamoyl)-3-methyl-butyl]-amide | 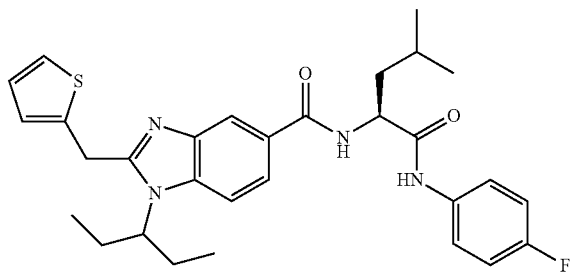 [SMILES: CCC(CC)n1c(Cc2cccs2)nc2cc(C(=O)N[C@@H](CC(C)C)C(=O)Nc3ccc(F)cc3)ccc21] | 535.2 | 6_3_1 | 1.65 |
| 229 | 1-(1-Ethyl-propyl)-2-thiophen-2-ylmethyl-1H-benzoimidazole-5-carboxylic acid [(S)-1-(2,6-dimethyl-morpholine-4-carbonyl)-3-methyl-butyl]-amide | 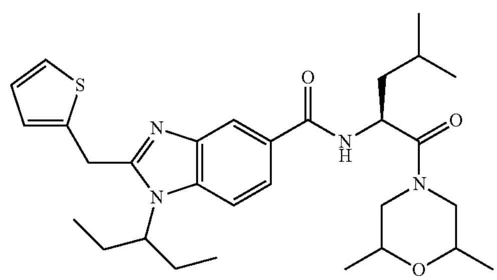 [SMILES: CCC(CC)n1c(Cc2cccs2)nc2cc(C(=O)N[C@@H](CC(C)C)C(=O)N3CC(C)OC(C)C3)ccc21] | 539.2 | 6_3_1 | 1.53 |
| 230 | 1-(1-Ethyl-propyl)-2-thiophen-2-ylmethyl-1H-benzoimidazole-5-carboxylic acid [(S)-3-methyl-1-(2-pyrrolidin-1-yl-ethylcarbamoyl)-butyl]-amide | 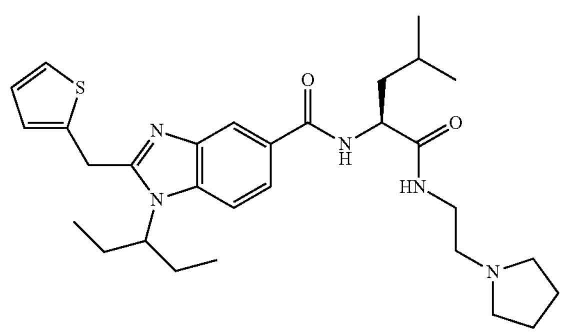 [SMILES: CCC(CC)n1c(Cc2cccs2)nc2cc(C(=O)N[C@@H](CC(C)C)C(=O)NCCN3CCCC3)ccc21] | 538.2 | 6_3_1 | 1.24 |
| 231 | 1-(1-Ethyl-propyl)-2-thiophen-2-ylmethyl-1H-benzoimidazole-5-carboxylic acid [(S)-3-methyl-1-(2-morpholin-4-yl-ethylcarbamoyl)-butyl]-amide | 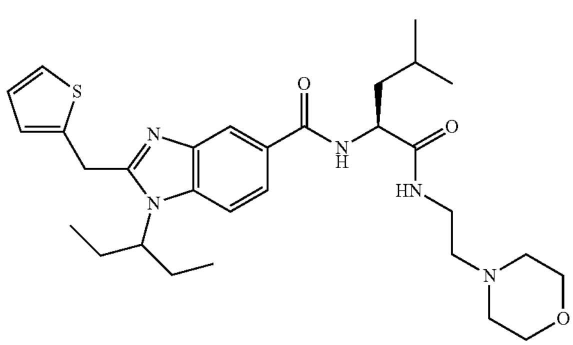 [SMILES: CCC(CC)n1c(Cc2cccs2)nc2cc(C(=O)N[C@@H](CC(C)C)C(=O)NCCN3CCOCC3)ccc21] | 554.2 | 6_3_1 | 1.22 |

-continued

| Exp. No. | Chemical Name | Structure | m/z [M + H]+ | LCMS method | R$_t$ [min] |
|---|---|---|---|---|---|
| 232 | 1-(1-Ethyl-propyl)-2-thiophen-2-ylmethyl-1H-benzoimidazole-5-carboxylic acid [(S)-1-(1,3-dimethyl-butylcarbamoyl)-3-methyl-butyl]-amide | 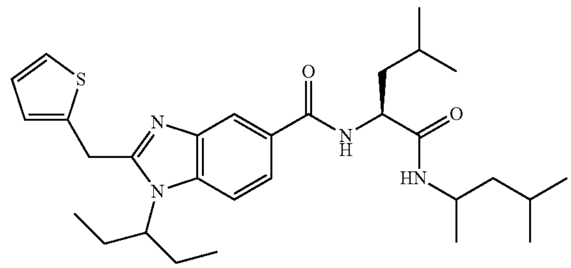 [SMILES: CCC(CC)n1c(Cc2cccs2)nc2cc(C(=O)N[C@@H](CC(C)C)C(=O)NC(C)CC(C)C)ccc21] | 525.2 | 6_3_1 | 1.67 |
| 233 | 1-(1-Ethyl-propyl)-2-thiophen-2-ylmethyl-1H-benzoimidazole-5-carboxylic acid [(S)-3-methyl-1-(2-piperidin-1-yl-ethylcarbamoyl)-butyl]-amide | 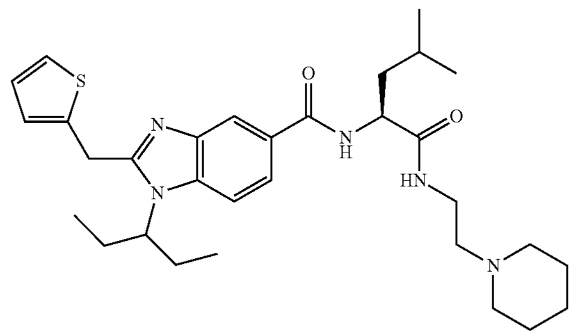 [SMILES: CCC(CC)n1c(Cc2cccs2)nc2cc(C(=O)N[C@@H](CC(C)C)C(=O)NCCN3CCCCC3)ccc21] | 552.3 | 6_3_1 | 1.30 |
| 234 | 1-(1-Ethyl-propyl)-2-thiophen-2-ylmethyl-1H-benzoimidazole-5-carboxylic acid [(S)-3-methyl-1-(3-morpholin-4-yl-propylcarbamoyl)-butyl]-amide | 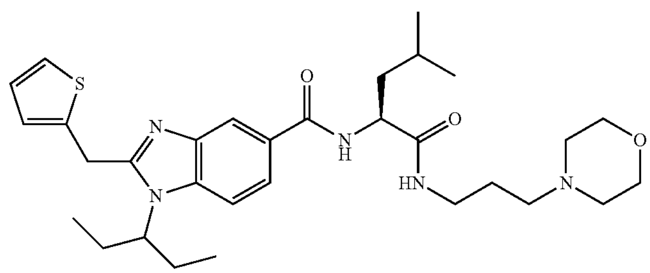 [SMILES: CCC(CC)n1c(Cc2cccs2)nc2cc(C(=O)N[C@@H](CC(C)C)C(=O)NCCCN3CCOCC3)ccc21] | 568.3 | 6_3_1 | 1.24 |
| 235 | 1-(1-Ethyl-propyl)-2-thiophen-2-ylmethyl-1H-benzoimidazole-5-carboxylic acid [(S)-3-methyl-1-(4-phenyl-piperazine-1-carbonyl)-butyl]-amide | 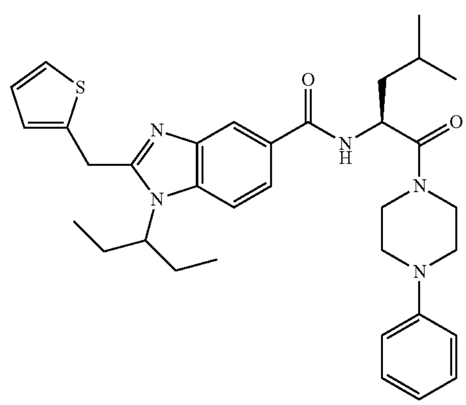 [SMILES: CCC(CC)n1c(Cc2cccs2)nc2cc(C(=O)N[C@@H](CC(C)C)C(=O)N3CCN(c4ccccc4)CC3)ccc21] | 586.2 | 6_3_1 | 1.63 |
| 236 | 1-(1-Ethyl-propyl)-2-thiophen-2-ylmethyl-1H-benzoimidazole-5-carboxylic acid [(S)-1-(4-methoxy-benzylcarbamoyl)-3-methyl-butyl]-amide | 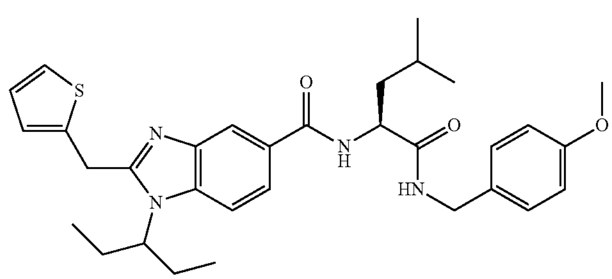 [SMILES: CCC(CC)n1c(Cc2cccs2)nc2cc(C(=O)N[C@@H](CC(C)C)C(=O)NCc3ccc(OC)cc3)ccc21] | 561.2 | 6_3_1 | 1.60 |

-continued

| Exp. No. | Chemical Name | Structure | m/z [M + H]+ | LCMS method | R$_t$ [min] |
|---|---|---|---|---|---|
| 237 | 1-(1-Ethyl-propyl)-2-thiophen-2-ylmethyl-1H-benzoimidazole-5-carboxylic acid ((S)-1-cyclopentylcarbamoyl-3-methyl-butyl)-amide | 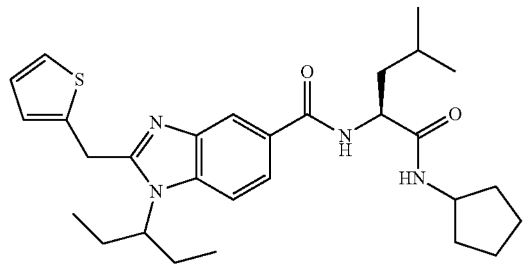 [SMILES: CCC(CC)n1c(Cc2cccs2)nc2cc(C(=O)N[C@@H](CC(C)C)C(=O)NC3CCCC3)ccc21] | 509.2 | 6_3_1 | 1.57 |
| 238 | 1-(1-Ethyl-propyl)-2-thiophen-2-ylmethyl-1H-benzoimidazole-5-carboxylic acid [(S)-1-(2-methoxy-benzylcarbamoyl)-3-methyl-butyl]-amide | 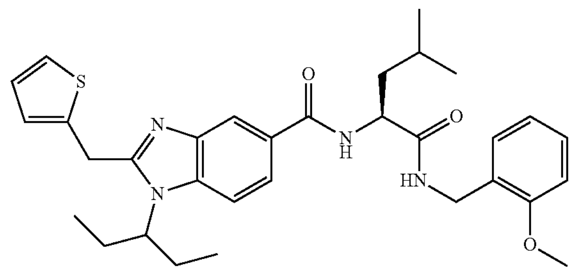 [SMILES: CCC(CC)n1c(Cc2cccs2)nc2cc(C(=O)N[C@@H](CC(C)C)C(=O)NCc3ccccc3OC)ccc21] | 561.2 | 6_3_1 | 1.61 |
| 239 | 1-(1-Ethyl-propyl)-2-thiophen-2-ylmethyl-1H-benzoimidazole-5-carboxylic acid {(S)-1-[(benzo[1,3]dioxol-5-ylmethyl)-carbamoyl]-3-methyl-butyl}-amide | 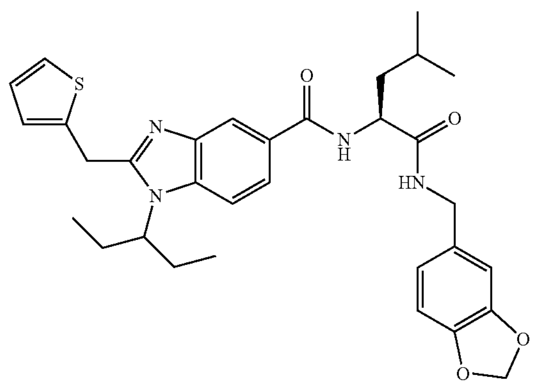 [SMILES: CCC(CC)n1c(Cc2cccs2)nc2cc(C(=O)N[C@@H](CC(C)C)C(=O)NCc3ccc4c(c3)OCO4)ccc21] | 575.3 | 6_1_1 | 1.87 |
| 240 | 1-(1-Ethyl-propyl)-2-thiophen-2-ylmethyl-1H-benzoimidazole-5-carboxylic acid {(S)-3-methyl-1-[methyl-(2-pyridin-2-yl-ethyl)-carbamoyl]-butyl}-amide | 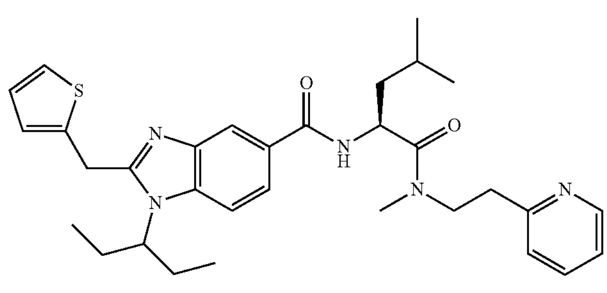 [SMILES: CCC(CC)n1c(Cc2cccs2)nc2cc(C(=O)N[C@@H](CC(C)C)C(=O)N(C)CCc3ccccn3)ccc21] | 560.4 | 6_1_1 | 1.35 |
| 241 | 1-(1-Ethyl-propyl)-2-thiophen-2-ylmethyl-1H-benzoimidazole-5-carboxylic acid [(S)-3-methyl-1-(3-pyrrolidin-1-yl-propylcarbamoyl)-butyl]-amide | 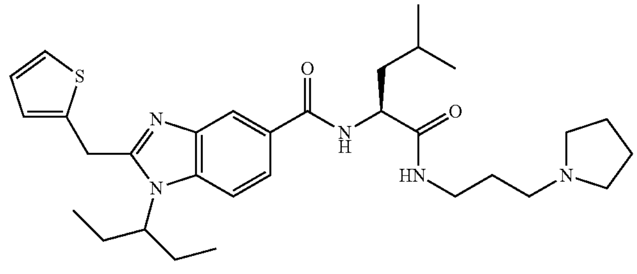 [SMILES: CCC(CC)n1c(Cc2cccs2)nc2cc(C(=O)N[C@@H](CC(C)C)C(=O)NCCCN3CCCC3)ccc21] | 552.3 | 6_3_1 | 1.26 |

| Exp. No. | Chemical Name | Structure | m/z [M + H]+ | LCMS method | R_t [min] |
|---|---|---|---|---|---|
| 242 | 1-(1-Ethyl-propyl)-2-thiophen-2-ylmethyl-1H-benzoimidazole-5-carboxylic acid [(S)-1-(4-diethylamino-phenylcarbamoyl)-3-methyl-butyl]-amide | 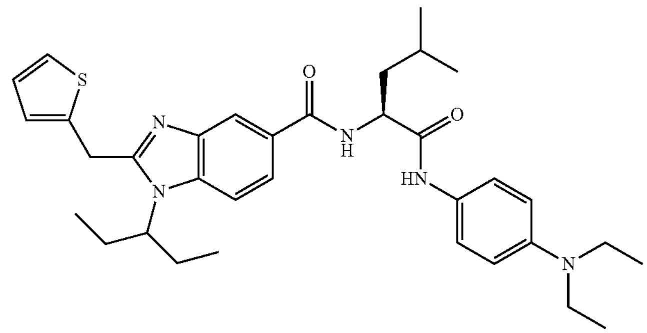 [SMILES: CCC(CC)n1c(Cc2cccs2)nc2cc(C(=O)N[C@@H](CC(C)C)C(=O)Nc3ccc(N(CC)CC)cc3)ccc21] | 588.4 | 6_3_1 | 1.33 |
| 243 | 1-(1-Ethyl-propyl)-2-thiophen-2-ylmethyl-1H-benzoimidazole-5-carboxylic acid [(S)-1-(2-dimethylamino-1-methyl-ethylcarbamoyl)-3-methyl-butyl]-amide | 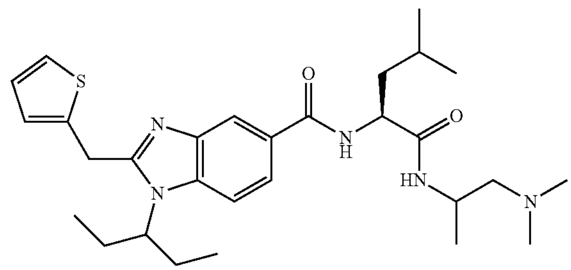 [SMILES: CCC(CC)n1c(Cc2cccs2)nc2cc(C(=O)N[C@@H](CC(C)C)C(=O)NC(C)CN(C)C)ccc21] | 526.3 | 6_3_1 | 1.25 |
| 244 | 1-(1-Ethyl-propyl)-2-thiophen-2-ylmethyl-1H-benzoimidazole-5-carboxylic acid [(S)-1-(4-fluoro-benzylcarbamoyl)-3-methyl-butyl]-amide | 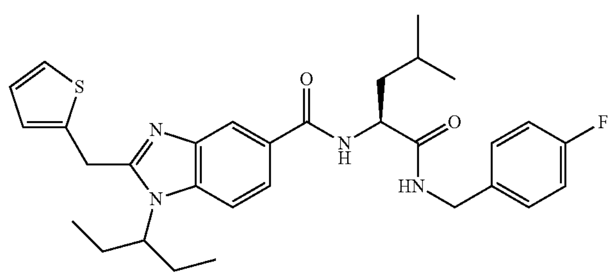 [SMILES: CCC(CC)n1c(Cc2cccs2)nc2cc(C(=O)N[C@@H](CC(C)C)C(=O)NCc3ccc(F)cc3)ccc21] | 549.2 | 6_3_1 | 1.60 |
| 245 | 1-(1-Ethyl-propyl)-2-thiophen-2-ylmethyl-1H-benzoimidazole-5-carboxylic acid [(S)-1-(4-dimethylamino-butylcarbamoyl)-3-methyl-butyl]-amide | 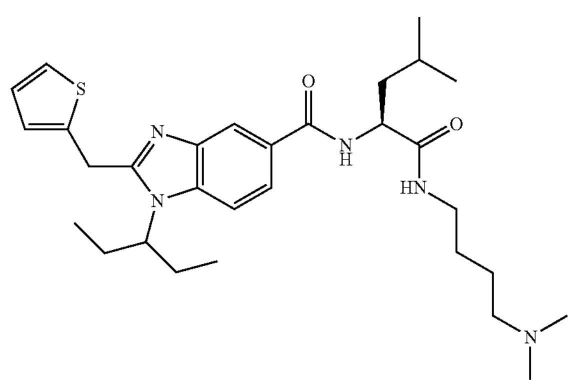 [SMILES: CCC(CC)n1c(Cc2cccs2)nc2cc(C(=O)N[C@@H](CC(C)C)C(=O)NCCCCN(C)C)ccc21] | 540.3 | 6_3_1 | 1.21 |

| Exp. No. | Chemical Name | Structure | m/z [M + H]+ | LCMS method | R$_t$ [min] |
|---|---|---|---|---|---|
| 246 | 1-(1-Ethyl-propyl)-2-thiophen-2-ylmethyl-1H-benzoimidazole-5-carboxylic acid {(S)-1-[1-(4-fluoro-phenyl)-ethylcarbamoyl]-3-methyl-butyl}-amide | 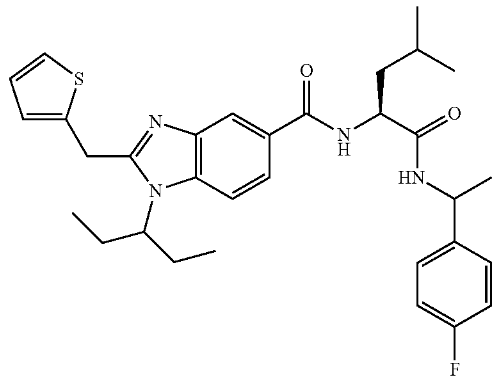 [SMILES: CCC(CC)n1c(Cc2cccs2)nc2cc(C(=O)N[C@@H](CC(C)C)C(=O)NC(C)c3ccc(F)cc3)ccc21] | 563.2 | 6_3_1 | 1.65 |
| 247 | 1-(1-Ethyl-propyl)-2-thiophen-2-ylmethyl-1H-benzoimidazole-5-carboxylic acid {(S)-1-[(S)-1-(4-methoxy-phenyl)-ethylcarbamoyl]-3-methyl-butyl}-amide | 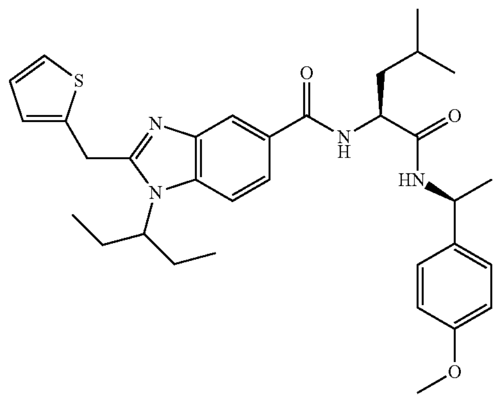 [SMILES: CCC(CC)n1c(Cc2cccs2)nc2cc(C(=O)N[C@@H](CC(C)C)C(=O)N[C@@H](C)c3ccc(OC)cc3)ccc21] | 575.3 | 6_3_1 | 1.62 |
| 248 | 1-(1-Ethyl-propyl)-2-thiophen-2-ylmethyl-1H-benzoimidazole-5-carboxylic acid [(S)-3-methyl-1-(3-methylsulfanyl-propylcarbamoyl)-butyl]-amide | 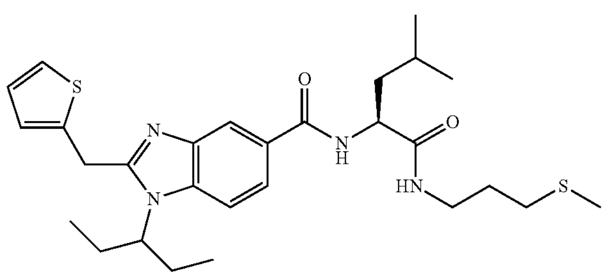 [SMILES: CCC(CC)n1c(Cc2cccs2)nc2cc(C(=O)N[C@@H](CC(C)C)C(=O)NCCCSC)ccc21] | 529.2 | 6_3_1 | 1.51 |
| 249 | 1-(1-Ethyl-propyl)-2-thiophen-2-ylmethyl-1H-benzoimidazole-5-carboxylic acid [(S)-3-methyl-1-(tetrahydro-pyran-4-ylcarbamoyl)-butyl]-amide | 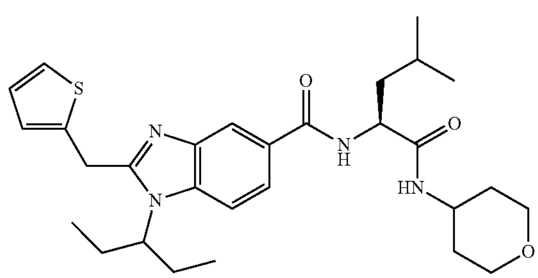 [SMILES: CCC(CC)n1c(Cc2cccs2)nc2cc(C(=O)N[C@@H](CC(C)C)C(=O)NC3CCOCC3)ccc21] | 525.3 | 6_3_1 | 1.40 |

| Exp. No. | Chemical Name | Structure | m/z [M + H]+ | LCMS method | R_t [min] |
|---|---|---|---|---|---|
| 250 | 1-(1-Ethyl-propyl)-2-thiophen-2-ylmethyl-1H-benzoimidazole-5-carboxylic acid {(S)-3-methyl-1-[(thiazol-2-ylmethyl)-carbamoyl]-butyl}-amide | 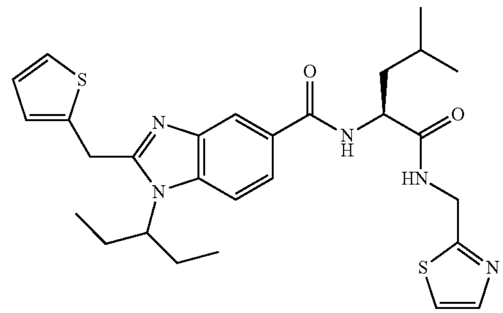 [SMILES: CCC(CC)n1c(Cc2cccs2)nc2cc(C(=O)N[C@@H](CC(C)C)C(=O)NCc3nccs3)ccc21] | 538.2 | 6_3_1 | 1.40 |
| 251 | 1-(-Ethyl-propyl)-2-thiophen-2-ylmethyl-1H-benzoimidazole-5-carboxylic acid [(S)-3-methyl-1-(3,3,3-trifluoro-propylcarbamoyl)-butyl]-amide | 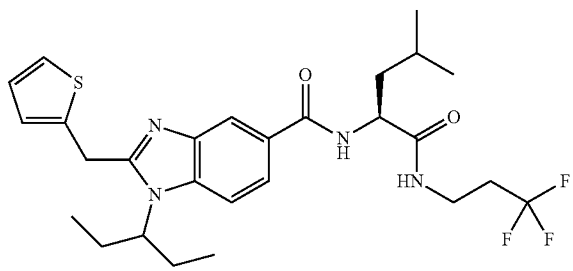 [SMILES: CCC(CC)n1c(Cc2cccs2)nc2cc(C(=O)N[C@@H](CC(C)C)C(=O)NCCC(F)(F)F)ccc21] | 537.2 | 6_3_1 | 1.54 |
| 252 | 1-(1-Ethyl-propyl)-2-thiophen-2-ylmethyl-1H-benzoimidazole-5-carboxylic acid [(S)-1-(3-dimethylamino-benzylcarbamoyl)-3-methyl-butyl]-amide | 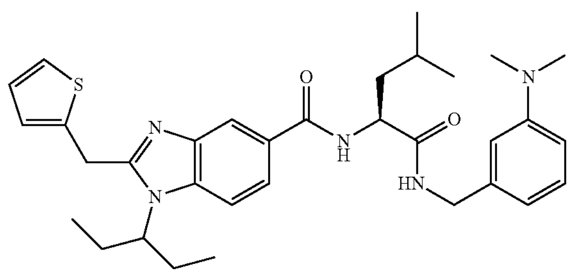 [SMILES: CCC(CC)n1c(Cc2cccs2)nc2cc(C(=O)N[C@@H](CC(C)C)C(=O)NCc3cccc(N(C)C)c3)ccc21] | 574.3 | 6_3_1 | 1.30 |
| 253 | 1-(1-Ethyl-propyl)-2-thiophen-2-ylmethyl-1H-benzoimidazole-5-carboxylic acid [(S)-3-methyl-1-(4-pyrrolidin-1-yl-butylcarbamoyl)-butyl]-amide | 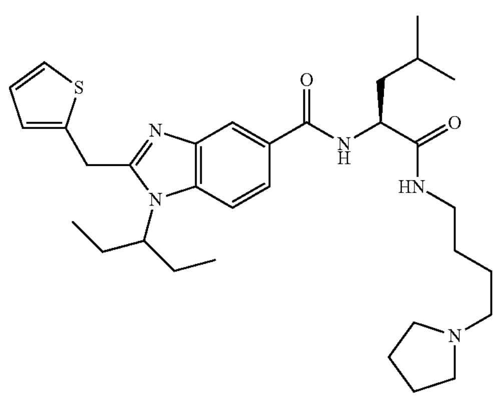 [SMILES: CCC(CC)n1c(Cc2cccs2)nc2cc(C(=O)N[C@@H](CC(C)C)C(=O)NCCCCN3CCCC3)ccc21] | 566.3 | 6_3_1 | 1.25 |
| 254 | 1-(1-Ethyl-propyl)-2-thiophen-2-ylmethyl-1H-benzoimidazole-5-carboxylic acid {(S)-3-methyl-1-[(oxazol-2-ylmethyl)-carbamoyl]-butyl}-amide | 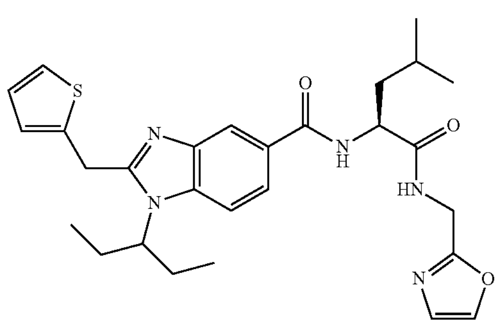 [SMILES: CCC(CC)n1c(Cc2cccs2)nc2cc(C(=O)N[C@@H](CC(C)C)C(=O)NCc3ncco3)ccc21] | 522.3 | 6_3_1 | 1.39 |

-continued

| Exp. No. | Chemical Name | Structure | m/z [M + H]+ | LCMS method | R$_t$ [min] |
|---|---|---|---|---|---|
| 255 | 1-(1-Ethyl-propyl)-2-thiophen-2-ylmethyl-1H-benzoimidazole-5-carboxylic acid [(S)-1-(2-methoxy-phenylcarbamoyl)-3-methyl-butyl]-amide | 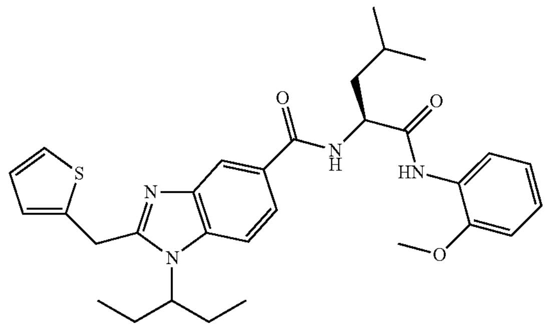 [SMILES: CCC(CC)n1c(Cc2cccs2)nc2cc(C(=O)N[C@@H](CC(C)C)C(=O)Nc3ccccc3OC)ccc21] | 547.2 | 6_3_1 | 1.67 |
| 256 | 1-(1-Ethyl-propyl)-2-thiophen-2-ylmethyl-1H-benzoimidazole-5-carboxylic acid {(S)-1-[(2-methoxy-benzyl)-methyl-carbamoyl]-3-methyl-butyl}-amide | 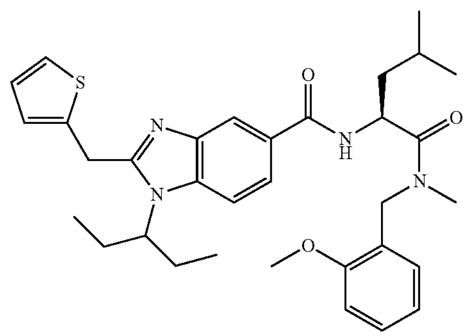 [SMILES: CCC(CC)n1c(Cc2cccs2)nc2cc(C(=O)N[C@@H](CC(C)C)C(=O)N(C)Cc3ccccc3OC)ccc21] | 575.2 | 6_3_1 | 1.69 |
| 257 | 1-(1-Ethyl-propyl)-2-thiophen-2-ylmethyl-1H-benzoimidazole-5-carboxylic acid {(S)-3-methyl-1-[(1-methyl-piperidin-2-ylmethyl)-carbamoyl]-butyl}-amide | 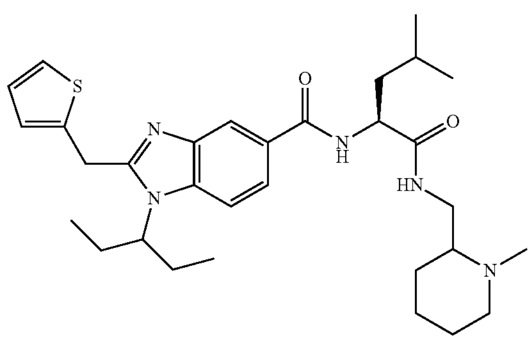 [SMILES: CCC(CC)n1c(Cc2cccs2)nc2cc(C(=O)N[C@@H](CC(C)C)C(=O)NCC3CCCCN3C)ccc21] | 552.3 | 6_3_1 | 1.26 |
| 258 | 1-(1-Ethyl-propyl)-2-thiophen-2-ylmethyl-1H-benzoimidazole-5-carboxylic acid [(S)-3-methyl-1-(2-methylsulfanyl-ethylcarbamoyl)-butyl]-amide | 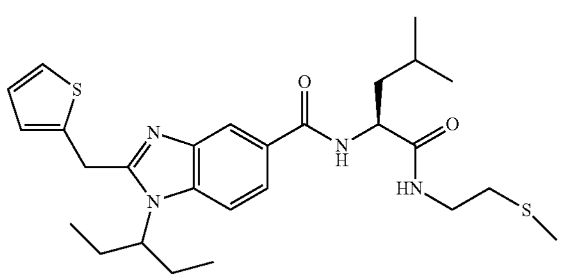 [SMILES: CCC(CC)n1c(Cc2cccs2)nc2cc(C(=O)N[C@@H](CC(C)C)C(=O)NCCSC)ccc21] | 515.2 | 6_3_1 | 1.47 |
| 259 | 1-(1-Ethyl-propyl)-2-thiophen-2-ylmethyl-1H-benzoimidazole-5-carboxylic acid [(S)-3-methyl-1-((1S,2R)-2-phenyl-cyclopropylcarbamoyl)-butyl]-amide | 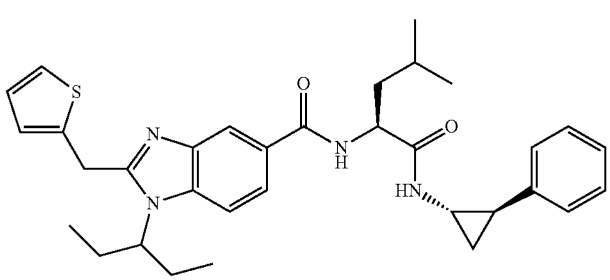 [SMILES: CCC(CC)n1c(Cc2cccs2)nc2cc(C(=O)N[C@@H](CC(C)C)C(=O)N[C@H]3C[C@@H]3c3ccccc3)ccc21] | 557.2 | 6_3_1 | 1.67 |

-continued

| Exp. No. | Chemical Name | Structure | m/z [M + H]+ | LCMS method | R_t [min] |
|---|---|---|---|---|---|
| 260 | 1-(1-Ethyl-propyl)-2-thiophen-2-ylmethyl-1H-benzoimidazole-5-carboxylic acid [(S)-1-((R)-3-dimethylamino-pyrrolidine-1-carbonyl)-3-methyl-butyl]-amide | 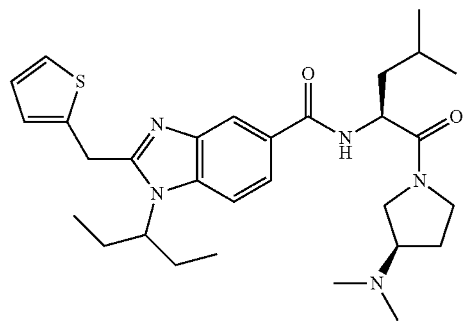 [SMILES: CCC(CC)n1c(Cc2cccs2)nc2cc(C(=O)N[C@@H](CC(C)C)C(=O)N3CC[C@@H](N(C)C)C3)ccc21] | 538.3 | 6_3_1 | 1.20 |
| 261 | 1-(1-Ethyl-propyl)-2-thiophen-2-ylmethyl-1H-benzoimidazole-5-carboxylic acid [(S)-1-(4-diethylamino-butylcarbamoyl)-3-methyl-butyl]-amide | 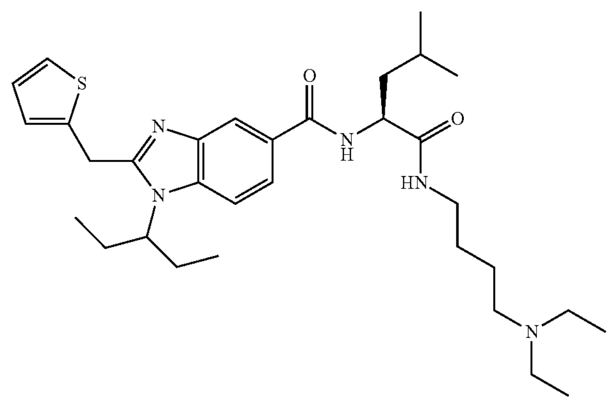 [SMILES: CCC(CC)n1c(Cc2cccs2)nc2cc(C(=O)N[C@@H](CC(C)C)C(=O)NCCCCN(CC)CC)ccc21] | 568.3 | 6_3_1 | 1.25 |
| 262 | 1-(1-Ethyl-propyl)-2-thiophen-2-ylmethyl-1H-benzoimidazole-5-carboxylic acid {(S)-1-[(S)-1-(2-fluoro-phenyl)-ethylcarbamoyl]-3-methyl-butyl}-amide | 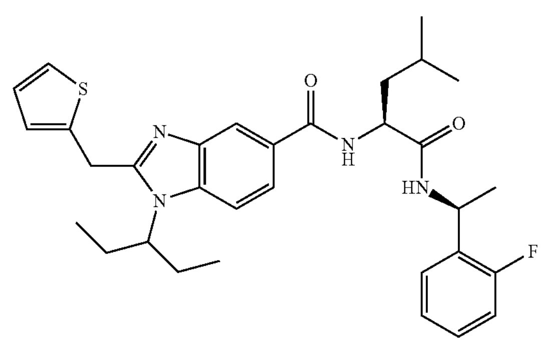 [SMILES: CCC(CC)n1c(Cc2cccs2)nc2cc(C(=O)N[C@@H](CC(C)C)C(=O)N[C@@H](C)c3ccccc3F)ccc21] | 563.2 | 6_3_1 | 1.65 |
| 263 | 1-(1-Ethyl-propyl)-2-thiophen-2-ylmethyl-1H-benzoimidazole-5-carboxylic acid [(S)-1-(benzyl-methyl-carbamoyl)-3-methyl-butyl]-amide | 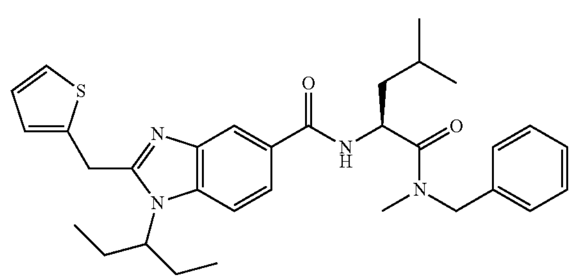 [SMILES: CCC(CC)n1c(Cc2cccs2)nc2cc(C(=O)N[C@@H](CC(C)C)C(=O)N(C)Cc3ccccc3)ccc21] | 545.2 | 6_3_1 | 1.67 |

-continued

| Exp. No. | Chemical Name | Structure | m/z [M + H]+ | LCMS method | R$_t$ [min] |
|---|---|---|---|---|---|
| 264 | 1-(1-Ethyl-propyl)-2-thiophen-2-ylmethyl-1H-benzoimidazole-5-carboxylic acid [(S)-3-methyl-1-(methyl-phenethyl-carbamoyl)-butyl]-amide | 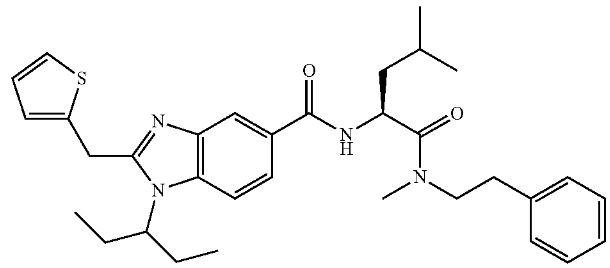 [SMILES: CCC(CC)n1c(Cc2cccs2)nc2cc(C(=O)N[C@@H](CC(C)C)C(=O)N(C)CCc3ccccc3)ccc21] | 559.2 | 6_3_1 | 1.71 |
| 265 | 1-(1-Ethyl-propyl)-2-thiophen-2-ylmethyl-1H-benzoimidazole-5-carboxylic acid [(S)-1-(4-methoxy-phenylcarbamoyl)-3-methyl-butyl]-amide | 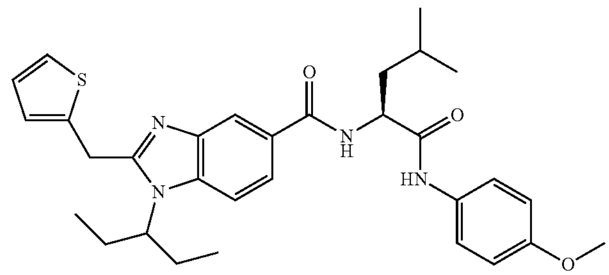 [SMILES: CCC(CC)n1c(Cc2cccs2)nc2cc(C(=O)N[C@@H](CC(C)C)C(=O)Nc3ccc(OC)cc3)ccc21] | 547.2 | 6_3_1 | 1.60 |
| 266 | 1-(1-Ethyl-propyl)-2-thiophen-2-ylmethyl-1H-benzoimidazole-5-carboxylic acid [(S)-1-(4-dimethylamino-benzylcarbamoyl)-3-methyl-butyl]-amide | 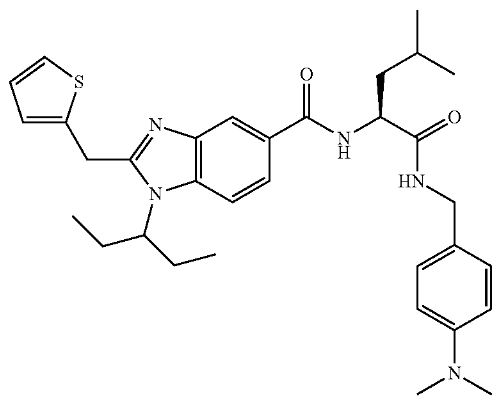 [SMILES: CCC(CC)n1c(Cc2cccs2)nc2cc(C(=O)N[C@@H](CC(C)C)C(=O)NCc3ccc(N(C)C)cc3)ccc21] | 574.3 | 6_3_1 | 1.28 |
| 267 | 1-(1-Ethyl-propyl)-2-thiophen-2-ylmethyl-1H-benzoimidazole-5-carboxylic acid [(S)-1-(2-dimethylamino-ethylcarbamoyl)-3-methyl-butyl]-amide | 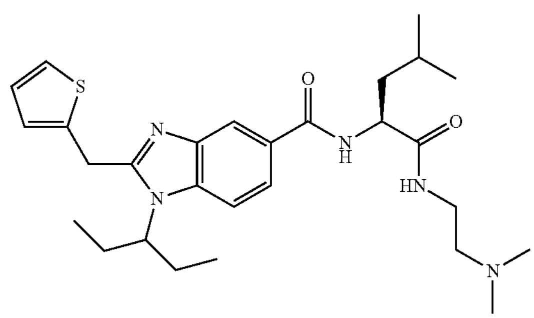 [SMILES: CCC(CC)n1c(Cc2cccs2)nc2cc(C(=O)N[C@@H](CC(C)C)C(=O)NCCN(C)C)ccc21] | 512.3 | 6_3_1 | 1.24 |
| 268 | 1-(1-Ethyl-propyl)-2-thiophen-2-ylmethyl-1H-benzoimidazole-5-carboxylic acid [(S)-1-(2-methoxy-ethylcarbamoyl)-3-methyl-butyl]-amide | 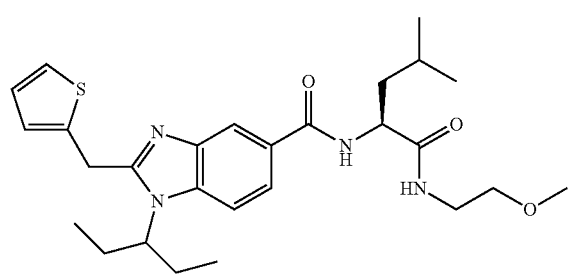 [SMILES: CCC(CC)n1c(Cc2cccs2)nc2cc(C(=O)N[C@@H](CC(C)C)C(=O)NCCOC)ccc21] | 499.2 | 6_3_1 | 1.38 |

-continued

| Exp. No. | Chemical Name | Structure | m/z [M + H]+ | LCMS method | $R_t$ [min] |
|---|---|---|---|---|---|
| 269 | 1-(1-Ethyl-propyl)-2-thiophen-2-ylmethyl-1H-benzoimidazole-5-carboxylic acid {(S)-3-methyl-1-[4-(3-trifluoromethyl-phenyl)-piperazine-1-carbonyl]-butyl}-amide | 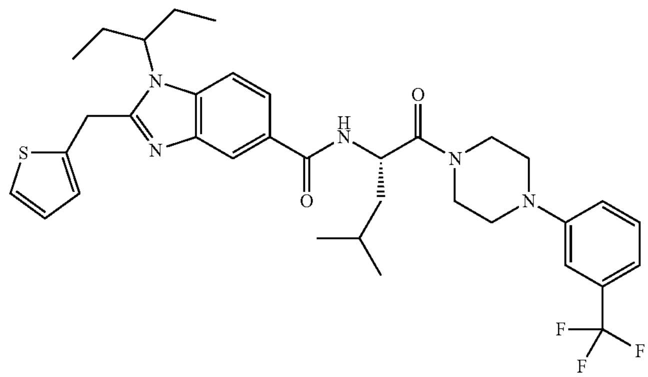 [SMILES: CCC(CC)n1c(Cc2cccs2)nc2cc(C(=O)N[C@@H](CC(C)C)C(=O)N3CCN(c4cccc(C(F)(F)F)c4)CC3)ccc21] | 654.2 | 6_1_1 | 3.67 |
| 270 | 1-(1-Ethyl-propyl)-2-thiophen-2-ylmethyl-1H-benzoimidazole-5-carboxylic acid {(S)-1-[4-(4-fluoro-phenyl)-piperazine-1-carbonyl]-3-methyl-butyl}-amide | 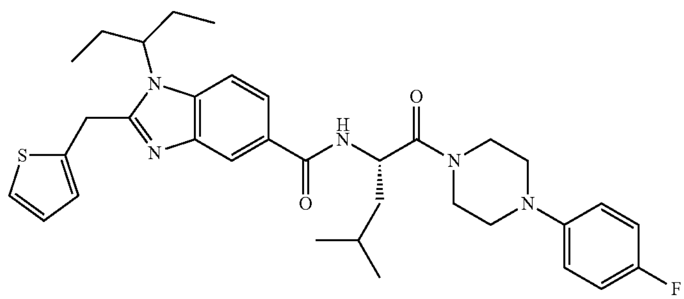 [SMILES: CCC(CC)n1c(Cc2cccs2)nc2cc(C(=O)N[C@@H](CC(C)C)C(=O)N3CCN(c4ccc(F)cc4)CC3)ccc21] | 604.2 | 6_1_1 | 3.32 |
| 271 | 1-(1-Ethyl-propyl)-2-thiophen-2-ylmethyl-1H-benzoimidazole-5-carboxylic acid [(S)-1-(4-benzyl-piperazine-1-carbonyl)-3-methyl-butyl]-amide | 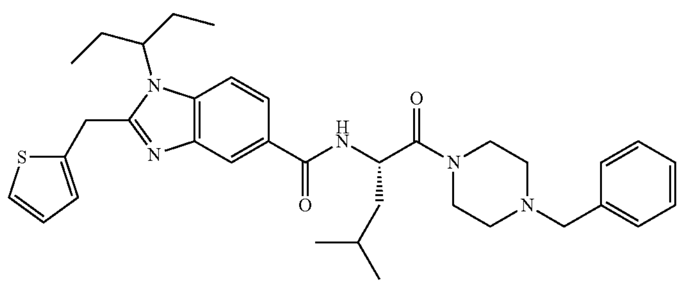 [SMILES: CCC(CC)n1c(Cc2cccs2)nc2cc(C(=O)N[C@@H](CC(C)C)C(=O)N3CCN(Cc4ccccc4)CC3)ccc21] | 600.2 | 6_1_1 | 2.75 |
| 272 | 1-(1-Ethyl-propyl)-2-thiophen-2-ylmethyl-1H-benzoimidazole-5-carboxylic acid [(S)-1-(4-isobutyl-piperazine-1-carbonyl)-3-methyl-butyl]-amide | 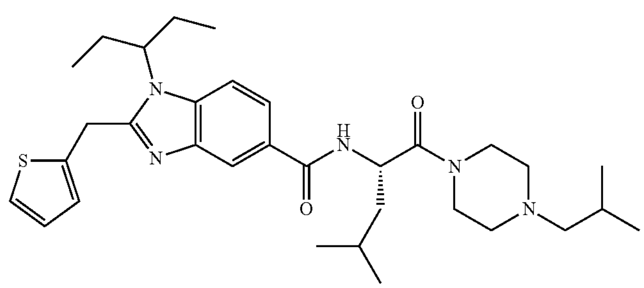 [SMILES: CCC(CC)n1c(Cc2cccs2)nc2cc(C(=O)N[C@@H](CC(C)C)C(=O)N3CCN(CC(C)C)CC3)ccc21] | 566.3 | 5_7_1 | 2.54 |
| 273 | 1-(1-Ethyl-propyl)-2-thiophen-2-ylmethyl-1H-benzoimidazole-5-carboxylic acid [(S)-3-methyl-1-((1R,5S)-8-methyl-8-aza-bicyclo[3.2.1]oct-3-ylcarbamoyl)-butyl]-amide | 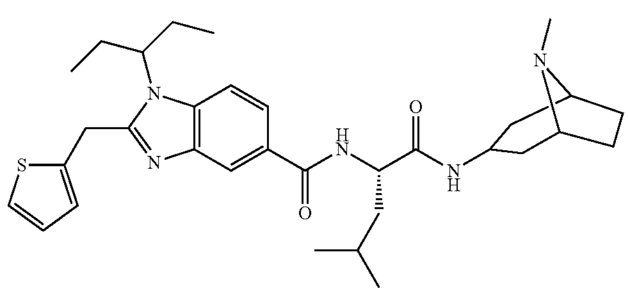 [SMILES: CCC(CC)n1c(Cc2cccs2)nc2cc(C(=O)N[C@@H](CC(C)C)C(=O)NC3CC4CCC(C3)N4C)ccc21] | 564.3 | 5_7_1 | 2.46 |

| Exp. No. | Chemical Name | Structure | m/z [M + H]+ | LCMS method | R_t [min] |
|---|---|---|---|---|---|
| 274 | 1-(1-Ethyl-propyl)-2-thiophen-2-ylmethyl-1H-benzoimidazole-5-carboxylic acid {(S)-1-[4-(2-chloro-6-fluoro-benzyl)-[1,4]diazepane-1-carbonyl]-3-methyl-butyl}-amide | 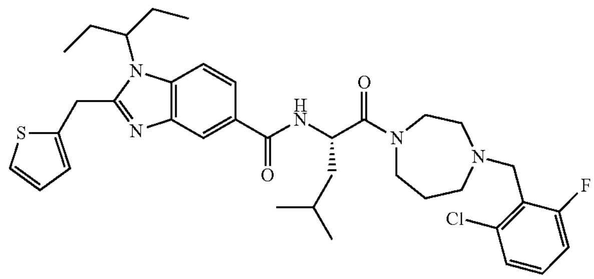 [SMILES: CCC(CC)n1c(Cc2cccs2)nc2cc(C(=O)N[C@@H](CC(C)C)C(=O)N3CCCN(Cc4c(F)cccc4Cl)CC3)ccc21] | 666.2 | 5_7_1 | 2.65 |
| 275 | 1-(1-Ethyl-propyl)-2-thiophen-2-ylmethyl-1H-benzoimidazole-5-carboxylic acid {(S)-3-methyl-1-[(octahydro-quinolizin-1-ylmethyl)-carbamoyl]-butyl}-amide | 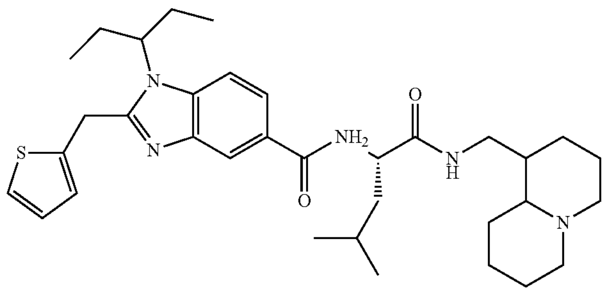 [SMILES: CCC(CC)n1c(Cc2cccs2)nc2cc(C(=O)N[C@@H](CC(C)C)C(=O)NCC3CCCN4CCCCC34)ccc21] | 592.3 | 5_7_1 | 2.52 |
| 276 | 1-(1-Ethyl-propyl)-2-thiophen-2-ylmethyl-1H-benzoimidazole-5-carboxylic acid [(S)-3-methyl-1-((3R)-8-methyl-8-aza-bicyclo[3.2.1]oct-3-ylcarbamoyl)-butyl]-amide | 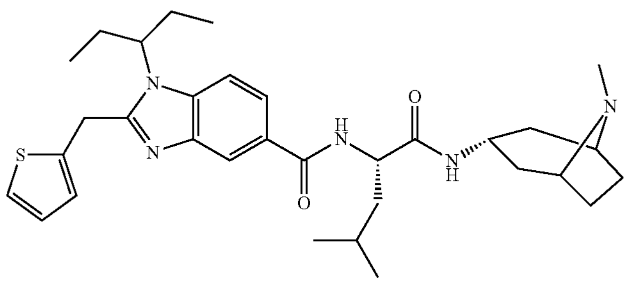 | 564.3 | 5_7_1 | 2.46 |
| 277 | 1-(1-Ethyl-propyl)-2-thiophen-2-ylmethyl-1H-benzoimidazole-5-carboxylic acid ((S)-1-{3-[4-(2-chloro-6-fluoro-benzyl)-piperazin-1-yl]-propylcarbamoyl}-3-methyl-butyl)-amide | 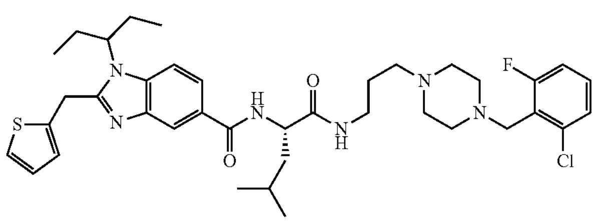 [SMILES: CCC(CC)n1c(Cc2cccs2)nc2cc(C(=O)N[C@@H](CC(C)C)C(=O)NCCCN3CCN(Cc4c(F)cccc4Cl)CC3)ccc21] | 709.3 | 5_7_1 | 2.72 |
| 278 | 1-(1-Ethyl-propyl)-2-thiophen-2-ylmethyl-1H-benzoimidazole-5-carboxylic acid {(S)-1-[3-{4-ethyl-piperazin-1-yl)-propylcarbamoyl]-3-methyl-butyl}-amide | 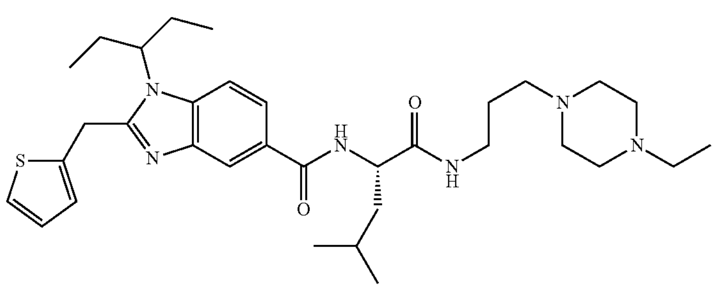 [SMILES: CCC(CC)n1c(Cc2cccs2)nc2cc(C(=O)N[C@@H](CC(C)C)C(=O)NCCCN3CCN(CC)CC3)ccc21] | 595.3 | 5_7_1 | 2.35 |

-continued

| Exp. No. | Chemical Name | Structure | m/z [M + H]+ | LCMS method | R_t [min] |
|---|---|---|---|---|---|
| 279 | 1-(1-Ethyl-propyl)-2-thiophen-2-ylmethyl-1H-benzoimidazole-5-carboxylic acid ((S)-1-{3-[4-(4-methoxy-phenyl)-piperazin-1-yl]-propylcarbamoyl}-3-methyl-butyl)-amide | 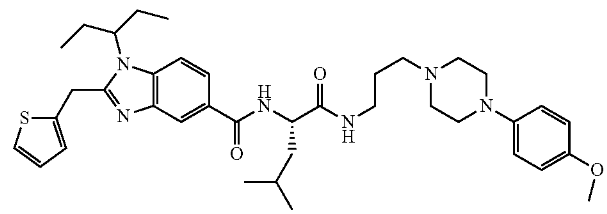 [SMILES: CCC(CC)n1c(Cc2cccs2)nc2cc(C(=O)N[C@@H](CC(C)C)C(=O)NCCCN3CCN(c4ccc(OC)cc4)CC3)ccc21] | 673.3 | 5_7_1 | 2.68 |
| 280 | 1-(1-Ethyl-propyl)-2-thiophen-2-ylmethyl-1H-benzoimidazole-5-carboxylic acid {(S)-3-methyl-1-[4-(4-methyl-piperazin-1-yl)-piperidine-1-carbonyl]-butyl}-amide | 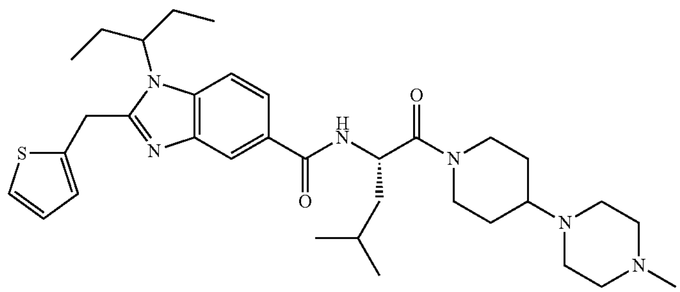 [SMILES: CCC(CC)n1c(Cc2cccs2)nc2cc(C(=O)N[C@@H](CC(C)C)C(=O)N3CCC(N4CCN(C)CC4)CC3)ccc21] | 607.3 | 5_7_1 | 2.35 |
| 281 | 1-(1-Ethyl-propyl)-2-thiophen-2-ylmethyl-1H-benzoimidazole-5-carboxylic acid [(S)-3-methyl-1-(3-methyl-[1,4']bipiperidinyl-1'-carbonyl)-butyl]-amide | 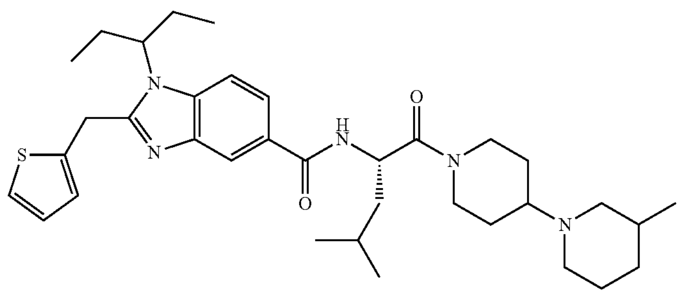 [SMILES: CCC(CC)n1c(Cc2cccs2)nc2cc(C(=O)N[C@@H](CC(C)C)C(=O)N3CCC(N4CCCC(C)C4)CC3)ccc21] | 606.3 | 5_7_1 | 2.57 |
| 282 | 1-(1-Ethyl-propyl)-2-thiophen-2-ylmethyl-1H-benzoimidazole-5-carboxylic acid [(S)-3-methyl-1-(4-methyl-[1,4']bipiperidinyl-1'-carbonyl)-butyl]-amide | 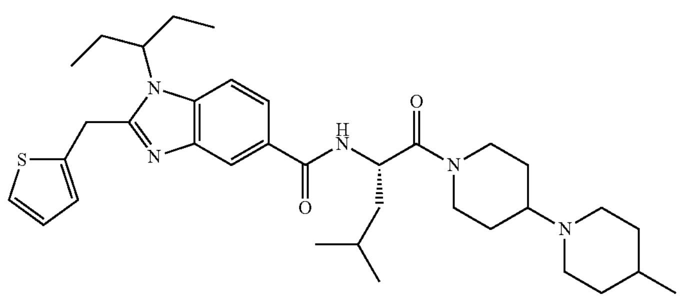 [SMILES: CCC(CC)n1c(Cc2cccs2)nc2cc(C(=O)N[C@@H](CC(C)C)C(=O)N3CCC(N4CCC(C)CC4)CC3)ccc21] | 606.3 | 5_7_1 | 2.57 |
| 283 | 1-(1-Ethyl-propyl)-2-thiophen-2-ylmethyl-1H-benzoimidazole-5-carboxylic acid {(S)-3-methyl-1-[4-(4-methyl-piperidin-1-ylmethyl)-phenylcarbamoyl]-butyl}-amide | 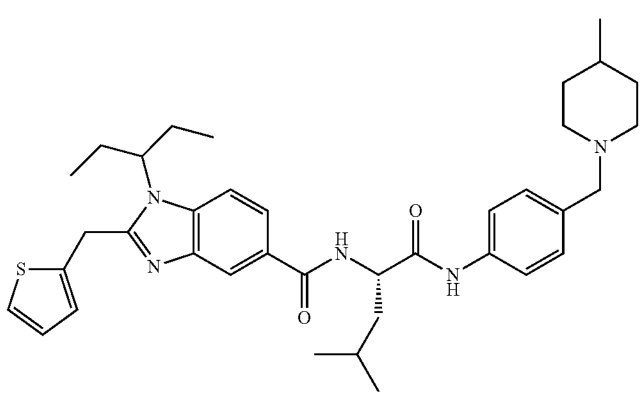 [SMILES: CCC(CC)n1c(Cc2cccs2)nc2cc(C(=O)N[C@@H](CC(C)C)C(=O)Nc3ccc(CN4CCC(C)CC4)cc3)ccc21] | 628.4 | 5_7_1 | 2.70 |

| Exp. No. | Chemical Name | Structure | m/z [M + H]+ | LCMS method | R_t [min] |
|---|---|---|---|---|---|
| 284 | 1-(1-Ethyl-propyl)-2-thiophen-2-ylmethyl-1H-benzoimidazole-5-carboxylic acid [(S)-1-(4-dipropylamino-piperidine-1-carbonyl)-3-methyl-butyl]-amide | 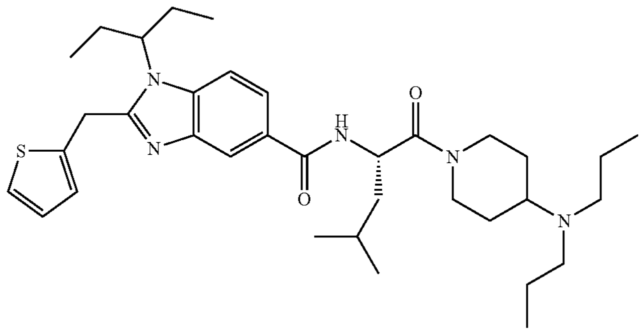 [SMILES: CCCN(CCC)C1CCN(C(=O)[C@H](CC(C)C)NC(=O)c2ccc3c(c2)nc(Cc2cccs2)n3C(CC)CC)CC1] | 608.3 | 5_7_1 | 2.61 |
| 285 | 1-(1-Ethyl-propyl)-2-thiophen-2-ylmethyl-1H-benzoimidazole-5-carboxylic acid [(S)-3-methyl-1-(1-propyl-piperidin-4-ylcarbamoyl)-butyl]-amide | 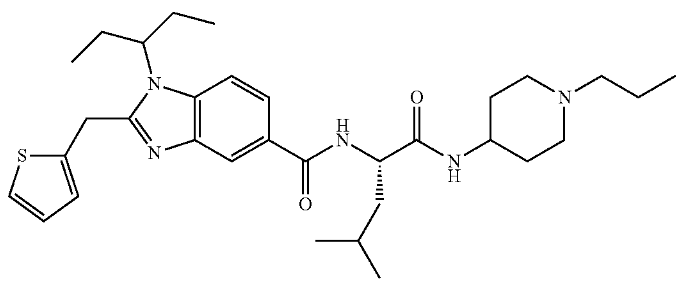 [SMILES: CCCN1CCC(NC(=O)[C@H](CC(C)C)NC(=O)c2ccc3c(c2)nc(Cc2cccs2)n3C(CC)CC)CC1] | 566.3 | 5_7_1 | 2.49 |
| 286 | 1-(1-Ethyl-propyl)-2-thiophen-2-ylmethyl-1H-benzoimidazole-5-carboxylic acid {(S)-1-[(1-benzyl-piperidin-3-ylmethyl)-carbamoyl]-3-methyl-butyl}-amide | 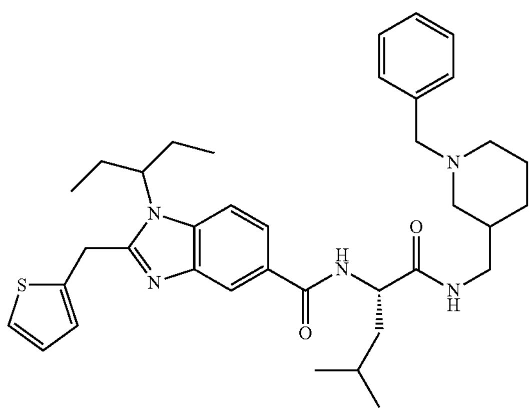 [SMILES: CCC(CC)n1c(Cc2cccs2)nc2cc(C(=O)N[C@@H](CC(C)C)C(=O)NCC3CCCN(Cc4ccccc4)C3)ccc21] | 628.3 | 6_1_1 | 2.82 |
| 287 | 1-(1-Ethyl-propyl)-2-thiophen-2-ylmethyl-1H-benzoimidazole-5-carboxylic acid [(S)-1-(3-azepan-1-yl-2,2-dimethyl-propylcarbamoyl)-3-methyl-butyl]-amide | 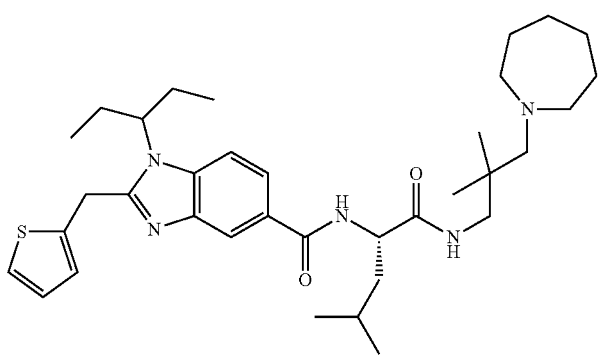 [SMILES: CCC(CC)n1c(Cc2cccs2)nc2cc(C(=O)N[C@@H](CC(C)C)C(=O)NCC(C)(C)CN3CCCCCC3)ccc21] | 608.3 | 6_1_1 | 2.84 |

-continued

| Exp. No. | Chemical Name | Structure | m/z [M + H]$^+$ | LCMS method | R$_t$ [min] |
|---|---|---|---|---|---|
| 288 | 1-(1-Ethyl-propyl)-2-thiophen-2-ylmethyl-1H-benzoimidazole-5-carboxylic acid {(S)-1-[1-(2,6-dimethoxy-benzyl)-piperidin-4-ylcarbamoyl]-3-methyl-butyl}-amide | 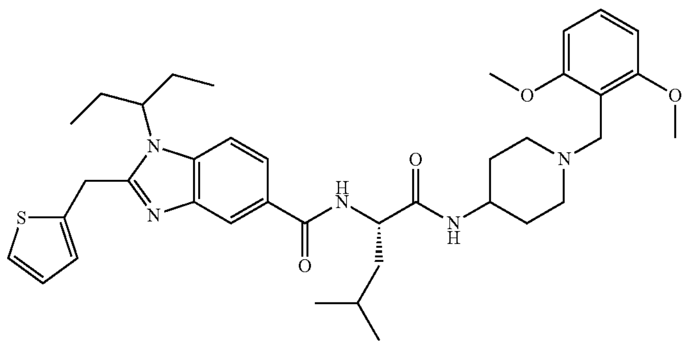 [SMILES: CCC(CC)n1c(Cc2cccs2)nc2cc(C(=O)N[C@@H](CC(C)C)C(=O)NC3CCN(Cc4c(OC)cccc4OC)CC3)ccc21] | 674.3 | 6_1_1 | 2.82 |
| 289 | 1-(1-Ethyl-propyl)-2-thiophen-2-ylmethyl-1H-benzoimidazole-5-carboxylic acid {(S)-3-methyl-1-[2-(1-methyl-piperidin-2-yl)-ethylcarbamoyl]-butyl}-amide | 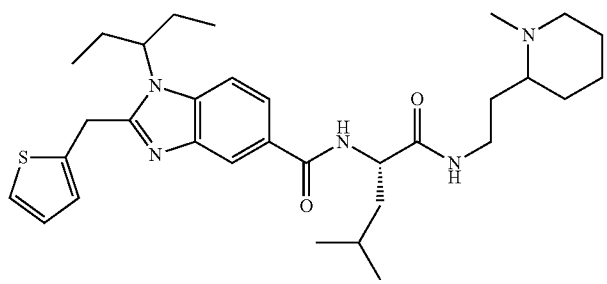 [SMILES: CCC(CC)n1c(Cc2cccs2)nc2cc(C(=O)N[C@@H](CC(C)C)C(=O)NCCC3CCCCN3C)ccc21] | 566.3 | 6_1_1 | 2.62 |
| 290 | 1-(1-Ethyl-propyl)-2-thiophen-2-ylmethyl-1H-benzoimidazole-5-carboxylic acid {(S)-1-[(1-benzyl-pyrrolidin-3-ylmethyl)-carbamoyl]-3-methyl-butyl}-amide | 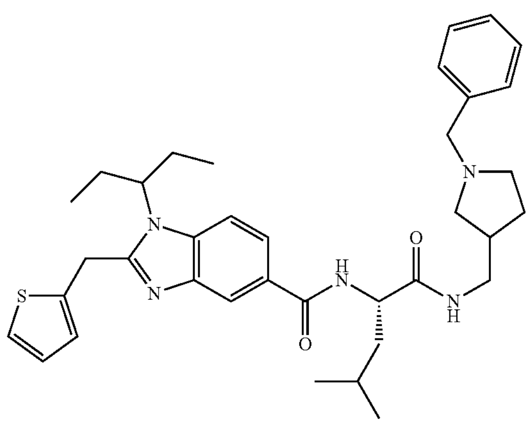 [SMILES: CCC(CC)n1c(Cc2cccs2)nc2cc(C(=O)N[C@@H](CC(C)C)C(=O)NCC3CCN(Cc4ccccc4)C3)ccc21] | 614.3 | 6_1_1 | 2.79 |
| 291 | 1-(1-Ethyl-propyl)-2-thiophen-2-ylmethyl-1H-benzoimidazole-5-carboxylic acid {(S)-3-methyl-1-[(1-phenethyl-pyrrolidin-3-ylmethyl)-carbamoyl]-butyl}-amide | 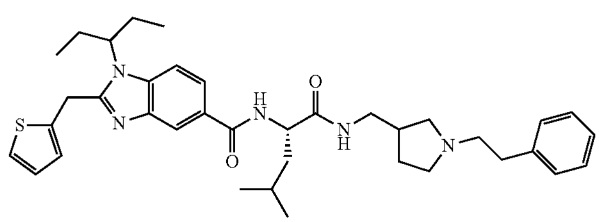 [SMILES: CCC(CC)n1c(Cc2cccs2)nc2cc(C(=O)N[C@@H](CC(C)C)C(=O)NCC3CCN(CCc4ccccc4)C3)ccc21] | 628.3 | 6_1_1 | 2.84 |

-continued

| Exp. No. | Chemical Name | Structure | m/z [M + H]+ | LCMS method | R_t [min] |
|---|---|---|---|---|---|
| 292 | 1-(1-Ethyl-propyl)-2-thiophen-2-ylmethyl-1H-benzoimidazole-5-carboxylic acid [(S)-3-methyl-1-(9-methyl-9-aza-bicyclo[3.3.1]non-3-ylcarbamoyl)-butyl]-amide | 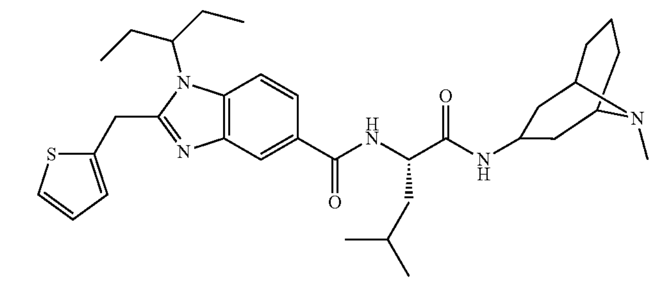 [SMILES: CCC(CC)n1c(Cc2cccs2)nc2cc(C(=O)N[C@@H](CC(C)C)C(=O)NC3CC4CCCC(C3)N4C)ccc21] | 578.3 | 6_1_1 | 2.64 |
| 293 | 1-(1-Ethyl-propyl)-2-thiophen-2-ylmethyl-1H-benzoimidazole-5-carboxylic acid [(S)-3-methyl-1-(3,4,5,6-tetrahydro-2H-[1,2']bipyridinyl-4-ylcarbamoyl)-butyl]-amide | 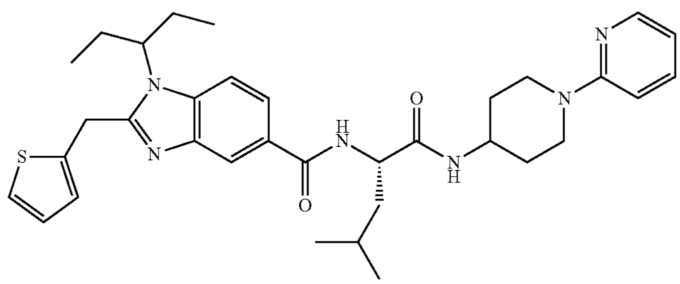 [SMILES: CCC(CC)n1c(Cc2cccs2)nc2cc(C(=O)N[C@@H](CC(C)C)C(=O)NC3CCN(c4ccccn4)CC3)ccc21] | 601.2 | 5_7_1 | 2.51 |
| 294 | 1-(1-Ethyl-propyl)-2-thiophen-2-ylmethyl-1H-benzoimidazole-5-carboxylic acid {(S)-1-[3-(2,6-dimethyl-morpholin-4-yl)-propylcarbamoyl]-3-methyl-butyl}-amide | 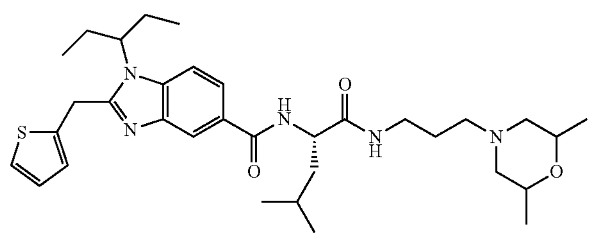 [SMILES: CCC(CC)n1c(Cc2cccs2)nc2cc(C(=O)N[C@@H](CC(C)C)C(=O)NCCCN3CC(C)OC(C)C3)ccc21] | 596.3 | 5_7_1 | 2.25 |
| 295 | 1-(1-Ethyl-propyl)-2-thiophen-2-ylmethyl-1H-benzoimidazole-5-carboxylic acid [(S)-3-methyl-1-(1-pyridin-2-ylmethyl-piperidin-4-ylcarbamoyl)-butyl]-amide | 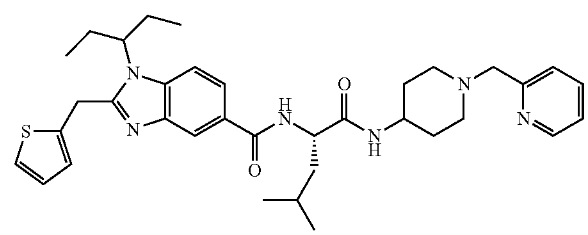 [SMILES: CCC(CC)n1c(Cc2cccs2)nc2cc(C(=O)N[C@@H](CC(C)C)C(=O)NC3CCN(Cc4ccccn4)CC3)ccc21] | 615.4 | 5_7_1 | 2.09 |
| 296 | 1-(1-Ethyl-propyl)-2-thiophen-2-ylmethyl-1H-benzoimidazole-5-carboxylic acid {(S)-1-[4-(3,4-dihydro-1H-isoquinolin-2-yl)-piperidine-1-carbonyl]-3-methyl-butyl}-amide | 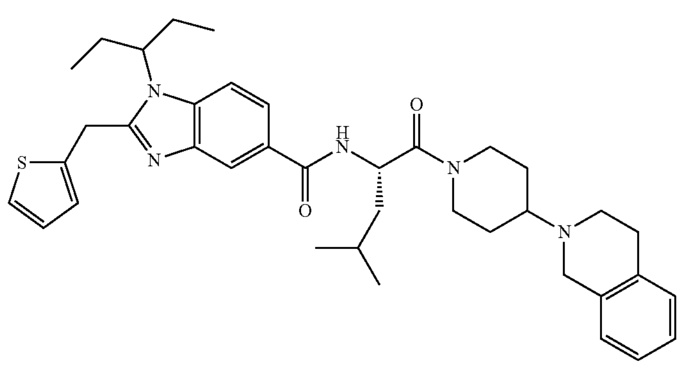 [SMILES: CCC(CC)n1c(Cc2cccs2)nc2cc(C(=O)N[C@@H](CC(C)C)C(=O)N3CCC(N4CCc5ccccc5C4)CC3)ccc21] | 640.3 | 5_7_1 | 2.61 |

-continued

| Exp. No. | Chemical Name | Structure | m/z [M + H]+ | LCMS method | R_t [min] |
|---|---|---|---|---|---|
| 297 | 1-(1-Ethyl-propyl)-2-thiophen-2-ylmethyl-1H-benzoimidazole-5-carboxylic acid {(S)-3-methyl-1-[(1-methyl-piperidin-3-ylmethyl)-carbamoyl]-butyl}-amide | 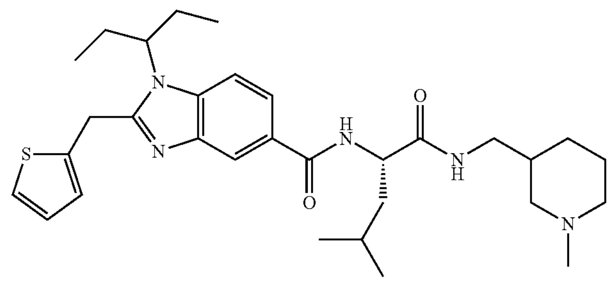 [SMILES: CCC(CC)n1c(Cc2cccs2)nc2cc(C(=O)N[C@@H](CC(C)C)C(=O)NCC3CCCN(C)C3)ccc21] | 552.3 | 5_7_1 | 2.43 |
| 298 | 1-(1-Ethyl-propyl)-2-thiophen-2-ylmethyl-1H-benzoimidazole-5-carboxylic acid [(S)-3-methyl-1-(1-pyridin-4-ylmethyl-piperidin-4-ylcarbamoyl)-butyl]-amide | 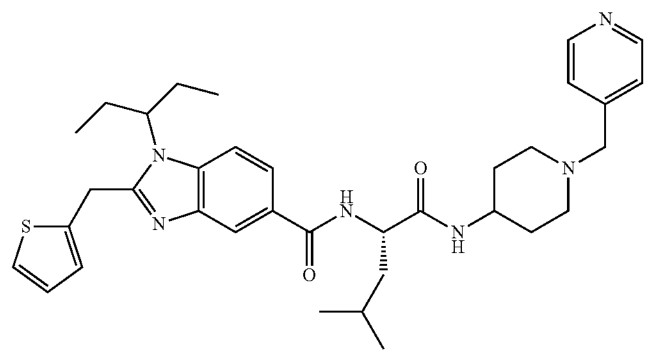 [SMILES: CCC(CC)n1c(Cc2cccs2)nc2cc(C(=O)N[C@@H](CC(C)C)C(=O)NC3CCN(Cc4ccncc4)CC3)ccc21] | 615.3 | 5_7_1 | 2.38 |
| 299 | 1-(1-Ethyl-propyl)-2-thiophen-2-ylmethyl-1H-benzoimidazole-5-carboxylic acid [(S)-3-methyl-1-(3-piperidin-1-yl-pyrrolidine-1-carbonyl)-butyl]-amide | 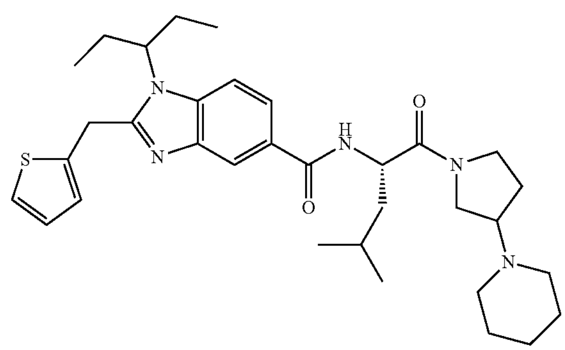 [SMILES: CCC(CC)n1c(Cc2cccs2)nc2cc(C(=O)N[C@@H](CC(C)C)C(=O)N3CCC(N4CCCCC4)C3)ccc21] | 578.3 | 5_7_1 | 2.46 |
| 300 | 1-(1-Ethyl-propyl)-2-thiophen-2-ylmethyl-1H-benzoimidazole-5-carboxylic acid {(S)-3-methyl-1-[3-(4-methyl-piperidin-1-yl)-pyrrolidine-1-carbonyl]-butyl}-amide | 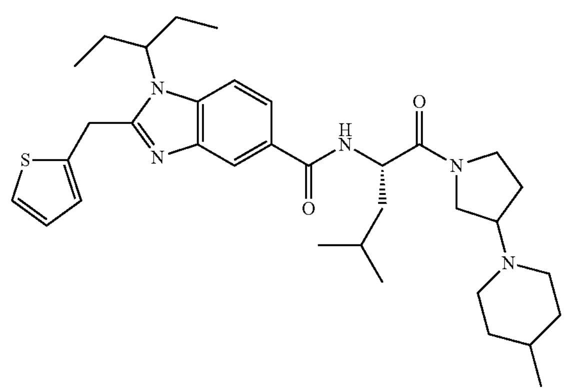 [SMILES: CCC(CC)n1c(Cc2cccs2)nc2cc(C(=O)N[C@@H](CC(C)C)C(=O)N3CCC(N4CCC(C)CC4)C3)ccc21] | 592.3 | 5_7_1 | 2.52 |

| Exp. No. | Chemical Name | Structure | m/z [M + H]+ | LCMS method | R_t [min] |
|---|---|---|---|---|---|
| 301 | 1-(1-Ethyl-propyl)-2-thiophen-2-ylmethyl-1H-benzoimidazole-5-carboxylic acid {(S)-1-[1-(3-fluoro-benzyl)-piperidin-4-ylcarbamoyl]-3-methyl-butyl}-amide | 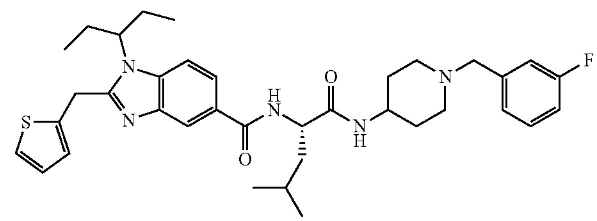 [SMILES: CCC(CC)n1c(Cc2cccs2)nc2cc(C(=O)N[C@@H](CC(C)C)C(=O)NC3CCN(Cc4cccc(F)c4)CC3)ccc21] | 632.3 | 5_7_1 | 2.59 |
| 302 | 1-(1-Ethyl-propyl)-2-thiophen-2-ylmethyl-1H-benzoimidazole-5-carboxylic acid {(S)-3-methyl-1-[(1-phenethyl-piperidin-3-ylmethyl)-carbamoyl]-butyl}-amide | 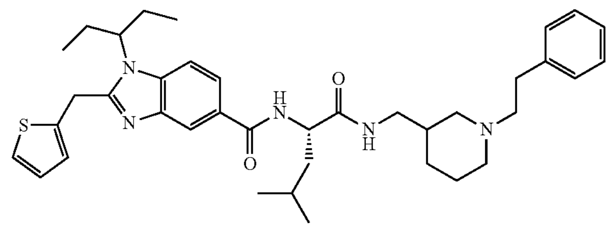 [SMILES: CCC(CC)n1c(Cc2cccs2)nc2cc(C(=O)N[C@@H](CC(C)C)C(=O)NCC3CCCN(CCc4ccccc4)C3)ccc21] | 642.3 | 5_7_1 | 2.99 |
| 303 | 1-(1-Ethyl-propyl)-2-thiophen-2-ylmethyl-1H-benzoimidazole-5-carboxylic acid {(S)-1-[(1-ethyl-piperidin-3-ylmethyl)-carbamoyl]-3-methyl-butyl}-amide | 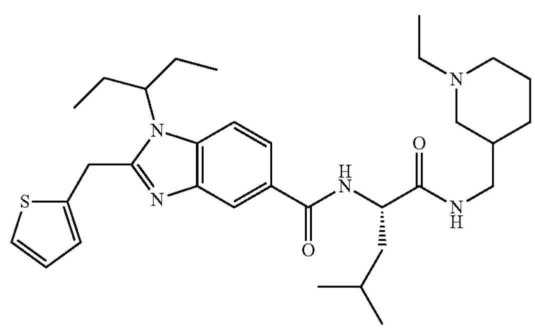 [SMILES: CCC(CC)n1c(Cc2cccs2)nc2cc(C(=O)N[C@@H](CC(C)C)C(=O)NCC3CCCN(CC)C3)ccc21] | 566.3 | 5_7_1 | 2.48 |
| 304 | 1-(1-Ethyl-propyl)-2-thiophen-2-ylmethyl-1H-benzoimidazole-5-carboxylic acid {(S)-1-[(1-isobutyl-pyrrolidin-3-ylmethyl)-carbamoyl]-3-methyl-butyl}-amide | 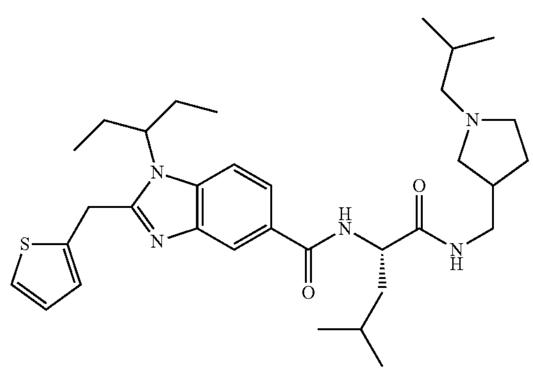 [SMILES: CCC(CC)n1c(Cc2cccs2)nc2cc(C(=O)N[C@@H](CC(C)C)C(=O)NCC3CCN(CC(C)C)C3)ccc21] | 580.3 | 5_7_1 | 2.55 |

| Exp. No. | Chemical Name | Structure | m/z [M + H]+ | LCMS method | R_t [min] |
|---|---|---|---|---|---|
| 305 | 1-(1-Ethyl-propyl)-2-thiophen-2-ylmethyl-1H-benzoimidazole-5-carboxylic acid ((S)-1-{[1-(2-methoxy-ethyl)-pyrrolidin-3-ylmethyl]-carbamoyl}-3-methyl-butyl)-amide | 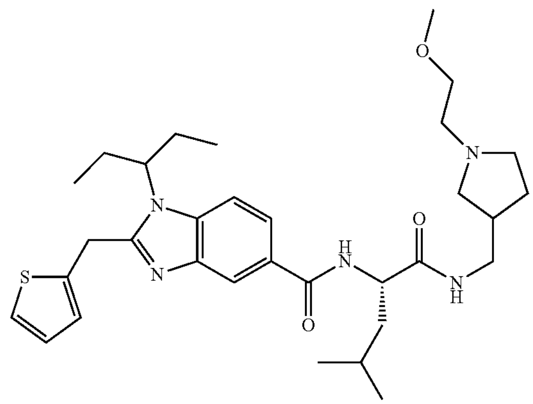 [SMILES: CCC(CC)n1c(Cc2cccs2)nc2cc(C(=O)N[C@@H](CC(C)C)C(=O)NCC3CCN(CCOC)C3)ccc21] | 582.3 | 5_7_1 | 2.55 |
| 306 | 1-(1-Ethyl-propyl)-2-thiophen-2-ylmethyl-1H-benzoimidazole-5-carboxylic acid [(S)-3-methyl-1-(1-methyl-3-morpholin-4-yl-propylcarbamoyl)-butyl]-amide | 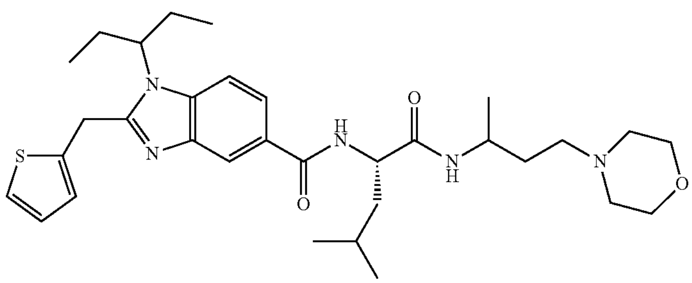 [SMILES: CCC(CC)n1c(Cc2cccs2)nc2cc(C(=O)N[C@@H](CC(C)C)C(=O)NC(C)CCN3CCOCC3)ccc21] | 582.3 | 5_7_1 | 2.48 |
| 307 | 1-(1-Ethyl-propyl)-2-thiophen-2-ylmethyl-1H-benzoimidazole-5-carboxylic acid {(S)-1-[2-(1-benzyl-piperidin-2-yl)-ethylcarbamoyl]-3-methyl-butyl}-amide | 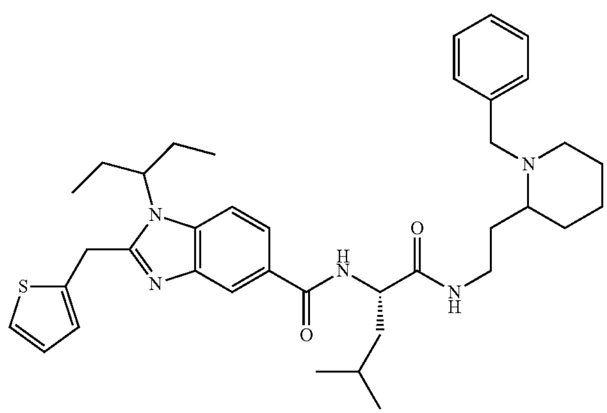 [SMILES: CCC(CC)n1c(Cc2cccs2)nc2cc(C(=O)N[C@@H](CC(C)C)C(=O)NCCC3CCCCN3Cc3ccccc3)ccc21] | 642.3 | 5_7_1 | 2.70 |
| 308 | 1-(1-Ethyl-propyl)-2-thiophen-2-ylmethyl-1H-benzoimidazole-5-carboxylic acid [(S)-3-methyl-1-(1-pyridin-3-ylmethyl-piperidin-4-ylcarbamoyl)-butyl]-amide | 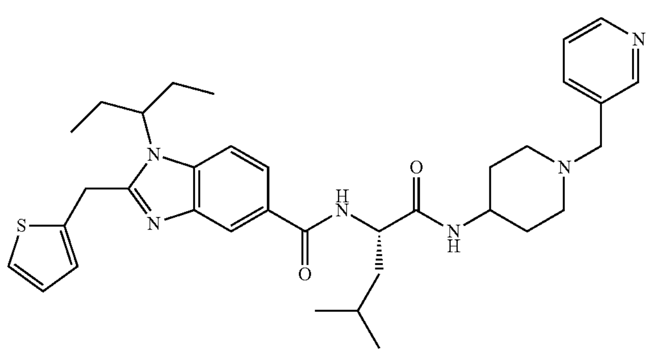 [SMILES: CCC(CC)n1c(Cc2cccs2)nc2cc(C(=O)N[C@@H](CC(C)C)C(=O)NC3CCN(Cc4cccnc4)CC3)ccc21] | 615.3 | 5_7_1 | 2.40 |

| Exp. No. | Chemical Name | Structure | m/z [M + H]+ | LCMS method | R_t [min] |
|---|---|---|---|---|---|
| 309 | 1-(1-Ethyl-propyl)-2-thiophen-2-ylmethyl-1H-benzoimidazole-5-carboxylic acid {(S)-3-methyl-1-[(1-propyl-piperidin-3-ylmethyl)-carbamoyl]-butyl}-amide | 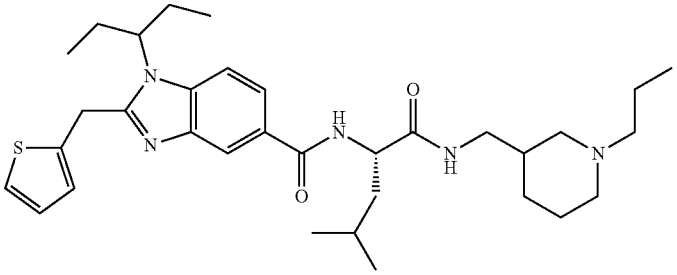 [SMILES: CCCN1CCCC(CNC(=O)[C@H](CC(C)C)NC(=O)c2ccc3c(c2)nc(Cc2cccs2)n3C(CC)CC)C1] | 580.3 | 5_7_1 | 2.58 |
| 310 | 1-(1-Ethyl-propyl)-2-thiophen-2-ylmethyl-1H-benzoimidazole-5-carboxylic acid ((S)-1-{4-[(2-dimethylamino-ethyl)-methyl-amino]-piperidine-1-carbonyl}-3-methyl-butyl)-amide | 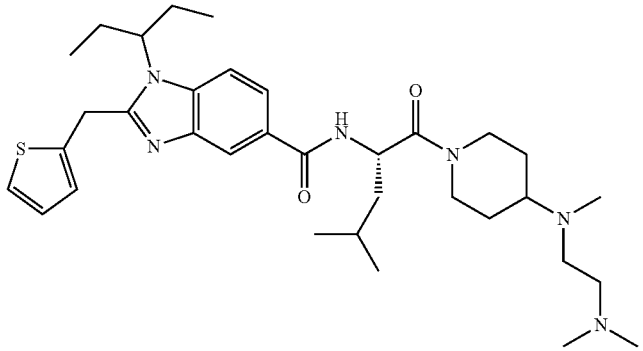 [SMILES: CCC(CC)n1c(Cc2cccs2)nc2cc(C(=O)N[C@@H](CC(C)C)C(=O)N3CCC(N(C)CCN(C)C)CC3)ccc21] | 609.3 | 5_7_1 | 2.33 |
| 311 | 1-(1-Ethyl-propyl)-2-thiophen-2-ylmethyl-1H-benzoimidazole-5-carboxylic acid [(S)-1-(4-benzo[1,3]dioxol-5-ylmethyl-piperazine-1-carbonyl)-3-methyl-butyl]-amide | 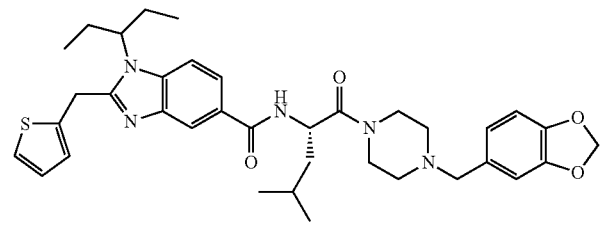 [SMILES: CCC(CC)n1c(Cc2cccs2)nc2cc(C(=O)N[C@@H](CC(C)C)C(=O)N3CCN(Cc4ccc5c(c4)OCO5)CC3)ccc21] | 644.2 | 5_7_1 | 2.62 |
| 312 | 1-(1-Ethyl-propyl)-2-thiophen-2-ylmethyl-1H-benzoimidazole-5-carboxylic acid [(S)-3-methyl-1-(4-pyridin-2-yl-piperazine-1-carbonyl)-butyl]-amide | 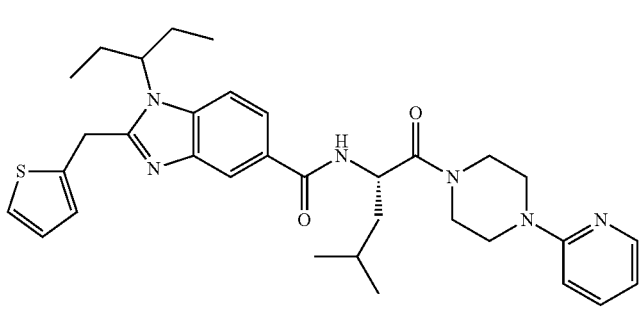 [SMILES: CCC(CC)n1c(Cc2cccs2)nc2cc(C(=O)N[C@@H](CC(C)C)C(=O)N3CCN(c4ccccn4)CC3)ccc21] | 587.3 | 5_7_1 | 2.50 |
| 313 | 1-(1-Ethyl-propyl)-2-thiophen-2-ylmethyl-1H-benzoimidazole-5-carboxylic acid [(S)-1-(1-benzyl-piperidin-4-ylcarbamoyl)-3-methyl-butyl]-amide | 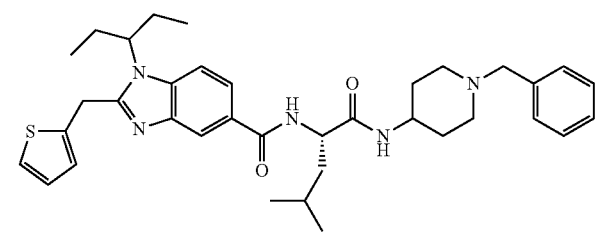 [SMILES: CCC(CC)n1c(Cc2cccs2)nc2cc(C(=O)N[C@@H](CC(C)C)C(=O)NC3CCN(Cc4ccccc4)CC3)ccc21] | 614.3 | 5_7_1 | 2.58 |

| Exp. No. | Chemical Name | Structure | m/z [M + H]+ | LCMS method | R_t [min] |
|---|---|---|---|---|---|
| 314 | 1-(1-Ethyl-propyl)-2-thiophen-2-ylmethyl-1H-benzoimidazole-5-carboxylic acid [(S)-1-(4-diethylamino-1-methyl-butylcarbamoyl)-3-methyl-butyl]-amide | 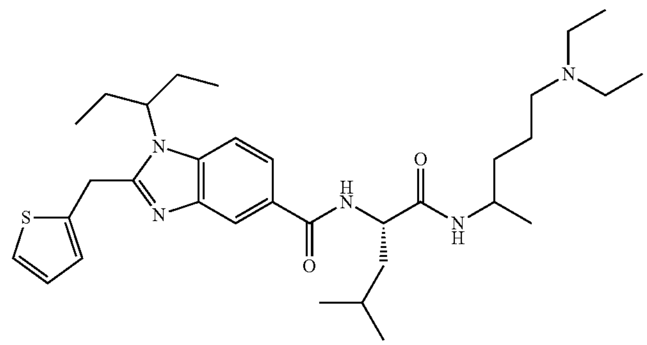 [SMILES: CCC(CC)n1c(Cc2cccs2)nc2cc(C(=O)N[C@@H](CC(C)C)C(=O)NC(C)CCCN(CC)CC)ccc21] | 582.3 | 5_7_1 | 2.54 |
| 315 | 1-(1-Ethyl-propyl)-2-thiophen-2-ylmethyl-1H-benzoimidazole-5-carboxylic acid {(S)-1-[4-(2-methoxy-phenyl)-piperazine-1-carbonyl]-3-methyl-butyl}-amide | 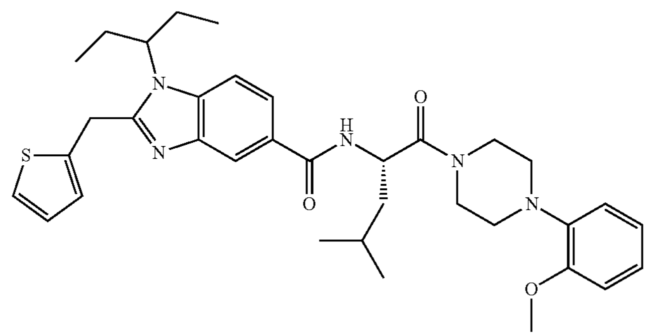 [SMILES: CCC(CC)n1c(Cc2cccs2)nc2cc(C(=O)N[C@@H](CC(C)C)C(=O)N3CCN(c4ccccc4OC)CC3)ccc21] | 616.3 | 5_7_1 | 3.34 |
| 316 | 1-(1-Ethyl-propyl)-2-thiophen-2-ylmethyl-1H-benzoimidazole-5-carboxylic acid [(S)-1-(3-dimethylamino-phenylcarbamoyl)-3-methyl-butyl]-amide | 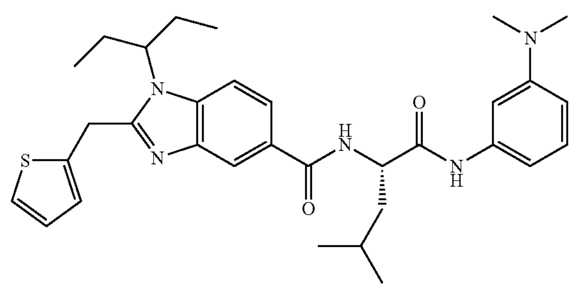 [SMILES: CCC(CC)n1c(Cc2cccs2)nc2cc(C(=O)N[C@@H](CC(C)C)C(=O)Nc3cccc(N(C)C)c3)ccc21] | 560.3 | 5_7_1 | 2.60 |
| 317 | 1-(1-Ethyl-propyl)-2-thiophen-2-ylmethyl-1H-benzoimidazole-5-carboxylic acid [(S)-3-methyl-1-(1-phenyl-piperidin-4-ylcarbamoyl)-butyl]-amide | 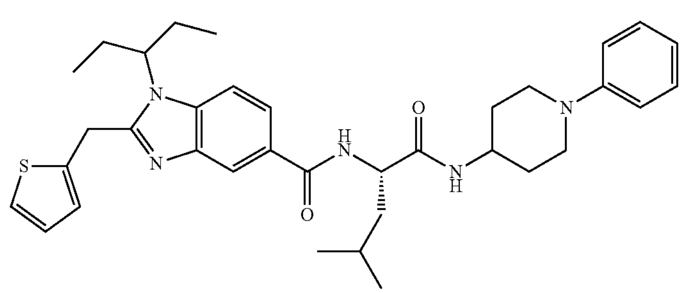 [SMILES: CCC(CC)n1c(Cc2cccs2)nc2cc(C(=O)N[C@@H](CC(C)C)C(=O)NC3CCN(c4ccccc4)CC3)ccc21] | 600.3 | 5_7_1 | 2.58 |

| Exp. No. | Chemical Name | Structure | m/z [M + H]+ | LCMS method | R$_t$ [min] |
|---|---|---|---|---|---|
| 318 | 1-(1-Ethyl-propyl)-2-thiophen-2-ylmethyl-1H-benzoimidazole-5-carboxylic acid [(S)-1-(4-cyclohexyl-piperazine-1-carbonyl)-3-methyl-butyl]-amide | 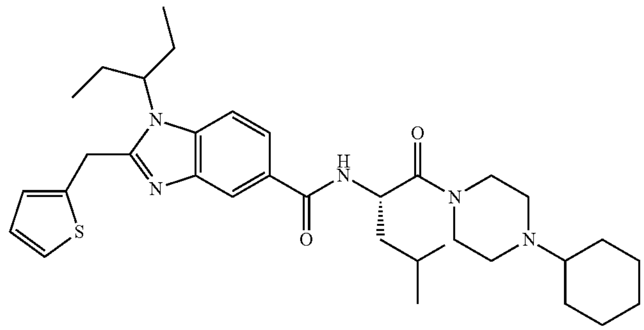 [SMILES: CCC(CC)n1c(Cc2cccs2)nc2cc(C(=O)N[C@@H](CC(C)C)C(=O)N3CCN(C4CCCCC4)CC3)ccc21] | 592.3 | 5_7_1 | 2.58 |
| 319 | 1-(1-Ethyl-propyl)-2-thiophen-2-ylmethyl-1H-benzoimidazole-5-carboxylic acid [(S)-1-(1-benzyl-pyrrolidin-3-ylcarbamoyl)-3-methyl-butyl]-amide | 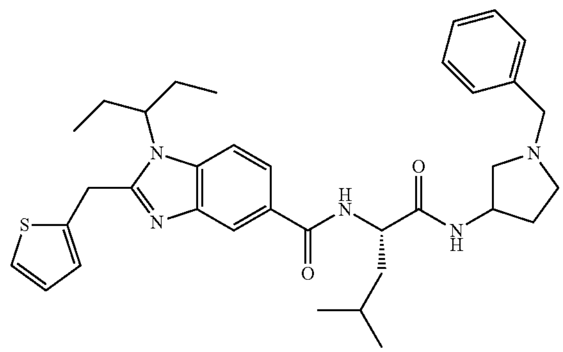 [SMILES: CCC(CC)n1c(Cc2cccs2)nc2cc(C(=O)N[C@@H](CC(C)C)C(=O)NC3CCN(Cc4ccccc4)C3)ccc21] | 600.2 | 5_7_1 | 2.61 |
| 320 | 1-(1-Ethyl-propyl)-2-thiophen-2-ylmethyl-1H-benzoimidazole-5-carboxylic acid {(S)-3-methyl-1-[3-(4-methyl-piperidin-1-yl)-propylcarbamoyl]-butyl}-amide | 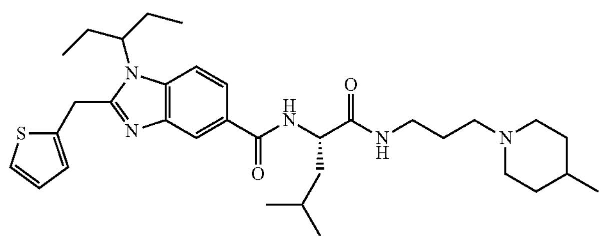 [SMILES: CCC(CC)n1c(Cc2cccs2)nc2cc(C(=O)N[C@@H](CC(C)C)C(=O)NCCCN3CCC(C)CC3)ccc21] | 580.3 | 5_7_1 | 2.56 |
| 321 | 1-(1-Ethyl-propyl)-2-thiophen-2-ylmethyl-1H-benzoimidazole-5-carboxylic acid [(S)-1-(4-cyclopentyl-piperazine-1-carbonyl)-3-methyl-butyl]-amide | 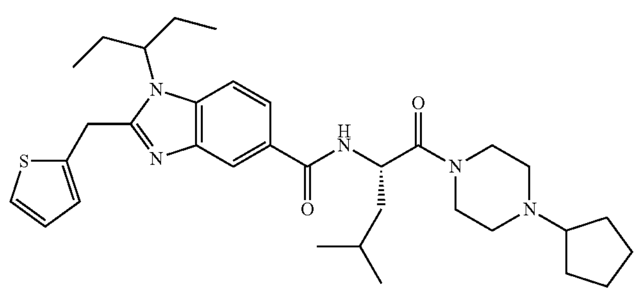 [SMILES: CCC(CC)n1c(Cc2cccs2)nc2cc(C(=O)N[C@@H](CC(C)C)C(=O)N3CCN(C4CCCC4)CC3)ccc21] | 578.3 | 5_7_1 | 2.52 |
| 322 | 1-(1-Ethyl-propyl)-2-thiophen-2-ylmethyl-1H-benzoimidazole-5-carboxylic acid [(S)-1-((S)-3-dimethylamino-pyrrolidine-1-carbonyl)-3-methyl-butyl]-amide | 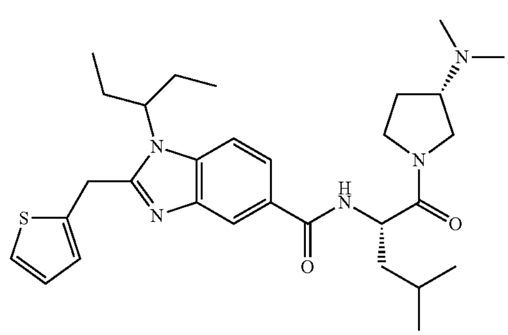 [SMILES: CCC(CC)n1c(Cc2cccs2)nc2cc(C(=O)N[C@@H](CC(C)C)C(=O)N3CC[C@H](N(C)C)C3)ccc21] | 538.2 | 5_7_1 | 2.40 |

-continued

| Exp. No. | Chemical Name | Structure | m/z [M + H]+ | LCMS method | R_t [min] |
|---|---|---|---|---|---|
| 323 | 1-(1-Ethyl-propyl)-2-thiophen-2-ylmethyl-1H-benzoimidazole-5-carboxylic acid [(S)-1-(4-benzyl-[1,4]diazepane-1-carbonyl)-3-methyl-butyl]-amide | 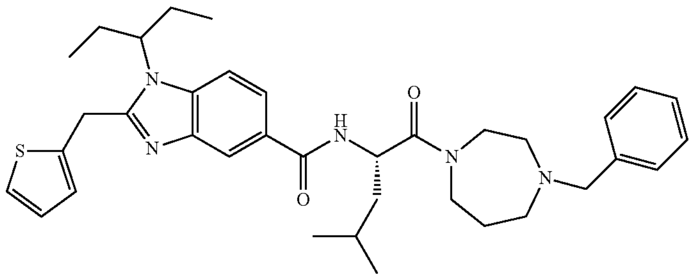 [SMILES: CCC(CC)n1c(Cc2cccs2)nc2cc(C(=O)N[C@@H](CC(C)C)C(=O)N3CCCN(Cc4ccccc4)CC3)ccc21] | 614.3 | 5_7_1 | 2.61 |
| 324 | 1-(1-Ethyl-propyl)-2-thiophen-2-ylmethyl-1H-benzoimidazole-5-carboxylic acid {(S)-1-[4-(4-fluoro-benzyl)-[1,4]diazepane-1-carbonyl]-3-methyl-butyl}-amide | 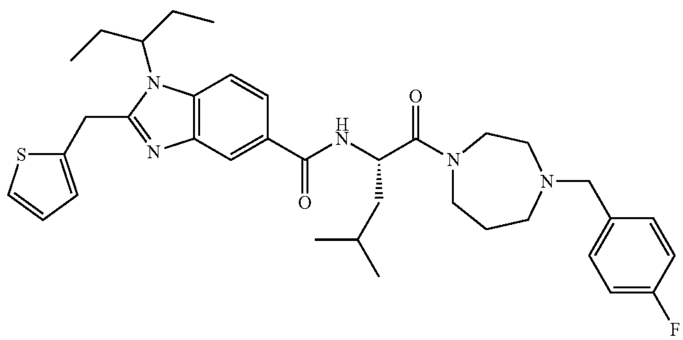 [SMILES: CCC(CC)n1c(Cc2cccs2)nc2cc(C(=O)N[C@@H](CC(C)C)C(=O)N3CCCN(Cc4ccc(F)cc4)CC3)ccc21] | 632.3 | 5_7_1 | 2.78 |
| 325 | 1-(1-Ethyl-propyl)-2-thiophen-2-ylmethyl-1H-benzoimidazole-5-carboxylic acid [(S)-1-((1R,4R)-5-benzyl-2,5-diaza-bicyclo[2.2.1]hept-ane-2-carbonyl)-3-methyl-butyl]-amide | 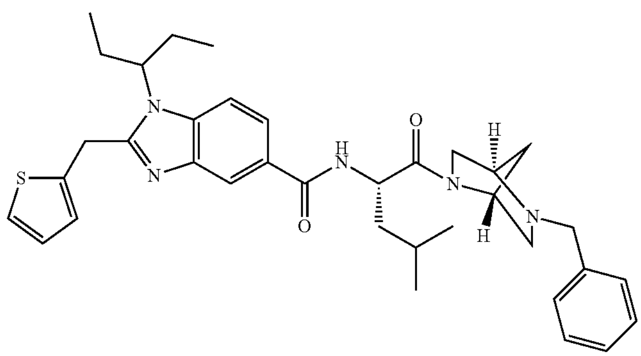 [SMILES: CCC(CC)n1c(Cc2cccs2)nc2cc(C(=O)N[C@@H](CC(C)C)C(=O)N3C[C@H]4C[C@@H]3CN4Cc3ccccc3)ccc21] | 612.2 | 5_7_1 | 2.61 |
| 326 | 1-(1-Ethyl-propyl)-2-thiophen-2-ylmethyl-1H-benzoimidazole-5-carboxylic acid {(S)-1-[5-(3-fluoro-phenyl)-2,5-diaza-bicyclo[2.2.1]hept-ane-2-carbonyl]-3-methyl-butyl}-amide | 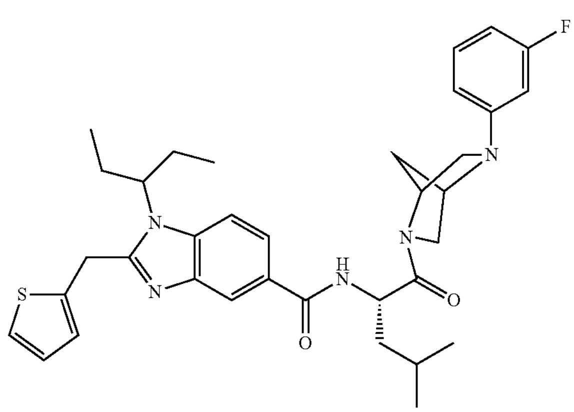 [SMILES: CCC(CC)n1c(Cc2cccs2)nc2cc(C(=O)N[C@@H](CC(C)C)C(=O)N3CC4CC3CN4c3cccc(F)c3)ccc21] | 616.2 | 5_7_1 | 3.17 |

-continued

| Exp. No. | Chemical Name | Structure | m/z [M + H]+ | LCMS method | R$_t$ [min] |
|---|---|---|---|---|---|
| 327 | 1-(1-Ethyl-propyl)-2-thiophen-2-ylmethyl-1H-benzoimidazole-5-carboxylic acid [(S)-3-methyl-1-(1-methyl-piperidin-4-ylcarbamoyl)-butyl]-amide | 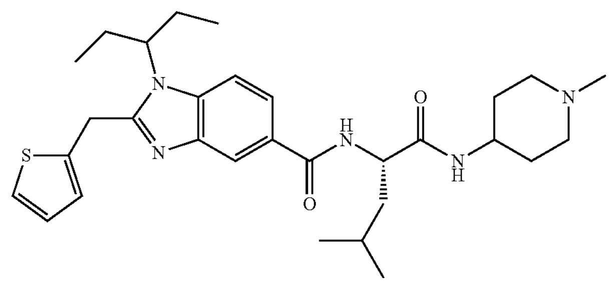 [SMILES: CCC(CC)n1c(Cc2cccs2)nc2cc(C(=O)N[C@@H](CC(C)C)C(=O)NC3CCN(C)CC3)ccc21] | 538.2 | 5_7_1 | 2.42 |
| 328 | 1-(1-Ethyl-propyl)-2-thiophen-2-ylmethyl-1H-benzoimidazole-5-carboxylic acid ((S)-1-{1-[2-(4-methoxy-phenyl)-ethyl]-piperidin-4-ylcarbamoyl}-3-methyl-butyl)-amide | 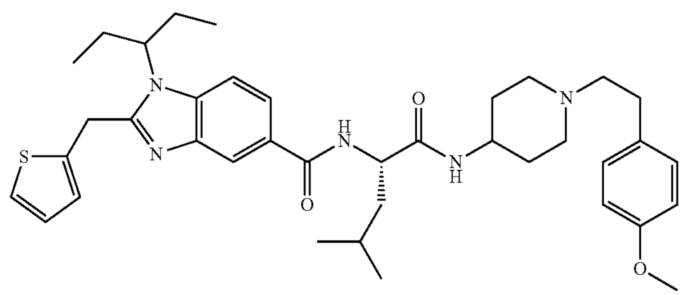 [SMILES: CCC(CC)n1c(Cc2cccs2)nc2cc(C(=O)N[C@@H](CC(C)C)C(=O)NC3CCN(CCc4ccc(OC)cc4)CC3)ccc21] | 658.3 | 5_7_1 | 2.64 |
| 329 | 1-(1-Ethyl-propyl)-2-thiophen-2-ylmethyl-1H-benzoimidazole-5-carboxylic acid [(S)-1-(3-diethylamino-pyrrolidine-1-carbonyl)-3-methyl-butyl]-amide | 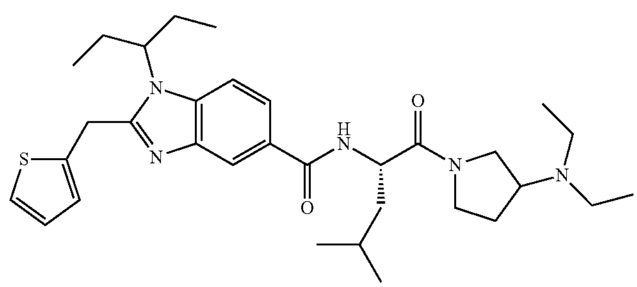 [SMILES: CCC(CC)n1c(Cc2cccs2)nc2cc(C(=O)N[C@@H](CC(C)C)C(=O)N3CCC(N(CC)CC)C3)ccc21] | 566.3 | 5_7_1 | 2.47 |
| 330 | 1-(1-Ethyl-propyl)-2-thiophen-2-ylmethyl-1H-benzoimidazole-5-carboxylic acid {(S)-1-[(4-benzyl-morpholin-2-ylmethyl)-carbamoyl]-3-methyl-butyl}-amide | 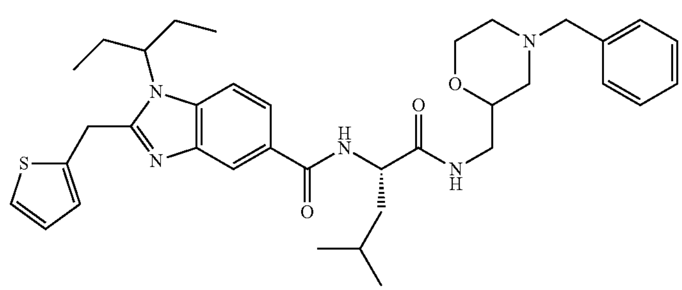 [SMILES: CCC(CC)n1c(Cc2cccs2)nc2cc(C(=O)N[C@@H](CC(C)C)C(=O)NCC3CN(Cc4ccccc4)CCO3)ccc21] | 630.3 | 5_7_1 | 2.60 |
| 331 | 1-(1-Ethyl-propyl)-2-thiophen-2-ylmethyl-1H-benzoimidazole-5-carboxylic acid {(S)-1-[(1-butyl-piperidin-4-ylmethyl)-carbamoyl]-3-methyl-butyl}-amide | 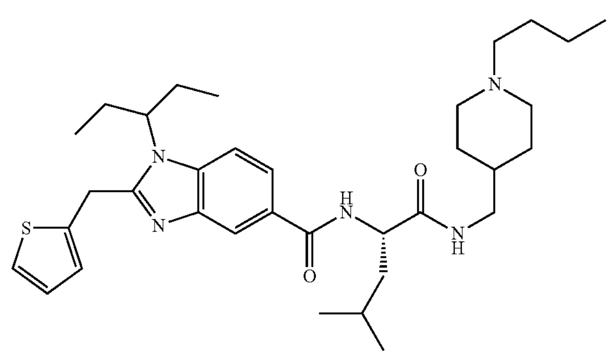 [SMILES: CCCCN1CCC(CNC(=O)[C@H](CC(C)C)NC(=O)c2ccc3c(c2)nc(Cc2cccs2)n3C(CC)CC)CC1] | 594.3 | 5_7_1 | 2.55 |

-continued

| Exp. No. | Chemical Name | Structure | m/z [M + H]$^+$ | LCMS method | R$_t$ [min] |
|---|---|---|---|---|---|
| 332 | 1-(1-Ethyl-propyl)-2-thiophen-2-ylmethyl-1H-benzoimidazole-5-carboxylic acid {(S)-1-[3-(3,5-dimethyl-piperidin-1-yl)-propylcarbamoyl]-3-methyl-butyl}-amide | 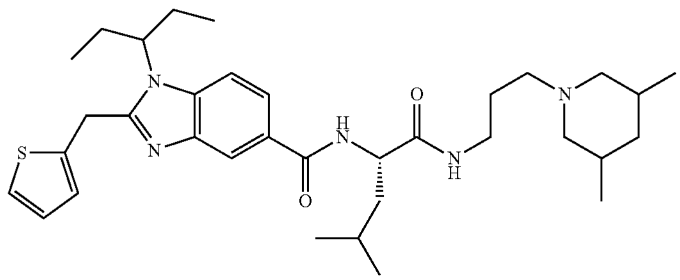 [SMILES: CCC(CC)n1c(Cc2cccs2)nc2cc(C(=O)N[C@@H](CC(C)C)C(=O)NCCCN3CC(C)CC(C)C3)ccc21] | 594.3 | 5_7_1 | 2.63 |
| 333 | 1-(1-Ethyl-propyl)-2-thiophen-2-ylmethyl-1H-benzoimidazole-5-carboxylic acid [(S)-3-methyl-1-(3-morpholin-4-yl-phenylcarbamoyl)-butyl]-amide | 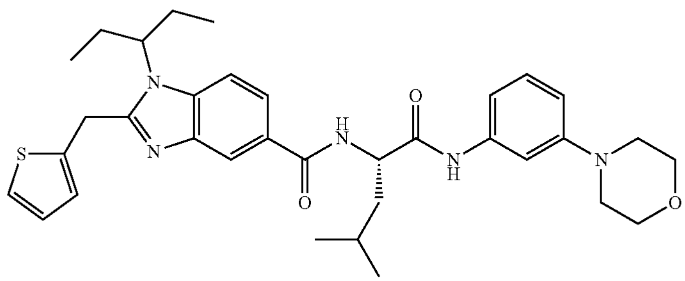 [SMILES: CCC(CC)n1c(Cc2cccs2)nc2cc(C(=O)N[C@@H](CC(C)C)C(=O)Nc3cccc(N4CCOCC4)c3)ccc21] | 602.2 | 5_7_1 | 2.85 |
| 334 | 1-(1-Ethyl-propyl)-2-thiophen-2-ylmethyl-1H-benzoimidazole-5-carboxylic acid [(S)-3-methyl-1-(4-morpholin-4-yl-piperidine-1-carbonyl)-butyl]-amide | 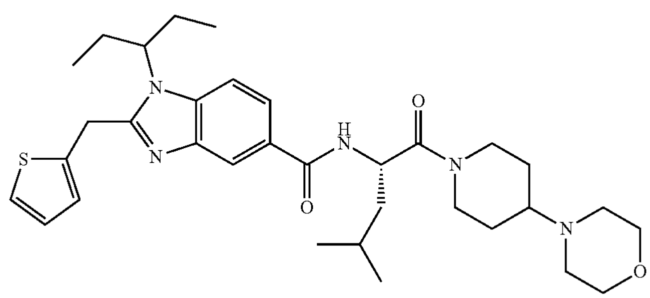 [SMILES: CCC(CC)n1c(Cc2cccs2)nc2cc(C(=O)N[C@@H](CC(C)C)C(=O)N3CCC(N4CCOCC4)CC3)ccc21] | 594.3 | 5_7_1 | 2.43 |
| 335 | 1-(1-Ethyl-propyl)-2-thiophen-2-ylmethyl-1H-benzoimidazole-5-carboxylic acid [(S)-1-(4-azepan-1-yl-piperidine-1-carbonyl)-3-methyl-butyl]-amide | 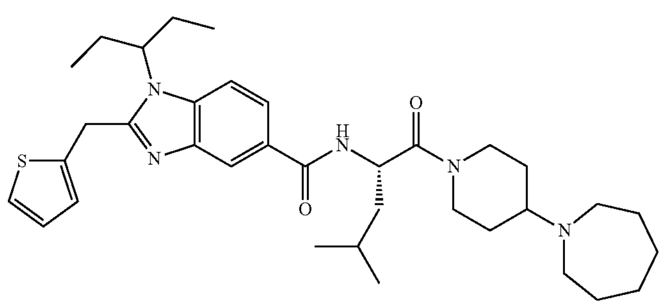 [SMILES: CCC(CC)n1c(Cc2cccs2)nc2cc(C(=O)N[C@@H](CC(C)C)C(=O)N3CCC(N4CCCCCC4)CC3)ccc21] | 606.3 | 5_7_1 | 2.53 |
| 336 | 1-(1-Ethyl-propyl)-2-thiophen-2-ylmethyl-1H-benzoimidazole-5-carboxylic acid {(S)-1-[4-(benzyl-ethyl-amino)-piperidine-1-carbonyl]-3-methyl-butyl}-amide | 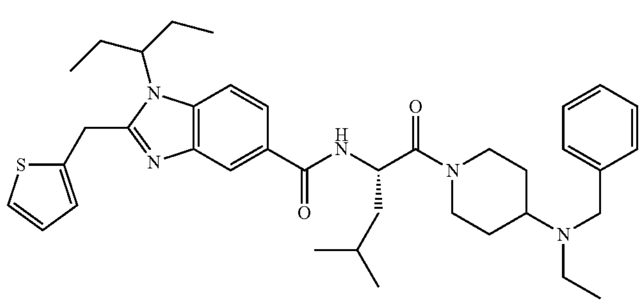 [SMILES: CCC(CC)n1c(Cc2cccs2)nc2cc(C(=O)N[C@@H](CC(C)C)C(=O)N3CCC(N(CC)Cc4ccccc4)CC3)ccc21] | 642.3 | 5_7_1 | 2.67 |

| Exp. No. | Chemical Name | Structure | m/z [M + H]+ | LCMS method | R_t [min] |
|---|---|---|---|---|---|
| 337 | 1-(1-Ethyl-propyl)-2-thiophen-2-ylmethyl-1H-benzoimidazole-5-carboxylic acid [(S)-1-(1-isobutyl-piperidin-4-ylcarbamoyl)-3-methyl-butyl]-amide | 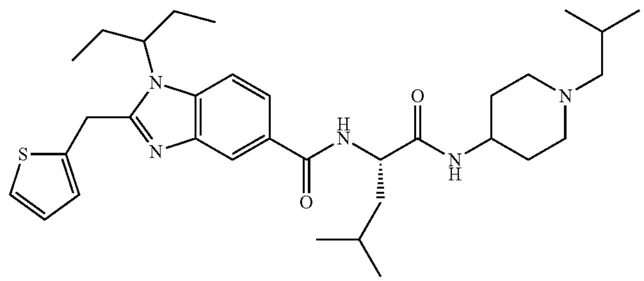 [SMILES: CCC(CC)n1c(Cc2cccs2)nc2cc(C(=O)N[C@@H](CC(C)C)C(=O)NC3CCN(CC(C)C)CC3)ccc21] | 580.3 | 5_7_1 | 2.51 |
| 338 | 1-(1-Ethyl-propyl)-2-thiophen-2-ylmethyl-1H-benzoimidazole-5-carboxylic acid [(S)-3-methyl-1-(1-phenethyl-piperidin-4-ylcarbamoyl)-butyl]-amide | 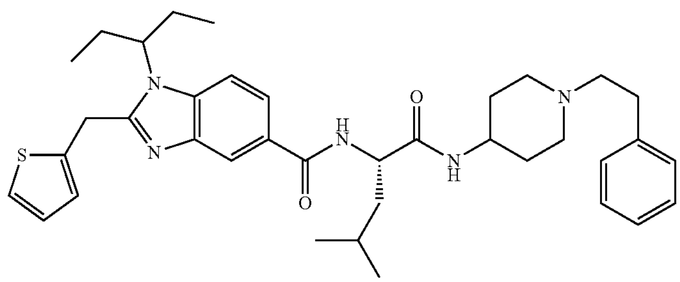 [SMILES: CCC(CC)n1c(Cc2cccs2)nc2cc(C(=O)N[C@@H](CC(C)C)C(=O)NC3CCN(CCc4ccccc4)CC3)ccc21] | 628.3 | 5_7_1 | 2.63 |
| 339 | 1-(1-Ethyl-propyl)-2-thiophen-2-ylmethyl-1H-benzoimidazole-5-carboxylic acid {(S)-3-methyl-1-[3-(3-methyl-piperidin-1-yl)-propylcarbamoyl]-butyl}-amide | 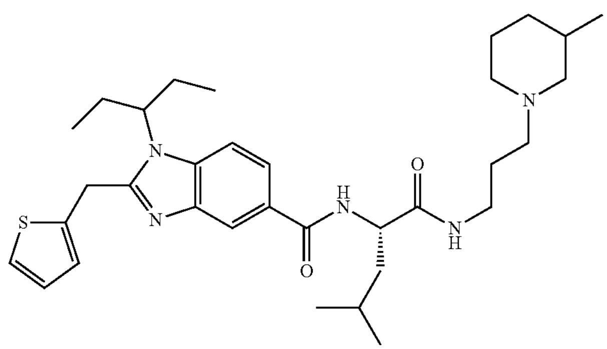 [SMILES: CCC(CC)n1c(Cc2cccs2)nc2cc(C(=O)N[C@@H](CC(C)C)C(=O)NCCCN3CCCC(C)C3)ccc21] | 580.3 | 5_7_1 | 2.57 |
| 340 | 1-(1-Ethyl-propyl)-2-thiophen-2-ylmethyl-1H-benzoimidazole-5-carboxylic acid [(S)-1-(1-ethyl-piperidin-4-ylcarbamoyl)-3-methyl-butyl]-amide | 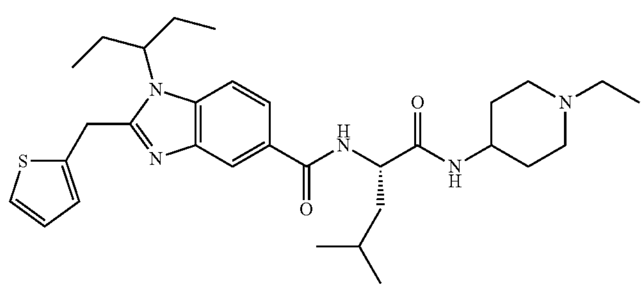 [SMILES: CCC(CC)n1c(Cc2cccs2)nc2cc(C(=O)N[C@@H](CC(C)C)C(=O)NC3CCN(CC)CC3)ccc21] | 552.3 | 5_7_1 | 2.44 |
| 341 | 1-(1-Ethyl-propyl)-2-thiophen-2-ylmethyl-1H-benzoimidazole-5-carboxylic acid {(S)-1-[3-(4-benzyl-piperazin-1-yl)-propylcarbamoyl]-3-methyl-butyl}-amide | 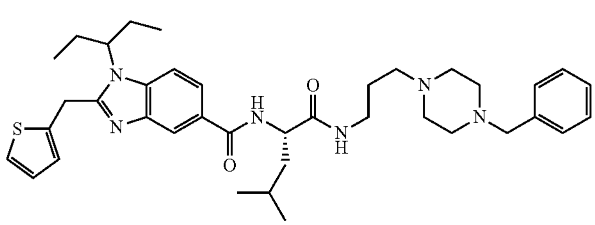 [SMILES: CCC(CC)n1c(Cc2cccs2)nc2cc(C(=O)N[C@@H](CC(C)C)C(=O)NCCCN3CCN(Cc4ccccc4)CC3)ccc21] | 657.3 | 5_7_1 | 2.48 |

-continued

| Exp. No. | Chemical Name | Structure | m/z [M + H]+ | LCMS method | R_t [min] |
|---|---|---|---|---|---|
| 342 | 1-(1-Ethyl-propyl)-2-thiophen-2-ylmethyl-1H-benzoimidazole-5-carboxylic acid {(S)-1-[3-(1,1-dioxo-1lambda6-thiomorpholin-4-yl)-propylcarbamoyl]-3-methyl-butyl}-amide | 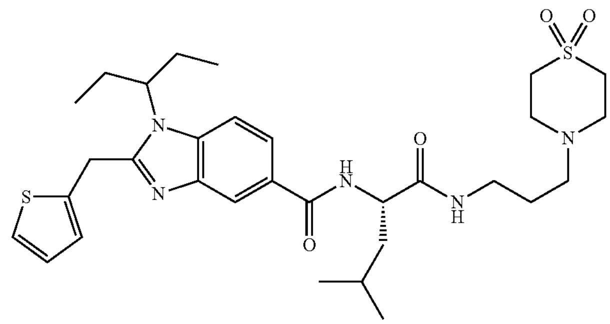 [SMILES: CCC(CC)n1c(Cc2cccs2)nc2cc(C(=O)N[C@@H](CC(C)C)C(=O)NCCCN3CCS(=O)(=O)CC3)ccc21] | 616.2 | 5_7_1 | 2.47 |
| 343 | 1-(1-Ethyl-propyl)-2-thiophen-2-ylmethyl-1H-benzoimidazole-5-carboxylic acid {(S)-3-methyl-1-[(4-methyl-morpholin-2-ylmethyl)-carbamoyl]-butyl}-amide | 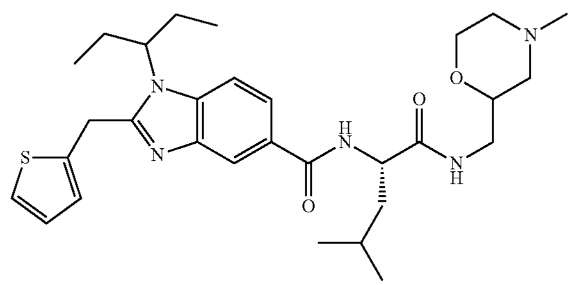 [SMILES: CCC(CC)n1c(Cc2cccs2)nc2cc(C(=O)N[C@@H](CC(C)C)C(=O)NCC3CN(C)CCO3)ccc21] | 554.2 | 5_7_1 | 2.43 |
| 344 | 1-(1-Ethyl-propyl)-2-thiophen-2-ylmethyl-1H-benzoimidazole-5-carboxylic acid [(S)-1-(1-cyclohexylmethyl-piperidin-4-ylcarbamoyl)-3-methyl-butyl]-amide | 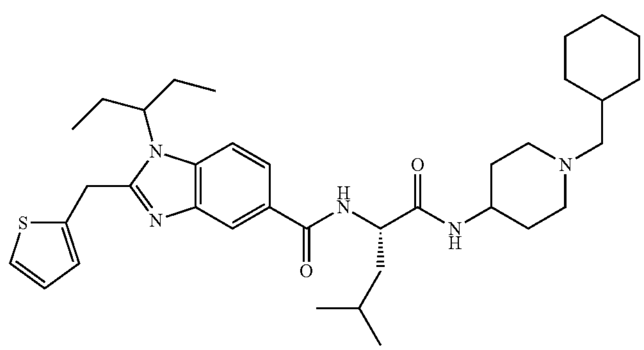 [SMILES: CCC(CC)n1c(Cc2cccs2)nc2cc(C(=O)N[C@@H](CC(C)C)C(=O)NC3CCN(CC4CCCCC4)CC3)ccc21] | 620.3 | 5_7_1 | 2.66 |
| 345 | 1-(1-Ethyl-propyl)-2-thiophen-2-ylmethyl-1H-benzoimidazole-5-carboxylic acid {(S)-1-[4-(benzyl-methyl-amino)-piperidine-1-carbonyl]-3-methyl-butyl}-amide | 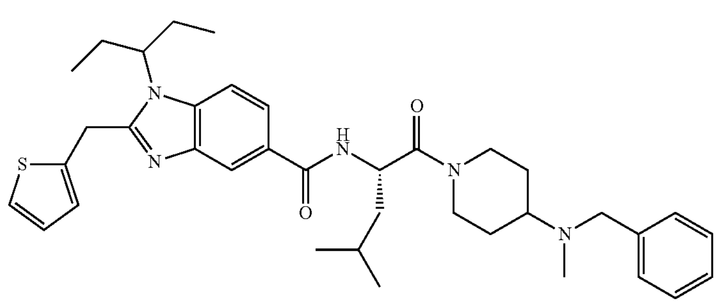 [SMILES: CCC(CC)n1c(Cc2cccs2)nc2cc(C(=O)N[C@@H](CC(C)C)C(=O)N3CCC(N(C)Cc4ccccc4)CC3)ccc21] | 628.3 | 5_7_1 | 2.61 |

| Exp. No. | Chemical Name | Structure | m/z [M + H]+ | LCMS method | R_t [min] |
|---|---|---|---|---|---|
| 346 | 1-(1-Ethyl-propyl)-2-thiophen-2-ylmethyl-1H-benzoimidazole-5-carboxylic acid {(S)-1-[3-(4-benzyl-piperidin-1-yl)-propylcarbamoyl]-3-methyl-butyl}-amide | 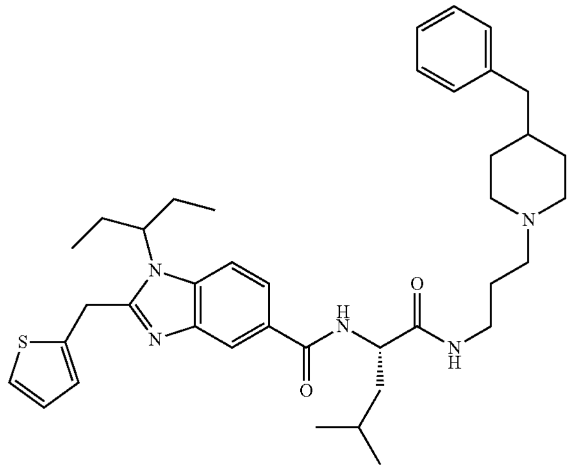 [SMILES: CCC(CC)n1c(Cc2cccs2)nc2cc(C(=O)N[C@@H](CC(C)C)C(=O)NCCCN3CCC(Cc4ccccc4)CC3)ccc21] | 656.3 | 5_7_1 | 2.78 |
| 347 | 1-(1-Ethyl-propyl)-2-thiophen-2-ylmethyl-1H-benzoimidazole-5-carboxylic acid [(S)-1-(5-ethyl-2,5-diaza-bicyclo[2.2.1]heptane-2-carbonyl)-3-methyl-butyl]-amide | 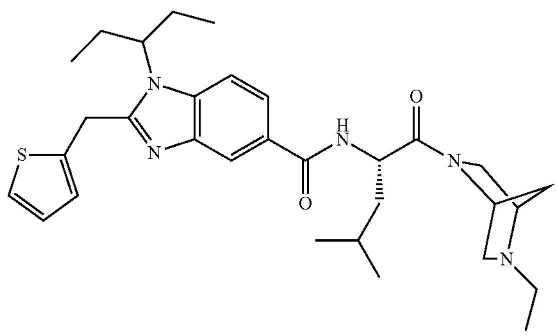 [SMILES: CCC(CC)n1c(Cc2cccs2)nc2cc(C(=O)N[C@@H](CC(C)C)C(=O)N3CC4CC3CN4CC)ccc21] | 550.2 | 5_7_1 | 2.42 |
| 348 | 1-(1-Ethyl-propyl)-2-thiophen-2-ylmethyl-1H-benzoimidazole-5-carboxylic acid [(S)-1-(5-isobutyl-2,5-diaza-bicyclo[2.2.1]heptane-2-carbonyl)-3-methyl-butyl]-amide | 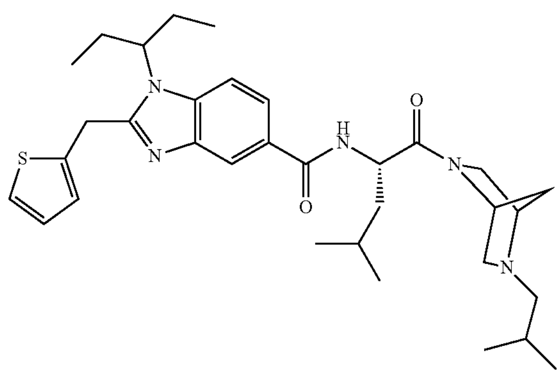 [SMILES: CCC(CC)n1c(Cc2cccs2)nc2cc(C(=O)N[C@@H](CC(C)C)C(=O)N3CC4CC3CN4CC(C)C)ccc21] | 578.3 | 5_7_1 | 2.52 |
| 349 | 1-(1-Ethyl-propyl)-2-thiophen-2-ylmethyl-1H-benzoimidazole-5-carboxylic acid [(S)-1-(5-cyclopentylmethyl-2,5-diaza-bicyclo[2.2.1]heptane-2-carbonyl)-3-methyl-butyl]-amide | 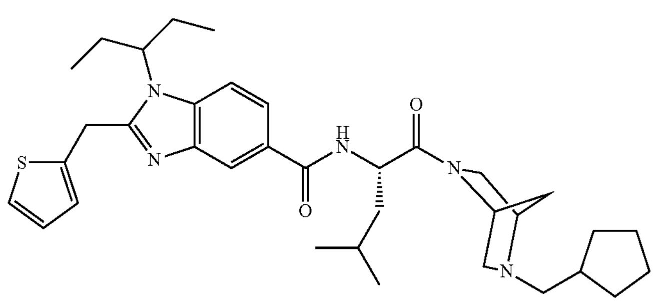 [SMILES: CCC(CC)n1c(Cc2cccs2)nc2cc(C(=O)N[C@@H](CC(C)C)C(=O)N3CC4CC3CN4CC3CCCC3)ccc21] | 604.3 | 5_7_1 | 2.62 |

| Exp. No. | Chemical Name | Structure | m/z [M + H]+ | LCMS method | R_t [min] |
|---|---|---|---|---|---|
| 350 | 1-(1-Ethyl-propyl)-2-thiophen-2-ylmethyl-1H-benzoimidazole-5-carboxylic acid {(S)-3-methyl-1-[5-(4-trifluoromethyl-benzyl)-2,5-diaza-bicyclo[2.2.1]heptane-2-carbonyl]-butyl}-amide | 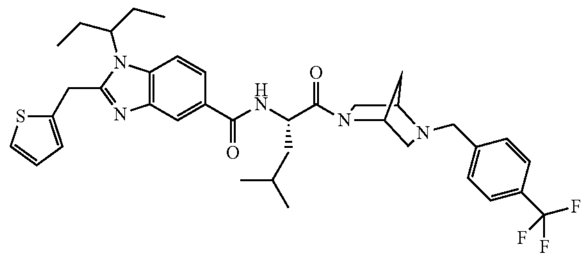 [SMILES: CCC(CC)n1c(Cc2cccs2)nc2cc(C(=O)N[C@@H](CC(C)C)C(=O)N3CC4CC3CN4Cc3ccc(C(F)(F)F)cc3)ccc21] | 680.2 | 5_7_1 | 2.76 |
| 351 | 1-(1-Ethyl-propyl)-2-thiophen-2-ylmethyl-1H-benzoimidazole-5-carboxylic acid {(S)-1-[5-(4-methoxy-benzyl)-2,5-diaza-bicyclo[2.2.1]heptane-2-carbonyl]-3-methyl-butyl}-amide | 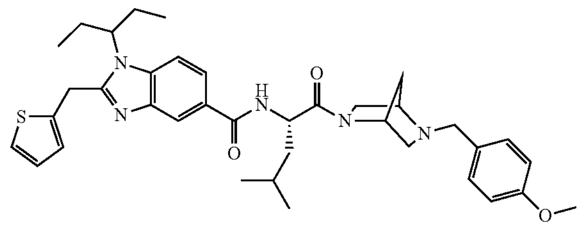 [SMILES: CCC(CC)n1c(Cc2cccs2)nc2cc(C(=O)N[C@@H](CC(C)C)C(=O)N3CC4CC3CN4Cc3ccc(OC)cc3)ccc21] | 642.3 | 5_7_1 | 2.62 |
| 352 | 1-(1-Ethyl-propyl)-2-thiophen-2-ylmethyl-1H-benzoimidazole-5-carboxylic acid [(S)-3-methyl-1-(1-pyrimidin-2-yl-piperidin-4-ylcarbamoyl)-butyl]-amide | 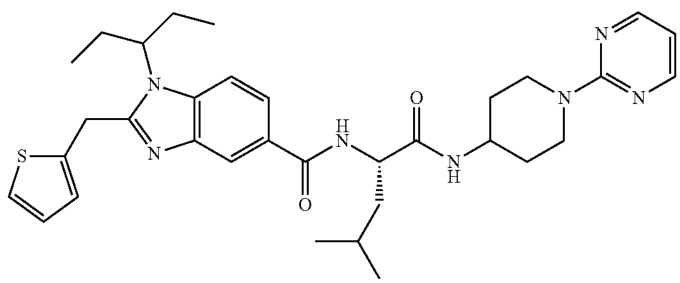 [SMILES: CCC(CC)n1c(Cc2cccs2)nc2cc(C(=O)N[C@@H](CC(C)C)C(=O)NC3CCN(c4ncccn4)CC3)ccc21] | 602.2 | 5_7_1 | 2.65 |
| 353 | 1-(1-Ethyl-propyl)-2-thiophen-2-ylmethyl-1H-benzoimidazole-5-carboxylic acid ((S)-3-methyl-1-{[1-(1-phenyl-ethyl)-pyrrolidin-3-ylmethyl]-carbamoyl}-butyl)-amide | 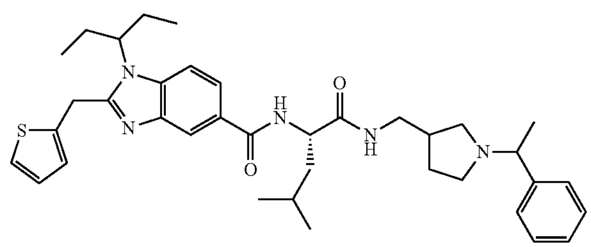 [SMILES: CCC(CC)n1c(Cc2cccs2)nc2cc(C(=O)N[C@@H](CC(C)C)C(=O)NCC3CCN(C(C)c4ccccc4)C3)ccc21] | 628.3 | 5_7_1 | 2.73 |
| 354 | 1-(1-Ethyl-propyl)-2-thiophen-2-ylmethyl-1H-benzoimidazole-5-carboxylic acid {(S)-3-methyl-1-[3-(4-propyl-piperidin-1-yl)-propylcarbamoyl]-butyl}-amide | 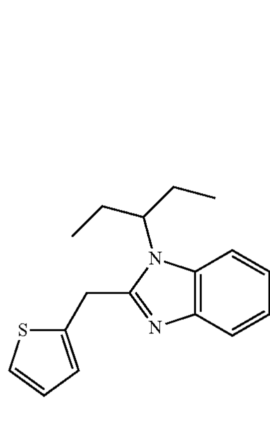 | 608.3 | 5_7_1 | 2.73 |

| Exp. No. | Chemical Name | Structure | m/z [M + H]+ | LCMS method | R$_t$ [min] |
|---|---|---|---|---|---|
| 355 | 1-(1-Ethyl-propyl)-2-thiophen-2-ylmethyl-1H-benzoimidazole-5-carboxylic acid {(S)-1-[(4-isobutyl-morpholin-2-ylmethyl)-carbamoyl]-3-methyl-butyl}-amide | 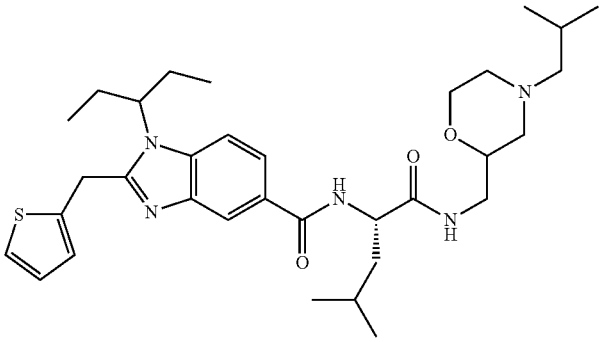 [SMILES: CCC(CC)n1c(Cc2cccs2)nc2cc(C(=O)N[C@@H](CC(C)C)C(=O)NCC3CN(CC(C)C)CCO3)ccc21] | 596.3 | 5_7_1 | 2.54 |
| 356 | 1-(1-Ethyl-propyl)-2-thiophen-2-ylmethyl-1H-benzoimidazole-5-carboxylic acid ((S)-1-{[4-(4-fluoro-benzyl)-morpholin-2-ylmethyl]-carbamoyl}-3-methyl-butyl)-amide | 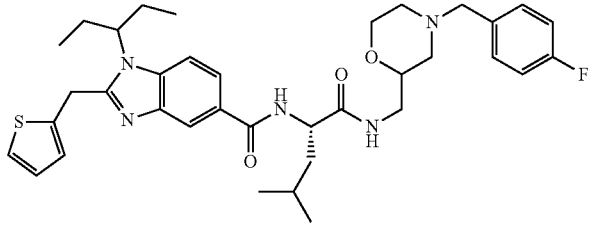 [SMILES: CCC(CC)n1c(Cc2cccs2)nc2cc(C(=O)N[C@@H](CC(C)C)C(=O)NCC3CN(Cc4ccc(F)cc4)CCO3)ccc21] | 648.3 | 5_7_1 | 2.62 |
| 357 | 1-(1-Ethyl-propyl)-2-thiophen-2-ylmethyl-1H-benzoimidazole-5-carboxylic acid ((S)-1-dimethyl-carbamoyl-3-methyl-butyl)-amide | 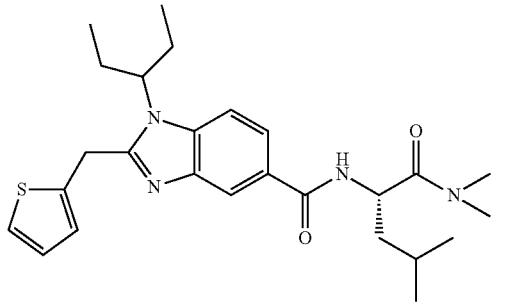 [SMILES: CCC(CC)n1c(Cc2cccs2)nc2cc(C(=O)N[C@@H](CC(C)C)C(=O)N(C)C)ccc21] | 469.2 | 5_7_1 | 3.03 |
| 358 | 1-(1-Ethyl-propyl)-2-thiophen-2-ylmethyl-1H-benzoimidazole-5-carboxylic acid [(S)-1-(3-isopropoxy-propylcarbamoyl)-3-methyl-butyl]-amide | 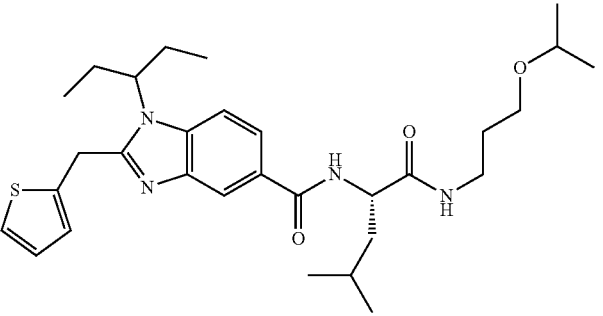 [SMILES: CCC(CC)n1c(Cc2cccs2)nc2cc(C(=O)N[C@@H](CC(C)C)C(=O)NCCCOC(C)C)ccc21] | 541.2 | 5_7_1 | 3.05 |
| 359 | 1-(1-Ethyl-propyl)-2-thiophen-2-ylmethyl-1H-benzoimidazole-5-carboxylic acid [(S)-1-(3-ethoxy-propylcarbamoyl)-3-methyl-butyl]-amide | 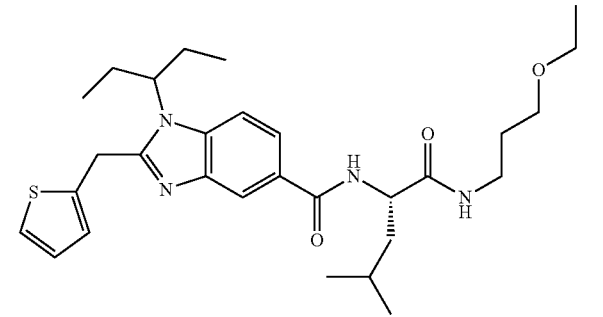 [SMILES: CCOCCCNC(=O)[C@H](CC(C)C)NC(=O)c1ccc2c(c1)nc(Cc1cccs1)n2C(CC)CC] | 527.2 | 5_7_1 | 2.96 |

-continued

| Exp. No. | Chemical Name | Structure | m/z [M + H]+ | LCMS method | R_t [min] |
|---|---|---|---|---|---|
| 360 | 1-(1-Ethyl-propyl)-2-thiophen-2-ylmethyl-1H-benzoimidazole-5-carboxylic acid {(S)-1-[2-(3-methoxy-phenyl)-ethylcarbamoyl]-3-methyl-butyl}-amide | 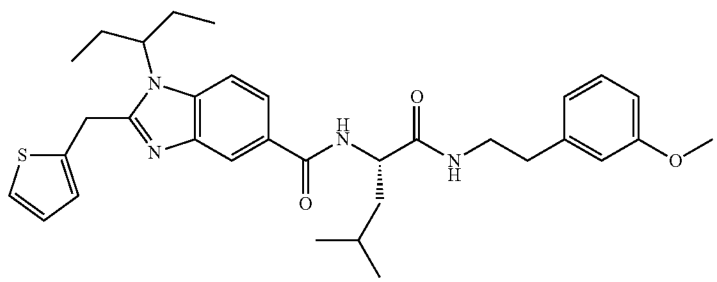 [SMILES: CCC(CC)n1c(Cc2cccs2)nc2cc(C(=O)N[C@@H](CC(C)C)C(=O)NCCc3cccc(OC)c3)ccc21] | 575.2 | 5_7_1 | 3.22 |
| 361 | 1-(1-Ethyl-propyl)-2-thiophen-2-ylmethyl-1H-benzoimidazole-5-carboxylic acid {(S)-1-[2-(4-methoxy-phenyl)-ethylcarbamoyl]-3-methyl-butyl}-amide | 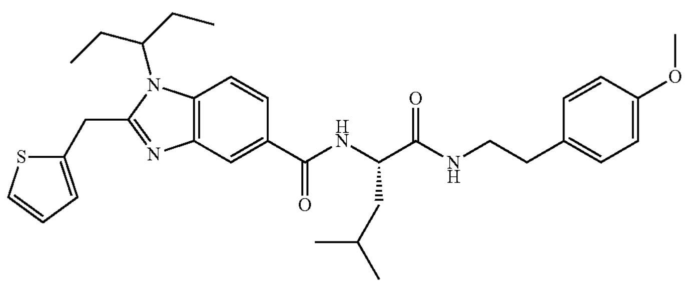 [SMILES: CCC(CC)n1c(Cc2cccs2)nc2cc(C(=O)N[C@@H](CC(C)C)C(=O)NCCc3ccc(OC)cc3)ccc21] | 575.2 | 5_7_1 | 3.16 |
| 362 | 1-(1-Ethyl-propyl)-2-thiophen-2-ylmethyl-1H-benzoimidazole-5-carboxylic acid {(S)-1-[2-(2-methoxy-phenyl)-ethylcarbamoyl]-3-methyl-butyl}-amide | 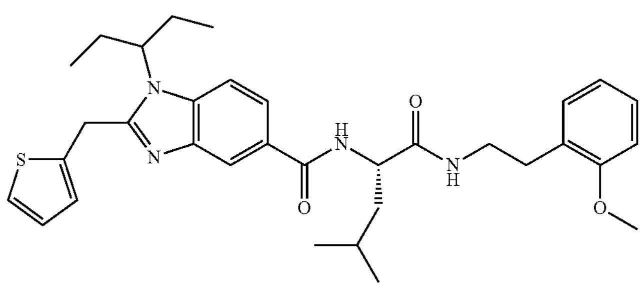 [SMILES: CCC(CC)n1c(Cc2cccs2)nc2cc(C(=O)N[C@@H](CC(C)C)C(=O)NCCc3ccccc3OC)ccc21] | 575.2 | 5_7_1 | 3.33 |
| 363 | 1-(1-Ethyl-propyl)-2-thiophen-2-ylmethyl-1H-benzoimidazole-5-carboxylic acid {(S)-1-[bis-(2-methoxy-ethyl)-carbamoyl]-3-methyl-butyl}-amide | 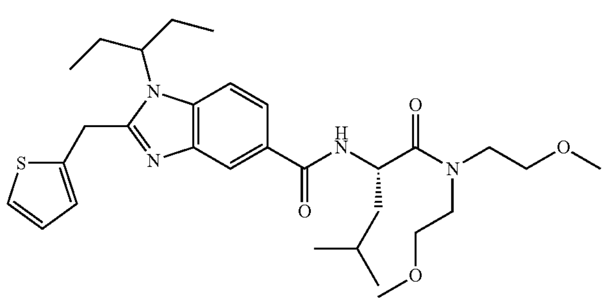 [SMILES: CCC(CC)n1c(Cc2cccs2)nc2cc(C(=O)N[C@@H](CC(C)C)C(=O)N(CCOC)CCOC)ccc21] | 557.3 | 6_1_1 | 3.05 |
| 364 | 1-(1-Ethyl-propyl)-2-thiophen-2-ylmethyl-1H-benzoimidazole-5-carboxylic acid [(S)-1-(3-methoxy-benzylcarbamoyl)-3-methyl-butyl]-amide | 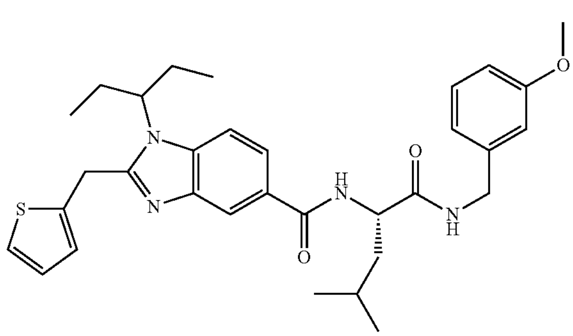 [SMILES: CCC(CC)n1c(Cc2cccs2)nc2cc(C(=O)N[C@@H](CC(C)C)C(=O)NCc3cccc(OC)c3)ccc21] | 561.2 | 5_7_1 | 3.16 |

| Exp. No. | Chemical Name | Structure | m/z [M + H]⁺ | LCMS method | R_t [min] |
|---|---|---|---|---|---|
| 365 | 1-(1-Ethyl-propyl)-2-thiophen-2-ylmethyl-1H-benzoimidazole-5-carboxylic acid [(S)-1-((R)-2-methoxymethyl-pyrrolidine-1-carbonyl)-3-methyl-butyl]-amide | 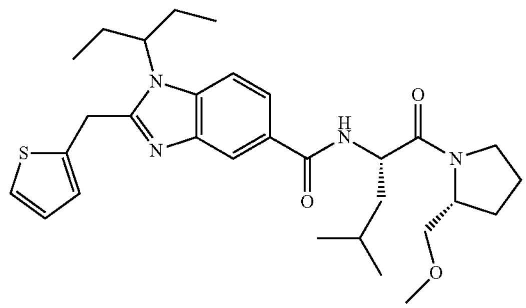 [SMILES: CCC(CC)n1c(Cc2cccs2)nc2cc(C(=O)N[C@@H](CC(C)C)C(=O)N3CCC[C@@H]3COC)ccc21] | 539.2 | 5_7_1 | 3.07 |
| 363 | 1-(1-Ethyl-propyl)-2-thiophen-2-ylmethyl-1H-benzoimidazole-5-carboxylic acid [(S)-3-methyl-1-(2-phenoxy-ethylcarbamoyl)-butyl]-amide | 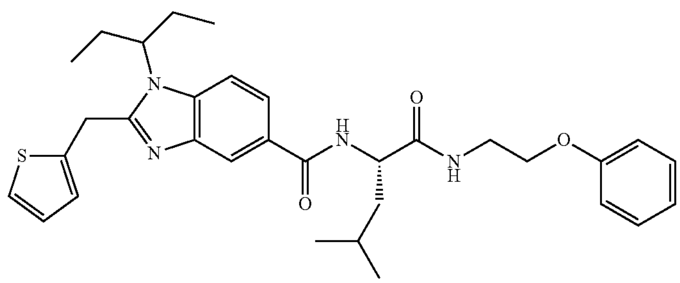 [SMILES: CCC(CC)n1c(Cc2cccs2)nc2cc(C(=O)N[C@@H](CC(C)C)C(=O)NCCOc3ccccc3)ccc21] | 561.2 | 5_7_1 | 3.21 |
| 367 | 1-(1-Ethyl-propyl)-2-thiophen-2-ylmethyl-1H-benzoimidazole-5-carboxylic acid ((S)-3-methyl-1-{[(R)-1-(tetrahydro-furan-2-yl)methyl]-carbamoyl}-butyl)-amide | 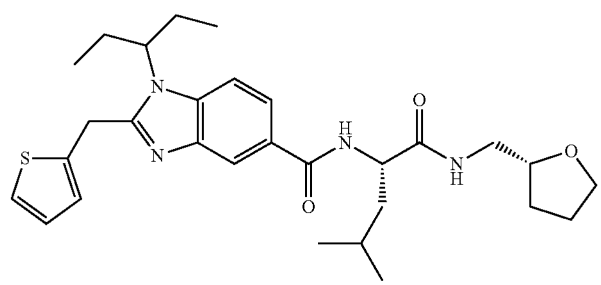 [SMILES: CCC(CC)n1c(Cc2cccs2)nc2cc(C(=O)N[C@@H](CC(C)C)C(=O)NC[C@H]3CCCO3)ccc21] | 525.2 | 5_7_1 | 2.89 |
| 368 | 1-(1-Ethyl-propyl)-2-thiophen-2-ylmethyl-1H-benzoimidazole-5-carboxylic acid ((S)-3-methyl-1-{[(S)-1-(tetrahydro-furan-2-yl)methyl]-carbamoyl}-butyl)-amide | 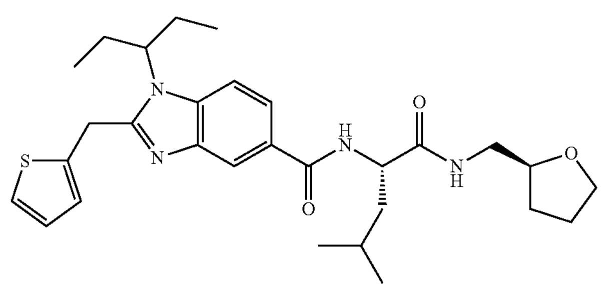 [SMILES: CCC(CC)n1c(Cc2cccs2)nc2cc(C(=O)N[C@@H](CC(C)C)C(=O)NC[C@@H]3CCCO3)ccc21] | 525.2 | 5_7_1 | 2.90 |
| 369 | 1-(1-Ethyl-propyl)-2-thiophen-2-ylmethyl-1H-benzoimidazole-5-carboxylic acid {(S)-3-methyl-1-[(tetrahydro-pyran-4-ylmethyl)-carbamoyl]-butyl}-amide | 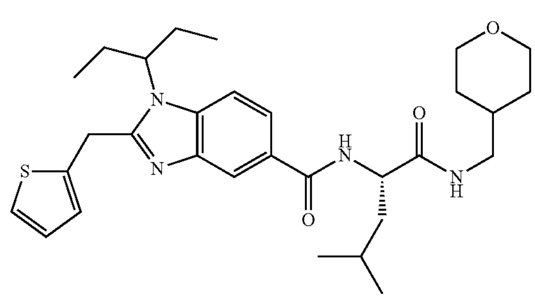 [SMILES: CCC(CC)n1c(Cc2cccs2)nc2cc(C(=O)N[C@@H](CC(C)C)C(=O)NCC3CCOCC3)ccc21] | 539.2 | 5_7_1 | 2.85 |

| Exp. No. | Chemical Name | Structure | m/z [M + H]+ | LCMS method | R$_t$ [min] |
|---|---|---|---|---|---|
| 370 | 1-(1-Ethyl-propyl)-2-thiophen-2-ylmethyl-1H-benzoimidazole-5-carboxylic acid [(S)-1-((S)-2-methoxy-1-methyl-ethylcarbamoyl)-3-methyl-butyl]-amide | 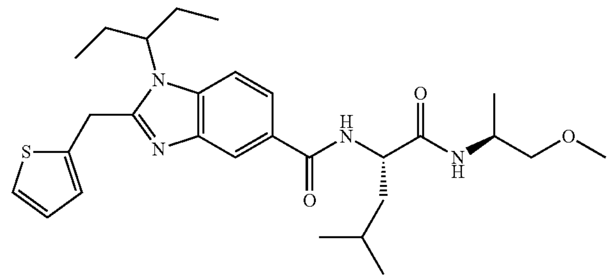 [SMILES: CCC(CC)n1c(Cc2cccs2)nc2cc(C(=O)N[C@@H](CC(C)C)C(=O)N[C@@H](C)COC)ccc21] | 513.2 | 5_7_1 | 2.90 |
| 371 | 1-(1-Ethyl-propyl)-2-thiophen-2-ylmethyl-1H-benzoimidazole-5-carboxylic acid [(S)-1-(2-isopropoxy-ethylcarbamoyl)-3-methyl-butyl]-amide | 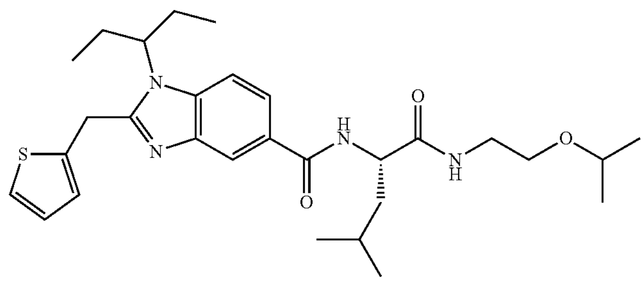 [SMILES: CCC(CC)n1c(Cc2cccs2)nc2cc(C(=O)N[C@@H](CC(C)C)C(=O)NCCOC(C)C)ccc21] | 527.2 | 5_7_1 | 3.07 |
| 372 | 1-(1-Ethyl-propyl)-2-thiophen-2-ylmethyl-1H-benzoimidazole-5-carboxylic acid {(S)-1-[(4-methoxy-benzyl)-methyl-carbamoyl]-3-methyl-butyl}-amide | 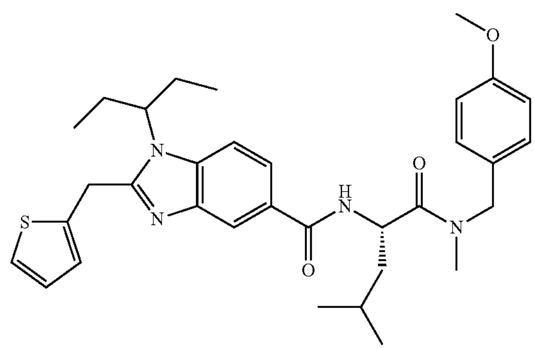 [SMILES: CCC(CC)n1c(Cc2cccs2)nc2cc(C(=O)N[C@@H](CC(C)C)C(=O)N(C)Cc3ccc(OC)cc3)ccc21] | 575.2 | 5_7_1 | 2.38 |
| 373 | 1-(1-Ethyl-propyl)-2-thiophen-2-ylmethyl-1H-benzoimidazole-5-carboxylic acid [(S)-1-(4-methoxy-piperidine-1-carbonyl)-3-methyl-butyl]-amide | 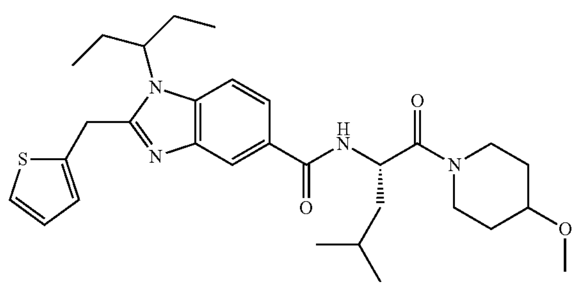 [SMILES: CCC(CC)n1c(Cc2cccs2)nc2cc(C(=O)N[C@@H](CC(C)C)C(=O)N3CCC(OC)CC3)ccc21] | 539.2 | 5_7_1 | 2.97 |
| 374 | 1-(1-Ethyl-propyl)-2-thiophen-2-ylmethyl-1H-benzoimidazole-5-carboxylic acid [(S)-1-(4-methoxymethyl-piperidine-1-carbonyl)-3-methyl-butyl]-amide | 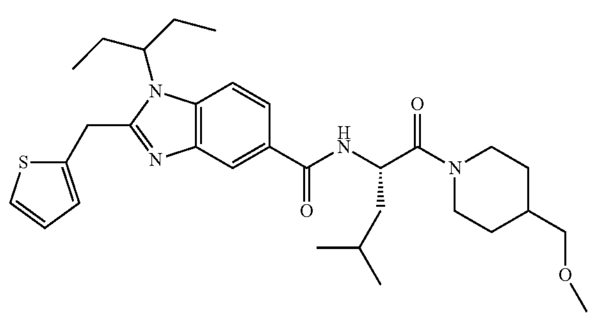 [SMILES: CCC(CC)n1c(Cc2cccs2)nc2cc(C(=O)N[C@@H](CC(C)C)C(=O)N3CCC(COC)CC3)ccc21] | 553.3 | 5_7_1 | 3.07 |

| Exp. No. | Chemical Name | Structure | m/z [M + H]+ | LCMS method | R_t [min] |
|---|---|---|---|---|---|
| 375 | 1-(1-Ethyl-propyl)-2-thiophen-2-ylmethyl-1H-benzoimidazole-5-carboxylic acid [(S)-1-(4-isopropoxy-piperidine-1-carbonyl)-3-methyl-butyl]-amide | 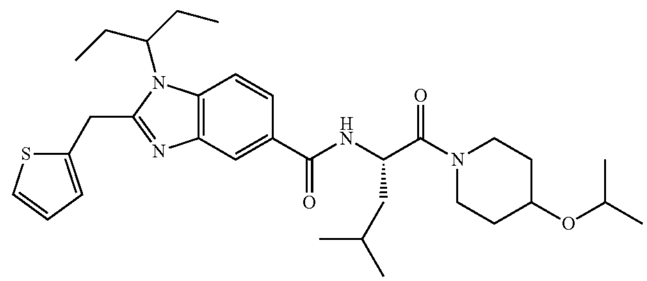 [SMILES: CCC(CC)n1c(Cc2cccs2)nc2cc(C(=O)N[C@@H](CC(C)C)C(=O)N3CCC(OC(C)C)CC3)ccc21] | 567.3 | 5_7_1 | 3.23 |
| 376 | 1-(1-Ethyl-propyl)-2-thiophen-2-ylmethyl-1H-benzoimidazole-5-carboxylic acid [(S)-1-(3-methoxy-piperidine-1-carbonyl)-3-methyl-butyl]-amide | 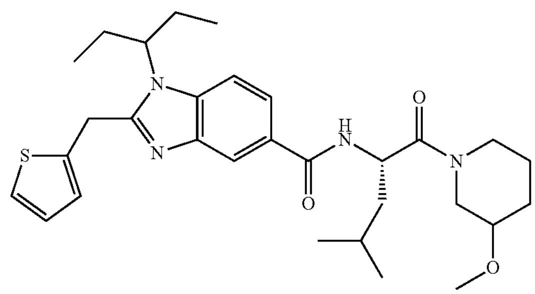 [SMILES: CCC(CC)n1c(Cc2cccs2)nc2cc(C(=O)N[C@@H](CC(C)C)C(=O)N3CCCC(OC)C3)ccc21] | 539.2 | 5_7_1 | 3.13 |
| 377 | 1-(1-Ethyl-propyl)-2-thiophen-2-ylmethyl-1H-benzoimidazole-5-carboxylic acid {(S)-3-methyl-1-[methyl-(tetrahydro-pyran-4-yl)-carbamoyl]-butyl}-amide | 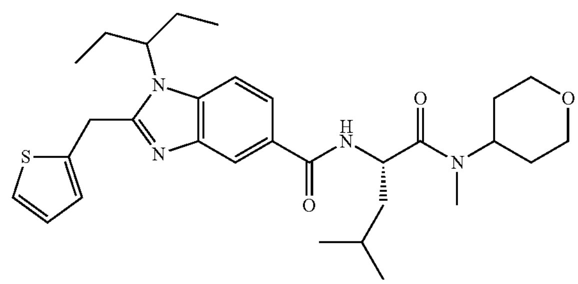 [SMILES: CCC(CC)n1c(Cc2cccs2)nc2cc(C(=O)N[C@@H](CC(C)C)C(=O)N(C)C3CCOCC3)ccc21] | 539.3 | 6_1_1 | 2.93 |
| 378 | 1-(1-Ethyl-propyl)-2-thiophen-2-ylmethyl-1H-benzoimidazole-5-carboxylic acid [(S)-1-(3-methoxymethyl-piperidine-1-carbonyl)-3-methyl-butyl]-amide | 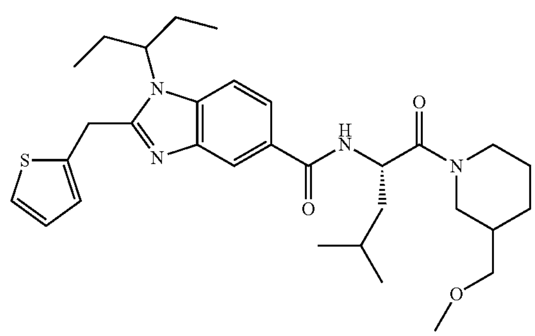 [SMILES: CCC(CC)n1c(Cc2cccs2)nc2cc(C(=O)N[C@@H](CC(C)C)C(=O)N3CCCC(COC)C3)ccc21] | 553.2 | 5_7_1 | 3.14 |
| 379 | 1-(1-Ethyl-propyl)-2-thiophen-2-ylmethyl-1H-benzoimidazole-5-carboxylic acid [(S)-3-methyl-1-(pyrrolidine-1-carbonyl)-butyl]-amide | 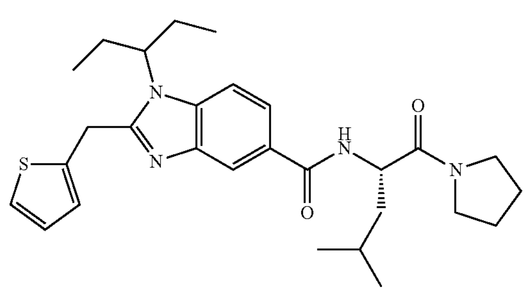 [SMILES: CCC(CC)n1c(Cc2cccs2)nc2cc(C(=O)N[C@@H](CC(C)C)C(=O)N3CCCC3)ccc21] | 495.2 | 5_7_1 | 2.98 |

| Exp. No. | Chemical Name | Structure | m/z [M + H]+ | LCMS method | R$_t$ [min] |
|---|---|---|---|---|---|
| 380 | 1-(1-Ethyl-propyl)-2-thiophen-2-ylmethyl-1H-benzoimidazole-5-carboxylic acid {(S)-1-[(2-methoxy-ethyl)-methyl-carbamoyl]-3-methyl-butyl}-amide | 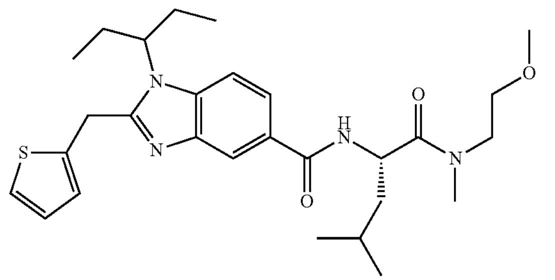 [SMILES: CCC(CC)n1c(Cc2cccs2)nc2cc(C(=O)N[C@@H](CC(C)C)C(=O)N(C)CCOC)ccc21] | 513.2 | 5_7_1 | 2.94 |
| 381 | 1-(1-Ethyl-propyl)-2-thiophen-2-ylmethyl-1H-benzoimidazole-5-carboxylic acid ((S)-3-methyl-1-methylcarbamoyl-butyl)-amide | 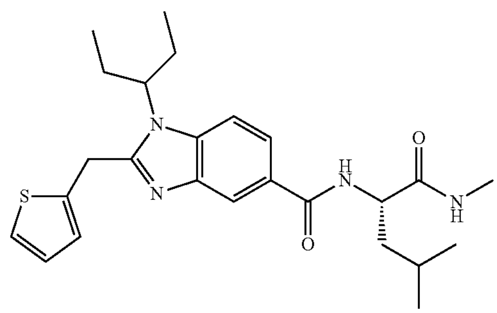 [SMILES: CCC(CC)n1c(Cc2cccs2)nc2cc(C(=O)N[C@@H](CC(C)C)C(=O)NC)ccc21] | 455.2 | 5_7_1 | 2.76 |
| 382 | 1-(1-Ethyl-propyl)-2-thiophen-2-ylmethyl-1H-benzoimidazole-5-carboxylic acid {(S)-3-methyl-1-[2-(tetrahydro-pyran-4-yl)-ethylcarbamoyl]-butyl}-amide | 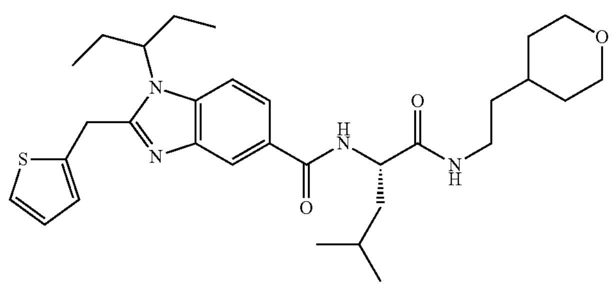 [SMILES: CCC(CC)n1c(Cc2cccs2)nc2cc(C(=O)N[C@@H](CC(C)C)C(=O)NCCC3CCOCC3)ccc21] | 553.2 | 5_7_1 | 2.95 |
| 383 | 1-(1-Ethyl-propyl)-2-thiophen-2-ylmethyl-1H-benzoimidazole-5-carboxylic acid [(S)-1-(2-ethoxy-ethylcarbamoyl)-3-methyl-butyl]-amide | 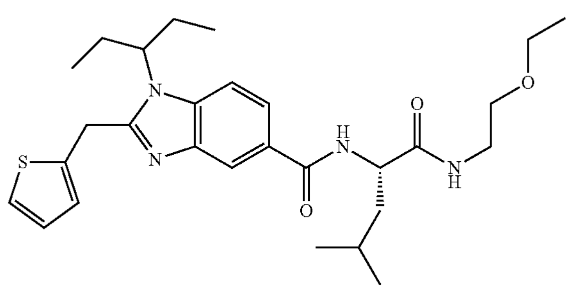 [SMILES: CCOCCNC(=O)[C@H](CC(C)C)NC(=O)c1ccc2c(c1)nc(Cc1cccs1)n2C(CC)CC] | 513.2 | 5_7_1 | 2.90 |
| 384 | 1-(1-Ethyl-propyl)-2-thiophen-2-ylmethyl-1H-benzoimidazole-5-carboxylic acid [(S)-1-((S)-2-methoxymethyl-pyrrolidine-1-carbonyl)-3-methyl-butyl]-amide | 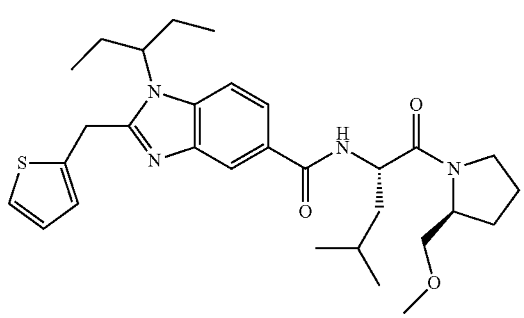 [SMILES: CCC(CC)n1c(Cc2cccs2)nc2cc(C(=O)N[C@@H](CC(C)C)C(=O)N3CCC[C@H]3COC)ccc21] | 539.2 | 5_7_1 | 3.08 |

-continued

| Exp. No. | Chemical Name | Structure | m/z [M + H]+ | LCMS method | R$_t$ [min] |
|---|---|---|---|---|---|
| 385 | 1-(1-Ethyl-propyl)-2-thiophen-2-ylmethyl-1H-benzoimidazole-5-carboxylic acid [(S)-3-methyl-1-(2-propoxy-ethylcarbamoyl)-butyl]-amide | 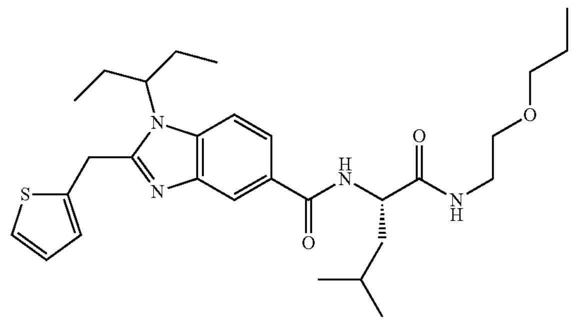 [SMILES: CCCOCCNC(=O)[C@H](CC(C)C)NC(=O)c1ccc2c(c1)nc(Cc1cccs1)n2C(CC)CC] | 527.2 | 5_7_1 | 3.04 |
| 386 | 1-(1-Ethyl-propyl)-2-thiophen-2-ylmethyl-1H-benzoimidazole-5-carboxylic acid {(S)-3-methyl-1-[(tetrahydro-pyran-2-ylmethyl)-carbamoyl]-butyl}-amide | 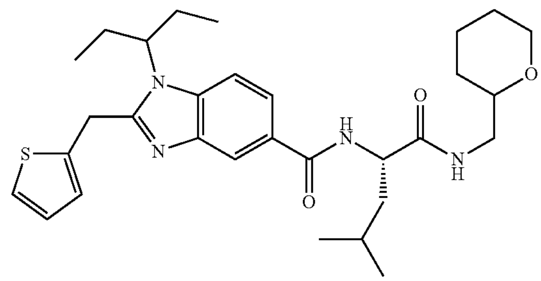 [SMILES: CCC(CC)n1c(Cc2cccs2)nc2cc(C(=O)N[C@@H](CC(C)C)C(=O)NCC3CCCCO3)ccc21] | 539.2 | 5_7_1 | 2.86 |
| 387 | 1-(1-Ethyl-propyl)-2-thiophen-2-ylmethyl-1H-benzoimidazole-5-carboxylic acid {(S)-3-methyl-1-[methyl-(tetrahydro-furan-2-ylmethyl)-carbamoyl]-butyl}-amide | 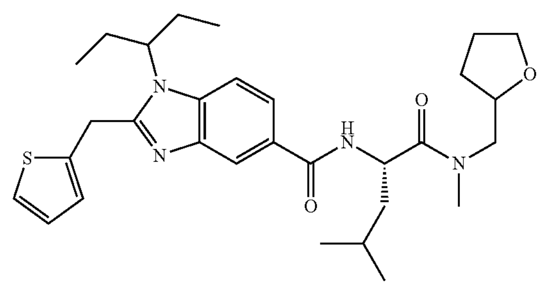 [SMILES: CCC(CC)n1c(Cc2cccs2)nc2cc(C(=O)N[C@@H](CC(C)C)C(=O)N(C)CC3CCCO3)ccc21] | 539.2 | 5_7_1 | 3.02 |
| 388 | 1-(1-Ethyl-propyl)-2-thiophen-2-ylmethyl-1H-benzoimidazole-5-carboxylic acid {(S)-3-methyl-1-[3-(tetrahydro-furan-2-ylmethoxy)-propylcarbamoyl]-butyl}-amide | 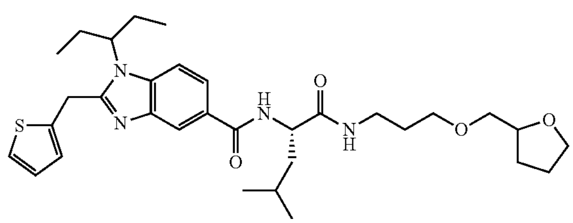 [SMILES: CCC(CC)n1c(Cc2cccs2)nc2cc(C(=O)N[C@@H](CC(C)C)C(=O)NCCCOCC3CCCO3)ccc21] | 583.3 | 5_7_1 | 2.95 |
| 389 | 1-(1-Ethyl-propyl)-2-thiophen-2-ylmethyl-1H-benzoimidazole-5-carboxylic acid [(S)-1-(3-benzyloxy-propylcarbamoyl)-3-methyl-butyl]-amide | 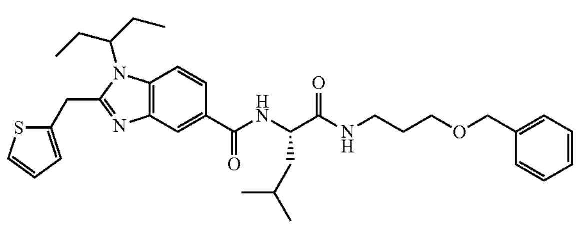 [SMILES: CCC(CC)n1c(Cc2cccs2)nc2cc(C(=O)N[C@@H](CC(C)C)C(=O)NCCCOCc3ccccc3)ccc21] | 589.2 | 5_7_1 | 3.24 |

| Exp. No. | Chemical Name | Structure | m/z [M + H]⁺ | LCMS method | R_t [min] |
|---|---|---|---|---|---|
| 390 | 1-(1-Ethyl-propyl)-2-thiophen-2-ylmethyl-1H-benzoimidazole-5-carboxylic acid [(S)-1-((S)-3-benzyloxy-pyrrolidine-1-carbonyl)-3-methyl-butyl]-amide | 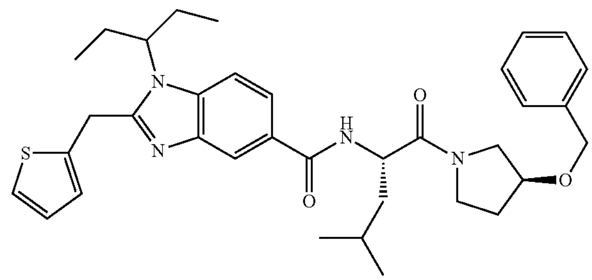 [SMILES: CCC(CC)n1c(Cc2cccs2)nc2cc(C(=O)N[C@@H](CC(C)C)C(=O)N3CC[C@H](OCc4ccccc4)C3)ccc21] | 601.2 | 5_7_1 | 3.38 |
| 391 | 1-(1-Ethyl-propyl)-2-thiophen-2-ylmethyl-1H-benzoimidazole-5-carboxylic acid [(S)-1-(3-cyclopropylmethoxy-propylcarbamoyl)-3-methyl-butyl]-amide | 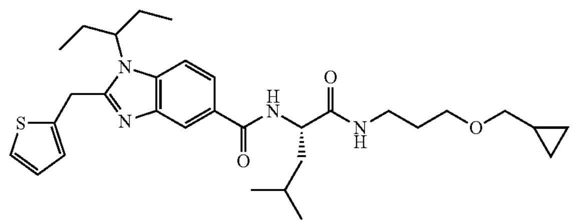 [SMILES: CCC(CC)n1c(Cc2cccs2)nc2cc(C(=O)N[C@@H](CC(C)C)C(=O)NCCCOCC3CC3)ccc21] | 553.2 | 5_7_1 | 3.08 |
| 392 | 1-(1-Ethyl-propyl)-2-thiophen-2-ylmethyl-1H-benzoimidazole-5-carboxylic acid ((S)-3-methyl-1-{methyl-[3-(tetrahydro-furan-2-yl)-propyl]-carbamoyl}-butyl)-amide | 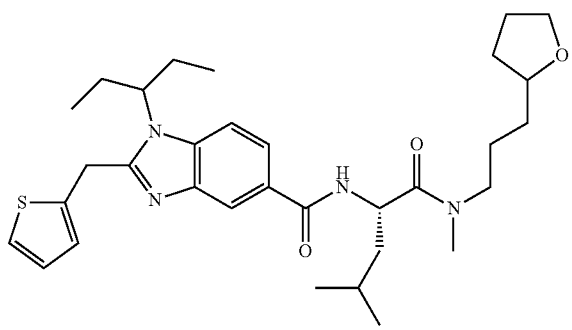 [SMILES: CCC(CC)n1c(Cc2cccs2)nc2cc(C(=O)N[C@@H](CC(C)C)C(=O)N(C)CCCC3CCCO3)ccc21] | 567.3 | 5_7_1 | 3.11 |
| 393 | 1-(1-Ethyl-propyl)-2-thiophen-2-ylmethyl-1H-benzoimidazole-5-carboxylic acid {(S)-1-[([1,4]dioxan-2-ylmethyl)-carbamoyl]-3-methyl-butyl}-amide | 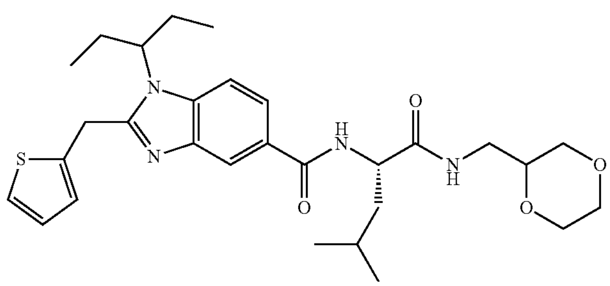 [SMILES: CCC(CC)n1c(Cc2cccs2)nc2cc(C(=O)N[C@@H](CC(C)C)C(=O)NCC3COCCO3)ccc21] | 541.2 | 5_7_1 | 2.80 |
| 394 | 1-(1-Ethyl-propyl)-2-thiophen-2-ylmethyl-1H-benzoimidazole-5-carboxylic acid [(S)-1-(2-methoxy-2-methyl-propylcarbamoyl)-3-methyl-butyl]-amide | 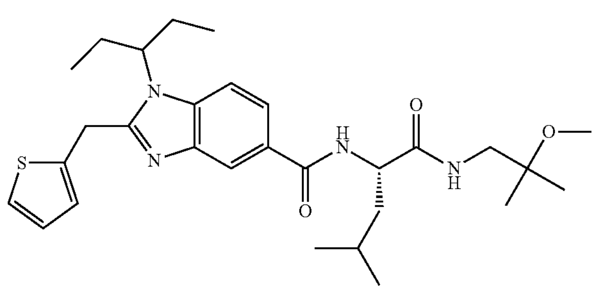 [SMILES: CCC(CC)n1c(Cc2cccs2)nc2cc(C(=O)N[C@@H](CC(C)C)C(=O)NCC(C)(C)OC)ccc21] | 527.2 | 5_7_1 | 3.05 |

| Exp. No. | Chemical Name | Structure | m/z [M+H]+ | LCMS method | R_t [min] |
|---|---|---|---|---|---|
| 395 | 1-(1-Ethyl-propyl)-2-thiophen-2-ylmethyl-1H-benzoimidazole-5-carboxylic acid {(S)-3-methyl-1-[methyl-(tetrahydro-pyran-2-ylmethyl)-carbamoyl]-butyl}-amide | 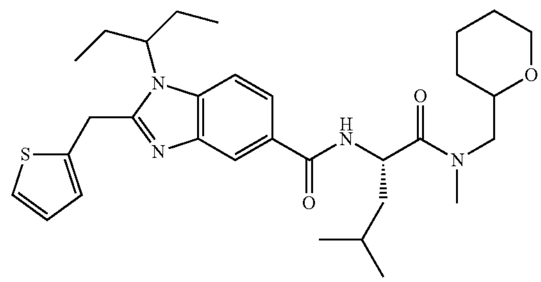 [SMILES: CCC(CC)n1c(Cc2cccs2)nc2cc(C(=O)N[C@@H](CC(C)C)C(=O)N(C)CC3CCCCO3)ccc21] | 553.2 | 5_7_1 | 3.23 |
| 396 | 1-(1-Ethyl-propyl)-2-thiophen-2-ylmethyl-1H-benzoimidazole-5-carboxylic acid {(S)-1-[ethyl-(tetrahydro-pyran-2-ylmethyl)-carbamoyl]-3-methyl-butyl}-amide | 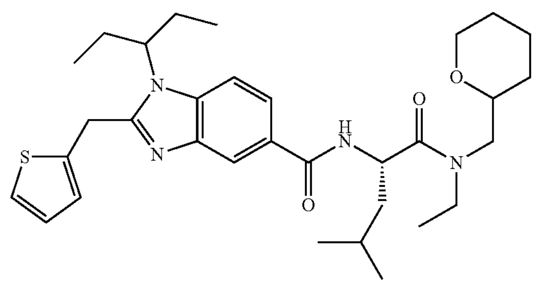 [SMILES: CCC(CC)n1c(Cc2cccs2)nc2cc(C(=O)N[C@@H](CC(C)C)C(=O)N(CC)CC3CCCCO3)ccc21] | 567.4 | 6_1_1 | 3.39 |
| 397 | 1-(1-Ethyl-propyl)-2-thiophen-2-ylmethyl-1H-benzoimidazole-5-carboxylic acid [(S)-3-methyl-1-(1-oxa-spiro[4.5]dec-3-ylcarbamoyl)-butyl]-amide | 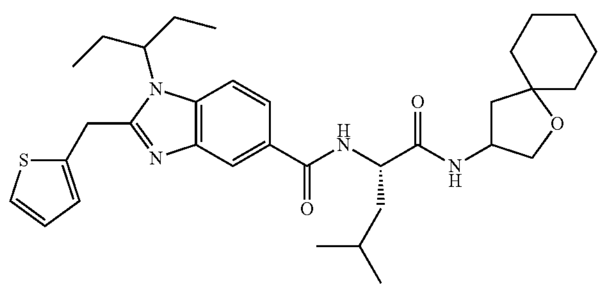 [SMILES: CCC(CC)n1c(Cc2cccs2)nc2cc(C(=O)N[C@@H](CC(C)C)C(=O)NC3COC4(CCCCC4)C3)ccc21] | 579.3 | 5_7_1 | 3.24 |
| 398 | 1-(1-Ethyl-propyl)-2-thiophen-2-ylmethyl-1H-benzoimidazole-5-carboxylic acid [(S)-3-methyl-1-(1-oxa-spiro[4.4]non-3-ylcarbamoyl)-butyl]-amide | 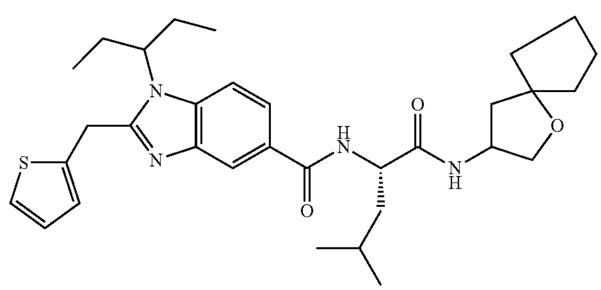 [SMILES: CCC(CC)n1c(Cc2cccs2)nc2cc(C(=O)N[C@@H](CC(C)C)C(=O)NC3COC4(CCCC4)C3)ccc21] | 565.2 | 5_7_1 | 3.20 |
| 399 | 1-(1-Ethyl-propyl)-2-thiophen-2-ylmethyl-1H-benzoimidazole-5-carboxylic acid {(S)-3-methyl-1-[(1H-tetrazol-5-ylmethyl)-carbamoyl]-butyl}-amide | 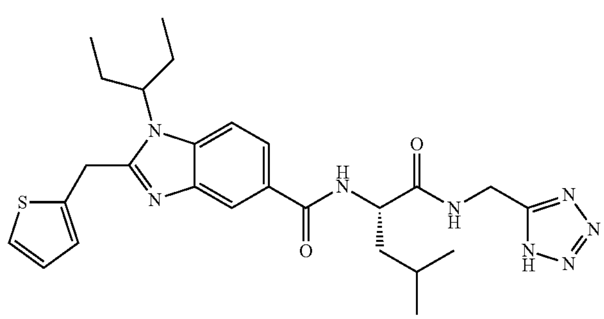 [SMILES: CCC(CC)n1c(Cc2cccs2)nc2cc(C(=O)N[C@@H](CC(C)C)C(=O)NCc3nnn[nH]3)ccc21] | 523.2 | 5_3_1 | 1.96 |

-continued

| Exp. No. | Chemical Name | Structure | m/z [M + H]+ | LCMS method | R_t [min] |
|---|---|---|---|---|---|
| 400 | 1-(1-Ethyl-propyl)-2-thiophen-2-ylmethyl-1H-benzoimidazole-5-carboxylic acid {(S)-3-methyl-1-[2-(1H-tetrazol-5-yl)-ethylcarbamoyl]-butyl}-amide | 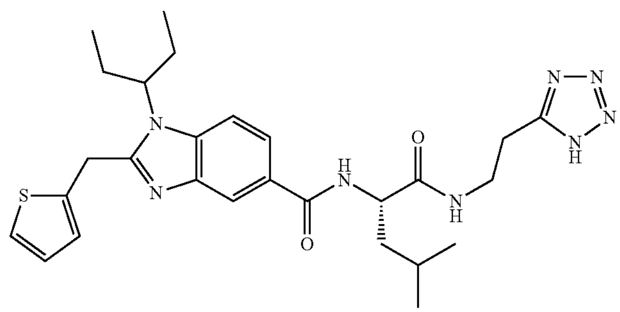 [SMILES: CCC(CC)n1c(Cc2cccs2)nc2cc(C(=O)N[C@@H](CC(C)C)C(=O)NCCc3nnn[nH]3)ccc21] | 537.2 | 5_3_1 | 2.08 |
| 401 | 1-(1-Ethyl-propyl)-2-thiophen-2-ylmethyl-1H-benzoimidazole-5-carboxylic acid [(S)-3-methyl-1-(2-sulfamoyl-ethylcarbamoyl)-butyl]-amide | 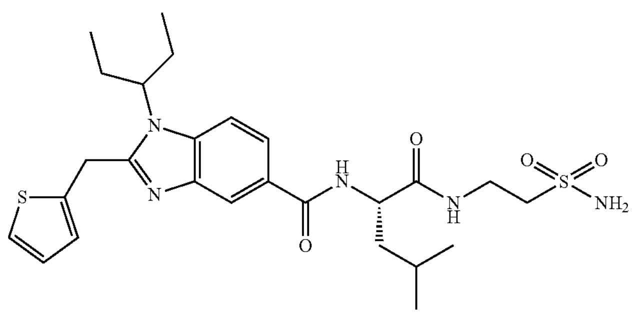 [SMILES: CCC(CC)n1c(Cc2cccs2)nc2cc(C(=O)N[C@@H](CC(C)C)C(=O)NCCS(N)(=O)=O)ccc21] | 548.2 | 3_2_1 | 1.31 |
| 402 | 1-(1-Ethyl-propyl)-2-thiophen-2-ylmethyl-1H-benzoimidazole-5-carboxylic acid [(S)-1-(2-methanesulfonylamino-ethylcarbamoyl)-3-methyl-butyl]-amide | 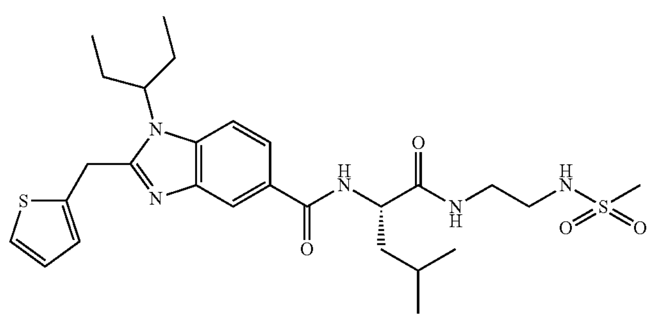 [SMILES: CCC(CC)n1c(Cc2cccs2)nc2cc(C(=O)N[C@@H](CC(C)C)C(=O)NCCNS(C)(=O)=O)ccc21] | 562.2 | 5_2_1 | 3.86 |
| 403 | 1-(1-Ethyl-propyl)-2-thiophen-2-ylmethyl-1H-benzoimidazole-5-carboxylic acid [(S)-1-(cyanomethyl-carbamoyl)-3-methyl-butyl]-amide | 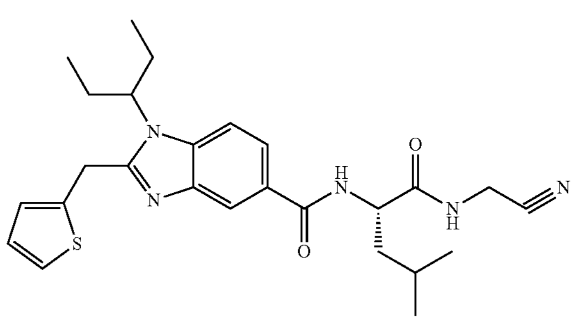 [SMILES: CCC(CC)n1c(Cc2cccs2)nc2cc(C(=O)N[C@@H](CC(C)C)C(=O)NCC#N)ccc21] | 478.3 | 4_1_1 | 1.19 |
| 404 | 1-(1-Ethyl-propyl)-2-thiophen-2-ylmethyl-1H-benzoimidazole-5-carboxylic acid [(S)-1-(2-cyano-ethylcarbamoyl)-3-methyl-butyl]-amide | 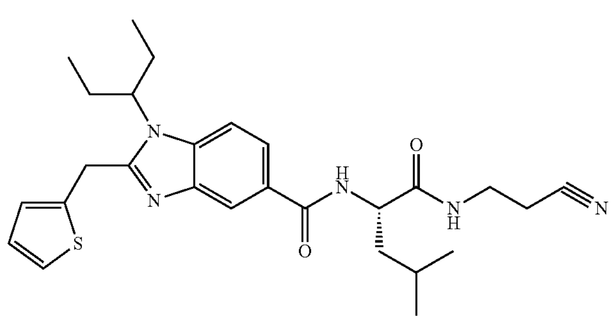 [SMILES: CCC(CC)n1c(Cc2cccs2)nc2cc(C(=O)N[C@@H](CC(C)C)C(=O)NCCC#N)ccc21] | 538.3 | 4_1_1 | 1.18 |

-continued

| Exp. No. | Chemical Name | Structure | m/z [M + H]+ | LCMS method | R_t [min] |
|---|---|---|---|---|---|
| 405 | 1-(1-Ethyl-propyl)-2-thiophen-2-ylmethyl-1H-benzoimidazole-5-carboxylic acid {(S)-3-methyl-1-[methyl-(5-oxo-4,5-dihydro-1H-[1,2,4]triazol-3-ylmethyl)-carbamoyl]-butyl}-amide | 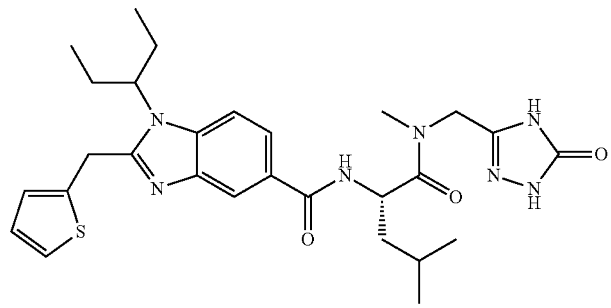 [SMILES: CCC(CC)n1c(Cc2cccs2)nc2cc(C(=O)N[C@@H](CC(C)C)C(=O)N(C)Cc3n[nH]c(=O)[nH]3)ccc21] | 552.3 | 3_2_1 | 1.30 |
| 406 | 1-(1-Ethyl-propyl)-2-thiophen-2-ylmethyl-1H-benzoimidazole-5-carboxylic acid {(S)-3-methyl-1-[2-(5-oxo-4,5-dihydro-1H-[1,2,4]triazol-3-yl)-ethylcarbamoyl]-butyl}-amide | 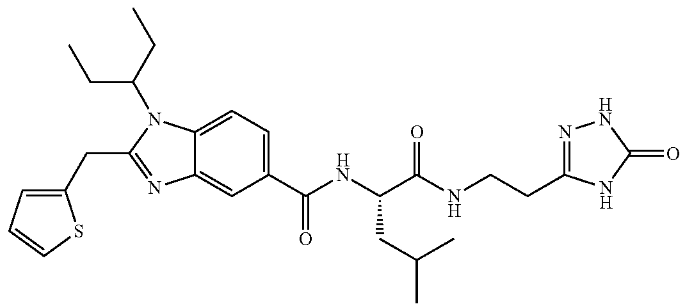 [SMILES: CCC(CC)n1c(Cc2cccs2)nc2cc(C(=O)N[C@@H](CC(C)C)C(=O)NCCc3n[nH]c(=O)[nH]3)ccc21] | 552.1 | 3_2_1 | 1.11 |
| 407 | 1-(1-Ethyl-propyl)-2-thiophen-2-ylmethyl-1H-benzoimidazole-5-carboxylic acid [(S)-1-(3-hydroxy-pyrrolidine-1-carbonyl)-3-methyl-butyl]-amide | 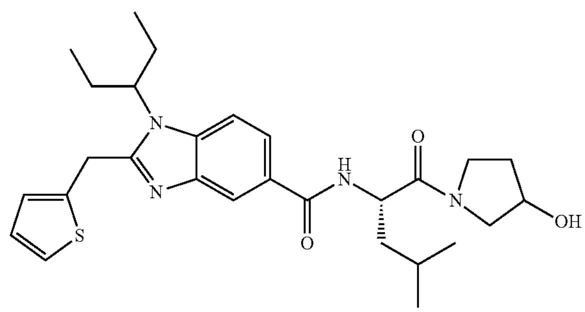 [SMILES: CCC(CC)n1c(Cc2cccs2)nc2cc(C(=O)N[C@@H](CC(C)C)C(=O)N3CCC(O)C3)ccc21] | 511.3 | 6_6_1 | 2.74 |

EXAMPLE 408

((S)-2-{[1-(1-Ethyl-propyl)-2-thiophen-2-ylmethyl-1H-benzoimidazole-5-carbonyl]-amino}-4-methyl-pentanoylamino)-acetic acid

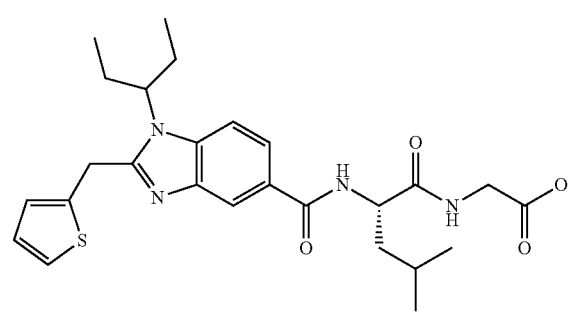

a) ((S)-2-{[1-(1-Ethyl-propyl)-2-thiophen-2-ylmethyl-1H-benzoimidazole-5-carbonyl]-amino}-4-methyl-pentanoylamino)-acetic acid tert.-butyl ester

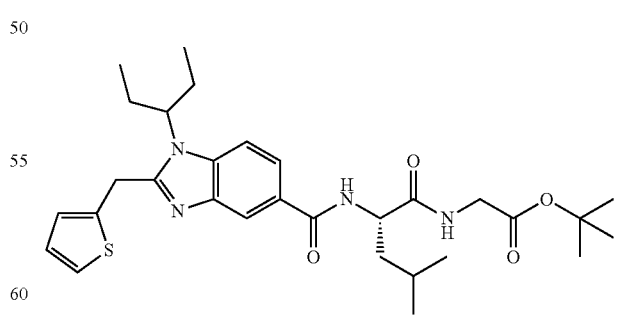

To a solution of 100 mg of (S)-2-{[1-(1-ethyl-propyl)-2-thiophen-2-ylmethyl-1H-benzoimidazole-5-carbonyl]-amino}-4-methyl-pentanoic acid in 1 ml of dry DMF 12 mg of HOAT, 41 mg of EDC and 0.13 ml of DIPEA were added at 0° C. After 15 min 30 mg of glycine tert.-butylester-hydrochloride and 0.03 ml of DIPEA were added and the reaction was stirred at it for 16 h. The reaction was then poured into water and the pH was adjusted to 3 by the addition of 2 M aqueous hydrochloric acid. The reaction was extracted with ethyl acetate three times. The combined organic phases were washed with saturated aqueous sodium bicarbonate solution and brine, dried over magnesium sulphate and concentrated. The crude product was purified by HPLC to yield 32 mg (32%) of ((S)-2-{[1-(1-ethyl-propyl)-2-thiophen-2-ylmethyl-1H-benzoimidazole-5-carbonyl]-amino}-4-methyl-pentanoylamino)-acetic acid tert.-butyl ester.

$C_{30}H_{42}N_4O_4S$ (554.75), LCMS (method 5_3_1): Rt=2.30 min, m/z=555.23 [M+H]$^+$ b) ((S)-2-{[1-(1-Ethyl-propyl)-2-thiophen-2-ylmethyl-1H-benzoimidazole-5-carbonyl]-amino}-4-methyl-pentanoylamino)-acetic acid 32 mg of ((S)-2-{[1-(1-ethyl-propyl)-2-thiophen-2-ylmethyl-1H-benzoimidazole-5-carbonyl]-amino}-4-methyl-pentanoylamino)-acetic acid tert.-butyl ester were reacted with 0.8 ml of 4 M hydrochloric acid in dioxane at rt over night. The reaction mixture was then concentrated in vacuo to yield 28 mg (91%) of ((S)-2-{[1-(1-Ethyl-propyl)-2-thiophen-2-ylmethyl-1H-benzoimidazole-5-carbonyl]-amino}-4-methyl-pentanoylamino)-acetic acid.

$C_{26}H_{34}N_4O_4S$ (498.64), LCMS (method 5_5_1): Rt=1.91 min, m/z=499.20 [M+H]$^+$

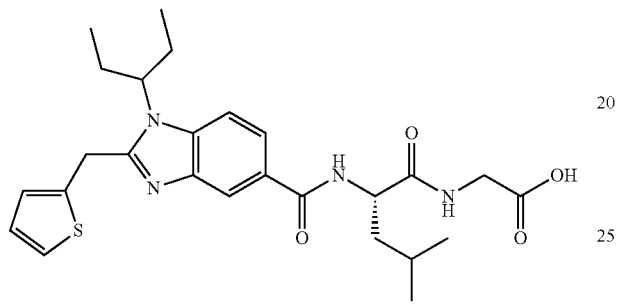

The following examples were prepared in analogy to example 408:

| Exp. No. | Chemical Name | Structure | m/z [M + H]$^+$ | LCMS method | R$_t$ [min] |
|---|---|---|---|---|---|
| 409 | (S)-1-((S)-2-{[1-(1-Ethyl-propyl)-2-thiophen-2-ylmethyl-1H-benzoimidazole-5-carbonyl]-amino}-4-methyl-pentanoyl)-pyrrolidine-2-carboxylic acid | 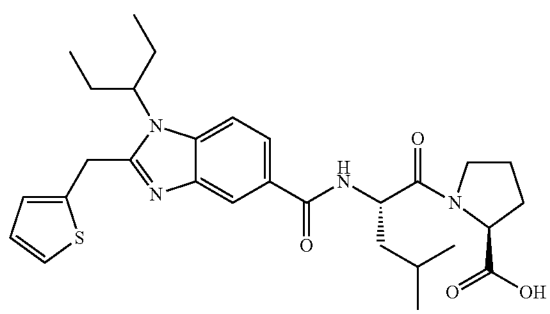 [SMILES: CCC(CC)n1c(Cc2cccs2)nc2cc(C(=O)N[C@@H](CC(C)C)C(=O)N3CCC[C@H]3C(=O)O)ccc21] | 539.3 | 6_6_1 | 2.87 |
| 410 | (R)-1-((S)-2-{[1-(1-Ethyl-propyl)-2-thiophen-2-ylmethyl-1H-benzoimidazole-5-carbonyl]-amino}-4-methyl-pentanoyl)-pyrrolidine-2-carboxylic acid | 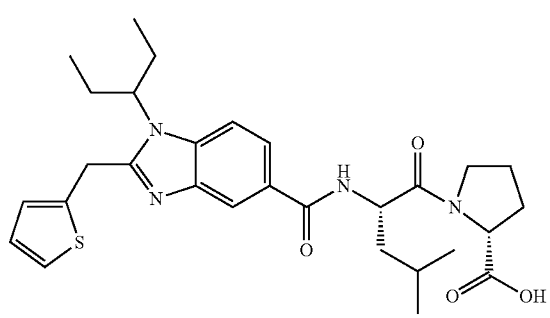 [SMILES: CCC(CC)n1c(Cc2cccs2)nc2cc(C(=O)N[C@@H](CC(C)C)C(=O)N3CCC[C@@H]3C(=O)O)ccc21] | 539.3 | 3_1_1 | 1.50 |

| Exp. No. | Chemical Name | Structure | m/z [M + H]⁺ | LCMS method | R$_t$ [min] |
|---|---|---|---|---|---|
| 411 | 1-((S)-2-{[1-(1-Ethyl-propyl)-2-thiophen-2-ylmethyl-1H-benzoimidazole-5-carbonyl]-amino}-4-methyl-pentanoyl)-azetidine-3-carboxylic acid | 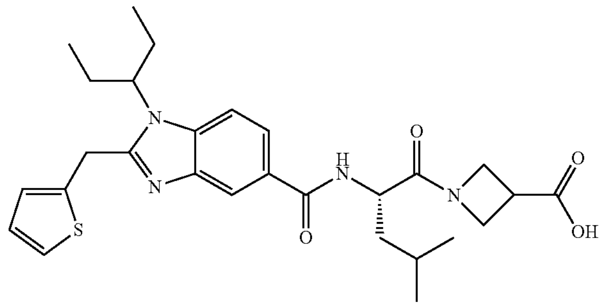 [SMILES: CCC(CC)n1c(Cc2cccs2)nc2cc(C(=O)N[C@@H](CC(C)C)C(=O)N3CC(C(=O)O)C3)ccc21] | 525.2 | 6_6_1 | 2.77 |

The following examples were obtained after separation of the diastereomeric mixtures using chiral stationary phases either by preparative HPLC using a Waters Alliance 2695 system (Flow rate 1 ml/min) or by SFC using a Thar system. The separation conditions are described below. (In the compounds described in the following table, the absolute configuration of the amino acid is as drawn, the diastereomers separated are the diastereomeric forms of the methyl-cyclohexylamine or methyl cyclopentyl amine part).

| Exp. No. | Structure and chemical name of diastereomeric mixture | Conditions of chiral sep. | No. of diastereomer | Rt [min] (sep.) | % de | Obs. Mass | LCMS method (non-chiral) | Rt [min] (non-chiral) |
|---|---|---|---|---|---|---|---|---|
| 412 | (S)-4-Methyl-2-{[1-(2-methyl-cyclohexyl)-2-thiophen-2-ylmethyl-1H-benzoimidazole-5-carbonyl]-amino}-pentanoic acid | Waters HPLC; Chiralpak IA-81; 250 × 4.6 mm; heptane + iPrOH + MeOH 6 + 1 + 1 + 0.1% NH₄Ac | 1 | 10.06 | >99 | 468.19 | 6_3_1 | 1.51 |
| 413 | | | 2 | 11.18 | 98.8 | 468.19 | 6_3_1 | 1.51 |
| 414 | | | 3 | 12.83 | >99 | 468.19 | 6_3_1 | 1.50 |
| 415 | | | 4 | 14.30 | 98.3 | 468.20 | 6_3_1 | 1.49 |
| 416 | (S)-2-{[2-Furan-2-ylmethyl-1-(2-methyl-cyclohexyl)-1H-benzoimidazole-5-carbonyl]-amino}-4-methyl-pentanoic acid | Waters HPLC; Chiralpak IA-81; 250 × 4.6 mm; heptane + iPrOH + MeOH 5 + 1 + 1 + 0.1% NH₄Ac | 1 | 7.93 | >99 | 452.41 | 6_2_1 | 1.92 |
| 417 | | | 2 | 8.94 | 94.6 | 452.41 | 6_2_1 | 1.89 |
| 418 | | | 3 | 9.70 | 79.0 | 452.41 | 6_2_1 | 1.87 |
| 419 | | | 4 | 10.42 | 76.1 | 452.41 | 6_2_1 | 1.89 |

-continued

| Exp. No. | Structure and chemical name of diastereomeric mixture | Conditions of chiral sep. | No. of diastereomer | Rt [min] (sep.) | % de | Obs. Mass | LCMS method (non-chiral) | Rt [min] (non-chiral) |
|---|---|---|---|---|---|---|---|---|
| 420 | 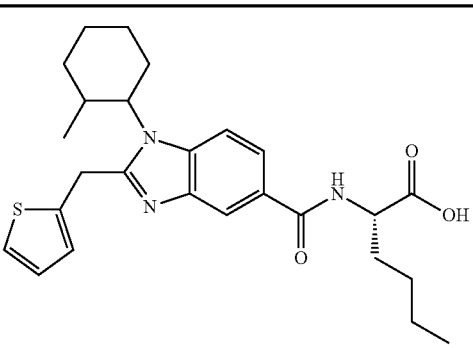 (S)-2-{[1-(2-Methyl-cyclohexyl)-2-thiophen-2-ylmethyl-1H-benzoimidazole-5-carbonyl]-amino}-hexanoic acid | Waters HPLC; Chiralpak IA-103; 250 × 4.6 mm; heptane + iPrOH + MeOH + MeCN 7 + 1 + 0.5 + 0.5 + 0.1% NH₄Ac | 1 | 16.84 | >99 | 468.27 | 5_7_1 | 3.02 |
| 421 | | | 2 | 19.90 | 98.7 | 468.14 | 5_7_1 | 2.99 |
| 422 | | | 3 | 21.52 | 97.9 | 468.22 | 5_7_1 | 2.94 |
| 423 | | | 4 | 26.32 | >99 | 468.24 | 5_7_1 | 2.94 |
| 424 | 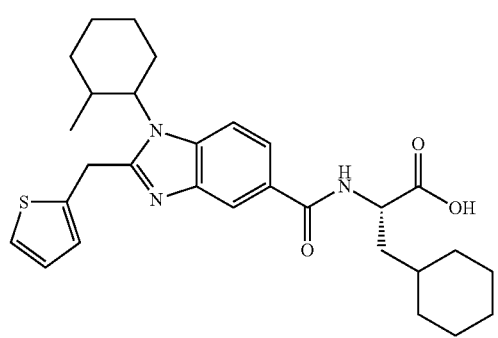 (S)-3-Cyclohexyl-2-{[1-(2-methyl-cyclohexyl)-2-thiophen-2-ylmethyl-1H-benzoimidazole-5-carbonyl]-amino}-propionic acid | Waters HPLC; Chiralpak IA-103; 250 × 4.6 mm; heptane + iPrOH + MeOH + MeCN 8 + 1 + 0.5 + 0.5 + 0.1% NH₄Ac | 1 | 18.44 | >99 | 508.20 | 5_7_1 | 3.16 |
| 425 | | | 2 | 23.22 | 86 | 508.20 | 5_7_1 | 3.17 |
| 426 | | | 3 | 24.72 | >99 | 508.26 | 5_7_1 | 3.16 |
| 427 | | | 4 | 30.44 | 95.8 | 508.24 | 5_7_1 | 3.15 |
| 428 | 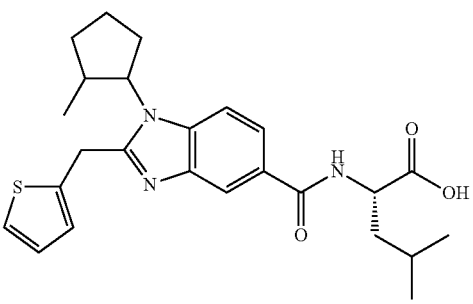 (S)-4-Methyl-2-{[1-(2-methyl-cyclopentyl)-2-thiophen-2-ylmethyl-1H-benzoimidazole-5-carbonyl]-amino}-pentanoic acid | Thar SFC; Chiralpak AD-H; 250 × 4.6 mm; MeOH 20% | 1 | 20.78 | >99 | 452.09 | 5_5_1 | 2.05 |
| 429 | | | 2 | 22.93 | 85.0 | 452.09 | 5_5_1 | 2.05 |
| 430 | | | 3 | 25.42 | 77.7 | 452.09 | 5_5_1 | 2.04 |
| 431 | | | 4 | 29.69 | 79.6 | 452.09 | 5_5_1 | 2.06 |

-continued

| Exp. No. | Structure and chemical name of diastereomeric mixture | Conditions of chiral sep. | No. of diastereomer | Rt [min] (sep.) | % de | Obs. Mass | LCMS method (non-chiral) | Rt [min] (non-chiral) |
|---|---|---|---|---|---|---|---|---|
| 432 | 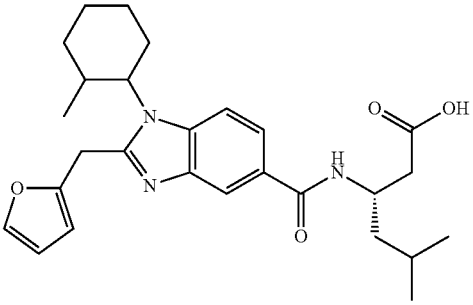 (S)-3-{[2-Furan-2-ylmethyl-1-(2-methyl-cyclohexyl)-1H-benzoimidazole-5-carbonyl]-amino}-5-methyl-hexanoic acid | Waters HPLC; Chiralpak IA-81; 250 × 4.6 mm; heptane + iPrOH + MeOH 4 + 1 + 1 + 0.3% NH₄Ac | 1 | 7.77 | >99 | 466.25 | 7_1_1 | 1.26 |
| 433 | | | 2* | 7.98 | >99 | 466.20 | 6_5_1 | 2.13 |
| 434 | | | 3* | 9.16 | 96.0 | 466.20 | 6_5_1 | 2.11 |
| 435 | | | 4 | 11.96 | 95.0 | 466.19 | 6_6_1 | 2.92 |
| 436 | 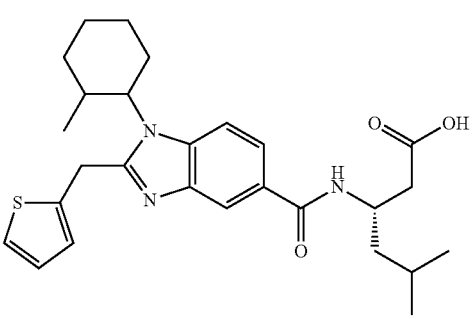 (S)-5-Methyl-3-{[1-(2-methyl-cyclohexyl)-2-thiophen-2-ylmethyl-1H-benzoimidazole-5-carbonyl]-amino}-hexanoic acid | Waters HPLC; Chiralpak IA-103; 250 × 4.6 mm; heptane + iPrOH + MeOH 5 + 1 + 1 + 0.1% NH₄Ac | 1 | 10.51 | >99 | 482.15 | 5_7_1 | 2.98 |
| 437 | | | 2 | 13.92 | >99 | 482.15 | 5_7_1 | 2.98 |
| 438 | | | 3 | 15.74 | 91 | 482.24 | 5_7_1 | 2.91 |
| 439 | | | 4 | 18.11 | 85 | 482.23 | 5_7_1 | 2.93 |

*In first run dia 22 and 23 eluted together at 10.40 min, in a second run this peak was separated into Dia22 and 23 using heptane + iPrOH + MeOH 8 + 1 + 1 + 0.1% NH₄Ac The following enantiomers or diastereomers were obtained after separation of the racemates or diastereomeric mixtures by preparative HPLC using a Waters Alliance 2695 system and chiral columns and solvent mixtures at a flow rate of 1 ml/min as given in the following table. In some cases more than one chiral center is present in the molecule, the starting mixtures consisted of epimers at the amino acid or amino alcohol chiral center.

| Exp. No. | Structure and chemical name of epimeric mixture | Conditions of chiral sep. | No. of enantiomer | Rt [min] (sep.) | % ee | Obs. Mass | LCMS method (non-chiral) | Rt [min] (non-chiral) |
|---|---|---|---|---|---|---|---|---|
| 440 441 | 2-{[1-(1-Ethyl-propyl)-2-thiophen-2-ylmethyl-1H-benzoimidazole-5-carbonyl]-amino}-2,4-dimethyl-pentanoic acid | LC_8, 1 ml/min, IA 103 4.6 × 250 mm, Hep:EtOH:MeOH 10:1:1 precond. TFA | 1 2 | 8.73 10.77 | >99.5 93 | 456.26 456.26 | 6_1_1 6_1_1 | 2.90 2.90 |
| 442 443 | 3-Cyclopentyl-2-{[1-((1R,2R)-2-methyl-cyclohexyl)-2-thiophen-2-ylmethyl-1H-benzoimidazole-5-carbonyl]-amino}-propionic acid | LC_3, 1 ml/min, Chiralpak AD-H, 67 4.6 × 250 mm, Hep:EtOH:MeOH 1:1:1 precond. TFA | 1 2 | 4.60 7.02 | 96.6 98.7 | 494.36 494.37 | 6_6_1 6_6_1 | 3.2 3.2 |
| 444 445 | 3-(4,4-Dimethyl-cyclohexyl)-2-{[1-(1-ethyl-propyl)-2-thiophen-2-ylmethyl-1H-benzoimidazole-5-carbonyl]-amino}-propionic acid | LC_01, 1 ml/min, Chiralpak AD-H, 55 4.6 × 250 mm, MeCN:MeOH 9:1, precond. TFA | 1 2 | 4.94 8.54 | >99.5 98 | 510.25 510.42 | 3_1_1 4_1_1 | 1.66 1.31 |

-continued

| Exp. No. | Structure and chemical name of epimeric mixture | Conditions of chiral sep. | No. of enantiomer | Rt [min] (sep.) | % ee | Obs. Mass | LCMS method (non-chiral) | Rt [min] (non-chiral) |
|---|---|---|---|---|---|---|---|---|
| 446 447 | 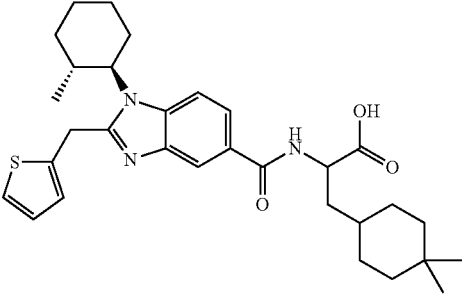 3-(4,4-Dimethyl-cyclohexyl)-2-{[1-((1R,2R)-2-methyl-cyclohexyl)-2-thiophen-2-ylmethyl-1H-benzoimidazole-5-carbonyl]-amino}-propionic acid | LC_01, 1 ml/min, Chiralpak AD-H-119 4.6 × 250 mm, MeCN:EtOH:MeOH 6:1:1, +0.1% DEA | 1 2 | 5.14 11.30 | >99.5 >99.5 | 536.45 536.43 | 4_1_1 4_1_1 | 1.39 1.40 |
| 448 449 | 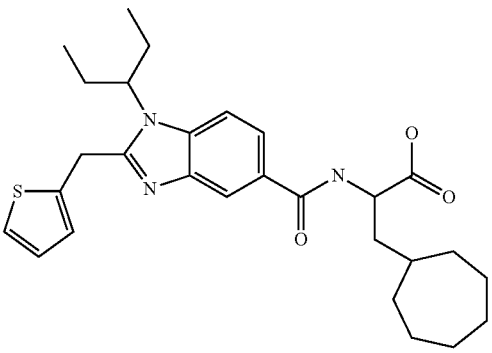 3-Cycloheptyl-2-{[1-(1-ethyl-propyl)-2-thiophen-2-ylmethyl-1H-benzoimidazole-5-carbonyl]-amino}-propionic acid | LC_04, 1 ml/min, Chiralpak AD-H 4.6 × 250 mm, Hep:EtOH:MeOH 6:1:1 precond. TFA | 1 2 | 9.22 14.68 | 99.6 99.7 | 496.2 496.26 | 4_1_1 4_1_1 | 1.3 1.3 |
| 450 451 | 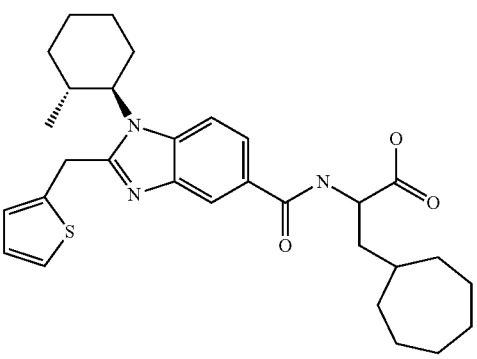 3-Cycloheptyl-2-{[1-((1R,2R)-2-methyl-cyclohexyl)-2-thiophen-2-ylmethyl-1H-benzoimidazole-5-carbonyl]-amino}-propionic acid | LC_04, 1 ml/min, Chiralpak AD-H, 4.6 × 250 mm, Hep:EtOH:MeOH 6:1:1 | 1 2 | 10.17 17.30 | >99.5 >99.5 | 522.45 522.45 | 4_1_1 4_1_1 | 1.35 1.36 |

-continued

| Exp. No. | Structure and chemical name of epimeric mixture | Conditions of chiral sep. | No. of enantiomer | Rt [min] (sep.) | % ee | Obs. Mass | LCMS method (non-chiral) | Rt [min] (non-chiral) |
|---|---|---|---|---|---|---|---|---|
| 452 453 | 3-{[1-(1-Ethyl-propyl)-2-thiophen-2-ylmethyl-1H-benzoimidazole-5-carbonyl]-amino}-heptanoic acid | LC_03, 1 ml/min, Chiralpak AD-H, 4.6 × 250 mm, Hep:EtOH:MeOH 10:1:1 | 1 2 | 9.20 13.20 | >99.5 >99.5 | 456.29 456.15 | 5_1_1 5_7_1 | 4.1 2.74 |
| 454 455 | 4-Cyclohexyl-3-{[1-(1-ethyl-propyl)-2-thiophen-2-ylmethyl-1H-benzoimidazole-5-carbonyl]-amino}-butyric acid | LC_03, 1 ml/min, Chiralpak AD-H, 4.6 × 250 mm, Hep:EtOH:MeOH 10:1:1 | 1 2 | 9.54 14.14 | >99.5 >99.5 | 496.18 496.17 | 5_7_1 5_7_1 | 3.00 2.96 |
| 456 457 | 4-Cyclohexyl-3-{[1-((1R,2R)-2-methyl-cyclohexyl)-2-thiophen-2-ylmethyl-1H-benzoimidazole-5-carbonyl]-amino]-butyric acid | LC_02, 1 ml/min, Chiralpak AD-H, 4.6 × 250 mm, Hep:EtOH:1:1, precond. DEA | 1 2 | 6.06 9.42 | >99.5 99.9 | 522.27 522.26 | 5_5_1 5_5_1 | 1.56 1.56 |

| Exp. No. | Structure and chemical name of epimeric mixture | Conditions of chiral sep. | No. of enantiomer | Rt [min] (sep.) | % ee | Obs. Mass | LCMS method (non-chiral) | Rt [min] (non-chiral) |
|---|---|---|---|---|---|---|---|---|
| 458<br>459 | 3-{[1-((1R,2R)-2-Methyl-cyclohexyl)-2-thiophen-2-ylmethyl-1H-benzoimidazole-5-carbonyl]-amino}-hexanoic acid | LC_04, 1 ml/min, Chiralpak AD-H, 4.6 × 250 mm, Hep:EtOH:MeOH 5:1:1 precond. DEA | 1<br>2 | 6.30<br>9.28 | >99.5<br>>99.5 | 468.20<br>468.20 | 3_2_1<br>3_2_1 | 1.38<br>1.39 |
| 460<br>461 | 3-{[1-((1R,2R)-2-Methyl-cyclohexyl)-2-thiophen-2-ylmethyl-1H-benzoimidazole-5-carbonyl]-amino}-heptanoic acid | LC_04, 1 ml/min, Chiralpak AD-H, 4.6 × 250 mm, Hep:EtOH:MeOH 5:1:1 precond. DEA | 1<br>2 | 5.83<br>8.23 | >99.5<br>>99.5 | 468.2<br>468.19 | 3_2_1<br>3_2_1 | 1.39<br>1.44 |
| 462<br>463 | 3-Cyclohexyl-3-{[1-((1R,2R)-2-methyl-cyclohexyl)-2-thiophen-2-ylmethyl-1H-benzoimidazole-5-carbonyl]-amino}-propionic acid | LC_05, 0.75 ml/min, Chiralpak AD-H, 4.6 × 250 mm, EtOH | 1<br>2 | 8.82<br>12.46 | >99.5<br>99.2 | 508.27<br>508.26 | 3_1_1<br>3_1_1 | 1.58<br>1.59 |

-continued

| Exp. No. | Structure and chemical name of epimeric mixture | Conditions of chiral sep. | No. of enantiomer | Rt [min] (sep.) | % ee | Obs. Mass | LCMS method (non-chiral) | Rt [min] (non-chiral) |
|---|---|---|---|---|---|---|---|---|
| 464 465 | 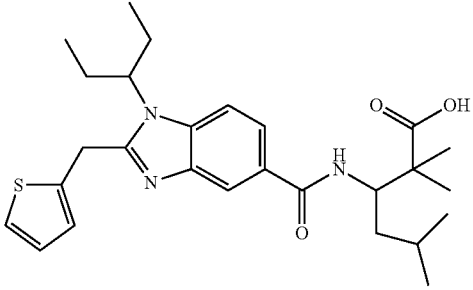<br>3-{[1-(1-Ethyl-propyl)-2-thiophen-2-ylmethyl-1H-benzoimidazole-5-carbonyl]-amino}-2,2,5-trimethyl-hexanoic acid | LC_11, 1 ml/min, Chiralpak AD-H, 4.6 × 250 mm, Hep:iPrtOH:MeOH 20:1:1 | 1<br>2 | 6.68<br>8.99 | >99.5<br>>99.5 | 484.26<br>484.26 | 6_6_1<br>6_6_1 | 4.04<br>4.04 |
| 466 467 | 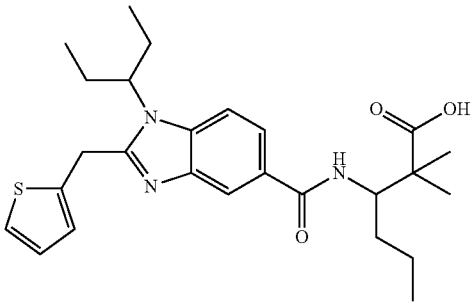<br>3-{[1-(1-Ethyl-propyl)-2-thiophen-2-ylmethyl-1H-benzoimidazole-5-carbonyl]-amino}-2,2-dimethyl-hexanoic acid | LC_03, 1 ml/min, Chiralpak AD-H, 4.6 × 250 mm, MeCN:MeOH 9:1, precond. TFA | 1<br>2 | 9.19<br>17.56 | >99.5<br>99.0 | 470.29<br>470.27 | 3_1_1<br>3_1_1 | 1.44<br>1.44 |
| 468 469 | 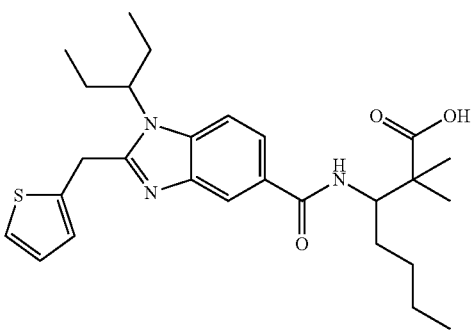<br>3-{[1-(1-Ethyl-propyl)-2-thiophen-2-ylmethyl-1H-benzoimidazole-5-carbonyl]-amino}-2,2-dimethyl-heptanoic acid | LC_03, 1 ml/min, Chiralpak AD-H, 4.6 × 250 mm, MeCN:MeOH 9:1, precond. TFA | 1<br>2 | 3.44<br>5.95 | 88.6<br>98.9 | 484.25<br>484.24 | 3_1_1<br>3_1_1 | 1.50<br>1.49 |

| Exp. No. | Structure and chemical name of epimeric mixture | Conditions of chiral sep. | No. of enantiomer | Rt [min] (sep.) | % ee | Obs. Mass | LCMS method (nonchiral) | Rt [min] (non-chiral) |
|---|---|---|---|---|---|---|---|---|
| 470 | 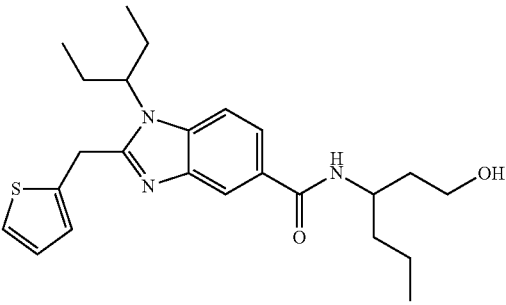 1-(1-Ethyl-propyl)-2-thiophen-2-ylmethyl-1H-benzoimidazole-5-carboxylic acid [1-(2-hydroxy-ethyl)-butyl]-amide | LC_01, 1 ml/min, Chiralpak AS-H 80 4.6 × 250 mm, Hep:iPrOH:MeOH 20:1:1 | 1 | 5.98 | >99.5 | 428.24 | 5_7_1 | 2.64 |
| 471 | | | 2 | 7.74 | >99.5 | 428.25 | 5_7_1 | 2.67 |

EXAMPLE 472

1-(1-Ethyl-propyl)-2-thiophen-2-ylmethyl-1H-benzoimidazole-5-carboxylic acid [(S)-3-methyl-1-(1H-tetrazol-5-ylmethyl)-butyl]-amide

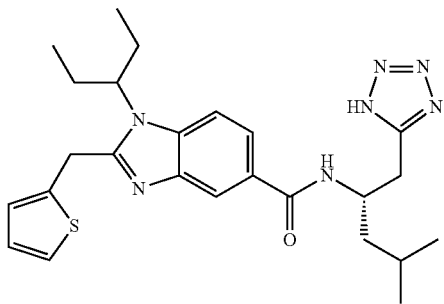 [SMILES: CCC(CC)n1c(Cc2cccs2)nc2cc(C(=O)N[C@H](Cc3nnn[nH]3)CC(C)C)ccc21]

a) 1-(1-Ethyl-propyl)-2-thiophen-2-ylmethyl-1H-benzoimidazole-5-carboxylic acid ((S)-1-cyanomethyl-3-methyl-butyl)-amide

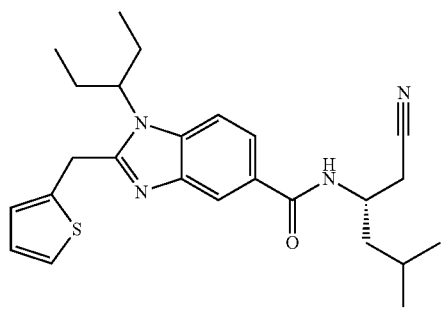 [SMILES: CCC(CC)n1c(Cc2cccs2)nc2cc(C(=O)N[C@H](CC#N)CC(C)C)ccc21]

To a solution of 4.93 g of 1-(1-ethyl-propyl)-2-thiophen-2-ylmethyl-1H-benzoimidazole-5-carboxylic acid in 50 ml of dry DMF 2.04 g of HOAT, 3.45 g of EDC and 4.35 ml of DIPEA were added at 0° C. After 30 min 3.29 g of (S)-3-Amino-5-methyl-hexanenitrile-hydrochloride and 4.35 ml of DIPEA were added and the reaction was stirred at rt for 4 h. The reaction was then poured into water and the pH was adjusted to 3 by the addition of 2 M aqueous sodium hydrogensulphate solution. The reaction was extracted with ethyl acetate three times. The combined organic phases were washed with saturated aqueous sodium bicarbonate solution and brine, dried over magnesium sulphate and concentrated. 5.90 g (90%) of 1-(1-Ethyl-propyl)-2-thiophen-2-ylmethyl-1H-benzoimidazole-5-carboxylic acid ((S)-1-cyanomethyl-3-methyl-butyl)-amide were obtained.

$C_{25}H_{32}N_4OS$ (436.62)), LCMS (method 5_1_1): Rt=4.58 min, m/z=437.21 [M+H]$^+$ b) 1-(1-Ethyl-propyl)-2-thiophen-2-ylmethyl-1H-benzoimidazole-5-carboxylic acid [(S)-3-methyl-1-(1H-tetrazol-5-ylmethyl)-butyl]-amide

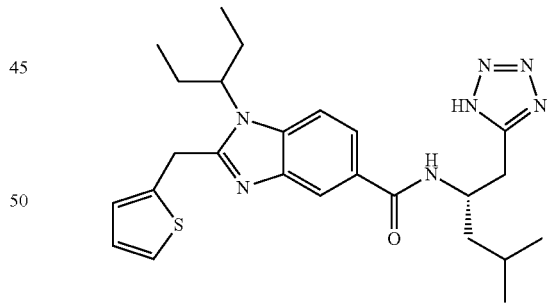

218 mg of 1-(1-ethyl-propyl)-2-thiophen-2-ylmethyl-1H-benzoimidazole-5-carboxylic acid ((S)-1-cyanomethyl-3-methyl-butyl)-amide and 124 mg of azidotrimethyltin in 10 ml of dry toluene were heated under Argon for 48 h. The precipitated crude product was isolated by suction and then dissolved in 10% aqueous sodium bicarbonate solution and filtered with addition of charcoal. The pH of the filtrated was adjusted to 5, and the precipitated product was isolated by suction, washed with water and dried in vacuo to obtain 100 mg (42%) of 1-(1-Ethyl-propyl)-2-thiophen-2-ylmethyl-1H-benzoimidazole-5-carboxylic acid [(S)-3-methyl-1-(1H-tetrazol-5-ylmethyl)-butyl]-amide.

C$_{25}$H$_{32}$N$_7$OS (479.65), LCMS (method 3_1_1): Rt=1.48 min, m/z=480.22 [M+H]$^+$

EXAMPLE 473

1-(1-Ethyl-propyl)-2-thiophen-2-ylmethyl-1H-benzoimidazole-5-carboxylic acid [(S)-1-(N-hydroxycarbamimidoylmethyl)-3-methyl-butyl]-amide Chiral

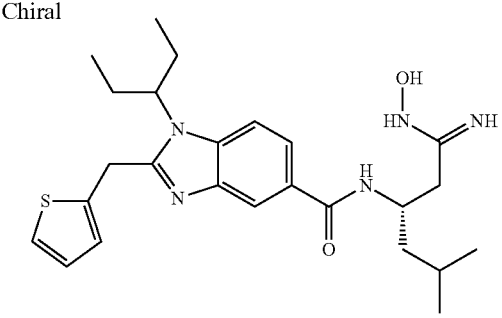

To 700 mg 1-(1-ethyl-propyl)-2-thiophen-2-ylmethyl-1H-benzoimidazole-5-carboxylic acid ((S)-1-cyanomethyl-3-methyl-butyl)-amide in 7 ml of dry THF and 7 ml of dry methanol was added 1.11 g hydroxylamine-hydrochloride, followed by the addition of 2.7 ml of triethylamine. The reaction was heated to reflux overnight, then it was diluted with ethyl acetate and washed with water. The layers were separated and the aqueous phase was extracted with ethyl acetate twice. The combined organic layers were dried over sodium sulphate and concentrated. The residue was purified by HPLC to obtain 175 mg (23%) of 1-(1-ethyl-propyl)-2-thiophen-2-ylmethyl-1H-benzoimidazole-5-carboxylic acid [(S)-1-(N-hydroxycarbamimidoylmethyl)-3-methyl-butyl]-amide.

C$_{25}$H$_{35}$N$_5$O$_2$S (469.65), LCMS (method 5_1_1): Rt=3.45 min, m/z=470.32 [M+H]$^+$

EXAMPLE 474

1-(1-Ethyl-propyl)-2-thiophen-2-ylmethyl-1H-benzoimidazole-5-carboxylic acid [(S)-3-methyl-1-(5-phenyl-[1,2,4]oxadiazol-3-ylmethyl)-butyl]-amide

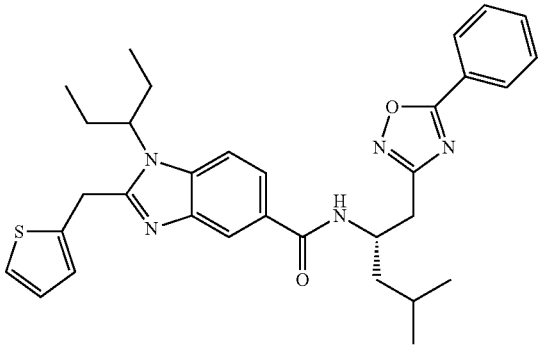 [SMILES: CCC(CC)n1c(Cc2cccs2)nc2cc(C(=O)N[C@H](Cc3noc(-c4ccccc4)n3)CC(C)C)ccc21]

A mixture of 88 mg 1-(1-Ethyl-propyl)-2-thiophen-2-ylmethyl-1H-benzoimidazole-5-carboxylic acid [(S)-1-(N-hydroxycarbamimidoylmethyl)-3-methyl-butyl]amide, 26 mg of benzoyl chloride and 78 mg of potassium carbonate in 0.5 ml of dry THF was reacted in a microwave reactor at 120° C. for 15 min. The reaction was taken up in water, the pH was adjusted to 7 by addition of 2 M aqueous hydrochloric acid, and the mixture was extracted with ethyl acetate twice. The combined organic layers were concentrated and the resulting residue was purified by HPLC to isolate 19 mg (18%) of 1-(1-Ethyl-propyl)-2-thiophen-2-ylmethyl-1H-benzoimidazole-5-carboxylic acid [(S)-3-methyl-1-(5-phenyl-[1,2,4]oxadiazol-3-ylmethyl)-butyl]-amide.

C$_{32}$H$_{37}$N$_5$O$_2$S (555.27), LCMS (method 5_7_1): Rt=3.59 min, m/z=556.26 [M+H]$^+$

EXAMPLE 475

1-(1-Ethyl-propyl)-2-thiophen-2-ylmethyl-1H-benzoimidazole-5-carboxylic acid [(S)-1-(5-cyclopropyl-[1,2,4]oxadiazol-3-ylmethyl)-3-methyl-butyl]-amide

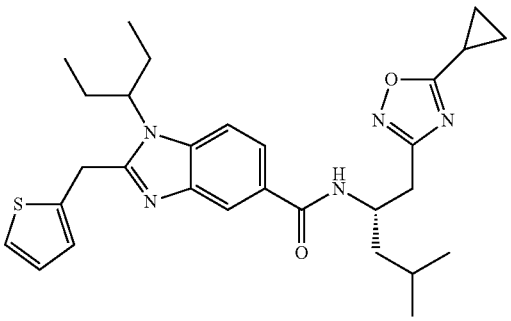 [SMILES: CCC(CC)n1c(Cc2cccs2)nc2cc(C(=O)N[C@H](Cc3noc(C4CC4)n3)CC(C)C)ccc21]

The title compound was prepared in analogy to example 474 by reaction of 1-(1-ethyl-propyl)-2-thiophen-2-ylmethyl-1H-benzoimidazole-5-carboxylic acid [(S)-1-(N-hydroxycarbamimidoylmethyl)-3-methyl-butyl]-amide and cyclopropanecarbonyl chloride.

C$_{29}$H$_{37}$N$_5$O$_2$S (519.71), LCMS (method 5_7_1): Rt=3.10 min, m/z=520.25 [M+H]$^+$

EXAMPLE 476

1-(1-Ethyl-propyl)-2-thiophen-2-ylmethyl-1H-benzoimidazole-5-carboxylic acid [(S)-3-methyl-1-(5-trifluoromethyl-1H-[1,2,4]triazol-3-ylmethyl)-butyl]-amide

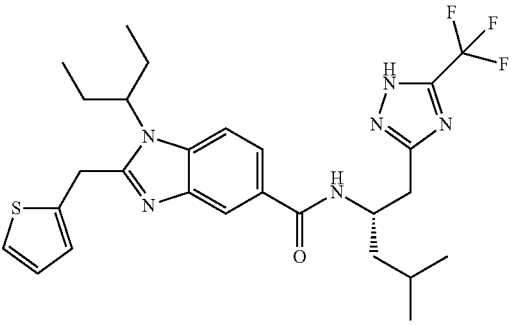 [SMILES: CCC(CC)n1c(Cc2cccs2)nc2cc(C(=O)N[C@H](Cc3n[nH]c(C(F)(F)F)n3)CC(C)C)ccc21]

A mixture of 50 mg 1-(1-ethyl-propyl)-2-thiophen-2-ylmethyl-1H-benzoimidazole-5-carboxylic acid ((S)-1-cyanomethyl-3-methyl-butyl)-amide, 45 mg of trifluoroacetic acid hydrazide and 4 mg of potassium carbonate in 0.6 ml of ethanol was heated to 200° C. in a microwave reactor for 24 h. The solvent was removed and the residue was purified by HPLC to obtain 6 mg (10%) of 1-(1-ethyl-propyl)-2-thiophen-2-ylmethyl-1H-benzoimidazole-5-carboxylic acid [(S)-3-methyl-1-(5-trifluoromethyl-1H-[1,2,4]triazol-3-ylmethyl)-butyl]-amide.

C$_{27}$H$_{33}$F$_3$N$_6$OS (546.66), LCMS (method 6_6_1): Rt=3.14 min, m/z=547.32 [M+H]$^+$

EXAMPLE 477

1-(1-Ethyl-propyl)-2-thiophen-2-ylmethyl-1H-benzoimidazole-5-carboxylic acid (1-pyridin-2-yl-butyl)-amide

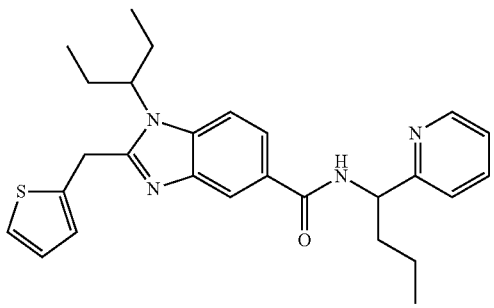 [SMILES: CCCC(NC(=O)c1ccc2c(c1)nc(Cc1cccs1)n2C(CC)CC)c1ccccn1]

To a solution of 50 mg of 1-(1-ethyl-propyl)-2-thiophen-2-ylmethyl-1H-benzoimidazole-5-carboxylic acid in 2 ml of dry DMF 10 mg of HOAT, 35 mg of EDC and 0.1 ml of DIPEA were added at 0° C. After 15 min 25 mg of 1-pyridin-2-ylbutylamine were added and the reaction was stirred at rt for 16 h. The reaction was then poured into water and the pH was adjusted to 4 by the addition of 2 M aqueous hydrochloric acid. The reaction was extracted with ethyl acetate three times. The combined organic phases were dried over magnesium sulphate and concentrated. 70 mg (100%) of 1-(1-ethyl-propyl)-2-thiophen-2-ylmethyl-1H-benzoimidazole-5-carboxylic acid (1-pyridin-2-yl-butyl)-amide were obtained.

$C_{27}H_{32}N_4OS$ (460.64), LCMS (method 5_6_1): Rt=1.79 min, m/z=461.19 [M+H]$^+$ The following examples were prepared in analogy to example 477:

| Exp. No. | Chemical Name | Structure | m/z [M + H]$^+$ | LCMS method | Rt [min] |
|---|---|---|---|---|---|
| 478 | 1-(1-Ethyl-propyl)-2-thiophen-2-ylmethyl-1H-benzoimidazole-5-carboxylic acid (3-methyl-1-pyridin-3-yl-butyl)-amide | 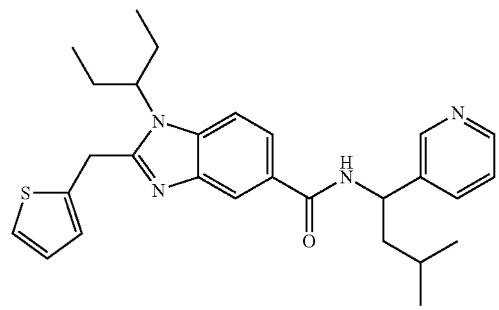 [SMILES: CCC(CC)n1c(Cc2cccs2)nc2cc(C(=O)NC(CC(C)C)c3cccnc3)ccc21] | 475.2 | 5_3_1 | 1.88 |
| 479 | 1-(1-Ethyl-propyl)-2-thiophen-2-ylmethyl-1H-benzoimidazole-5-carboxylic acid (3-methyl-1-thiazol-2-yl-butyl)-amide | 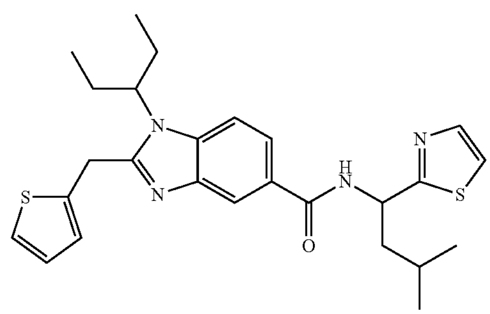 [SMILES: CCC(CC)n1c(Cc2cccs2)nc2cc(C(=O)NC(CC(C)C)c3nccs3)ccc21] | 481.2 | 3_2_1 | 1.46 |
| 480 | 1-(1-Ethyl-propyl)-2-thiophen-2-ylmethyl-1H-benzoimidazole-5-carboxylic acid [1-(4,5-dimethyl-thiazol-2-yl)-3-methyl-butyl]-amide | 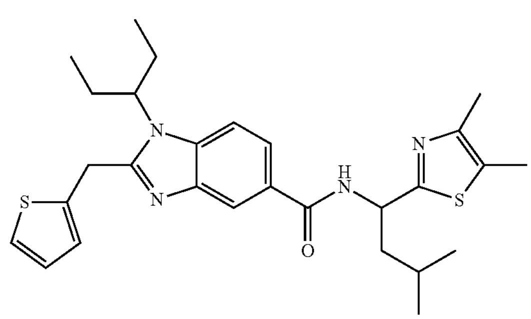 [SMILES: CCC(CC)n1c(Cc2cccs2)nc2cc(C(=O)NC(CC(C)C)c3nc(C)c(C)s3)ccc21] | 509.3 | 3_2_1 | 1.49 |

| Exp. No. | Chemical Name | Structure | m/z [M + H]+ | LCMS method | Rt [min] |
|---|---|---|---|---|---|
| 481 | 1-(1-Ethyl-propyl)-2-thiophen-2-ylmethyl-1H-benzoimidazole-5-carboxylic acid [3-methyl-1-(5-methyl-[1,3,4]oxadiazol-2-yl)-butyl]-amide | 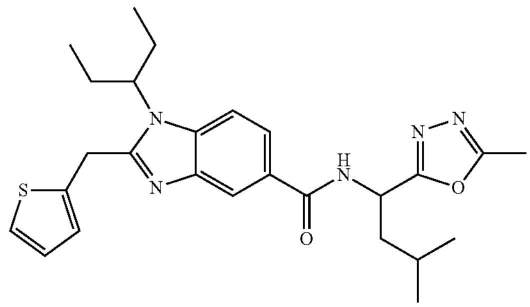 [SMILES: CCC(CC)n1c(Cc2cccs2)nc2cc(C(=O)NC(CC(C)C)c3nnc(C)o3)ccc21] | 480.2 | 6_6_1 | 2.97 |
| 482 | 1-(1-Ethyl-propyl)-2-thiophen-2-ylmethyl-1H-benzoimidazole-5-carboxylic acid [(S)-1-(5-methoxymethyl-2H-[1,2,4]triazol-3-yl)-2-methyl-propyl]-amide | 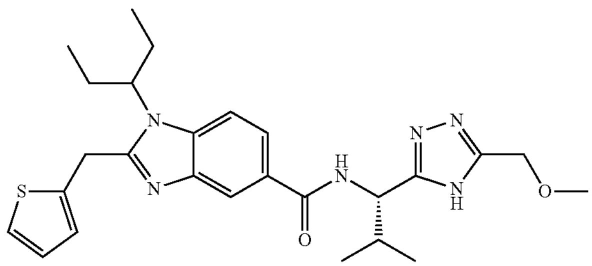 [SMILES: CCC(CC)n1c(Cc2cccs2)nc2cc(C(=O)N[C@H](c3nnc(COC)[nH]3)C(C)C)ccc21] | 495.3 | 3_1_1 | 1.36 |

EXAMPLE 483

1-(1-Ethyl-propyl)-2-thiophen-2-ylmethyl-1H-benzoimidazole-5-carboxylic acid [(S)-3-methyl-1-(4H-[1,2,4]triazol-3-ylsulfanylmethyl)-butyl]-amide

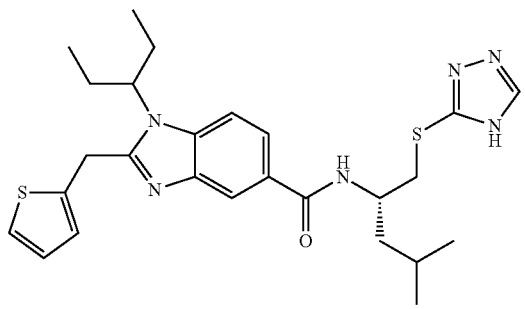 [SMILES: CCC(CC)n1c(Cc2cccs2)nc2cc(C(=O)N[C@H](CSc3nnc[nH]3)CC(C)C)ccc21]

a) Toluene-4-sulfonic acid (S)-2-tert-butoxycarbonylamino-4-methyl-pentyl ester

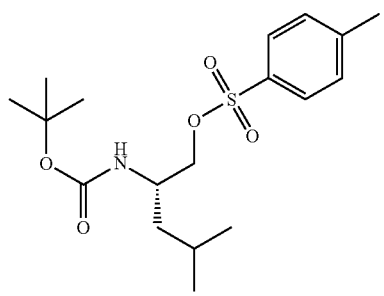 [SMILES: Cc1ccc(S(=O)(=O)OC[C@H](CC(C)C)NC(=O)OC(C)(C)C)cc1]

To a solution of 4.50 g of Boc-L-leucinol in 30 ml of THF were added 4.74 g of p-toluenesulfonylchloride, 7.2 ml of TEA and 0.25 g of DMAP. The reaction was stirred at rt overnight. The pH of the reaction was then adjusted to 6 by the addition of 1 M aqueous hydrochloric acid. The phases were separated and the aqueous phase was extracted with ethyl acetate twice. The combined organic layers were dried over sodium sulphate and concentrated to yield 6.94 g of toluene-4-sulfonic acid (S)-2-tert-butoxycarbonylamino-4-methyl-pentyl ester.

$C_{18}H_{29}NO_5S$ (371.50) MS (ESI LCMS (method 8_1_1): Rt=1.14 min, m/z=271.90 [M+H-Boc]+ b) [(S)-3-Methyl-1-(4H-[1,2,4]triazol-3-ylsulfanylmethyl)-butyl]-carbamic acid tert-butyl ester

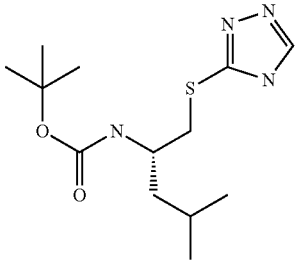 [SMILES: CC(C)C[C@@H](CSc1nnc[nH]1)NC(=O)OC(C)(C)C]

To 250 mg of toluene-4-sulfonic acid (S)-2-tert-butoxycarbonylamino-4-methyl-pentyl ester in 2.5 ml acetone and 0.5 ml water were added 112 mg of potassium carbonate, followed by the addition of 75 mg 4H-1,2,4-triazole-3-thiol. The reaction was heated in a microwave reactor for 5 min to 100° C. The pH was then adjusted to 7 by the addition of 2 M aqueous hydrochloric acid and the mixture was extracted with ethyl acetate twice. The combined organic phases were dried over sodium sulphate and concentrated in vacuo. 161 mg (80%) of [(S)-3-Methyl-1-(4H-[1,2,4]triazol-3-ylsulfanylmethyl)-butyl]-carbamic acid tert-butyl ester were obtained.

$C_{13}H_{24}N_4O_2S$ (300.43), LCMS (method 8_1_1): Rt=0.84 min, m/z=301.00 [M+H]$^+$ c) (S)-3-Methyl-1-(4H-[1,2,4]triazol-3-ylsulfanylmethyl)-butylamine-hydrochloride

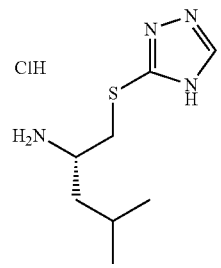

160 mg of [(S)-3-Methyl-1-(4H-[1,2,4]triazol-3-ylsulfanylmethyl)-butyl]-carbamic acid tert-butyl ester were reacted with 2.6 ml of 4M hydrochloric acid in dioxane at it for 2 h. The reaction was concentrated in vacuo and the resulting crude product was used without further purification. 125 mg (100%) of (S)-3-methyl-1-(4H-[1,2,4]triazol-3-ylsulfanylmethyl)-butylamine-hydrochloride were obtained.

$C_8H_{16}N_4S$ (200.31), LCMS (method 8_1_1): Rt=0.18 min, m/z=201.00 [M+H]$^+$ d) 1-(1-Ethyl-propyl)-2-thiophen-2-ylmethyl-1H-benzoimidazole-5-carboxylic acid [(S)-3-methyl-1-(4H-[1,2,4]triazol-3-ylsulfanylmethyl)-butyl]-amide

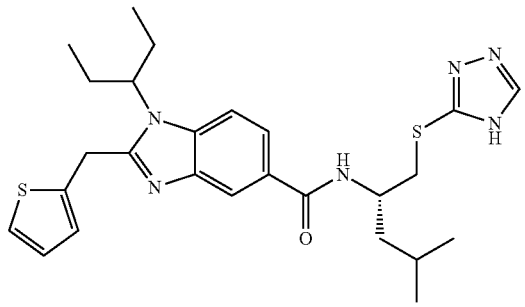 [SMILES: CCC(CC)n1c(Cc2cccs2)nc2cc(C(=O)N[C@H](CSc3nnc[nH]3)CC(C)C)ccc21]

To a solution of 185 mg of 1-(1-ethyl-propyl)-2-thiophen-2-ylmethyl-1H-benzoimidazole-5-carboxylic acid in 3 ml of dry DMF 84 mg of HOAT, 151 mg of EDC and 0.47 ml of DIPEA were added at 0° C. After 15 min 133 mg of (S)-3-methyl-1-(4H-[1,2,4]triazol-3-ylsulfanylmethyl)-butylamine-hydrochloride were added and the reaction was stirred at it for 20 h. The reaction was then poured into water and the pH was adjusted to 3 by the addition of 2 M aqueous hydrochloric acid. The reaction was extracted with ethyl acetate three times. The combined organic phases were washed with 2 M aqueous hydrochloric acid, saturated sodium bicarbonate solution and brine, dried over magnesium sulphate and concentrated. After purification by HPLC 64 mg (22%) of 1-(1-Ethyl-propyl)-2-thiophen-2-ylmethyl-1H-benzoimidazole-5-carboxylic acid [(S)-3-methyl-1-(4H-[1,2,4]triazol-3-ylsulfanylmethyl)-butyl]-amide were obtained.

$C_{26}H_{34}N_6OS_2$ (510.73); LCMS (method 3_1_1): Rt=1.50 min, m/z=511.18 [M+H]$^+$

EXAMPLE 484

1-(1-Ethyl-propyl)-2-thiophen-2-ylmethyl-1H-benzoimidazole-5-carboxylic acid [(S)-3-methyl-1-(4H-[1,2,4]triazole-3-sulfonylmethyl)-butyl]-amide

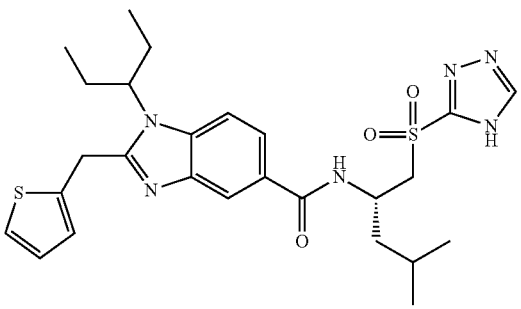 [SMILES: CCC(CC)n1c(Cc2cccs2)nc2cc(C(=O)N[C@@H](CC(C)C)CS(=O)(=O)c3nnc[nH]3)ccc21]

a) [(S)-3-Methyl-1-(4H-[1,2,4]triazole-3-sulfonylmethyl)-butyl]-carbamic acid tert-butyl ester

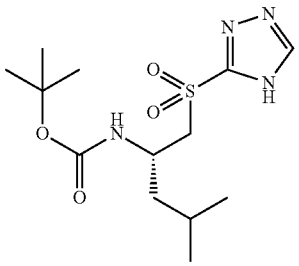 [SMILES: CC(C)C[C@@H](CS(=O)(=O)c1nnc[nH]1)NC(=O)OC(C)(C)C]

To 750 mg of [(S)-3-Methyl-1-(4H-[1,2,4]triazol-3-ylsulfanylmethyl)-butyl]-carbamic acid tert-butyl ester in 10 ml acetonitrile and 1 ml water was added 6 mg of sodium tungstate and 0.2 ml of hydrogen peroxide (35%). The reaction was stirred overnight, then another 6 mg of sodium tungstate and 0.2 ml of hydrogen peroxide (35%) were added and after 24 h the reaction was diluted with ethyl acetate and water. The phases were separated and the organic phase was concentrated and the resulting residue was purified by HPLC to obtain 126 mg (18%) of [(S)-3-Methyl-1-(4H-[1,2,4]triazole-3-sulfonylmethyl)-butyl]-carbamic acid tert-butyl ester.

$C_{13}H_{24}N_4O_4S$ (332.42), LCMS (method 8_1_1): Rt=0.75 min, m/z=233.10 [M+H-Boc]$^+$ b) (S)-3-Methyl-1-(4H-[1,2,4]triazole-3-sulfonylmethyl)-butylamine-hydrochloride

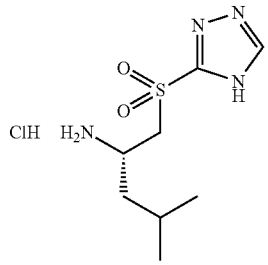

200 mg of [(S)-3-Methyl-1-(4H-[1,2,4]triazole-3-sulfonylmethyl)-butyl]-carbamic acid tert-butyl ester were dissolved in 6 ml of dioxane and reacted with 2.2 ml of 4M hydrochloric acid in dioxane at rt for 16 h. The reaction was concentrated in vacuo and the resulting crude product was used without further purification. 120 mg (100%) of S)-3-Methyl-1-(4H-[1,2,4]triazole-3-sulfonylmethyl)-butylamine-hydrochloride were obtained.

$C_8H_{16}N_4O_2S$ (232.31), LCMS (method 8_1_1): Rt=0.17 min, m/z=233.15 [M+H]$^+$ c) 1-(1-Ethyl-propyl)-2-thiophen-2-ylmethyl-1H-benzoimidazole-5-carboxylic acid [(S)-3-methyl-1-(4H-[1,2,4]triazole-3-sulfonylmethyl)-butyl]-amide

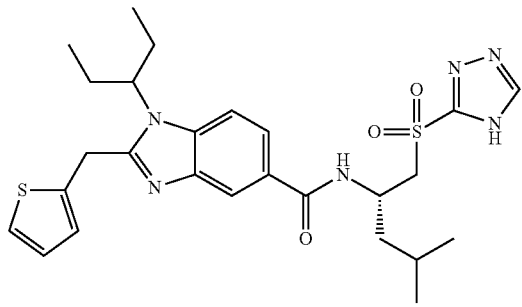 [SMILES: CCC(CC)n1c(Cc2cccs2)nc2cc(C(=O)N[C@@H](CC(C)C)CS(=O)(=O)c3nnc[nH]3)ccc21]

To a solution of 120 mg of 1-(1-ethyl-propyl)-2-thiophen-2-ylmethyl-1H-benzoimidazole-5-carboxylic acid in 1 ml of dry DMF 25 mg of HOAT, 85 mg of EDC and 0.36 ml of DIPEA were added at 0° C. After 15 min 108 mg of (S)-3-Methyl-1-(4H-[1,2,4]triazole-3-sulfonylmethyl)-butylamine-hydrochloride were added and the reaction was stirred at rt for 20 h. The reaction was then poured into water and the pH was adjusted to 3 by the addition of 2 M aqueous hydrochloric acid. The reaction was extracted with ethyl acetate three times. The combined organic phases were washed with 2 M aqueous hydrochloric acid, saturated sodium bicarbonate solution and brine, dried over magnesium sulphate and concentrated. After purification by HPLC 163 mg (82%) of 1-(1-Ethyl-propyl)-2-thiophen-2-ylmethyl-1H-benzoimidazole-5-carboxylic acid [(S)-3-methyl-1-(4H-[1,2,4]-triazole-3-sulfonylmethyl)-butyl]-amide were obtained.

$C_{26}H_{34}N_6O_3S_2$ (542.73), LCMS (method 3_1_1): Rt=1.45 min, m/z=543.24 [M+H]$^+$

EXAMPLE 485

1-(1-Ethyl-propyl)-2-thiophen-2-ylmethyl-1H-benzoimidazole-5-carboxylic acid ((S)-3-methyl-1-methylsulfamoylmethyl-butyl)-amide

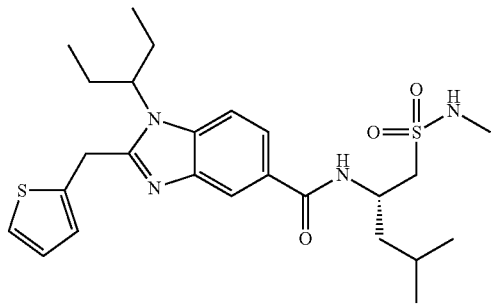 [SMILES: CCC(CC)n1c(Cc2cccs2)nc2cc(C(=O)N[C@@H](CC(C)C)CS(=O)(=O)NC)ccc21]

a) Thioacetic acid S—((S)-2-tert-butoxycarbonylamino-4-methyl-pentyl)ester

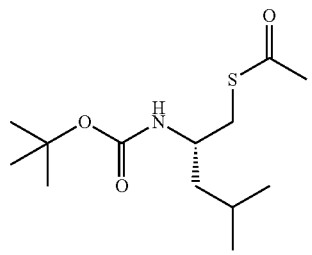 [SMILES: CC(=O)SC[C@H](CC(C)C)NC(=O)OC(C)(C)C]

To 1.00 g of toluene-4-sulfonic acid (S)-2-tert-butoxycarbonylamino-4-methyl-pentyl ester in 10 ml DMF were added 308 mg of potassium thioacetate. After 24 h at room temperature, the reaction was poured unto water, the pH was then adjusted to 9 and the mixture was extracted with ethyl acetate twice. The combined organic phases were washed with brine until neutral, dried over sodium sulphate and concentrated in vacuo. 0.67 g (90%) of Thioacetic acid S—((S)-2-tert-butoxycarbonylamino-4-methyl-pentyl)ester were obtained.

$C_{13}H_{25}NO_3S$ (275.41), LCMS (method 8_1_1): Rt=1.00 min, m/z=176.15 [M+H-Boc]$^+$ b) ((S)-3-Methyl-1-methylsulfamoylmethyl-butyl)-carbamic acid tert-butyl ester

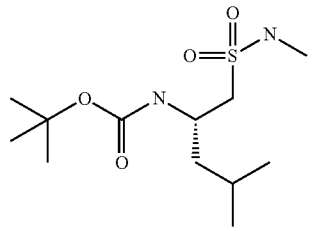 [SMILES: CNS(=O)(=O)C[C@H](CC(C)C)NC(=O)OC(C)(C)C]

At 10° C. 920 mg Thioacetic acid S—((S)-2-tert-butoxycarbonylamino-4-methyl-pentyl) ester were added in several portions to a solution of 1.78 g N-chlorosuccinimide in 5 ml acetonitrile and 1 ml 2M aqueous hydrochloric acid. The reaction was kept a 0° C. for 30 min and at room temperature for 30 min. It was then diluted with THF, the layers were separated. The organic layer was washed with brine and concentrated in vacuo at room temperature. The crude sulfonyl chloride was dissolved in 10 ml THF and treated with 30 ml of 2M methylamine solution in THF. After 16 h at it the reaction was diluted with ethyl acetate and sat. aqueous sodium bicarbonate solution. The layers were separated and the aqueous layer was extracted with ethyl acetate twice. The combined organic layers were dried over sodium sulphate, concentrated and the resulting residue was purified by HPLC to obtain 53 mg (5%) of ((S)-3-Methyl-1-methylsulfamoylmethyl-butyl)-carbamic acid tert-butyl ester.

C$_{12}$H$_{26}$N$_2$O$_4$S (294.42), LCMS (method 8_1_1): Rt=0.87 min, nm/z=195.10 [M+H-Boc]$^+$ c) (S)-2-Amino-4-methyl-pentane-1-sulfonic acid methylamide-hydrochloride

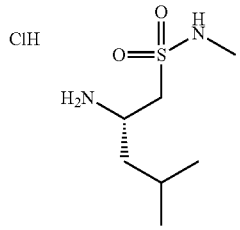

105 mg of ((S)-3-Methyl-1-methylsulfamoylmethyl-butyl)-carbamic acid tert-butyl ester were dissolved in 2 ml of dioxane and reacted with 1.3 ml of 4M hydrochloric acid in dioxane at it for 16 h. The reaction was concentrated in vacuo and the resulting crude product was used without further purification. 60 mg (100%) of (S)-2-Amino-4-methyl-pentane-1-sulfonic acid methylamide-hydrochloride were obtained.

C$_7$H$_{18}$N$_2$O$_2$S (194.30), LCMS (method 8_1_1): Rt=0.18 min, m/z=195.15 [M+H]$^+$ d) 1-(1-Ethyl-propyl)-2-thiophen-2-ylmethyl-1H-benzoimidazole-5-carboxylic acid ((S)-3-methyl-1-methylsulfamoylmethyl-butyl)-amide

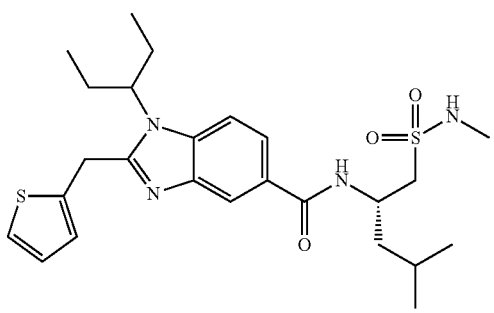 [SMILES: CCC(CC)n1c(Cc2cccs2)nc2cc(C(=O)N[C@@H](CC(C)C)CS(=O)(=O)NC)ccc21]

To a solution of 80 mg of 1-(1-ethyl-propyl)-2-thiophen-2-ylmethyl-1H-benzoimidazole-5-carboxylic acid in 0.5 ml of dry DMF 17 mg of HOAT, 56 mg of EDC and 0.24 ml of DIPEA were added at 0° C. After 15 min 60 mg of (S)-2-Amino-4-methyl-pentane-1-sulfonic acid methylamide-hydrochloride were added and the reaction was stirred at it for 20 h. The reaction was then poured into water and the pH was adjusted to 3 by the addition of 2 M aqueous hydrochloric acid. The reaction was extracted with ethyl acetate three times. The combined organic phases were washed with 2 M aqueous hydrochloric acid, saturated sodium bicarbonate solution and brine, dried over magnesium sulphate and concentrated. After purification by HPLC 55 mg (45%) of 1-(1-Ethyl-propyl)-2-thiophen-2-ylmethyl-1H-benzoimidazole-5-carboxylic acid ((S)-3-methyl-1-methylsulfamoylmethyl-butyl)-amide were obtained.

C$_{25}$H$_{33}$N$_4$O$_3$S$_2$ (504.72), LCMS (method 3_1_1): Rt=1.49 min, m/z=505.24 [M+H]$^+$ Preparation of Intermediates 1-(1-Ethyl-propyl)-2-thiophen-2-ylmethyl-1H-benzoimidazole-5-carboxylic acid

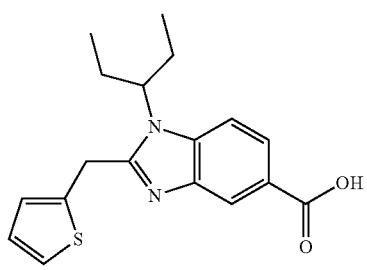

a) 4-Fluoro-3-nitro-benzoic acid methyl ester

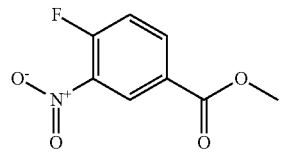

5.55 g of 4-Fluoro-3-nitro-benzoic acid were dissolved in 50 ml of methanol, 6.4 ml of concentrated sulfuric acid were added and the reaction was heated to reflux for 3 h. The reaction was cooled, poured unto ice and the precipitated product was collected by suction and dried in vacuo. 5.40 g (90%) of 4-fluoro-3-nitro-benzoic acid methyl ester were obtained.

C$_8$H$_6$FNO$_4$ (199.14), LCMS (method 7_1_1): Rt=1.28 min, m/z=200.05 [M+H]$^+$ b) 4-(1-Ethyl-propylamino)-3-nitro-benzoic acid methyl ester

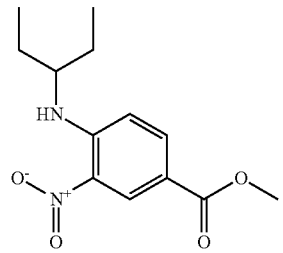 [SMILES: CCC(CC)Nc1ccc(C(=O)OC)cc1[N+](=O)[O-]]

To a solution of 5.38 g of 4-fluoro-3-nitro-benzoic acid methyl ester in 25 ml of abs. DMF was added 5.60 g of potassium carbonate, followed by 2.67 g of 3-aminopentane. After 3 h at rt, the mixture was poured into water, and extracted with ethyl acetate three times. The combined organic phases were washed with water, dried over sodium sulphate and concentrated to yield 7.01 g (97%) of 4-(1-Ethyl-propylamino)-3-nitro-benzoic acid methyl ester as a light brown oil.

$C_{13}H_{18}N_2O_4$ (266.30), LCMS (method 7_1_1): Rt=1.80 min, m/z=267.15 [M+H]$^+$ c) 3-Amino-4-(1-ethyl-propylamino)-benzoic acid methyl ester

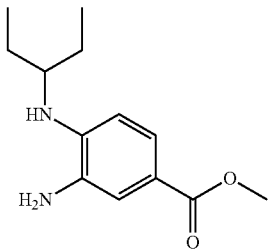 [SMILES: CCC(CC)Nc1ccc(C(=O)OC)cc1N]

7.00 g of 4-(1-Ethyl-propylamino)-3-nitro-benzoic acid methyl ester were dissolved in 70 ml ethanol, 0.35 g of palladium on carbon (10%) were added and the mixture was hydrogenated at 5 bar for 4 h. The catalyst was removed by filtration over celite, the filtrate was concentrated and after crystallization from diethylether 5.00 g (65%) of 3-Amino-4-(1-ethyl-propylamino)-benzoic acid methyl ester were obtained.

$C_{13}H_{20}N_2O_2$ (236.31), LCMS (method 7_1_1): Rt=1.09 min, m/z=237.15 [M+H]$^+$ d) 4-(1-Ethyl-propylamino)-3-(2-thiophen-2-yl-acetylamino)-benzoic acid methyl ester

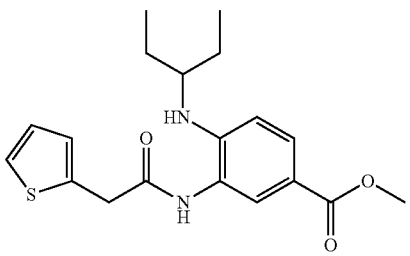 [SMILES: CCC(CC)Nc1ccc(C(=O)OC)cc1NC(=O)Cc1cccs1]

To a solution of 1.56 g of thiophen-2-yl-acetic acid in 25 ml of dry DMF 1.49 g of HOBT, 2.11 g of EDC and 2.6 ml of DIPEA were added at 0° C. After 30 min 2.36 g of 3-amino-4-(1-ethyl-propylamino)-benzoic acid methyl ester and 2.6 ml of DIPEA were added and the reaction was stirred at rt for 16 h. The reaction was then poured into water and extracted with ethyl acetate three times. The combined organic phases were washed with saturated aqueous sodium bicarbonate solution and brine, dried over magnesium sulphate and concentrated. The crude product was purified by crystallization from diethylether to yield 2.78 g (77%) of 4-(1-ethyl-propylamino)-3-(2-thiophen-2-yl-acetylamino)-benzoic acid methyl ester.

$C_{19}H_{24}N_2O_3S$ (360.48), LCMS (method 7_1_1): Rt=1.63 min, m/z=361.15 [M+H]$^+$ e) 1-(1-Ethyl-propyl)-2-thiophen-2-ylmethyl-1H-benzoimidazole-5-carboxylic acid methyl ester

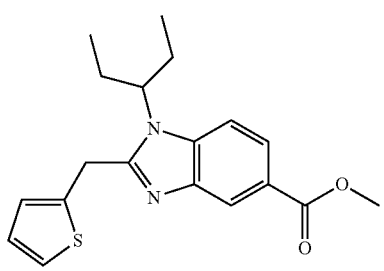 [SMILES: CCC(CC)n1c(Cc2cccs2)nc2cc(C(=O)OC)ccc21]

0.72 g of 4-(1-ethyl-propylamino)-3-(2-thiophen-2-yl-acetylamino)-benzoic acid methyl ester were dissolved in 5 ml of dry dioxane and 10 ml of 4M hydrochloric acid in dioxane were added. The reaction was heated in a microwave reactor to 120° C. for 10 min and concentrated to yield 0.69 g (100%) of 1-(1-ethyl-propyl)-2-thiophen-2-ylmethyl-1H-benzoimidazole-5-carboxylic acid methyl ester as a brown solid which was used in the next step without further purification.

$C_{19}H_{22}N_2O_2S$ (342.46), LCMS (method 7_1_1): Rt=1.25 min, m/z=343.15 [M+H]$^+$ f) 1-(1-Ethyl-propyl)-2-thiophen-2-ylmethyl-1H-benzoimidazole-5-carboxylic acid

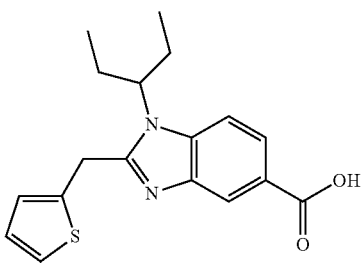

To 0.69 g of 1-(1-ethyl-propyl)-2-thiophen-2-ylmethyl-1H-benzoimidazole-5-carboxylic acid methyl ester 4 ml of methanol and 4 ml of 1 M aqueous sodium hydroxide solution were added and the reaction was heated in a microwave reactor to 110° C. for 5 min. The reaction mixture was adjusted to pH 5 by the addition of 2M aqueous hydrochloric acid and was extracted with ethyl acetate three times. The combined organic phases were dried over sodium sulphate and concentrated in vacuo. After crystallization from diisopropylether 0.46 g (96%) of 1-(1-ethyl-propyl)-2-thiophen-2-ylmethyl-1H-benzoimidazole-5-carboxylic acid were obtained.

$C_{18}H_{20}N_2O_2S$ (328.43), LCMS (method 7_1_1): Rt=1.04 min, m/z=329.15 [M+H]$^+$ (S)-2-[3-Amino-4-(1-isopropyl-2-methyl-propylamino)-benzoylamino]-4-methyl-pentanoic acid tert-butyl ester

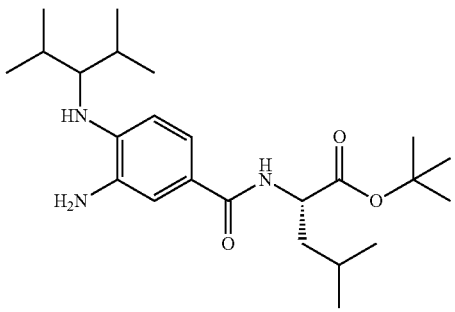 [SMILES: CC(C)C[C@H](NC(=O)c1ccc(NC(C(C)C)C(C)C)c(N)c1)C(=O)OC(C)(C)C]

a) (S)-2-(4-Fluoro-3-nitro-benzoylamino)-4-methyl-pentanoic acid tert-butyl ester

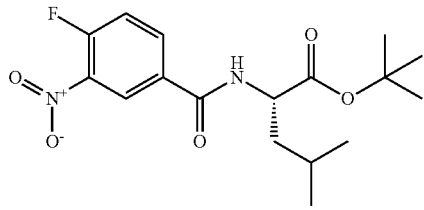 [SMILES: CC(C)C[C@H](NC(=O)c1ccc(F)c([N+](=O)[O-])c1)C(=O)OC(C)(C)C]

To a solution of 9.26 g of 4-fluoro-3-nitro-benzoic acid in 100 ml of dry DMF 7.43 g of HOBT, 10.54 g of EDC and 8.9 ml of DIPEA were added at 0° C. After 30 min 12.31 g of L-leucin-tert.-butylester-hydrochloride and 8.9 ml of DIPEA were added and the reaction was stirred at it for 4 h. The reaction was then concentrated to about a fifth of its volume and poured into water. It was then extracted with ethyl acetate three times. The combined organic phases were washed with saturated aqueous sodium carbonate solution and brine, dried over magnesium sulphate and concentrated to yield 17.65 g (100%) of (S)-2-(4-Fluoro-3-nitro-benzoylamino)-4-methyl-pentanoic acid tert-butyl ester as a brown oil, which was used without further purification in the subsequent step.

$C_{17}H_{23}FN_2O_5$ (354.38), LCMS (method 7_1_1): Rt=1.71 min, m/z=299.15 [M+H$^+$-tBu]

b) (S)-2-[4-(1-Isopropyl-2-methyl-propylamino)-3-nitro-benzoylamino]-4-methyl-pentanoic acid tert-butyl ester

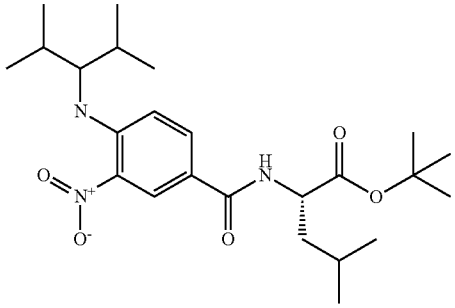 [SMILES: CC(C)C[C@H](NC(=O)c1ccc(NC(C(C)C)C(C)C)c([N+](=O)[O-])c1)C(=O)OC(C)(C)C]

To a solution of 1.06 g of 4(S)-2-(4-Fluoro-3-nitro-benzoylamino)-4-methyl-pentanoic acid tert-butyl ester in 10 ml of abs. DMF was added 0.42 g of potassium carbonate, followed by 0.38 g of 3-amino-2,4-dimethylpentane. After 3 h at rt, the mixture was poured into water, and extracted with ethyl acetate three times. The combined organic phases were dried over magnesium sulphate and concentrated to yield 1.30 g (96%) of (S)-2-[4-(1-Isopropyl-2-methyl-propylamino)-3-nitro-benzoylamino]-4-methyl-pentanoic acid tert-butyl ester as a brown oil, which was used in the next step without further purification.

c) (S)-2-[3-Amino-4-(1-isopropyl-2-methyl-propylamino)-benzoylamino]-4-methyl-pentanoic acid tert-butyl ester

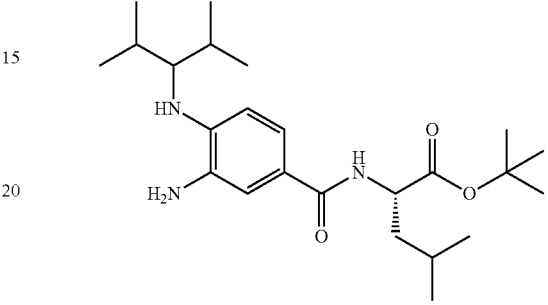

1.35 g of (S)-2-[4-(1-Isopropyl-2-methyl-propylamino)-3-nitro-benzoylamino]-4-methyl-pentanoic acid tert-butyl ester were dissolved in 14 ml ethanol, 0.30 g of palladium on carbon (10%) were added and the mixture was hydrogenated at 5 bar for 4 h. The catalyst was removed by filtration over celite, and the reaction mixture was concentrated to yield 1.00 g (79%) of (S)-2-[3-Amino-4-(1-isopropyl-2-methyl-propylamino)-benzoylamino]-4-methyl-pentanoic acid tert-butyl ester as a viscous oil, which was used without further purification.

$C_{24}H_{41}N_3O_3$ (419.61), LCMS (method 7_1_1): Rt=1.57 min, m/z=420.36 [M+H]$^+$ (S)-2-[3-Amino-4-(1-ethyl-propylamino)-benzoylamino]-4-methyl-pentanoic acid tert-butyl ester

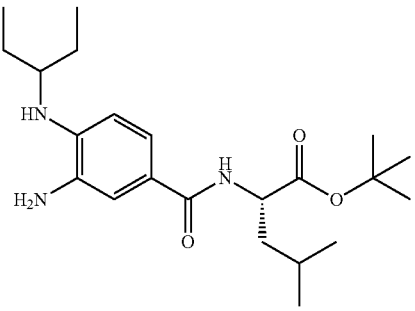 [SMILES: CCC(CC)Nc1ccc(C(=O)N[C@@H](CC(C)C)C(=O)OC(C)(C)C)cc1N]

a) 4-(1-Ethyl-propylamino)-3-nitro-benzoic acid ethyl ester

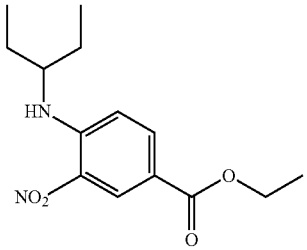 [SMILES: CCOC(=O)c1ccc(NC(CC)CC)c([N+](=O)[O-])c1]

To a solution of 25.0 g of 4-fluoro-3-nitro-benzoic acid ethyl ester in 100 ml of abs. DMF was added 24.3 g of potassium carbonate, followed by 11.6 g of 3-aminopentane. After 2 h at rt, the mixture was poured into water, and extracted with ethyl acetate three times. The combined organic phases were dried over magnesium sulphate and concentrated to yield 32.8 g (100%) of 4-(1-Ethyl-propylamino)-3-nitro-benzoic acid ethyl ester as a yellow oil.

$C_{14}H_{20}N_2O_4$ (280.32), LCMS (method 7_1_1): Rt=1.90 min, m/z=281.35 [M+H]$^+$ b) 4-(1-Ethyl-propylamino)-3-nitro-benzoic acid

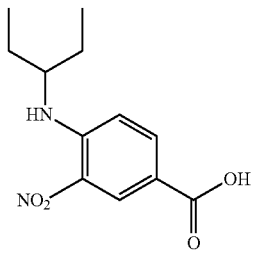 [SMILES: CCC(CC)Nc1ccc(C(=O)O)cc1[N+](=O)[O-]]

30.0 g of 4-(1-ethyl-propylamino)-3-nitro-benzoic acid ethyl ester were dissolved in 100 ml ethanol and 10 ml THF and 107 ml of 2 M aqueous sodium hydroxide solution were added. After stirring at room temperature over night, the reaction mixture was brought to pH 1 by addition of 2 M aqueous hydrochloric acid and extracted with ethyl acetate three times. The combined organic phases were dried over magnesium sulphate and concentrated to yield 27.0 g (100%) of 4-(1-ethyl-propylamino)-3-nitro-benzoic acid as a yellow solid.

$C_{12}H_{16}N_2O_4$ (252.27), LCMS (method 7_1_1): Rt=1.48 min, m/z=253.35 [M+H]$^+$ c) (S)-2-[4-(1-Ethyl-propylamino)-3-nitro-benzoylamino]-4-methyl-pentanoic acid tert-butyl ester

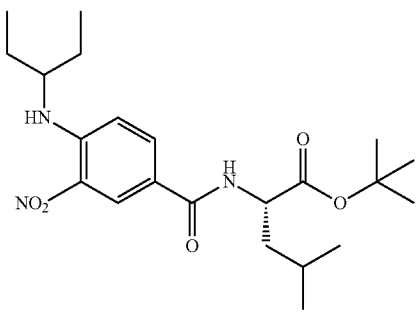 [SMILES: CCC(CC)Nc1ccc(C(=O)N[C@@H](CC(C)C)C(=O)OC(C)(C)C)cc1[N+](=O)[O-]]

To a solution of 6.80 g of 4-(1-ethyl-propylamino)-3-nitro-benzoic acid in 210 ml of dry DMF 1.82 g of HOBT, 7.23 g of EDC and 6.6 ml of DIPEA were added at 0° C. After 30 min 7.24 g of L-leucin-tert.-butylester-hydrochloride and 4.7 ml of DIPEA were added and the reaction was stirred at rt for 4 h. The reaction was then concentrated to about a fifth of its volume and poured into water. It was then extracted with ethyl acetate three times. The combined organic phases were washed with saturated aqueous sodium carbonate solution and brine, dried over magnesium sulphate and concentrated to yield 11.50 g (100%) of (S)-2-[4-(1-ethyl-propylamino)-3-nitro-benzoylamino]-4-methyl-pentanoic acid tert-butyl ester.

$C_{22}H_{36}N_3O_5$ (421.54), LCMS (method 7_1_1): Rt=2.02 min, m/z=366.45 [M+H-tBu]$^+$ d) (S)-2-[3-Amino-4-(1-ethyl-propylamino)-benzoylamino]-4-methyl-pentanoic acid tert-butyl ester

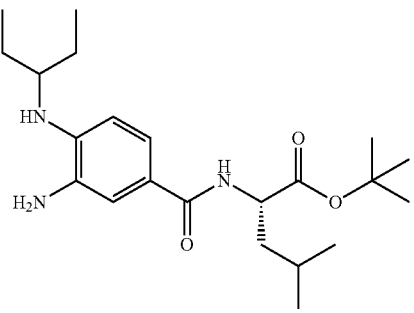 [SMILES: CCC(CC)Nc1ccc(C(=O)N[C@@H](CC(C)C)C(=O)OC(C)(C)C)cc1N]

11.5 g of (S)-2-[4-(1-ethyl-propylamino)-3-nitro-benzoylamino]-4-methyl-pentanoic acid tert-butyl ester were dissolved in 100 ml ethanol, 1.0 g of palladium on carbon (10%) were added and the mixture was hydrogenated at 5 bar for 4 h. the catalyst was removed by filtration over celite, and the reaction mixture was concentrated and purified by chromatography (silica, heptane/ethyl acetate) to yield 6.5 g (61%) of (S)-2-[3-amino-4-(1-ethyl-propylamino)-benzoylamino]-4-methyl-pentanoic acid tert-butyl ester as a colourless oil.

$C_{22}H_{37}N_3O_3$ (391.55), LCMS (method 7_1_1): Rt=1.45 min, m/z=392.65 [M+H]$^+$

2-Cyclopentylmethyl-1-(1-ethyl-propyl)-1H-benzoimidazole-5-carboxylic acid

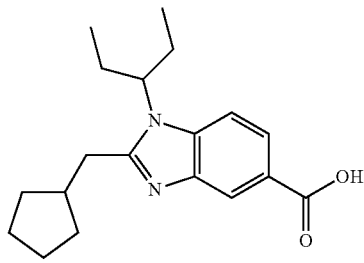

a) 3-(2-Cyclopentyl-acetylamino)-4-(1-ethyl-propylamino)-benzoic acid methyl ester

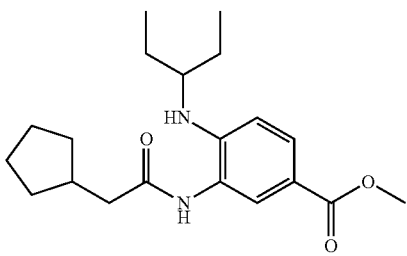 [SMILES: CCC(CC)Nc1ccc(C(=O)OC)cc1NC(=O)CC1CCCC1]

To a solution of 16.41 g of cyclopentyl-acetic acid in 600 ml of dry DMF 17.30 g of HOBT, 24.54 g of EDC and 30 ml of DIPEA were added at 0° C. After 1 h 27.51 g of 3-amino-4-(1-ethyl-propylamino)-benzoic acid methyl ester and 30 ml of DIPEA were added and the reaction was stirred at rt for 16 h. The reaction was then poured into water and extracted with ethyl acetate three times. The combined organic phases were washed with saturated aqueous sodium bicarbonate solution and brine, dried over magnesium sulphate and concentrated. The crude product was purified by crystallization from diisopropylether to yield 29.35 g (73%) of 3-(2-cyclopentyl-acetylamino)-4-(1-ethyl-propylamino)-benzoic acid methyl ester as an off-white solid.

$C_{20}H_{30}N_2O_3$ (346.47), LCMS (method 6_4_1): Rt=2.04 min, m/z=347.32 [M+H]$^+$ b) 2-Cyclopentylmethyl-1-(1-ethyl-propyl)-1H-benzoimidazole-5-carboxylic acid methyl ester

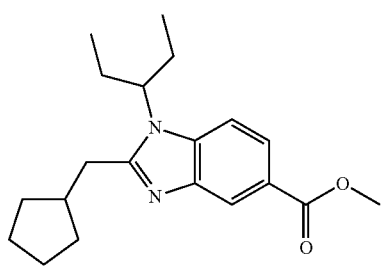 [SMILES: CCC(CC)n1c(CC2CCCC2)nc2cc(C(=O)OC)ccc21]

2.93 g of 3-(2-Cyclopentyl-acetylamino)-4-(1-ethyl-propylamino)-benzoic acid methyl ester were dissolved in 7.5 ml of dry dioxane and 7.5 ml of 4M hydrochloric acid in dioxane were added. The reaction was heated in a microwave reactor to 140° C. for 30 min. The reaction mixture was concentrated, the residue was taken up in ethyl acetate, washed with saturated aqueous sodium bicarbonate solution, dried over magnesium sulphate and concentrated to yield 26.9 g (97%) of 2-Cyclopentylmethyl-1-(1-ethyl-propyl)-1H-benzoimidazole-5-carboxylic acid methyl ester as a brown solid which was used in the next step without further purification.

No analytical data c) 2-Cyclopentylmethyl-1-(1-ethyl-propyl)-1H-benzoimidazole-5-carboxylic acid

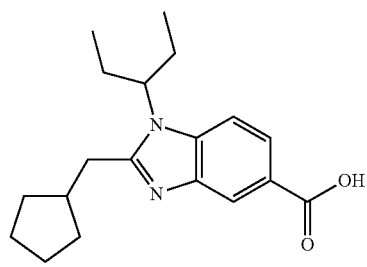

To 3.22 g of -Cyclopentylmethyl-1-(1-ethyl-propyl)-1H-benzoimidazole-5-carboxylic acid methyl ester 5 ml of methanol and 7 ml of 2 M aqueous sodium hydroxide solution were added and the reaction was heated in a microwave reactor to 140° C. for 1 h. The methanol was removed by distillation and the mixture was adjusted to pH 5 by the addition of 2M aqueous hydrochloric acid. The precipitated product was collected by filtration, washed with water and dried in vacuo. 2.22 g (65%) of Cyclopentylmethyl-1-(1-ethyl-propyl)-1H-benzoimidazole-5-carboxylic acid were obtained as light-brown solid.

$C_{19}H_{26}N_2O_2$ (314.43), LCMS (method 6_4_1): Rt=1.31 min, m/z=315.18 [M+H]$^+$ 2-Cyclopentylmethyl-1-(1-ethyl-propyl)-1H-benzoimidazole-5-carbonyl chloride

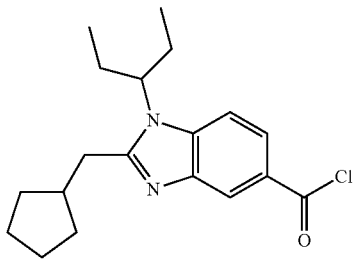 [SMILES: CCC(CC)n1c(CC2CCCC2)nc2cc(C(=O)Cl)ccc21]

To 8.00 g of 2-cyclopentylmethyl-1-(1-ethyl-propyl)-1H-benzoimidazole-5-carboxylic acid in 100 ml of dichloromethane 0.1 ml of DMF and 4 ml of oxalyl chloride were added. The reaction was stirred at it for 16 h, then concentrated and co-distilled with toluene to obtain 8.45 g (100%) of the crude product as a brown solid, which was used without further purification.

No analytical data 1-(1-Ethyl-propyl)-2-thiophen-2-ylmethyl-1H-benzoimidazole-5-carbonyl chloride

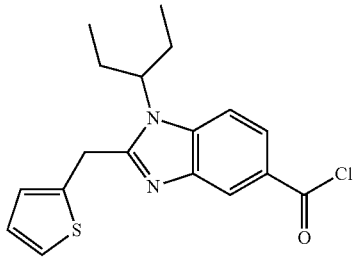 [SMILES: CCC(CC)n1c(Cc2cccs2)nc2cc(C(=O)Cl)ccc21]

To 8.00 g of 1-(1-Ethyl-propyl)-2-thiophen-2-ylmethyl-1H-benzoimidazole-5-carboxylic acid in 100 ml of dichloromethane 0.1 ml of DMF and 4 ml of oxalyl chloride were added. The reaction was stirred at rt for 16 h, then concentrated and co-distilled with toluene to obtain 8.47 g (100%) of the crude product as a brown solid, which was used without further purification.

No analytical data 1-(1-Ethyl-propyl)-2-furan-2-ylmethyl-1H-benzoimidazole-5-carboxylic acid

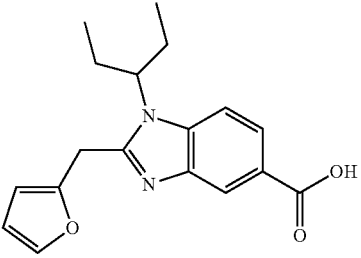 [SMILES: CCC(CC)n1c(Cc2ccco2)nc2cc(C(=O)O)ccc21]

a) 4-(1-Ethyl-propylamino)-3-(2-furan-2-yl-acetylamino)-benzoic acid methyl ester

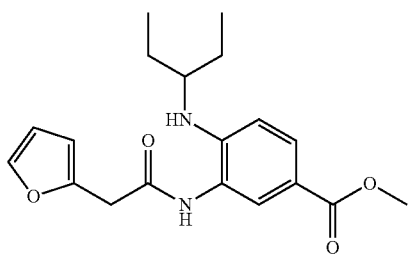 [SMILES: CCC(CC)Nc1ccc(C(=O)OC)cc1NC(=O)Cc1ccco1]

To a solution of 4.48 g of 2-furylacetic acid in 30 ml of dry DMF 1.00 g of HOBT, 3.97 g of EDC and 1.8 ml of DIPEA were added at 0° C. After 30 min 3.50 g of 3-amino-4-(1-ethyl-propylamino)-benzoic acid methyl ester and 1.8 ml of DIPEA were added and the reaction was stirred at it for 16 h. The reaction was then poured into water and extracted with ethyl acetate three times. The combined organic phases were washed with saturated aqueous sodium carbonate solution and saturated aqueous ammonium chloride solution, dried over magnesium sulphate and concentrated to obtain 4.44 g (87%) of 4-(1-Ethyl-propylamino)-3-(2-furan-2-yl-acetylamino)-benzoic acid methyl ester.

$C_{19}H_{24}N_2O_4$ (344.41), LCMS (method 7_1_1): Rt=1.51 min, m/z=345.15 [M+H]$^+$ b) 1-(1-Ethyl-propyl)-2-furan-2-ylmethyl-1H-benzoimidazole-5-carboxylic acid methyl ester

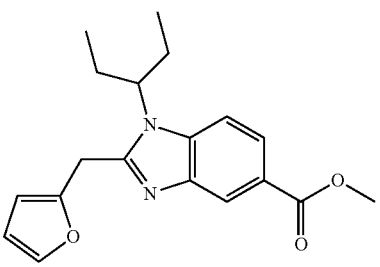 [SMILES: CCC(CC)n1c(Cc2ccco2)nc2cc(C(=O)OC)ccc21]

4.70 g of 4-(1-Ethyl-propylamino)-3-(2-furan-2-yl-acetylamino)-benzoic acid methyl ester were dissolved in 25 ml of dry dioxane and 50 ml of 4M hydrochloric acid in dioxane were added. The reaction was heated to reflux for 10 h and concentrated to yield 4.70 g (100%) of 1-(1-Ethyl-propyl)-2-furan-2-ylmethyl-1H-benzoimidazole-5-carboxylic acid methyl ester which was used in the next step without further purification.

$C_{19}H_{22}N_2O_3$ (326.40), LCMS (method 7_1_1): Rt=1.18 min, m/z=327.35 [M+H]$^+$ c) 1-(1-Ethyl-propyl)-2-furan-2-ylmethyl-1H-benzoimidazole-5-carboxylic acid

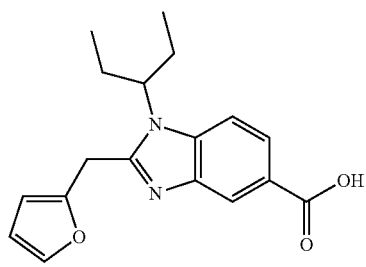 [SMILES: CCC(CC)n1c(Cc2ccco2)nc2cc(C(=O)O)ccc21]

To 5.30 g of 1-(1-Ethyl-propyl)-2-furan-2-ylmethyl-1H-benzoimidazole-5-carboxylic acid methyl ester 12 ml of methanol and 22 ml THF 22 ml of 1 M aqueous sodium hydroxide solution were added and the reaction was stirred for 16 h. The reaction mixture was adjusted to pH 5 by the addition of 2M aqueous hydrochloric acid and was extracted with ethyl acetate three times. The combined organic phases were dried over sodium sulphate and concentrated in vacuo. 4.83 g (85%) of 1-(1-Ethyl-propyl)-2-furan-2-ylmethyl-1H-benzoimidazole-5-carboxylic acid were obtained.

$C_{18}H_2O_2O_3$ (312.37), LCMS (method 6_4_1): Rt=1.25 min, m/z=313.07 [M+H]$^+$

1-(1-Ethyl-propyl)-2-(tetrahydro-furan-2-ylmethyl)-1H-benzoimidazole-5-carboxylic acid

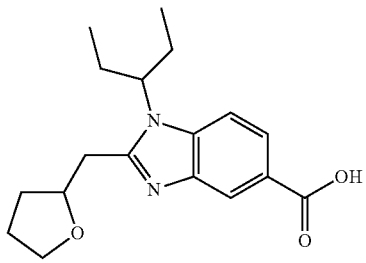 [SMILES: CCC(CC)n1c(CC2CCCO2)nc2cc(C(=O)O)ccc21]

A solution of 348 mg of 1-(1-ethyl-propyl)-2-furan-2-yl-methyl-1H-benzoimidazole-5-carboxylic acid in 5 ml of ethanol was hydrogenated at 5 bar for 24 h in the presence of 10 mg platinum oxide. The catalyst was removed by filtration, and the filtrate was concentrated in vacuo. The resulting residue was purified by HPLC to obtain 55 mg (17%) of 1-(1-Ethyl-propyl)-2-(tetrahydro-furan-2-ylmethyl)-1H-benzoimidazole-5-carboxylic acid.

$C_{18}H_{24}N_2O_3$ (316.40), LCMS (method 7_1_1): Rt=0.97 min, m/z=317.25 [M+H]$^+$

2-(5-Chloro-thiophen-2-ylmethyl)-1-(1-ethyl-propyl)-1H-benzoimidazole-5-carboxylic acid

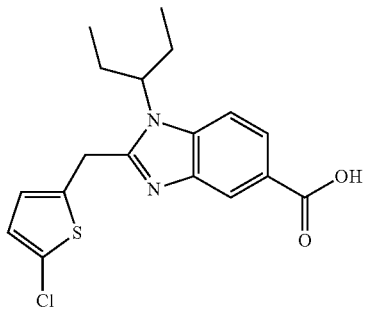 [SMILES: CCC(CC)n1c(Cc2ccc(Cl)s2)nc2cc(C(=O)O)ccc21]

a) 3-[2-(5-Chloro-thiophen-2-yl)-acetylamino]-4-(1-ethyl-propylamino)-benzoic acid methyl ester

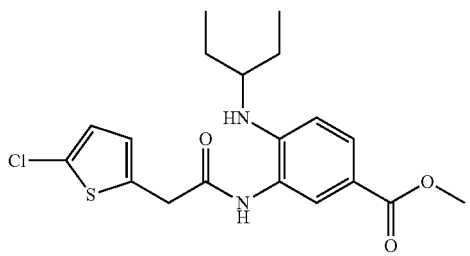 [SMILES: CCC(CC)Nc1ccc(C(=O)OC)cc1NC(=O)Cc1ccc(Cl)s1]

To a solution of 1.00 g of 5-Chlorothiophen-2-yl-acetic acid in 15 ml of dry DMF 0.84 g of HOBT, 1.19 g of EDC and 1.5 ml of DIPEA were added at 0° C. After 30 min 1.33 g of 3-amino-4-(1-ethyl-propylamino)-benzoic acid methyl ester and 1.5 ml of DIPEA were added and the reaction was stirred at rt for 16 h. The reaction was then poured into water and extracted with ethyl acetate three times. The combined organic phases were washed with saturated aqueous sodium bicarbonate solution and brine, dried over magnesium sulphate and concentrated. The crude product was purified by crystallization from diethylether to yield 2.00 g (89%) of 3-[2-(5-Chloro-thiophen-2-yl)-acetylamino]-4-(1-ethyl-propylamino)-benzoic acid methyl ester.

$C_{19}H_{23}ClN_2O_3S$ (394.92), LCMS (method 7_1_1): Rt=1.71 min, m/z=395.25 [M+H]$^+$ b) 2-(5-Chloro-thiophen-2-ylmethyl)-1-(1-ethyl-propyl)-1H-benzoimidazole-5-carboxylic acid methyl ester

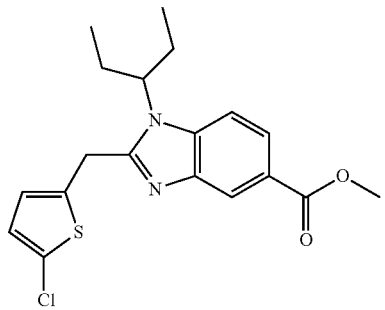 [SMILES: CCC(CC)n1c(Cc2ccc(Cl)s2)nc2cc(C(=O)OC)ccc21]

0.99 g 3-[2-(5-Chloro-thiophen-2-yl)-acetylamino]-4-(1-ethyl-propylamino)-benzoic acid methyl ester were reacted with 10 ml of 4M hydrochloric acid in dioxane in a microwave reactor at 130° C. for 15 min. The reaction was concentrated. The residue was dissolved in ethyl actate, washed with saturated aqueous sodium bicarbonate solution and brine, dried over sodium sulphate and concentrated to yield 0.73 g (77%) of 2-(5-Chloro-thiophen-2-ylmethyl)-1-(1-ethyl-propyl)-1H-benzoimidazole-5-carboxylic acid methyl ester.

$C_{19}H_{21}ClN_2O_2S$ (376.91), LCMS (method 7_1_1): Rt=1.41 min, m/z=377.20 [M+H]$^+$ c) 2-(5-Chloro-thiophen-2-ylmethyl)-1-(1-ethyl-propyl)-1H-benzoimidazole-5-carboxylic acid

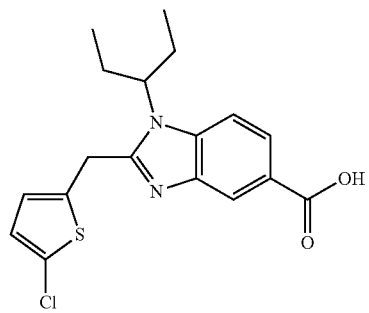 [SMILES: CCC(CC)n1c(Cc2ccc(Cl)s2)nc2cc(C(=O)O)ccc21]

To 0.57 g of 2-(5-Chloro-thiophen-2-ylmethyl)-1-(1-ethyl-propyl)-1H-benzoimidazole-5-carboxylic acid methyl ester in 3 ml of methanol were added 0.08 g of lithium hydroxide and 1 ml of water. The reaction was heated to reflux for 1 h. The reaction mixture was adjusted to pH 5 by the addition of 2M aqueous hydrochloric acid and was extracted with ethyl acetate three times. The combined organic phases were dried over sodium sulphate and concentrated in vacuo. The product precipitated after treatment with diethylether and 0.30 g (55%) of 2-(5-Chloro-thiophen-2-ylmethyl)-1-(1-ethyl-propyl)-1H-benzoimidazole-5-carboxylic acid were obtained.

$C_{18}H_{19}ClN_2O_2S$ (362.88), LCMS (method 7_1_1): Rt=1.19 min, m/z=363.15 [M+H]$^+$ 1-(1-Ethyl-propyl)-2-thiazol-4-ylmethyl-1H-benzoimidazole-5-carboxylic acid

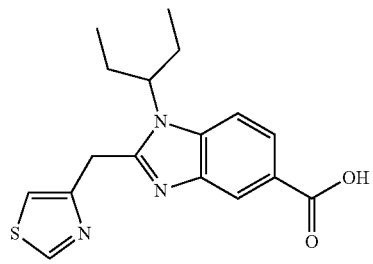 [SMILES: CCC(CC)n1c(Cc2cscn2)nc2cc(C(=O)O)ccc21]

1-(1-Ethyl-propyl)-2-thiazol-4-ylmethyl-1H-benzoimidazole-5-carboxylic acid was synthesized in analogy to 2-(5-Chloro-thiophen-2-ylmethyl)-1-(1-ethyl-propyl)-1H-benzoimidazole-5-carboxylic acid.

$C_{17}H_{19}N_3O_2S$ (329.42); LCMS (method 6_4_1): Rt=1.05 min, m/z=330.12 [M+H]$^+$ 1-(1-Ethyl-propyl)-2-thiazol-5-ylmethyl-1H-benzoimidazole-5-carboxylic acid

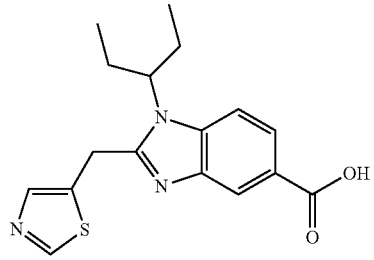

a) 4-(1-Ethyl-propylamino)-3-(2-thiazol-5-yl-acetylamino)-benzoic acid methyl ester

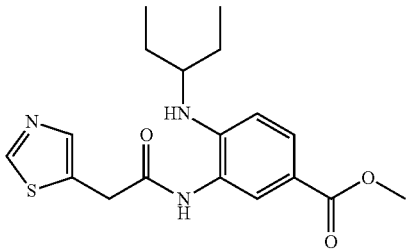

To a solution of 1.00 g of Thiazol-5-yl-acetic acid in 17 nil of dry DMF 0.48 g of HOAT, 1.61 g of EDC and 2.3 ml of DIPEA were added at 0° C. After 30 min 1.65 g of 3-Amino-4-(1-ethyl-propylamino)-benzoic acid methyl ester were added, followed by the addition of 2 ml of DIPEA and the reaction was stirred at it for 48 h. The reaction was then poured into water and extracted with ethyl acetate three times. The combined organic phases were washed with saturated aqueous sodium bicarbonate solution and brine, dried over magnesium sulphate and concentrated to obtain 2.16 g (85%)

of 4-(1-Ethyl-propylamino)-3-(2-thiazol-5-yl-acetylamino)-benzoic acid methyl ester, which was used without further purification.

$C_{18}H_{23}N_3O_3S$ (361.47), LCMS (method 8_1_1): Rt=0.83 min, m/z=362.15 [M+H]$^+$ b) 1-(1-Ethyl-propyl)-2-thiazol-5-ylmethyl-1H-benzoimidazole-5-carboxylic acid

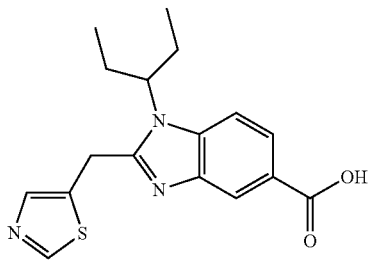 [SMILES: CCC(CC)n1c(Cc2cncs2)nc2cc(C(=O)O)ccc21]

To 2.16 g of 4-(1-Ethyl-propylamino)-3-(2-thiazol-5-yl-acetylamino)-benzoic acid methyl ester were added 15 ml of 4M hydrochloric acid in dioxane. The reaction was divided in three portions and each was heated at 130° C. in a microwave reactor for 15 min. 2 ml of water were added to each vial and the reaction mixtures were heated to 140° C. for 15 min. The combined reaction mixtures were concentrated and the residue purified by chromatography (silica, ethyl acetate/heptane) to yield 1.50 g (77%) of 1-(1-Ethyl-propyl)-2-thiazol-5-ylmethyl-1H-benzoimidazole-5-carboxylic acid.

$C_{17}H_{19}N_3O_2S$ (329.42), LCMS (method 8_1_1): Rt=0.62 min, m/z=330.10 [M+H]$^+$ 1-(1-Ethyl-propyl)-2-pyrazol-1-ylmethyl-1H-benzoimidazole-5-carboxylic acid

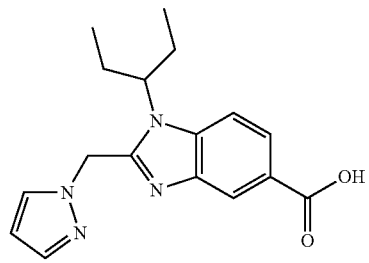 [SMILES: CCC(CC)n1c(Cn2cccn2)nc2cc(C(=O)O)ccc21]

a) 4-(1-Ethyl-propylamino)-3-(2-pyrazol-1-yl-acetylamino)-benzoic acid methyl ester

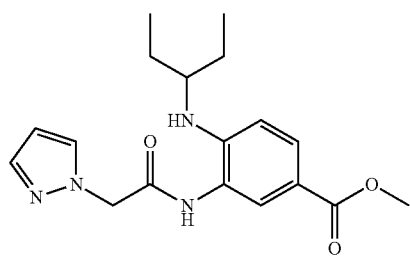 [SMILES: CCC(CC)Nc1ccc(C(=O)OC)cc1NC(=O)Cn1cccn1]

To a solution of 1.76 g of Pyrazol-1-yl-acetic acid in 20 ml of dry DMF 2.09 g of HOAT, 3.75 g of EDC and 6.9 ml of DIPEA were added at 0° C. After 30 min 3.3 g of 3-amino-4-(1-ethyl-propylamino)-benzoic acid methyl ester were added and the reaction was stirred at rt for 16 h. The reaction was then poured into water and extracted with ethyl acetate three times. The combined organic phases were washed with saturated aqueous sodium bicarbonate solution and brine, dried over magnesium sulphate and concentrated. The crude product was purified by precipitation from heptane to yield 2.28 g (47%) of 4-(1-Ethyl-propylamino)-3-(2-pyrazol-1-yl-acetylamino)-benzoic acid methyl ester.

$C_{18}H_{24}N_4O_3$ (344.42), LCMS (method 8_1_1): Rt=0.85 min, m/z=345.15 [M+H]$^+$ b) 1-(1-Ethyl-propyl)-2-pyrazol-1-ylmethyl-1H-benzoimidazole-5-carboxylic acid

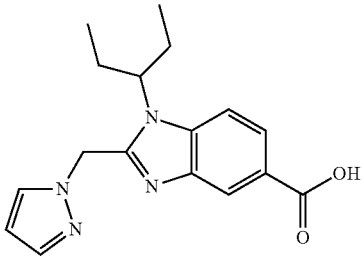 [SMILES: CCC(CC)n1c(Cn2cccn2)nc2cc(C(=O)O)ccc21]

To 2.28 g 4-(1-Ethyl-propylamino)-3-(2-pyrazol-1-yl-acetylamino)-benzoic acid methyl ester were added 50 ml of 4M hydrochloric acid in dioxane. Divided into five portions the reaction mixture was heated to 110° C. for 15 min in a microwave reactor. After cooling to the reaction mixture 6 ml of 10 M aqueous sodium hydroxide solution were added slowly. After 30 min at rt the reaction mixture was concentrated to a third of its volume and adjusted to pH 4 by the addition of 2M aqueous hydrochloric acid. It was extracted with ethyl acetate three times. The combined organic phases were dried over sodium sulphate and concentrated in vacuo. 1.86 g (90%) of 1-(1-Ethyl-propyl)-2-pyrazol-1-ylmethyl-1H-benzoimidazole-5-carboxylic acid were obtained.

$C_{17}H_{20}H_4O_2$ (312.37), LCMS (method 8_1_1): Rt=0.65 min, m/z=313.15 [M+H]$^+$ 1-(1-Ethyl-propyl)-2-isoxazol-5-ylmethyl-1H-benzoimidazole-5-carboxylic acid

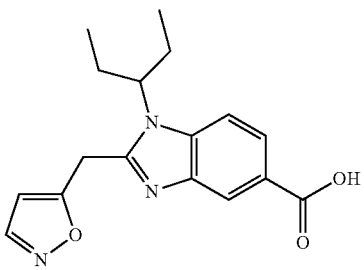 [SMILES: CCC(CC)n1c(Cc2ccno2)nc2cc(C(=O)O)ccc21]

a) 4-(1-Ethyl-propylamino)-3-(2-isoxazol-5-yl-acetylamino)-benzoic acid methyl ester

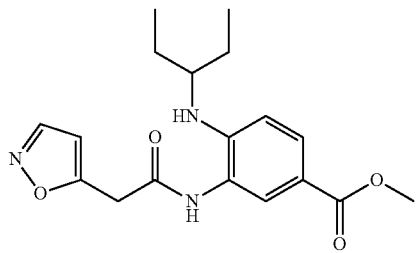 [SMILES: CCC(CC)Nc1ccc(C(=O)OC)cc1NC(=O)Cc1ccno1]

To a solution of 0.71 g of Isoxazol-5-yl-acetic acid in 15 ml of dry DMF 0.38 g of HOAT, 1.29 g of EDC and 3 ml of DIPEA were added at 0° C. After 30 min 1.32 g of 3-amino-4-(1-ethyl-propylamino)-benzoic acid methyl ester were added and the reaction was stirred at it for 16 h. The reaction was then poured into water and extracted with ethyl acetate three times. The combined organic phases were washed with saturated aqueous sodium bicarbonate solution and brine, dried over magnesium sulphate and concentrated. The crude product was purified by precipitation from diisoprpylether to yield 1.06 g (55%) of 4-(1-Ethyl-propylamino)-3-(2-isoxazol-5-yl-acetylamino)-benzoic acid methyl ester.

$C_{18}H_{23}N_3O_4$ (345.40), LCMS (method 8_1_1): Rt=0.86 min, m/z=346.15 [M+H]$^+$ b) 1-(1-Ethyl-propyl)-2-isoxazol-5-ylmethyl-1H-benzoimidazole-5-carboxylic acid

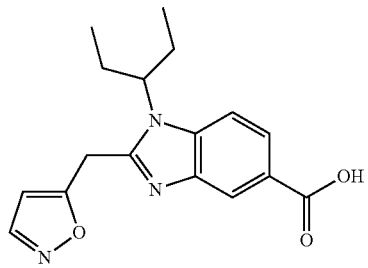 [SMILES: CCC(CC)n1c(Cc2ccno2)nc2cc(C(=O)O)ccc21]

To 1.06 g 4-(1-Ethyl-propylamino)-3-(2-isoxazol-5-yl-acetylamino)-benzoic acid methyl ester were added 7.5 ml of 4M hydrochloric acid in dioxane. The reaction mixture was heated to 130° C. for 20 min in a microwave reactor. After cooling to rt 2 ml of water were added and the reaction was again heated to 130° C. for 20 min. The reaction was concentrated and the residue purified by chromatography (silica, ethyl acetate/heptane) to yield 0.85 g (90%) of 1-(1-Ethyl-propyl)-2-isoxazol-5-ylmethyl-1H-benzoimidazole-5-carboxylic acid.

$C_{17}H_{19}N_3O_3$ (313.36), LCMS (method 8_1_1): Rt=0.62 min, m/z=314.15 [M+H]$^+$ 1-Cyclohexylmethyl-2-thiophen-2-ylmethyl-1H-benzoimidazole-5-carboxylic acid

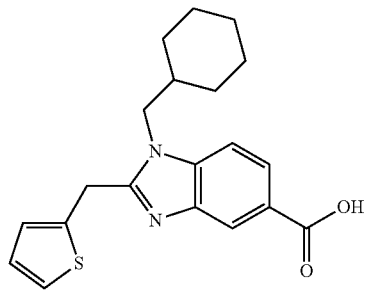 [SMILES: O=C(O)c1ccc2c(c1)nc(Cc1cccs1)n2CC1CCCCC1]

a) 4-(Cyclohexylmethyl-amino)-3-nitro-benzoic acid methyl ester

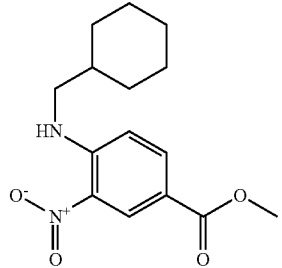 [SMILES: COC(=O)c1ccc(NCC2CCCCC2)c([N+](=O)[O-])c1]

To a solution of 25.0 g of 4-fluoro-3-nitro-benzoic acid methyl ester in 100 ml of abs. DMF was added 26.0 g of potassium carbonate, followed by 14.2 g of (cycloheylmethyl)amine. After 16 h at rt, the mixture was poured into water, and extracted with ethyl acetate three times. The combined organic phases were washed with water, dried over sodium sulphate and concentrated to yield 36.7 g (100%) of 4-(Cyclohexylmethyl-amino)-3-nitro-benzoic acid methyl ester as an orange solid.

$C_{15}H_{20}N_2O_4$ (292.33), LCMS (method 6_4_1): Rt=2.32 min, m/z=293.17 [M+H]$^+$ b) 3-Amino-4-(cyclohexylmethyl-amino)-benzoic acid methyl ester

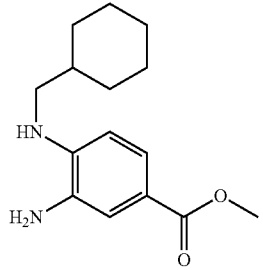 [SMILES: COC(=O)c1ccc(NCC2CCCCC2)c(N)c1]

12.00 g 4-(Cyclohexylmethyl-amino)-3-nitro-benzoic acid methyl ester were dissolved in 75 ml ethyl acetate and 75 ml methanol, 0.45 g of palladium on carbon (10%) were added and the mixture was hydrogenated at 5 bar for 4 h. The catalyst was removed by filtration over celite, the filtrate was concentrated and after precipitation with cyclohexane 12.00 g (93%) of 3-Amino-4-(cyclohexylmethyl-amino)-benzoic acid methyl ester were obtained.

$C_{15}H_{22}N_2O_2$ (262.35), LCMS (method 7_1_1): Rt=1.27 min, m/z=263.25 [M+H]$^+$ c) 4-(Cyclohexylmethyl-amino)-3-(2-thiophen-2-yl-acetylamino)-benzoic acid methyl ester

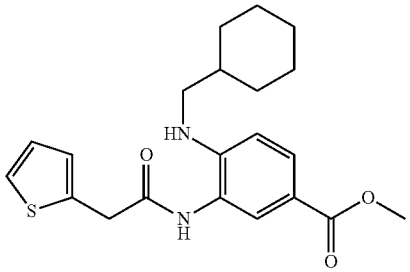 [SMILES: COC(=O)c1ccc(NCC2CCCCC2)c(NC(=O)Cc2cccs2)c1]

To a solution of 8.94 g of thiophen-2-yl-acetic acid in 130 ml of dry DMF 8.56 g of HOAT, 12.06 g of EDC and 30 ml of DIPEA were added at 0° C. After 30 min 15.00 g of 3-Amino-4-(cyclohexylmethyl-amino)-benzoic acid methyl ester were added and the reaction was stirred at 80° C. for 48 h. The reaction was then poured into water and extracted with ethyl acetate three times. The combined organic phases were washed with saturated aqueous sodium bicarbonate solution and brine, dried over magnesium sulphate and concentrated. The crude product was purified by chromatography (silica, ethyl acetate/heptane) to yield 22.00 g (100%) of 4-(Cyclohexylmethyl-amino)-3-(2-thiophen-2-yl-acetylamino)-benzoic acid methyl ester.

$C_{21}H_{26}N_2O_3S$ (386.51); LCMS (method 6_4_1): Rt=2.05 min, m/z=387.16 [M+H]$^+$ d) 1-Cyclohexylmethyl-2-thiophen-2-ylmethyl-1H-benzoimidazole-5-carboxylic acid methyl ester

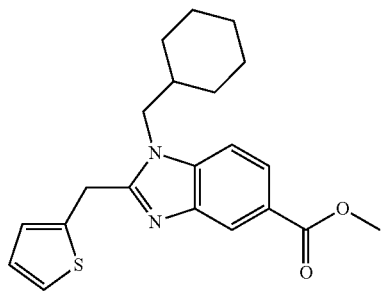 [SMILES: COC(=O)c1ccc2c(c1)nc(Cc1cccs1)n2CC1CCCCC1]

20.0 g 4-(Cyclohexylmethyl-amino)-3-(2-thiophen-2-yl-acetylamino)-benzoic acid methyl ester were dissolved in 65 ml dioxane and reacted with 33 ml of 4M hydrochloric acid in dioxane at rt for 4 h. The reaction was concentrated and the residue purified by chromatography (silica, ethyl acetate/heptane) to yield 13.6 g (71%) of 1-Cyclohexylmethyl-2-thiophen-2-ylmethyl-1H-benzoimidazole-5-carboxylic acid methyl ester.

$C_{21}H_{24}N_2O_2S$ (368.50), LCMS (method 6_4_1): Rt=1.63 min, m/z=369.06 [M+H]$^+$ e) 1-Cyclohexylmethyl-2-thiophen-2-ylmethyl-1H-benzoimidazole-5-carboxylic acid

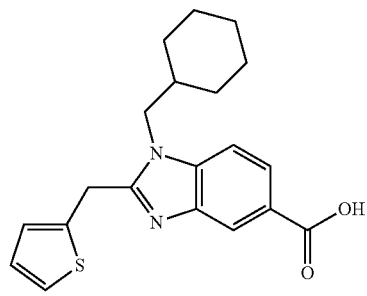 [SMILES: O=C(O)c1ccc2c(c1)nc(Cc1cccs1)n2CC1CCCCC1]

To 13.60 g of 1-Cyclohexylmethyl-2-thiophen-2-ylmethyl-1H-benzoimidazole-5-carboxylic acid methyl ester in 25 ml of methanol and 100 ml of THF were added 37 ml of 2 M aqueous sodium hydroxide solution. The reaction stirred at rt for 6 h. The reaction mixture was adjusted to pH 4 by the addition of 2M aqueous hydrochloric acid and was extracted with ethyl acetate three times. The combined organic phases were dried over sodium sulphate and concentrated in vacuo. The residue was purified by chromatography (silica, heptane/ ethyl acetate) to yield 11.1 g (85%) of 1-Cyclohexylmethyl-2-thiophen-2-ylmethyl-1H-benzoimidazole-5-carboxylic acid.

$C_{20}H_{22}N_2O_2S$ (354.47) LCMS (method 6_4_1): Rt=1.42 min, m/z=355.06 [M+H]$^+$ (S)-2-[3-Amino-4-(2-chloro-phenylamino)-benzoylamino]-4-methyl-pentanoic acid tert-butyl ester

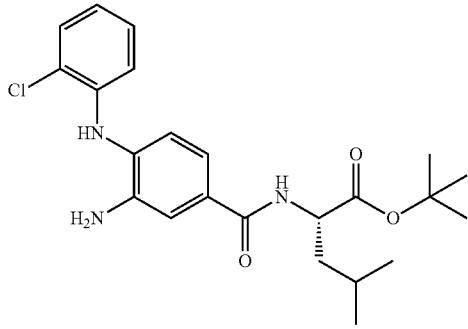 [SMILES: CC(C)C[C@H](NC(=O)c1ccc(Nc2ccccc2Cl)c(N)c1)C(=O)OC(C)(C)C]

a) (S)-2-[4-(2-Chloro-phenylamino)-3-nitro-benzoylamino]-4-methyl-pentanoic acid tert-butyl ester

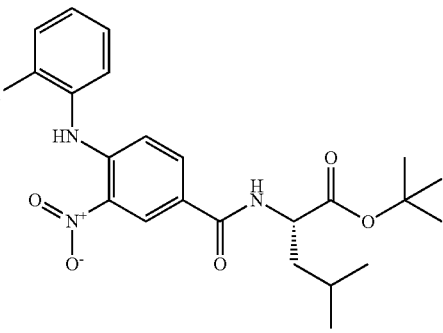

To a solution of 300 mg of (S)-2-(4-Fluoro-3-nitro-benzoylamino)-4-methyl-pentanoic acid tert-butyl ester in 1.6 ml of abs. DMF was added 1044 mg of cesium carbonate, followed by 90 mg of 2-chloroaniline. The reaction was heated in a microwave reactor to 80° C. for 2 min. The mixture was poured into water, and extracted with ethyl acetate three times. The combined organic phases were dried over magnesium sulphate and concentrated to yield 149 mg (50%) of (S)-2-[4-(2-Chloro-henylamino)-3-nitro-benzoylamino]-4-methyl-pentanoic acid tert-butyl.

$C_{23}H_{28}ClN_3O_5$ (461.94), LCMS (method 7_1_1): Rt=1.93 min, m/z=406.10 [M+H-tBu]$^+$ b) (S)-2-[3-Amino-4-(2-chloro-phenylamino)-benzoylamino]-4-methyl-pentanoic acid tert-butyl ester

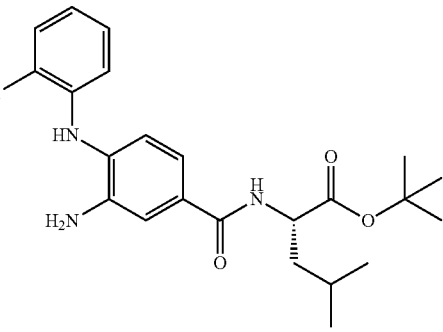

140 mg of (S)-2-[4-(2-Chloro-phenylamino)-3-nitro-benzoylamino]-4-methyl-pentanoic acid tert-butyl ester were dissolved in 5 ml ethyl acetate, 342 mg of tin(II)chloride-dihydrate were added and the mixture was stirred at rt for 4 h. Water was added to the reaction. The mixture was filtrated over celite. The pH of the filtrate was adjusted to 7, the layers were separated and the organic layer was extracted with ethyl acetate twice. The combined organic layers were dried over sodium sulphate and concentrated to yield 103 mg (79%) of (S)-2-[3-Amino-4-(2-chloro-phenylamino)-benzoylamino]-4-methyl-pentanoic acid tert-butyl ester.

$C_{23}H_{30}ClN_3O_3$ (431.96), LCMS (method 7_1_1): Rt=1.72 min, m/z=432.20 [M+H]$^+$ (S)-2-[3-Amino-4-(1,3-dimethyl-butylamino)-benzoylamino]-4-methyl-pentanoic acid tert-butyl ester

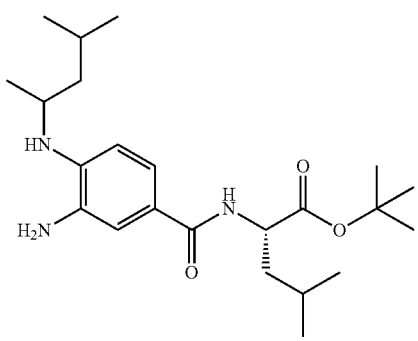 [SMILES: CC(C)CC(C)Nc1ccc(C(=O)N[C@@H](CC(C)C)C(=O)OC(C)(C)C)cc1N]

a) (S)-2-[4-(1,3-Dimethyl-butylamino)-3-nitro-benzoylamino]-4-methyl-pentanoic acid tert-butyl ester

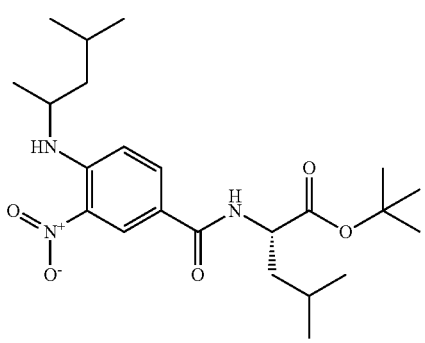 [SMILES: CC(C)CC(C)Nc1ccc(C(=O)N[C@@H](CC(C)C)C(=O)OC(C)(C)C)cc1[N+](=O)[O-]]

To a solution of 200 mg of 4(S)-2-(4-chloro-3-nitro-benzoylamino)-4-methyl-pentanoic acid tert-butyl ester in 1.4 ml of abs. DMF was added 878 mg of cesium carbonate, followed by 60 mg of 1,3-dimethylbutylamine. The reaction was heated in a microwave reactor to 100° C. for 10 min. Then the mixture was poured into water, and extracted with ethyl acetate three times. The combined organic phases were dried over magnesium sulphate and concentrated. The resulting residue was purified by HPLC to yield 56 mg (24%) of (S)-2-[3-Amino-4-(1,3-dimethyl-butylamino)-benzoylamino]-4-methyl-pentanoic acid tert-butyl ester.

$C_{23}H_{37}N_3O_5$ (435.56) LCMS (method 6_4_1): Rt=2.44 min, m/z=436.25 [M+H]$^+$ b) (S)-2-[3-Amino-4-(1,3-dimethyl-butylamino)-benzoylamino]-4-methyl-pentanoic acid tert-butyl ester

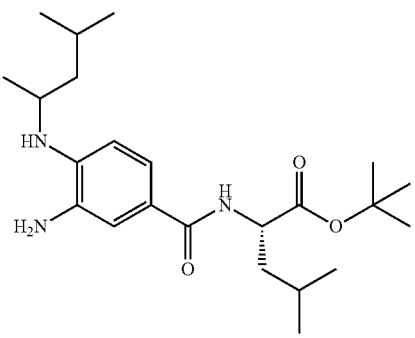 [SMILES: CC(C)CC(C)Nc1ccc(C(=O)N[C@@H](CC(C)C)C(=O)OC(C)(C)C)cc1N]

50 mg of (S)-2-[4-(1,3-Dimethyl-butylamino)-3-nitro-benzoylamino]-4-methyl-pentanoic acid tert-butyl ester were dissolved in 0.5 ml, ethanol, 5 mg of palladium on carbon (10%) were added and the mixture was hydrogenated at 5 bar for 4 h. The catalyst was removed by filtration over celite, and the reaction mixture was concentrated to yield 45 mg (99%) of (S)-2-[3-Amino-4-(1,3-dimethyl-butylamino)-benzoylamino]-4-methyl-pentanoic acid tert-butyl ester, which was used without further purification.

$C_{23}H_{39}N_3O_3$ (405.59), LCMS (method 7_1_1): Rt=1.50 min, m/z=406.25 [M+H]$^+$ 1-(2-Methyl-cyclohexyl)-2-thiophen-2-ylmethyl-1H-benzoimidazole-5-carboxylic acid

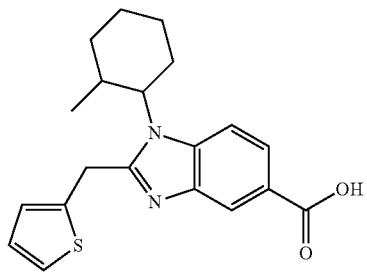 [SMILES: CC1CCCCC1n1c(Cc2cccs2)nc2cc(C(=O)O)ccc21]

a) 4-(2-Methyl-cyclohexylamino)-3-nitro-benzoic acid methyl ester

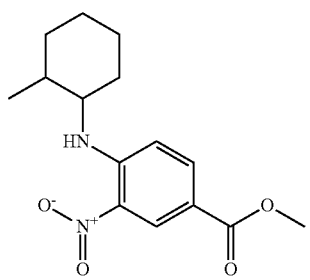

To a solution of 20.0 g of 4-fluoro-3-nitro-benzoic acid methyl ester in 100 ml of abs. DMF was added 27.8 g of potassium carbonate, followed by 12.5 g of 2-methylcyclohexylamine. After 16 h at rt, the mixture was poured into water, the pH was adjusted to 4 by the addition of 2 M aqueous hydrochloric acid, and the reaction mixture was extracted with ethyl acetate three times. The combined organic phases were washed with water, dried over sodium sulphate and concentrated to yield 29.4 g (100%) of 4-(2-Methyl-cyclohexylamino)-3-nitro-benzoic acid methyl ester. $C_{15}H_{20}N_2O_4$ (292.34), LCMS (method 7_1_1): Rt=1.85 min, m/z=293.25 $[M+H]^+$ b) 3-Amino-4-(2-methyl-cyclohexylamino)-benzoic acid methyl ester

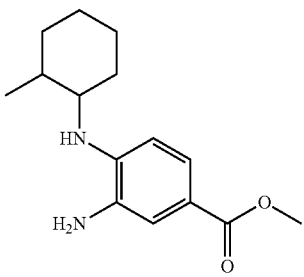

13.50 g 4-(2-Methyl-cyclohexylamino)-3-nitro-benzoic acid methyl ester were dissolved in 60 ml methanol, 0.49 g of palladium on carbon (10%) were added and the mixture was hydrogenated at 5 bar for 4 h. The catalyst was removed by filtration over celite, the filtrate was concentrated to obtain 12.00 g (99%) of 3-Amino-4-(2-methyl-cyclohexylamino)-benzoic acid methyl ester.

$C_{16}H_{22}N_2O_2$ (262.35), LCMS (method 7_1_1): Rt=1.20 min, m/z=263.50 $[M+H]^+$ c) 4-(2-Methyl-cyclohexylamino)-3-(2-thiophen-2-yl-acetylamino)-benzoic acid methyl ester

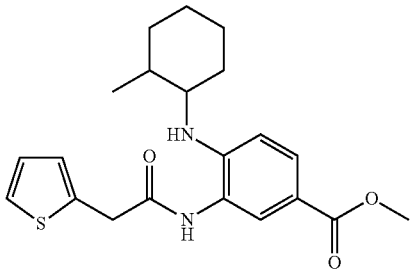 [SMILES: COC(=O)c1ccc(NC2CCCCC2C)c(NC(=O)Cc2cccs2)c1]

To a solution of 4.34 g of thiophen-2-yl-acetic acid in 40 ml of dry DMF 2.08 g of HOAT, 8.77 g of EDC and 13 ml of DIPEA were added at 0° C. After 30 min 8.00 g of 3-Amino-4-(2-methyl-cyclohexylamino)-benzoic acid methyl ester were added, followed by the addition of 6 ml of DIPEA and the reaction was stirred at rt for 48 h. The reaction was then poured into water and extracted with ethyl acetate three times. The combined organic phases were washed with saturated aqueous sodium bicarbonate solution and brine, dried over magnesium sulphate and concentrated to obtain 11.75 g (100%) of 4-(2-Methyl-cyclohexylamino)-3-(2-thiophen-2-yl-acetylamino)-benzoic acid methyl ester, which was used without further purification.

$C_{21}H_{26}N_2O_3S$ (386.52), LCMS (method 7_1_1): Rt=1.69 min, m/z=387.35 $[M+H]^+$ d) 1-(2-Methyl-cyclohexyl)-2-thiophen-2-ylmethyl-1H-benzoimidazole-5-carboxylic acid

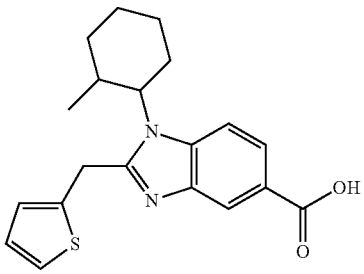 [SMILES: CC1CCCCC1n1c(Cc2cccs2)nc2cc(C(=O)O)ccc21]

0.77 g 4-(2-Methyl-cyclohexylamino)-3-(2-thiophen-2-yl-acetylamino)-benzoic acid methyl ester were reacted with 5 ml of 4M hydrochloric acid in dioxane at 100° C. in a microwave reactor for 5 min. 1 ml water was added and the mixture was heated to 135° C. for 15 min. The reaction was concentrated and the residue purified by chromatography (silica, ethyl acetate/heptane) to yield 0.65 g (91%) of 1-((1R,2R)-2-Methyl-cyclohexyl)-2-thiophen-2-ylmethyl-1H-benzoimidazole-5-carboxylic acid.

$C_{20}H_{22}N_2O_2S$ (354.47), LCMS (method 7_1_1): Rt=1.16 min, m/z=355.25 $[M+H]^+$ (1R,2R)-2-Methyl-cyclohexylamine-hydrochloride and (1S,2S)-2-Methyl-cyclohexyl-amine-hydrochloride

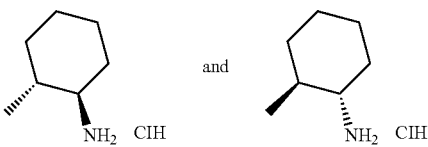

a) 7-(Toluene-4-sulfonyl)-7-aza-bicyclo[4.1.0]heptane

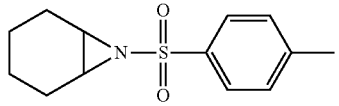 [SMILES: Cc1ccc(S(=O)(=O)N2C3CCCCC32)cc1]

To a solution of 200 g cyclohexene and 30.7 g iodine in 800 ml of anhydrous dioxane was added 611.7 g of chloramine T. The mixture was stirred at 80° C. for 10 h. After cooling to room temperature the mixture was poured into ice water and extracted with ethyl acetate twice. The combined organic phases were dried over sodium sulphate and concentrated and the residue was purified by chromatography (Silica, hexane/Ethyl acetate) to afford 180 g (29%) of 7-(Toluene-4-sulfonyl)-7-aza-bicyclo[4.1.0]heptane as a white solid.

¹H-NMR (400 MHz, CDCl₃): δ=7.78 (dd, 2H, J=1.6 Hz, J=1.6 Hz), 7.30 (dd, 2H, J=0.4 Hz, J=10 Hz), 2.94 (d, 2H, J=1.6 Hz), 2.38 (t, 3H, J=4.6 Hz), 1.77 (t, 4H, J=4.6 Hz), 1.38 (m, 2H), 1.32 (m, 2H)

b) 4-Methyl-N-((1S,2S)-2-methyl-cyclohexyl)-benzenesulfonamide and 4-Methyl-N-((1R,2R)-2-methyl-cyclohexyl)-benzenesulfonamide

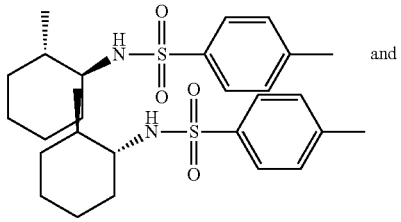

To the solution of 180 g of) 7-(Toluene-4-sulfonyl)-7-azabicyclo[4.1.0]heptane and 18 g of Copper(II)acetyl acetonate in 1500 ml of dry THF was added 86 ml of a 10 M solution of methyllithium dropwise over 30 min. The mixture was stirred under nitrogen atmosphere for 8 h. It was then washed with water and extracted with ethyl acetate twice. The combined organic layers were concentrated. The resulting residue was purified by chromatography (silica, hexan/ethyl acetate) to afford 120 g (62%) of 4-Methyl-N-(trans-2-methyl-cyclohexyl)-benzenesulfonamide ¹H-NMR (400 MHz, CDCl₃): δ=7.78 (dd, 2H, J=2 Hz, J=1.6 Hz), 7.27 (t, 2H, J=4 Hz), 4.76 (d, 1H, J=8.4 Hz), 2.69 (q, 1H, J=4.2 Hz), 2.39 (s, 3H), 1.57 (m, 4H), 1.20 (m, 4H), 1.08 (m, 1H); 0.79 (t, 3H, J=3.2 Hz)

The two diastereomers of 4-methyl-N-(trans-2-methyl-cyclohexyl)-benzenesulfonamide were separated using a Berger Multigram SFC instrument from MEttler Toledo on a ChiralPak AD, 20 µm column (300×50 mm) from Daicel Chemical Industries with a mobile phase of supercritical carbon dioxide and IPA 70/30 at 200 ml/min at 38° C. Retention time of the first diastereomer was 7.5 min with >99% ee, retention time of the second diastereomer was 9.2 min with 98.2% ee.

c) ((1S,2S)-2-Methyl-cyclohexyl)-carbamic acid tert-butyl ester and ((1R,2R)-2-Methyl-cyclohexyl)-carbamic acid tert-butyl ester

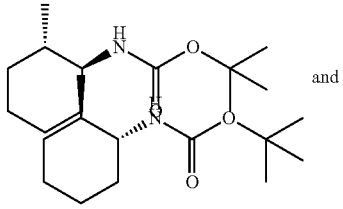

To a solution of 2.0 g of the first diastereomer of 4-methyl-N-(trans-2-methyl-cyclohexyl)-benzenesulfonamide (rt=7.5 min) in 20 ml dra THF and 20 of liquid ammonia was added 1 g of sodium at −78° C. under nitrogen atmosphere and the solution was stirred for 5 h. Then 20 ml of ethanol and 20 ml of water were added and ammonia was evaporated. The solution was cooled to 0° C. and 2.5 g of Boc₂O was added. The resulting solution was stirred overnight, the solvent was removed and the residue was dissolved in ethyl acetate, washed with water and brine and dried over magnesium sulphate. The solvent was evaporated and the resulting residue was purified by chromatography (silica, ethyl acetate/hexane) to obtain 1.2 g (75%) of the first diastereomer of trans-2-Methyl-cyclohexyl)-carbamic acid tert-butyl ester.

¹H-NMR (400 MHz, CDCl₃): δ=4.25 (s, 1H), 3.05 (s, 1H), 1.91 (m, 2H), 1.67 (m, 2H), 1.57 (m, 1H), 1.48 (s, 9H), 1.28 (m, 2H), 1.18 (m, 2H), 1.11 (d, 3H, J=6 Hz).

The second diastereomer of trans-2-Methyl-cyclohexyl)-carbamic acid tert-butyl ester was obtained in analogous manner starting from the second diastereomer of 4-methyl-N-(trans-2-methyl-cyclohexyl)-benzenesulfonamide (rt=9.2 min).

¹H-NMR (400 MHz, CDCl₃): δ=4.25 (s, 1H), 3.05 (s, 1H), 1.91 (m, 2H), 1.67 (m, 2H), 1.57 (m, 1H), 1.48 (s, 9H), 1.28 (m, 2H), 1.18 (m, 2H), 1.11 (d, 3H, J=6 Hz).

d) (1R,2R)-2-Methyl-cyclohexylamine-hydrochloride and (1S,2S)-2-Methyl-cyclohexylamine-hydrochloride

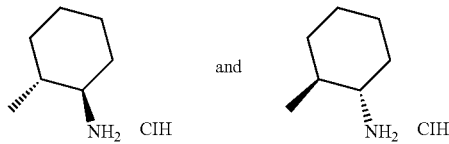

To 20 g of the first diastereomer of trans-2-Methyl-cyclohexyl)-carbamic acid tert-butyl ester was added 150 ml of hydrochloric acid (2M in diethyl ether) and the mixture was stirred for 30 min at rt. Then the mixture was filtered and the solid was washed with diethyl ether. 13.6 g (96%) of the first diastereomer of trans-Methyl-cyclohexylamine-hydrochloride were obtained.

¹H-NMR (400 MHz, CD₃OD): δ=2.72 (d, 1H, J=3.2 Hz), 2.03 (q, 1H, J=1.6 Hz), 1.81 (m, 2H), 1.72 (m, 1H), 1.60 (m, 1H), 1.38 (m, 4H), 1.31 (m, 1H), 1.28 (d, 2H, J=3.2 Hz).

The optical rotation for this first diastereomer of trans-2-Methyl-cyclohexylamine-hydrochloride was determined at rt as $[\alpha]_D = -24.66 \pm 0.18°$ (c=4, MeOH). Therefore an (1R,2R)-configuration was assigned to this first diastereomer based on the comparison of the optical rotation described for (1S,2S)-2-Methyl-cyclohexylamine-hydrochloride, which was synthesized by H. C. Brown using a chiral-pool derived borane and for which an optical rotation at 21° C. of $[\alpha]_D = +26.63°$ (c=4, MeOH) was reported (J. Am. Chem. Soc. 1986, 108, 21, 6761).

To 21 g of the second diastereomer of trans-2-Methyl-cyclohexyl)-carbamic acid tert-butyl ester was added 150 ml of hydrochloric acid (2M in diethyl ether) and the mixture was stirred for 30 min at rt. Then the mixture was filtered and the solid was washed with diethyl ether. 14.2 g (97%) of the second diastereomer of trans-Methyl-cyclohexylamine-hydrochloride were obtained.

¹H-NMR (400 MHz, CD₃OD): δ=2.72 (d, 1H, J=3.2 Hz), 2.03 (q, 1H, J=1.6 Hz), 1.81 (m, 2H), 1.72 (m, 1H), 1.60 (m, 1H), 1.38 (m, 4H), 1.31 (m, 1H), 1.28 (d, 2H, J=3.2 Hz).

The optical rotation for this second diastereomer of trans-2-Methyl-cyclohexylamine-hydrochloride was determined at it as $[\alpha]_D = +25.15 \pm 0.12°$ (c=4, MeOH). Therefore an (1S, 2S)-configuration was assigned to this second diastereomer based on the comparison of the optical rotation described for (1S,2S)-2-Methyl-cyclohexylamine-hydrochloride, which was synthesized by H. C. Brown using a chiral-pool derived borane and for which an optical rotation at 21° C. of $[\alpha]_D$= +26.63° (c=4, MeOH) was reported (*J. Am. Chem. Soc.* 1986, 108, 21, 6761).

1-((1R,2R)-2-Methyl-cyclohexyl)-2-thiazol-5-ylm-ethyl-1H-benzoimidazole-5-carboxylic acid

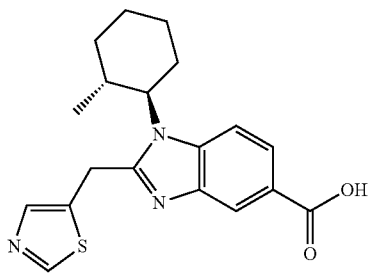 [SMILES: C[C@@H]1CCCC[C@H]1n1c(Cc2cncs2)nc2cc(C(=O)O)ccc21]

a) 4-((1R,2R)-2-Methyl-cyclohexylamino)-3-nitro-benzoic acid methyl ester

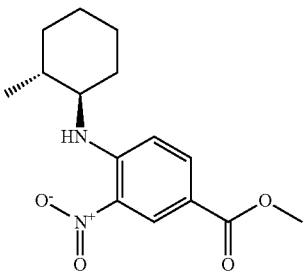

To a solution of 6.47 g of 4-fluoro-3-nitro-benzoic acid methyl ester in 35 ml of abs. DMF was added 13.47 g of potassium carbonate, followed by 4.96 g of (1R,2R)-2-Methyl-cyclohexylamine-hydrochloride. After 1.5 h at 60° C., the mixture was poured into water, the pH was adjusted to 5-6 by the addition of 2 M aqueous hydrochloric acid, and the reaction mixture was extracted with ethyl acetate three times. The combined organic phases were washed with water, dried over sodium sulphate and concentrated to yield 9.28 g (98%) of 4-((1R,2R)-2-Methyl-cyclohexylamino)-3-nitro-benzoic acid methyl ester.

$C_{15}H_{20}N_2O_4$ (292.34), LCMS (method 8_1_1): Rt=1.11 min, m/z=293.15 [M+H]$^+$ b) 3-Amino-4-((1R,2R)-2-methyl-cyclohexylamino)-benzoic acid methyl ester

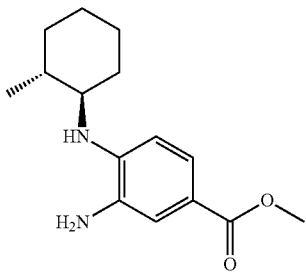

9.27 g 4-((1R,2R)-2-Methyl-cyclohexylamino)-3-nitro-benzoic acid methyl ester were dissolved in 100 ml ethanol, 0.20 g of palladium on carbon (10%) were added and the mixture was hydrogenated at 5 bar for 3 h. The catalyst was removed by filtration over celite, the filtrate was concentrated to obtain 8.20 g (99%) of 3-Amino-4-((1R,2R)-2-methyl-cyclohexylamino)-benzoic acid methyl ester. $C_{15}H_{22}N_2O_2$ (262.35), LCMS (method 8_1_1): Rt=0.77 min, m/z=263.15 [M+H]$^+$ c) 4-((1R,2R)-2-Methyl-cyclohexylamino)-3-(2-thiazol-5-yl-acetylamino)-benzoic acid methyl ester

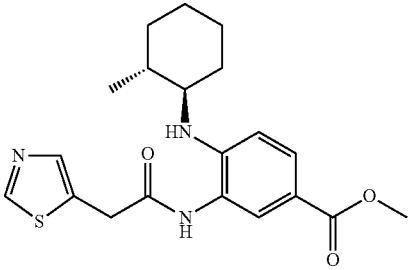 [SMILES: COC(=O)c1ccc(N[C@@H]2CCCC[C@H]2C)c(NC(=O)Cc2cncs2)c1]

To a solution of 0.49 g of thiazol-5-yl-acetic acid in 10 ml of dry DMF 0.27 g of HOAT, 0.79 g of EDC and 1 ml of DIPEA were added at 0° C. After 30 min 0.9 g of 3-Amino-4-((1R,2R)-2-methyl-cyclohexylamino)-benzoic acid methyl ester were added, followed by the addition of 1 ml of DIPEA and the reaction was stirred at it for 48 h. The reaction was then poured into water, brought to pH3 by the addition of 2 M aqueous hydrochloric acid and extracted with ethyl acetate three times. The combined organic phases were washed with saturated aqueous sodium bicarbonate solution and brine, dried over magnesium sulphate and concentrated to obtain 1.25 g (94%) of 4-((1R,2R)-2-Methyl-cyclohexylamino)-3-(2-thiazol-5-yl-acetylamino)-benzoic acid methyl ester, which was used without further purification.

$C_{20}H_{25}N_3O_3S$ (387.50), L_CMS (method 8_1_1): Rt=0.92 min, m/z=388.10 [M+H]$^+$ d) 1-((1R,2R)-2-Methyl-cyclohexyl)-2-thiazol-5-ylmethyl-1H-benzoimidazole-5-carboxylic acid methyl ester

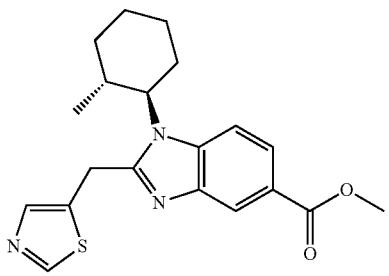 [SMILES: COC(=O)c1ccc2c(c1)nc(Cc1cncs1)n2[C@@H]1CCCC[C@H]1C]

To 1.26 g 4-((1R,2R)-2-Methyl-cyclohexylamino)-3-(2-thiazol-5-yl-acetylamino)-benzoic acid methyl ester in 10 ml dioxane were added 12 ml of 4M hydrochloric acid in dioxane and the mixture was heated to reflux for 2 h. The reaction was concentrated and the residue was taken up in ethyl acetate and washed with saturated aqueous sodium bicarbonate solution and brine. The organic layers were dried over sodium sulphate and concentrated. The resulting residue was purified by HPLC to yield 0.37 g (31%) of 1-((1R,2R)-2-Methyl-cyclohexyl)-2-thiazol-5-ylmethyl-1H-benzoimidazole-5-carboxylic acid methyl ester.

e) 1-((1R,2R)-2-Methyl-cyclohexyl)-2-thiazol-5-ylmethyl-1H-benzoimidazole-5-carboxylic acid

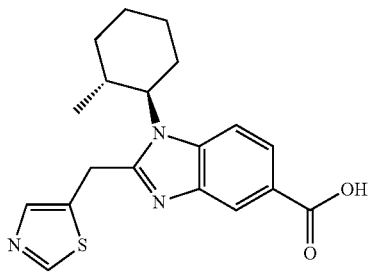 [SMILES: C[C@@H]1CCCC[C@H]1n1c(Cc2cncs2)nc2cc(C(=O)O)ccc21]

0.35 g 4-((1R,2R)-2-Methyl-cyclohexylamino)-3-(2-thiazol-5-yl-acetylamino)-benzoic acid methyl ester was dissolved in 6 ml of THF and 3 ml of methanol and 7 ml of 2 M aqueous sodium hydroxide solution were added at rt for 4 h. The reaction was concentrated and the pH was adjusted to 5 by addition of 2 M aqueous hydrochloric acid, and the mixture was extracted with ethyl acetate twice. The combined organic layers were dried over sodium sulphate and concentrated to afford 0.32 g (95%) of 1-((1R,2R)-2-Methyl-cyclohexyl)-2-thiazol-5-ylmethyl-1H-benzoimidazole-5-carboxylic acid.

$C_{19}H_{21}N_3O_2S$ (355.46), LCMS (method 7_1_1): Rt=0.65 min, m/z=356.10 [M+H]$^+$ 1-((1R,2R)-2-Methyl-cyclohexyl)-2-thiophen-2-ylmethyl-1H-benzoimidazole-5-carboxylic acid

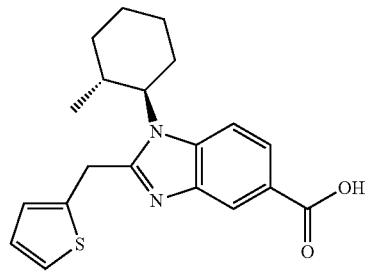 [SMILES: C[C@@H]1CCCC[C@H]1n1c(Cc2cccs2)nc2cc(C(=O)O)ccc21]

a) 4-((1R,2R)-2-Methyl-cyclohexylamino)-3-(2-thiophen-2-yl-acetylamino)-benzoic acid methyl ester

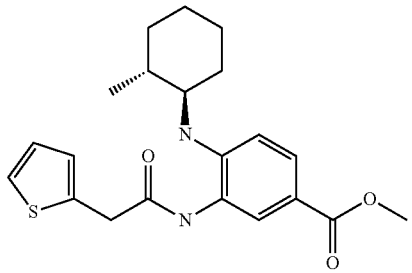 [SMILES: COC(=O)c1ccc(N[C@@H]2CCCC[C@H]2C)c(NC(=O)Cc2cccs2)c1]

To a solution of 4.46 g of 2-thienyl-acetic acid in 80 ml of dry DMF 1.94 g of HOAT, 6.56 g of EDC and 9 ml of DIPEA were added at 0° C. After 30 min 7.48 g of 3-Amino-4-((1R,2R)-2-methyl-cyclohexylamino)-benzoic acid methyl ester were added, followed by the addition of 9 ml of DIPEA and the reaction was stirred at rt for 16 h. The reaction was then poured into water, brought to pH3 by the addition of 2 M aqueous hydrochloric acid and extracted with ethyl acetate three times. The combined organic phases were washed with saturated aqueous sodium bicarbonate solution and brine, dried over magnesium sulphate and concentrated to obtain 9.52 g (86%) of 4-((1R,2R)-2-Methyl-cyclohexylamino)-3-(2-thiophen-2-yl-acetylamino)-benzoic acid methyl ester, which was used without further purification.

$C_{16}H_{26}N_2O_3S$ (386.52), LCMS (method 8_1_1): Rt=1.05 min, m/z=387.15 [M+H]$^+$ b) 1-((1R,2R)-2-Methyl-cyclohexyl)-2-thiophen-2-ylmethyl-1H-benzoimidazole-5-carboxylic acid

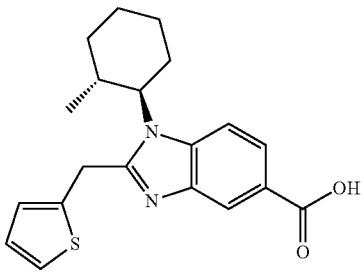 [SMILES: C[C@@H]1CCCC[C@H]1n1c(Cc2cccs2)nc2cc(C(=O)O)ccc21]

To 8.32 g 4-((1R,2R)-2-Methyl-cyclohexylamino)-3-(2-thiophen-2-yl-acetylamino)-benzoic acid methyl ester were added 40 ml of 4M hydrochloric acid in dioxane and the mixture was heated in four portions in a microwave reactor to 130° C. for 20 min. 2 ml of water were added to each vial and the reactions were heated to 130° C. for 40 min. The reactions were then combined and concentrated and the pH was adjusted to 6 by addition of saturated aqueous sodium bicarbonate. The resulting mixture was extracted with ethyl acetate twice. The combined organic layers were dried over sodium sulphate and concentrated. The product precipitated upon treatment with diisopropylether and 5.65 g (76%) of 1-((1R,2R)-2-Methyl-cyclohexyl)-2-thiophen-2-ylmethyl-1H-benzoimidazole-5-carboxylic acid were obtained.

$C_{20}H_{22}N_2O_2S$ (354.47), LCMS (method 8_1_1): Rt=0.75 min, m/z=355.15 [M+H]$^+$ 1-((1S,2S)-2-Methyl-cyclohexyl)-2-thiophen-2-ylmethyl-1H-benzoimidazole-5-carboxylic acid

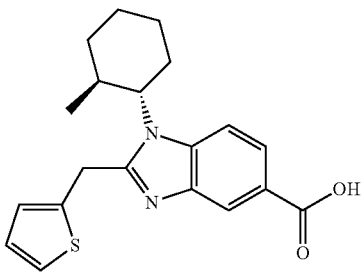 [SMILES: C[C@H]1CCCC[C@@H]1n1c(Cc2cccs2)nc2cc(C(=O)O)ccc21]

1-((1S,2S)-2-Methyl-cyclohexyl)-2-thiophen-2-ylmethyl-1H-benzoimidazole-5-carboxylic acid was prepared in analogy to the synthesis of 1-((1R,2R)-2-Methyl-cyclohexyl)-2-thiophen-2-ylmethyl-1H-benzoimidazole-5-carboxylic acid via 3-Amino-4-((1S,2S)-2-methyl-cyclohexylamino)-benzoic acid methyl ester and starting from (1S,2S)-2-Methyl-cyclohexylamine-hydrochloride.

$C_{20}H_{22}N_2O_2S$ (354.47), LCMS (method 8_1_1): Rt=0.75 min, m/z=355.15 $[M+H]^+$ 2-Furan-2-ylmethyl-1-(2-methyl-cyclohexyl)-1H-benzoimidazole-5-carboxylic acid

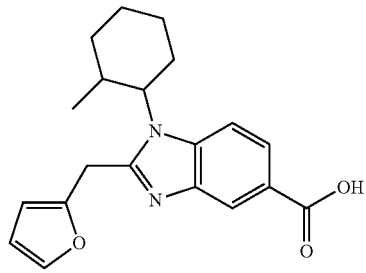

a) 3-(2-Furan-2-yl-acetylamino)-4-(2-methyl-cyclohexylamino)-benzoic acid methyl ester

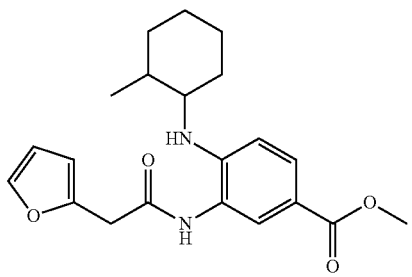 [SMILES: COC(=O)c1ccc(NC2CCCCC2C)c(NC(=O)Cc2ccco2)c1]

To a solution of 1.26 g of 2-furyl-acetic acid in 15 ml of dry DMF 1.50 g of HOAT, 2.11 g of EDC and 8 ml of DIPEA were added at 0° C. After 30 min 1.31 g of 3-Amino-4-(2-methyl-cyclohexylamino)-benzoic acid methyl ester were added, and the reaction was stirred at rt for 16 h. The reaction was then poured into water and extracted with ethyl acetate three times. The combined organic phases were washed with saturated aqueous sodium bicarbonate solution and brine, dried over magnesium sulphate and concentrated to obtain 1.85 g (100%) of 3-(2-Furan-2-yl-acetylamino)-4-(2-methyl-cyclohexylamino)-benzoic acid methyl ester, which was used without further purification.

$C_{21}H_{26}N_2O_4$ (370.45), LCMS (method 7_1_1): Rt=1.61 min, m/z=371.15 $[M+H]^+$ b) 2-Furan-2-ylmethyl-1-(2-methyl-cyclohexyl)-1H-benzoimidazole-5-carboxylic acid methyl ester

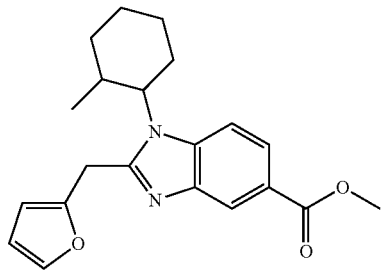 [SMILES: COC(=O)c1ccc2c(c1)nc(Cc1ccco1)n2C1CCCCC1C]

1.48 g 3-(2-Furan-2-yl-acetylamino)-4-(2-methyl-cyclohexylamino)-benzoic acid methyl ester with 15 ml of 4M hydrochloric acid in dioxane were heated in a microwave reactor to 130° C. for 15 min. Water was added to the reaction mixture and the pH was adjusted to 7 by the addition of saturated sodium bicarbonate solution. The phases were separated, and the aqueous layer was extracted with ethyl acetate twice. The combined organic layers were dried over sodium sulphate, concentrated and 1.31 g (93%) of 2-Furan-2-ylmethyl-1-(2-methyl-cyclohexyl)-1H-benzoimidazole-5-carboxylic acid methyl ester were obtained.

$C_{21}H_{24}N_2O_3$ (352.43), LCMS (method 7_1_1): Rt=1.29 min, m/z=353.15 $[M+H]^+$ c) 2-Furan-2-ylmethyl-1-(2-methyl-cyclohexyl)-1H-benzoimidazole-5-carboxylic acid

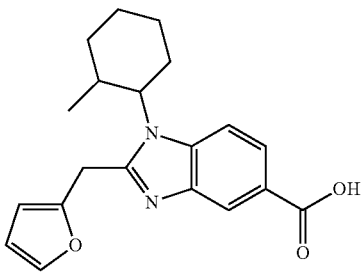

To 1.30 g of 2-Furan-2-ylmethyl-1-(2-methyl-cyclohexyl)-1H-benzoimidazole-5-carboxylic acid methyl ester in 15 ml of methanol were added 6 ml of 2 M aqueous sodium hydroxide solution. The reaction stirred at it for 16 h. The reaction mixture was adjusted to pH 5 by the addition of 2M aqueous hydrochloric acid and was extracted with ethyl acetate three times. The combined organic phases were dried over sodium sulphate and concentrated in vacuo. The residue was precipitated using heptane to yield 0.68 g (54%) of 2-Furan-2-ylmethyl-1-(2-methyl-cyclohexyl)-1H-benzoimidazole-5-carboxylic acid.

$C_{20}H_{22}N_2O_3$ (338.41), LCMS (method 7_1_1): Rt=1.13 min, m/z=339.15 $[M+H]^+$ 2-Thiophen-2-ylmethyl-1-(2-trifluoromethyl-cyclohexyl)-1H-benzoimidazole-5-carboxylic acid

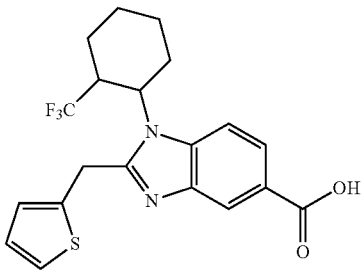

a) 3-Nitro-4-(2-trifluoromethyl-cyclohexylamino)-benzoic acid methyl ester

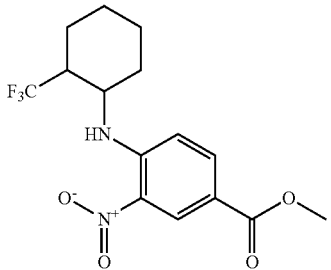 [SMILES: COC(=O)c1ccc(NC2CCCCC2C(F)(F)F)c([N+](=O)[O-])c1]

To a solution of 0.92 g of 4-fluoro-3-nitro-benzoic acid methyl ester in 15 ml of abs. DMF was added 0.84 ml of DIPEA, followed by 0.85 g of 2-(trifluoromethyl)cyclohexylamine. After 16 h at rt, the mixture was poured into water, the pH was adjusted to 4 by the addition of 1 M aqueous hydrochloric acid, and the reaction mixture was extracted with ethyl acetate three times. The combined organic phases were washed with water, dried over sodium sulphate and concentrated to yield 1.62 g (100%) of 3-Nitro-4-(2-trifluoromethyl-cyclohexylamino)-benzoic acid methyl ester.

$C_{15}H_{17}F_3N_2O_4$ (346.31), LCMS (method 7_1_1): Rt=1.75 min, m/z=347.10 [M+H]$^+$ b) 3-Amino-4-(2-trifluoromethyl-cyclohexylamino)-benzoic acid methyl ester

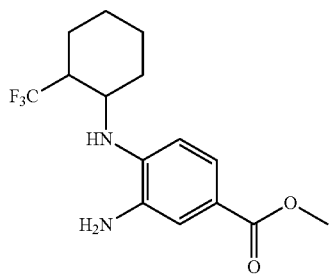 [SMILES: COC(=O)c1ccc(NC2CCCCC2C(F)(F)F)c(N)c1]

1.63 g 3-Nitro-4-(2-trifluoromethyl-cyclohexylamino)-benzoic acid methyl ester were dissolved in 25 ml methanol, 0.03 g of palladium on carbon (10%) were added and the mixture was hydrogenated at 5 bar for 16 h. The catalyst was removed by filtration over celite, the filtrate was concentrated to obtain 1.44 g (97%) of 3-Amino-4-(2-trifluoromethyl-cyclohexylamino)-benzoic acid methyl ester.

$C_{15}H_{19}F_3N_2O_2$ (316.33), LCMS (method 7_1_1): Rt=1.31 min, m/z=317.15 [M+H]$^+$ c) 3-(2-Thiophen-2-yl-acetylamino)-4-(2-trifluoromethyl-cyclohexylamino)-benzoic acid methyl ester

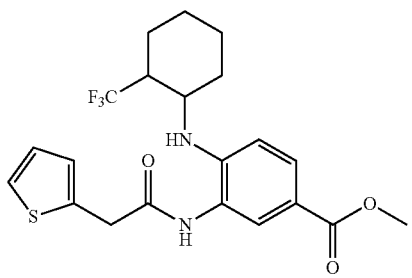 [SMILES: COC(=O)c1ccc(NC2CCCCC2C(F)(F)F)c(NC(=O)Cc2cccs2)c1]

To a solution of 0.71 g of thiophen-2-yl-acetic acid in 10 ml of dry DMF 0.68 g of HOAT, 1.22 g of EDC and 2.25 ml of DIPEA were added at 0° C. After 30 min 1.44 g of 3-Amino-4-(2-trifluoromethyl-cyclohexylamino)-benzoic acid methyl ester were added, and the reaction was stirred at rt for 16 h. The reaction was then poured into water and extracted with ethyl acetate three times. The combined organic phases were washed with saturated aqueous sodium bicarbonate solution and brine, dried over magnesium sulphate and concentrated to obtain 2.00 g (100%) of 3-(2-Thiophen-2-yl-acetylamino)-4-(2-trifluoromethyl-cyclohexylamino)-benzoic acid methyl ester, which was used without further purification.

$C_{21}H_{23}F_3N_2O_3S$ (440.49), LCMS (method 7_1_1): Rt=1.56 min, m/z=441.15 [M+H]$^+$ d) 2-Thiophen-2-ylmethyl-1-(2-trifluoromethyl-cyclohexyl)-1H-benzoimidazole-5-carboxylic acid

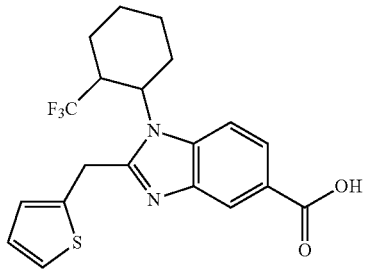

0.75 g 3-(2-Thiophen-2-yl-acetylamino)-4-(2-trifluoromethyl-cyclohexylamino)-benzoic acid methyl ester with 10 ml of 4M hydrochloric acid in dioxane were heated in a microwave reactor to 110° C. for 5 h. 3 ml water was added to the reaction mixture, which was reacted again to 110° C. for 2 h. The mixture was then concentrated in vacuo, the residue taken up in ethyl acetate and water, and the pH of the aqueous phase was brought to 4. The phases were separated, and the aqueous layer was extracted with ethyl acetate twice. The combined organic layers were dried over magnesium sulphate, concentrated and 0.75 g (100%) of 2-Thiophen-2-ylmethyl-1-(2-trifluoromethyl-cyclohexyl)-1H-benzoimidazole-5-carboxylic acid were obtained.

$C_{20}H_{19}F_3N_2O_2S$ (408.45), LCMS (method 7_1_1): Rt=1.26 min, m/z=409.10 [M+H]$^+$ 1-(2-Methyl-cyclopentyl)-2-thiophen-2-ylmethyl-1H-benzoimidazole-5-carboxylic acid

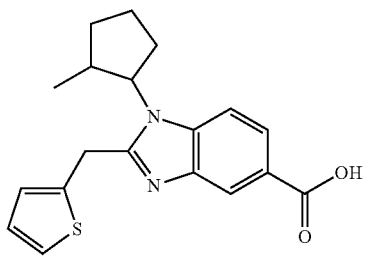 [SMILES: CC1CCCC1n1c(Cc2cccs2)nc2cc(C(=O)O)ccc21]

a) 4-(2-Methyl-cyclopentylamino)-3-nitro-benzoic acid methyl ester

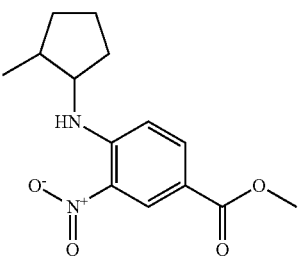

To a solution of 9.32 g of 4-fluoro-3-nitro-benzoic acid methyl ester in 30 ml of abs. DMF was added 16.47 g of potassium carbonate, followed by 5.00 g of 2-methyl-cyclopentylamine. After 16 h at rt, the mixture was poured into water, the pH was adjusted to 5 by the addition of 2 M aqueous hydrochloric acid, and the reaction mixture was extracted with ethyl acetate three times. The combined organic phases were washed with water, dried over sodium sulphate and concentrated to yield 12.74 g (100%) of 4-(2-Methyl-cyclopentylamino)-3-nitro-benzoic acid methyl ester.

$C_{14}H_{18}N_2O_4$ (278.31), LCMS (method 8_1_1): Rt=1.10 min, m/z=279.05 [M+H]+ b) 3-Amino-4-(2-methyl-cyclopentylamino)-benzoic acid methyl ester

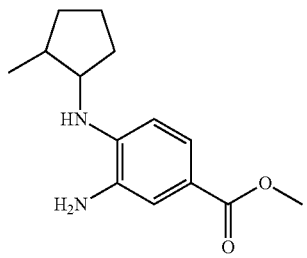

12.74 g 4-(2-Methyl-cyclopentylamino)-3-nitro-benzoic acid methyl ester were dissolved in 80 ml methanol, 0.39 g of palladium on carbon (10%) were added and the mixture was hydrogenated at 5 bar for 16 h. The catalyst was removed by filtration over celite, the filtrate was concentrated and the residue purified by chromatography (silica, ethyl acetate/hexane) to obtain 8.17 g (72%) of 3-Amino-4-(2-methyl-cyclopentylamino)-benzoic acid methyl ester.

$C_{14}H_2O_2O_2$ (248.32), LCMS (method 5_1_1): Rt=4.25 min, m/z=249.29 [M+H]+ c) 4-(2-Methyl-cyclopentylamino)-3-(2-thiophen-2-yl-acetylamino)-benzoic acid methyl ester

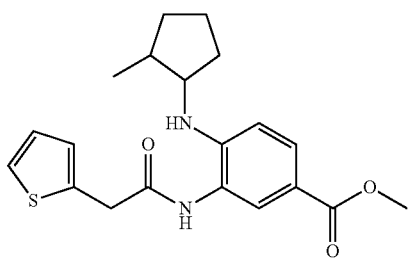 [SMILES: COC(=O)c1ccc(NC2CCCC2C)c(NC(=O)Cc2cccs2)c1]

To a solution of 3.44 g of thiophen-2-yl-acetic acid in 40 ml of dry DMF 3.62 g of HOAT, 6.48 g of EDC and 12 ml of DIPEA were added at 0° C. After 30 min 6.00 g of 3-Amino-4-(2-methyl-cyclopentylamino)-benzoic acid methyl ester were added, and the reaction was stirred at rt for 16 h. The reaction was then poured into water and the pH was adjusted to 3 by the addition of 2 m aqueous hydrochloric acid. Ethyl acetate was added and the layers were separated. The aqueous layer was extracted with ethyl acetate three times. The combined organic phases were washed with saturated aqueous sodium bicarbonate solution and brine, dried over magnesium sulphate and concentrated to obtain 9.03 g (100%) of 4-(2-Methyl-cyclopentylamino)-3-(2-thiophen-2-yl-acetylamino)-benzoic acid methyl ester, which was used without further purification.

$C_{20}H_{24}N_2O_3S$ (372.49), LCMS (method 8_1_1): Rt=0.97 min, m/z=373.15 [M+H]+ d) 1-(2-Methyl-cyclopentyl)-2-thiophen-2-ylmethyl-1H-benzoimidazole-5-carboxylic acid methyl ester

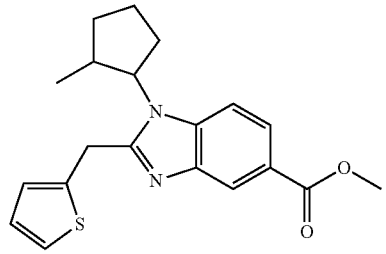 [SMILES: COC(=O)c1ccc2c(c1)nc(Cc1cccs1)n2C1CCCC1C]

0.88 g 4-(2-Methyl-cyclopentylamino)-3-(2-thiophen-2-yl-acetylamino)-benzoic acid methyl ester were reacted with 10 ml of 4M hydrochloric acid in dioxane at 110° C. in a microwave reactor for 30 min. The reaction was concentrated and 0.98 g (99%) of 1-(2-Methyl-cyclopentyl)-2-thiophen-2-ylmethyl-1H-benzoimidazole-5-carboxylic acid were obtained.

$C_{20}H_{22}N_2O_2S$ (354.47), LCMS (method 8_1_1): Rt=0.82 min, m/z=335.15 [M+H]+ e) 1-(2-Methyl-cyclopentyl)-2-thiophen-2-ylmethyl-1H-benzoimidazole-5-carboxylic acid

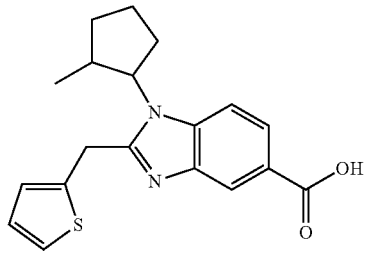 [SMILES: CC1CCCC1n1c(Cc2cccs2)nc2cc(C(=O)O)ccc21]

To 9.85 g of 21-(2-Methyl-cyclopentyl)-2-thiophen-2-ylmethyl-1H-benzoimidazole-5-carboxylic acid methyl ester in 75 ml of methanol and 40 ml of THF were added 50 ml of 2 M aqueous sodium hydroxide solution. The reaction was stirred at it for 16 h. The reaction mixture was concentrated in vacuo to a fifth of its volume and the pH was adjusted to 4 by the addition of 2M aqueous hydrochloric acid. The precipitated product was collected by filtration, washed with water and dried in vacuo. 7.28 g (85%) of 1-(2-Methyl-cyclopentyl)-2-thiophen-2-ylmethyl-1H-benzoimidazole-5-carboxylic acid were obtained.

$C_{19}H_{20}N_2O_2S$ (340.45), LCMS (method 8_1_1): Rt=0.71 min, m/z=341.15 [M+H]+

1-(2-Ethyl-cyclohexyl)-2-thiophen-2-ylmethyl-1H-benzoimidazole-5-carboxylic acid

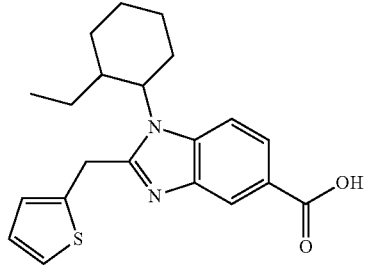 [SMILES: CCC1CCCCC1n1c(Cc2cccs2)nc2cc(C(=O)O)ccc21]

a) 4-(2-Ethyl-cyclohexylamino)-3-nitro-benzoic acid methyl ester

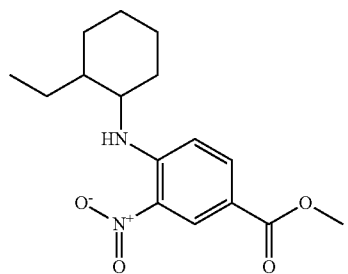 [SMILES: CCC1CCCCC1Nc1ccc(C(=O)OC)cc1[N+](=O)[O-]]

To a solution of 0.48 g of 4-fluoro-3-nitro-benzoic acid methyl ester in 1.5 ml of abs. DMF was added 1.00 g of potassium carbonate, followed by 0.31 g of 2-ethylcyclohexylamine. After 16 h at rt, the mixture was poured into water, the pH was adjusted to 4 by the addition of 2 M aqueous hydrochloric acid, and the reaction mixture was extracted with ethyl acetate three times. The combined organic phases were washed with water, dried over sodium sulphate and concentrated to yield 0.44 g (60%) of 4-(2-Ethyl-cyclohexylamino)-3-nitro-benzoic acid methyl ester.

$C_{16}H_{22}N_2O_4$ (306.36), LCMS (method 8_1_1): Rt=1.22 min, m/z=307.15 $[M+H]^+$ b) 3-Amino-4-(2-ethyl-cyclohexylamino)-benzoic acid methyl ester

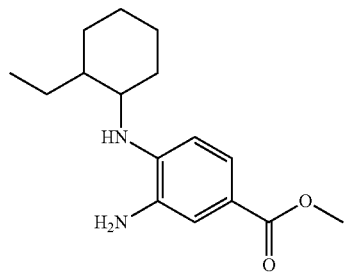 [SMILES: CCC1CCCCC1Nc1ccc(C(=O)OC)cc1N]

0.45 g 4-(2-Ethyl-cyclohexylamino)-3-nitro-benzoic acid methyl ester were dissolved in 60 ml methanol, 0.02 g of palladium on carbon (10%) were added and the mixture was hydrogenated at 5 bar for 4 h. The catalyst was removed by filtration over celite, the filtrate was concentrated to obtain 0.40 g (100%) of 3-Amino-4-(2-ethyl-cyclohexylamino)-benzoic acid methyl ester.

$C_{16}H_{24}N_2O_2$ (276.38), LCMS (method 8_1_1): Rt=0.84 min, m/z=277.15 $[M+H]^+$ c) 4-(2-Ethyl-cyclohexylamino)-3-(2-thiophen-2-yl-acetylamino)-benzoic acid methyl ester

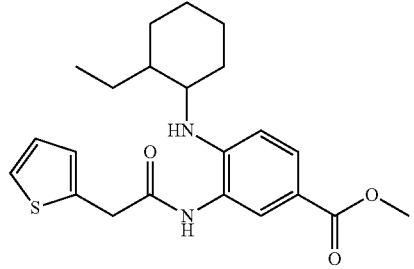 [SMILES: CCC1CCCCC1Nc1ccc(C(=O)OC)cc1NC(=O)Cc1cccs1]

To a solution of 0.24 g of thiophen-2-yl-acetic acid in 40 ml of dry DMF 0.11 g of HOAT, 0.36 g of EDC and 0.5 ml of DIPEA were added at 0° C. After 30 min 0.41 g of 3-Amino-4-(2-ethyl-cyclohexylamino)-benzoic acid methyl ester were added, followed by the addition of 0.5 ml of DIPEA and the reaction was stirred at rt for 48 h. The reaction was then poured into water and extracted with ethyl acetate three times. The combined organic phases were washed with saturated aqueous sodium bicarbonate solution and brine, dried over magnesium sulphate and concentrated to obtain 0.60 g (97%) of 4-(2-Ethyl-cyclohexylamino)-3-(2-thiophen-2-yl-acetylamino)-benzoic acid methyl ester, which was used without further purification.

$C_{22}H_{28}N_{12}O_3S$ (400.54), LCMS (method 8_1_1): Rt=1.09 min, m/z=401.20 $[M+H]^+$ d) 1-(2-Ethyl-cyclohexyl)-2-thiophen-2-ylmethyl-1H-benzoimidazole-5-carboxylic acid

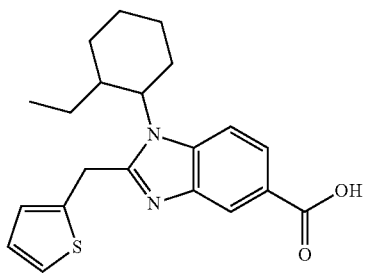

0.59 g 4-(2-Ethyl-cyclohexylamino)-3-(2-thiophen-2-yl-acetylamino)-benzoic acid methyl ester were reacted with 10 ml of 4M hydrochloric acid in dioxane at 130° C. in a microwave reactor for 20 min. 1 ml water was added and the mixture was heated to 130° C. for 30 min. The reaction was concentrated and the residue purified by chromatography (silica, ethyl acetate/heptane) to yield 0.47 g (88%) of 1-(2-Ethyl-cyclohexyl)-2-thiophen-2-ylmethyl-1H-benzoimidazole-5-carboxylic acid.

$C_{21}H_{24}N_2O_2S$ (368.50), LCMS (method 8_1_1): Rt=0.79 min, m/z=369.15 $[M+H]^+$ Determination of Agonism on the Human Apelin Receptor by a Calcium Fluorescence Assay (FLIPR)

The assay is based on the detection of intracellular calcium changes detected by the selective, calcium-chelating dye Fluo-4 (Molecular Probes). A large fluorescence intensity increase is observed upon calcium association with Fluo-4. The dye is delivered to the cell interior using an acetoxymethylester form of Fluo-4, where the intracellular esterase activity results in the charged species being released and trapped within the cytoplasm of the cell. Hence, influx of calcium to this cytoplasmic pocket, via release from intracellular pools and the phospholipase C cascade can be detected. By co-expressing the human apelin receptor and a promiscuous $G_{iaq}$ protein, agonism of the apelin receptor couples to phospholipase-C resulting in intracellular calcium mobilization.

The HEK293 cells were stably transfected with the human apelin receptor and the $G_{iaq}$ protein. Cells were selected and maintained in a log phase of growth at 37° and 5% CO2 in the Iscove's minimal essential medium, 10% fetal calf serum, 1× Penicillin-Streptomycin, 400 µg/mL G418. One day prior the assay, cells were passaged by accutase and plated at a density of 50,000 cells/well onto a 96-well plates with black border but clear bottom (Costar, cat#3904) in a final volume of 200 µl growth medium.

In order to load the cells the next day with the calcium-sensitive dye, growth medium was carefully replaced by dye solution (100 μl/well) containing Fluo-4 (4 μM) in basic measurement buffer (135 mM NaCl, 5 mM KCl, 1 mM magnesium sulphate, 5 mM glucose, 20 mM Hepes, 2.5 mM probenecid; adjusted to pH 7.4). Cells were incubated for 1 h at 37° C., and then washed 3× with buffer containing no dye. The washer was programmed to leave a remaining volume of 150 μl after the third wash in the plate.

During the dye-loading of the cells, a serial compound dilution was performed in a separate 96-well plate with overall 4× increased concentrations. Small aliquots of DMSO stock solutions of the compounds (10 mM in 100% DMSO were aliquoted into 150 μl buffer in the first rows of the 96-well plates, and then serially diluted by a factor of 1:3 transferring each time 30 μl to the next rows already containing 60 μl buffer. All compounds were tested in a least 7 concentrations, each condition was performed in triplicates. As comparator, we used freshly prepared apelin-13 solutions, for which also a concentration-response curve was determined at each measurement day. The compound plate was incubated for 10 min after the final dilutions steps at 37° C. before transferring the dye-loaded cell plate and the compound plate into a FLIPR Tetra reader (Molecular Devices). Measurement within this reader started by pipetting the agonist solution (50 μl) on the cell plate. Overall perform 60 reads were performed with an interval of 2 sec. The maximum of the fluorescence transient was used to calculate the agonistic response of the cells. In order to normalize this response, which may vary from plate to plate we set the maximum fluorescence achieved by 1 μM apelin-13 on this plate as 100%.

EC-50 values for apelin-13 and the apelin receptor compounds described in this patent were determined by standard algorithms using a specific software package. Compounds exhibit agonism in this Apelin receptor calcium fluorescence assay in a range of about 0.01 nM to 100000 nM.

APJ Agonism for Example Compounds:

| Example No. | EC50 [μM] |
| --- | --- |
| 1 | 0.359 |
| 2 | 20.07 |
| 3 | 1.199 |
| 4 | 16.77 |
| 5 | 9.873 |
| 6 | 3.818 |
| 7 | 44.331 |
| 8 | 0.107 |
| 9 | 0.585 |
| 10 | 1.699 |
| 11 | 0.065 |
| 12 | 0.818 |
| 13 | 0.535 |
| 14 | 1.344 |
| 15 | 0.254 |
| 16 | 0.117 |
| 17 | 0.935 |
| 18 | 0.15 |
| 19 | 5.03 |
| 20 | 1.828 |
| 21 | 0.443 |
| 22 | 0.08 |
| 23 | 0.106 |
| 24 | 0.219 |
| 25 | 4.753 |
| 26 | 5.301 |
| 27 | 1.86 |
| 28 | 18.52 |
| 29 | 5.658 |
| 30 | 2.199 |
| 31 | 4.11 |
| 32 | 4.569 |
| 33 | 3.209 |
| 34 | 0.489 |
| 35 | 0.291 |
| 36 | 1.262 |
| 37 | 0.886 |
| 38 | 0.115 |
| 39 | 1.14 |
| 40 | 0.915 |
| 41 | 2.428 |
| 42 | 1.103 |
| 43 | 14.49 |
| 44 | 0.258 |
| 45 | 0.552 |
| 46 | 0.112 |
| 47 | 2.585 |
| 48 | 4.187 |
| 49 | 7.066 |
| 50 | 0.205 |
| 51 | 0.211 |
| 52 | 12.33 |
| 53 | 0.048 |
| 54 | 0.115 |
| 55 | 0.196 |
| 56 | 0.157 |
| 57 | 0.475 |
| 58 | 0.172 |
| 59 | 0.576 |
| 60 | 0.046 |
| 61 | 0.075 |
| 62 | 0.193 |
| 63 | 0.343 |
| 64 | 0.176 |
| 65 | 0.056 |
| 66 | 0.087 |
| 67 | 0.079 |
| 68 | 0.018 |
| 69 | 0.339 |
| 70 | 0.179 |
| 71 | 0.073 |
| 72 | 0.047 |
| 73 | 0.065 |
| 74 | 0.14 |
| 75 | 0.066 |
| 76 | 0.062 |
| 77 | 0.053 |
| 78 | 0.101 |
| 79 | 0.08 |
| 80 | 1.671 |
| 81 | <0.041 |
| 82 | 23.3 |
| 83 | 18.24 |
| 84 | 2.951 |
| 85 | 7.797 |
| 86 | 0.088 |
| 87 | 0.882 |
| 88 | 0.754 |
| 89 | 9.331 |
| 90 | 0.472 |
| 91 | 0.137 |
| 92 | <0.041 |
| 93 | 0.291 |
| 94 | 0.781 |
| 95 | 0.095 |
| 96 | <0.041 |
| 97 | 38.959 |
| 98 | 2.189 |
| 99 | 0.046 |
| 100 | 5.842 |
| 101 | 0.106 |
| 102 | 0.247 |
| 103 | 10.99 |
| 104 | 0.479 |
| 105 | 5.466 |
| 106 | 0.048 |
| 107 | 0.047 |

| Example No. | EC50 [μM] |
|---|---|
| 108 | 1.061 |
| 109 | 3.863 |
| 110 | 2.029 |
| 111 | 0.579 |
| 112 | 12.77 |
| 113 | 21.71 |
| 114 | 0.185 |
| 115 | 34.593 |
| 116 | 6.713 |
| 117 | 0.419 |
| 118 | 0.222 |
| 119 | 33.117 |
| 120 | 24.09 |
| 121 | 0.074 |
| 122 | 4.378 |
| 123 | 1.879 |
| 124 | 9.35 |
| 125 | 0.078 |
| 126 | 3.933 |
| 127 | 15 |
| 128 | 10 |
| 129 | 2.675 |
| 130 | 0.293 |
| 131 | 0.185 |
| 132 | 0.7 |
| 133 | 2.35 |
| 134 | 7.15 |
| 135 | 3.8 |
| 136 | 2.7 |
| 137 | 9.5 |
| 138 | 2.93 |
| 139 | 0.285 |
| 140 | 3.8 |
| 141 | 23 |
| 142 | 12 |
| 143 | 2.45 |
| 144 | 23 |
| 145 | 18 |
| 146 | 0.328 |
| 147 | 4.55 |
| 148 | 15 |
| 149 | 27 |
| 150 | 2.8 |
| 151 | 0.89 |
| 152 | 3.95 |
| 153 | 0.35 |
| 154 | 0.27 |
| 155 | 0.5 |
| 156 | 0.21 |
| 157 | 10 |
| 158 | 0.515 |
| 159 | 15 |
| 160 | 0.82 |
| 161 | 2.3 |
| 162 | 1.105 |
| 163 | 0.051 |
| 164 | 6.345 |
| 165 | 1.01 |
| 166 | 3.043 |
| 167 | 7.548 |
| 168 | 4.533 |
| 169 | 6.654 |
| 170 | 10.11 |
| 171 | 0.748 |
| 172 | 4.888 |
| 173 | 6.703 |
| 174 | 0.301 |
| 175 | 0.501 |
| 176 | 8.906 |
| 177 | 2.425 |
| 178 | 17.45 |
| 179 | 25.17 |
| 180 | 6.165 |
| 181 | 6.949 |
| 182 | 10.99 |
| 183 | 26.35 |
| 184 | 2.902 |
| 185 | 14.12 |
| 186 | 4.673 |
| 187 | 29 |
| 188 | 4.52 |
| 189 | 12.17 |
| 190 | 6.283 |
| 191 | 6.295 |
| 192 | 14.02 |
| 193 | 6.218 |
| 194 | 0.96 |
| 195 | 15.17 |
| 196 | 0.922 |
| 197 | 1.039 |
| 198 | 8.88 |
| 199 | 0.71 |
| 200 | 8.184 |
| 201 | 0.334 |
| 202 | 14.42 |
| 203 | 24.71 |
| 204 | 1.99 |
| 205 | 1.751 |
| 206 | 2.297 |
| 207 | 0.554 |
| 208 | 1.16 |
| 209 | 0.254 |
| 210 | 10.24 |
| 211 | 0.705 |
| 212 | 9.294 |
| 213 | 29.94 |
| 214 | 0.926 |
| 215 | 1.449 |
| 216 | 1.729 |
| 217 | 2.21 |
| 218 | 2.013 |
| 219 | 0.274 |
| 220 | 2.863 |
| 221 | 1.828 |
| 222 | 3.986 |
| 223 | 6.959 |
| 224 | 0.3 |
| 225 | 0.775 |
| 226 | 4.874 |
| 227 | 0.287 |
| 228 | 8.497 |
| 229 | 1.942 |
| 230 | 0.288 |
| 231 | 0.525 |
| 232 | 2.918 |
| 233 | 0.394 |
| 234 | 0.344 |
| 235 | 1.302 |
| 236 | 3.868 |
| 237 | 2.48 |
| 238 | 6.554 |
| 239 | 5.585 |
| 240 | 0.614 |
| 241 | 0.257 |
| 242 | 5.932 |
| 243 | 0.771 |
| 244 | 4.283 |
| 245 | 0.291 |
| 246 | 6.841 |
| 247 | 7.216 |
| 248 | 1.798 |
| 249 | 0.407 |
| 250 | 0.52 |
| 251 | 2.559 |
| 252 | 6.99 |
| 253 | 0.242 |
| 254 | 0.233 |
| 255 | 6.669 |
| 256 | 5.918 |
| 257 | 0.425 |
| 258 | 1.334 |
| 259 | 6.648 |
| 260 | 0.17 |
| 261 | 0.269 |

| Example No. | EC50 [μM] |
|---|---|
| 262 | 4.555 |
| 263 | 4.301 |
| 264 | 3.338 |
| 265 | 8.658 |
| 266 | 2.717 |
| 267 | 0.383 |
| 268 | 0.552 |
| 269 | 18.51 |
| 270 | 10.8 |
| 271 | 3.255 |
| 272 | 2.768 |
| 273 | 0.212 |
| 274 | 12.56 |
| 275 | 0.242 |
| 276 | 0.105 |
| 277 | 2.099 |
| 278 | 0.405 |
| 279 | 2.269 |
| 280 | 0.219 |
| 281 | 1.215 |
| 282 | 0.43 |
| 283 | 4.496 |
| 284 | 0.252 |
| 285 | 0.295 |
| 286 | 1.097 |
| 287 | 0.408 |
| 288 | 0.512 |
| 289 | 0.341 |
| 290 | 0.506 |
| 291 | 0.408 |
| 292 | 1.216 |
| 293 | 2.644 |
| 294 | 0.722 |
| 295 | 1.828 |
| 296 | 1.032 |
| 297 | 0.39 |
| 298 | 1.26 |
| 299 | 0.776 |
| 300 | 0.732 |
| 301 | 2.461 |
| 302 | 0.386 |
| 303 | 0.214 |
| 304 | 0.461 |
| 305 | 0.319 |
| 306 | 1.26 |
| 307 | 1.826 |
| 308 | 0.672 |
| 309 | 0.482 |
| 310 | 0.162 |
| 311 | 21.23 |
| 312 | 2.963 |
| 313 | 1.888 |
| 314 | 0.474 |
| 315 | 2.453 |
| 316 | 22 |
| 317 | 13.97 |
| 318 | 2.861 |
| 319 | 1.524 |
| 320 | 0.386 |
| 321 | 1.525 |
| 322 | 0.244 |
| 323 | 6.745 |
| 324 | 16.76 |
| 325 | 4.407 |
| 326 | 16.35 |
| 327 | 0.111 |
| 328 | 1.271 |
| 329 | 0.362 |
| 330 | 2.475 |
| 331 | 0.267 |
| 332 | 0.692 |
| 333 | 27.31 |
| 334 | 0.412 |
| 335 | 0.384 |
| 336 | 1.262 |
| 337 | 0.331 |
| 338 | 1.593 |
| 339 | 0.444 |
| 340 | 0.185 |
| 341 | 0.918 |
| 342 | 0.999 |
| 343 | 0.419 |
| 344 | 1.687 |
| 345 | 1.666 |
| 346 | 1.315 |
| 347 | 0.809 |
| 348 | 2.663 |
| 349 | 3.037 |
| 350 | 29.14 |
| 351 | 9.291 |
| 352 | 2.981 |
| 353 | 0.787 |
| 354 | 0.998 |
| 355 | 1.521 |
| 356 | 4.26 |
| 357 | 0.389 |
| 358 | 2.57 |
| 359 | 2.135 |
| 360 | 21.24 |
| 361 | 24.97 |
| 362 | 27.06 |
| 363 | 1.715 |
| 364 | 13.55 |
| 365 | 2.752 |
| 366 | 16.5 |
| 367 | 1.662 |
| 368 | 1.881 |
| 369 | 2.212 |
| 370 | 2.853 |
| 371 | 3.574 |
| 372 | 13.23 |
| 373 | 1.838 |
| 374 | 2.179 |
| 375 | 2.88 |
| 376 | 1.83 |
| 377 | 1.145 |
| 378 | 2.445 |
| 379 | 1.803 |
| 380 | 0.586 |
| 381 | 0.97 |
| 382 | 3.564 |
| 383 | 2.121 |
| 384 | 1.626 |
| 385 | 2.506 |
| 386 | 2.226 |
| 387 | 1.141 |
| 388 | 1.593 |
| 389 | 17.08 |
| 390 | 10.91 |
| 391 | 2.179 |
| 392 | 1.377 |
| 393 | 1.358 |
| 394 | 2.329 |
| 395 | 1.758 |
| 396 | 4.039 |
| 397 | 8.739 |
| 398 | 5.458 |
| 399 | 0.099 |
| 400 | 0.07 |
| 401 | 0.6 |
| 402 | 0.777 |
| 403 | 1.606 |
| 404 | 0.788 |
| 405 | 0.842 |
| 406 | 1.112 |
| 407 | 0.708 |
| 408 | 0.447 |
| 409 | 0.491 |
| 410 | 0.578 |
| 411 | 0.822 |
| 412 | 0.106 |
| 413 | 1.016 |
| 414 | 0.664 |
| 415 | 0.532 |

-continued

| Example No. | EC50 [μM] |
|---|---|
| 416 | 0.025 |
| 417 | 0.715 |
| 418 | 0.248 |
| 419 | 0.313 |
| 420 | 0.014 |
| 421 | 20.02 |
| 422 | 1.859 |
| 423 | 9.731 |
| 424 | 0.389 |
| 425 | 2.685 |
| 426 | 1.627 |
| 427 | 1.319 |
| 428 | 0.266 |
| 429 | 0.891 |
| 430 | 1.31 |
| 431 | 3.474 |
| 432 | 0.032 |
| 433 | 1.723 |
| 434 | 0.425 |
| 435 | 0.226 |
| 436 | 0.024 |
| 437 | 4.911 |
| 438 | 0.661 |
| 439 | 0.662 |
| 440 | 6.59 |
| 441 | 1.522 |
| 442 | 0.134 |
| 443 | 1.446 |
| 444 | 3.913 |
| 445 | 8.814 |
| 446 | 2.137 |
| 447 | |
| 448 | 0.706 |
| 449 | 0.853 |
| 450 | 0.72 |
| 451 | 1.227 |
| 452 | 0.049 |
| 453 | 0.781 |
| 454 | 0.126 |
| 455 | 0.16 |
| 456 | 0.152 |
| 457 | 1.462 |
| 458 | 0.124 |
| 459 | |
| 460 | 0.122 |
| 461 | 3.431 |
| 462 | 0.137 |
| 463 | 2.483 |
| 464 | 0.126 |
| 465 | 0.948 |
| 466 | 4.716 |
| 467 | 0.265 |
| 468 | 0.719 |
| 469 | 0.06 |
| 470 | 0.235 |
| 471 | 5.023 |
| 472 | 0.038 |
| 473 | 0.173 |
| 474 | 34.546 |
| 475 | 2.818 |
| 476 | 3.954 |
| 477 | 2.717 |
| 478 | 3.146 |
| 479 | 16.9 |
| 480 | 20.04 |
| 481 | 3.483 |
| 482 | 15.72 |
| 483 | 2.085 |
| 484 | 0.014 |
| 485 | 0.813 |

The invention claimed is:

1. A compound of the formula I,

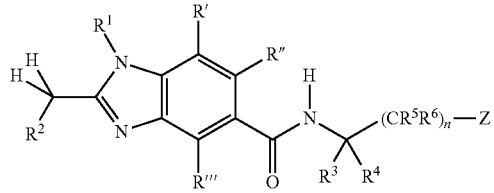

wherein

R', R", and R''' are independently of each other H, halogen, $CF_3$, $OCF_3$, or $O$—$(C_1$-$C_3)$-alkyl;

$R^1$ is
a) $(C_4$-$C_7)$-alkyl;
b) $(C_5$-$C_7)$-cycloalkyl, which is unsubstituted or mono-substituted by $(C_1$-$C_2)$-alkyl or $CF_3$;
c) methylene-cyclohexyl; or
d) phenyl, which is unsubstituted or mono-substituted by methyl or Cl;

$R^2$ is
a) a 5-membered heteroaryl which contains 1 or 2 identical or different ring heteroatoms selected from the group consisting of N, O and S, wherein said 5-membered heteroaryl is unsubstituted or mono-substituted by Cl or $(C_1$-$C_4)$-alkyl;
b) phenyl;
c) $(C_5$-$C_6)$-cycloalkyl; or
d) tetrahydrofuranyl;

$R^3$ is H or $(C_1$-$C_2)$-alkyl;
and
$R^4$ is
a) $(C_3$-$C_5)$-alkyl, which may be optionally substituted by 1-3 F or S—$(C_1$-$C_4)$-alkyl,
b) $(C_0$-$C_1)$-alkylene-$(C_3$-$C_7)$-cycloalkyl, wherein said cycloalkyl is unsubstituted or mono- or di-substituted by methyl;
c) $(C_0$-$C_2)$-alkylene-phenyl, wherein said phenyl is unsubstituted or mono- or di-substituted by F, Cl, $(C_1$-$C_4)$-alkyl or $CF_3$; or
d) thienyl; or
$R_3$ and $R_4$
are, together with the carbon atom to which they are attached, a 5- to 7-membered cycloalkyl ring, which is unsubstituted or mono-substituted by $(C_1$-$C_4)$-alkyl;

$R^5$ is H, $(C_1$-$C_4)$-alkyl or OH;
$R^6$ is H or $(C_1$-$C_4)$-alkyl;
n is 0, 1 or 2; and
Z is
$CO_2$—$R^7$, $OR^8$, $C(O)NR^9R^{10}$, $S(O)_2NR^{11}R^{12}$,

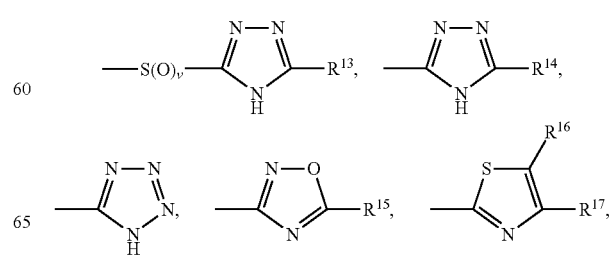

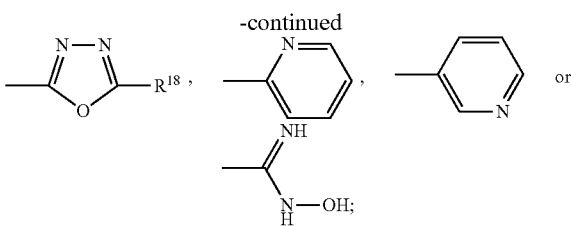

wherein
v is 0 or 2;
$R^7$ is H or $(C_1-C_4)$-alkyl;
$R^8$ is H or $(C_1-C_4)$-alkyl;
$R^9$ is H, $(C_1-C_4)$-alkyl or ethylene-O—$(C_1-C_4)$-alkyl; and
$R^{10}$ is
a) H;
b) $(C_1-C_6)$-alkyl, which is unsubstituted or mono-substituted by $CF_3$;
c) $(C_1-C_2)$-alkyl, which is substituted by CN or $CO_2R^{19}$; wherein
$R^{19}$ is H or $(C_1-C_6)$-alkyl;
d) $(C_2-C_4)$-alkyl, which is mono-substituted by a substituent selected from the group consisting of S-methyl, $SO_2NR^{20}R^{21}$, O—$R^{22}$ and $NR^{23}R^{24}$;
wherein
$R^{20}$ is H;
$R^{21}$ is H;
$R^{22}$ is H, $(C_1-C_3)$-alkyl, methylene-cyclopropyl, methylene-phenyl, or methylene-2-tetrahydrofurane;
$R^{23}$ is H or $(C_1-C_2)$-alkyl; and
$R^{24}$ is $(C_1-C_2)$-alkyl or $SO_2$-methyl;
e) $(C_3-C_5)$-cycloalkyl, which is unsubstituted or mono-substituted by phenyl;
f) $(C_0-C_2)$-alkylene-heterocycloalkyl, wherein said heterocycloalkyl is five or six membered and contains 1 or 2 O atoms in non-adjacent positions, and wherein said heterocycloalkyl is unsubstituted or geminally disubstituted with a spiro cyclopentyl ring or a spiro cyclohexyl ring;
g) $(C_2-C_5)$-alkylene-heterocycloalkyl, wherein said heterocycloalkyl is a five-, six- or seven-membered ring, which contains at least one N atom, and which is attached via said N-atom, and which may additionally contain one heteroatom selected from the group consisting of O, $S(O)_x$ and $NR^{25}$ in a position not adjacent to the N atom by which the ring is attached to the alkylene, and wherein any carbon atom within said heterocycloalkyl is unsubstituted or substituted by 1 or 2 substituents selected from the group consisting of $(C_1-C_3)$alkyl and methylene-phenyl; wherein
x is 2; and
$R^{25}$ is H, $(C_1-C_2)$alkyl, methylene-phenyl or phenyl, which is unsubstituted or substituted by 1 or 2 substituents selected from the group consisting of F, Cl and O—$(C_1-C_4)$-alkyl;
h) $(C_0-C_3)$-alkylene-heterocycloalkyl, wherein said heterocycloalkyl is a five- or six-membered ring, which contains at least one N atom, and which is not attached via said N-atom, and which may additionally contain one O atom in a position not adjacent to the N atom, and wherein said N-atom is unsubstituted or substituted by a substituent selected from the group consisting of
i) $(C_1-C_4)$-alkyl, which is unsubstituted or mono-substituted by $O(C_1-C_4)$-alkyl;
ii) methylene-cyclohexyl;
iii) $(C_0-C_2)$-alkylene-phenyl, wherein said phenyl is unsubstituted or substituted by 1 or 2 substituents selected from the group consisting of F and $O(C_1-C_4)$-alkyl;
iv) $(C_0-C_1)$-alkylene-pyridyl; and
v) pyrimidinyl;
i) 8-methyl-8-aza-bicyclo[3.2.1]oct-3yl;
j) 9-methyl-9-aza-bicyclo[3.3.1]non-3-yl;
k) methylene-4-(octahydro-quinolizinyl);
l) $(C_0-C_2)$-alkylene-phenyl, wherein phenyl is unsubstituted or monosubstituted by a substituent selected from the group consisting of F, $O(C_1-C_4)$-alkyl, $N((C_1-C_4)$-alkyl$)_2$, 4-morpholinyl and methylene-(4-methyl-piperidin)-1-yl or disubstituted on adjacent positions by the group —$O(CH_2)O$—; or
m) $(C_1-C_2)$-alkylene-heteroaryl, wherein said heteroaryl ring is a five- or six-membered ring containing 1, 2, 3 or 4 heteroatoms selected from the group consisting of O, S and N; and wherein said heteroaryl ring is unsubstituted;
or
$R^9$ and $R^{10}$ together with the N-atom carrying them are
a) a four-, five- or six-membered heterocycloalkyl ring containing one heteroatom, which is the N atom to which $R^9$ and $R^{10}$ are attached, and wherein said heterocycloalkyl ring is unsubstituted or mono-substituted by a substituent selected from the group consisting of
i) $(C_0-C_1)$-alkylene-$OR^{26}$, wherein $R^{26}$ is H, $(C_1-C_3)$ alkyl or methylene-phenyl;
ii) $CO_2R^{27}$, wherein $R^{27}$ is H or $(C_1-C_6)$-alkyl;
ii) $NR^{28}R^{29}$, wherein $R^{28}$ is $(C_1-C_2)$-alkyl and $R^{29}$ is $(C_1-C_2)$-alkyl, methylene-phenyl or ethylene-$N((C_1-C_4)$-alkyl$)_2$;
iii) 1-piperidinyl, which is unsubstituted or mono-substituted by methyl;
iv) 1-piperazinyl, which is unsubstituted or mono-substituted by methyl;
v) 4-morpholinyl;
vi) 1-azepanyl; and
vii) 2-(2,3-dihydro-1H-isoindolyl);
b) a six- or seven-membered heterocycloalkyl ring containing the N atom to which $R^9$ and $R^{10}$ are attached and one additional heteroatom selected from O, S or $NR^{30}$ in a position non-adjacent to the N atom to which $R^9$ and $R^{10}$ are attached, wherein the carbon atoms in said heterocycloalkyl ring are unsubstituted or mono- or disubstituted by methyl and wherein
$R^{30}$ is
i) H;
ii) $(C_1-C_4)$-alkyl;
iii) $(C_5-C_6)$-cycloalkyl;
iv) phenyl, which is unsubstituted or mono-substituted by F, $CF_3$ or O—$(C_1-C_4)$-alkyl;
v) methylene-phenyl, which is unsubstituted or mono- or di-substituted by F or Cl or disubstituted on adjacent positions by the group —$O(CH_2)O$—; or
vi) pyridyl; or
c) a 2,5-diaza-bicyclo[2.2.1]heptyl-ring, which is unsubstituted or substituted on the N atom in the 5-position by a substituent selected from the group consisting of $(C_1-C_4)$-alkyl, methylene-cyclopentyl, phenyl, which is unsubstituted or mono-substituted by F, and methylene-phenyl, wherein said phenyl is unsubstituted or mono-substituted by O—$(C_1-C_4)$-alkyl or $CF_3$;
$R^{11}$ is H;
$R^{12}$ is $(C_1-C_4)$-alkyl;
$R^{13}$ is H;
$R^{14}$ is $CF_3$ or methylene-O—$(C_1-C_4)$-alkyl;

$R^{15}$ is cyclopropyl or phenyl;
$R^{16}$ is H or $(C_1-C_4)$-alkyl;
$R^{17}$ is H or $(C_1-C_4)$-alkyl;
and
$R^{18}$ is $(C_1-C_4)$-alkyl;
in any of its stereoisomeric forms, or a mixture of stereoisomeric forms in any ratio, or a physiologically acceptable salt thereof, or a physiologically acceptable solvate of any of them.

2. A compound of the formula I,

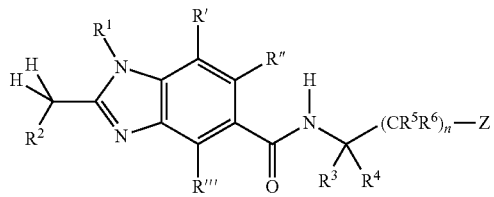

wherein
R', R'', and R''' are each H;
$R^1$ is
a) iso-butyl, sec-butyl, 1-ethyl-propyl, 2-methyl-butyl, 1,3-dimethyl-butyl, or 1-isopropyl-2-methyl-propyl;
b) cyclopentyl, 2-methyl-cyclopentyl, cyclohexyl, 2-methyl-cyclohexyl, 2-(trifluoromethyl)-cyclohexyl, 2-ethyl-cyclohexyl, or cycloheptyl;
c) methylene-cyclohexyl; or
d) phenyl, 2-chloro-phenyl, or 4-tolyl;
$R^2$ is
a) 2-furanyl, 3-furanyl, 2-thienyl, 3-thienyl, 4-thiazolyl, 5-thiazolyl, 1-pyrazolyl; 5-isoxazolyl, 5-methyl-thien-2-yl, or 5-chloro-thien-2-yl;
b) phenyl;
c) $(C_5-C_6)$-cycloalkyl; or
d) 2-tetrahydrofuranyl;
$R^3$ is H or methyl;
and
$R^4$ is
a) $(C_3-C_5)$-alkyl, which may be optionally substituted by 1-3 F or S-methyl; or
b) methylene-$(C_4-C_6)$-cycloalkyl;
or
$R^3$ and $R^4$
are, together with the carbon atom to which they are attached, a 5- to 7-membered cycloalkyl ring;
$R^5$ is H, methyl or OH;
$R^6$ is H or methyl;
n is 0, 1 or 2; and
Z is $CO_2$—$R^7$, $OR^8$, $C(O)NR^9R^{10}$, $S(O)_2NR^{11}R^{12}$,

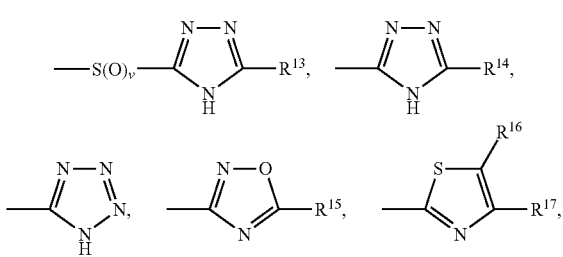

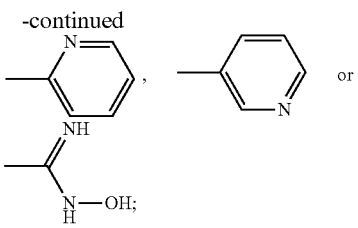

wherein
v is 0 or 2;
$R^7$ is H;
$R^8$ is H or $(C_1-C_4)$-alkyl;
$R^9$ is H or $CH_3$;
and
$R^{10}$ is
a) H;
b) $(C_1-C_6)$-alkyl, which is unsubstituted or mono-substituted by $CF_3$; or
c) $(C_1-C_2)$-alkyl, which is substituted by CN or $CO_2R^{19}$;
wherein
$R^{19}$ is H;
d) $(C_2-C_4)$-alkyl, which is mono-substituted by a substituent selected from the group consisting of S—$CH_3$, $SO_2NR^{20}R^{21}$, O—$R^{22}$ and $NR^{23}R^{24}$;
wherein
$R^{20}$ is H;
$R^{21}$ is H;
$R^{22}$ is H, $(C_1-C_3)$-alkyl, methylene-cyclopropyl, methylene-phenyl, or methylene-2-tetrahydrofuran;
$R^{23}$ is H or $(C_1-C_2)$-alkyl; and
$R^{24}$ is $(C_1-C_2)$-alkyl or $SO_2CH_3$;
e) cyclobutyl, cyclopentyl or 2-phenyl-cyclopropyl;
f) $(C_0-C_2)$-alkylene-heterocycloalkyl, wherein said heterocycloalkyl is selected from the group consisting of 2-tetrahydrofuranyl, 3-tetrahydrofuranyl, 2-tetrahydropyranyl, 3-tetrahydropyranyl, 4-tetrahydropyranyl and 1,4-dioxan-2-yl;
g) $(C_2-C_5)$-alkylene-heterocycloalkyl, wherein said heterocycloalkyl is selected from the group consisting of 1-pyrrolidinyl, 1-piperidinyl, 1-azepanyl, 4-morpholinyl 1,1-dioxo-thiomorpholin-4-yl, and 1-piperazinyl; wherein said heterocycloalkyl is unsubstituted or substituted by 1 or 2 substituents selected from the group consisting of $(C_1-C_2)$alkyl and methylene-phenyl;
h) $(C_0-C_3)$-alkylene-heterocycloalkyl, wherein said heterocycloalkyl is selected from the group consisting of 3-pyrrolidinyl, 2-piperidinyl, 3-piperidinyl, 4-piperidinyl and 2-morpholinyl and wherein said heterocycloalkyl is substituted by a substituent selected from the group consisting of
i) $(C_1-C_4)$-alkyl;
ii) methylene-cyclohexyl;
iii) $(C_0-C_2)$-alkylene-phenyl;
iv) $(C_0-C_1)$-alkylene-pyridyl; or
v) pyrimidinyl;
i) 8-methyl-8-aza-bicyclo[3.2.1]oct-3yl;
j) 9-methyl-9-aza-bicyclo[3.3.1]non-3-yl;
k) methylene-4-(octahydro-quinolizinyl);
l) $(C_0-C_2)$-alkylene-phenyl, wherein said phenyl is unsubstituted or monosubstituted by a substituent selected from the group consisting of F, O—$CH_3$ and $N(CH_3)_2$;
or
m) $(C_1-C_2)$-alkylene-heteroaryl, wherein said heteroaryl ring is selected from the group consisting of 2-thienyl, 2-furanyl, 2-thiazolyl, 2-oxazolyl, 5-tetrazolyl and 5-Oxo-4,5-dihydro-1H-[1,2,4]triazol-3-yl;
or
$R^9$ and $R^{10}$ together with the N-atom carrying them are
a) azetidinyl substituted by $CO_2H$;
b) pyrrolidinyl, which is unsubstituted or mono-substituted by a substituent selected from the group consisting of
  i) OH;
  ii) methylene-$OCH_3$;
  iii) methylene-O-methylene-phenyl;
  iv) $CO_2H$;
  v) $NR^{28}R^{29}$, wherein $R^{28}$ is $(C_1-C_2)$-alkyl and $R^{29}$ is $(C_1-C_2)$-alkyl; and
  vi) 1-piperazinyl, which is unsubstituted or mono-substituted by methyl;
c) piperidinyl, which is mono-substituted by a substituent selected from the group consisting of
  i) O—$(C_1-C_3)$alkyl;
  ii) methylene-O—$CH_3$;
  iii) $NR^{28}R^{29}$, wherein $R^{28}$ is $(C_1-C_2)$-alkyl and $R^{29}$ is methylene-phenyl or ethylene-$N(CH_3)_2$;
  iv) 1-piperidinyl, which is mono-substituted by methyl;
  v) 1-piperazinyl, which is unsubstituted or mono-substituted by methyl;
  vi) 4-morpholinyl;
  vii) 1-azepanyl; and
  viii) 2-(2,3-dihydro-1H-isoindolyl);
d) 4-morpholinyl, which is disubstituted by methyl;
e) 4-thiomorpholinyl;
f) piperazinyl, which is substituted on the nitrogen in the 4-position with a substituent selected from the group consisting of
  i) $(C_1-C_4)$-alkyl;
  ii) $(C_5-C_6)$-cycloalkyl;
  iii) phenyl, which is unsubstituted or mono-substituted by F, $CF_3$ or $OCH_3$;
  iv) methylene-phenyl, which is unsubstituted or disubstituted on adjacent positions by the group —$O(CH_2)O$—; and
  v) pyridyl;
g) azepanyl, which is substituted by methylene-phenyl, which is unsubstituted or mono- or di-substituted by F or Cl;
h) a 2,5-diaza-bicyclo[2.2.1]heptyl-ring, which is substituted on the N atom in the 5-position by a substituent selected from the group consisting of $(C_1-C_4)$-alkyl, methylene-cyclopentyl, phenyl, which is mono-substituted by F, and methylene-phenyl, wherein said phenyl is unsubstituted or mono-substituted by $OCH_3$ or $CF_3$;
$R^{11}$ is H;
$R^{12}$ is $CH_3$;
$R^{13}$ is H;
$R^{14}$ is $CF_3$ or methylene-$OCH_3$;
$R^{15}$ is cyclopropyl or phenyl;
$R^{16}$ is H or $CH_3$;
$R^{17}$ is H or $CH_3$;
and
$R^{18}$ is $CH_3$;
in any of its stereoisomeric forms, or a mixture of stereoisomeric forms in any ratio, or a physiologically acceptable salt thereof, or a physiologically acceptable solvate of any of them.

3. The compound of claim 1 wherein
R', R'', and R''' are each H;
$R^1$ is 1-ethyl-propyl;
$R^2$ is 3-thienyl;
$R^3$ is H;
$R^4$ is 2-methyl-propyl;
n is 0, 1, or 2;
and
Z is $C(O)NR^9R^{10}$.

4. The compound of claim 1 wherein
R', R'', and R''' are each H;
$R^1$ is 1-ethyl-propyl or 2-methyl-cyclohexyl;
$R^2$ is 3-thienyl;
$R^3$ is H or $(C_1-C_2)$-alkyl;
and
$R^4$ is
a) $(C_3-C_5)$-alkyl, which may be optionally substituted by 1-3 F or S—$(C_1-C_4)$-alkyl; or
b) $(C_0-C_1)$-alkylene-$(C_3-C_7)$-cycloalkyl, wherein said cycloalkyl is unsubstituted or mono- or di-substituted by methyl;
or
$R^3$ and $R^4$
are, together with the carbon atom to which they are attached, a 5- to 7-membered cycloalkyl ring, which is unsubstituted or mono-substituted by $(C_1-C_4)$-alkyl;
n is 0; and
Z is $CO_2$—H.

5. The compound of claim 1 wherein
R', R'', and R''' are each H;
$R^1$ is 1-ethyl-propyl or 2-methyl-cyclohexyl;
$R^2$ is 3-thienyl;
$R^3$ is H or $(C_1-C_2)$-alkyl;
and
$R^4$ is
a) $(C_3-C_5)$-alkyl, which may be optionally substituted by 1-3 F or S—$(C_1-C_4)$-alkyl; or
b) $(C_0-C_1)$-alkylene-$(C_3-C_7)$-cycloalkyl, wherein said cycloalkyl is unsubstituted or mono- or di-substituted by methyl;
or
$R^3$ and $R^4$
are, together with the carbon atom to which they are attached, a 5- to 7-membered cycloalkyl ring, which is unsubstituted or mono-substituted by $(C_1-C_4)$-alkyl;
$R^5$ is H, $(C_1-C_4)$-alkyl or OH;
$R^6$ is H or $(C_1-C_4)$-alkyl;
n is 1;
and
Z is $CO_2$—H.

6. The compound of claim 1 wherein
R', R'', and R''' are each H;
$R^1$ is 1-ethyl-propyl or 2-methyl-cyclohexyl;
$R^2$ is 3-thienyl;
$R^3$ is H or $(C_1-C_2)$-alkyl;
and
$R^4$ is
a) $(C_3-C_5)$-alkyl, which may be optionally substituted by 1-3 F or S—$(C_1-C_4)$-alkyl; or
b) $(C_0-C_1)$-alkylene-$(C_3-C_7)$-cycloalkyl, wherein said cycloalkyl is unsubstituted or mono- or di-substituted by methyl;
or
$R^3$ and $R^4$
are, together with the carbon atom to which they are attached, a 5- to 7-membered cycloalkyl ring, which is unsubstituted or mono-substituted by $(C_1-C_4)$-alkyl;
$R^5$ is H, $(C_1-C_4)$-alkyl or OH;
$R^6$ is H or $(C_1-C_4)$-alkyl;
n is 2;
and
Z is $CO_2$—H.

7. The compound of claim 1
wherein
R', R", and R'" are each H;
$R^1$ is 1-ethyl-propyl;
$R^2$ is 3-thienyl;
$R^3$ is H or $(C_1-C_2)$-alkyl;
and
$R^4$ is
a) $(C_3-C_5)$-alkyl, which may be optionally substituted by 1-3 F or S—$(C_1-C_4)$-alkyl; or
b) $(C_0-C_1)$-alkylene-$(C_3-C_7)$-cycloalkyl, wherein said cycloalkyl is unsubstituted or mono- or di-substituted by methyl;
or
$R^3$ and $R^4$
are, together with the carbon atom to which they are attached, a 5- to 7-membered cycloalkyl ring, which is unsubstituted or mono-substituted by $(C_1-C_4)$-alkyl;
$R^5$ is H, $(C_1-C_4)$-alkyl or OH;
$R^6$ is H or $(C_1-C_4)$-alkyl;
n is 1 or 2;
and
Z is $OR^8$, $S(O)_2NR^{11}R^{12}$,

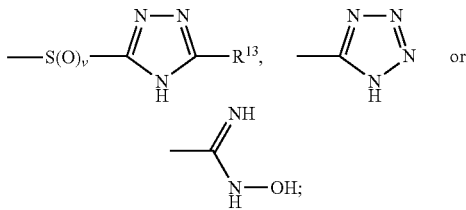

wherein v is 0 or 2;
$R^8$ is H;
$R^{11}$ is H;
$R^{12}$ is $CH_3$; and
$R^{13}$ is H.
8. The compound of claim 1
wherein
R', R", and R'" are each H;
$R^1$ is 1-ethyl-propyl;
$R^2$ is 3-thienyl;
$R^3$ is H;
$R^4$ is 2-methyl-propyl;
n is 0;
and
Z is $C(O)NR^9R^{10}$;
wherein
$R^9$ is H or methyl;
and
$R^{10}$ is
c) $(C_1-C_2)$-alkyl, which is substituted by CN;
d) $(C_2-C_4)$-alkyl, which is mono-substituted by $NR^{23}R^{24}$;
wherein
$R^{23}$ is H;
$R^{24}$ is $(C_1-C_2)$-alkyl or $SO_2$Methyl; or
m) $(C_1-C_2)$-alkylene-heteroaryl, wherein said heteroaryl ring is a five- or six-membered ring containing 1, 2, 3 or 4 heteroatoms selected from the group consisting of O, S and N; and wherein said heteroaryl ring is unsubstituted;
or
$R^9$ and $R^{10}$ together with the N-atom carrying them are
a) a four-, five- or six-membered heterocycloalkyl ring containing one heteroatom, which is the N atom to which $R^9$ and $R^{10}$ are attached, and wherein said heterocycloalkyl ring is unsubstituted or mono-substituted by a substituent selected from the group consisting of
i) $(C_0-C_1)$-alkylene-$OR^{26}$, wherein $R^{26}$ is H; and
ii) $CO_2R^{27}$, wherein $R^{27}$ is H.
9. The compound of claim 1, selected from the group consisting of
1-{[1-(1-Ethyl-propyl)-2-thiophen-2-ylmethyl-1H-benzoimidazole-5-carbonyl]-amino}-cycloheptanecarboxylic acid;
1-{[1-(1-Ethyl-propyl)-2-thiophen-2-ylmethyl-1H-benzoimidazole-5-carbonyl]-amino}-cyclopentanecarboxylic acid;
3-Cyclopentyl-2-{[1-(1-ethyl-propyl)-2-thiophen-2-ylmethyl-1H-benzoimidazole-5-carbonyl]-amino}-propionic acid;
2-{[1-(1-Ethyl-propyl)-2-thiophen-2-ylmethyl-1H-benzoimidazole-5-carbonyl]-amino}-2,4-dimethyl-pentanoic acid;
(S)-3-Cyclohexyl-2-{[1-(2-methyl-cyclohexyl)-2-thiophen-2-ylmethyl-1H-benzoimidazole-5-carbonyl]-amino}-propionic acid;
(S)-2-{[1-(2-Methyl-cyclohexyl)-2-thiophen-2-ylmethyl-1H-benzoimidazole-5-carbonyl]-amino}-hexanoic acid;
(S)-2-{[1-(1-Ethyl-propyl)-2-thiophen-2-ylmethyl-1H-benzoimidazole-5-carbonyl]-amino}-hexanoic acid;
(S)-3-Cyclopropyl-2-{[1-(1-ethyl-propyl)-2-thiophen-2-ylmethyl-1H-benzoimidazole-5-carbonyl]-amino}-propionic acid;
(S)-3-Cyclobutyl-2-{[1-(1-ethyl-propyl)-2-thiophen-2-ylmethyl-1H-benzoimidazole-5-carbonyl]-amino}-propionic acid;
(S)-3-Cyclobutyl-2-{[1-((1R,2R)-2-methyl-cyclohexyl)-2-thiophen-2-ylmethyl-1H-benzoimidazole-5-carbonyl]-amino}-propionic acid;
1-{[1-(1-Ethyl-propyl)-2-thiophen-2-ylmethyl-1H-benzoimidazole-5-carbonyl]-amino}-cyclohexanecarboxylic acid;
2-{[1-(1-Ethyl-propyl)-2-thiophen-2-ylmethyl-1H-benzoimidazole-5-carbonyl]-amino}-2-methyl-pentanoic acid;
2-{[1-(1-Ethyl-propyl)-2-thiophen-2-ylmethyl-1H-benzoimidazole-5-carbonyl]-amino}-5,5,5-trifluoro-pentanoic acid;
5,5,5-Trifluoro-2-{[1-((1R,2R)-2-methyl-cyclohexyl)-2-thiophen-2-ylmethyl-1H-benzoimidazole-5-carbonyl]-amino}-pentanoic acid;
3-(4,4-Dimethyl-cyclohexyl)-2-{[1-(1-ethyl-propyl)-2-thiophen-2-ylmethyl-1H-benzoimidazole-5-carbonyl]-amino}-propionic acid;
3-(4,4-Dimethyl-cyclohexyl)-2-{[1-((1R,2R)-2-methyl-cyclohexyl)-2-thiophen-2-ylmethyl-1H-benzoimidazole-5-carbonyl]-amino}-propionic acid;
1-{[1-(1-Ethyl-propyl)-2-thiophen-2-ylmethyl-1H-benzoimidazole-5-carbonyl]-amino}-4-methyl-cyclohexanecarboxylic acid;
4-Methyl-1-{[1-((1R,2R)-2-methyl-cyclohexyl)-2-thiophen-2-ylmethyl-1H-benzoimidazole-5-carbonyl]-amino}-cyclohexanecarboxylic acid;
2-{[1-(1-Ethyl-propyl)-2-thiophen-2-ylmethyl-1H-benzoimidazole-5-carbonyl]-amino}-3-(4-methyl-cyclohexyl)-propionic acid;
1-{[1-((1R,2R)-2-Methyl-cyclohexyl)-2-thiophen-2-ylmethyl-1H-benzoimidazole-5-carbonyl]-amino}-cyclohexanecarboxylic acid;

3-Cycloheptyl-2-{[1-(1-ethyl-propyl)-2-thiophen-2-ylmethyl-1H-benzoimidazole-5-carbonyl]-amino}-propionic acid;
3-Cycloheptyl-2-{[1-((1R,2R)-2-methyl-cyclohexyl)-2-thiophen-2-ylmethyl-1H-benzoimidazole-5-carbonyl]-amino}-propionic acid;
3-Cyclohexyl-3-{[1-(1-ethyl-propyl)-2-thiophen-2-ylmethyl-1H-benzoimidazole-5-carbonyl]-amino}-propionic acid;
3-{[1-(1-Ethyl-propyl)-2-thiophen-2-ylmethyl-1H-benzoimidazole-5-carbonyl]-amino}-heptanoic acid;
4-Cyclohexyl-3-{[1-(1-ethyl-propyl)-2-thiophen-2-ylmethyl-1H-benzoimidazole-5-carbonyl]-amino}-butyric acid;
3-{[1-(1-Ethyl-propyl)-2-thiophen-2-ylmethyl-1H-benzoimidazole-5-carbonyl]-amino}-5,5-dimethyl-hexanoic acid;
(R)-3-{[1-(1-Ethyl-propyl)-2-thiophen-2-ylmethyl-1H-benzoimidazole-5-carbonyl]-amino}-5-methyl-hexanoic acid;
4-Cyclohexyl-3-{[1-((1R,2R)-2-methyl-cyclohexyl)-2-thiophen-2-ylmethyl-1H-benzoimidazole-5-carbonyl]-amino}-butyric acid;
4-Cyclohexyl-3-{[1-((1S,2S)-2-methyl-cyclohexyl)-2-thiophen-2-ylmethyl-1H-benzoimidazole-5-carbonyl]-amino}-butyric acid;
(3R,4S)-4-Methyl-3-{[1-((1R,2R)-2-methyl-cyclohexyl)-2-thiophen-2-ylmethyl-1H-benzoimidazole-5-carbonyl]-amino}-hexanoic acid;
(3R,4S)-3-{[1-(1-Ethyl-propyl)-2-thiophen-2-ylmethyl-1H-benzoimidazole-5-carbonyl]-amino}-4-methyl-hexanoic acid;
3-{[1-((1R,2R)-2-Methyl-cyclohexyl)-2-thiophen-2-ylmethyl-1H-benzoimidazole-5-carbonyl]-amino}-hexanoic acid;
3-{[1-((1R,2R)-2-Methyl-cyclohexyl)-2-thiophen-2-ylmethyl-1H-benzoimidazole-5-carbonyl]-amino}-heptanoic acid;
3-Cyclohexyl-3-{[1-((1R,2R)-2-methyl-cyclohexyl)-2-thiophen-2-ylmethyl-1H-benzoimidazole-5-carbonyl]-amino}-propionic acid;
3-{[1-(1-Ethyl-propyl)-2-thiophen-2-ylmethyl-1H-benzoimidazole-5-carbonyl]-amino}-2,2-dimethyl-heptanoic acid;
4-Ethyl-3-{[1-(1-ethyl-propyl)-2-thiophen-2-ylmethyl-1H-benzoimidazole-5-carbonyl]-amino}-hexanoic acid;
(S)-4-Cyclopentyl-3-{[1-(1-ethyl-propyl)-2-thiophen-2-ylmethyl-1H-benzoimidazole-5-carbonyl]-amino}-butyric acid;
(S)-4-Cyclopentyl-3-{[1-((1R,2R)-2-methyl-cyclohexyl)-2-thiophen-2-ylmethyl-1H-benzoimidazole-5-carbonyl]-amino}-butyric acid;
3-{[1-(1-Ethyl-propyl)-2-thiophen-2-ylmethyl-1H-benzoimidazole-5-carbonyl]-amino}-2,2,5-trimethyl-hexanoic acid;
3-{[1-(1-Ethyl-propyl)-2-thiophen-2-ylmethyl-1H-benzoimidazole-5-carbonyl]-amino}-2,2-dimethyl-hexanoic acid;
(1-{[1-(1-Ethyl-propyl)-2-thiophen-2-ylmethyl-1H-benzoimidazole-5-carbonyl]-amino}-cyclohexyl)-acetic acid;
(1-{[1-((1R,2R)-2-Methyl-cyclohexyl)-2-thiophen-2-ylmethyl-1H-benzoimidazole-5-carbonyl]-amino}-cyclohexyl)-acetic acid;
(2R,3S)-3-{[1-(1-Ethyl-propyl)-2-thiophen-2-ylmethyl-1H-benzoimidazole-5-carbonyl]-amino}-2-hydroxy-5-methyl-hexanoic acid;
(2S,3S)-3-{[1-(1-Ethyl-propyl)-2-thiophen-2-ylmethyl-1H-benzoimidazole-5-carbonyl]-amino}-2-hydroxy-5-methyl-hexanoic acid;
(R)-6-Methyl-4-{[1-((1R,2R)-2-methyl-cyclohexyl)-2-thiophen-2-ylmethyl-1H-benzoimidazole-5-carbonyl]-amino}-heptanoic acid;
(4R,5S)-4-{[1-(1-Ethyl-propyl)-2-thiophen-2-ylmethyl-1H-benzoimidazole-5-carbonyl]-amino}-5-methyl-heptanoic acid;
(4R,5S)-5-Methyl-4-{[1-((1R,2R)-2-methyl-cyclohexyl)-2-thiophen-2-ylmethyl-1H-benzoimidazole-5-carbonyl]-amino}-heptanoic acid;
(3R,4S)-5-Cyclohexyl-4-{[1-(1-ethyl-propyl)-2-thiophen-2-ylmethyl-1H-benzoimidazole-5-carbonyl]-amino}-3-hydroxy-pentanoic acid;
(3R,4S)-5-Cyclohexyl-3-hydroxy-4-{[1-((1R,2R)-2-methyl-cyclohexyl)-2-thiophen-2-ylmethyl-1H-benzoimidazole-5-carbonyl]-amino}-pentanoic acid;
(3S,4S)-4-{[1-(1-Ethyl-propyl)-2-thiophen-2-ylmethyl-1H-benzoimidazole-5-carbonyl]-amino}-3-hydroxy-6-methyl-heptanoic acid;
(3R,4S)-4-{[1-(1-Ethyl-propyl)-2-thiophen-2-ylmethyl-1H-benzoimidazole-5-carbonyl]-amino}-3-hydroxy-6-methyl-heptanoic acid;
(3R,4S)-3-Hydroxy-6-methyl-4-{[1-((1R,2R)-2-methyl-cyclohexyl)-2-thiophen-2-ylmethyl-1H-benzoimidazole-5-carbonyl]-amino}-heptanoic acid;
(3S,4S)-3-Hydroxy-6-methyl-4-{[1-((1R,2R)-2-methyl-cyclohexyl)-2-thiophen-2-ylmethyl-1H-benzoimidazole-5-carbonyl]-amino}-heptanoic acid;
(3S,4S)-5-Cyclohexyl-4-{[1-(1-ethyl-propyl)-2-thiophen-2-ylmethyl-1H-benzoimidazole-5-carbonyl]-amino}-3-hydroxy-pentanoic acid;
(S)-2-{[1-((1R,2R)-2-Methyl-cyclohexyl)-2-thiophen-2-ylmethyl-1H-benzoimidazole-5-carbonyl]-amino}-pentanoic acid;
(2S,3S)-3-Methyl-2-{[1-((1R,2R)-2-methyl-cyclohexyl)-2-thiophen-2-ylmethyl-1H-benzoimidazole-5-carbonyl]-amino}-pentanoic acid;
(S)-2-{[1-(1-Ethyl-propyl)-2-thiophen-2-ylmethyl-1H-benzoimidazole-5-carbonyl]-amino}-pentanoic acid;
(S)-3-{[1-(1-Ethyl-propyl)-2-thiophen-2-ylmethyl-1H-benzoimidazole-5-carbonyl]-amino}-5-methyl-hexanoic acid;
(S)-5-Methyl-3-{[1-(2-methyl-cyclohexyl)-2-thiophen-2-ylmethyl-1H-benzoimidazole-5-carbonyl]-amino}-hexanoic acid;
(S)-3-{[1-(1-Ethyl-propyl)-2-thiophen-2-ylmethyl-1H-benzoimidazole-5-carbonyl]-amino}-5-methyl-hexanoic acid;
(S)-2-{[1-(1-Ethyl-propyl)-2-thiophen-2-ylmethyl-1H-benzoimidazole-5-carbonyl]-amino}-4-methyl-pentanoic acid;
(S)-2-{[1-(1-Ethyl-propyl)-2-thiophen-2-ylmethyl-1H-benzoimidazole-5-carbonyl]-amino}-3-methyl-pentanoic acid;
(S)-2-{[1-(1-Ethyl-propyl)-2-thiophen-2-ylmethyl-1H-benzoimidazole-5-carbonyl]-amino}-4-methylsulfanyl-butyric acid;
(S)-3-Cyclohexyl-2-{[1-(1-ethyl-propyl)-2-thiophen-2-ylmethyl-1H-benzoimidazole-5-carbonyl]-amino}-propionic acid;

(S)-2-{[1-(1-Ethyl-propyl)-2-thiophen-2-ylmethyl-1H-benzoimidazole-5-carbonyl]-amino}-5-methyl-hexanoic acid;

(S)-4-Methyl-2-{[1-(2-methyl-cyclohexyl)-2-thiophen-3-ylmethyl-1H-benzoimidazole-5-carbonyl]-amino}-pentanoic acid;

(S)-4-Methyl-2-{[1-(2-methyl-cyclohexyl)-2-thiophen-2-ylmethyl-1H-benzoimidazole-5-carbonyl]-amino}-pentanoic acid;

(2S,3R)-2-{[1-(1-Ethyl-propyl)-2-thiophen-2-ylmethyl-1H-benzoimidazole-5-carbonyl]-amino}-3-methyl-pentanoic acid;

3-{[1-(1-Ethyl-propyl)-2-thiophen-2-ylmethyl-1H-benzoimidazole-5-carbonyl]-amino}-hexanoic acid;

(R)-3-{[1-(1-Ethyl-propyl)-2-thiophen-2-ylmethyl-1H-benzoimidazole-5-carbonyl]-amino}-4-methyl-pentanoic acid;

(R)-4-{[1-(1-Ethyl-propyl)-2-thiophen-2-ylmethyl-1H-benzoimidazole-5-carbonyl]-amino}-5-methyl-hexanoic acid;

(R)-4-{[1-(1-Ethyl-propyl)-2-thiophen-2-ylmethyl-1H-benzoimidazole-5-carbonyl]-amino}-6-methyl-heptanoic acid;

(S)-4-Methyl-2-{[1-((1R,2R)-2-methyl-cyclohexyl)-2-thiophen-2-ylmethyl-1H-benzoimidazole-5-carbonyl]-amino}-pentanoic acid;

(S)-4-Methyl-2-{[1-((1S,2S)-2-methyl-cyclohexyl)-2-thiophen-2-ylmethyl-1H-benzoimidazole-5-carbonyl]-amino}-pentanoic acid;

(S)-4-Methyl-2-{[1-((1R,2S)-2-methyl-cyclohexyl)-2-thiophen-2-ylmethyl-1H-benzoimidazole-5-carbonyl]-amino}-pentanoic acid;

(S)-4-Methyl-2-{[1-((1S,2R)-2-methyl-cyclohexyl)-2-thiophen-2-ylmethyl-1H-benzoimidazole-5-carbonyl]-amino}-pentanoic acid;

(S)-2-{[1-(2-Methyl-cyclohexyl)-2-thiophen-2-ylmethyl-1H-benzoimidazole-5-carbonyl]-amino}-hexanoic acid;

(S)-2-{[1-(2-Methyl-cyclohexyl)-2-thiophen-2-ylmethyl-1H-benzoimidazole-5-carbonyl]-amino}-hexanoic acid;

(S)-2-{[1-(2-Methyl-cyclohexyl)-2-thiophen-2-ylmethyl-1H-benzoimidazole-5-carbonyl]-amino}-hexanoic acid;

(S)-2-{[1-(2-Methyl-cyclohexyl)-2-thiophen-2-ylmethyl-1H-benzoimidazole-5-carbonyl]-amino}-hexanoic acid;

(S)-3-Cyclohexyl-2-{[1-(2-methyl-cyclohexyl)-2-thiophen-2-ylmethyl-1H-benzoimidazole-5-carbonyl]-amino}-propionic acid;

(S)-3-Cyclohexyl-2-{[1-(2-methyl-cyclohexyl)-2-thiophen-2-ylmethyl-1H-benzoimidazole-5-carbonyl]-amino}-propionic acid;

(S)-3-Cyclohexyl-2-{[1-(2-methyl-cyclohexyl)-2-thiophen-2-ylmethyl-1H-benzoimidazole-5-carbonyl]-amino}-propionic acid;

(S)-3-Cyclohexyl-2-{[1-(2-methyl-cyclohexyl)-2-thiophen-2-ylmethyl-1H-benzoimidazole-5-carbonyl]-amino}-propionic acid;

(S)-5-Methyl-3-{[1-(2-methyl-cyclohexyl)-2-thiophen-2-ylmethyl-1H-benzoimidazole-5-carbonyl]-amino}-hexanoic acid;

(S)-5-Methyl-3-{[1-(2-methyl-cyclohexyl)-2-thiophen-2-ylmethyl-1H-benzoimidazole-5-carbonyl]-amino}-hexanoic acid;

(S)-5-Methyl-3-{[1-(2-methyl-cyclohexyl)-2-thiophen-2-ylmethyl-1H-benzoimidazole-5-carbonyl]-amino}-hexanoic acid;

(S)-5-Methyl-3-{[1-(2-methyl-cyclohexyl)-2-thiophen-2-ylmethyl-1H-benzoimidazole-5-carbonyl]-amino}-hexanoic acid;

(R)-2-{[1-(1-Ethyl-propyl)-2-thiophen-2-ylmethyl-1H-benzoimidazole-5-carbonyl]-amino}-2,4-dimethyl-pentanoic acid;

(S)-2-{[1-(1-Ethyl-propyl)-2-thiophen-2-ylmethyl-1H-benzoimidazole-5-carbonyl]-amino}-2,4-dimethyl-pentanoic acid;

3-Cyclopentyl-2-{[1-((1R,2R)-2-methyl-cyclohexyl)-2-thiophen-2-ylmethyl-1H-benzoimidazole-5-carbonyl]-amino}-propionic acid;

3-Cyclopentyl-2-{[1-((1R,2R)-2-methyl-cyclohexyl)-2-thiophen-2-ylmethyl-1H-benzoimidazole-5-carbonyl]-amino}-propionic acid;

(S)-3-Cycloheptyl-2-{[1-(1-ethyl-propyl)-2-thiophen-2-ylmethyl-1H-benzoimidazole-5-carbonyl]-amino}-propionic acid;

(R)-3-Cycloheptyl-2-{[1-(1-ethyl-propyl)-2-thiophen-2-ylmethyl-1H-benzoimidazole-5-carbonyl]-amino}-propionic acid;

3-Cycloheptyl-2-{[1-((1R,2R)-2-methyl-cyclohexyl)-2-thiophen-2-ylmethyl-1H-benzoimidazole-5-carbonyl]-amino}-propionic acid;

3-Cycloheptyl-2-{[1-((1R,2R)-2-methyl-cyclohexyl)-2-thiophen-2-ylmethyl-1H-benzoimidazole-5-carbonyl]-amino}-propionic acid;

(S)-3-{[1-(1-Ethyl-propyl)-2-thiophen-2-ylmethyl-1H-benzoimidazole-5-carbonyl]-amino}-heptanoic acid;

(R)-3-{[1-(1-Ethyl-propyl)-2-thiophen-2-ylmethyl-1H-benzoimidazole-5-carbonyl]-amino}-heptanoic acid;

(S)-4-Cyclohexyl-3-{[1-(1-ethyl-propyl)-2-thiophen-2-ylmethyl-1H-benzoimidazole-5-carbonyl]-amino}-butyric acid;

(R)-4-Cyclohexyl-3-{[1-(1-ethyl-propyl)-2-thiophen-2-ylmethyl-1H-benzoimidazole-5-carbonyl]-amino}-butyric acid;

4-Cyclohexyl-3-{[1-((1R,2R)-2-methyl-cyclohexyl)-2-thiophen-2-ylmethyl-1H-benzoimidazole-5-carbonyl]-amino}-butyric acid;

4-Cyclohexyl-3-{[1-((1R,2R)-2-methyl-cyclohexyl)-2-thiophen-2-ylmethyl-1H-benzoimidazole-5-carbonyl]-amino}-butyric acid;

3-{[1-((1R,2R)-2-Methyl-cyclohexyl)-2-thiophen-2-ylmethyl-1H-benzoimidazole-5-carbonyl]-amino}-hexanoic acid;

3-{[1-((1R,2R)-2-Methyl-cyclohexyl)-2-thiophen-2-ylmethyl-1H-benzoimidazole-5-carbonyl]-amino}-hexanoic acid;

3-{[1-((1R,2R)-2-Methyl-cyclohexyl)-2-thiophen-2-ylmethyl-1H-benzoimidazole-5-carbonyl]-amino}-heptanoic acid;

3-{[1-((1R,2R)-2-Methyl-cyclohexyl)-2-thiophen-2-ylmethyl-1H-benzoimidazole-5-carbonyl]-amino}-heptanoic acid;

3-Cyclohexyl-3-{[1-((1R,2R)-2-methyl-cyclohexyl)-2-thiophen-2-ylmethyl-1H-benzoimidazole-5-carbonyl]-amino}-propionic acid;

3-Cyclohexyl-3-{[1-((1R,2R)-2-methyl-cyclohexyl)-2-thiophen-2-ylmethyl-1H-benzoimidazole-5-carbonyl]-amino}-propionic acid;

(R)-3-{[1-(1-Ethyl-propyl)-2-thiophen-2-ylmethyl-1H-benzoimidazole-5-carbonyl]-amino}-2,2,5-trimethyl-hexanoic acid;

(S)-3-{[1-(1-Ethyl-propyl)-2-thiophen-2-ylmethyl-1H-benzoimidazole-5-carbonyl]-amino}-2,2,5-trimethyl-hexanoic acid;

(R)-3-{[1-(1-Ethyl-propyl)-2-thiophen-2-ylmethyl-1H-benzoimidazole-5-carbonyl]-amino}-2,2-dimethyl-hexanoic acid;

(S)-3-{[1-(1-Ethyl-propyl)-2-thiophen-2-ylmethyl-1H-benzoimidazole-5-carbonyl]-amino}-2,2-dimethyl-hexanoic acid;

(S)-3-{[1-(1-Ethyl-propyl)-2-thiophen-2-ylmethyl-1H-benzoimidazole-5-carbonyl]-amino}-2,2-dimethyl-heptanoic acid; and (R)-3-{[1-(1-Ethyl-propyl)-2-thiophen-2-ylmethyl-1H-benzoimidazole-5-carbonyl]-amino}-2,2-dimethyl-heptanoic acid;

or a physiologically acceptable salt thereof, or a physiologically acceptable solvate thereof.

10. A pharmaceutical composition comprising at least one compound of claim 1 or a physiologically acceptable solvate thereof, and a pharmaceutically acceptable carrier and/or excipient.

11. A pharmaceutical composition comprising at least one compound of claim 2 or a physiologically acceptable solvate thereof, and a pharmaceutically acceptable carrier and/or excipient.

* * * * *